United States Patent
Mohammadi et al.

(10) Patent No.: US 9,657,075 B2
(45) Date of Patent: May 23, 2017

(54) CHIMERIC FIBROBLAST GROWTH FACTOR 23 PROTEINS AND METHODS OF USE

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/839,051

(22) Filed: Mar. 15, 2013

(65) Prior Publication Data

US 2013/0331325 A1    Dec. 12, 2013

Related U.S. Application Data

(60) Provisional application No. 61/656,887, filed on Jun. 7, 2012, provisional application No. 61/664,097, filed on Jun. 25, 2012.

(51) Int. Cl.
| | | |
|---|---|---|
| *A61K 38/18* | (2006.01) | |
| *C07K 14/50* | (2006.01) | |
| *A61K 45/06* | (2006.01) | |

(52) U.S. Cl.
CPC .......... *C07K 14/50* (2013.01); *A61K 38/1825* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,132,408 A | 7/1992 | Baird et al. | |
| 5,478,804 A | 12/1995 | Calabresi et al. | |
| 5,648,260 A | 7/1997 | Winter et al. | |
| 6,326,484 B1 | 12/2001 | Gage et al. | |
| 6,982,170 B1 | 1/2006 | Maciag et al. | |
| 7,223,563 B2 | 5/2007 | Econs et al. | |
| 7,314,618 B2 | 1/2008 | Econs et al. | |
| 7,491,697 B2 | 2/2009 | Beals et al. | |
| 7,582,607 B2 | 9/2009 | Frye et al. | |
| 7,622,445 B2 | 11/2009 | Frye et al. | |
| 7,655,627 B2 | 2/2010 | Frye et al. | |
| 7,745,406 B2 | 6/2010 | Econs et al. | |
| 7,947,810 B2 | 5/2011 | Econs et al. | |
| 7,956,033 B2 | 6/2011 | Cheng et al. | |
| 8,168,591 B2 | 5/2012 | Takada et al. | |
| 8,642,546 B2 | 2/2014 | Belouski et al. | |
| 8,889,426 B2 | 11/2014 | Mohammadi et al. | |
| 8,889,621 B2 | 11/2014 | Mohammadi et al. | |
| 8,906,854 B2 | 12/2014 | Jonker et al. | |
| 8,951,966 B2 | 2/2015 | Ling et al. | |
| 8,999,929 B2 | 4/2015 | Mohammadi et al. | |
| 9,072,708 B2 | 7/2015 | Jonker et al. | |
| 9,272,017 B2 | 3/2016 | Mohammadi et al. | |
| 9,464,126 B2 | 10/2016 | Mohammadi et al. | |
| 9,474,785 B2 | 10/2016 | Mohammadi et al. | |
| 9,475,856 B2 | 10/2016 | Mohammadi et al. | |
| 2002/0082205 A1 | 6/2002 | Itoh et al. | |
| 2003/0105302 A1 | 6/2003 | Itoh et al. | |
| 2004/0043457 A1 | 3/2004 | Schumacher et al. | |
| 2004/0097414 A1 | 5/2004 | Itoh et al. | |
| 2004/0259780 A1 | 12/2004 | Glasebrook et al. | |
| 2006/0160181 A1 | 7/2006 | Luethy et al. | |
| 2006/0281679 A1 | 12/2006 | Itoh et al. | |
| 2007/0142278 A1 | 6/2007 | Beals et al. | |
| 2007/0237768 A1 | 10/2007 | Glaesner et al. | |
| 2007/0265200 A1 | 11/2007 | Glaesner et al. | |
| 2007/0293430 A1 | 12/2007 | Frye et al. | |
| 2007/0299007 A1 | 12/2007 | Frye et al. | |
| 2008/0103096 A1 | 5/2008 | Frye et al. | |
| 2008/0255045 A1 | 10/2008 | Cujec et al. | |
| 2008/0261875 A1 | 10/2008 | Etgen et al. | |

(Continued)

FOREIGN PATENT DOCUMENTS

| | | |
|---|---|---|
| EP | 0 645 451 B1 | 8/2001 |
| JP | 2008/0117661 A | 4/2008 |

(Continued)

OTHER PUBLICATIONS

Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).

Zakrzewska et al., "Increased Protein Stability of FGF1 Can Compensate for Its Reduced Affinity for Heparin," J. Biol. Chem. 284(37):25388-403 (2009).

Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780 (12):1432-40 (2008).

(Continued)

*Primary Examiner* — Marianne P Allen
(74) *Attorney, Agent, or Firm* — LeClairRyan, a Professional Corporation

(57) ABSTRACT

The present invention relates to a chimeric protein that includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification. The present invention also relates to pharmaceutical compositions including chimeric proteins according to the present invention, methods for treating a subject suffering from a disorder, and methods of screening for compounds with enhanced binding affinity for the αKlotho-FGF receptor complex involving the use of chimeric proteins of the present invention.

40 Claims, 11 Drawing Sheets

(56) References Cited

U.S. PATENT DOCUMENTS

| | | |
|---|---|---|
| 2009/0111742 A1 | 4/2009 | Kharitonenkov et al. |
| 2009/0118190 A1 | 5/2009 | Beals et al. |
| 2009/0305986 A1 | 12/2009 | Belouski et al. |
| 2010/0062984 A1 | 3/2010 | Kumar et al. |
| 2010/0158914 A1 | 6/2010 | Desnoyers |
| 2010/0184665 A1 | 7/2010 | Suzuki et al. |
| 2010/0216715 A1 | 8/2010 | Tagmose et al. |
| 2010/0285131 A1 | 11/2010 | Belouski et al. |
| 2010/0286042 A1 | 11/2010 | Imamura et al. |
| 2010/0323954 A1 | 12/2010 | Li et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0171218 A1 | 7/2011 | Seehra et al. |
| 2011/0172401 A1 | 7/2011 | Cujec et al. |
| 2011/0190207 A1 | 8/2011 | Mohammadi et al. |
| 2011/0195077 A1 | 8/2011 | Gass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0172275 A1 | 7/2013 | Mohammadi et al. |
| 2013/0184211 A1 | 7/2013 | Mohammadi et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0111821 A1 | 4/2015 | Suh et al. |
| 2015/0343022 A1 | 12/2015 | Jonker et al. |

FOREIGN PATENT DOCUMENTS

| | | |
|---|---|---|
| WO | WO 01/66595 A2 | 9/2001 |
| WO | WO 01/66596 A2 | 9/2001 |
| WO | WO 2009/133905 A1 | 11/2009 |
| WO | 2010075037 A1 | 7/2010 |
| WO | 2011/047267 A1 | 4/2011 |
| WO | 2011/130729 A2 | 10/2011 |
| WO | WO 2013/027191 A1 | 2/2013 |
| WO | 2013/184958 A1 | 12/2013 |
| WO | 2013/184960 A2 | 12/2013 |
| WO | 2013/184962 A1 | 12/2013 |
| WO | 2015/149069 A1 | 10/2015 |

OTHER PUBLICATIONS

Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).

Kharitonenkov et al., "The Metabolic State of Diabetic Monkeys is Regulated by Fibroblast Growth Factor-21," Endocrinology 148(2):774-81 (2007).

Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).

Goetz et al., "Molecular Insights Into the Klotho-Dependent, Endocrine Mode of Action of Fibroblast Growth Factor 19 Subfamily Members," Mol. Cell. Biol. 27(9):3417-3428 (2007).

Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).

Wu et al., "FGF19 Regulates Cell Proliferation, Glucose and Bile Acid Metabolism Via FGFR4-Dependent and Independent Pathways," PLoS One 6(3):e17868 (Mar. 8, 2011).

Wu et al., "Selective Activation of FGFR4 by an FGF19 Variant Does Not Improve Glucose Metabolism in OB/OB Mice," Proc. Nat'l. Acad. Sci U.S.A. 106(34):14379-84 (2009).

Mohammadi et al., "Structural Basis for Fibroblast Growth Factor Receptor Activation," Cytokine & Growth Factor Reviews 16:107-137 (2005).

Hutley et al., "Fibroblast Growth Factor 1: A Key Regulator of Human Adipogenesis," Diabetes 53:3097-3106 (2004).

Imamura et al., "Recovery of Mitogenic Activity of a Growth Factor Mutant with Nuclear Translocation Sequence," Science 249:1567-1570 (Sep. 28, 1990).

Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).

Razzaque, "The FGF23-Klotho Axis: Endocrine Regulation of Phosphate Homeostasis," Nat. Rev. Endocrinol. 5(11):611-19 (2009).

Yie et al., "FGF21 N- and C-Termini Play Different Roles in Receptor Interaction and Activation," FEBS Lett. 583:19-24 (2009).

Andrukhova et al., "FGF23 Acts Directly on Renal Proximal Tubules to Induce Phosphaturia Through Activation of the ERK1/2-SKG1 Signaling Pathway," Bone 51(3):621-8 (Jun. 12, 2012).

Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).

Jonker et al., "A PPARgamma-FGF1 Axis Is Required for Adaptive Adipose Remodelling and Metabolic Homeostasis," Nature 485(7398):391-394 (Apr. 22, 2012).

Wu et al., "A Unique FGF23 With the Ability to Activate FGFR Signaling Through Both alphaKlotho and betaKlotho," J Mol. Biol. 418:82-89 (2012).

Beenken & Mohammadi, "The Structural Biology of the FGF19 Subfamily," Adv. Exp. Med. Biol. 728:1-24 (2012).

Wu et al., "C-Terminal Tail of FGF19 Determines Its Specificity Toward Klotho Co-Receptors," J. Biol. Chem. 283 (48):33304-33309 (2008).

Goetz et al., "Conversion of a Paracrine Fibroblast Growth Factor Into an Endocrine Fibrobalst Growth Factor," J. Biol. Chem. 287(34):29134-29146 (Jun. 25, 2012).

Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).

Olsen et al., "Insights Into the Molecular Basis for Fibroblast Growth Factor Receptor Autoinhibition and Ligand-Binding Promiscuity,"Proc. Nat'l. Acad. Sci. USA 101(4):935-940 (2004).

Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).

Wu et al., "Separating Mitogenic and Metabolic Activities of Fibroblast Growth Factor 19 (FGF19)," Proc. Nat'l. Acad. Sci. USA 107(32):14158-14163 (2010).

Wu et al., "FGF19-Induced Hepatocyte Proliferation Is Mediated Through FGFR4 Activation," J. Biol. Chem. 285(8):5165-5170 (2009).

Zhang et al., "Receptor Specificity of the Fibroblast Growth Factor Family," J. Biol. Chem. 281(23):15694-15700 (2006).

Abraham et al., "Human Basic Fibroblast Growth Factor: Nucleotide Sequence and Genomic Organization," EMBO J. 5(10):2523-2528 (1986).

Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).

Kurosu et al., "The Klotho Gene Family as a Regulator of Endocrine Fibroblast Growth Factors," Mol. Cel. Endocrin. 299:72-78 (2009).

Ono et al., "Novel Regulation of Fibroblast Growth Factor 2 (FGF2)-Mediated Cell Growth by Polysialic Acid," J. Biol. Chem. 287(6):3710-3722 (2012).

Schlessinger et al., "Crystal Structure of a Ternary FGF-FGFR-Heparin Complex Reveals a Dual Role for Heparin in FGFR Binding and Dimerization," Molecular Cell 6:743-750 (2000).

(56) References Cited

OTHER PUBLICATIONS

Thompson et al., "Energetic Characterization of the Basic Fibroblast Growth Factor-Heparin Interaction: Identification of the Heparin Binding Domains," Biochemistry 33:3831-3840 (1994).
Suh et al., "Endocrinization of FGF1 Produces a Neomorphic and Potent Insulin Sensitizer," Author Manuscript, Nature 513(7518): 436-439 (2014).
Shalhoub et al. "FGF23 Neutralization Improves Chronic Kidney Disease-Associated Hyperparathyroidism yet Increases Mortality," J. Clin. Invest. 122(7):2543-2553 (2012).
Nallamsetty et al., "Gateway Vectors for the Production of Combinatorially-Tagged His6-MBP Fusion Proteins in the Cytoplasm and Periplasm of *Escherichia coli*," Protein Sci. 14:2964-2971 (2005).
Isakova et al., "Fibroblast Growth Factor 23 is Elevated Before Parathyroid Hormone and Phosphate in Chronic Kidney Disease," Kidney International 79:1370-1378 (2011).
Faul et al., "FGF23 Induces Left Ventricular Hypertrophy," J. Clin. Invest. 121:4393-4408 (2011).
Andrukhova et al., "FGF23 Drives Progression of Chronic Kidney Disease in Mice," Abstract No. TH-OR105, Kidney Week, Nov. 2015, San Diego, CA.
Fliser et al., "Fibroblast Growth Factor 23 (FGF23) Predicts Progression of Chronic Kidney Disease: The Mild to Moderate Kidney Disease (MMKD) Study," J Am Soc Nephrol 18(9):2600-2608 (2007).
Gutierrez et al., "Fibroblast Growth Factor-23 Mitigates Hyperphosphatemia but Accentuates Calcitriol Deficiency in Chronic Kidney Disease," J Am Soc Nephrol 16(7):2205-2215 (2005).
Gutierrez et al., "Fibroblast Growth Factor 23 and Mortality Among Patients Undergoing Hemodialysis," N Engl J Med 359(6):584-592 (2008).
Gutierrez et al., "Fibroblast Growth Factor 23 and Left Ventricular Hypertrophy in Chronic Kidney Disease," Circulation 119(19):2545-2552 (2009).
Hasegawa et al., "Direct Evidence for a Causative Role of FGF23 in the Abnormal Renal Phosphate Handling and Vitamin D Metabolism in Rats with Early-Stage Chronic Kidney Disease," Kidney International 78:975-980 (2010).
Hsu HJ and Wu MS, "Fibroblast Growth Factor 23: A Possible Cause of Left Ventricular Hypertrophy in Hemodialysis Patients," Am J Med Sci 337(2):116-122 (2009).
Jean et al., "High Levels of Serum Fibroblast Growth Factor (FGF)-23 are Associated with Increased Mortality in Long Haemodialysis Patients," Nephrol Dial Transplant 24(9):2792-2796 (2009).
Larsson et al., "Circulating Concentration of FGF-23 Increases as Renal Function Declines in Patients with Chronic Kidney Disease, but does not Change in Response to Variation in Phosphate Intake in Healthy Volunteers," Kidney Int 64(6):2272-2279 (2003).
Mirza et al., "Circulating Fibroblast Growth Factor-23 is Associated with Vascular Dysfunction in the Community," Atherosclerosis 205(2):385-390 (2009).
Mirza et al., "Serum Intact FGF23 Associate with Left Ventricular Mass, Hypertrophy and Geometry in an Elderly Population," Atherosclerosis 207(2):546-551 (2009).
Mirza et al., "Circulating Fibroblast Growth Factor-23 is Associated with Fat Mass and Dyslipidemia in Two Independent Cohorts of Elderly Individuals," Arterioscler. Thromb. Vasc. Biol. 31:219-227 (2011).
Nakanishi et al., "Serum Fibroblast Growth Factor-23 Levels Predict the Future Refractory Hyperparathyroidism in Dialysis Patients," Kidney Int 67(3):1171-1178 (2005).
Nasrallah et al., "Fibroblast Growth Factor-23 (FGF-23) Is Independently Correlated to Aortic Calcification in Haemodialysis Patients," Nephrol Dial Transplant 25(8):2679-2685 (2010).
Shigematsu et al., "Possible Involvement of Circulating Fibroblast Growth Factor 23 in the Development of Secondary Hyperparathyroidism Associated with Renal Insufficiency," Am J Kidney Dis 44(2):250-256 (2004).
Westerberg et al., "Regulation of Fibroblast Growth Factor-23 in Chronic Kidney Disease," Nephrol Dial Transplant 22(11):3202-3207 (2007).
Beenken et al., "The FGF Family. Biology, Pathophysiology and Therapy," Nat Rev Drug Discov. 8(3):235-53 (Mar. 2009).
Perwad et al., "Fibroblast Growth Factor 23 Impairs Phosphorus and Vitamin D Metabolism in vivo and Suppresses 25-Hydroxyvitamin D-1α-Hydroxylase Expression in vitro," American J. of Phys. Renal Phys. 293(5):F1577-F1583 (2007).
Aono et al., "Therapeutic Effects of Anti-FGF23 Antibodies in Hypophosphatemic Rickets/Osteomalacia," J. Bone Miner. Res. 24(11):1879-1888 (available online May 4, 2009).
Aono et al., "The Neutralization of FGF-23 Ameliorates Hypophosphatemia and Rickets in Hyp Mice," Abstract, Oral Presentation, No. 1056, 25th American Society for Bone and Mineral Research Meeting, Sep. 19-23, 2003, Minneapolis, Minnesota, J. Bone Miner. Res. 18 (Suppl. S1): S15 (2003).
Shimada et al., "Mutant FGF-23 Responsible for Autosomal Dominant Hypophosphatemic Rickets Is Resistant to Proteolytic Cleavage and Causes Hypophosphatemia in Vivo," Endocrinology 143(8):3179-82 (2002).
Shimada et al., "Neutralization of Intrinsic FGF-23 Action by Antibodies Reveals the Essential Role of FGF-23 in Physiological Phosphate and Vitamin D Metabolism," Abstract, Poster Presentation, Nos. SA414 and F414, 25th American Society for Bone and Mineral Research Meeting, Sep. 19-23, 2003, Minneapolis, Minnesota, J. Bone Miner. Res. 18 (Suppl. S1): S93, S164 (2003).
Yamazaki et al., "Anti-FGF23 Neutralizing Antibodies Show the Physiological Role and Structural Features of FGF23," J. Bone Miner. Res. 23(9):1509-1518 (available online Apr. 1, 2008).
Berndt et al., "Biological Activity of FGF-23 Fragments," Eur J Physiol 454:615-623 (2007).
Hu et al., "C-terminal Fragments of Fibroblast Growth Factor (FGF) 23 Inhibit Renal Phosphate (Pi) Excretion as an FGF23 Antagonist by Displacing FGF23 from its Receptor," Abstract SA-FC345, J. Am. Soc. Nephrol. 19:78A (2008).
Hu et al., "C-terminal Fragment of Fibroblast Growth Factor (FGF) 23 Inhibits Renal Phosphate (Pi) Excretion as an FGF23 Antagonist by Displacing FGF23 from its Receptor," Oral Presentation at the 41st Annual Meeting of the American Society of Nephrology (Renal Week 2008) Philadelphia, PA, Nov. 4-9 2008.
Shimada, "Possible Roles of Fibroblast Growth Factor 23 in Developing X-Linked Hypophosphatemia," Clin. Pediatr. Endocrinol. 14(Suppl 23):33-37 (2005).
Kurosu et al. "Regulation of Fibroblast Growth Factor-23 Signaling by Klotho," J. Biol. Chem. 281(10): 6120-6123 (2006).
Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).
Micanovic et al., "Different Roles of N- and C- Termini in the Functional Activity of FGF21," J. Cell. Physiol. 219:227-234 (2009).
Kharitonenkov et al.,"FGF-21/FGF-21 Receptor Interaction and Activation is Determined by βKlotho," J. Cell. Physiol. 215:1-7 (2008).
Neyra et al., "Fibroblast Growth Factor 23 and Acute Kidney Injury," Pediatr Nephrol. 30(11):1909-18 (2015).
Hu et al., "Fibroblast Growth Factor 23 and Klotho: Physiology and Pathophysiology of an Endocrine Network of Mineral Metabolism," Annu Rev Physiol. 75:503-33 (2013).
Yao et al., "Expression and Pharmacological Evaluation of Fusion Protein FGF21-L-Fc," Acta Pharmaceutica Sinica 46(7):787-92 (2011) (Abstract in English).
Pellegrini et al., "Crystal Structure of Fibroblast Growth Factor Receptor Ectodomain Bound to Ligand and Heparin," Nature 407:1029-1034 (2000).
Pellegrini et al., Protein Data Bank, 1E0O, "Crystal Structure of a Ternary FGF1-FGFR2-Heparin Complex," (Released Oct. 23, 2000).

SEQUENCE LISTING

<160> NUMBER OF SEQ ID NOS: 334

<210> SEQ ID NO 1
<211> LENGTH: 155
<212> TYPE: PRT
<213> ORGANISM: Homo sapiens

<400> SEQUENCE: 1

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 2
<211> LENGTH: 155
<212> TYPE: PRT
<213> ORGANISM: Papio Anubis

<400> SEQUENCE: 2

Met Ala Glu Gly Glu Ile Thr Thr Phe Thr Ala Leu Thr Glu Lys Phe
1               5                   10                  15

Asn Leu Pro Pro Ala Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 3
<211> LENGTH: 155
<212> TYPE: PRT
<213> ORGANISM: Pongo abelii

<400> SEQUENCE: 3

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 4
<211> LENGTH: 155
<212> TYPE: PRT
<213> ORGANISM: Callithrix jacchus

<400> SEQUENCE: 4

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 5
<211> LENGTH: 155
<212> TYPE: PRT

<213> ORGANISM: Equus caballus

<400> SEQUENCE: 5

```
Met Ala Glu Gly Glu Ile Thr Thr Phe Thr Ala Leu Thr Glu Lys Phe
1               5                   10                  15
Asn Leu Pro Pro Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Ser Thr Glu Thr Gly Gln Tyr Leu
65                  70                  75                  80
Ala Met Asp Thr Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Thr Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
    130                 135                 140
Ile Leu Phe Leu Pro Leu Pro Val Ser Ser Asp
145                 150                 155
```

<210> SEQ ID NO 6
<211> LENGTH: 155
<212> TYPE: PRT
<213> ORGANISM: Pan troglodytes

<400> SEQUENCE: 6

```
Met Ala Glu Gly Glu Ile Thr Thr Phe Thr Ala Leu Thr Glu Lys Phe
1               5                   10                  15
Asn Leu Pro Ser Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Ser Thr Glu Thr Gly Gln Tyr Leu
65                  70                  75                  80
Ala Met Asp Thr Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Ile Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
    130                 135                 140
Ile Leu Phe Leu Pro Leu Pro Val Ser Ser Asp
145                 150                 155
```

<210> SEQ ID NO 7
<211> LENGTH: 155
<212> TYPE: PRT
<213> ORGANISM: Loxodonta africana

<400> SEQUENCE: 7

Met Ala Glu Gly Glu Ile Thr Thr Phe Thr Ala Leu Thr Glu Lys Phe
1               5                   10                  15

Asn Leu Pro Pro Gly Asn Tyr Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 8
<211> LENGTH: 155
<212> TYPE: PRT
<213> ORGANISM: Canis lupus familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Ailuropoda melanoleuca

<400> SEQUENCE: 9

Met Ala Glu Gly Glu Ile Thr Thr Phe Thr Ala Leu Thr Glu Lys Phe
1               5                   10                  15

```
Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 10
<211> LENGTH: 155
<212> TYPE: PRT
<213> ORGANISM: Saimiri boliviensis boliviensis

<400> SEQUENCE: 10

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 11
<211> LENGTH: 155
<212> TYPE: PRT
<213> ORGANISM: Sus scrofa

<400> SEQUENCE: 11

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30
```

-continued

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Ser Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 12
<211> LENGTH: 155
<212> TYPE: PRT
<213> ORGANISM: Otolemur garnettii

<400> SEQUENCE: 12

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Gln Asp Arg Ser Asp Gln His Ile Gln Leu Gln Leu Ser Ala Glu
        50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 13
<211> LENGTH: 155
<212> TYPE: PRT
<213> ORGANISM: Rhinolophus ferrumequinum

<400> SEQUENCE: 13

Met Ala Glu Gly Glu Val Thr Thr Phe Thr Ala Leu Thr Glu Lys Phe
1               5                   10                  15

Asn Leu Pro Thr Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

```
Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 14
<211> LENGTH: 155
<212> TYPE: PRT
<213> ORGANISM: Sorex araneus

<400> SEQUENCE: 14

Met Ala Glu Gly Glu Ile Thr Thr Phe Gly Ala Leu Met Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly His Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 15
<211> LENGTH: 155
<212> TYPE: PRT
<213> ORGANISM: Oryctolagus cuniculus

<400> SEQUENCE: 15

Met Ala Glu Gly Glu Val Thr Thr Phe Thr Ala Leu Thr Glu Lys Phe
1               5                   10                  15

Asn Leu Pro Ala Gly Asn Tyr Lys Leu Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60
```

-continued

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 16
<211> LENGTH: 155
<212> TYPE: PRT
<213> ORGANISM: Cricetulus griseus

<400> SEQUENCE: 16

Met Ala Glu Gly Glu Ile Thr Thr Phe Ser Ala Leu Thr Glu Arg Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Ala Gly Glu Val Tyr Ile Lys Gly Thr Glu Thr Gly Gln Tyr Arg
65                  70                  75                  80

Asn Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 17
<211> LENGTH: 155
<212> TYPE: PRT
<213> ORGANISM: Sarcophilus harrisii

<400> SEQUENCE: 17

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Arg Asp Arg Asn Asp Gln His Ile Gln Leu Gln Leu Ser Ala Glu
        50                  55                  60

Ser Val Gly Glu Val Tyr Ile Lys Ser Thr Glu Ser Gly Gln Tyr Leu
65                  70                  75                  80

```
Ala Met Asp Thr Asp Gly Leu Leu Tyr Gly Ser Gln Thr Pro Thr Glu
            85                  90                  95

Glu Cys Leu Phe Leu Glu Arg Leu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Glu
145                 150                 155

<210> SEQ ID NO 18
<211> LENGTH: 155
<212> TYPE: PRT
<213> ORGANISM: Mus musculus

<400> SEQUENCE: 18

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
            85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 19
<211> LENGTH: 154
<212> TYPE: PRT
<213> ORGANISM: Cavia porcellus

<400> SEQUENCE: 19

Met Ala Glu Gly Glu Ile Thr Thr Phe Ala Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Gly Val Gly Glu Val Tyr Ile Gln Ser Thr Glu Thr Gly Gln Tyr Leu
65                  70                  75                  80

Ala Met Asp Thr Asp Gly Leu Leu Tyr Gly Ser Gln Thr Pro Ser Glu
            85                  90                  95
```

```
Glu Cys Leu Phe Leu Glu Arg Leu Glu Glu Asn His Tyr Asn Thr Tyr
                100                 105                 110

Thr Ser Lys Lys His Val Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Asp
145                 150

<210> SEQ ID NO 20
<211> LENGTH: 155
<212> TYPE: PRT
<213> ORGANISM: Monodelphis domestica

<400> SEQUENCE: 20

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Thr Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
            115                 120                 125

Asn Gly Ser Cys Lys Lys Gly Pro Arg Thr His Tyr Gly Gln Lys Ala
        130                 135                 140

Ile Leu Phe Leu Pro Leu Pro Val Ser Ser Glu
145                 150                 155

<210> SEQ ID NO 21
<211> LENGTH: 155
<212> TYPE: PRT
<213> ORGANISM: Desmodus rotundus

<400> SEQUENCE: 21

Met Ala Glu Gly Glu Val Thr Thr Phe Thr Ala Leu Thr Glu Lys Phe
1               5                   10                  15

Asn Leu Pro Leu Glu Ser Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Gly Ser Gly Gln Tyr Leu
65                  70                  75                  80

Ala Met Asp Ser Ala Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110
```

```
Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Asn Ser Asp
145                 150                 155

<210> SEQ ID NO 22
<211> LENGTH: 155
<212> TYPE: PRT
<213> ORGANISM: Bos taurus

<400> SEQUENCE: 22

Met Ala Glu Gly Glu Thr Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Thr Val Asp Gly
        35                  40                  45

Thr Lys Asp Arg Ser Asp Gln His Ile Gln Leu Gln Leu Cys Ala Glu
    50                  55                  60

Ser Ile Gly Glu Val Tyr Ile Lys Ser Thr Glu Thr Gly Gln Phe Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys His Trp Phe Val Gly Leu Lys Lys
        115                 120                 125

Asn Gly Arg Ser Lys Leu Gly Pro Arg Thr His Phe Gly Gln Lys Ala
    130                 135                 140

Ile Leu Phe Leu Pro Leu Pro Val Ser Ser Asp
145                 150                 155

<210> SEQ ID NO 23
<211> LENGTH: 155
<212> TYPE: PRT
<213> ORGANISM: Ornithorhynchus anatinus

<400> SEQUENCE: 23

Met Ala Glu Gly Glu Ile Thr Thr Phe Thr Ala Leu Met Glu Lys Phe
1               5                   10                  15

Asp Leu Pro Leu Gly Asn Tyr Lys Lys Pro Arg Leu Leu Tyr Cys Ser
            20                  25                  30

Asn Gly Gly Tyr Phe Leu Arg Ile Gln Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly His Tyr Leu
65                  70                  75                  80

Ala Met Asp Thr Glu Gly Leu Leu Tyr Gly Ser Gln Ala Pro Ser Glu
                85                  90                  95

Asp Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125
```

```
Asn Gly Ser Cys Lys Arg Gly Pro Arg Thr His Tyr Gly Gln Lys Ala
            130                 135                 140

Ile Leu Phe Leu Pro Leu Pro Val Ala Ser Asp
145                 150                 155

<210> SEQ ID NO 24
<211> LENGTH: 155
<212> TYPE: PRT
<213> ORGANISM: Taeniopygia guttata

<400> SEQUENCE: 24

Met Ala Glu Gly Glu Ile Thr Thr Phe Ser Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Val Val His Ile Gln Ser Thr Gln Ser Gly Gln Tyr Leu
65                  70                  75                  80

Ala Met Asp Thr Asn Gly Leu Leu Tyr Gly Ser Gln Leu Pro Pro Gly
                85                  90                  95

Glu Cys Leu Phe Leu Glu Arg Leu Glu Glu Asn His Tyr Asn Thr Tyr
                100                 105                 110

Val Ser Lys Met His Ala Asp Lys Asn Trp Phe Val Gly Leu Lys Lys
            115                 120                 125

Asn Gly Thr Ser Lys Leu Gly Pro Arg Thr His Tyr Gly Gln Lys Ala
        130                 135                 140

Ile Leu Phe Leu Pro Leu Pro Val Ala Ala Asp
145                 150                 155

<210> SEQ ID NO 25
<211> LENGTH: 155
<212> TYPE: PRT
<213> ORGANISM: Dasypus novemcinctus

<400> SEQUENCE: 25

Met Ala Glu Gly Glu Ile Thr Thr Phe Met Ala Leu Met Glu Lys Phe
1               5                   10                  15

Asn Leu Pro Leu Glu Asn Tyr Lys His Pro Arg Leu Leu Tyr Cys Arg
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Ala Glu Thr Gly Gln Tyr Leu
65                  70                  75                  80

Ala Met Asp Thr Asp Gly Leu Leu Tyr Gly Ser Glu Thr Pro Ser Glu
                85                  90                  95

Glu Cys Leu Phe Met Glu Lys Leu Glu Glu Asn Asn Tyr Asn Thr Tyr
                100                 105                 110

Ile Ser Lys Lys His Ala Glu Lys Lys Trp Phe Val Gly Leu Lys Lys
            115                 120                 125

Asp Gly Ser Ser Lys Arg Gly Pro Gln Thr His Tyr Gly Gln Lys Ala
        130                 135                 140
```

```
Ile Leu Phe Leu Pro Leu Pro Val Ser Ser Asp
145                 150                 155

<210> SEQ ID NO 26
<211> LENGTH: 155
<212> TYPE: PRT
<213> ORGANISM: Xenopus Silurana tropicalis

<400> SEQUENCE: 26

Met Ala Glu Gly Asp Ile Thr Thr Phe Asn Pro Ile Ala Glu Ser Phe
1               5                   10                  15

Ser Leu Pro Ile Gly Asn Tyr Lys Lys Pro Lys Leu Leu Tyr Cys Asn
            20                  25                  30

Asn Gly Gly Tyr Phe Leu Arg Ile Leu Pro Asp Gly Val Val Asp Gly
        35                  40                  45

Thr Arg Asp Arg Asp Asp Leu Tyr Ile Thr Leu Lys Leu Ser Ala Gln
    50                  55                  60

Ser Gln Gly Glu Val His Ile Lys Ser Thr Glu Thr Gly Ser Tyr Leu
65                  70                  75                  80

Ala Met Asp Ser Ser Gly Gln Leu Tyr Gly Thr Leu Thr Pro Asn Glu
                85                  90                  95

Glu Ser Leu Phe Leu Glu Thr Leu Glu Glu Asn His Tyr Asn Thr Tyr
            100                 105                 110

Lys Ser Lys Lys Tyr Ala Glu Asn Asn Trp Phe Val Gly Ile Lys Lys
        115                 120                 125

Asn Gly Ala Ser Lys Lys Gly Ser Arg Thr His Tyr Gly Gln Lys Ala
    130                 135                 140

Ile Leu Phe Leu Pro Leu Pro Ala Ser Pro Asp
145                 150                 155

<210> SEQ ID NO 27
<211> LENGTH: 155
<212> TYPE: PRT
<213> ORGANISM: Heterocephalus glaber

<400> SEQUENCE: 27

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asp Gln His Ile Gln Leu Gln Leu Ser Ala Glu
    50                  55                  60

Gly Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Ala Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

```
<210> SEQ ID NO 28
<211> LENGTH: 155
<212> TYPE: PRT
<213> ORGANISM: Pteropus alecto

<400> SEQUENCE: 28
```

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

```
<210> SEQ ID NO 29
<211> LENGTH: 155
<212> TYPE: PRT
<213> ORGANISM: Tupaia chinensis

<400> SEQUENCE: 29
```

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Ala Leu Lys Lys
        115                 120                 125

Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155

```
<210> SEQ ID NO 30
```

```
<211> LENGTH: 155
<212> TYPE: PRT
<213> ORGANISM: Columba livia

<400> SEQUENCE: 30

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Gln Ser Gly Gln Tyr Leu
65                  70                  75                  80

Ala Met Asp Pro Thr Gly Leu Leu Tyr Gly Ser Gln Leu Leu Gly Glu
                85                  90                  95

Glu Cys Leu Phe Leu Glu Arg Ile Glu Glu Asn His Tyr Asn Thr Tyr
            100                 105                 110

Val Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155

<210> SEQ ID NO 31
<211> LENGTH: 155
<212> TYPE: PRT
<213> ORGANISM: Ovis aries

<400> SEQUENCE: 31

Met Ala Glu Gly Glu Thr Thr Thr Phe Arg Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Arg Val Asp Gly
        35                  40                  45

Thr Lys Asp Arg Ser Asp Gln His Ile Gln Leu Gln Leu Tyr Ala Glu
    50                  55                  60

Ser Ile Gly Glu Val Tyr Ile Lys Ser Thr Glu Thr Gly Gln Phe Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Ile Gly Leu Lys Lys
        115                 120                 125

Asn Gly Ser Ser Lys Leu Gly Pro Arg Thr His Phe Gly Gln Lys Ala
    130                 135                 140

Ile Leu Phe Leu Pro Leu Pro Val Ser Ser Asp
145                 150                 155

<210> SEQ ID NO 32
<211> LENGTH: 155
<212> TYPE: PRT
<213> ORGANISM: Gallus gallus
```

<400> SEQUENCE: 32

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Asp Val Gly Glu Val Tyr Ile Lys Ser Thr Ala Ser Gly Gln Tyr Leu
65                  70                  75                  80

Ala Met Asp Thr Asn Gly Leu Leu Tyr Gly Ser Gln Leu Pro Gly Glu
                85                  90                  95

Glu Cys Leu Phe Leu Glu Arg Leu Glu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155

<210> SEQ ID NO 33
<211> LENGTH: 98
<212> TYPE: PRT
<213> ORGANISM: Vicugna pacos

<400> SEQUENCE: 33

Gln Leu Gln Leu Ser Ala Glu Ser Val Gly Glu Val Tyr Ile Lys Ser
1               5                   10                  15

Thr Glu Thr Gly Gln Tyr Leu Ala Met Asp Thr Asp Gly Leu Leu His
            20                  25                  30

Gly Ser Gln Thr Pro Asn Glu Glu Cys Leu Phe Leu Glu Arg Leu Glu
        35                  40                  45

Glu Asn His Tyr Asn Thr Tyr Thr Ser Lys Lys His Ala Glu Lys Asn
    50                  55                  60

Trp Phe Val Gly Leu Lys Lys Asn Gly Ser Cys Lys Arg Gly Pro Arg
65                  70                  75                  80

Thr His Tyr Gly Gln Lys Ala Ile Leu Phe Leu Pro Leu Pro Val Ser
                85                  90                  95

Ser Asp

<210> SEQ ID NO 34
<211> LENGTH: 155
<212> TYPE: PRT
<213> ORGANISM: Anolis carolinensis

<400> SEQUENCE: 34

Met Ala Glu Gly Glu Ile Thr Thr Phe Thr Ala Leu Thr Glu Arg Phe
1               5                   10                  15

Ala Leu Pro Met Glu Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Met Asp Arg Asn Asp Ser Tyr Ile Gln Leu Leu Leu Thr Ala Glu

```
                  50                  55                  60

Asp Val Gly Val Val Tyr Ile Lys Gly Thr Glu Thr Gly Gln Tyr Leu
 65                  70                  75                  80

Ala Met Asp Ala Asn Gly His Leu Tyr Gly Ser Gln Leu Pro Thr Glu
                 85                  90                  95

Glu Cys Leu Phe Val Glu Thr Leu Glu Asn His Tyr Asn Thr Tyr
                100                 105                 110

Thr Ser Lys Met His Gly Asp Lys Lys Trp Tyr Val Gly Leu Lys Lys
            115                 120                 125

Asn Gly Lys Gly Lys Leu Gly Pro Arg Thr His Arg Gly Gln Lys Ala
130                 135                 140

Ile Leu Phe Leu Pro Leu Pro Val Ser Pro Asp
145                 150                 155

<210> SEQ ID NO 35
<211> LENGTH: 155
<212> TYPE: PRT
<213> ORGANISM: Otolemur garnettii

<400> SEQUENCE: 35

Met Ala Glu Gly Glu Ile Thr Thr Phe Thr Ala Leu Thr Glu Lys Phe
  1               5                  10                  15

Asn Leu Pro Leu Gly Asn Tyr Lys Lys Pro Lys Leu Leu Tyr Cys Ser
             20                  25                  30

Asn Gly Gly His Phe Leu Arg Ile Leu Pro Asp Gly Thr Val Asp Gly
            35                  40                  45

Thr Gln Asp Arg Ser Asp Gln His Ile Gln Leu Gln Leu Ser Ala Glu
 50                  55                  60

Ser Val Gly Glu Val Tyr Ile Lys Ser Thr Gln Thr Gly Gln Tyr Leu
 65                  70                  75                  80

Ala Met Asp Ser Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 36
<211> LENGTH: 155
<212> TYPE: PRT
<213> ORGANISM: Felis catus

<400> SEQUENCE: 36

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
             20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
```

```
                65                  70                  75                  80
Ala Met Asp Thr Asp Gly Leu Leu Tyr Gly Ser Gln Thr Pro Asn Glu
                85                  90                  95

Glu Cys Leu Phe Leu Glu Arg Leu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 37
<211> LENGTH: 155
<212> TYPE: PRT
<213> ORGANISM: Pelodiscus sinensis

<400> SEQUENCE: 37

Met Ala Glu Gly Glu Ile Thr Thr Phe Thr Ala Leu Thr Glu Lys Phe
1               5                   10                  15

Asn Leu Pro Leu Gly Asn Tyr Lys Asn Pro Lys Leu Leu Tyr Cys Ser
            20                  25                  30

Asn Gly Gly Tyr Phe Leu Arg Ile His Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Phe Leu
65                  70                  75                  80

Ala Met Asp Ala Asn Gly Leu Leu Tyr Gly Ser Leu Ser Pro Ser Glu
                85                  90                  95

Glu Cys Leu Phe Leu Glu Arg Met Glu Asn His Tyr Asn Thr Tyr
            100                 105                 110

Ile Ser Lys Lys His Ala Asp Lys Asn Trp Phe Val Gly Leu Lys Lys
            115                 120                 125

Asn Gly Ser Cys Lys Leu Gly Pro Arg Thr His Tyr Gly Gln Lys Ala
        130                 135                 140

Val Leu Phe Leu Pro Leu Pro Val Ser Ala Asp
145                 150                 155

<210> SEQ ID NO 38
<211> LENGTH: 155
<212> TYPE: PRT
<213> ORGANISM: Latimeria chalumnae

<400> SEQUENCE: 38

Met Ala Glu Asp Lys Ile Thr Thr Leu Lys Ala Leu Ala Glu Lys Phe
1               5                   10                  15

Asn Leu Pro Met Gly Asn Tyr Lys Lys Ala Lys Leu Leu Tyr Cys Ser
            20                  25                  30

Asn Gly Gly Tyr Phe Leu Arg Ile Pro Pro Asp Gly Lys Val Glu Gly
        35                  40                  45

Ile Arg Glu Arg Ser Asp Lys Tyr Ile Gln Leu Gln Met Asn Ala Glu
    50                  55                  60

Ser Leu Gly Met Val Ser Ile Lys Gly Val Glu Ala Gly Gln Tyr Leu
65                  70                  75                  80

Ala Met Asn Thr Asn Gly Leu Leu Tyr Gly Ser Gln Ser Leu Thr Glu
```

```
            85                  90                  95
Glu Cys Leu Phe Met Glu Lys Met Glu Glu Asn His Tyr Asn Thr Tyr
            100                 105                 110

Arg Ser Lys Thr His Ala Asp Lys Asn Trp Tyr Val Gly Ile Arg Lys
        115                 120                 125

Asn Gly Ser Ile Lys Pro Gly Pro Arg Thr His Ile Gly Gln Lys Ala
    130                 135                 140

Val Leu Phe Leu Pro Leu Pro Ala Ser Ser Asp
145                 150                 155

<210> SEQ ID NO 39
<211> LENGTH: 155
<212> TYPE: PRT
<213> ORGANISM: Tursiops truncatus

<400> SEQUENCE: 39

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ala Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 40
<211> LENGTH: 155
<212> TYPE: PRT
<213> ORGANISM: Mustela putorius furo

<400> SEQUENCE: 40

Met Ala Glu Gly Glu Ile Thr Thr Phe Thr Ala Leu Met Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
```

```
                100             105             110
Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 41
<211> LENGTH: 155
<212> TYPE: PRT
<213> ORGANISM: Nomascus leucogenys

<400> SEQUENCE: 41

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
        130                 135                 140

Ile Leu Phe Leu Pro Leu Pro Val Ser Ser Asp
145                 150                 155

<210> SEQ ID NO 42
<211> LENGTH: 155
<212> TYPE: PRT
<213> ORGANISM: Gorilla gorilla

<400> SEQUENCE: 42

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
```

```
            115                 120                 125
Asn Gly Ser Cys Lys Arg Gly Pro Arg Thr His Tyr Gly Gln Lys Ala
        130                 135                 140
Ile Leu Phe Leu Pro Leu Pro Val Ser Ser Asp
145                 150                 155

<210> SEQ ID NO 43
<211> LENGTH: 155
<212> TYPE: PRT
<213> ORGANISM: Erinaceus europaeus

<400> SEQUENCE: 43

Met Ala Glu Gly Glu Ile Thr Thr Phe Thr Ala Leu Thr Glu Lys Phe
1               5                   10                  15
Asn Leu Pro Leu Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Ser Thr Glu Thr Gly Gln Tyr Leu
65                  70                  75                  80
Ala Met Asp Thr Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Thr Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
    130                 135                 140
Ile Leu Phe Leu Pro Leu Pro Val Ser Ser Asp
145                 150                 155

<210> SEQ ID NO 44
<211> LENGTH: 91
<212> TYPE: PRT
<213> ORGANISM: Procavia capensis

<400> SEQUENCE: 44

Met Ala Glu Gly Glu Ile Thr Thr Phe Thr Ala Leu Thr Glu Lys Phe
1               5                   10                  15
Asn Leu Pro Leu Glu Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Gly Thr Glu Thr Gly Gln Tyr Leu
65                  70                  75                  80
Ala Met Asp Thr Asp Gly Leu Leu Tyr Gly Ser
                85                  90

<210> SEQ ID NO 45
<211> LENGTH: 114
<212> TYPE: PRT
<213> ORGANISM: Dipodomys ordii

<400> SEQUENCE: 45
```

```
Met Ala Glu Gly Glu Ile Thr Thr Phe Thr Ala Leu Thr Glu Arg Phe
1               5                   10                  15

Gln Leu Gln Leu Ser Ala Glu Ser Val Gly Glu Val Tyr Ile Lys Ser
            20                  25                  30

Thr Glu Thr Gly Gln Tyr Leu Ala Met Asp Ala Asp Gly Leu Leu Tyr
        35                  40                  45

Gly Ser Gln Thr Pro Asp Glu Glu Cys Leu Phe Leu Glu Arg Leu Glu
    50                  55                  60

Glu Asn His Tyr Asn Thr Tyr Ile Ala Lys Lys His Ala Glu Lys Asn
65                  70                  75                  80

Trp Phe Val Gly Leu Lys Lys Asn Gly Ser Cys Lys Arg Gly Pro Arg
                85                  90                  95

Thr His Tyr Gly Gln Lys Ala Ile Leu Phe Leu Pro Leu Pro Val Ser
                100                 105                 110

Ser Asp
```

```
<210> SEQ ID NO 46
<211> LENGTH: 92
<212> TYPE: PRT
<213> ORGANISM: Petromyzon marinus

<400> SEQUENCE: 46

Met Glu Val Gly His Ile Gly Thr Leu Pro Val Val Pro Ala Gly Pro
1               5                   10                  15

Val Phe Pro Gly Ser Phe Lys Glu Pro Arg Arg Leu Tyr Cys Arg Ser
            20                  25                  30

Ala Gly His His Leu Gln Ile Leu Gly Asp Gly Thr Val Ser Gly Thr
        35                  40                  45

Gln Asp Glu Asn Glu Pro His Ala Val Leu Gln Leu Gln Ala Val Arg
    50                  55                  60

Arg Gly Val Val Thr Ile Arg Gly Leu Cys Ala Glu Arg Phe Leu Ala
65                  70                  75                  80

Met Ser Thr Glu Gly His Leu Tyr Gly Ala Val Arg
                85                  90
```

```
<210> SEQ ID NO 47
<211> LENGTH: 98
<212> TYPE: PRT
<213> ORGANISM: Echinops telfairi

<400> SEQUENCE: 47

Gln Leu Lys Leu Val Ala Glu Ser Val Gly Val Val Tyr Ile Lys Ser
1               5                   10                  15

Ile Lys Thr Gly Gln Tyr Leu Ala Met Asn Pro Asp Gly Leu Leu Tyr
            20                  25                  30

Gly Ser Glu Thr Pro Glu Glu Cys Leu Phe Leu Glu Thr Leu Glu
        35                  40                  45

Glu Asn His Tyr Thr Thr Phe Lys Ser Lys Lys His Val Glu Lys Asn
50                  55                  60

Trp Phe Val Gly Leu Arg Lys Asn Gly Arg Val Lys Ile Gly Pro Arg
65                  70                  75                  80

Thr His Gln Gly Gln Lys Ala Ile Leu Phe Leu Pro Leu Pro Val Ser
                85                  90                  95

Ser Asp
```

<210> SEQ ID NO 48
<211> LENGTH: 155
<212> TYPE: PRT
<213> ORGANISM: Macaca mulatta

<400> SEQUENCE: 48

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 49
<211> LENGTH: 155
<212> TYPE: PRT
<213> ORGANISM: Pteropus vampyrus

<400> SEQUENCE: 49

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 50
<211> LENGTH: 155
<212> TYPE: PRT

-continued

<213> ORGANISM: Myotis lucifugus

<400> SEQUENCE: 50

Met Ala Glu Gly Glu Val Thr Thr Phe Thr Ala Leu Thr Glu Arg Phe
1               5                   10                  15

Asn Leu Pro Leu Glu Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 51
<211> LENGTH: 155
<212> TYPE: PRT
<213> ORGANISM: Microcebus murinus

<400> SEQUENCE: 51

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Ser Thr Gln Thr Gly Arg Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 52
<211> LENGTH: 144
<212> TYPE: PRT
<213> ORGANISM: Ochotona princeps

<400> SEQUENCE: 52

```
Met Ala Glu Gly Glu Val Thr Thr Phe Ser Ala Leu Thr Glu Lys Phe
1               5                   10                  15

Asn Leu Pro Gly Gly Asn Tyr Lys Leu Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Leu His Glu Val Phe Ile Lys Ser Thr Glu
50                  55                  60

Thr Gly Gln Tyr Leu Ala Met Asp Thr Asp Gly Leu Leu Tyr Gly Ser
65                  70                  75                  80

Gln Thr Pro Ser Glu Glu Cys Leu Phe Leu Glu Arg Leu Glu Glu Asn
                85                  90                  95

His Tyr Asn Thr Tyr Thr Ser Lys Lys His Ala Glu Lys Asn Trp Phe
            100                 105                 110

Val Gly Ile Lys Lys Asn Gly Ser Cys Lys Arg Gly Pro Arg Thr His
        115                 120                 125

Tyr Gly Gln Lys Ala Ile Leu Phe Leu Pro Leu Pro Val Ser Ser Asp
    130                 135                 140

<210> SEQ ID NO 53
<211> LENGTH: 155
<212> TYPE: PRT
<213> ORGANISM: Rattus norvegicus

<400> SEQUENCE: 53

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 54
<211> LENGTH: 155
<212> TYPE: PRT
<213> ORGANISM: Choloepus hoffmanni

<400> SEQUENCE: 54

Met Ala Glu Gly Glu Ile Thr Thr Phe Thr Ala Leu Met Glu Lys Phe
1               5                   10                  15

Asn Leu Pro Pro Gly Asn Tyr Met Lys Pro Lys Leu Leu Tyr Cys Ser
                20                  25                  30
```

Asn Gly Gly His Phe Leu Arg Ile Leu Pro Asp Gly Thr Val Asp Gly
            35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Ala Glu Thr Gly Gln Tyr Leu
65                  70                  75                  80

Ala Met Asp Thr Gly Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
            115                 120                 125

Asn Gly Ser Ser Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 55
<211> LENGTH: 155
<212> TYPE: PRT
<213> ORGANISM: Ictidomys tridecemlineatus

<400> SEQUENCE: 55

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 56
<211> LENGTH: 155
<212> TYPE: PRT
<213> ORGANISM: Tarsius syrichta

<400> SEQUENCE: 56

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
            35                  40                  45

```
Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Val Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155
```

<210> SEQ ID NO 57
<211> LENGTH: 155
<212> TYPE: PRT
<213> ORGANISM: Tupaia belangeri

<400> SEQUENCE: 57

```
Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Ala Leu Lys Lys
            115                 120                 125

Asn Gly Ser Cys Lys Leu Gly Pro Arg Thr His Tyr Gly Gln Lys Ala
            130                 135                 140

Ile Leu Phe Leu Pro Leu Pro Val Ser Ser Asp
145                 150                 155
```

<210> SEQ ID NO 58
<211> LENGTH: 56
<212> TYPE: PRT
<213> ORGANISM: Meleagris gallopavo

<400> SEQUENCE: 58

```
Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Lys Val Asp Gly
            35                  40                  45

Thr Arg Asp Arg Ser Asp Gln His
    50                  55
```

<210> SEQ ID NO 59
<211> LENGTH: 155
<212> TYPE: PRT
<213> ORGANISM: Macropus eugenii

<400> SEQUENCE: 59

```
Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155
```

<210> SEQ ID NO 60
<211> LENGTH: 147
<212> TYPE: PRT
<213> ORGANISM: Danio rerio

<400> SEQUENCE: 60

```
Met Thr Glu Ala Asp Ile Ala Val Lys Ser Ser Pro Arg Asp Tyr Lys
1               5                   10                  15

Lys Leu Thr Arg Leu Tyr Cys Met Asn Gly Gly Phe His Leu Gln Ile
            20                  25                  30

Leu Ala Asp Gly Thr Val Ala Gly Ala Ala Asp Glu Asn Thr Tyr Ser
        35                  40                  45

Ile Leu Arg Ile Lys Ala Thr Ser Pro Gly Val Val Ile Glu Gly
    50                  55                  60

Ser Glu Thr Gly Leu Tyr Leu Ser Met Asn Glu His Gly Lys Leu Tyr
65                  70                  75                  80

Ala Ser Ser Leu Val Thr Asp Glu Ser Tyr Phe Leu Glu Lys Met Glu
                85                  90                  95

Glu Asn His Tyr Asn Thr Tyr Gln Ser Gln Lys His Gly Glu Asn Trp
            100                 105                 110

Tyr Val Gly Ile Lys Lys Asn Gly Lys Met Lys Arg Gly Pro Arg Thr
        115                 120                 125

His Ile Gly Gln Lys Ala Ile Phe Phe Leu Pro Arg Gln Val Glu Gln
    130                 135                 140

Glu Glu Asp
145
```

<210> SEQ ID NO 61

<211> LENGTH: 468
<212> TYPE: DNA
<213> ORGANISM: Homo sapiens

<400> SEQUENCE: 61

```
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctatatat ccaagaagca tgcagagaag     360
aattggtttg ttggcctcaa gaagaatggg agctgcaaac gcggtcctcg gactcactat     420
ggccagaaag caatcttgtt tctccccctg ccagtctctt ctgattaa                  468
```

<210> SEQ ID NO 62
<211> LENGTH: 468
<212> TYPE: DNA
<213> ORGANISM: Olive Baboon

<400> SEQUENCE: 62

```
atggctgaag gggaaatcac cacgttcaca gccctgaccg agaagtttaa tctgcctcca      60
gcgaattaca agaagcccaa actgctctac tgtagcaacg ggggacactt cttgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctacatat ccaagaagca cgcagagaag     360
aattggtttg ttggcctcaa gaagaatgga agctgcaaac gtggtcctcg gactcactat     420
ggccagaaag caatcttgtt tcttccccctg ccagtctctt ctgattaa                 468
```

<210> SEQ ID NO 63
<211> LENGTH: 468
<212> TYPE: DNA
<213> ORGANISM: Sumatran orangutan

<400> SEQUENCE: 63

```
atggctgaag gggaaatcac caccttcaca gccctgaccg agaagtttaa tctgcctcca      60
gggaattaca agaagcccaa actcctctac tgtagcaacg ggggccactt cttgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac caaatgagga atgtttgttc     300
ctggaaaggc tggaggagaa ccattacaac acctatatat ccaagaagca tgcagagaag     360
aattggtttg ttggcctcaa gaagaatgga agctgcaaac gcggtcctcg gactcactat     420
ggccagaaag caatcttgtt tctccccctg ccagtctctt ccgattaa                  468
```

<210> SEQ ID NO 64
<211> LENGTH: 468
<212> TYPE: DNA
<213> ORGANISM: White-tufted-ear marmoset

<400> SEQUENCE: 64

```
atggctgaag gggaaatcac caccttcaca gccctgaccg agaagtttga tctgcctcca      60
```

```
gggaattaca agaagcccaa actcctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggagaggc tggaggagaa ccattacaac acctatatat ccaagaaaca tgcagagaag    360
aattggtttg tcggcctcaa gaagaatgga agctgtaaac gtggtcctcg gactcactat    420
ggtcagaaag cgatcttgtt tctcccccctg ccagtttctt ctgattaa                468
```

<210> SEQ ID NO 65
<211> LENGTH: 468
<212> TYPE: DNA
<213> ORGANISM: Horse

<400> SEQUENCE: 65

```
atggctgaag gagaaatcac aaccttcacg gccctgaccg agaagtttaa tctgcctcca    60
gggaattaca agaagcccaa actcctctac tgtagcaatg ggggccactt cctgaggatc    120
cttccagatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct gttgtacggc tcacagacac caaacgagga atgtttgttc    300
ctggaaaggc tggaggaaaa ccattacaac acctacacat ccaagaagca tgcagagaag    360
aactggttcg ttggtctcaa gaagaatggg agctgcaaac gcggtcctcg gactcactat    420
gggcagaaag caatcttgtt tcttcccctg cccgtctcct ctgactaa                468
```

<210> SEQ ID NO 66
<211> LENGTH: 468
<212> TYPE: DNA
<213> ORGANISM: Chimpanzee

<400> SEQUENCE: 66

```
atggctgaag gggaaatcac caccttcaca gccctgaccg agaagtttaa tctgccttca    60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaacggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctcccccctg ccagtctctt ccgattaa                468
```

<210> SEQ ID NO 67
<211> LENGTH: 468
<212> TYPE: DNA
<213> ORGANISM: Elephant

<400> SEQUENCE: 67

```
atggccgaag gggaaatcac aactttcaca gccctgacag agaagttcaa cctgcctcca    60
gggaattaca agaagcccaa actcctctac tgtagcaatg gaggtcactt cttaaggatc    120
cttccagatg gcacagtgga tgcaccagg gacaggagtg accagcacat tcagctgcag    180
ctcagtgcgg aaagcgtggg ggaggtgtat ataagggca ccgagactgg ccagtacttg    240
```

```
gccatggaca ccgacgggct tttatacggc tcacagacac caaatgagga atgtttgttc    300
ctggaaaggc tggaggaaaa ccattacaac acctacacat ccaagaagca cgcagagaag    360
aattggttcg ttggtctcaa gaagaatgga agctgcaaac gcggtcctcg gactcactat    420
ggccagaaag caatcttgtt tctccccctg ccagtctcct ctgattaa                 468
```

<210> SEQ ID NO 68
<211> LENGTH: 468
<212> TYPE: DNA
<213> ORGANISM: Dog

<400> SEQUENCE: 68

```
atggctgaag ggaaaatcac aaccttcact gccctgacgg agaagtttaa tctgcctccg    60
gggaattaca tgaagcccaa actcctctac tgtagcaacg ggggccactt cctgaggatc   120
cttccagatg gcacagtgga tgggacaagg gacaggagcc accagcacat tcagctgcag   180
ctcagcgcgg aaagcgtggg ggaggtgtat ataaagagca ccgagactgg ccagtacttg   240
gccatggaca ccgatgggct tctgtacggc tcacagacac cgaatgagga atgtttgttc   300
ctggaaaggc tggaggaaaa ccattacaac acctacacat ccaagaagca tgcagaaaaa   360
aattggtttg ttggtctcaa gaagaatgga agctgcaaac gcggtcctcg gactcactat   420
ggtcaaaaag caattttgtt tctccccctg ccagtgtcct ctgattaa                 468
```

<210> SEQ ID NO 69
<211> LENGTH: 468
<212> TYPE: DNA
<213> ORGANISM: Giant panda

<400> SEQUENCE: 69

```
atggctgaag ggagatcac aaccttcacc gccctgacgg agaagtttaa tctgcctgcg     60
gggaattaca agaagcccaa actcctctac tgtagcaacg ggggccactt cctgaggatc   120
cttccagatg gcacagtgga cgggacgagg gacaggagcg accagcacat tcaactgcag   180
ctcagcgcgg aaagcgtagg ggaggtgtac ataaagagca ccgagaccgg ccagtacttg   240
gccatggaca ccgatgggct tctgtacggc tcacagacac caaatgagga atgtttgttc   300
ctggaaaggc tggaggaaaa ccattacaac acctacacat ccaagaagca cgcggagaag   360
aattggtttg ttggtctcaa gaagaatgga agctgcaaac gtggtcctcg gactcactat   420
ggccagaaag caattctgtt tctccccctg ccagtctcct ctgattaa                 468
```

<210> SEQ ID NO 70
<211> LENGTH: 468
<212> TYPE: DNA
<213> ORGANISM: Bolivian squirrel monkey

<400> SEQUENCE: 70

```
atggctgaag ggaaaatcac cacctttaca gccctgaccg agaagtttga tctgcctcca    60
gggaattaca agaagcccaa actcctctac tgtagcaacg ggggccactt cttgaggatc   120
cttccggatg gcacagtgga tgggaccagg gacaggagcg atcttcacat tcagctgcag   180
ctcagtgcgg aaagcgtggg ggaggtgtat ataaagagta ccgagactgg ccagtacttg   240
gccatggaca ccgacgggct tttatacggc tcacagacac caaatgagga atgtttgttc   300
ctggaaaggc tggaggagaa ccattacaac acctatatat ccaagaaaca cgcagagaag   360
aattggtttg ttggcctcaa gaagaatgga agctgcaagc gcggtcctcg gactcactat   420
ggccagaaag caatcttgtt tctccccctg ccagtctctt ctgattaa                 468
```

<210> SEQ ID NO 71
<211> LENGTH: 468
<212> TYPE: DNA
<213> ORGANISM: Pig

<400> SEQUENCE: 71

```
atggctgaag gcgaaatcac aaccttcacg gccctgaccg agaagtttaa tctgcctcca        60
ggaaattaca agaagcccaa gctcctctac tgcagcaacg ggggccattt cctcaggatc       120
cttccagatg gcacagtgga tgggaccagg acaggagcg accagcacat tcagctgcag        180
ctcagtgcgg aaagcgtggg ggaggtgtat ataaagagta cggagactgg ccagtacttg       240
gccatggaca ccagcgggct tttgtacggc tcacagacac ccagtgagga gtgtttgttc       300
ctggagaggc tggaggaaaa ccattacaat acctacacat ccaagaagca cgcagagaag       360
aactggttcg ttggcctcaa gaagaatgga agctgcaaac gcggtcctcg gactcactat       420
ggccagaaag ccatcctgtt tctcccctg ccagtatcct cggattaa                     468
```

<210> SEQ ID NO 72
<211> LENGTH: 468
<212> TYPE: DNA
<213> ORGANISM: Small-eared galago

<400> SEQUENCE: 72

```
atggctgaag gggaaatcac aaccttcaca gccctcacag agaagtttaa tctgcctcta        60
ggaaattaca agaagcccaa gctcctctac tgtagcaacg ggggtcactt tctgaggatc       120
ctgccggatg gcaccgtgga tgggacacaa gacaggagcg accagcacat tcagctgcag       180
ctcagtgcgg aaagcgtggg ggaggtgtat ataaagagta cccagactgg ccagtacttg       240
gccatggact ccgacgggct tttatacggc tcacaaacac caaatgagga tgcctgttc        300
ctggaacggc tggaggaaaa ccattacaac acctatgtgt ccaagaagca cgccgagaag       360
aattggtttg tcggtctcaa gaagaacgga agttgcaaac gtggtcctcg gactcactac       420
ggccagaaag caatcttgtt tctcccctg ccagtctcct ctgattaa                     468
```

<210> SEQ ID NO 73
<211> LENGTH: 468
<212> TYPE: DNA
<213> ORGANISM: Greater horseshoe bat

<400> SEQUENCE: 73

```
ttaatcagag gagactggca ggggagaaa caggattgct ttctggccat agtgagtccg         60
aggaccgcgc ttgcagcttc cattcttctt gagcccaacg aaccaattct tttctgcgtg       120
cttcttggac gtgtaggtgt tgtaatggtt ttcctccagc cttccagga acagacattc        180
ctcatttggt gtctgtgagc cgtacaaaag cccgtcggag tccatggcca agtactggcc       240
actctcggtg ctctttatat acacctcccc cacgctttcc gcactgagct gcagctgaat       300
gtgctggtca ctcttgtccc ttgtcccatc cactgtgcca tctggaagga tcctcaggaa       360
gtggccccg ttgctgcagt agagaagttt gggtttcttg taattccctg taggcagatt       420
aaacttctca gtaagggctg tgaacgtggt gacttcccct tcggccat                    468
```

<210> SEQ ID NO 74
<211> LENGTH: 468
<212> TYPE: DNA
<213> ORGANISM: European shrew

<400> SEQUENCE: 74

```
ctagtcggag gagacgggca gggggagaaa caagatcgct ttctggccgt agtgagtccg      60
gggaccacgc ttgcagcttc cgttcttctt cagaccaaca aaccaattct tctcggcatg    120
cttcttggag gtataggtgt tgtaatggtt ttcctccagc ctttccagaa acagacattc    180
ctcattcggt gtttgtgagc cgtataaaag cccgtcggtg tccatggcca agtaatggcc    240
agtctccgtg ctctttatat acacctcccc cacgctttcc gcactgagct gcagctgaat    300
gtgctggtcg ctgccggtccc tggtcccatc cactgtgccg tccgggagga tgcgcaggaa   360
gtggccccg ttgctgcagt acaggagttt gggcttcttg tagttccctg gtggcaggtt     420
aaacttctcc atgagggccc caaaggtggt gatctccccc tcggccat                 468
```

<210> SEQ ID NO 75
<211> LENGTH: 468
<212> TYPE: DNA
<213> ORGANISM: Rabbit

<400> SEQUENCE: 75

```
atggctgagg gggaggtcac caccttcaca gccctgaccg agaagttcaa cctgcctgca     60
gggaactaca agttgcccaa actcctctac tgcagcaacg ggggccactt cctgaggatc    120
ctgccggacg gcactgtgga cggcacaagg gacaggagcg accagcacat tcagctgcag    180
ctgagtgcgg aaagcgtggg ggaggtgtat ataaagagta cggagaccgg ccagtacttg    240
gccatggaca ccgacggcct tttatacggc tcgcaaacgc ccagtgagga gtgtttgttc    300
ctggaacggc tggaggagaa ccactacaac acctacacgt ccaagaagca cgccgagaag    360
aactggttcg tggggctgaa gaaaaacggg agctgcaagc gcggtcctcg gactcactac    420
ggccagaaag ccatcttgtt cctcccccctg ccggtctcct ccgactaa                468
```

<210> SEQ ID NO 76
<211> LENGTH: 468
<212> TYPE: DNA
<213> ORGANISM: Chinese hamster

<400> SEQUENCE: 76

```
atggctgaag gagaaatcac caccttctca gccctgacag agagatttaa tctgcctcca     60
ggaaactaca agaagcccaa actgctctac tgcagcaacg ggggccactt cttgaggatc    120
cttccagatg gcacagtgga tgggacaagg gacaggagtg accagcacat tcagctgcag    180
ctgagtgcgg aaagcgcggg cgaagtgtat ataaagggta cagagacagg ccagtacagg    240
aacatggaca cggatggcct tttatacggc tcacagacac caaatgaaga tgcctgttc     300
ctggaaaggc tggaagaaaa ccattacaac acttatacat ccaagaagca cgcagagaag    360
aactggtttg tgggcctcaa gaaaaacggg agctgcaagc gtggtcctcg gactcactat    420
ggccagaaag caatcttgtt tctccccctg cctgtatctt ctgactag                 468
```

<210> SEQ ID NO 77
<211> LENGTH: 468
<212> TYPE: DNA
<213> ORGANISM: Tasmanian devil

<400> SEQUENCE: 77

```
atggccgaag gggagatcac aaccttcaca gccctgaccg aaagatttaa tctgccactg     60
gggaattaca agaagcccaa gcttctctac tgtagcaatg ggggccactt tttgaggatt    120
cttcctgatg gtaaagtgga tgggacaagg gacagaaatg atcaacacat tcaactgcaa    180
```

```
ctaagcgcgg aaagcgtggg tgaggtgtat ataaagagca ctgagtctgg ccagtatttg      240
gctatggaca ccgatggact tttatacggc tcacagacac ccactgaaga atgcttgttc      300
ctggagagat tggaggagaa tcattacaac acctacatat caaagaagca tgcggagaaa      360
aattggtttg tgggcctcaa gaaaaatgga agctgcaaaa gaggtcccag gactcactat      420
ggccagaaag ccatcctctt ccttccccts cctgtgtcct ctgagtaa                   468
```

<210> SEQ ID NO 78
<211> LENGTH: 468
<212> TYPE: DNA
<213> ORGANISM: House mouse

<400> SEQUENCE: 78

```
atggctgaag gggagatcac aaccttcgca gccctgaccg agaggttcaa cctgcctcta       60
ggaaactaca aaaagcccaa actgctctac tgcagcaacg ggggccactt cttgaggatc      120
cttcctgatg caccgtggga tgggacaagg gacaggagcg accagcacat tcagctgcag      180
ctcagtgcgg aaagtgcggg cgaagtgtat ataaaggggta cggagaccgg ccagtacttg      240
gccatggaca ccgaagggct tttatacggc tcgcagacac caaatgagga atgtctgttc      300
ctggaaaggc tggaagaaaa ccattataac acttacacct caagaagca tgcggagaag       360 aactggtttg tgggcctcaa gaagaacggg agctgtaagc gcggtcctcg gactcactat      420
ggccagaaag ccatcttgtt tctgcccctc ccggtgtctt ctgactag                   468
```

<210> SEQ ID NO 79
<211> LENGTH: 465
<212> TYPE: DNA
<213> ORGANISM: Domestic guinea pig

<400> SEQUENCE: 79

```
atggctgaag gagaaatcac aacttttgca gccctgactg agaagtttaa tctgcctcca       60
gggaattata agaagcccaa actgctctac tgcagcaatg ggggccactt cctgaggatc      120
cttccagacg gcacagtgga cggcacaaga gacaggagcg accagcacat tcagctgcag      180
ctcagtgcgg aaggcgtggg ggaggtgtat atacagagca ccgagaccgg ccagtacttg      240
gccatggaca ccgacgggct tttatacggc tcacagacac caagtgagga atgcttgttc      300 ctggaaggc tggaggaaaa ccattacaac acctacacat caagaagca tgtggagaag        360 aattggtttg ttggcctcaa gaagaacgga agctgcaagc gtggtcctcg gactcactat      420
ggccagaaag caatcttgtt cctccccttg ccagtctctg attag                      465
```

<210> SEQ ID NO 80
<211> LENGTH: 468
<212> TYPE: DNA
<213> ORGANISM: Gray short-tailed opossum

<400> SEQUENCE: 80

```
atggccgaag gggagatcac aaccttcaca gccctgactg aaagatttaa cctgccactg       60
gggaattaca agaaacccaa gcttctctac tgtagcaatg ggggccattt cttgaggatc      120
cttcctgatg caaagtgga tgggacacgg gacagaaatg atcaacacat tcaactgcag       180
ctgagcacgg aaagtgtggg tgaggtgtat ataaagagca ctgagtctgg ccagtatttg      240
gctatggaca ccgatggact tttatatggc tcacagacac ccagtgaaga atgcttgttt      300
ctggagaggt tggaggagaa tcattacaac acctacacat cgaagaagca tgcagagaaa      360
```
aattggtttg ttggtctcaa gaagaatgga agctgcaaaa agggtcccag gactcactac    420
ggccagaaag ccatcctgtt ccttcccctc cctgtgtcct ctgagtaa                 468

<210> SEQ ID NO 81
<211> LENGTH: 468
<212> TYPE: DNA
<213> ORGANISM: Common vampire bat

<400> SEQUENCE: 81
atggctgaag gggaagtcac cacgttcaca gctctgactg agaagtttaa tctgcctctg    60
gagagttaca agaagcccaa acttctctac tgcagcaacg gtggccactt cctgaggatc   120
cttccagatg gtacagtgga tgggacaagg gacaagagcg accagcacat tcagctgcag   180
ctcagtgcgg aaagcgtggg ggaggtgtac ataaagagca ccgggagtgg ccagtacttg   240
gccatggact ccgccgggct tttgtatggc tcacagacac caaatgagga atgtttgttc   300
ctggaaaggc tggaggaaaa ccattacaac acctacacat ccaagaagca tgcagaaaag   360
aattggttcg tggggctcaa gaagaatgga agctgcaagc gtggccccg gactcattat    420 ggccagaaag caatcttgtt tctcccctg ccagtcaact ctgattaa                 468

<210> SEQ ID NO 82
<211> LENGTH: 468
<212> TYPE: DNA
<213> ORGANISM: Cattle

<400> SEQUENCE: 82
atggctgaag gagaaaccac gaccttcacg gccctgactg agaagtttaa cctgcctcta    60
ggcaattaca agaagcccaa gctcctctac tgcagcaacg ggggctactt cctgagaatc   120
ctcccagatg gcacagtgga tgggacgaag gacaggagcg accagcacat tcagctgcag   180
ctctgtgcgg aaagcatagg ggaggtgtat attaagagta cggagactgg ccagttcttg   240
gccatggaca ccgacgggct tttgtacggc tcacagacac ccaatgagga atgtttgttc   300
ctggaaaggt tggaggaaaa ccattacaac acctacatat ccaagaagca tgcagagaag   360
cattggttcg ttggtctcaa gaagaacgga aggtctaaac tcggtcctcg gactcacttc   420
ggccagaaag ccatcttgtt tctcccctg ccagtctcct ctgattaa                 468

<210> SEQ ID NO 83
<211> LENGTH: 468
<212> TYPE: DNA
<213> ORGANISM: Platypus

<400> SEQUENCE: 83
atggcggagg gtgaaatcac cacgttcaca gccctgatgg agaagttcga cctacccctg    60
ggcaactaca aaaagcctag gctgctctac tgcagcaatg gcggctactt cctgcgcatc   120
cagccagacg gtaaagtgga cgggaccagg gatcggagcg atcagcacat tcaactgcag   180
ctaagcgcgg aaagcgtggg cgaggtgtat ataaagagca ccgagtctgg ccactatttg   240
gctatggaca ccgaaggact tttatatggc tcacaggcac ccagtgaaga ctgcttgttc   300
ctggagcggc tggaggagaa ccactataac acgtacgtgt ccaagaagca cgctgagaag   360
aattggtttg tcggtctcaa gaagaacggg agctgcaaac gaggtccccg gactcactac   420
ggccagaaag ccatcctctt cctcccgctc cccgtggcat ccgactag                468

<210> SEQ ID NO 84
<211> LENGTH: 468

<212> TYPE: DNA
<213> ORGANISM: Zebra finch

<400> SEQUENCE: 84

```
atggccgagg gggagatcac caccttcagc gccctgacgg agaagttcaa cctgccccg      60 gggaactaca agaagcccaa actgctgtac tgcagcaacg gggggcattt cctgcgcatc    120
ctcccggacg gcaccgtgga tggcaccagg accgcagcg accagcacat tcagctccag     180
ctgagtgcag agagcgtggg ggtggtgcac atccagagca cccagtcggg gcagtacctg    240
gccatggaca ccaacgggct gctctacggc tcgcagctgc acccggtga gtgtctgttc     300 ctggaaaggc tggaggagaa ccattacaac acctacgtct ccaaaatgca cgcggacaag    360
aactggtttg tggggctgaa gaagaacggg acaagcaagc tgggcccgcg gactcactac    420
ggccagaagg cgatcctgtt cctgccgctg cccgtggcgg ccgactga                 468
```

<210> SEQ ID NO 85
<211> LENGTH: 468
<212> TYPE: DNA
<213> ORGANISM: Nine-banded armadillo

<400> SEQUENCE: 85

```
ttaatcagag gagactggca ggggaagaaa caagatagct ttctggccat agtgagtctg    60
aggaccacgt ttgctgcttc cgtccttctt gagaccaaca aaccatttct tctctgcatg   120
cttcttggat atgtaggtgt tgtaattgtt ttcttccagc ttttccatga acaagcattc   180
ctcacttggt gtctctgagc catataaaag cccgtcggtg tccatggcta agtactggcc   240
ggtctctgca ctctttatat acacctcccc cacgctttcc gcactgagct gcagctgaat   300
gtgttggtcg ctcctgtccc ttgtcccatc caccgtgcca tctggaagga tcctcaagaa   360 gtggccccg tttctgcagt agaggagtct ggggtgcttg taattttcta ggggcaggtt    420
gaacttctcc atcagggcca tgaaggttgt gatctccct tcagccat                 468
```

<210> SEQ ID NO 86
<211> LENGTH: 468
<212> TYPE: DNA
<213> ORGANISM: Xenopus Silurana tropicalis

<400> SEQUENCE: 86

```
atggcagagg gagacatcac aacattcaac cccattgcag agtccttcag tcttccaatt    60
ggcaactaca agaaaccaaa acttctgtac tgtaataatg gagggtattt tttgcgcatc   120
ctcccagatg gggttgtgga tggaacaaga gacagagatg acctttacat tacactgaag   180
ttaagcgcac aaagccaagg ggaggtgcat atcaaaagca cagagacagg gagttactta   240
gccatggact ccagtggaca gttgtatgga actctcacac caaatgaaga aagcctgttt    300
ctggagacat tagaagagaa tcactataac acatacaagt caaagaagta tgcagaaaat    360
aactggtttg tggggataaa gaagaacggg gcaagcaaaa agggatcaag gactcactat    420
ggacaaaaag ccatccttttt tctgccgctg ccagcatcac ctgactag                468
```

<210> SEQ ID NO 87
<211> LENGTH: 465
<212> TYPE: DNA
<213> ORGANISM: Heterocephalus glaber

<400> SEQUENCE: 87

```
atggcggaag gcgaaattac caccttttacc gcgctgaccg aaaaatttaa cctgccgccg    60
```

```
ggcaactata aaaaaccgaa actgctgtat tgcagcaacg gcggccattt tctgcgcatt      120
ctgccggatg gcaaagtgga tggcacccgc gatcgcagcg atcagcatat tcagctgcag      180
ctgagcgcgg aaggcgtggg cgaagtgtat attaaaagca ccgaaaccgg ccagtatctg      240
gcgatggata ccgatggcct gctgtatggc agccagaccg cgagcgaaga atgcctgttt      300
ctggaacgcc tggaagaaaa ccattataac acctatatta gcaaaaaaca tgcggaaaaa      360
aactggtttg tgggcctgaa aaaaaacggc agctgcaaac gcggcccgcg cacccattat      420
ggccagaaag cgattctgtt tctgccgctg ccggtgagca gcgat                     465

<210> SEQ ID NO 88
<211> LENGTH: 465
<212> TYPE: DNA
<213> ORGANISM: Black flying fox

<400> SEQUENCE: 88
atggcggaag gcgaagtgac cacctttacc gcgctgaccg aacgctttaa cctgccgccg       60
ggcaactata aaaaaccgaa actgctgtat tgcagcaacg gcggccattt tctgcgcatt      120
ctgccggatg gcaccgtgga tggcacccgc gataaaagcg atcagcatat tcagctgcag      180
ctgagcgcgg aaagcgtggg cgaagtgtat attaaaagca ccgaaagcgg ccagtatctg      240
gcgatggata gcgatggcct gctgtatggc agccagaccc cggatgaaga ttgcctgttt      300
ctggaacgcc tggaagaaaa ccattataac acctatacca gcaaaaaaca tgcggaaaaa      360
aactggtttg tgggcctgaa aaaaaacggc agctgcaaac gcggcccgcg cacccattat      420
ggccagaaag cgattctgtt tctgccgctg ccggtgagca gcgat                     465

<210> SEQ ID NO 89
<211> LENGTH: 465
<212> TYPE: DNA
<213> ORGANISM: Chinese tree shrew

<400> SEQUENCE: 89
atggcggaag gcgaaattac cacctttgcg gcgctgaccg aaaaatttga tctgccgccg       60
ggcaactata aaaaaccgaa actgctgtat tgcagcaacg gcggccattt tctgcgcatt      120
ctgccggatg gcaccgtgga tggcacccgc gatcgcagcg atcagcatat tcagctgcag      180
ctgaccgcgg aaaacgtggg cgaagtgtat attaaaagca ccgaaaccgg ccagtatctg      240
gcgatggatg cggatggcct gctgtatggc agccagaccc cgaacgaaga atgcctgttt      300
ctggaacgcc tggaagaaaa ccattataac acctatatta gcaaaaaaca tgcggaaaaa      360
aactggtttg tggcgctgaa aaaaaacggc agctgcaaac tgggcccgcg cacccattat      420
ggccagaaag cgattctgtt tctgccgctg ccggtgagca gcgat                     465

<210> SEQ ID NO 90
<211> LENGTH: 465
<212> TYPE: DNA
<213> ORGANISM: Rock pigeon

<400> SEQUENCE: 90
atggcggaag gcgaaattac cacctttacc gcgctgaccg aaaaatttaa cctgccgccg       60
ggcaactata aaaaaccgaa actgctgtat tgcagcaacg gcggccattt tctgcgcatt      120
ctgccggatg gcaaagtgga tggcacccgc gatcgcagcg atcagcatat tcagctgcag      180
ctgagcgcgg aaagcgtggg cgaagtgtat attaaaagca cccagagcgg ccagtatctg      240
gcgatggatc cgaccggcct gctgtatggc agccagctgc tgggcgaaga atgcctgttt      300
```

```
ctggaacgca ttgaagaaaa ccattataac acctatgtga gcaaaaaaca tgcggataaa      360
aactggtttg tgggcctgaa aaaaaacggc aacagcaaac tgggcccgcg cacccattat      420
ggccagaaag cgattctgtt tctgccgctg ccggtgagcg cggat                      465
```

```
<210> SEQ ID NO 91
<211> LENGTH: 468
<212> TYPE: DNA
<213> ORGANISM: Sheep

<400> SEQUENCE: 91
atggctgaag agaaaccac aaccttcagg gccctgactg agaagtttaa cctgcctcta       60
ggcaattaca agaagcccaa gctcctctat tgcagcaacg ggggctactt cctgagaatc      120
ctcccagatg gcagagtgga tgggacgaag acaggagcg accagcacat tcagctgcag      180
ctctatgcgg aaagcatagg ggaggtgtat attaagagta cggagactgg ccagttcttg      240
gccatggaca ccaacgggct tttgtacggc tcacaaacac ccagtgagga atgtttgttc      300
ctggaaaggc tggaggaaaa ccattataac acctacatat ccaagaagca tgcagagaag      360
aattggttca ttggtctcaa gaagaacgga agctccaaac tcggtcctcg gactcacttc      420
ggccagaaag ccatcttgtt tctccccctg ccagtttcct ctgattaa                   468
```

```
<210> SEQ ID NO 92
<211> LENGTH: 468
<212> TYPE: DNA
<213> ORGANISM: Chicken

<400> SEQUENCE: 92
atggccgagg gggagataac caccttcacc gccctgaccg agcgcttcgg cctgccgctg      60
ggcaactaca agaagcccaa actcctgtac tgcagcaacg ggggccactt cctacggatc      120
ctgccggacg gcaaggtgga cgggacgcgg gaccggagtg accagcacat tcagctgcag      180
ctcagcgcgg aagatgtggg cgaggtctat ataaagagca cagcgtcggg gcagtacctg      240
gcaatggaca ccaacgggct cctgtatggc tcgcagctac caggcgagga gtgcttgttc      300
cttgagaggc tcgaggagaa ccattacaac acatacatct ccaaaaagca cgcagacaag      360
aactggttcg tcgggctgaa gaaaaacggg aacagcaagc tggggccgcg gactcactat      420
gggcaaaagg cgatcctctt cctcccattg ccggtgtcgg ctgactga                   468
```

```
<210> SEQ ID NO 93
<211> LENGTH: 297
<212> TYPE: DNA
<213> ORGANISM: Alpaca

<400> SEQUENCE: 93
cagctgcagc tcagtgcgga aagcgtgggg gaggtgtata taaagagtac cgagactggc      60
cagtacttgg ccatggacac cgacgggctt ttgcacggct cacagacacc aaatgaggaa      120
tgtttgttcc tggaaaggct ggaggagaac cattacaaca cctacacgtc caagaagcac      180
gccgaaaaga attggtttgt tggtctcaag aagaatggaa gctgcaaacg cggtcctcgg      240
actcactacg gccagaaggc gatcttgttt ctccccttgc cagtctcctc tgattaa        297
```

```
<210> SEQ ID NO 94
<211> LENGTH: 468
<212> TYPE: DNA
<213> ORGANISM: Anole lizard
```

<400> SEQUENCE: 94

```
atggctgaag gtgaaataac aacattcaca gccttgaccg agaggtttgc tctcccaatg      60
gagaattaca agaagcccaa actcctgtat tgcagcaatg gaggccactt cctgaggatc     120
cttccagatg gaaaagtgga tggcaccatg gaccggaatg acagctatat tcagttgctg     180
ttaacagcag aagatgtggg tgtggtatat ataaaaggca ctgagaccgg gcagtacttg     240
gccatggatg ccaatggaca tttatatggc tcgcagttgc aacagaaga gtgtttattt      300
gtggaaacgc tggaagaaaa ccattacaat acatatacct caaagatgca tggcgataag     360
aagtggtatg ttggcttgaa aaagaatggg aaaggcaaac tggggccacg gactcatcgc     420
ggccaaaagg caatactttt ccttccactg ccagtatcac ctgattag                  468
```

<210> SEQ ID NO 95
<211> LENGTH: 468
<212> TYPE: DNA
<213> ORGANISM: Bushbaby

<400> SEQUENCE: 95

```
atggctgaag gggaaatcac aaccttcaca gccctcacag agaagtttaa tctgcctcta     60
ggaaattaca agaagcccaa gctcctctac tgtagcaacg ggggtcactt tctgaggatc    120
ctgccggatg gcaccgtgga tgggacacaa gacaggagcg accagcacat tcagctgcag    180
ctcagtgcgg aaagcgtggg ggaggtgtat ataaagagta cccagactgg ccagtacttg    240
gccatggact ccgacgggct tttatacggc tcacaaacac caaatgagga atgcctgttc    300
ctggaacggc tggaggaaaa ccattacaac acctatgtgt ccaagaagca cgccgagaag    360
aattggtttg tcggtctcaa gaagaacgga agttgcaaac gtggtcctcg gactcactac    420
ggccagaaag caatcttgtt tctccccctg ccagtctcct ctgattaa                 468
```

<210> SEQ ID NO 96
<211> LENGTH: 468
<212> TYPE: DNA
<213> ORGANISM: Cat

<400> SEQUENCE: 96

```
atggctgaag gggaaatcac aaccttcacg ccctgacgg agaagttcaa tctgcctcca      60
gggaattaca agaaacccaa actcctctac tgtagcaacg ggggccactt cctgaggatc    120
cttccagatg gcacagtgga tgggacgagg gacaggagcg accagcacat tcagctgcag    180
ctcagtgcgg aaagcgtggg ggaggtgtat ataaagagta ccgagactgg ccagtacttg    240
gccatggaca ccgacgggct tttgtacggc tcacagacac caaatgagga atgcttgttc    300
ctggaaggc tggaagaaaa ccattacaac acctacacat ccaagaagca cgcagaaaag     360
aattggtttg tgggtctcaa gaagaatgga agctgcaaac gcggtccccg gactcactat    420
ggccagaagg caattttgtt tctccccctg ccagtctcct ctgattaa                 468
```

<210> SEQ ID NO 97
<211> LENGTH: 468
<212> TYPE: DNA
<213> ORGANISM: Chinese softshell turtle

<400> SEQUENCE: 97

```
atggctgaag gggaaataac aacgttcacc gccctgaccg aaaaattcaa ccttcccctg      60
gggaattaca agaatcccaa actcttatat tgcagcaatg gaggctactt cttgaggata    120
catccagatg gcaaagtaga tgggacaagg gaccgaagtg accaacacat tcagctgcag    180
```

-continued

```
ctaagtgcgg aaagcgtggg tgaggtatat ataaagagca ctgagtctgg acagttttg     240 gctatggacg ccaatggact tttatatgga tcactgtcac cgagtgagga atgcttattc    300
ttggaaagaa tggaagaaaa tcattataac acctacatct ccaagaagca tgcagacaag    360
aactggttcg ttggcttaaa gaagaatgga agctgcaaac tgggaccgcg gacgcactac    420
ggccaaaagg ccgtcctttt ccttccactg ccagtgtcag ctgattaa                 468
```

<210> SEQ ID NO 98
<211> LENGTH: 468
<212> TYPE: DNA
<213> ORGANISM: Coelacanth
<400> SEQUENCE: 98

```
atggctgaag acaaaataac aacactgaag gccttggctg aaaaatttaa ccttcctatg     60
ggaaattaca agaaagcaaa actcctctac tgcagcaacg gagggtattt cctgcgaata    120
cccccagacg ggaaagtgga aggaattaga gaacgaagcg acaagtacat tcagctgcaa    180
atgaatgcag aaagtttagg catggtgtct ataaagggtg tggaggcagg gcaatacctag  240 gctatgaata caaatggact cctgtatgga tctcagtctc taactgaaga atgcctttc    300 atggaaaaga tggaagaaaa ccactacaac acatacaggt ctaagacaca tgcagataaa    360
aactggtatg ttggcattag aaagaacggt agcatcaaac caggaccaag gactcacatt    420
ggccaaaagg ctgttctttt tctccctctg cctgcctcga gtgattag                468
```

<210> SEQ ID NO 99
<211> LENGTH: 468
<212> TYPE: DNA
<213> ORGANISM: Dolphin
<400> SEQUENCE: 99

```
atggctgaag gggaaatcac aaccttcaca gccctgaccg agaagtttaa tctgcctcca     60
gggaattaca agaagcccaa actcctctac tgtagcaacg ggggccactt cctgaggatc    120
cttccagatg gcacagtgga tgggacaagg gacaggagtg accagcacat tcagctgcag    180
ctcagtgcgg aaagcgtggg ggaggtgtat ataaagagta cggagactgg ccagtacttg    240
gccatggaca ccgacgggct tttgtacggc tcacagacac ccaatgagga atgtttgttc    300
ctggaaaggt tggaggaaaa ccattacaac acctacgcat ccaagaagca tgcagaaaag    360
aattggttcg ttggtctcaa gaagaacgga agctgcaaac gcggtcctcg gactcactac    420
ggccagaaag caatcttgtt tctcccctg ccagtctcct ccgattaa                  468
```

<210> SEQ ID NO 100
<211> LENGTH: 468
<212> TYPE: DNA
<213> ORGANISM: Ferret
<400> SEQUENCE: 100

```
atggctgaag gggaaatcac aaccttcaca gccctgatgg agaagtttaa tctgcctgcg     60
gggaattaca agaagcccaa actcctctac tgtagcaatg ggggccactt cctgaggatc    120
cttccagatg gcacagtgga cggcacaagg gacaggagcg accagcacat tcagctgcag    180
ctcagtgcgg aaagcgtggg ggaggtgtac ataaagagta ccgagactgg ccagtacttg    240
gccatggaca ccgatgggct tttgtacggc tcacaaacac caaatgagga atgtctgttc    300 ctggaaggc tggaggaaaa ccattacaac acctacacat ccaagaagca cgctgagaag    360
```

```
aattggtttg taggtctcaa gaagaacgga agctgcaaac gcggtcctcg gactcactat    420
ggccagaaag caattctgtt tctccccctg ccagtctcct ctgattaa                 468
```

<210> SEQ ID NO 101
<211> LENGTH: 468
<212> TYPE: DNA
<213> ORGANISM: Gibbon

<400> SEQUENCE: 101

```
atggccgaag gggaaatcac caccttcaca gccctgaccg agaagtttaa tctgcctcca    60
gggaattaca agaagcccaa actcctctac tgtagcaacg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ctgattaa                 468
```

<210> SEQ ID NO 102
<211> LENGTH: 468
<212> TYPE: DNA
<213> ORGANISM: Gorilla

<400> SEQUENCE: 102

```
atggctgaag gggaaatcac caccttcaca gccctgaccg agaagtttaa tctgcctcca    60
gggaattaca agaagcccaa actcctctac tgtagcaatg ggggccactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatgga agctgcaaac gcggtcctcg gactcactat    420
ggccagaaag caatcttgtt tctccccctg ccagtctctt ccgattaa                 468
```

<210> SEQ ID NO 103
<211> LENGTH: 468
<212> TYPE: DNA
<213> ORGANISM: Hedgehog

<400> SEQUENCE: 103

```
atggctgaag gagaaatcac caccttcacg gccctgactg agaagtttaa tctgccacta    60
gggaattaca agaagcccaa gctcctctac tgtagcaacg ggggccactt cctgaggatc    120
cttccagatg gcaccgtgga tgggacaagg gacaggagcg accagcatat tcagctgcag    180
ctcagtgcgg aaagcgtggg ggaggtgtat ataaagagta cggagactgg ccagtacttg    240
gccatggaca ccgacgggct tttatacggc tcacaaacac caaatgagga atgtctgttc    300
cttgaaaggc tggaagagaa ccattacaat acctacacat ccaagaagca tgccgagaag    360
aactggtttg ttggcctcaa gaagaatgga agctgcaagc gtggtcctcg gactcattat    420
ggccagaaag ctattttgtt tctccccctg ccagtttcct ctgattaa                 468
```

<210> SEQ ID NO 104
<211> LENGTH: 273

<212> TYPE: DNA
<213> ORGANISM: Hyrax

<400> SEQUENCE: 104

```
atggctgaag gcgaaatcac aaccttcaca gccctgactg agaagtttaa cctgccacta      60
gagaattaca agaagcccaa actcctctac tgtagcaacg gaggccactt cctgaggatc     120
cttccggacg gcacagtgga tggcaccagg acaggagtg accagcacat tcagctgcag      180
ctcagtgcgg aaagcgtggg ggaggtgtat ataaagggca ccgagactgg ccagtacttg     240
gccatggaca ccgacgggct tttatatggc tca                                   273
```

<210> SEQ ID NO 105
<211> LENGTH: 349
<212> TYPE: DNA
<213> ORGANISM: Kangaroo rat

<400> SEQUENCE: 105

```
atggctgaag gggaaatcac aaccttcaca gccctgacgg aaaggtttaa ttcagctgca      60
actgagtgcg gaaagcgtgg gggaggtcta tataagagc accgagactg gccaatactt      120
ggccatggat gccgacgggc ttttatacgg ctcacagaca cctgatgaag aatgcttgtt     180
cctggagagg ctggaagaaa atcattataa cacctacata gccaagaaac atgctgaaaa     240
gaattggttt gtcggcctca aaaagaatgg aagctgcaag cgtggcctc ggactcacta      300
tggccagaaa gcaatcctgt tcctcccctt gcctgtctcc tctgattag                 349
```

<210> SEQ ID NO 106
<211> LENGTH: 276
<212> TYPE: DNA
<213> ORGANISM: Lamprey

<400> SEQUENCE: 106

```
atggaggtgg gccacatcgg cacgctgccc gtggtccccg cggggcccgt gttcccggc      60
agtttcaagg agccacggcg cctctactgc cgcagcgcgg ccaccacct ccagatcctg      120
ggggacggca ccgtgagtgg cacccaggac gagaacgagc ccacgccgt tctgcagctg      180
caggcggtgc gccgcggggt ggtgacgatc cgtgggctct gcgccgagag gttcctcgcc     240
atgagcacgg agggacacct gtacggggcg gtgagg                               276
```

<210> SEQ ID NO 107
<211> LENGTH: 297
<212> TYPE: DNA
<213> ORGANISM: Lesser hedgehog tenrec

<400> SEQUENCE: 107

```
cagctgaagc tcgttgccga aagcgtgggg gtggtgtata taaagagcat caagaccggc      60
cagtacttgg ccatgaaccc cgacgggctt ttatacggct ccgagacccc agaggaagaa     120
tgcttgttcc tggaaacgct ggaggaaaac cactacacca ccttcaaatc taagaagcac     180
gtagagaaga attggttcgt tggtctccgg aagaatggaa gggtcaagat cgggcctcgg     240
actcaccaag gccagaaagc aatcttgttc ctgcccctcc cggtgtcctc tgattaa        297
```

<210> SEQ ID NO 108
<211> LENGTH: 468
<212> TYPE: DNA
<213> ORGANISM: Rhesus monkey

<400> SEQUENCE: 108

```
atggctgaag gggaaatcac cacgttcaca gccctgaccg agaagtttaa tctgcctcca    60
gggaattaca agaagcccaa actgctctac tgtagcaatg ggggccactt cttgaggatc   120
cttccggatg gcacagtgga tgggacaagg gacaggagcg accagcacat tcagctgcag   180
ctcagtgcgg aaagcgtggg ggaggtgtat ataaagagta ccgagactgg ccagtacttg   240
gccatggaca ccgacgggct tttatacggc tcacagacac caaatgagga atgtttgttc   300
ctggaaaggc tggaggagaa ccattacaac acctatacat ccaagaagca cgcagagaag   360
aattggtttg ttggcctcaa gaagaatgga agctgcaaac gtggtcctcg gactcactat   420
ggccagaaag caatcttgtt tcttcccctg ccagtctctt ctgattaa                 468
```

<210> SEQ ID NO 109
<211> LENGTH: 468
<212> TYPE: DNA
<213> ORGANISM: Megabat

<400> SEQUENCE: 109

```
atggccgagg gggaagtcac gacgttcacg gccctgaccg agaggtttaa cctgcctcca    60
gggaattaca agaagcccaa acttctctac tgcagcaacg ggggccactt cctgaggatc   120
ctcccagatg gcacagtgga tgggacaagg gacaagagcg accagcacat tcagctgcag   180
ctcagtgcgg aaagtgtggg ggaggtgtat ataaagagca ccgagagtgg ccagtacttg   240
gccatggact ccgacgggct tttgtacggc tcacagacac cagatgagga ctgtttgttc   300
ctggaaaggc tggaggaaaa ccattacaac acctacacat ccaagaagca cgcagagaag   360
aattggtttg ttgggctcaa gaagaatgga agctgcaagc gcggtccccg gactcactac   420
ggccagaaag cgatcctgtt tctccccctg ccagtctcct ctgattag                 468
```

<210> SEQ ID NO 110
<211> LENGTH: 468
<212> TYPE: DNA
<213> ORGANISM: Microbat

<400> SEQUENCE: 110

```
atggctgagg gggaagtcac cacattcacg gccctgaccg agaggttcaa tctgcctctg    60
gagaactaca agaagcccaa gcttctctac tgcagcaacg ggggccactt cctgcggatc   120
ctcccagacg gcaccgtgga cgggacgagg gacaggagcg accagcacat tcagctgcag   180
ctcagtgcgg aaagcgtggg ggaggtgtat ataaagagca ccgagagtgg ccagtacttg   240
gccatggact ccgacgggct tttgtacggc tcacaaacac ccaatgagga atgtttgttc   300
ctggaaaggc tggaggagaa ccactacaac acctacacgt ccaagaagca cgcagaaaag   360
aattggttcg ttgggctcaa gaagaacgga agctgcaagc gtggtcctcg gacgcattat   420
ggccagaaag caatcttgtt tctccccctg ccagtctcct ccgattaa                 468
```

<210> SEQ ID NO 111
<211> LENGTH: 468
<212> TYPE: DNA
<213> ORGANISM: Mouse lemur

<400> SEQUENCE: 111

```
atggccgaag gggagatcac aaccttcacg gccctcaccg agaagtttaa cctgcctccg    60
gggaactaca agaagcccaa gctcctctac tgcagcaacg gcggccactt cctgcgcatc   120
cttcccgacg gcaccgtgga tgcacgagag gacaggagcg accagcacat tcagctgcag   180
ctcagtgcgg aaagcgcggg ggaggtgtat ataaagagca cccagactgg ccggtacttg   240
```

```
gccatggacg ccgacgggct tttatacggc tcacaaacac caaatgagga atgtttgttc    300
ctggaaaggc tggaggaaaa ccattacaac acctacgtat ccaagaagca cgcagagaag    360
aattggtttg ttggcctcaa gaagaatgga agttgcaaac gcggcccccg gactcactat    420
ggccagaaag caatcttgtt tctgcccctg ccagtctcct ctgattaa                 468
```

<210> SEQ ID NO 112
<211> LENGTH: 436
<212> TYPE: DNA
<213> ORGANISM: Pika

<400> SEQUENCE: 112

```
atggccgagg gagaagtcac caccttctca gccctgacgg agaagttcaa tctgcctgga     60
ggaaactaca gttgcccaa gctcctttac tgtagcaacg gaggccactt cctgaggatc    120
cttccagatg gcacagtgga tgggaccagg gacaggagcg acctgcacag aggtgtttat    180
aaagagtacg gagactggcc agtacttggc tatggacacc gatggccttt tatatggctc    240
gcagacaccc cagtgaggagt gtttgttcct ggagcggctg gaggagaacc actacaacac    300
ctacacatcc aagaagcatg ccgagaagaa ctggtttgtg ggcatcaaga gaatggaag    360 ctgcaagcgt ggtcctcgga ctcactacgg ccagaaagcc atcttgtttc tccctctgcc    420
agtctcttct gactaa                                                   436
```

<210> SEQ ID NO 113
<211> LENGTH: 468
<212> TYPE: DNA
<213> ORGANISM: Rat

<400> SEQUENCE: 113

```
atggccgaag gggagatcac aacctttgca gccctgaccg agaggttcaa tctgcctcta     60
gggaactaca aaaacccaa actgctctac tgcagcaacg ggggccactt cttgaggatt    120
cttcccgatg gcaccgtgga tgggaccagg gacaggagcg accagcacat tcagctgcag    180
ctcagtgcgg aaagcgcggg cgaagtgtat ataaagggta cagagactgg ccagtacttg    240
gccatggaca ccgaagggct tttatacggc tcgcagacac caaatgaaga atgcctattc    300
ctggaaaggc tagaagaaaa ccattataac acttacacat ccaagaagca cgcggagaag    360
aactggtttg tgggcctcaa gaagaacggg agttgtaagc gcggtcctcg gactcactac    420
ggccagaaag ccatcttgtt tctccccctc ccggtatctt ctgactaa                468
```

<210> SEQ ID NO 114
<211> LENGTH: 468
<212> TYPE: DNA
<213> ORGANISM: Sloth

<400> SEQUENCE: 114

```
atggctgaag gggaaatcac aaccttcaca gctctgatgg agaagtttaa cctgccacca     60
gggaattaca tgaagcccaa actcctctac tgtagcaacg ggggccactt cttgaggatc    120
cttccagacg gcacagtgga tgggacaagg gacaggagcg acctgcacat tcagctgcag    180
ctcagtgcgg aaagcgtggg ggaggtgtat ataaagagtg cggagaccgg ccagtactta    240
gccatggaca ccggcgggct tttatacggc tcacagacac caagtgagga atgcctgttc    300
ctagaaaggc tggaggaaaa ccattacaac acctacgtat ccaagaagca tgcggagaag    360
aactggttcg ttggcctaaa gaagaatgga agcagcaaac gcggcccccg gactcactat    420
```

```
ggccagaaag ccatcttgtt tcttcccctg ccagtctcct ctgattaa        468
```

<210> SEQ ID NO 115
<211> LENGTH: 468
<212> TYPE: DNA
<213> ORGANISM: Squirrel

<400> SEQUENCE: 115

```
atggctgaag gggaaatcac aaccttcaca gccctgaccg agaagttcaa tctgcctcca        60
gggaactaca agaagcccaa actgctctac tgtagcaacg gaggccactt cttgaggatc       120
cttcctgatg gcacagtgga tgggacaaga gacaggagcg accaacacat tcagctgcag       180
ctcagtgcgg aaagcgtggg ggaggtgtat ataaagagta ccgagaccgg ccagtacttg       240
gccatggaca ccgacgggct tttatatggc tcacagaccc caaatgagga atgcttattc       300
ctggaaaggc tggaggaaaa ccattacaac acgtacacat ccaagaagca tgcagagaag       360
aattggtttg ttggcctcaa gaagaacgga agctgcaagc gcggtccccg gactcactat       420
ggccagaaag cgatcttgtt tctcccactg cctgtctcct ctgattag                    468
```

<210> SEQ ID NO 116
<211> LENGTH: 468
<212> TYPE: DNA
<213> ORGANISM: Tarsier

<400> SEQUENCE: 116

```
atggccgaag gggaaatcac aaccttcaca gccctgaccg agaagttcaa cctgcccccg        60
gggaattaca agaagcccaa actcctctac tgcagcaacg gggccactt cttgaggatc        120
cttccggatg gcactgtgga tggaacgagg acaggagcg accagcacat tcagctgcag       180
ctcagcgcgg aaagcgtggg ggaggtgtat ataaagagta ccgagaccgg ccagtacttg       240
gccatggaca ccgacgggct tttgtacggc tcacagacac caaatgagga gtgtctgttc       300
ctggaaaggc tggaagagaa tcattacaat acctacgtgt ccaagaagca tgcggagaag       360
aattggtttg tcggcctcaa gaagaatgga agctgcaaac gcggtcctcg gactcactat       420
ggccagaaag caatcttgtt tctcccccctg ccagtttcct ctgattaa                   468
```

<210> SEQ ID NO 117
<211> LENGTH: 468
<212> TYPE: DNA
<213> ORGANISM: Tree shrew

<400> SEQUENCE: 117

```
atggctgaag gggaaatcac gaccttcgca gccctgaccg agaagtttga tctgcctcca        60
gggaattaca agaagcccaa acttctctac tgtagcaacg gggccatttt cttgaggatt       120
cttccagatg gcaccgtgga tgggacaaga gacaggagcg accagcacat tcagctgcag       180
ctcactgcgg aaaacgtggg ggaggtgtac ataaagagta cggagactgg ccagtacttg       240
gccatggacg ccgacgggct tttatatggc tcacagacac caaacgagga atgtttgttc       300
ctggaaaggc tggaggagaa ccattacaac acctacatat ccaagaagca cgcagagaag       360
aattggtttg ttgccctcaa gaagaacgga agctgcaaac tcggtcctcg gactcactat       420
ggccagaaag caatcttgtt tctccccctg ccagtctcct ctgattaa                    468
```

<210> SEQ ID NO 118
<211> LENGTH: 168
<212> TYPE: DNA
<213> ORGANISM: Turkey

<400> SEQUENCE: 118

```
atggccgagg gggagataac caccttcaca gccctgaccg agcgcttcgg cctgccgctg      60
ggcaactaca agaagcccaa actcctgtac tgcagcaacg ggggccactt cctacggatc     120
ctgccgacg gcaaggtgga cgggacgcgg gaccggagcg accagcac                   168
```

<210> SEQ ID NO 119
<211> LENGTH: 468
<212> TYPE: DNA
<213> ORGANISM: Wallaby

<400> SEQUENCE: 119

```
atggccgaag gggagatcac aaccttcaca gccctgaccg aaagatttaa cctgccactg      60
gggaattaca agaagcccaa gcttctctac tgtagcaatg ggggccactt tttgaggatc     120
cttcctgatg gcaaagtgga tgggacaagg acagaaatg atcaacacat tcaactgcaa     180
ctaagcgcgg aaagcgtggg tgaggtgtat ataaagagca ctgagtctgg gcagtatttg     240
gccatggaca ccaatggact tttatatggc tcacagaccc ccagcgaaga tgcttattc     300
ctggagaggt tggaggagaa tcattacaac acctacatat caagaagca tgcggagaaa     360
aattggtttg ttggcctcaa gaagaacgga agttgcaaaa gaggtcccag gactcactat     420
ggccagaaag ccatcctatt ccttcccctc cctgtgtcct ctgagtaa                  468
```

<210> SEQ ID NO 120
<211> LENGTH: 444
<212> TYPE: DNA
<213> ORGANISM: Zebrafish

<400> SEQUENCE: 120

```
atgaccgagg ccgatattgc ggtaaagtcc agcccgcgcg actataaaaa actgacgcgg      60
ctgtactgta tgaatggagg atttcacctt cagatcctgg cggacgggac agtggctgga     120
gcagcagacg aaaacacata cagcatactg cgcataaaag caacaagtcc aggagtggtg     180
gtgatcgaag gatcagaaac aggtctttac ctctcgatga atgaacatgg caagctgtac     240
gcttcatcat tagtgacgga tgaaagttat ttcctggaga agatggagga aaaccactac     300
aacacatatc agtctcaaaa gcacggtgaa aactggtacg tcggaataaa aagaacggg      360
aaaatgaaac ggggcccaag aactcacatc ggacaaaagg ccattttctt tcttccacga     420
caggtggagc aggaagagga ctga                                             444
```

<210> SEQ ID NO 121
<211> LENGTH: 155
<212> TYPE: PRT
<213> ORGANISM: Homo sapiens

<400> SEQUENCE: 121

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80
```

```
Arg Tyr Leu Ala Met Lys Glu Asp Gly Arg Leu Leu Ala Ser Lys Cys
                 85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
                115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 122
<211> LENGTH: 155
<212> TYPE: PRT
<213> ORGANISM: Gorilla gorilla

<400> SEQUENCE: 122

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
                115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 123
<211> LENGTH: 155
<212> TYPE: PRT
<213> ORGANISM: Pongo abelii

<400> SEQUENCE: 123

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95
```

Val Thr Asp Glu Cys Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 124
<211> LENGTH: 155
<212> TYPE: PRT
<213> ORGANISM: Macaca mulatta

<400> SEQUENCE: 124

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 125
<211> LENGTH: 155
<212> TYPE: PRT
<213> ORGANISM: Pan troglodytes

<400> SEQUENCE: 125

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

```
Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 126
<211> LENGTH: 155
<212> TYPE: PRT
<213> ORGANISM: Pan paniscus

<400> SEQUENCE: 126

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 127
<211> LENGTH: 155
<212> TYPE: PRT
<213> ORGANISM: Saimiri boliviensis boliviensis

<400> SEQUENCE: 127

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125
```

```
Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 128
<211> LENGTH: 155
<212> TYPE: PRT
<213> ORGANISM: Nomascus leucogenys

<400> SEQUENCE: 128

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 129
<211> LENGTH: 155
<212> TYPE: PRT
<213> ORGANISM: Equus caballus

<400> SEQUENCE: 129

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140
```

Ala Ile Leu Phe Leu Pro Met Ser Ala Lys Ser
145                 150                 155

<210> SEQ ID NO 130
<211> LENGTH: 155
<212> TYPE: PRT
<213> ORGANISM: Bos taurus

<400> SEQUENCE: 130

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ala Ser Lys Ser
145                 150                 155

<210> SEQ ID NO 131
<211> LENGTH: 155
<212> TYPE: PRT
<213> ORGANISM: Papio anubis

<400> SEQUENCE: 131

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ala Ser Lys Ser
145                 150                 155

<210> SEQ ID NO 132
<211> LENGTH: 155
<212> TYPE: PRT
<213> ORGANISM: Vicugna pacos

<400> SEQUENCE: 132

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 133
<211> LENGTH: 155
<212> TYPE: PRT
<213> ORGANISM: Ovis aries

<400> SEQUENCE: 133

Met Ala Ala Gly Ser Ile Thr Thr Leu Pro Ala Leu Pro Glu Asp Gly
1               5                   10                  15

Gly Ser Ser Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 134

```
<211> LENGTH: 108
<212> TYPE: PRT
<213> ORGANISM: Capreolus capreolus

<400> SEQUENCE: 134

Arg Ile His Pro Asp Gly Arg Val Asp Gly Val Arg Glu Lys Ser Asp
1               5                   10                  15

Pro His Ile Lys Leu Gln Leu Gln Ala Glu Glu Arg Gly Val Val Ser
                20                  25                  30

Ile Lys Gly Val Cys Ala Asn Arg Tyr Leu Ala Met Lys Glu Asp Gly
            35                  40                  45

Arg Leu Leu Ala Ser Lys Cys Val Thr Asp Glu Cys Phe Phe Phe Glu
    50                  55                  60

Arg Leu Glu Ser Asn Asn Tyr Asn Thr Tyr Arg Ser Arg Lys Tyr Ser
65                  70                  75                  80

Ser Trp Tyr Val Ala Leu Lys Arg Thr Gly Gln Tyr Lys Leu Gly Pro
                85                  90                  95

Lys Thr Gly Pro Gly Gln Lys Ala Ile Leu Phe Leu
                100                 105

<210> SEQ ID NO 135
<211> LENGTH: 96
<212> TYPE: PRT
<213> ORGANISM: Loxodonta africana

<400> SEQUENCE: 135

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
                20                  25                  30

Leu Ala Ser Arg Cys Val Thr Asp Glu Cys Phe Phe Phe Glu Arg Leu
            35                  40                  45

Glu Ser Asn Asn Tyr Asn Thr Tyr Arg Ser Arg Lys Tyr Thr Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
                85                  90                  95

<210> SEQ ID NO 136
<211> LENGTH: 120
<212> TYPE: PRT
<213> ORGANISM: Sus scrofa

<400> SEQUENCE: 136

Asn Gly Gly Phe Phe Leu Arg Ile His Pro Asp Gly Arg Val Asp Gly
1               5                   10                  15

Val Arg Glu Lys Ser Asp Pro His Ile Lys Leu Gln Leu Gln Ala Glu
                20                  25                  30

Glu Arg Gly Val Val Ser Ile Lys Gly Val Cys Ala Asn Arg Tyr Leu
            35                  40                  45

Ala Met Lys Glu Asp Gly Arg Leu Leu Ala Ser Lys Cys Val Thr Asp
    50                  55                  60

Glu Cys Phe Phe Phe Glu Arg Leu Glu Ser Asn Asn Tyr Asn Thr Tyr
65                  70                  75                  80

Arg Ser Arg Lys Tyr Ser Ser Trp Tyr Val Ala Leu Lys Arg Thr Gly
                85                  90                  95
```

-continued

```
Gln Tyr Lys Leu Gly Pro Lys Thr Gly Pro Gln Lys Ala Ile Leu
            100                 105                 110

Phe Leu Pro Met Ser Ala Lys Ser
        115                 120

<210> SEQ ID NO 137
<211> LENGTH: 96
<212> TYPE: PRT
<213> ORGANISM: Ailuropoda melanoleuca

<400> SEQUENCE: 137

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95

<210> SEQ ID NO 138
<211> LENGTH: 155
<212> TYPE: PRT
<213> ORGANISM: Choloepus hoffmanni

<400> SEQUENCE: 138

Met Ala Ala Gly Ser Ile Thr Thr Leu Pro Ala Leu Pro Glu Asp Gly
1               5                   10                  15

Gly Ser Gly Ala Leu Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Gln Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155

<210> SEQ ID NO 139
<211> LENGTH: 155
<212> TYPE: PRT
<213> ORGANISM: Bubalus bubalis

<400> SEQUENCE: 139

Met Ala Ala Gly Ser Ile Thr Thr Leu Pro Pro Leu Pro Glu Asp Gly
```

```
            1               5                  10                 15
Gly Ser Gly Ala Phe Pro Pro Gly His Phe Lys Asp Pro Lys Arg Leu
            20                 25                 30

Tyr Cys Lys Asn Gly Gly Phe Phe Leu Arg Ile His Pro Asp Gly Arg
            35                 40                 45

Val Asp Gly Val Arg Glu Lys Ser Asp Pro His Ile Lys Leu Gln Leu
        50                 55                 60

Gln Ala Glu Glu Arg Gly Val Val Ser Ile Lys Gly Val Cys Ala Asn
65                  70                 75                     80

Arg Tyr Leu Ala Met Lys Glu Asp Gly Arg Leu Leu Ala Ser Lys Cys
                85                 90                 95

Val Thr Asp Glu Cys Phe Phe Phe Glu Arg Leu Glu Ser Ser Asn Tyr
                100                105                110

Asn Thr Tyr Arg Ser Arg Lys Tyr Ser Ser Trp Tyr Val Ala Leu Lys
                115                120                125

Arg Thr Gly Gln Tyr Lys Leu Gly Pro Lys Thr Gly Pro Gly Gln Lys
                130                135                140

Ala Ile Leu Phe Leu Pro Met Ser Ala Lys Ser
145                 150                155

<210> SEQ ID NO 140
<211> LENGTH: 155
<212> TYPE: PRT
<213> ORGANISM: Canis lupus familiaris

<400> SEQUENCE: 140

Met Ala Ala Gly Ser Ile Thr Thr Leu Pro Ala Leu Pro Glu Asp Gly
1               5                  10                 15

Gly Ser Gly Ala Phe Pro Pro Gly His Phe Lys Asp Pro Lys Arg Leu
            20                 25                 30

Tyr Cys Lys Lys Gly Gly Phe Phe Leu Arg Ile His Pro Asp Gly Arg
            35                 40                 45

Val Asp Gly Val Arg Glu Lys Ser Asp Pro His Val Lys Leu Gln Leu
        50                 55                 60

Gln Ala Glu Glu Arg Gly Val Val Ser Ile Lys Gly Val Cys Ala Asn
65                  70                 75                     80

Arg Tyr Leu Ala Met Lys Glu Asp Gly Arg Leu Leu Ala Ser Lys Cys
                85                 90                 95

Val Thr Asp Glu Cys Phe Phe Phe Glu Arg Leu Glu Ser Asn Asn Tyr
                100                105                110

Asn Thr Tyr Arg Ser Arg Lys Tyr Ser Ser Trp Tyr Val Ala Leu Lys
                115                120                125

Arg Thr Gly Gln Tyr Lys Leu Gly Pro Lys Thr Gly Pro Gly Gln Lys
                130                135                140

Ala Ile Leu Phe Leu Pro Met Ser Ala Lys Ser
145                 150                155

<210> SEQ ID NO 141
<211> LENGTH: 154
<212> TYPE: PRT
<213> ORGANISM: Rattus norvegicus

<400> SEQUENCE: 141

Met Ala Ala Gly Ser Ile Thr Ser Leu Pro Ala Leu Pro Glu Asp Gly
1               5                  10                 15

Gly Gly Ala Phe Pro Pro Gly His Phe Lys Asp Pro Lys Arg Leu Tyr
```

```
            20                  25                  30
Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
 50                  55                  60

Ala Glu Glu Arg Gly Val Val Ser Ile Lys Gly Val Cys Ala Asn Arg
 65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150

<210> SEQ ID NO 142
<211> LENGTH: 134
<212> TYPE: PRT
<213> ORGANISM: Heterocephalus glaber

<400> SEQUENCE: 142

Pro Pro Gly His Phe Lys Asp Pro Lys Arg Leu Tyr Cys Lys Asn Gly
 1               5                  10                  15

Gly Phe Phe Leu Arg Ile His Pro Asp Gly Arg Val Asp Gly Val Arg
                20                  25                  30

Glu Lys Ser Asp Pro His Val Lys Leu Gln Leu Gln Ala Glu Glu Arg
            35                  40                  45

Gly Val Val Ser Ile Lys Gly Val Cys Ala Asn Arg Tyr Leu Ala Met
        50                  55                  60

Lys Glu Asp Gly Arg Leu Leu Ala Ser Lys Cys Val Thr Asp Glu Cys
 65                  70                  75                  80

Phe Phe Phe Glu Arg Leu Glu Ser Asn Asn Tyr Asn Thr Tyr Arg Ser
                85                  90                  95

Arg Lys Tyr Ser Ser Trp Tyr Val Ala Leu Lys Arg Thr Gly Gln Tyr
            100                 105                 110

Lys Leu Gly Ser Lys Thr Gly Pro Gly Gln Lys Ala Ile Leu Phe Leu
        115                 120                 125

Pro Met Ser Ala Lys Ser
    130

<210> SEQ ID NO 143
<211> LENGTH: 155
<212> TYPE: PRT
<213> ORGANISM: Otolemur garnettii

<400> SEQUENCE: 143

Met Ala Ala Gly Ser Ile Thr Thr Leu Pro Ser Leu Pro Glu Asp Gly
 1               5                  10                  15

Gly Ser Asp Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro Tyr Ile Lys Leu Gln Leu
```

```
                50                  55                  60
Gln Ala Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Leu
                 85                  90                  95

Ile Thr Asp Glu Cys Phe Phe Phe Glu Arg Leu Glu Ser Asn Asn Tyr
                100                 105                 110

Asn Thr Tyr Arg Ser Arg Lys Tyr Ser Ser Trp Tyr Val Ala Leu Lys
                115                 120                 125

Arg Thr Gly Gln Tyr Lys Leu Gly Ser Lys Thr Gly Pro Gly Gln Lys
                130                 135                 140

Ala Ile Leu Phe Leu Pro Met Ser Ala Lys Ser
145                 150                 155

<210> SEQ ID NO 144
<211> LENGTH: 154
<212> TYPE: PRT
<213> ORGANISM: Mus musculus

<400> SEQUENCE: 144

Met Ala Ala Ser Gly Ile Thr Ser Leu Pro Ala Leu Pro Glu Asp Gly
 1               5                  10                  15

Gly Ala Ala Phe Pro Pro Gly His Phe Lys Asp Pro Lys Arg Leu Tyr
                20                  25                  30

Cys Lys Asn Gly Gly Phe Phe Leu Arg Ile His Pro Asp Gly Arg Val
                35                  40                  45

Asp Gly Val Arg Glu Lys Ser Asp Pro His Val Lys Leu Gln Leu Gln
 50                  55                  60

Ala Glu Glu Arg Gly Val Val Ser Ile Lys Gly Val Cys Ala Asn Arg
 65                  70                  75                  80

Tyr Leu Ala Met Lys Glu Asp Gly Arg Leu Leu Ala Ser Lys Cys Val
                 85                  90                  95

Thr Glu Glu Cys Phe Phe Phe Glu Arg Leu Glu Ser Asn Asn Tyr Asn
                100                 105                 110

Thr Tyr Arg Ser Arg Lys Tyr Ser Ser Trp Tyr Val Ala Leu Lys Arg
                115                 120                 125

Thr Gly Gln Tyr Lys Leu Gly Ser Lys Thr Gly Pro Gly Gln Lys Ala
                130                 135                 140

Ile Leu Phe Leu Pro Met Ser Ala Lys Ser
145                 150

<210> SEQ ID NO 145
<211> LENGTH: 144
<212> TYPE: PRT
<213> ORGANISM: Ictidomys tridecemlineatus

<400> SEQUENCE: 145

Leu Pro Glu Asp Gly Gly Gly Ala Phe Pro Pro Gly His Phe Lys
 1               5                  10                  15

Asp Pro Lys Arg Leu Tyr Cys Lys Asn Gly Gly Phe Phe Leu Arg Ile
                20                  25                  30

His Pro Asp Gly Arg Val Asp Gly Val Arg Glu Lys Ser Asp Pro His
                35                  40                  45

Ile Lys Leu Gln Leu Gln Ala Glu Asp Arg Gly Val Val Ser Ile Lys
 50                  55                  60

Gly Val Cys Ala Asn Arg Tyr Leu Ala Met Lys Glu Asp Gly Arg Leu
```

```
            65                  70                  75                  80
Leu Ala Ser Lys Cys Val Thr Asp Glu Cys Phe Phe Phe Glu Arg Leu
                85                  90                  95

Glu Ser Asn Asn Tyr Asn Thr Tyr Arg Ser Arg Lys Tyr Ser Ser Trp
            100                 105                 110

Tyr Val Ala Leu Lys Arg Thr Gly Gln Tyr Lys Leu Gly Ser Lys Thr
        115                 120                 125

Gly Pro Gly Gln Lys Ala Ile Leu Phe Leu Pro Met Ser Ala Lys Ser
    130                 135                 140

<210> SEQ ID NO 146
<211> LENGTH: 106
<212> TYPE: PRT
<213> ORGANISM: Felis catus

<400> SEQUENCE: 146

His Phe Lys Asp Pro Lys Arg Leu Tyr Cys Lys Asn Gly Gly Phe Phe
1               5                  10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Ser Ser Trp Tyr Val Ala Leu Lys Arg Thr
            100                 105

<210> SEQ ID NO 147
<211> LENGTH: 96
<212> TYPE: PRT
<213> ORGANISM: Cavia porcellus

<400> SEQUENCE: 147

Val Lys Leu Gln Leu Gln Ala Glu Asp Arg Gly Val Val Ser Ile Lys
1               5                  10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
                85                  90                  95

<210> SEQ ID NO 148
<211> LENGTH: 156
<212> TYPE: PRT
<213> ORGANISM: Sarcophilus harrisii

<400> SEQUENCE: 148

Met Ala Ala Gly Ser Ile Thr Thr Leu Pro Ala Leu Ala Gly Asp Gly
1               5                  10                  15
```

```
Ala Ser Gly Gly Ala Phe Pro Pro Gly His Phe Gln Asp Pro Lys Arg
            20                  25                  30

Leu Tyr Cys Lys Asn Gly Gly Phe Phe Leu Arg Ile His Pro Asp Gly
        35                  40                  45

His Val Asp Gly Ile Arg Glu Lys Ser Asp Pro His Ile Lys Leu Gln
 50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Cys Val Thr Glu Glu Cys Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 149
<211> LENGTH: 156
<212> TYPE: PRT
<213> ORGANISM: Monodelphis domestica

<400> SEQUENCE: 149

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
 50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155

<210> SEQ ID NO 150
<211> LENGTH: 155
<212> TYPE: PRT
<213> ORGANISM: Oryctolagus cuniculus

<400> SEQUENCE: 150

Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30
```

```
Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
            115                 120                 125

Arg Thr Gly Gln Tyr Lys Leu Gly Ser Lys Thr Gly Pro Gly Gln Lys
            130                 135                 140

Ala Ile Leu Phe Leu Pro Met Ser Ala Lys Ser
145                 150                 155

<210> SEQ ID NO 151
<211> LENGTH: 125
<212> TYPE: PRT
<213> ORGANISM: Meleagris gallopavo

<400> SEQUENCE: 151

Arg Leu Tyr Cys Lys Asn Gly Gly Phe Phe Leu Arg Ile Asn Pro Asp
 1               5                  10                  15

Gly Arg Val Asp Gly Val Arg Glu Lys Ser Asp Pro His Ile Lys Leu
                20                  25                  30

Gln Leu Gln Ala Glu Glu Arg Gly Val Val Ser Ile Lys Gly Val Ser
            35                  40                  45

Ala Asn Arg Phe Leu Ala Met Lys Glu Asp Gly Arg Leu Leu Ala Leu
 50                  55                  60

Lys Cys Ala Thr Glu Glu Cys Phe Phe Phe Glu Arg Leu Glu Ser Asn
 65                  70                  75                  80

Asn Tyr Asn Thr Tyr Arg Ser Arg Lys Tyr Ser Asp Trp Tyr Val Ala
                 85                  90                  95

Leu Lys Arg Thr Gly Gln Tyr Lys Pro Gly Pro Lys Thr Gly Pro Gly
            100                 105                 110

Gln Lys Ala Ile Leu Phe Leu Pro Met Ser Ala Lys Ser
            115                 120                 125

<210> SEQ ID NO 152
<211> LENGTH: 158
<212> TYPE: PRT
<213> ORGANISM: Gallus gallus

<400> SEQUENCE: 152

Met Ala Ala Gly Ala Ala Gly Ser Ile Thr Thr Leu Pro Ala Leu Pro
 1               5                  10                  15

Asp Asp Gly Gly Gly Gly Ala Phe Pro Pro Gly His Phe Lys Asp Pro
                20                  25                  30

Lys Arg Leu Tyr Cys Lys Asn Gly Gly Phe Phe Leu Arg Ile Asn Pro
            35                  40                  45

Asp Gly Arg Val Asp Gly Val Arg Glu Lys Ser Asp Pro His Ile Lys
 50                  55                  60

Leu Gln Leu Gln Ala Glu Glu Arg Gly Val Val Ser Ile Lys Gly Val
 65                  70                  75                  80
```

```
Ser Ala Asn Arg Phe Leu Ala Met Lys Glu Asp Gly Arg Leu Leu Ala
                85                  90                  95

Leu Lys Cys Ala Thr Glu Glu Cys Phe Phe Glu Arg Leu Glu Ser
           100                 105                 110

Asn Asn Tyr Asn Thr Tyr Arg Ser Arg Lys Tyr Ser Asp Trp Tyr Val
            115                 120                 125

Ala Leu Lys Arg Thr Gly Gln Tyr Lys Pro Gly Pro Lys Thr Gly Pro
        130                 135                 140

Gly Gln Lys Ala Ile Leu Phe Leu Pro Met Ser Ala Lys Ser
145                 150                 155
```

<210> SEQ ID NO 153
<211> LENGTH: 153
<212> TYPE: PRT
<213> ORGANISM: Taeniopygia guttata

<400> SEQUENCE: 153

```
Met Ala Ala Ala Gly Gly Ile Ala Thr Leu Pro Asp Asp Gly Gly Ser
1               5                   10                  15

Gly Ala Phe Pro Pro Gly His Phe Lys Asp Pro Lys Arg Leu Tyr Cys
            20                  25                  30

Lys Asn Gly Gly Phe Phe Leu Arg Ile Asn Pro Asp Gly Lys Val Asp
        35                  40                  45

Gly Val Arg Glu Lys Ser Asp Pro His Ile Lys Leu Gln Leu Gln Ala
    50                  55                  60

Glu Glu Arg Gly Val Val Ser Ile Lys Gly Val Ser Ala Asn Arg Phe
65                  70                  75                  80

Leu Ala Met Lys Glu Asp Gly Arg Leu Leu Ala Leu Lys Tyr Ala Thr
                85                  90                  95

Glu Glu Cys Phe Phe Phe Glu Arg Leu Glu Ser Asn Asn Tyr Asn Thr
            100                 105                 110

Tyr Arg Ser Arg Lys Tyr Ser Asp Trp Tyr Val Ala Leu Lys Arg Thr
        115                 120                 125

Gly Gln Tyr Lys Pro Gly Pro Lys Thr Gly Pro Gly Gln Lys Ala Ile
    130                 135                 140

Leu Phe Leu Pro Met Ser Ala Lys Ser
145                 150
```

<210> SEQ ID NO 154
<211> LENGTH: 155
<212> TYPE: PRT
<213> ORGANISM: Cynops pyrrhogaster

<400> SEQUENCE: 154

```
Met Ala Ala Gly Ser Ile Thr Ser Leu Pro Ala Leu Pro Glu Asp Gly
1               5                   10                  15

Asn Gly Gly Thr Phe Thr Pro Gly Gly Phe Lys Glu Pro Lys Arg Leu
            20                  25                  30

Tyr Cys Lys Asn Gly Gly Phe Phe Leu Arg Ile Asn Ser Asp Gly Lys
        35                  40                  45

Val Asp Gly Ala Arg Glu Lys Ser Asp Ser Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Asp Asp Gly Arg Leu Met Ala Leu Lys Trp
                85                  90                  95
```

```
Ile Thr Asp Glu Cys Phe Phe Glu Arg Leu Glu Ser Asn Asn Tyr
            100                 105                 110

Asn Thr Tyr Arg Ser Arg Lys Tyr Ser Asp Trp Tyr Val Ala Leu Lys
        115                 120                 125

Arg Thr Gly Gln Tyr Lys Asn Gly Ser Lys Thr Gly Ala Gly Gln Lys
    130                 135                 140

Ala Ile Leu Phe Leu Pro Met Ser Ala Lys Ser
145                 150                 155

<210> SEQ ID NO 155
<211> LENGTH: 155
<212> TYPE: PRT
<213> ORGANISM: Xenopus laevis

<400> SEQUENCE: 155

Met Ala Ala Gly Ser Ile Thr Thr Leu Pro Thr Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
        35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Lys Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Asn Gly Ser Ser Thr Gly Pro Gly Gln Lys
    130                 135                 140

Ala Ile Leu Phe Leu Pro Met Ser Ala Lys Ser
145                 150                 155

<210> SEQ ID NO 156
<211> LENGTH: 156
<212> TYPE: PRT
<213> ORGANISM: Didelphis albiventris

<400> SEQUENCE: 156

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Glu Arg Leu Glu Ser Asn Asn
            100                 105                 110
```

```
Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
130                 135                 140

Lys Ala Ile Leu Phe Ser Pro Cys Leu Leu Arg Cys
145                 150                 155
```

<210> SEQ ID NO 157
<211> LENGTH: 96
<212> TYPE: PRT
<213> ORGANISM: Myotis lucifugus

<400> SEQUENCE: 157

```
Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
                20                  25                  30

Gln Ala Ser Lys Cys Val Thr Asp Glu Cys Phe Phe Phe Glu Arg Leu
            35                  40                  45

Glu Ser Asn Asn Tyr Asn Thr Tyr Arg Ser Arg Lys Tyr Ser Ser Trp
50                  55                  60

Tyr Val Ala Leu Lys Arg Asn Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95
```

<210> SEQ ID NO 158
<211> LENGTH: 140
<212> TYPE: PRT
<213> ORGANISM: Anolis carolinensis

<400> SEQUENCE: 158

```
Ala Ala Ala Ala Ser Phe Pro Pro Gly Pro Phe Lys Asp Pro Lys Arg
1               5                   10                  15

Leu Tyr Cys Lys Asn Gly Gly Phe Phe Leu Arg Ile Asn Pro Asp Gly
                20                  25                  30

Gly Val Asp Gly Val Arg Glu Lys Ser Asp Pro Asn Ile Lys Leu Leu
            35                  40                  45

Leu Gln Ala Glu Glu Arg Gly Val Val Ser Ile Lys Gly Val Cys Ala
        50                  55                  60

Asn Arg Phe Leu Ala Met Asn Glu Asp Gly Arg Leu Leu Ala Leu Lys
65                  70                  75                  80

Tyr Val Thr Asp Glu Cys Phe Phe Phe Glu Arg Leu Glu Ser Asn Asn
                85                  90                  95

Tyr Asn Thr Tyr Arg Ser Arg Lys Tyr Arg Asp Trp Tyr Ile Ala Leu
                100                 105                 110

Lys Arg Thr Gly Gln Tyr Lys Leu Gly Pro Lys Thr Gly Arg Gly Gln
            115                 120                 125

Lys Ala Ile Leu Phe Leu Pro Met Ser Ala Lys Ser
        130                 135                 140
```

<210> SEQ ID NO 159
<211> LENGTH: 94
<212> TYPE: PRT
<213> ORGANISM: Dasypus novemcinctus

<400> SEQUENCE: 159

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
                35                  40                  45

Val Asp Gly Val Arg Glu Lys Ser Asp Pro Asn Ile Lys Leu Gln Leu
    50                  55                  60

Gln Ala Glu Glu Arg Gly Val Val Ser Ile Gly Val Cys Ala Asn
65                  70                  75                  80

Arg Tyr Leu Ala Met Arg Glu Asp Gly Arg Leu Gln Ala Ser
                85                  90
```

<210> SEQ ID NO 160
<211> LENGTH: 189
<212> TYPE: PRT
<213> ORGANISM: Tupaia belangeri

<400> SEQUENCE: 160

```
Ala Gly Val Arg Ala Glu Arg Glu Ala Pro Gly Ser Gly Asp Ser
1               5                   10                  15

Arg Gly Thr Asp Pro Ala Ala Arg Ser Leu Ile Arg Arg Pro Asp Ala
            20                  25                  30

Ala Ala Arg Glu Ala Leu Leu Gly Ala Arg Ser Arg Val Gln Gly Ser
                35                  40                  45

Ser Thr Ser Trp Pro Ala Ser Ser Arg Thr Gly Ile Lys Leu Pro Asp
    50                  55                  60

Asp Ser Gly Gln Gly Met Gly Gly Tyr Pro Leu Asp Arg Pro Ser Arg
65                  70                  75                  80

Ser Thr Gly Arg Gly Leu Gly Gly Ala Pro Asp Pro Ala Val Lys Leu
                85                  90                  95

Gln Leu Gln Ala Glu Glu Arg Gly Val Val Ser Ile Lys Gly Val Cys
            100                 105                 110

Ala Asn Arg Tyr Leu Ala Met Lys Glu Asp Gly Arg Leu Leu Ala Ser
                115                 120                 125

Lys Cys Val Thr Asp Glu Cys Phe Phe Glu Arg Leu Glu Ser Asn
            130                 135                 140

Asn Tyr Asn Thr Tyr Arg Ser Arg Lys Tyr Ser Ser Trp Tyr Val Ala
145                 150                 155                 160

Leu Lys Arg Thr Gly Gln Tyr Lys Leu Gly Ser Lys Thr Gly Pro Gly
                165                 170                 175

Gln Lys Ala Ile Leu Phe Leu Pro Met Ser Ala Lys Ser
            180                 185
```

<210> SEQ ID NO 161
<211> LENGTH: 154
<212> TYPE: PRT
<213> ORGANISM: Xenopus silurana tropicalis

<400> SEQUENCE: 161

```
Met Ala Ala Gly Ser Ile Thr Thr Leu Pro Thr Glu Ser Glu Asp Gly
1               5                   10                  15

Asn Thr Pro Phe Pro Pro Gly Asn Phe Lys Asp Pro Lys Arg Leu Tyr
            20                  25                  30

Cys Lys Asn Gly Gly Tyr Phe Leu Arg Ile Asn Ser Asp Gly Arg Val
                35                  40                  45
```

```
Asp Gly Ser Arg Asp Lys Ser Asp Leu His Ile Lys Leu Gln Leu Gln
 50                  55                  60

Ala Val Glu Arg Gly Val Val Ser Ile Lys Gly Ile Thr Ala Asn Arg
 65                  70                  75                  80

Tyr Leu Ala Met Lys Glu Asp Gly Arg Leu Thr Ser Leu Lys Cys Ile
                 85                  90                  95

Thr Asp Glu Cys Phe Phe Tyr Glu Arg Leu Glu Ala Asn Asn Tyr Asn
                100                 105                 110

Thr Tyr Arg Ser Arg Lys Asn Asn Ser Trp Tyr Val Ala Leu Lys Arg
                115                 120                 125

Thr Gly Gln Tyr Lys Asn Gly Ser Thr Thr Gly Pro Gly Gln Lys Ala
        130                 135                 140

Ile Leu Phe Leu Pro Met Ser Ala Lys Ser
145                 150

<210> SEQ ID NO 162
<211> LENGTH: 155
<212> TYPE: PRT
<213> ORGANISM: Latimeria chalumnae

<400> SEQUENCE: 162

Met Ala Ala Gly Gly Ile Thr Thr Leu Pro Ala Val Pro Glu Asp Gly
 1               5                  10                  15

Gly Ser Ser Thr Phe Pro Pro Gly Asn Phe Lys Glu Pro Lys Arg Leu
                 20                  25                  30

Tyr Cys Lys Asn Gly Gly Tyr Phe Leu Arg Ile Asn Pro Asp Gly Arg
                 35                  40                  45

Val Asp Gly Thr Arg Glu Lys Asn Asp Pro Tyr Ile Lys Leu Gln Leu
 50                  55                  60

Gln Ala Glu Ser Ile Gly Val Val Ser Ile Lys Gly Val Cys Ser Asn
 65                  70                  75                  80

Arg Tyr Leu Ala Met Asn Glu Asp Cys Arg Leu Phe Gly Leu Lys Tyr
                 85                  90                  95

Pro Thr Asp Glu Cys Phe Phe His Glu Arg Leu Glu Ser Asn Asn Tyr
                100                 105                 110

Asn Thr Tyr Arg Ser Lys Lys Tyr Ser Asp Trp Tyr Val Ala Leu Lys
                115                 120                 125

Arg Thr Gly Gln Tyr Lys Pro Gly Pro Lys Thr Gly Leu Gly Gln Lys
        130                 135                 140

Ala Ile Leu Phe Leu Pro Met Ser Ala Lys Ser
145                 150                 155

<210> SEQ ID NO 163
<211> LENGTH: 155
<212> TYPE: PRT
<213> ORGANISM: Tetraodon nigroviridis

<400> SEQUENCE: 163

Met Ala Thr Gly Gly Ile Thr Thr Leu Pro Ser Thr Pro Glu Asp Gly
 1               5                  10                  15

Gly Ser Ser Gly Phe Pro Pro Gly Ser Phe Lys Asp Pro Lys Arg Leu
                 20                  25                  30

Tyr Cys Lys Asn Gly Gly Phe Phe Leu Arg Ile Lys Ser Asp Gly Val
                 35                  40                  45

Val Asp Gly Ile Arg Glu Lys Ser Asp Pro His Ile Lys Leu Gln Leu
 50                  55                  60
```

```
Gln Ala Thr Ser Val Gly Glu Val Val Ile Lys Gly Val Cys Ala Asn
 65                  70                  75                  80

Arg Tyr Leu Ala Met Asn Arg Asp Gly Arg Leu Phe Gly Thr Lys Arg
                 85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Thr Met Phe Val Gly Leu Thr
            115                 120                 125

Arg Thr Gly Gln Tyr Lys Ser Gly Ser Lys Thr Gly Pro Gly Gln Lys
        130                 135                 140

Ala Ile Leu Phe Leu Pro Met Ser Ala Lys Cys
145                 150                 155

<210> SEQ ID NO 164
<211> LENGTH: 155
<212> TYPE: PRT
<213> ORGANISM: Gasterosteus aculeatus

<400> SEQUENCE: 164

Met Ala Thr Ala Gly Phe Ala Thr Leu Pro Ser Thr Pro Glu Asp Gly
  1               5                  10                  15

Gly Ser Gly Gly Phe Thr Pro Gly Gly Phe Lys Asp Pro Lys Arg Leu
                 20                  25                  30

Tyr Cys Lys Asn Gly Gly Phe Phe Leu Arg Ile Arg Ser Asp Gly Gly
             35                  40                  45

Val Asp Gly Ile Arg Glu Lys Ser Asp Ala His Ile Lys Leu Gln Ile
         50                  55                  60

Gln Ala Thr Ser Val Gly Glu Val Val Ile Lys Gly Val Cys Ala Asn
 65                  70                  75                  80

Arg Tyr Leu Ala Met Asn Arg Asp Gly Arg Leu Phe Gly Val Arg Arg
                 85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Gly Met Tyr Val Ala Leu Lys
            115                 120                 125

Arg Thr Gly Gln Tyr Lys Ser Gly Ser Lys Thr Gly Pro Gly Gln Lys
        130                 135                 140

Ala Ile Leu Phe Leu Pro Met Ser Ala Lys Cys
145                 150                 155

<210> SEQ ID NO 165
<211> LENGTH: 155
<212> TYPE: PRT
<213> ORGANISM: Takifugu rubripes

<400> SEQUENCE: 165

Met Ala Thr Gly Gly Ile Thr Thr Leu Pro Ser Thr Pro Glu Asp Gly
  1               5                  10                  15

Gly Ser Gly Gly Phe Pro Pro Gly Ser Phe Lys Asp Pro Lys Arg Leu
                 20                  25                  30

Tyr Cys Lys Asn Gly Gly Phe Phe Leu Arg Ile Arg Ser Asp Gly Ala
             35                  40                  45

Val Asp Gly Thr Arg Glu Lys Thr Asp Pro His Ile Lys Leu Gln Leu
         50                  55                  60

Gln Ala Thr Ser Val Gly Glu Val Val Ile Lys Gly Val Cys Ala Asn
 65                  70                  75                  80
```

Arg Tyr Leu Ala Met Asn Arg Asp Gly Arg Leu Phe Gly Met Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Asn Met Phe Val Gly Leu Thr
            115                 120                 125

Arg Thr Gly Asn Tyr Lys Ser Gly Thr Lys Thr Gly Pro Cys Gln Lys
        130                 135                 140

Ala Ile Leu Phe Leu Pro Met Ser Ala Lys Tyr
145                 150                 155

<210> SEQ ID NO 166
<211> LENGTH: 155
<212> TYPE: PRT
<213> ORGANISM: Oncorhynchus mykiss

<400> SEQUENCE: 166

Met Ala Thr Gly Glu Ile Thr Thr Leu Pro Ala Thr Pro Glu Asp Gly
1               5                   10                  15

Gly Ser Gly Gly Phe Leu Pro Gly Asn Phe Lys Glu Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Asp Lys Asn Asp Pro His Asn Lys Leu Gln Leu
    50                  55                  60

Gln Ala Thr Ser Val Gly Glu Val Val Ile Lys Gly Val Ser Ala Asn
65                  70                  75                  80

Arg Tyr Leu Ala Met Asn Ala Asp Gly Arg Leu Phe Gly Pro Arg Arg
                85                  90                  95

Thr Thr Asp Glu Cys Tyr Phe Met Glu Arg Leu Glu Ser Asn Asn Tyr
            100                 105                 110

Asn Thr Tyr Arg Ser Arg Lys Tyr Pro Glu Met Tyr Val Ala Leu Lys
            115                 120                 125

Arg Thr Gly Gln Tyr Lys Ser Gly Ser Lys Thr Gly Pro Gly Gln Lys
        130                 135                 140

Ala Ile Leu Phe Leu Pro Met Ser Ala Arg Arg
145                 150                 155

<210> SEQ ID NO 167
<211> LENGTH: 150
<212> TYPE: PRT
<213> ORGANISM: Salmo salar

<400> SEQUENCE: 167

Met Ala Thr Gly Glu Ile Thr Thr Leu Pro Ala Thr Pro Glu Asp Gly
1               5                   10                  15

Gly Ser Gly Gly Phe Pro Pro Gly Asn Phe Lys Asp Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Glu Lys Asn Asp Pro His Lys Gln Pro Gln Phe
    50                  55                  60

Val Arg Ala Trp Thr Leu Gln Gly Val Lys Arg Ser Thr Gly Met Leu
65                  70                  75                  80

Ala His Val Asp Ser Asn Ala Ser His Asn Cys Val Lys Val Ala Gly
                85                  90                  95

```
Cys Ser Leu Gly Glu Phe Gly Ser Met Ser Asn Arg Pro His Asn Arg
                100                 105                 110

Arg Pro Arg Val Ala Thr Pro Ala Gln Asp Leu His Ile Arg Leu Leu
            115                 120                 125

His Leu Arg Asp Arg Leu Lys Pro Ala Thr Arg Thr Ala Asp Lys Thr
130                 135                 140

Glu Glu Tyr Phe Cys Leu
145             150

<210> SEQ ID NO 168
<211> LENGTH: 154
<212> TYPE: PRT
<213> ORGANISM: Danio rerio

<400> SEQUENCE: 168

Met Ala Thr Gly Gly Ile Thr Thr Leu Pro Ala Ala Pro Asp Ala Glu
1               5                   10                  15

Asn Ser Ser Phe Pro Ala Gly Ser Phe Arg Asp Pro Lys Arg Leu Tyr
            20                  25                  30

Cys Lys Asn Gly Gly Phe Phe Leu Arg Ile Asn Ala Asp Gly Arg Val
        35                  40                  45

Asp Gly Ala Arg Asp Lys Ser Asp Pro His Ile Arg Leu Gln Leu Gln
    50                  55                  60

Ala Thr Ala Val Gly Glu Val Leu Ile Lys Gly Ile Cys Thr Asn Arg
65                  70                  75                  80

Phe Leu Ala Met Asn Ala Asp Gly Arg Leu Phe Gly Thr Lys Arg Thr
                85                  90                  95

Thr Asp Glu Cys Tyr Phe Leu Glu Arg Leu Glu Ser Asn Asn Tyr Asn
            100                 105                 110

Thr Tyr Arg Ser Arg Lys Tyr Pro Asp Trp Tyr Val Ala Leu Lys Arg
        115                 120                 125

Thr Gly Gln Tyr Lys Ser Gly Ser Lys Thr Ser Pro Gly Gln Lys Ala
    130                 135                 140

Ile Leu Phe Leu Pro Met Ser Ala Lys Cys
145                 150

<210> SEQ ID NO 169
<211> LENGTH: 155
<212> TYPE: PRT
<213> ORGANISM: Oreochromis niloticus

<400> SEQUENCE: 169

Met Ala Thr Gly Gly Ile Thr Thr Leu Pro Ala Thr Pro Glu Asp Gly
1               5                   10                  15

Gly Ser Ser Gly Phe Pro Pro Gly Asn Phe Lys Asp Pro Lys Arg Leu
            20                  25                  30

Tyr Cys Lys Asn Gly Gly Phe Phe Leu Arg Ile Lys Ser Asp Gly Gly
        35                  40                  45

Val Asp Gly Ile Arg Glu Lys Asn Asp Pro His Ile Lys Leu Gln Leu
    50                  55                  60

Gln Ala Thr Ser Val Gly Glu Val Val Ile Lys Gly Ile Cys Ala Asn
65                  70                  75                  80

Arg Tyr Leu Ala Met Asn Arg Asp Gly Arg Leu Phe Gly Ala Arg Arg
                85                  90                  95

Ala Thr Asp Glu Cys Tyr Phe Leu Glu Arg Leu Glu Ser Asn Asn Tyr
            100                 105                 110
```

Asn Thr Tyr Arg Ser Arg Lys Tyr Pro Asn Met Tyr Val Ala Leu Lys
            115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 170
<211> LENGTH: 155
<212> TYPE: PRT
<213> ORGANISM: Oryzias latipes

<400> SEQUENCE: 170

Met Ala Thr Gly Glu Ile Thr Thr Leu Pro Ser Pro Ala Glu Asn Ser
1               5                   10                  15

Arg Ser Asp Gly Phe Pro Pro Gly Asn Tyr Lys Asp Pro Lys Arg Leu
            20                  25                  30

Tyr Cys Lys Asn Gly Gly Leu Phe Leu Arg Ile Lys Pro Asp Gly Gly
        35                  40                  45

Val Asp Gly Ile Arg Glu Lys Lys Asp Pro His Val Lys Leu Arg Leu
 50                  55                  60

Gln Ala Thr Ser Ala Gly Glu Val Val Ile Lys Gly Val Cys Ser Asn
65                  70                  75                  80

Arg Tyr Leu Ala Met His Gly Asp Gly Arg Leu Phe Gly Val Arg Gln
                85                  90                  95

Ala Thr Glu Glu Cys Tyr Phe Leu Glu Arg Leu Glu Ser Asn Asn Tyr
            100                 105                 110

Asn Thr Tyr Arg Ser Lys Lys Tyr Pro Asn Met Tyr Val Ala Leu Lys
            115                 120                 125

Arg Thr Gly Gln Tyr Lys Pro Gly Asn Lys Thr Gly Pro Gly Gln Lys
    130                 135                 140

Ala Ile Leu Phe Leu Pro Met Ser Ala Lys Tyr
145                 150                 155

<210> SEQ ID NO 171
<211> LENGTH: 468
<212> TYPE: DNA
<213> ORGANISM: Homo sapiens

<400> SEQUENCE: 171
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagaggagg gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468

<210> SEQ ID NO 172
<211> LENGTH: 468
<212> TYPE: DNA
<213> ORGANISM: Gorilla

<400> SEQUENCE: 172

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
cgttaccttg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga                468

<210> SEQ ID NO 173
<211> LENGTH: 468
<212> TYPE: DNA
<213> ORGANISM: Sumatran orangutan

<400> SEQUENCE: 173
atggcagccg ggagcatcac cacgctgccc gccttgcccg aggatggcgg cagcggcgcc    60
ttcccgccgg gccacttcaa ggaccccaag cggctgtact gcaaaaacgg gggcttcttc   120
ctgcgcatcc accccgacgg ccgagttgac ggggtccgag agaagagcga ccctcacatc   180
aaactacaac ttcaagcaga agaaagagga gttgtgtcta tcaaaggagt gtgtgctaac   240
cgctaccttg ctatgaagga agatggaaga ttactggctt ctaaatgtgt tacggatgag   300
tgtttctttt ttgaacgatt ggaatctaat aactacaata cttaccggtc aaggaaatac   360
accagttggt atgtggcact gaaacgaact gggcagtata aacttggatc caaaacagga   420
cctgggcaga aagctatact ttttcttcca atgtctgcta agagctga                468

<210> SEQ ID NO 174
<211> LENGTH: 468
<212> TYPE: DNA
<213> ORGANISM: Rhesus monkey

<400> SEQUENCE: 174
atggcagccg ggagcatcac cacgctgccc gccttgcccg aggatggcgg cagcggcgcc    60
ttcccgcctg gccacttcaa ggaccccaag cggctgtact gcaaaaacgg gggcttcttc   120
ctgcgcattc accccgacgg ccgagttgac ggggtccggg agaagagcga ccgtcacatc   180
aaattacaac ttcaagcaga agagagagga gttgtgtcta tcaaaggagt gtgtgctaac   240
cgttaccttg ctatgaagga agatggaaga ttactggctt ctaaatgtgt tacagatgag   300
tgtttctttt ttgaacgatt ggaatctaat aactacaata cttaccggtc aaggaaatac   360
accagttggt atgtggcact gaaacgaact gggcaatata aacttggatc caaaacagga   420
cctgggcaga aagctatact ttttcttcca atgtctgcta agagctga                468

<210> SEQ ID NO 175
<211> LENGTH: 468
<212> TYPE: DNA
<213> ORGANISM: Chimpanzee

<400> SEQUENCE: 175
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc   120
ctgcgcatcc accccgacgg ccgagttgac ggggtccggg agaagagcga ccctcacatc   180
aagctacaac ttcaagcaga agagagagga gttgtgtcta tcaaaggagt gtgtgctaac   240
```

```
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                468
```

<210> SEQ ID NO 176
<211> LENGTH: 468
<212> TYPE: DNA
<213> ORGANISM: Pygmy chimpanzee

<400> SEQUENCE: 176

```
atggcagccg ggagcatcac cacgctgccc gccttgcccg aggatggcgg cagcggcgcc     60
ttcccgcccg gccacttcaa ggaccccaag cggctgtact gcaaaaacgg gggcttcttc    120
ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
cctgggcaga aagctatact ttttcttcca atgtctgcta agagctga                468
```

<210> SEQ ID NO 177
<211> LENGTH: 468
<212> TYPE: DNA
<213> ORGANISM: Bolivian squirrel monkey

<400> SEQUENCE: 177

```
atggcagccg ggagcatcac cacgctgccc gccctgcccg aagacggcgg cagcggcgcc     60
ttcccgcccg gccacttcaa agaccccaag cggctgtact gcaaaaacgg gggcttcttc    120
ctgcgaatcc accccgacgg ccgagtggac ggggtccggg agaagagcga ccctcacatc    180
aaactacaac ttcaagcaga agagagagga gttgtatcta tcaaaggagt gtgtgctaac    240
cgttaccttg ctatgaagga agatggaaga ttactggctt ctaaatgtgt tacggacgag    300
tgtttctttt ttgaacgatt ggaatctaat aactacaata cttaccgatc aaggaaatac    360
accagttggt atgtggcact gaaacgaact gggcagtata aacttggatc caaaacagga    420
cctgggcaga aagctatact ttttcttcca atgtctgcta agagctga                468
```

<210> SEQ ID NO 178
<211> LENGTH: 468
<212> TYPE: DNA
<213> ORGANISM: Northern white-cheeked gibbon

<400> SEQUENCE: 178

```
atggcagccg ggagcatcac cacgctgccc gccttgccgg aggatggcgg cagcggcgcc     60
ttcccgcccg gccacttcaa ggaccccaag cggctgtact gcaaaaacgg gggtttcttc    120
ctgcgcatcc accccgacgg tcgagttgac ggggtccggg agaagagcga ccctcacatc    180
aaactacaac ttcaagcaga agagagagga gttgtgtcta tcaaaggagt gtgtgctaac    240
cgttaccttg ctatgaagga agatggaaga ttactggctt ctaaatgtgt tacggatgag    300
tgtttctttt ttgaacgatt ggaatctaat aactacaata cttaccggtc aaggaaatac    360
accagttggt atgtggcact gaaacgaact gggcagtata aacttggatc caaaacagga    420
```
cctgggcaga aagctatact ttttcttcca atgtctgcta agagctga 468

<210> SEQ ID NO 179
<211> LENGTH: 468
<212> TYPE: DNA
<213> ORGANISM: Horse

<400> SEQUENCE: 179
atggcagccg ggagcatcac cacgctgccc gccctgcccg aggacggcgg cagcggcgcc 60
ttcccgcccg gccacttcaa ggaccccaag cggctctact gcaaaaacgg gggcttcttc 120
ctgcgcatcc accccgacgg ccgagtggac ggggtccggg agaagagcga ccctcacatc 180
aaactacaac ttcaagcaga agagagaggg gttgtgtcta tcaaaggagt gtgtgcgaac 240
cgttatcttg ctatgaagga agatggaagg ttactggctt ctaaatgtgt tacggacgag 300
tgtttctttt ttgaacgatt ggaatctaat aactacaata cttaccggtc aaggaaatac 360
tccagttggt atgtggccct gaaacgaacg gggcagtata aacttggacc caaaacagga 420
cctggacaga aagctatact ttttcttcca atgtctgcta agagctga 468

<210> SEQ ID NO 180
<211> LENGTH: 468
<212> TYPE: DNA
<213> ORGANISM: Cattle

<400> SEQUENCE: 180
atggccgccg ggagcatcac cacgctgcca gccctgccgg aggacggcgg cagcggcgct 60
ttcccgccgg ccacttcaa ggaccccaag cggctgtact gcaagaacgg gggcttcttc 120
ctgcgcatcc accccgacgg ccgagtggac ggggtccgcg agaagagcga cccacacatc 180
aaactacaac ttcaagcaga agagagaggg gttgtgtcta tcaaaggagt gtgtgcaaac 240
cgttaccttg ctatgaaaga agatggaaga ttactagctt ctaaatgtgt tacagacgag 300
tgtttctttt ttgaacgatt ggagtctaat aactacaata cttaccggtc aaggaaatac 360
tccagttggt atgtggcact gaaacgaact gggcagtata aacttggacc caaaacagga 420
cctgggcaga aagctatact ttttcttcca atgtctgcta agagctga 468

<210> SEQ ID NO 181
<211> LENGTH: 468
<212> TYPE: DNA
<213> ORGANISM: Olive baboon

<400> SEQUENCE: 181
atggcagccg ggagcatcac cacgctgccc gccttgcccg aggatggcgg cagcggcgcc 60
ttcccgcccg gccacttcaa ggaccccaag cggctgtact gcaaaaacgg gggcttcttc 120
ctgcgcattc accccgacgg ccgagttgac ggggtccggg agaagagcga ccctcacatc 180
aaattacaac ttcaagcaga agagagagga gttgtgtcta tcaaaggagt gtgtgctaac 240
cgttaccttg ctatgaagga agatggaaga ttactggctt ctaaatgtgt tacggatgag 300
tgtttctttt ttgaacgatt ggaatctaat aactacaata cttaccggtc aaggaaatac 360
accagttggt atgtggcact gaaacgaact gggcagtata aacttggatc caaaacagga 420
cctgggcaga aagctatact ttttcttcca atgtctgcta agagctga 468

<210> SEQ ID NO 182
<211> LENGTH: 468
<212> TYPE: DNA
<213> ORGANISM: Alpaca

<400> SEQUENCE: 182

```
atggcagctg ggagcatcac cacgctgccc gccctgccgg aggacggcgg cagcggcgcc    60
ttcccgcccg gccacttcaa ggaccccaag cggttgtact gcaaaaacgg gggcttcttc   120
ctgcgcatcc accccgacgg ccgagtggac ggggtccggg agaagagcga ccctcacatc   180
aaactacaac ttcaagcaga agagagaggg gtcgtgtcta tcaaaggagt gtgtgcaaac   240
cgttaccttg ctatgaagga agatggaaga ttactggctt ctaaatgtgt cacagacgag   300
tgtttcttt ttgaacgatt ggaatctaat aactacaata cttaccggtc aaggaaatac   360
tccagttggt atgtggcact gaaacgaact gggcagtaca acttggacc caaaacagga   420
cctgggcaga aagctatact tttccttcca atgtctgcta agagctga              468
```

<210> SEQ ID NO 183
<211> LENGTH: 468
<212> TYPE: DNA
<213> ORGANISM: Sheep

<400> SEQUENCE: 183

```
atggccgccg ggagcatcac cacgctgcca gccctgccgg aggacggcgg cagcagcgct    60
ttcccgcccg ccactttaa ggaccccaag cggctgtact gcaagaacgg gggcttcttc   120
ctgcgcatcc accccgacgg ccgagtggac ggggtccgcg agaagagcga ccctcacatc   180
aaactacaac ttcaagcaga agagagaggg gttgtgtcta tcaaaggagt gtgtgcaaac   240
cgttaccttg ctatgaaaga agatggaaga ttactagctt ctaaatgtgt tacagacgag   300
tgtttcttt ttgaacgatt ggagtctaat aactacaata cttaccggtc aaggaaatac   360
tccagttggt atgtggcact gaaacgaact gggcagtata acttggacc caaaacagga   420
cctgggcaga aagctatact ttttcttcca atgtctgcta agagctga              468
```

<210> SEQ ID NO 184
<211> LENGTH: 325
<212> TYPE: DNA
<213> ORGANISM: Western roe deer

<400> SEQUENCE: 184

```
gcgcatccac cccgacggcc gagtggacgg ggtccgcgag aagagtgacc ctcacatcaa    60
actacaactt caagcagaag agagggggt tgtgtctatc aaaggagtgt gtgcgaaccg   120
ttatcttgct atgaaagaag acggaagatt attggcttca aatgtgtta cagacgaatg   180
tttcttttt gaacgattgg agtctaataa ctacaatact taccggtcaa ggaaatactc   240
cagttggtat gtggcactga acgaactgg gcagtataaa cttggaccca aaacaggacc   300
tgggcagaaa gctatacttt ttctt                                        325
```

<210> SEQ ID NO 185
<211> LENGTH: 288
<212> TYPE: DNA
<213> ORGANISM: Elephant

<400> SEQUENCE: 185

```
gttaaactac agcttcaagc agaagagaga ggtgttgtgt ctatcaaagg agtgtgtgcc    60
aaccgttatc tggctatgaa ggaagatgga agattgctgg cttctagatg tgtgacagat   120
gaatgtttct tctttgaacg actgaatct aataactaca atacttaccg gtcaaggaaa   180
tacaccagtt ggtatgtggc actgaaacga acggggcagt ataaacttgg atccaaaaca   240
```

```
ggacctggac agaaagctat actttttctt cccatgtctg ctaagagc              288
```

<210> SEQ ID NO 186
<211> LENGTH: 361
<212> TYPE: DNA
<213> ORGANISM: Pig

<400> SEQUENCE: 186

```
gaacggggc ttcttcctgc gcatccaccc cgacggccga gtggatgggg tccgggagaa    60
gagcgaccct cacatcaaac tacaacttca agcagaagag agaggggttg tgtctatcaa   120
aggagtgtgt gcaaaccgtt atcttgctat gaaggaagat ggaagattac tggcttctaa   180
atgtgttaca gacgagtgtt tctttttga acgactggaa tctaataact acaatactta    240
ccggtcgagg aaatactcca gttggtatgt ggcactgaaa cgaactgggc agtataaact    300
tggacccaaa acaggacctg gcagaaaagc tatactttt cttccaatgt ctgctaagag     360
c                                                                   361
```

<210> SEQ ID NO 187
<211> LENGTH: 288
<212> TYPE: DNA
<213> ORGANISM: Panda

<400> SEQUENCE: 187

```
gtcaaactgc aacttcaagc ggaagagaga ggggttgtat ccatcaaagg agtatgtgca    60
aatcgctatc ttgccatgaa ggaagatgga agattactgg cttctaaatg tgttaccgat   120
gagtgtttct tttttgagcg actggaatct aataactaca atacttaccg gtcaaggaaa   180
tactccagtt ggtatgtggc actgaaacga actgggcagt ataaacttgg acccaaaaca    240
ggacctgggc agaaagctat acttttctt ccaatgtctg ctaagagc                  288
```

<210> SEQ ID NO 188
<211> LENGTH: 468
<212> TYPE: DNA
<213> ORGANISM: Sloth

<400> SEQUENCE: 188

```
atggcagccg ggagcatcac cacgctgccc gccctgcccg aggacggagg cagcggcgcc    60
ttaccgcccg ccacttcaa agatcccaag cggctctact gcaaaaacgg ggcttcttc    120
ctgcgtatcc atcccgacgg cagagtggac ggggtccggg agaagagcga ccccacatc    180
aaactacaac ttcaagcaga agagagaggg gttgtgtcta tcaaaggtgt gtgtgcaaac    240
cgatatcttg ctatgaagga agatggaaga ttacaggctt ctaaatgtgt aacggacgag    300
tgtttctttt ttgaacgatt ggaatctaat aactacaata cgtaccgatc aaggaaatac    360
tccagttggt atgtggcact gaaacgaact gggcaatata aacttggacc caaaacagga    420
cctgggcaga aagccatact ttttcttcca atgtctgcta agagctga                 468
```

<210> SEQ ID NO 189
<211> LENGTH: 468
<212> TYPE: DNA
<213> ORGANISM: Water buffalo

<400> SEQUENCE: 189

```
atggccgccg ggagcatcac cacgctgcca cccctgccgg aggacggcgg cagcggcgct    60
ttcccgcccg ccacttcaa ggaccccaag cggctgtact gcaagaacgg ggcttcttc    120
ctgcgcatcc accccgacgg ccgagtggac ggggtccgcg agaagagcga cccacacatc    180
```

```
aaactacaac ttcaagcaga agagagaggg gttgtgtcta tcaaggagt gtgtgcaaac    240 cgttaccttg ctatgaaaga agatggaaga ttactagctt ccaaatgtgt tacagacgag    300
tgtttctttt ttgaacgatt ggagtctagt aactacaata cttaccggtc aaggaaatac    360
tccagttggt atgtggcact gaaacgaact gggcagtata aacttggacc aaaacagga     420 cctgggcaga aagctatact ttttcttcca atgtctgcta agagctga                 468

<210> SEQ ID NO 190
<211> LENGTH: 468
<212> TYPE: DNA
<213> ORGANISM: Dog

<400> SEQUENCE: 190
atggcagccg ggagcatcac cacgctgccc gccctgccgg aggacggcgg cagcggcgcc     60
ttcccgcccg gccacttcaa ggaccccaag aggctgtact gcaaaaaagg gggcttcttc    120
ctgcggatcc accccgacgg ccgggtggac ggggtccggg agaagagcga tccccacgtc    180
aaattgcaac ttcaagcaga agagagaggc gttgtgtcca tcaaggagt atgtgcaaat     240 cgctatcttg ctatgaagga agatggaaga ttactggctt ctaaatgtgt tactgacgag    300
tgcttctttt ttgaacgatt ggaatctaat aactacaata cttaccggtc aaggaaatac    360
tccagttggt atgtggcact gaaacgaact gggcagtata aacttggacc aaaaacagga    420
cctgggcaga aagctatact ttttcttcca atgtctgcta agagctga                 468

<210> SEQ ID NO 191
<211> LENGTH: 465
<212> TYPE: DNA
<213> ORGANISM: Norway rat

<400> SEQUENCE: 191
atggctgccg gcagcatcac ttcgcttccc gcactgccgg aggacggcgg cggcgccttc     60
ccacccggcc acttcaagga tcccaagcgg ctctactgca gaacggcgg cttcttcctg    120 cgcatccatc cagacggccg cgtggacggc gtcggggaga gagcgaccc acacgtcaaa    180 ctacagctcc aagcagaaga gagaggagtt gtgtccatca agggagtgtg tgcgaaccgg    240
tacctggcta tgaaggaaga tggacggctg ctggcttcta agtgtgttac agaagagtgt    300 ttcttcttg aacgcctgga gtccaataac tacaacactt accggtcacg gaatactcc     360 agttggtatg tggcactgaa acgaactggg cagtataaac tcggatccaa acggggcct    420 ggacagaagg ccatactgtt tcttccaatg tctgctaaga gctga                    465

<210> SEQ ID NO 192
<211> LENGTH: 405
<212> TYPE: DNA
<213> ORGANISM: Naked mole-rat

<400> SEQUENCE: 192
ccacccggcc acttcaagga cccaaagcgg ctgtactgca aaaacggggg cttcttcctg     60
cgcatccacc ccgacggccg cgtggacggg gtccgggaga gagcgaccc tcacgtcaaa    120 ctacaacttc aagcagaaga gagaggagtt gtgtctatta agggagtgtg tgcgaaccgt    180
taccttgcta tgaaggaaga tggaagatta ctggcttcta aatgtgttac agatgagtgt    240
ttcttttttg aacgattgga atctaataac tacaatactt atcggtcaag gaatactcc     300 agttggtatg tggcactgaa acgaactgga caatataaac ttggatccaa aacaggaccg    360
```

```
gggcagaaag ctatacttttt tcttccaatg tctgctaaga gctga              405
```

<210> SEQ ID NO 193
<211> LENGTH: 468
<212> TYPE: DNA
<213> ORGANISM: Bushbaby

<400> SEQUENCE: 193

```
atggcagccg ggagcatcac cacgctgccc tccctgcccg aggacggcgg cagcgacgcc    60
tttccgcccg gccacttcaa ggaccccaag cgactgtact gcaaaaacgg gggcttcttc   120
ctgcgcatcc accccgacgg ccgagtggac ggggtccggg agaagagcga cccttacatc   180
aaactacaac ttcaagcaga agagaggagga gttgtgtcta tcaaaggagt gtgtgcgaac   240
cgttaccttg ctatgaagga agacggaaga ttgctggctt ctaaattgat tacagacgag   300
tgcttctttt ttgaacgact ggaatctaat aactacaata cttaccggtc aagaaaatac   360
tccagttggt atgtggcact gaaacgaact ggacagtata aacttggatc caaaacagga   420
cctgggcaga aagctatact ttttcttcca atgtctgcta agagctga               468
```

<210> SEQ ID NO 194
<211> LENGTH: 465
<212> TYPE: DNA
<213> ORGANISM: House mouse

<400> SEQUENCE: 194

```
atggctgcca gcggcatcac ctcgcttccc gcactgccgg aggacggcgg cgccgccttc    60
ccaccaggcc acttcaagga ccccaagcgg ctctactgca agaacggcgg cttcttcctg   120
cgcatccatc ccgacggccg cgtggatggc gtccgcgaga gagcgacccc acacgtcaaa   180
ctacaactcc aagcagaaga gaggagtt gtgtctatca agggagtgtg tgccaaccgg   240
taccttgcta tgaaggaaga tggacggctg ctggcttcta agtgtgttac agaagagtgt   300
ttcttctttg aacgactgga atctaataac tacaatactt accggtcacg gaaatactcc   360
agttggtatg tggcactgaa acgaactggg cagtataaac tcggatccaa aacgggacct   420
ggacagaagg ccatactgtt tcttccaatg tctgctaaga gctga                  465
```

<210> SEQ ID NO 195
<211> LENGTH: 432
<212> TYPE: DNA
<213> ORGANISM: Squirrel

<400> SEQUENCE: 195

```
ctgcccgagg acggcggcgg cggcgccttc ccgcccggcc actttaagga ccccaagcgg    60
ctctactgca aaaacggagg cttcttcctg cgcatccacc ccgacggccg agtggacggg   120
gtccgggaga agagcgaccc ccacatcaag ctccagcttc aagccgaaga ccgagggggtt   180
gtgtccatca agggagtgtg tgcaaaccga tacctggcca tgaaggagga cgggaggctc   240
ctggcttcta aatgtgttac ggacgagtgt ttcttttttg aacgactgga atcaaataac   300
tacaatactt accggtcaag gaaatactcc agttggtatg tggccctgaa acgaacaggg   360
cagtataaac ttggatccaa aacaggacct gggcagaaag ctatactttt tcttccaatg   420
tctgctaaga gc                                                      432
```

<210> SEQ ID NO 196
<211> LENGTH: 318
<212> TYPE: DNA
<213> ORGANISM: Domestic cat

```
<400> SEQUENCE: 196
ccacttcaag accccaagc gtctgtactg caaaaacggg ggcttcttcc tgcgcatcca      60
ccccgacggc cgagtggatg gggtccggga agagcgac cctcacatca aactgcaact     120
tcaggcagaa gagagagggg ttgtgtccat caaggagtc tgtgcaaacc gctatcttgc    180
catgaaggaa gatggaagat tactggcttc taaatgtgtt acggacgagt gtttctttttt  240 tgaacgattg gaatctaata actacaatac ttatcggtca aggaaatact ccagctggta   300
tgtggcactg aaacgaac                                                 318

<210> SEQ ID NO 197
<211> LENGTH: 288
<212> TYPE: DNA
<213> ORGANISM: Guinea pig

<400> SEQUENCE: 197 gttaaaactac aacttcaagc cgaagacaga ggagttgtgt ctatcaaggg agtctgtgcg    60
aaccgttacc ttgctatgaa ggaagacgga agattattgg cttccaaatg tgttacagat   120
gaatgtttct tttttgaacg actggaatct aataactaca acacttaccg gtcaaggaaa    180
tactccagtt ggtatgtggc actgaaacga actggacaat ataaacttgg gtccaaaaca    240
ggaccagggc agaaagccat acttttttctt ccaatgtctg cgaagagc              288

<210> SEQ ID NO 198
<211> LENGTH: 471
<212> TYPE: DNA
<213> ORGANISM: Tasmanian devil

<400> SEQUENCE: 198
atggccgcgg gcagcatcac cacgttgccg gccctggccg gggatggagc cagcggggc     60 gcctttcccc cgggccactt ccaggacccc aagcggctgt actgcaagaa cggaggcttc    120
ttcttgcgca tccatcccga cggtcacgtg gacggcatcc gcgagaagag cgatccgcac    180
attaaacttc agcttcaggc agaagagaga ggagtagtgt ctattaaagg agtttgtgcc    240
aaccgctatc ttgccatgaa gaggatggca agattactgg ctctgaaatg tgtgactgaa    300
gagtgtttct tctttgaacg tctagagtcc aacaattaca cacttatcg ctcaaggaaa     360 tactccaatt ggtatgtggc attgaaacgc acaggccagt ataagcttgg atccaagact    420
ggaccagggc agaaagccat cctttttcctt cccatgtctg ctaagagctg a             471

<210> SEQ ID NO 199
<211> LENGTH: 471
<212> TYPE: DNA
<213> ORGANISM: Gray short-tailed opossum

<400> SEQUENCE: 199
atggccgcag gcagcatcac cacgctgcca gccctgtccg gggacggagg cggcggggc     60 gcctttcccc cgggccactt caaggacccc aagcggctgt actgcaagaa cggaggcttc   120
ttcctgcgca tccaccccga cggccgtgtg gacggcatcc gcgagaagag cgacccgaac   180
attaaactac aacttcaggc agaagagaga ggagtggtgt ctattaaagg agtatgtgcc   240
aatcgctatc ttgccatgaa ggaagatgga agattattgg ctttgaaata tgtgaccgaa   300
gagtgtttct tttcgaacg cttggagtcc aacaactaca cacttatcg ctcgaggaaa    360 tattccaatt ggtacgtggc actgaaacga acggggcagt acaagcttgg atccaagact   420
```

```
ggcccggggc agaaagccat ccttttcctc cccatgtctg ctaagagctg a        471
```

<210> SEQ ID NO 200
<211> LENGTH: 468
<212> TYPE: DNA
<213> ORGANISM: Rabbit

<400> SEQUENCE: 200

```
atggcagccg agagcatcac cacgctgccc gccctgccgg aggatggagg cagcggcgcc    60
ttcccgcccg gccacttcaa ggaccccaag cggctgtact gcaaaaacgg gggtttcttc   120
ctgcgtatcc accccgacgg ccgcgtggac ggggtccggg agaagagcga cccacacatc   180
aaattacaac ttcaagcaga agagagagga gttgtatcca tcaaaggtgt gtgtgcaaac   240
cgttaccttg ctatgaagga agatggaaga ctgctggctt ctaaatgtgt tacagacgag   300
tgcttctttt ttgaacgact ggagtctaat aactacaata cttaccggtc aaggaaatat   360
tccagctggt atgtggcact gaaacgaact gggcagtata aacttggatc caaaacagga   420
cctgggcaga aggctatact ttttcttcca atgtctgcta gagctga               468
```

<210> SEQ ID NO 201
<211> LENGTH: 375
<212> TYPE: DNA
<213> ORGANISM: Turkey

<400> SEQUENCE: 201

```
cggctctact gtaagaacgg cggcttcttc ctgcgcatca atcccgacgg cagagtggac    60
ggcgtccgcg agaagagcga tccgcacatc aaactgcagc ttcaggcaga agaaagagga   120
gtggtatcaa tcaaaggtgt aagtgcaaac cgctttctgg ctatgaagga ggatggcaga   180
ttgctggcac tgaaatgtgc aacagaagaa tgtttctttt tgagcgtttt ggaatctaat   240
aattataaca cttaccggtc acggaagtac tctgattggt atgtggcact gaaaagaact   300
ggacagtaca agcccggacc aaaaactgga cctggacaga agctatcct ttttcttcca   360
atgtctgcta aaagc                                                    375
```

<210> SEQ ID NO 202
<211> LENGTH: 477
<212> TYPE: DNA
<213> ORGANISM: Gallus gallus

<400> SEQUENCE: 202

```
atggcggcgg gggcggcggg gagcatcacc acgctgccgg cgctgcccga cgacgggggc    60
ggcggcgctt ttccccccgg gcacttcaag gaccccaagc ggctctactg caagaacggc   120
ggcttcttcc tgcgcatcaa ccccgacggc agggtggacg gcgtccgcga gaagagcgat   180
ccgcacatca aactgcagct tcaagcagaa gaaagaggag tagtatcaat caaaggcgta   240
agtgcaaacc gctttctggc tatgaaggag gatggcagat tgctggcact gaaatgtgca   300
acagaggaat gtttctttt cgagcgcttg gaatctaata actataacac ttaccggtca   360
cggaagtact ctgattggta tgtggcactg aaaaggactg acagtacaa gcccggacca   420
aaaactggac ctggacagaa agctatcctt tttcttccaa tgtctgctaa agctga      477
```

<210> SEQ ID NO 203
<211> LENGTH: 462
<212> TYPE: DNA
<213> ORGANISM: Zebra finch

<400> SEQUENCE: 203

```
atggcggcgg cggggggcat cgctacgctg cccgacgacg gcggcagcgg cgccttccc    60 ccggggcact tcaaggaccc caagcgcctg tactgcaaga cggcggctt cttcctgcgc   120 atcaaccccg acgggaaggt ggacggcgtc cgcgagaaga gcgacccgca catcaagctg   180
cagcttcagg cggaggaacg aggagtggtg tccatcaaag tgtcagtgc caatcgcttc    240 ctggccatga agaggatgg cagattgctg gccttgaaat atgcaacaga agaatgtttc    300
ttttttgaac gtttggaatc caataactat aacacttacc ggtcacgaaa atactcggat   360
tggtatgtgg cactgaaaag aactggacag tacaaacctg gaccaaaaac tggacctgga   420
cagaaagcta tccttttcct tcctatgtct gctaaaagct ga                      462

<210> SEQ ID NO 204
<211> LENGTH: 468
<212> TYPE: DNA
<213> ORGANISM: Japanese firebelly newt

<400> SEQUENCE: 204
atggctgctg ggagcatcac cagtctccct gccctacccg aggacgggaa tggcggcacc    60
ttcacacccg gcggattcaa agagccgaag aggctgtact gcaagaacgg ggcttctttt   120
ctccggatca actccgacgg caaggtggac ggagcccggg agaagagcga ctcctacatt   180
aaactgcagc ttcaagcaga agagcgcggt gtggtgtcca tcaagggagt atgtgcaaac   240
cgctatctcg ctatgaagga tgatggcagg ctgatggcgc tgaaatggat aaccgatgaa   300
tgcttctttt tcgagcgact ggagtccaac aactataaca cgtatcgatc acggaaatat   360
tccgattggt atgtggcgct gaaaagaact gggcaataca aaaatggatc aaaaaccgga   420
gcaggacaga aagcaatcct ttttctaccc atgtcggcca agagttga                468

<210> SEQ ID NO 205
<211> LENGTH: 468
<212> TYPE: DNA
<213> ORGANISM: African clawed frog

<400> SEQUENCE: 205
atggcggcag ggagcatcac aactctgcca actgaatccg aggatggggg aaacactcct    60
ttttcaccag ggagttttaa agaccccaag aggctctact gcaagaacgg ggcttcttc   120 ctcaggataa actcagacgg gagagtggac gggtcaaggg acaaaagtga ctcgcacata   180
aaattacagc tacaagctgt agagcgggga gtggtatcaa taagggaat cactgcaaat    240 cgctaccttg ccatgaagga agatgggaga ttaacatcgc tgaggtgtat aacagatgaa   300
tgcttctttt ttgaacgact ggaagctaat aactacaaca cttaccggtc tcggaaatac   360
agcagctggt atgtggcact aaagcgaacc gggcagtaca aaaatggatc gagcactgga   420
ccgggacaaa aagctatttt atttctccca atgtccgcaa agagctga                468

<210> SEQ ID NO 206
<211> LENGTH: 471
<212> TYPE: DNA
<213> ORGANISM: White-eared opossum

<400> SEQUENCE: 206
atggcagcag gcagcatcac cacattgccg gccctgtccg ggacggagg cggcggggga    60 gcctttcctc caggccactt caaggacccc aagcggctgt actgcaagaa cggaggcttc   120
ttcctgcgca tccaccccga cggccgcgtg gacggcatcc gcgagaagag cgacccgaac   180
```

```
attaaactac aacttcaggc agaagagaga ggagtagtgt ctattaaagg agtatgtgcc    240
aaccgatatc ttgccatgaa ggaggatggc agattattgg ctttgaaata tgtgaccgaa    300
gagtgtttct ttttgaacg tttggagtcc aacaactaca acacttatcg ctcaagaaaa     360
tattccaatt ggtatgtggc actgaaacga acggggcagt ataagcttgg atccaagact    420
ggcccggggc agaaagccat cctttctcc ccatgtctgc taagatgctg a               471

<210> SEQ ID NO 207
<211> LENGTH: 288
<212> TYPE: DNA
<213> ORGANISM: Microbat

<400> SEQUENCE: 207
gtcaaactcc aacttcaagc agaagagaga ggggtcgtgt ctatcaaagg agtgtgtgcc    60
aaccgctatc tcgctatgaa ggaggacggc cggttacagg cttctaaatg tgttacggat   120
gagtgtttct ttttgaacg gttggaatcc aataactaca acacttaccg gtcaagaaag    180
tactccagtt ggtatgtggc attgaagcgg aatgggcagt ataaacttgg acccaaaaca   240
ggacctggcc agaaagccat acttttctct cccatgtctg ctaagagc                288

<210> SEQ ID NO 208
<211> LENGTH: 420
<212> TYPE: DNA
<213> ORGANISM: Anole lizard

<400> SEQUENCE: 208
gcggcggcgg cctctttccc cccgggcccc ttcaaggacc ccaagcgcct ctactgcaag    60
aacgggggct tcttcctgcg gatcaacccc gacggcggcg tggacggcgt ccgagagaag   120
agcgacccca acatcaaatt gctgctccag gcagaggaga gaggtgtagt gtccatcaaa    180
ggtgtatgcg caaaccgttt cctggctatg aatgaagacg gtcgattgtt agcactgaaa   240
tacgtaacag atgaatgctt ctttttgaa cgcttggaat ctaataatta caatacttat    300
cggtctcgta aataccgtga ttggtacatt gcactgaaac gaactggtca gtacaaactt   360
ggaccaaaaa ctggacgagg ccagaaagct atccttttcc ttccaatgtc tgccaaaagt   420

<210> SEQ ID NO 209
<211> LENGTH: 282
<212> TYPE: DNA
<213> ORGANISM: Armadillo

<400> SEQUENCE: 209
atggcagccg ggagcatcac cacgctgccc gctctgcccg aggacggcgg cagcggcgcc    60
ttcccgccgg gccacttcaa ggaccccaag cggctgtact gcaaaaacgg ggcttcttc    120 ctgcgcatcc atcccgacgg ccgagtggac ggggtccggg agaagagcga ccctaacatc   180
aaactacaac ttcaagcaga agagaggg gtcgtgtcta tcaaaggcgt gtgtgcgaac     240
cgttaccttg ctatgcggga agacggaaga ctccaggcgt ct                       282

<210> SEQ ID NO 210
<211> LENGTH: 567
<212> TYPE: DNA
<213> ORGANISM: Tree shrew

<400> SEQUENCE: 210
gcgggggtta gagctgagag ggaggaggca ccggggagcg gtgacagccg ggggaccgat    60
cccgccgcgc gttcgctcat caggaggccg gatgctgcag cgcgagaggc gcttcttgga   120
```

```
gccaggagcc gggttcaggg cagctccacc tcctggccag cctcgtcacg aaccgggatc    180
aagttgccgg acgactcagg tcaaggaatg ggcggctatc ctctggaccg cccgagccgg    240
agcacagggc gagggctggg cggtgccccg gaccctgccg taaaactaca gcttcaagcg    300
gaagagagag gggtcgtgtc tatcaaagga gtgtgtgcaa accgttacct ggccatgaag    360
gaggatgggc gactgctggc ttctaaatgt gttacagatg agtgtttctt ttttgaacga    420
ctggaatcta ataactacaa tacttaccgg tcccgaaagt actccagctg gtatgtggca    480
ctgaaacgaa ctgggcagta taaacttgga tccaaaacag gacctgggca gaaagctata    540 cttttcttc caatgtctgc taaaagc                                        567

<210> SEQ ID NO 211
<211> LENGTH: 465
<212> TYPE: DNA
<213> ORGANISM: Western clawed frog

<400> SEQUENCE: 211
atggcagcag gaagcatcac aaccctacca accgaatctg aggatggaaa cactcctttc     60
ccaccgggga actttaagga ccccaagagg ctctactgca agaatggggg ctacttcctc    120
aggattaact cagacgggag agtggacgga tcaagggata aaagtgactt acacataaaa    180
ttacagctac aagcagtaga gcggggagtg gtatcaataa agggaatcac tgcaaatcgc    240
taccttgcca tgaaggaaga tgggagatta acatcgctga agtgtataac agatgaatgc    300 ttctttatg aacgattgga agctaataac tacaacactt accggtctcg gaaaacaaac    360
agctggtatg tggcactaaa gcgaactggg cagtataaaa atggatcgac cactggacca    420
ggacaaaaag ctatttgtt tctcccaatg tcagcaaaaa gctga                    465

<210> SEQ ID NO 212
<211> LENGTH: 468
<212> TYPE: DNA
<213> ORGANISM: Coelacanth

<400> SEQUENCE: 212
atggctgcgg gaggaatcac taccctgccg gcggtacctg aggatggagg cagcagcacc     60
ttccctccag gaaacttcaa ggagcccaag agactttact gtaagaatgg aggctatttc    120
ttaaggataa accccgatgg aagagtggat ggaacaaggg agaaaaatga tcctatata    180 aaattacaac tgcaagctga atctatagga gtggtgtcga taagggagt ttgttcaaac    240 cgttacctag cgatgaatga agactgtaga cttttggat tgaaatatcc aacggatgaa    300
tgtttcttcc atgagaggct ggagtccaac aactacaata cttatcgttc aaagaagtat    360
tcggattggt atgtggcgct gaaacggact ggtcagtaca aacctgggcc aaaaactgga    420
ctgggacaaa aagcaatcct tttccttccg atgtctgcca agagttga                468

<210> SEQ ID NO 213
<211> LENGTH: 468
<212> TYPE: DNA
<213> ORGANISM: Spotted green pufferfish

<400> SEQUENCE: 213
atggccacgg gagggatcac gacgcttcca tccacacctg aagacggcgg cagcagcggc     60
tttcctcccg gcagcttcaa ggatcccaaa aggctctact gtaaaaacgg aggtttcttc    120
ctgaggatca agtccgacgg ggtcgtggac ggaatccggg agaagagtga cccccacata    180
```

| aagcttcagc tccaggcgac ctctgtgggg gaggtggtca tcaagggggt gtgcgctaac | 240 |
| cgctatctgg ccatgaacag agatggacgg ctgttcggaa cgaaacgagc cacggacgaa | 300 |
| tgccatttct tagagcggct tgagagcaac aactacaaca cttaccgctc caggaagtac | 360 |
| ccaaccatgt ttgtgggact gacgcggacg ggccagtaca agtctgggag caaaactgga | 420 |
| ccgggccaaa aggccatcct tttcttccg atgtccgcca aatgctaa | 468 |

<210> SEQ ID NO 214
<211> LENGTH: 468
<212> TYPE: DNA
<213> ORGANISM: Stickleback

<400> SEQUENCE: 214

| atggccacgg caggcttcgc gacgcttccc tccacgcccg aagacggcgg cagcggcggc | 60 |
| ttcaccccg ggggattcaa ggatcccaag aggctgtact gcaaaaacgg gggcttcttc | 120 |
| ttgaggatca ggtccgacgg aggtgtagat ggaatcaggg agaagagcga cgcccacata | 180 |
| aagctccaaa tccaggcgac gtcggtgggg gaggtggtca tcaaggagt ctgtgccaac | 240 |
| cgctatctgg ccatgaacag agacggccgg ctgttcggag tgagacgggc gacggacgaa | 300 |
| tgctacttcc tggagcggct ggagagtaac aactacaaca cctaccgctc caggaagtac | 360 |
| cccggcatgt acgtggctct gaagcggacc ggccagtaca agtccgggag caaaaccgga | 420 |
| cccggtcaaa aggccattct gttcctcccc atgtcggcta agtgctaa | 468 |

<210> SEQ ID NO 215
<211> LENGTH: 468
<212> TYPE: DNA
<213> ORGANISM: Fugu rubripes

<400> SEQUENCE: 215

| atggccacgg gagggatcac aacacttcca tccacacctg aagacggcgg cagcggcggt | 60 |
| tttcctcccg ggagcttcaa ggatcccaaa aggctgtact gtaaaaacgg cggcttcttc | 120 |
| ctgaggatca ggtccgacgg ggccgtggac ggaacccggg agaagactga cccccacata | 180 |
| aagcttcagc tccaggcgac ctctgtgggg gaggtggtca tcaagggggt ttgtgctaat | 240 |
| cgttatctgg ccatgaacag agatggacga ctgtttggaa tgaaacgagc gacggatgaa | 300 |
| tgccacttct tagagcggct cgagagcaac aactacaaca cctaccgctc caggaagtac | 360 |
| cccaacatgt ttgtgggact gacgcgaact ggcaactaca agtctgggac taaaactgga | 420 |
| ccgggccaaa aggccatcct cttcttccg atgtcggcca atactaa | 468 |

<210> SEQ ID NO 216
<211> LENGTH: 468
<212> TYPE: DNA
<213> ORGANISM: Rainbow trout

<400> SEQUENCE: 216

| atggccacag gagaaatcac cactctaccc gccacacctg aagatggagg cagtggcggc | 60 |
| ttccttccag gaaactttaa ggagcccaag aggttgtact gtaaaaatgg aggctacttc | 120 |
| ttgaggataa actctaacgg aagcgtggac gggatcagag ataagaacga cccccacaat | 180 |
| aagcttcaac tccaggcgac ctcagtgggg gaagtagtaa tcaaggggt ctcagccaac | 240 |
| cgctatctgg ccatgaatgc agatggaaga ctgtttggac cgagacggac aacagatgaa | 300 |
| tgctacttca tggagaggct ggagagtaac aactacaaca cctaccgctc tcgaaagtac | 360 |
| cctgaaatgt atgtggcact gaaaaggact ggccagtaca agtcaggatc caaaactgga | 420 |

```
cccggccaaa aagccatcct cttcctcccc atgtcagcca gacgctga        468
```

<210> SEQ ID NO 217
<211> LENGTH: 453
<212> TYPE: DNA
<213> ORGANISM: Salmon

<400> SEQUENCE: 217

```
atggccacag gagaaatcac cactctaccc gccacacctg aagatggagg cagtggcggc     60
ttccctccag gaaactttaa ggatcccaag aggctgtact gtaaaaacgg gggctacttc   120
ttgagaataa actctaatgg aagcgtggac gggatccgag agaagaacga ccccacaaa    180
cagcctcaat ttgtcagggc atggactctt caaggtgtca aacgttccac agggatgctg   240
gcccatgttg actccaacgc ttcccacaat tgtgtcaagg tggctggatg ttctttggga   300
gaatttggca gtatgtccaa ccggcctcat aaccgcagac cacgtgtagc tacaccagcc   360
caggacctcc acatccggct tcttcatcta cgggatcgtc tgaaaccagc cacccgaaca   420
gctgataaaa ctgaggagta tttctgtctg taa                                 453
```

<210> SEQ ID NO 218
<211> LENGTH: 465
<212> TYPE: DNA
<213> ORGANISM: Zebrafish

<400> SEQUENCE: 218

```
atggccaccg gagggatcac cacactcccg gccgctccgg acgccgaaaa cagcagcttt     60
cccgcgggca gcttcaggga tcccaagcgc ctgtactgca aaaacggagg attcttcctg   120
cggatcaacg cggacggccg agtggacgga gcccgagaca gagcgaccc gcacattcgt    180
ctgcagctgc aggcgacggc agtgggtgaa gtactcatta aggcatctg taccaaccgt    240
ttccttgcca tgaacgcaga cggacgactg ttcgggacga aaaggaccac agatgaatgt   300
tatttcctgg agcgcctgga gtccaacaac tacaacacat acagatcccg caagtatccc   360
gactggtacg tggctctgaa gagaaccggc cagtataaaa gcggctctaa aaccagcccg   420
ggacagaagg ccatcctgtt tctgcccatg tcggccaaat gctga                   465
```

<210> SEQ ID NO 219
<211> LENGTH: 468
<212> TYPE: DNA
<213> ORGANISM: Nile tilapia

<400> SEQUENCE: 219

```
atggccacgg gaggaatcac aacacttccc gctacacctg aagacggcgg cagcagcggc     60
tttcctcctg ggaacttcaa ggaccctaaa aggctgtact gtaaaaatgg tggcttcttc   120
ttgaggataa aatctgatgg aggagtggat ggaatacgag agaaaaacga ccccacata    180
aagcttcaac tccaggcgac ctcagtggga gaagtggtca tcaaagggat ttgtgcaaac   240
cgatatctgg caatgaacag agatggacga ctgtttggag cgagaagagc aacagatgag   300
tgctacttct tagagcggct cgagagcaac aactacaaca cctaccgctc caggaagtac   360
ccaaacatgt acgtggcgct gaagcggact ggccagtaca agtctggaag caaaactgga   420
ccgggtcaaa aggcaattct ctttctccca atgtctgcta aatgctaa                 468
```

<210> SEQ ID NO 220
<211> LENGTH: 468
<212> TYPE: DNA

<213> ORGANISM: Medaka

<400> SEQUENCE: 220

```
atggctacgg gagaaatcac aacacttccc tccccagctg aaaacagcag aagcgatggc      60
tttcctccag ggaactacaa ggatcctaag aggctctact gtaaaaatgg aggtttgttt     120
ttgaggatta aacctgatgg aggagtggat ggaatccggg aaaaaaaaga tccccacgtt     180
aagcttcgcc ttcaggctac ctcagcggga gaggtggtga tcaaaggagt ttgttcaaac     240
agatatctgg cgatgcatgg agatggacgt ctatttggag tgagacaagc aacagaggaa     300
tgctacttct tggagcgact agagagcaac aactataaca cctatcgctc taaaaagtac     360
ccaaacatgt acgtggcact gaagcggaca ggccagtaca aacctggaaa caaaactgga     420
ccaggtcaaa aggccattct ctttctgcct atgtctgcca agtactaa                  468
```

<210> SEQ ID NO 221
<211> LENGTH: 206
<212> TYPE: PRT
<213> ORGANISM: Homo sapiens

<400> SEQUENCE: 221

```
Met Ser Gly Pro Gly Thr Ala Ala Val Ala Leu Leu Pro Ala Val Leu
 1               5                  10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
        50                  55                  60

Lys Glu Ala Ala Val Gln Ser Gly Ala Gly Asp Tyr Leu Leu Gly Ile
 65                  70                  75                  80

Lys Arg Leu Arg Arg Leu Tyr Cys Asn Val Gly Ile Gly Phe His Leu
                 85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205
```

<210> SEQ ID NO 222
<211> LENGTH: 268
<212> TYPE: PRT
<213> ORGANISM: Homo sapiens

<400> SEQUENCE: 222

```
Met Ser Leu Ser Phe Leu Leu Leu Phe Phe Ser His Leu Ile Leu
 1               5                  10                  15

Ser Ala Trp Ala His Gly Glu Lys Arg Leu Ala Pro Lys Gly Gln Pro
```

```
            20                  25                  30
Gly Pro Ala Thr Asp Arg Asn Pro Arg Gly Ser Ser Arg Gln
            35                  40                  45
Ser Ser Ser Ala Met Ser Ser Ser Ala Ser Ser Pro Ala
50                  55                  60
Ala Ser Leu Gly Ser Gln Ser Gly Leu Glu Gln Ser Ser Phe Gln
65                  70                  75                  80
Trp Ser Pro Ser Gly Arg Thr Gly Ser Leu Tyr Cys Arg Val Gly
                85                  90                  95
Ile Gly Phe His Leu Gln Ile Tyr Pro Asp Gly Lys Val Asn Gly Ser
                100                 105                 110
His Glu Ala Asn Met Leu Ser Val Leu Glu Ile Phe Ala Val Ser Gln
                115                 120                 125
Gly Ile Val Gly Ile Arg Gly Val Phe Ser Asn Lys Phe Leu Ala Met
                130                 135                 140
Ser Lys Lys Gly Lys Leu His Ala Ser Ala Lys Phe Thr Asp Asp Cys
145                 150                 155                 160
Lys Phe Arg Glu Arg Phe Gln Glu Asn Ser Tyr Asn Thr Tyr Ala Ser
                165                 170                 175
Ala Ile His Arg Thr Glu Lys Thr Gly Arg Glu Trp Tyr Val Ala Leu
                180                 185                 190
Asn Lys Arg Gly Lys Ala Lys Arg Gly Cys Ser Pro Arg Val Lys Pro
                195                 200                 205
Gln His Ile Ser Thr His Phe Leu Pro Arg Phe Lys Gln Ser Glu Gln
                210                 215                 220
Pro Glu Leu Ser Phe Thr Val Thr Val Pro Glu Lys Lys Pro Pro
225                 230                 235                 240
Ser Pro Ile Lys Pro Lys Ile Pro Leu Ser Ala Pro Arg Lys Asn Thr
                245                 250                 255
Asn Ser Val Lys Tyr Arg Leu Lys Phe Arg Phe Gly
                260                 265

<210> SEQ ID NO 223
<211> LENGTH: 208
<212> TYPE: PRT
<213> ORGANISM: Homo sapiens

<400> SEQUENCE: 223

Met Ala Leu Gly Gln Lys Leu Phe Ile Thr Met Ser Arg Gly Ala Gly
1               5                   10                  15
Arg Leu Gln Gly Thr Leu Trp Ala Leu Val Phe Leu Gly Ile Leu Val
                20                  25                  30
Gly Met Val Val Pro Ser Pro Ala Gly Thr Arg Ala Asn Asn Thr Leu
            35                  40                  45
Leu Asp Ser Arg Gly Trp Gly Thr Leu Leu Ser Arg Ser Arg Ala Gly
        50                  55                  60
Leu Ala Gly Glu Ile Ala Gly Val Asn Trp Glu Ser Gly Tyr Leu Val
65                  70                  75                  80
Gly Ile Lys Arg Gln Arg Arg Leu Tyr Cys Asn Val Gly Ile Gly Phe
                85                  90                  95
His Leu Gln Val Leu Pro Asp Gly Arg Ile Ser Gly Thr His Glu Glu
                100                 105                 110
Asn Pro Tyr Ser Leu Leu Glu Ile Ser Thr Val Glu Arg Gly Val Val
                115                 120                 125
```

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                    165                 170                 175

Gln Gly Thr Tyr Ile Ala Leu Ser Lys Tyr Gly Arg Val Lys Arg Gly
                180                 185                 190

Ser Lys Val Ser Pro Ile Met Thr Val Thr His Phe Leu Pro Arg Ile
                195                 200                 205

<210> SEQ ID NO 224
<211> LENGTH: 208
<212> TYPE: PRT
<213> ORGANISM: Homo sapiens

<400> SEQUENCE: 224

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205

<210> SEQ ID NO 225
<211> LENGTH: 207
<212> TYPE: PRT
<213> ORGANISM: Homo sapiens

<400> SEQUENCE: 225

Met Ala Glu Val Gly Gly Val Phe Ala Ser Leu Asp Trp Asp Leu His
1               5                   10                  15

Gly Phe Ser Ser Ser Leu Gly Asn Val Pro Leu Ala Asp Ser Pro Gly
                20                  25                  30

Phe Leu Asn Glu Arg Leu Gly Gln Ile Glu Gly Lys Leu Gln Arg Gly
            35                  40                  45

```
Ser Pro Thr Asp Phe Ala His Leu Lys Gly Ile Leu Arg Arg Arg Gln
    50                  55                  60

Leu Tyr Cys Arg Thr Gly Phe His Leu Glu Ile Phe Pro Asn Gly Thr
65              70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
            115                 120                 125

Leu Thr Arg Glu Cys Val Phe Arg Glu Gln Phe Glu Glu Asn Trp Tyr
    130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
            195                 200                 205

<210> SEQ ID NO 226
<211> LENGTH: 211
<212> TYPE: PRT
<213> ORGANISM: Homo sapiens

<400> SEQUENCE: 226

Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
                20                  25                  30

Arg Pro Pro Leu Leu Gly Glu Arg Arg Ser Ala Ala Glu Arg Ser Ala
            35                  40                  45

Arg Gly Gly Pro Gly Ala Ala Gln Leu Ala His Leu His Gly Ile Leu
        50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210
```

<210> SEQ ID NO 227
<211> LENGTH: 621
<212> TYPE: DNA
<213> ORGANISM: Homo sapiens

<400> SEQUENCE: 227

```
atgtcggggc cgggacggc cgcggtagcg ctgctcccgg cggtcctgct ggccttgctg      60
gcgccctggg cgggccgagg gggcgccgcc gcacccactg cacccaacgg cacgctggag    120
gccgagctgg agcgccgctg ggagagcctg gtggcgctct cgttggcgcg cctgccggtg    180
gcagcgcagc ccaaggaggc ggccgtccag agcggcgccg cgactacct gctgggcatc     240
aagcggctgc ggcggctcta ctgcaacgtg gcatcggct tccacctcca ggcgctcccc     300
gacggccgca tcggcggcgc gcacgcggac acccgcgaca gctgctgga gctctcgccc    360
gtggagcggg gcgtggtgag catcttcggc gtggccagcc ggttcttcgt ggccatgagc    420
agcaagggca agctctatgg ctcgcccttc ttcaccgatg agtgcacgtt caaggagatt    480
ctccttccca caactacaa cgcctacgag tcctacaagt accccggcat gttcatcgcc    540
ctgagcaaga atgggaagac caagaagggg aaccgagtgt cgcccaccat gaaggtcacc    600
cacttcctcc ccaggctgtg a                                              621
```

<210> SEQ ID NO 228
<211> LENGTH: 807
<212> TYPE: DNA
<213> ORGANISM: Homo sapiens

<400> SEQUENCE: 228

```
atgagcttgt ccttcctcct cctcctcttc ttcagccacc tgatcctcag cgcctgggct    60
cacggggaga agcgtctcgc ccccaaaggg caacccggac ccgctgccac tgataggaac   120
cctagaggct ccagcagcag acagagcagc agtagcgcta tgtcttcctc ttctgcctcc    180
tcctcccccg cagcttctct gggcagccaa ggaagtggct tggagcagag cagtttccag    240
tggagcccct cggggcgccg gaccggcagc ctctactgca gagtgggcat cggtttccat    300
ctgcagatct acccggatgg caaagtcaat ggatcccacg aagccaatat gttaagtgtt    360
ttggaaatat ttgctgtgtc tcaggggatt gtaggaatac gaggagtttt cagcaacaaa    420
tttttagcga tgtcaaaaaa aggaaaactc catgcaagtg ccaagttcac agatgactgc    480
aagttcaggg agcgttttca agaaaatagc tataatacct atgcctcagc aatacataga    540
actgaaaaaa cagggcggga gtggtatgtg gccctgaata aaagaggaaa agccaaacga    600
gggtgcagcc cccgggttaa accccagcat atctctaccc attttctgcc aagattcaag    660
cagtcggagc agccagaact ttcttcacg gttactgttc ctgaaaagaa aaagccacct    720
agccctatca agccaaagat tcccctttct gcacctcgga aaataccaa ctcagtgaaa    780
tacagactca gtttcgctt tggataa                                         807
```

<210> SEQ ID NO 229
<211> LENGTH: 627
<212> TYPE: DNA
<213> ORGANISM: Homo sapiens

<400> SEQUENCE: 229

```
atggccctgg acagaaaact gttcatcact atgtcccggg gagcaggacg tctgcagggc     60
acgctgtggg ctctcgtctt cctaggcatc ctagtgggca tggtggtgcc ctcgcctgca    120
```

```
ggcacccgtg ccaacaacac gctgctggac tcgagggggct ggggcaccct gctgtccagg      180
tctcgcgcgg ggctagctgg agagattgcc ggggtgaact gggaaagtgg ctatttggtg      240
gggatcaagc ggcagcggag gctctactgc aacgtgggca tcggctttca cctccaggtg      300
ctccccgacg gccggatcag cgggacccac gaggagaacc cctacagcct gctggaaatt      360
tccactgtgg agcgaggcgt ggtgagtctc tttggagtga aagtgccct cttcgttgcc       420 atgaacagta aaggaagatt gtacgcaacg cccagcttcc aagaagaatg caagttcaga      480
gaaaccctcc tgcccaacaa ttacaatgcc tacgagtcag acttgtacca agggacctac      540
attgccctga gcaaatacgg acgggtaaag cggggcagca aggtgtcccc gatcatgact      600
gtcactcatt tccttcccag gatctaa                                          627

<210> SEQ ID NO 230
<211> LENGTH: 627
<212> TYPE: DNA
<213> ORGANISM: Homo sapiens

<400> SEQUENCE: 230
atggctccct taggtgaagt tgggaactat ttcggtgtgc aggatgcggt accgtttggg      60
aatgtgcccg tgttgccggt ggacagcccg gttttgttaa gtgaccacct gggtcagtcc      120
gaagcagggg ggctccccag gggacccgca gtcacggact tggatcattt aaaggggatt      180
ctcaggcgga ggcagctata ctgcaggact ggatttcact agaaatcttc ccccaatggt      240
actatccagg gaaccaggaa agaccacagc cgatttggca ttctggaatt tatcagtata      300 gcagtggggcc tggtcagcat tcgaggcgtg gacagtggac tctacctcgg gatgaatgag      360
aagggggagc tgtatggatc agaaaaacta acccaagagt gtgtattcag agaacagttc      420
gaagaaaact ggtataatac gtactcatca aacctatata gcacgtggaa cactggaagg      480
cgatactatg ttgcattaaa taaagatggg accccgagag aagggactag gactaaacgg      540
caccagaaat tcacacattt tttacctaga ccagtggacc ccgacaaagt acctgaactg      600
tataaggata ttctaagcca aagttga                                          627

<210> SEQ ID NO 231
<211> LENGTH: 624
<212> TYPE: DNA
<213> ORGANISM: Homo sapiens

<400> SEQUENCE: 231
atggcagagg tgggggggcgt cttcgcctcc ttggactggg atctacacgg cttctcctcg      60
tctctgggga acgtgcccttt agctgactcc ccaggtttcc tgaacgagcg cctgggccaa      120
atcgagggga agctgcagcg tggctcaccc acagacttcg cccacctgaa ggggatcctg      180
cggcgccgcc agctctactg ccgcaccggc ttccacctgg atcttccc caacggcacg       240 gtgcacggga cccgccacga ccacagccgc ttcggaatcc tggagtttat cagcctggct      300
gtggggctga tcagcatccg gggagtggac tctggcctgt acctaggaat gaatgagcga      360
ggagaactct atgggtcgaa gaaactcaca cgtgaatgtg ttttccggga acagtttgaa      420
gaaaactggt acaacaccta tgcctcaacc ttgtacaaac attcggactc agagagacag      480
tattacgtgg ccctgaacaa agatggctca ccccgggagg gatacaggac taaacgacac      540
cagaaattca ctcactttttt acccaggcct gtagatcctt ctaagttgcc ctccatgtcc      600
agagacctct ttcactatag gtaa                                             624
```

<210> SEQ ID NO 232
<211> LENGTH: 636
<212> TYPE: DNA
<213> ORGANISM: Homo sapiens

<400> SEQUENCE: 232

```
atggctccct tagccgaagt cgggggcttt ctgggcggcc tggagggctt gggccagcag      60
gtgggttcgc atttcctgtt gcctcctgcc ggggagcggc cgccgctgct gggcgagcgc     120
aggagcgcgg cggagcggag cgcgcgcggc gggccggggg ctgcgcagct ggcgcacctg     180
cacggcatcc tgcgccgccg gcagctctat tgccgcaccg gcttccacct gcagatcctg     240
cccgacggca gcgtgcaggg cacccggcag gaccacagcc tcttcggtat cttggaattc     300
atcagtgtgg cagtgggact ggtcagtatt agaggtgtgg acagtggtct ctatcttgga     360
atgaatgaca aggagaact  ctatggatca gagaaactta cttccgaatg catctttagg     420
gagcagtttg aagagaactg gtataacacc tattcatcta acatatataa acatggagac     480
actggccgca ggtattttgt ggcacttaac aaagacggaa ctccaagaga tggcgccagg     540
tccaagaggc atcagaaatt tacacatttc ttacctagac cagtggatcc agaaagagtt     600
ccagaattgt acaaggacct actgatgtac acttga                                636
```

<210> SEQ ID NO 233
<211> LENGTH: 251
<212> TYPE: PRT
<213> ORGANISM: Homo sapiens

<400> SEQUENCE: 233

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220
```

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 234
<211> LENGTH: 251
<212> TYPE: PRT
<213> ORGANISM: Gorilla gorilla

<400> SEQUENCE: 234

Met Leu Gly Ala Arg Leu Arg Leu Trp Val Cys Ala Leu Cys Ser Val
1               5                   10                  15

Cys Ser Leu Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
                180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
        210                 215                 220

Gly Val Val Arg Gly Arg Val Asn Thr Tyr Ala Gly Gly Thr Gly
225                 230                 235                 240

Pro Glu Gly Cys Arg Pro Phe Pro Lys Phe Ile
                245                 250

<210> SEQ ID NO 235
<211> LENGTH: 251
<212> TYPE: PRT
<213> ORGANISM: Nomascus leucogenys

<400> SEQUENCE: 235

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

-continued

```
Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
                100                 105                 110

Cys Arg Phe Gln His Gln Thr Leu Glu Asn Gly Tyr Asp Val Tyr His
                115                 120                 125

Ser Pro Gln His His Phe Leu Val Ser Leu Gly Arg Ala Lys Arg Ala
130                 135                 140

Phe Leu Pro Gly Met Asn Pro Pro Tyr Ser Gln Phe Leu Ser Arg
145                 150                 155                 160

Arg Asn Glu Ile Pro Leu Leu His Phe Asn Thr Pro Thr Pro Arg Arg
                165                 170                 175

His Thr Arg Ser Ala Glu Asp Asp Ser Glu Arg Asp Pro Leu Asn Val
                180                 185                 190

Leu Lys Pro Arg Ala Arg Met Thr Pro Ala Pro Ala Ser Cys Ser Gln
                195                 200                 205

Glu Leu Leu Ser Ser Glu Asp Asn Ser Pro Met Ala Ser Asp Pro Leu
210                 215                 220

Gly Val Val Arg Gly Arg Val Asn Thr His Ala Gly Gly Thr Gly
225                 230                 235                 240

Pro Glu Gly Cys Arg Pro Phe Pro Lys Phe Ile
                245                 250

<210> SEQ ID NO 236
<211> LENGTH: 251
<212> TYPE: PRT
<213> ORGANISM: Macaca mulatta

<400> SEQUENCE: 236

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
                100                 105                 110

Cys Arg Phe Arg His Trp Thr Leu Glu Asn Gly Tyr Asp Val Tyr His
                115                 120                 125

Ser Pro Gln His His Phe Leu Val Ser Leu Gly Arg Ala Lys Arg Ala
130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175
```

```
His Thr Arg Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Gly Gly Arg Val Asn Thr His Ala Gly Gly Thr Gly
225                 230                 235                 240

Pro Glu Ala Cys Arg Pro Phe Pro Lys Phe Ile
                245                 250

<210> SEQ ID NO 237
<211> LENGTH: 251
<212> TYPE: PRT
<213> ORGANISM: Macaca fascicularis

<400> SEQUENCE: 237

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Arg Pro Arg Arg
                165                 170                 175

His Thr Arg Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Ala Gly Arg Val Asn Thr His Ala Gly Gly Thr Gly
225                 230                 235                 240

Pro Glu Ala Cys Arg Pro Phe Pro Lys Phe Ile
                245                 250

<210> SEQ ID NO 238
<211> LENGTH: 251
<212> TYPE: PRT
<213> ORGANISM: Pan troglodytes

<400> SEQUENCE: 238
```

```
Met Leu Gly Ala Arg Leu Arg Leu Trp Val Cys Ala Leu Cys Ser Val
1               5                   10                  15

Cys Ser Val Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
                100                 105                 110

Cys Arg Phe Gln His Gln Thr Leu Glu Asn Gly Tyr Asp Val Tyr Tyr
            115                 120                 125

Ser Pro Gln Tyr His Phe Leu Val Ser Leu Gly Arg Ala Lys Arg Ala
            130                 135                 140

Phe Leu Pro Ser Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
                180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
            210                 215                 220

Gly Val Val Arg Gly Gly Arg Val Asn Thr His Ala Gly Gly Thr Gly
225                 230                 235                 240

Pro Glu Gly Cys Arg Pro Phe Pro Lys Phe Ile
                245                 250
```

<210> SEQ ID NO 239
<211> LENGTH: 251
<212> TYPE: PRT
<213> ORGANISM: Callithrix jacchus

<400> SEQUENCE: 239

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Ala Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Leu Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
                100                 105                 110

Cys Arg Phe Arg Pro Gln Arg Leu Glu Asn Gly Tyr Asp Val Tyr Gln
```

```
            115                 120                 125
Ser Pro Gln His His Phe Leu Val Ser Leu Gly Arg Ala Lys Arg Ala
        130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Lys Pro Arg Arg
                165                 170                 175
His Thr Arg Ser Ala Glu Asp Asp Pro Glu Leu Asp Pro Leu Asn Val
            180                 185                 190
Leu Lys Ser Arg Val Arg Met Thr Pro Ala Pro Ala Ser Cys Ser Gln
        195                 200                 205
Glu Leu Leu Ser Ala Glu Asp Asn Ser Pro Val Gly Ser Asp Pro Leu
    210                 215                 220
Gly Met Val Arg Gly Arg Val Asn Ser His Ala Glu Gly Thr Gly
225                 230                 235                 240
Pro Glu Gly Cys Ser Pro Phe Pro Lys Leu Ile
                245                 250
```

<210> SEQ ID NO 240
<211> LENGTH: 251
<212> TYPE: PRT
<213> ORGANISM: Loxodonta Africana

<400> SEQUENCE: 240

```
Met Leu Gly Ala Arg Leu Arg Leu Trp Val Cys Thr Leu Cys Ser Ala
1               5                   10                  15
Cys Ser Met Cys Ser Val Arg Ala Tyr Pro Asn Ala Ser Pro Leu Leu
            20                  25                  30
His Ser Ser Trp Gly Gly Leu Thr His Leu Tyr Thr Ala Thr Ala Arg
        35                  40                  45
Asn Ser Tyr His Leu Gln Ile His Lys Asp Gly His Val Asp Gly Thr
    50                  55                  60
Pro Asp Gln Thr Ile Tyr Ser Ala Leu Ile Ile Arg Ser Glu Glu Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asn Pro Glu Asn
            100                 105                 110
Cys Arg Phe Lys His Trp Thr Leu Glu Asn Gly Tyr Asp Val Tyr His
        115                 120                 125
Ser Pro Gln His His Phe Leu Val Ser Leu Gly Arg Val Lys Lys Ala
    130                 135                 140
Phe Leu Pro Gly Met Asn Pro Pro Tyr Ser Gln Phe Leu Ser Arg
145                 150                 155                 160
Arg Asn Glu Ile Pro Leu Ile Tyr Phe Asn Thr Pro Lys Pro Arg Arg
                165                 170                 175
His Thr Arg Ser Ala Glu Asp Asp Ser Glu Arg Asp Pro Leu Asn Val
            180                 185                 190
Leu Lys Pro Arg Pro Arg Met Thr Pro Ala Pro Ala Ser Cys Ser Gln
        195                 200                 205
Glu Leu Leu Ser Ala Glu Asp Asn Ser Val Val Ala Asn Asp Pro Leu
    210                 215                 220
Gly Val Val Arg Ser Asn Arg Val Asn Thr His Ala Gly Gly Ile Gly
225                 230                 235                 240
```

```
Val Glu Arg Cys Arg Pro Phe Pro Lys Phe Ile
                245                 250

<210> SEQ ID NO 241
<211> LENGTH: 250
<212> TYPE: PRT
<213> ORGANISM: Erinaceus telfairi

<400> SEQUENCE: 241

Met Leu Gly Ala His Leu Arg Leu Trp Val Cys Ala Leu Cys Ser Val
1               5                   10                  15

Ser Ala Met Tyr His Val Arg Ala Tyr Pro Asn Ala Ser Pro Leu Leu
            20                  25                  30

Gly Thr Ser Trp Ala Gly Leu Thr His Leu Tyr Thr Ala Thr Ala Arg
        35                  40                  45

Asn Ser Phe His Leu Gln Ile His Lys Asp Gly His Val Asp Gly Thr
    50                  55                  60

Pro His Gln Thr Ile Tyr Ser Ala Leu Met Ile Arg Ser Glu Asp Ser
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Thr Ala Asp Ser
            100                 105                 110

Cys Arg Phe Arg Gln Arg Thr Leu Glu Asn Gly Tyr Asp Val Tyr His
        115                 120                 125

Ser Pro Gln His His Phe Leu Ile Ser Leu Gly Arg Ala Lys Arg Val
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Glu Val Glu Gln Asp Pro Leu Asn Val
            180                 185                 190

Leu Lys Pro Arg Pro Arg Met Thr Pro Ala Pro Ala Ser Cys Ser Gln
        195                 200                 205

Glu Leu Pro Ser Ala Glu Asp Asn Ser Ala Leu Ala Ser Asp Pro Leu
    210                 215                 220

Gly Val Val Arg Gly Lys Lys Leu Asn Thr His Ala Val Gly Met Gly
225                 230                 235                 240

Ala Glu Arg Cys Arg Pro Phe Pro Lys Phe
                245                 250

<210> SEQ ID NO 242
<211> LENGTH: 235
<212> TYPE: PRT
<213> ORGANISM: Erinaceus europaeus

<400> SEQUENCE: 242

Met Leu Gly Ala His Leu Gly Leu Val Val Cys Ala Leu Val Ser Arg
1               5                   10                  15

Ala Tyr Pro Asn Ala Ser Pro Leu Leu Gly Phe Ser Trp Gly Gly Leu
            20                  25                  30

Thr His Leu Tyr Thr Ala Thr Ala Arg Asn Ser Tyr His Leu Gln Ile
        35                  40                  45

His Lys Asp Gly His Val Asp Gly Ser Pro Gln Gln Thr Ile Tyr Ala
    50                  55                  60
```

```
Gly Phe Val Met Ile Thr Gly Val Met Ser Arg Arg Tyr Leu Cys Met
65                  70                  75                  80

Asp Phe Arg Ser Asn Ile Phe Gly Ser His His Phe Ala Pro Glu Ser
                85                  90                  95

Cys Arg Phe Arg His Arg Thr Leu Glu Asn Gly Tyr Asp Val Tyr His
            100                 105                 110

Ser Pro Gln His His Phe Leu Val Ser Leu Gly Arg Ala Lys Arg Ala
        115                 120                 125

Phe Leu Pro Gly Thr Asn Pro Pro Tyr Ser Gln Phe Leu Ser Arg
130                 135                 140

Arg Asn Glu Val Pro Leu Ile His Phe Asn Thr Pro Arg Pro Arg Arg
145                 150                 155                 160

His Thr Arg Ser Ala Glu Asp Asn Ser Glu Leu Asp Pro Leu Asn Val
                165                 170                 175

Leu Lys Pro Arg Pro Arg Met Thr Pro Ala Pro Ala Ser Cys Ser Gln
            180                 185                 190

Glu Leu Pro Ser Ala Glu Asp Asn Ser Met Val Ala Ser Asp Pro Leu
        195                 200                 205

Gly Val Val Arg Ala Asn Arg Val Asn Thr His Ala Gly Gly Leu Gly
210                 215                 220

Val Asp Lys Cys Arg Pro Phe Pro Lys Phe Ile
225                 230                 235

<210> SEQ ID NO 243
<211> LENGTH: 252
<212> TYPE: PRT
<213> ORGANISM: Otolemur garnettii

<400> SEQUENCE: 243

Met Leu Gly Thr Cys Leu Arg Leu Trp Val Cys Ala Leu Cys Ser Val
1               5                   10                  15

Cys Ser Val Ser Ile Val Arg Ala Tyr Pro Asn Ala Ser Pro Leu Leu
                20                  25                  30

Ser Ser Ser Trp Gly Gly Leu Thr His Leu Tyr Thr Ala Ser Ala Arg
            35                  40                  45

Asn Ser Tyr His Leu Gln Ile His Lys Asp Gly His Val Asp Gly Thr
50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Lys Gly Asn Ile Phe Gly Ser His Ser Phe His Pro Glu Ser
            100                 105                 110

Cys Arg Phe Arg His Arg Thr Leu Glu Asn Gly Tyr Asp Val Tyr Leu
        115                 120                 125

Ser Pro Gln His His Phe Leu Val Ser Leu Gly Arg Ser Lys Arg Pro
130                 135                 140

Phe Leu Pro Gly Met Asn Pro Pro Phe Ser Gln Phe Leu Ser Arg
145                 150                 155                 160

Arg Asn Asp Ile Pro Leu Ile His Phe Asn Thr Pro Arg Pro Arg Arg
                165                 170                 175

His Thr Arg Ser Ala Glu Asp Asn Asp Ser Glu Leu Asp Pro Leu Asn
            180                 185                 190

Val Leu Lys Pro Arg Pro Arg Ala Thr Pro Gly Pro Ala Ser Cys Ser
        195                 200                 205
```

Gln Glu Leu Pro Ser Ala Glu Asp Asn Ser Leu Val Ala Ser Asp Pro
    210                 215                 220

Leu Gly Val Val Arg Gly Asn Arg Val Asn Ala His Ala Gly Arg Ala
225                 230                 235                 240

Gly Leu Asp Arg Cys Arg Pro Phe Pro Arg Tyr Phe
            245                 250

<210> SEQ ID NO 244
<211> LENGTH: 252
<212> TYPE: PRT
<213> ORGANISM: Oryctolagus cuniculus

<400> SEQUENCE: 244

Met Leu Gly Ala Arg Leu Leu Arg Leu Leu Val Cys Ala Leu Gly Ser
1               5                   10                  15

Val Cys Ser Trp Cys Val Val Arg Ala Tyr Pro Asp Thr Ser Pro Leu
            20                  25                  30

Leu Ser Ser Ser Trp Ala Gly Leu Thr His Leu Tyr Thr Ala Thr Ala
        35                  40                  45

Arg Asn Ser Tyr His Leu Gln Ile His Lys Asp Gly Gln Val Asp Gly
    50                  55                  60

Thr Pro His Gln Thr Ile Tyr Ser Ala Leu Met Ile Arg Ser Glu Asp
65                  70                  75                  80

Ala Gly Phe Val Val Ile Thr Gly Val Met Ser Arg Arg Tyr Leu Cys
                85                  90                  95

Met Asp Phe Arg Gly Asn Ile Phe Gly Ser His Tyr Phe Asp Pro Gln
            100                 105                 110

Asn Cys Arg Phe Arg His Arg Thr Leu Glu Asn Gly Tyr Asp Val Tyr
        115                 120                 125

His Ser Pro Glu His His Phe Leu Val Ser Leu Gly Arg Ala Lys Arg
    130                 135                 140

Pro Phe Leu Pro Gly Met Asn Pro Pro Tyr Ser Gln Phe Leu Ser
145                 150                 155                 160

Arg Arg Asn Glu Ile Pro Leu Ile His Phe Asn Thr Pro Arg Pro Arg
                165                 170                 175

Arg His Thr Arg Ser Ala Glu Asp Ala Trp Glu Gln Asp Pro Leu Asn
            180                 185                 190

Val Leu Lys Pro Arg Phe Arg Leu Thr Pro Ala Pro Ala Ser Cys Ser
        195                 200                 205

Gln Glu Ala Pro Ser Ala Glu Asp Asn Gly Leu Val Ala Ser Asp Pro
    210                 215                 220

Phe Gly Val Leu Arg Gly Asn Arg Val Asn Met His Gly Asp Arg Met
225                 230                 235                 240

Gly Pro Glu Arg Cys His His Phe Pro Lys Phe Ile
                245                 250

<210> SEQ ID NO 245
<211> LENGTH: 246
<212> TYPE: PRT
<213> ORGANISM: Equus caballus

<400> SEQUENCE: 245

Met Ser Gly Pro Cys Leu Gly Leu Leu Val Tyr Val Leu Cys Ser Ala
1               5                   10                  15

Val Lys Ala Tyr Pro Asn Ala Ser Pro Leu Leu Asp Ser Ser Trp Gly
            20                  25                  30

```
Ser Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
 50                  55                  60

Tyr Ser Ala Leu Met Ile Arg Ser Glu Asp Ala Gly Phe Val Val Ile
 65                  70                  75                  80

Thr Gly Val Met Ser Arg Arg Tyr Leu Cys Met Asp Phe Arg Gly Asn
                 85                  90                  95

Ile Phe Gly Ser His His Phe Ser Pro Glu Ser Cys Ser Phe Arg Gln
                100                 105                 110

Arg Thr Leu Glu Asn Gly Tyr Asp Val Tyr His Ser Pro Gln His Arg
            115                 120                 125

Phe Leu Val Ser Leu Gly Arg Ala Lys Arg Ala Phe Leu Pro Gly Thr
        130                 135                 140

Asn Pro Pro Tyr Ser Gln Phe Leu Ser Arg Arg Asn Glu Ile Pro
145                 150                 155                 160

Leu Val His Phe Asn Thr Pro Arg Pro Arg His Thr Arg Ser Ala
                165                 170                 175

Glu Asp Asn Ser Glu Arg Asp Pro Leu Asn Val Leu Lys Pro Arg Pro
            180                 185                 190

Arg Met Thr Pro Ala Pro Ala Ser Cys Ser Gln Glu Leu Pro Ser Ala
        195                 200                 205

Glu Asp Asn Ser Val Leu Ala Ser Asp Pro Leu Gly Val Val Arg Gly
    210                 215                 220

Asn Arg Val Asn Thr His Ala Gly Gly Ala Gly Val Glu Arg Cys Arg
225                 230                 235                 240

Pro Phe Pro Lys Phe Phe
                245

<210> SEQ ID NO 246
<211> LENGTH: 245
<212> TYPE: PRT
<213> ORGANISM: Ailuropoda melanoleuca

<400> SEQUENCE: 246

Met Ser Gly Thr Arg Leu Gly Leu Leu Val Ser Val Leu Cys Trp Val
 1               5                  10                  15

Gly Arg Ala Tyr Pro Asn Thr Ser Pro Leu Leu Gly Ser Ser Trp Gly
            20                  25                  30

Gly Leu Thr His Leu Tyr Thr Ala Ser Ala Arg Asn Ser Tyr His Leu
        35                  40                  45

Gln Ile His Lys Asp Gly His Val Asp Gly Thr Pro His Gln Thr Ile
 50                  55                  60

Tyr Ser Ala Leu Met Ile Arg Ser Glu Asp Ala Gly Phe Val Val Ile
 65                  70                  75                  80

Thr Gly Val Met Ser Arg Arg Tyr Leu Cys Met Asp Leu Arg Gly Asn
                 85                  90                  95

Ile Phe Gly Ser His Leu Phe Ser Pro Glu Ser Cys Arg Phe Arg Gln
                100                 105                 110

Arg Thr Leu Glu Asn Gly Tyr Asp Val Tyr His Ser Pro Gln His Arg
            115                 120                 125

Phe Leu Val Ser Leu Gly Gln Ala Lys Arg Thr Phe Leu Pro Gly Thr
        130                 135                 140

Asn Pro Pro Tyr Ser Gln Phe Leu Ser Arg Arg Asn Glu Ile Pro
```

```
            145                 150                 155                 160
Leu Ile His Phe Asn Thr Pro Arg Pro Arg Arg His Thr Arg Ser Ala
                165                 170                 175
Glu Asp Thr Glu Arg Asp Pro Leu Asn Val Leu Lys Pro Arg Pro Arg
                180                 185                 190
Met Thr Pro Ala Pro Ala Ser Cys Ser Gln Glu Leu Pro Ser Ala Glu
                195                 200                 205
Asp Asn Ser Val Val Ala Ser Asp Pro Leu Gly Val Leu Arg Gly Asn
                210                 215                 220
Arg Val Asn Ala His Ala Gly Gly Met Gly Val Asp Arg Cys Arg Pro
225                 230                 235                 240
Phe Pro Lys Phe Ile
                245

<210> SEQ ID NO 247
<211> LENGTH: 250
<212> TYPE: PRT
<213> ORGANISM: Ochotona princeps

<400> SEQUENCE: 247

Met Leu Gly Gly Leu Gly Leu Trp Val Cys Val Leu Gly Ser Val Cys
1               5                   10                  15
Ser Trp Arg Gly Val Arg Ala Tyr Pro Asp Thr Ser Pro Leu Leu Gly
                20                  25                  30
Ser Ser Trp Thr Gly Leu Thr His Leu Tyr Thr Ala Thr Ala Arg Asn
                35                  40                  45
Ser Phe His Leu Gln Ile His Lys Asp Gly His Val Asp Gly Thr Pro
                50                  55                  60
Gln Gln Thr Ile Tyr Ser Ala Leu Met Ile Arg Ser Glu Asp Ala Gly
65                  70                  75                  80
Phe Val Val Ile Thr Gly Val Met Ser Arg Arg Tyr Leu Cys Met Asp
                85                  90                  95
Phe Arg Gly Asn Ile Phe Gly Ser His Tyr Phe Glu Pro Gln Asn Cys
                100                 105                 110
Arg Phe Gln Gln Arg Thr Leu Glu Asn Gly Tyr Asp Ile Tyr His Ser
                115                 120                 125
Pro Gln His Asp Phe Leu Val Ser Leu Gly Arg Ala Lys Arg Pro Phe
                130                 135                 140
Leu Pro Gly Met Asn Pro Pro Tyr Ser Gln Phe Leu Ser Arg Arg
145                 150                 155                 160
Asn Glu Ile Pro Leu Ile Leu Phe Asn Thr Pro Arg Pro Arg Arg His
                165                 170                 175
Thr Arg Ser Ala Glu Glu Gly Trp Glu Arg Asp Pro Leu Asn Val Leu
                180                 185                 190
Lys Ser Arg Pro Arg Met Thr Pro Ala Pro Ala Ser Cys Ser Arg Glu
                195                 200                 205
Ala Pro Ser Ala Glu Asp Asp Gly Leu Leu Ala Ser Asp Pro Met Gly
                210                 215                 220
Val Leu Arg Gly His Arg Val Asp Val His Gly Gly Thr Gly Arg
225                 230                 235                 240
Asp Arg Cys Arg Pro Phe Pro Arg Phe Ile
                245                 250

<210> SEQ ID NO 248
<211> LENGTH: 245
```

```
<212> TYPE: PRT
<213> ORGANISM: Bos Taurus

<400> SEQUENCE: 248

Met Leu Gly Ala Arg Leu Gly Leu Trp Val Cys Thr Leu Ser Cys Val
1               5                   10                  15

Val Gln Ala Tyr Pro Asn Ser Ser Pro Leu Leu Gly Ser Ser Trp Gly
            20                  25                  30

Gly Leu Thr His Leu Tyr Thr Ala Thr Ala Arg Asn Ser Tyr His Leu
            35                  40                  45

Gln Ile His Gly Asp Gly His Val Asp Gly Ser Pro Gln Gln Thr Val
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Thr Gly Asn
                85                  90                  95

Ile Phe Gly Ser His His Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
130                 135                 140

Asn Pro Pro Pro Tyr Ala Gln Phe Leu Ser Arg Arg Asn Glu Ile Pro
145                 150                 155                 160

Leu Pro His Phe Ala Ala Thr Ala Arg Pro Arg Arg His Thr Arg Ser
                165                 170                 175

Ala His Asp Ser Gly Asp Pro Leu Ser Val Leu Lys Pro Arg Ala Arg
            180                 185                 190

Ala Thr Pro Val Pro Ala Ala Cys Ser Gln Glu Leu Pro Ser Ala Glu
        195                 200                 205

Asp Ser Gly Pro Ala Ala Ser Asp Pro Leu Gly Val Leu Arg Gly His
210                 215                 220

Arg Leu Asp Val Arg Ala Gly Ser Ala Gly Ala Glu Arg Cys Arg Pro
225                 230                 235                 240

Phe Pro Gly Phe Ala
                245

<210> SEQ ID NO 249
<211> LENGTH: 244
<212> TYPE: PRT
<213> ORGANISM: Sus scrofa

<400> SEQUENCE: 249

Met Leu Gly Ala Arg Leu Gly Leu Trp Val Cys Thr Leu Cys Cys Ala
1               5                   10                  15

Ala Arg Ala Tyr Pro Asp Thr Ser Pro Leu Leu Ser Ser Gly Trp Gly
            20                  25                  30

Gly Leu Thr His Leu Tyr Thr Ala Thr Ala Arg Asn Ser Tyr His Leu
            35                  40                  45

Gln Ile His Lys Asp Gly His Val Asp Gly Ser Pro Gln Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Leu Arg Gly Asn
                85                  90                  95
```

```
Ile Phe Gly Ser Leu His Phe Ser Pro Glu Ser Cys Arg Phe Arg Gln
                100                 105                 110

Arg Thr Leu Glu Asn Gly Tyr Asp Val Tyr His Ser Pro His Tyr Arg
            115                 120                 125

Phe Leu Val Ser Leu Gly Arg Ala Lys Arg Ala Phe Leu Pro Gly Thr
        130                 135                 140

Asn Pro Pro Tyr Ala Gln Phe Leu Ser Arg Arg Asn Glu Ile Pro
145                 150                 155                 160

Leu Leu His Phe Ala Thr Ala Arg Pro Arg His Thr Arg Ser Ala
                165                 170                 175

His Asp Gly Gly Asp Pro Leu Ser Val Leu Lys Pro Arg Ala Arg Ala
                180                 185                 190

Thr Pro Ala Pro Val Ser Cys Ser Arg Glu Leu Pro Ser Ala Glu Asp
            195                 200                 205

Gly Gly Pro Ala Ala Ser Asp Pro Leu Gly Val Leu Arg Gly Gln Arg
        210                 215                 220

Leu Asp Ala Arg Ala Gly Val Gly Gly Ala Glu Arg Cys Arg Pro Phe
225                 230                 235                 240

Pro Ser Phe Ala

<210> SEQ ID NO 250
<211> LENGTH: 312
<212> TYPE: PRT
<213> ORGANISM: Canis lupus familiaris

<400> SEQUENCE: 250

Met Trp Thr Val Glu Phe Phe Leu Phe Asp Val Thr Gly Pro Pro Phe
1               5                   10                  15

Lys Ser Leu Arg Glu Lys Arg Arg Glu Ser Ser Leu Gly Leu Ser Arg
            20                  25                  30

Lys Ile Pro Thr Lys Lys Arg Lys Arg Pro Val Arg His Ser Arg
        35                  40                  45

Gly Ile Lys Glu Ala Val Ser Gly Phe Lys Leu Gln Pro Ala Ile Gln
    50                  55                  60

Arg Ala Val Met Ser Gly Thr Arg Leu Gly Phe Leu Val Ser Val Leu
65                  70                  75                  80

Cys Trp Val Val Arg Ala Tyr Ser Asn Thr Ser Pro Leu Leu Gly Ser
                85                  90                  95

Ser Trp Gly Ser Leu Thr His Leu Tyr Thr Ala Thr Ala Arg Asn Ser
                100                 105                 110

Tyr His Leu Gln Ile His Lys Asp Gly His Val Asp Gly Thr Pro His
            115                 120                 125

Gln Thr Ile Tyr Ser Ala Leu Met Ile Arg Ser Glu Asp Ala Gly Phe
        130                 135                 140

Val Val Ile Thr Gly Val Met Ser Arg Arg Tyr Leu Cys Met Asp Phe
145                 150                 155                 160

Arg Gly Asn Ile Phe Gly Ser His Leu Phe Ser Pro Glu Ser Cys Arg
                165                 170                 175

Phe Arg Gln Arg Thr Leu Glu Asn Gly Tyr Asp Val Tyr His Ser Pro
            180                 185                 190

Gln His Arg Phe Leu Val Ser Leu Gly Gln Ala Lys Arg Ala Phe Leu
        195                 200                 205

Pro Gly Thr Asn Pro Pro Tyr Ser Gln Phe Leu Ser Arg Arg Asn
        210                 215                 220
```

Glu Ile Pro Leu Val His Phe His Thr Pro Arg Pro Arg Arg His Thr
225                 230                 235                 240

Arg Ser Ala Glu Ala Pro Glu Arg Asp Pro Leu Asn Val Leu Lys Pro
            245                 250                 255

Arg Pro Arg Leu Ala Pro Ala Pro Ala Ser Cys Ser Gln Glu Leu Pro
            260                 265                 270

Ser Ala Glu Asp Pro Gly Ala Pro Ala Ser Asp Pro Leu Gly Val Leu
        275                 280                 285

Arg Gly His Arg Ala Asn Ala Arg Ala Gly Gly Val Gly Val Asp Arg
        290                 295                 300

Cys Arg Ala Phe Pro Thr Pro Ile
305                 310

<210> SEQ ID NO 251
<211> LENGTH: 243
<212> TYPE: PRT
<213> ORGANISM: Cavia porcellus

<400> SEQUENCE: 251

Met Leu Gly Thr Cys Leu Gly Leu Leu Ala Cys Thr Val Ser Leu Val
1               5                   10                  15

Gly Ala Tyr Pro Asp Ala Ser Pro Leu Leu Thr Ser Ser Trp Gly Gly
            20                  25                  30

Leu Ile His Leu Tyr Thr Ala Thr Ala Arg Asn Ser Tyr His Leu Gln
        35                  40                  45

Ile His Lys Asp Gly His Ile Asp Gly Ala Pro Tyr Pro Thr Ile Tyr
    50                  55                  60

Ser Ala Leu Met Ile Arg Ser Glu Asp Ala Gly Phe Val Val Ile Thr
65                  70                  75                  80

Gly Val Thr Ser Arg Arg Phe Leu Cys Met Asp Phe Arg Gly Asn Ile
                85                  90                  95

Phe Gly Ser His His Phe Asn Pro Gln Asp Cys Arg Phe Gln His Arg
            100                 105                 110

Thr Leu Glu Asn Gly Tyr Asp Val Tyr Leu Ser Pro Glu His His Phe
        115                 120                 125

Leu Ile Ser Leu Gly Arg Thr Lys Lys Phe Phe Leu Pro Gly Thr Asn
    130                 135                 140

Pro Pro Pro Tyr Ser Gln Phe Leu Ser Arg Arg Asn Glu Leu Pro Leu
145                 150                 155                 160

Ala Arg Phe Val Thr Pro Gly Pro Arg Arg His Thr Arg Ser Ala Glu
                165                 170                 175

Glu Asp Gln Gly Arg Asp Pro Leu Ser Val Leu Lys Leu Arg Pro Arg
            180                 185                 190

Ala Thr Pro Ala Pro Ala Ser Cys Ser Gln Glu Leu Pro Ser Ala Glu
        195                 200                 205

Asp Ala Ala Gln Ala Ser Asp Pro Leu Gly Val Leu Arg Gly Ala Arg
    210                 215                 220

Val His Ala His Gly Gly Pro Arg Pro Ala Arg Cys Arg Pro Gly Pro
225                 230                 235                 240

Gly Ala Lys

<210> SEQ ID NO 252
<211> LENGTH: 251
<212> TYPE: PRT
<213> ORGANISM: Cricetulus griseus

```
<400> SEQUENCE: 252

Met Leu Gly Thr Cys Leu Arg Leu Leu Val Gly Val Leu Cys Ser Ala
1               5                   10                  15

Cys Ser Leu Gly Thr Val Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Lys Asp Gly Arg Val Asp Gly Thr
    50                  55                  60

Pro His Gln Thr Ile Tyr Ser Ala Leu Met Ile Arg Ser Glu Asp Ala
65                  70                  75                  80

Gly Phe Val Ile Ile Thr Gly Ala Val Thr Arg Arg Phe Leu Cys Met
                85                  90                  95

Asp Leu Arg Gly Asn Ile Phe Gly Ser His His Phe Ser Pro Glu Asn
            100                 105                 110

Cys Arg Phe Arg Gln Arg Thr Leu Glu Asn Gly Tyr Asp Val Tyr Leu
        115                 120                 125

Ser Pro Gln His His Tyr Leu Val Ser Leu Gly Arg Ala Lys Arg Pro
    130                 135                 140

Phe Glu Pro Gly Thr Asn Pro Pro Phe Ser Gln Phe Leu Ala Arg
145                 150                 155                 160

Arg Asn Glu Val Pro Leu Leu Arg Phe His Thr Ala Arg Pro Arg Arg
                165                 170                 175

His Thr Arg Ser Ala Glu Asp Pro Pro Glu Trp Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Asp Leu Ala Ala Ser Asp Pro Leu
    210                 215                 220

Gly Val Leu Arg Arg Gly Arg Gly Asp Ala Arg Gly Gly Ala Gly Gly
225                 230                 235                 240

Val Asp Arg Cys Arg Pro Phe Pro Arg Phe Ala
                245                 250

<210> SEQ ID NO 253
<211> LENGTH: 180
<212> TYPE: PRT
<213> ORGANISM: Tupaia belangeri

<400> SEQUENCE: 253

Ala Leu Leu Ile Arg Pro Glu Glu Ala Gly Phe Ala Val Ile Thr Gly
1               5                   10                  15

Val Met Ser Arg Arg Tyr Leu Cys Met Asp Phe Arg Gly Asn Ile Phe
            20                  25                  30

Gly Ser His Leu Phe Ser Pro Glu Ser Cys Arg Phe Arg Gln Arg Ala
        35                  40                  45

Leu Glu Asn Gly Tyr Asp Val Tyr His Pro Gln His His Phe Leu
    50                  55                  60

Val Ser Leu Gly Arg Pro Lys Arg Ala Phe Val Pro Gly Thr Asn Pro
65                  70                  75                  80

Pro Pro Tyr Ser Gln Phe Leu Ala Arg Lys Asn Glu Ile Pro Leu Ile
                85                  90                  95

His Phe Asn Thr Pro Lys Pro Arg Arg His Thr Arg Ser Ala Glu Asp
            100                 105                 110
```

Asn Ser Gly Arg Asp Pro Leu Asn Val Leu Lys Pro Arg Pro Arg Met
        115                 120                 125

Thr Pro Ala Pro Ala Ser Cys Ser Gln Glu Leu Pro Ser Ala Glu Asp
    130                 135                 140

Asn Ser Val Val Ala Ser Asp Pro Leu Gly Val Leu Arg Gly Asn Arg
145                 150                 155                 160

Val Asn Thr His Ala Gly Gly Trp Gly Val Asp Arg Cys Arg Pro Phe
                165                 170                 175

Pro Arg Phe Ile
        180

<210> SEQ ID NO 254
<211> LENGTH: 251
<212> TYPE: PRT
<213> ORGANISM: Rattus norvegicus

<400> SEQUENCE: 254

Met Leu Gly Ala Cys Leu Arg Leu Leu Val Gly Ala Leu Cys Thr Val
1               5                   10                  15

Cys Ser Leu Gly Thr Ala Arg Ala Tyr Ser Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Ile Gly Ala Met Thr Arg Arg Phe Leu Cys Met
                85                  90                  95

Asp Leu Arg Gly Asn Ile Phe Gly Ser Tyr His Phe Ser Pro Glu Asn
            100                 105                 110

Cys Arg Phe Arg Gln Trp Thr Leu Glu Asn Gly Tyr Asp Val Tyr Leu
        115                 120                 125

Ser Pro Lys His His Tyr Leu Val Ser Leu Gly Arg Ser Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Ala Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Ile Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Arg Gly Ala Gly Gly
225                 230                 235                 240

Thr Asp Arg Cys Arg Pro Phe Pro Arg Phe Val
                245                 250

<210> SEQ ID NO 255
<211> LENGTH: 251
<212> TYPE: PRT
<213> ORGANISM: Mus musculus

<400> SEQUENCE: 255

```
Met Leu Gly Thr Cys Leu Arg Leu Leu Val Gly Ala Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 256
<211> LENGTH: 248
<212> TYPE: PRT
<213> ORGANISM: Pteropus vampyrus

<400> SEQUENCE: 256

Met Pro Arg Gly Ser Leu Gly Leu Leu Val Cys Ile Leu Cys Cys Arg
1               5                   10                  15

Ala Tyr Pro Asp Ala Ser Pro Leu Leu Ser Ser Ser Leu Gly Gly Leu
            20                  25                  30

Ile His Leu Tyr Thr Ala Thr Ala Arg Asn Gly Tyr His Leu Gln Ile
        35                  40                  45

His Lys Asp Gly His Val Asp Gly Thr Pro His Gln Thr Ile Tyr Ser
    50                  55                  60

Ala Leu Met Ile Arg Ser Glu Asp Ser Gly Phe Val Val Ile Ile Gly
65                  70                  75                  80

Val Met Ser Arg Arg Tyr Leu Cys Met Asp Phe Lys Gly Asn Ile Phe
                85                  90                  95

Gly Ser His His Phe Ser Pro Glu Ser Cys Lys Phe Arg Gln Arg Thr
            100                 105                 110

Leu Glu Asn Gly Tyr Asp Val Tyr His Ser Pro Gln His His Phe Phe
        115                 120                 125
```

Val Ser Leu Gly Arg Ala Lys Arg Ala Phe Leu Pro Gly Thr Asn Pro
            130                 135                 140

Pro Pro Tyr Ser Gln Phe Leu Ser Arg Arg Asn Glu Ile Pro Leu Phe
145                 150                 155                 160

Gln Phe Asn Thr Pro Arg Pro Arg Arg His Thr Arg Ser Val Glu Asp
                165                 170                 175

Tyr Lys Asp Tyr Asp Leu Asp Pro Asp Pro Leu Lys Val Leu Arg Pro
            180                 185                 190

Arg Pro Arg Trp Val Pro Ala Leu Pro Ser Cys Ser Gln Glu Leu Pro
        195                 200                 205

Ser Ala Glu Asp Asn Ser Val Val Ala Asn Asp Pro Leu Gly Val Leu
        210                 215                 220

Arg Pro Ser Arg Val Asn Ile Tyr Arg Glu Arg Met Gly Lys Gly Arg
225                 230                 235                 240

Cys Arg Pro His Pro Glu Phe Val
                245

<210> SEQ ID NO 257
<211> LENGTH: 248
<212> TYPE: PRT
<213> ORGANISM: Myotis lucifugus

<400> SEQUENCE: 257

Met Pro Gly Ala Arg Leu Gly Leu Leu Val Cys Val Leu Ala Leu Arg
1               5                   10                  15

Cys Val Val Arg Ala Tyr Pro Asn Ala Ser Pro Leu Leu Gly Ser Ser
            20                  25                  30

Trp Gly Gly Leu Thr His Leu Tyr Thr Ala Ser Ala Arg Asn Ser Tyr
        35                  40                  45

His Leu Gln Ile His Lys Asp Gly His Val Asp Gly Thr Pro His Gln
    50                  55                  60

Thr Ile Tyr Ser Ala Leu Met Ile Arg Ser Glu Asp Ala Gly Phe Val
65                  70                  75                  80

Val Ile Thr Gly Val Met Ser Arg Arg Tyr Leu Cys Met Asp Phe Arg
                85                  90                  95

Gly Asn Ile Phe Gly Ser Leu Phe Ser Pro Ser Asn Phe Ser Phe
            100                 105                 110

Leu Glu Trp Lys Lys Glu Ser Gly Met Asp His Trp Ile Ser Arg Gln
        115                 120                 125

Thr His Phe Leu Val Ser Pro Gly Pro Ser Gln Glu Gly Leu Pro Ala
    130                 135                 140

Gly His Asn Pro Pro Tyr Ser Gln Phe Leu Ser Arg Asn Glu Ile
145                 150                 155                 160

Pro Leu Phe His Phe Asn Thr Pro Ala Pro Arg Arg His Thr Arg Ser
                165                 170                 175

Ala Glu Glu Asn Ser Ala Ala Asp Pro Leu Val Val Leu Lys Pro Val
            180                 185                 190

Pro Arg Leu Thr Pro Pro Ala Ser Cys Ser Arg Glu Leu Ser Ser
        195                 200                 205

Ala Glu Asp Asn Ser Val Ala Ala His Asp Pro Leu Gly Val Leu Arg
        210                 215                 220

Ser Ser Asn Arg Val Asn Ser His Ala Pro Pro Gly Pro Arg
225                 230                 235                 240

Thr Arg Gln Gly Met Leu Leu Val

-continued

```
                  245

<210> SEQ ID NO 258
<211> LENGTH: 245
<212> TYPE: PRT
<213> ORGANISM: Sarcophilus harrisii

<400> SEQUENCE: 258

Met Ser Gly Gly Cys Leu Arg Leu Leu Phe Ala Leu Cys Ser Leu
1               5                   10                  15

Arg Ala Ile Gln Ala Phe Pro Asn Ala Ser Pro Leu Leu Ser Leu Gly
            20                  25                  30

Trp Gly Gly Leu Thr His Leu Tyr Thr Ala Thr Ala Arg Asn Ser Tyr
        35                  40                  45

His Leu Gln Ile His Lys Asp Gly His Val Asp Gly Ser Pro His Gln
    50                  55                  60

Thr Ile Tyr Ser Ala Leu Met Ile Arg Ser Glu Asp Ala Gly Leu Val
65                  70                  75                  80

Ile Ile Thr Gly Val Met Ser Arg Arg Tyr Leu Cys Met Asp Ile Arg
                85                  90                  95

Gly Asn Ile Phe Gly Ser His Phe Phe Ser Pro Asp Asn Cys Arg Phe
            100                 105                 110

Lys His Arg Thr Leu Glu Asn Gly Tyr Asp Ile Tyr His Ser Pro Gln
        115                 120                 125

Asn Asn Phe Leu Ile Ser Leu Gly Lys Ala Lys Arg Ala Phe Leu Pro
    130                 135                 140

Gly Met Asn Pro Pro Tyr Ser Gln Phe Leu Ser Arg Arg Asn Glu
145                 150                 155                 160

Ile Pro Ile Ile His Phe Asn Thr Pro Glu Pro His Arg His Thr Arg
                165                 170                 175

Ser Ala Glu Asn Ser Pro Asp Leu Asp Pro Met Asn Val Leu Lys Leu
            180                 185                 190

Arg Pro Arg Ile Thr Pro Cys Ser Gln Glu Leu His Ser Ala Glu Glu
        195                 200                 205

Asn Ser Val Val Asp Asp Pro Leu Glu Val Leu Arg Asn Ser Asn
    210                 215                 220

Arg Leu Lys Pro Tyr Pro Gly Arg Met Ser Leu Glu Arg Cys Leu His
225                 230                 235                 240

Val Pro Lys Ala Ala
            245

<210> SEQ ID NO 259
<211> LENGTH: 191
<212> TYPE: PRT
<213> ORGANISM: Monodelphis domestica

<400> SEQUENCE: 259

Met Ala Asn Cys Arg Glu Lys Glu Leu Glu Met Tyr Ile Cys Ala Leu
1               5                   10                  15

Met Ile Arg Ser Glu Asp Ala Gly Leu Val Ile Ile Thr Gly Val Met
            20                  25                  30

Ser Arg Arg Tyr Leu Cys Met Asp Ile Arg Gly Asn Ile Phe Gly Ser
        35                  40                  45

His Phe Phe Asn Pro Asp Asn Cys Lys Phe Lys His Arg Thr Leu Glu
    50                  55                  60

Asn Gly Tyr Asp Ile Tyr His Ser Pro Gln Asn Asn Phe Leu Ile Ser
```

```
                65                  70                  75                  80
Leu Gly Lys Ala Lys Arg Ala Phe Leu Pro Gly Met Asn Pro Pro Pro
                    85                  90                  95

Tyr Ser Gln Phe Leu Ser Arg Lys Asn Glu Ile Pro Ile Ile His Phe
                100                 105                 110

Asn Thr Pro Glu Pro His Arg His Thr Arg Ser Ala Glu Asn Ser Pro
                115                 120                 125

Asp Leu Asp Pro Met Asn Val Leu Lys Pro Arg Pro Arg Met Thr Pro
130                 135                 140

Cys Ser Gln Glu Leu Tyr Ser Ala Glu Glu Asn Ser Val Val Asp Asp
145                 150                 155                 160

Asp Pro Leu Glu Val Leu Arg Asn Ser Asn Arg Leu Lys Pro Phe Pro
                165                 170                 175

Gly Arg Leu Gly Leu Glu Arg Cys His His Val Pro Lys Thr Asp
                180                 185                 190

<210> SEQ ID NO 260
<211> LENGTH: 180
<212> TYPE: PRT
<213> ORGANISM: Dasypus novemcinctus

<400> SEQUENCE: 260

Ala Leu Met Ile Ser Ser Glu Asp Ala Gly Phe Val Val Ile Thr Gly
1               5                   10                  15

Val Met Ser Arg Arg Tyr Leu Cys Met Asp Phe Arg Gly Asn Ile Phe
                20                  25                  30

Gly Ser His Asp Phe Thr Pro Asp Ser Cys Arg Phe Gln Arg Thr
                35                  40                  45

Leu Glu Asn Gly Tyr Asp Val Tyr His Ser Pro Gln His His Phe Leu
50                  55                  60

Val Ser Leu Gly Arg Ala Lys Arg Ala Phe Gln Pro Gly Ser Asn Pro
65                  70                  75                  80

Pro Pro Tyr Ser Gln Phe Leu Ser Arg Arg Asn Glu Ile Pro Leu Met
                85                  90                  95

Arg Phe Ser Thr Pro Arg Pro Arg His Thr Arg Ser Ala Gln Asp
                100                 105                 110

His Ala Asp Pro Asp Pro Leu Arg Val Leu Lys Pro Arg Leu Arg Leu
                115                 120                 125

Thr Pro Ala Pro Ala Ser Cys Ser Gln Glu Leu Pro Ser Asp Glu Asp
130                 135                 140

Asp Gly Ala Val Ala Ser Asp Pro Leu Arg Val Val Leu Gly Arg Arg
145                 150                 155                 160

Pro His Ala Arg Ala Ala Gly Ala Gly Gly Glu Arg Cys Arg Pro Gly
                165                 170                 175

Pro Gln Leu Ser
            180

<210> SEQ ID NO 261
<211> LENGTH: 177
<212> TYPE: PRT
<213> ORGANISM: Macropus eugenii

<400> SEQUENCE: 261

Ala Leu Met Ile Arg Ser Glu Asp Ala Gly Leu Val Ile Ile Ser Gly
1               5                   10                  15

Val Met Ser Arg Arg Tyr Leu Cys Met Asp Leu Arg Gly Asn Ile Phe
```

```
            20                  25                  30
Gly Ser His Phe Phe Ser Pro Asp Asn Cys Arg Phe Lys His Arg Thr
         35                  40                  45
Leu Glu Asn Gly Tyr Asp Ile Tyr His Ser Pro Gln Asn Asn Leu Leu
 50                  55                  60
Ile Ser Leu Gly Lys Ala Lys Arg Ala Phe Leu Pro Gly Met Asn Pro
 65                  70                  75                  80
Pro Pro Tyr Ser Gln Phe Leu Ser Arg Arg Asn Glu Ile Pro Ile Ile
                 85                  90                  95
His Phe Asn Thr Pro Glu Pro Arg Arg His Thr Arg Ser Ala Glu Asn
                100                 105                 110
Ser Pro Asp Leu Asp Pro Met Asn Val Leu Lys Pro Arg Pro Arg Val
                115                 120                 125
Thr Pro Cys Ser Gln Glu Leu Arg Ser Ala Glu Asn Ser Val Val
                130                 135                 140
Asp Asp Asp Pro Leu Glu Val Leu Arg Asn Ser Asn Arg Leu Lys Pro
145                 150                 155                 160
Tyr Pro Gly Arg Met Ser Leu Glu Arg Cys Leu Gln Val Pro Lys Ala
                165                 170                 175
Ala

<210> SEQ ID NO 262
<211> LENGTH: 256
<212> TYPE: PRT
<213> ORGANISM: Taeniopygia guttata

<400> SEQUENCE: 262

Met Glu Trp Arg Ala Thr Leu Gln Gly Ile Pro Cys Ser Ser Leu Leu
 1               5                  10                  15
Leu Leu Leu Cys Ser Leu Lys Ala Ser Leu Ala Phe Pro Asn Ser Ser
                 20                  25                  30
Pro Leu Leu Ser Pro Ser Trp Gly Asn Gly Asp Arg Leu Met His Leu
                 35                  40                  45
Tyr Thr Asp Thr Glu Arg Ser Ser Phe His Leu Gln Ile Asn Ala Asp
 50                  55                  60
Gly Tyr Ile Asp Gly Ala Pro His Gln Thr Ile Tyr Ser Ala Leu Met
 65                  70                  75                  80
Ile Lys Ser Glu Gly Ala Gly Ser Val Ile Ile Thr Gly Val Lys Ser
                 85                  90                  95
Gly Arg Tyr Leu Cys Met Asp Met Lys Gly Asn Ile Phe Gly Ser His
                100                 105                 110
Tyr Phe Ser Gln Glu Asp Cys Met Phe Asn His Arg Thr Leu Glu Asn
                115                 120                 125
Gly Tyr Asp Val Tyr Gln Ser Pro Lys His His Phe Leu Val Ser Leu
                130                 135                 140
Gly Arg Val Lys Gln Val Phe Ser Pro Gly Met Asn Pro Pro Tyr
145                 150                 155                 160
Ser Gln Phe Leu Ser Arg Lys Asn Glu Ile Pro Leu Phe Arg Phe Asn
                165                 170                 175
Thr Pro Glu Pro His Arg His Thr Arg Ser Ala Asp Val Asp Pro Val
                180                 185                 190
Asp Pro His Gln Ile Leu Val Pro Gln Arg Lys Thr Pro Val Phe Gly
                195                 200                 205
Ser Leu Gln Gln Gln Pro Ala Asp Phe Pro His Met Pro Arg Glu Pro
```

```
                    210                 215                 220
Met Arg Ile Asn Gln Asn Asp Val Val Asn Pro Asp Pro His Ala
225                 230                 235                 240

Met Met Glu Ala Arg Arg Tyr Pro Ser Pro Arg Phe Tyr Ile Thr Arg
                245                 250                 255
```

<210> SEQ ID NO 263
<211> LENGTH: 254
<212> TYPE: PRT
<213> ORGANISM: Gallus gallus

<400> SEQUENCE: 263

```
Met Pro His Thr Ser Pro Cys Ser Cys Leu Glu Tyr Met Leu Leu Val
1               5                   10                  15

Leu Cys Ile Leu Lys Ala Ala Val Ala Phe Pro Asn Ser Ser Pro Leu
                20                  25                  30

Leu Asn Pro Ser Trp Gly Asn Gly Asp Gln Leu Met His Leu Tyr Thr
            35                  40                  45

Ser Thr Glu Arg Asn Ser Phe His Leu Gln Ile Asn Ala Asp Gly His
        50                  55                  60

Ile Asn Gly Val Pro His Gln Thr Ile Tyr Ser Ala Leu Met Ile Lys
65                  70                  75                  80

Ser Glu Gly Ala Gly Cys Val Ile Ile Thr Gly Val Lys Ser Gly Arg
                85                  90                  95

Tyr Leu Cys Met Asp Met Lys Gly Asp Ile Phe Gly Ser Tyr Tyr Phe
                100                 105                 110

Ser Gln Glu Asp Cys Val Phe Asn Gln Arg Thr Leu Glu Asn Gly Tyr
            115                 120                 125

Asp Val Tyr Gln Ser Pro Lys His Asn Phe Leu Val Ser Leu Gly Arg
        130                 135                 140

Thr Lys Gln Val Phe Phe Pro Gly Met Asn Pro Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Leu Asp Pro
                180                 185                 190

His Gln Ile Leu Val Pro Gln Arg Lys Val Ser Ala Leu Gly Ser Gln
            195                 200                 205

Leu Gln Leu Gln Met Asp Phe Ser His Val Pro Arg Glu Pro Met Arg
        210                 215                 220

Val Asn Gln Asn Asp Val Val Asn Pro Asp Pro His Ala Met Met
225                 230                 235                 240

Asp Ala Arg Arg Tyr Ala Ser Pro Arg Phe Tyr Ile Thr Arg
                245                 250
```

<210> SEQ ID NO 264
<211> LENGTH: 254
<212> TYPE: PRT
<213> ORGANISM: Meleagris gallopavo

<400> SEQUENCE: 264

```
Met Pro His Thr Ser Pro Cys Ser Cys Leu Glu Tyr Met Leu Leu Val
1               5                   10                  15

Leu Cys Ile Leu Lys Ala Ala Val Ser Phe Pro Asn Ser Ser Pro Leu
                20                  25                  30

Leu Asn Pro Ser Trp Gly Asn Gly Asp Gln Leu Met His Leu Tyr Thr
```

```
                35                  40                  45
Ser Thr Glu Arg Asn Ser Phe His Leu Gln Ile Asn Ala Asp Gly His
 50                  55                  60

Ile Ser Gly Val Pro Tyr Gln Thr Ile Tyr Ser Ala Leu Met Ile Lys
 65                  70                  75                  80

Ser Glu Gly Ala Gly Ser Val Ile Ile Thr Gly Val Lys Ser Gly Arg
                 85                  90                  95

Tyr Leu Cys Met Asp Met Lys Gly Asp Ile Phe Gly Ser His Tyr Phe
                100                 105                 110

Ser Gln Glu Asp Cys Val Phe Asn Gln Arg Thr Leu Glu Asn Gly Tyr
                115                 120                 125

Asp Val Tyr Gln Ser Pro Lys His Asn Phe Leu Val Ser Leu Gly Arg
130                 135                 140

Thr Lys Gln Val Phe Phe Pro Gly Met Asn Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Met Asp Pro
                180                 185                 190

His Gln Ile Leu Val Pro Gln Arg Lys Val Ser Ala Ile Glu Ser Gln
                195                 200                 205

Leu Gln Leu Gln Met Asp Phe Ser His Val Pro Arg Glu Pro Met Arg
210                 215                 220

Val Asn Gln Asn Asp Val Val Asn Pro Asp Asp Pro His Ala Met Met
225                 230                 235                 240

Asp Ala Arg Arg Tyr Ala Ser Pro Arg Phe Tyr Ile Thr Arg
                245                 250

<210> SEQ ID NO 265
<211> LENGTH: 242
<212> TYPE: PRT
<213> ORGANISM: Anolis carolinensis

<400> SEQUENCE: 265

Met Val Gln Ala Thr Leu Tyr Ser Phe Leu Lys Tyr Met Leu Leu Ala
 1               5                  10                  15

Thr Cys Ser Trp Lys Ala Ile Ala Ala Phe Pro Asn Ala Ser Pro Leu
                20                  25                  30

Leu Ser Leu Asn Trp Gly Asn Ser Asp Ser Leu Leu His Leu Tyr Thr
                35                  40                  45

Ser Thr Ala Arg Asn Ser Phe His Leu Gln Ile His Ser Asn Gly Tyr
 50                  55                  60

Val Asp Gly Ser Pro Tyr Gln Thr Ile Tyr Ser Ala Leu Met Ile Lys
 65                  70                  75                  80

Ser Glu Val Ala Gly Tyr Val Ile Ile Asn Gly Val Lys Ser Gly Arg
                 85                  90                  95

Phe Leu Cys Met Asp Met Asn Gly Asn Ile Phe Gly Ser His Phe Phe
                100                 105                 110

Ser Tyr Glu Asp Cys Thr Phe Lys His Trp Val Leu Glu Asn Gly Tyr
                115                 120                 125

Asp Val Tyr Gln Ser Pro Lys Tyr Asn Tyr Leu Val Ser Leu Gly Lys
130                 135                 140

Ala Lys Gln Pro Leu Phe Pro Asn Met Asn Pro Pro Tyr Ser Gln
145                 150                 155                 160
```

Phe Leu Ser Arg Arg Asn Glu Ile Pro Leu Val Gln Phe Asn Thr Pro
              165                 170                 175

Lys Pro His Arg His Thr Arg Ser Ala Asn Ala Asp Pro Cys Gly Ser
            180                 185                 190

Ile Ile Ser Ser Gly Asn Ile Ala Lys Glu Asn Leu Gln Leu Gln Pro
            195                 200                 205

Leu Met Tyr Asn Thr Lys Met Asn Ser Asn Ser Glu Asp Glu Asp Pro
        210                 215                 220

Asn Ser Ala Ile Ile Asn Arg Arg Phe Leu Ser Pro Arg Thr Asp Val
225                 230                 235                 240

Arg Ser

<210> SEQ ID NO 266
<211> LENGTH: 249
<212> TYPE: PRT
<213> ORGANISM: Latimeria chalumnae

<400> SEQUENCE: 266

Leu Glu Ser Ala Leu Leu Ala Phe Ser Met Ala Ile Phe Tyr Ser Phe
1               5                   10                  15

Lys Ala Val Ser Ser Phe Pro Asn Ser Ser Pro Leu Leu Asn Pro Val
            20                  25                  30

Trp Gly Asn Thr Asp Asn Leu Ile His Leu Tyr Thr Ala Ser Glu Thr
        35                  40                  45

Asn Ser Phe His Leu Gln Ile Asn Ser Asp Gly His Val Asp Gly Thr
    50                  55                  60

Pro His Gln Thr Ala Tyr Ser Ala Leu Leu Ile Lys Ser Glu Glu Ala
65                  70                  75                  80

Gly Ser Val Val Ile Leu Gly Val Lys Ser Gly Arg Tyr Leu Cys Met
                85                  90                  95

Asp Ile Lys Gly Asn Ile Ile Gly Leu His His Phe Ser Lys Glu Asp
            100                 105                 110

Cys Thr Phe Lys Gln Glu Gly Leu Glu Asn Gly Phe Asp Val Leu Arg
        115                 120                 125

Ser Pro Lys His Asn Ile Leu Val Ser Leu Asp Lys Thr Lys Arg Ser
    130                 135                 140

Tyr Ile Pro Gly Met Asn Leu Pro Pro Tyr Ser Gln Phe Leu Ser Arg
145                 150                 155                 160

Gln Asn Glu Val Ala Leu Ile Asn Phe Ile Asn Thr Pro Asp Ile His
                165                 170                 175

Arg His Ser Arg Asn Val Asp Val Asp Pro Ser Asp Pro His Gly Met
            180                 185                 190

Ile Ile Gln Pro Asp Val Gly Val Ser Phe Arg Lys Ser Ser Ser Leu
        195                 200                 205

Phe Ser Asp Leu Pro Arg Asp Ser Met Arg Thr Ser His Asn Gly Met
    210                 215                 220

Asp Met Val Asp Pro Ala Asp Pro His Gly Met Leu Asp Ser Arg Arg
225                 230                 235                 240

Arg Pro Ser Pro Arg Phe Phe Ala Arg
                245

<210> SEQ ID NO 267
<211> LENGTH: 254
<212> TYPE: PRT
<213> ORGANISM: Xenopus silurana tropicalis -continued

```
<400> SEQUENCE: 267

Met Thr Lys Gln Gln Thr Arg Leu Gly Leu Val Leu Thr Val Leu Ala
1               5                   10                  15

Ser Ile Lys Val Ile Ser Ala Phe Pro Asn Ser Pro Ile Ile Ser
            20                  25                  30

Gly Gly Trp Gly Val Pro Asp Arg Leu Met His Leu Tyr Thr Ala Ser
            35                  40                  45

Asp Trp Asn Ser Phe His Leu Gln Ile Asn His Asp Gly Ser Ile Asp
50                  55                  60

Gly Thr Pro Thr Gln Thr Ile Tyr Ser Ala Ile Met Ile Lys Ser Glu
65                  70                  75                  80

Ser Ala Gly His Val Val Ile Thr Gly Val Lys Thr Asn Arg Tyr Leu
                85                  90                  95

Cys Met Asp Lys Ser Gly Asn Ile Phe Gly Tyr His Phe Asn His
            100                 105                 110

Asp Asp Cys Val Phe Lys His Glu Thr Leu Glu Asn Asn Phe Asp Val
        115                 120                 125

Tyr His Ser Pro Lys His Asn Phe Val Ile Ser Leu Lys Glu Pro Lys
130                 135                 140

His His Phe Arg Leu Gly Met Asp Leu Pro Pro Tyr Ser Gln Phe Leu
145                 150                 155                 160

Ser Leu Glu Asn Glu Ile Pro Ile Thr Arg Phe Asn Ala Pro Glu Pro
                165                 170                 175

Glu Met Arg Ile Pro Glu Gly Asn Phe Ala Asp Pro Ser Asp Ile Ile
            180                 185                 190

Lys Asn Pro Arg Asn Trp Asp Phe Ser Gln Ser Ile His Asn Pro Phe
        195                 200                 205

Gln Asp Val Trp Leu Pro Phe Pro Ser Gly Ser Leu Pro Ile Ile Arg
    210                 215                 220

Ala Ser Leu Pro Ile Ile His Asn Asn Val Ile Asn Thr Asp Asp Pro
225                 230                 235                 240

Glu Glu Ile Val Lys Met Lys Arg Tyr Arg Tyr Phe Lys Arg
                245                 250

<210> SEQ ID NO 268
<211> LENGTH: 199
<212> TYPE: PRT
<213> ORGANISM: Felis catus

<400> SEQUENCE: 268

Met Ser Gly Thr Arg Leu Gly Leu Leu Val Ser Val Leu Cys Trp Val
1               5                   10                  15

Val Arg Ala Tyr Pro Asn Thr Ser Pro Leu Leu Gly Ser Ser Trp Gly
            20                  25                  30

Gly Leu Thr His Leu Tyr Thr Ala Thr Ala Arg Asn Ser Tyr His Leu
            35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Gln Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110
```

```
Arg Thr Leu Glu Asn Gly Tyr Asp Val Tyr His Ser Pro Gln His Arg
            115                 120                 125

Phe Leu Val Ser Leu Gly Pro Ala Lys Arg Ala Phe Leu Pro Gly Thr
130                 135                 140

Asn Arg Met Thr Pro Ala Pro Ala Ser Cys Ser Gln Glu Leu Pro Ser
145                 150                 155                 160

Ala Glu Asp Ser Gly Val Val Ala Ser Asp Pro Leu Gly Val Leu Arg
                165                 170                 175

Gly Asn Arg Val Asn Ala His Ala Gly Gly Met Gly Val Glu Arg Cys
            180                 185                 190

Arg Pro Phe Pro Lys Phe Asn
        195

<210> SEQ ID NO 269
<211> LENGTH: 250
<212> TYPE: PRT
<213> ORGANISM: Pelodiscus sinensis

<400> SEQUENCE: 269

Met Ser Gln Pro Ser Gln Cys Ser Cys Leu Asn Phe Met Leu Phe Val
1               5                   10                  15

Leu Cys Ser Phe Lys Ala Ile Ala Ala Phe Pro Phe Ser Ser Leu
                20                  25                  30

Leu Asn Pro Ser Trp Gly Glu Thr Asp Ser Leu Ile His Leu Tyr Thr
            35                  40                  45

Ala Thr Glu Lys Asn Ser Phe His Leu Gln Ile Asn Pro Asp Gly Tyr
        50                  55                  60

Val Asp Gly Thr Pro His Gln Thr Ile Tyr Ser Ala Leu Met Ile Lys
65                  70                  75                  80

Ser Glu Asp Ala Gly Tyr Val Val Ile Ser Gly Val Lys Ser Gly Arg
                85                  90                  95

Tyr Leu Cys Met Asp Ile Lys Gly Asn Ile Phe Gly Ser His Tyr Phe
            100                 105                 110

Ser Gln Glu Asp Cys Met Phe Lys His Arg Thr Leu Glu Asn Gly Tyr
        115                 120                 125

Asp Val Tyr Gln Ser Pro Lys His Asn Phe Leu Val Ser Leu Gly Arg
    130                 135                 140

Asn Lys Gln Ala Phe Phe Pro Gly Met Asn Leu Pro Pro Tyr Ser Gln
145                 150                 155                 160

Phe Leu Pro Arg Arg Asn Glu Ile Pro Leu Ile Arg Phe Asn Thr Pro
                165                 170                 175

Glu Pro His Arg His Thr Arg Asn Ala Asp Val Asp Pro Leu Gln Ile
            180                 185                 190

Leu Ile Pro Arg Gly Glu Ala Phe Asp Thr Gly Pro Gln Arg Leu Gln
        195                 200                 205

Thr His Phe Asp His Leu Pro Arg Glu Pro Met Arg Ile Asn Pro Asn
    210                 215                 220

Asp Val Val Ser Pro Asp Pro Leu Ala Met Met Asp Val Arg Arg
225                 230                 235                 240

Asn Ala Ser Pro Arg Leu Tyr Ile Thr Arg
                245                 250

<210> SEQ ID NO 270
<211> LENGTH: 245
<212> TYPE: PRT
<213> ORGANISM: Mustela putorius furo
```

```
<400> SEQUENCE: 270

Met Ser Val Thr Arg Leu Gly Leu Leu Val Ser Val Leu Cys Trp Val
1               5                   10                  15

Val Arg Ala Tyr Pro Asn Ala Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Gln Ala Lys Arg Ala Phe Leu Pro Gly Thr
    130                 135                 140

Asn Pro Pro Tyr Ser Gln Phe Leu Ser Arg Arg Asn Glu Ile Pro
145                 150                 155                 160

Leu Ile His Phe Asn Thr Pro Arg Pro Arg His Thr Arg Ser Ala
                165                 170                 175

Glu Asp Met Glu His Asp Pro Leu Asn Val Leu Lys Pro Arg Pro Arg
            180                 185                 190

Met Thr Pro Ala Pro Ala Ser Cys Ser Gln Glu Leu Pro Ser Ala Glu
        195                 200                 205

Asp Asn Ser Val Val Ala Ser Asp Pro Leu Gly Val Leu Arg Gly Asn
    210                 215                 220

Arg Val Asn Val His Ala Gly Gly Met Gly Val Asp Arg Cys Arg Pro
225                 230                 235                 240

Leu Pro Lys Phe Ile
                245

<210> SEQ ID NO 271
<211> LENGTH: 206
<212> TYPE: PRT
<213> ORGANISM: Microcebus murinus

<400> SEQUENCE: 271

Met Leu Gly Ala Cys Leu Arg Leu Trp Val Cys Ala Leu Cys Ser Val
1               5                   10                  15

Cys Gly Val Ser Val Val Arg Ala Tyr Pro Asn Ala Ser Pro Leu Leu
            20                  25                  30

Ala Ser Ser Trp Gly Gly Leu Ile His Leu Tyr Thr Ala Thr Ala Arg
        35                  40                  45

Asn Ser Tyr His Leu Gln Ile His Lys Asp Gly His Val Asp Gly Thr
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Val Phe Ser Ala Glu Ser
            100                 105                 110
```

```
Cys Arg Phe Arg Gln Arg Thr Leu Glu Asn Gly Phe Asp Val Tyr Gln
            115                 120                 125

Ser Pro Gln His His Phe Leu Val Ser Leu Gly Arg Ala Lys Gly Ala
        130                 135                 140

Phe Pro Ala Gly Ala Lys Pro Pro Phe Pro Gln Phe Leu Pro Arg
145                 150                 155                 160

Gly Asn Glu Ala Pro Gly Arg Lys Thr Arg Gly Pro Glu Glu Lys Gly
                165                 170                 175

Ala Pro His Pro Leu Arg Gly Val Glu Ser Gly Gly Arg Lys Gly Gly
                180                 185                 190

Ala Pro Pro Leu Cys Leu Glu Arg Leu Ser Arg Ala Arg Glu
                195                 200                 205

<210> SEQ ID NO 272
<211> LENGTH: 193
<212> TYPE: PRT
<213> ORGANISM: Pongo abelii

<400> SEQUENCE: 272

Met Arg Asn Glu Ser Leu Pro Cys Leu Val Phe Ser Ile Gly Ala Leu
1               5                   10                  15

Met Ile Arg Ser Glu Asp Ala Gly Phe Val Val Ile Thr Gly Val Met
                20                  25                  30

Ser Arg Arg Tyr Leu Cys Met Asp Phe Arg Gly Asn Ile Phe Gly Ser
            35                  40                  45

His Tyr Phe Asn Pro Glu Asn Cys Arg Phe Gln His Gln Thr Leu Glu
        50                  55                  60

Asn Gly Tyr Asp Val Tyr His Ser Pro Gln His His Phe Leu Val Ser
65                  70                  75                  80

Leu Gly Arg Val Lys Arg Ala Phe Leu Pro Gly Met Pro Pro Pro Tyr
                85                  90                  95

Ser Gln Phe Leu Ser Arg Arg Asn Glu Ile Pro Leu Ile His Phe Asn
            100                 105                 110

Thr Pro Val Pro Arg Arg His Thr Arg Ser Ala Glu Asp Asp Thr Glu
        115                 120                 125

Arg Asp Pro Leu Lys Val Leu Lys Pro Arg Ala Arg Met Thr Pro Ala
    130                 135                 140

Pro Ala Ser Cys Ser Gln Glu Leu Pro Ser Ser Glu Asp Asn Ser Pro
145                 150                 155                 160

Met Ala Ser Asp Pro Leu Gly Val Val Arg Gly Gly Arg Val Asn Thr
                165                 170                 175

His Ala Gly Gly Thr Gly Pro Glu Gly Cys Arg Pro Phe Pro Lys Phe
            180                 185                 190

Ile

<210> SEQ ID NO 273
<211> LENGTH: 188
<212> TYPE: PRT
<213> ORGANISM: Sorex araneus

<400> SEQUENCE: 273

Met Trp Gly Leu Arg Leu Gly Leu Leu Val Gly Leu Leu Gly Cys Val
1               5                   10                  15

Asp Arg Ala Ser Pro Met Leu Ala Ser Ser Trp Gly Gly Leu Thr His
                20                  25                  30
```

Leu Tyr Thr Ala Thr Ala Arg Asn Ser Tyr His Leu Gln Ile His Lys
                35                  40                  45

Asp Gly Leu Val Asp Gly Ser Pro Gln Gln Thr Val Tyr His His Phe
 50                  55                  60

Ser Pro Glu Ser Cys Arg Phe Gln Gln Arg Thr Leu Glu Asn Gly Tyr
 65                  70                  75                  80

Asp Val Tyr Gln Ser Pro Gln His Arg Phe Leu Val Ser Leu Gly Arg
                 85                  90                  95

Pro Lys Arg Ala Phe Gln Pro Gly Ala Asn Pro Pro Tyr Ala Gln
                100                 105                 110

Phe Leu Ala Arg Arg Asn Glu Val Pro Leu Ala Arg Phe His Thr Pro
                115                 120                 125

Ala Pro Arg Arg His Thr Arg Ser Ala His Asp Asn Gly Asp Ala Asp
130                 135                 140

Pro Leu Asn Val Leu Ala Pro Arg Ala Ala Ala Ala Ser Cys Ser
145                 150                 155                 160

His Glu Leu Pro Ser Ala Glu Asp Asn Ser Val Val Ala Ser Asp Pro
                165                 170                 175

Leu Gly Val Ile Arg Ser Asn Arg Phe Arg Thr His
                180                 185

<210> SEQ ID NO 274
<211> LENGTH: 263
<212> TYPE: PRT
<213> ORGANISM: Tetraodon nigroviridis

<400> SEQUENCE: 274

Met Asp Val Asn Arg Arg Ile Gly Val Lys Asp Ala Leu Leu Ala Leu
 1               5                  10                  15

Leu Leu Ala Leu Leu Gln Gly Cys Pro Leu Gly Glu Thr Ala Pro Asn
                 20                  25                  30

Ala Ser Pro Leu Val Gly Ser Asn Trp Gly Asn Pro Arg Arg Tyr Val
                 35                  40                  45

His Leu Gln Thr Ser Thr Asp Met Ser Asn Phe Tyr Leu Glu Ile Arg
 50                  55                  60

Leu Asp Gly Thr Val Arg Lys Ser Thr Ala Arg Thr Ser Tyr Ser Val
 65                  70                  75                  80

Ile Leu Leu Lys Ala Asp Thr Arg Glu Arg Ile Ala Ile Leu Gly Val
                 85                  90                  95

Lys Ser Asn Arg Tyr Leu Cys Met Asp Leu Glu Gly Ser Pro Phe Ser
                100                 105                 110

Ser Pro Thr Cys Ile Arg Asp Asp Cys Leu Phe Asn His Ser Leu Leu
                115                 120                 125

Glu Asn Asn Arg Asp Val Tyr Tyr Ser Ser Arg Thr Gly Ile Leu Phe
                130                 135                 140

Asn Leu Glu Gly Ser Arg Gln Val Phe Val Val Gly Gln Asn Val Pro
145                 150                 155                 160

Gln Thr Ser Leu Phe Leu Pro Arg Thr Asn Thr Val Pro Leu Glu Arg
                165                 170                 175

Leu Leu Leu His Arg Asp Lys Arg Asn Gln Val Asp Pro Ser Asp
                180                 185                 190

Pro His Arg Val Ala Val Gly Arg Ala Glu Glu Gly Ser Asp Ser Arg
                195                 200                 205

Ala Leu Gln Glu Asp Asp Ala Asp Leu Glu Val Glu Thr Glu Val Glu
210                 215                 220

```
Val Gly Asp Asp Gly Arg Asn Ala Ser Arg Glu Arg Leu Gln Ala Pro
225                 230                 235                 240

Ser Asp His Asp Pro Trp Gly Val Phe Ser Ser Asn Pro Gly Ser Pro
                245                 250                 255

Arg Ser Ser Gly Thr Val Gly
            260

<210> SEQ ID NO 275
<211> LENGTH: 255
<212> TYPE: PRT
<213> ORGANISM: Oreochromis niloticus

<400> SEQUENCE: 275

Met Asp Val Asn Arg Arg Met Gly Met Arg Asp Thr Val Leu Ala Leu
1               5                   10                  15

Phe Leu Ala Val Leu Gln Gly Phe Pro Leu Gly Asp Thr Val Pro Asn
            20                  25                  30

Pro Ser Pro Leu Ala Gly Ser Asn Trp Gly Asn Pro Arg Arg Tyr Val
        35                  40                  45

His Leu Gln Thr Ser Thr Asp Leu Asn Asn Phe Tyr Leu Glu Ile Arg
    50                  55                  60

Leu Asp Gly Ser Val Arg Lys Thr Thr Ser Arg Ser Thr Tyr Ser Val
65                  70                  75                  80

Ile Leu Leu Lys Ser Glu Ala Arg Asp Arg Val Ala Ile Leu Gly Val
                85                  90                  95

Lys Ser Ser Arg Tyr Leu Cys Met Asp Leu Glu Gly Asn Pro Phe Ser
            100                 105                 110

Ser Pro Val Cys Leu Arg Asp Asp Cys Leu Phe Asn His Lys Leu Leu
        115                 120                 125

Glu Asn Asn Arg Asp Val Tyr Tyr Ser Ser Arg Thr Gly Ile Leu Phe
    130                 135                 140

Asn Leu Glu Gly Ser Arg Gln Val Tyr Ser Val Gly Gln Asn Leu Pro
145                 150                 155                 160

Gln Thr Ser Leu Phe Leu Pro Arg Lys Asn Thr Val Pro Leu Glu Arg
                165                 170                 175

Leu Leu Leu His Arg Glu Lys Arg Asn Arg Gly Gln Thr Glu Glu Gly
            180                 185                 190

Ser Asp Ser Arg Ala Val Pro Glu Glu Leu Glu Glu Arg Glu Val Glu
        195                 200                 205

Met Glu Thr Glu Ile Glu Thr Glu Val Gly Asp Asp Gly Arg Asn Val
    210                 215                 220

Ser Arg Glu Lys Leu Ala Ala Pro Ser Ser His Asp Pro Trp Asn Val
225                 230                 235                 240

His Phe Ser Asn Pro Ala Ser Pro Arg Ser Thr Gly Thr Val Gly
                245                 250                 255

<210> SEQ ID NO 276
<211> LENGTH: 258
<212> TYPE: PRT
<213> ORGANISM: Danio rerio

<400> SEQUENCE: 276

Met Arg Cys Ala Leu Ser Asn Leu His Met Leu His Ser Ser Val Leu
1               5                   10                  15

Ala Leu Trp Phe Thr Ala Leu Gln Gly Leu Arg Pro Ala Asp Ala Ala
            20                  25                  30
```

```
Pro Asn Pro Ser Pro Leu Leu Gly Ser Asn Trp Gly Asn Pro Arg Arg
         35                  40                  45

Tyr Ile His Leu Gln Thr Thr Ser Asp Leu Asn Asn Tyr Tyr Leu Glu
 50                  55                  60

Ile Ser Pro Ser Gly His Val Arg Lys Thr Thr Asn Arg Gly Ser Tyr
 65                  70                  75                  80

Ser Val Ile Leu Leu Lys Thr Glu Ser Arg Asp Arg Leu Ala Ile Phe
                 85                  90                  95

Gly Val Lys Ser Asn Arg Phe Leu Cys Met Asp Thr Gly Gly Thr Leu
                100                 105                 110

Phe Thr Ser Thr Ile Cys Asn Lys Glu Asp Cys Leu Phe His His Lys
             115                 120                 125

Leu Leu Glu Asn His Arg Asp Val Tyr Tyr Ser Thr Lys His Ser Ile
130                 135                 140

Leu Leu Asn Leu Asp Gly Asp Lys Gln Ala Phe Ile Ala Gly Gln Asn
145                 150                 155                 160

Leu Pro Gln Ser Ser Leu Phe Leu Ser Glu Lys Asn Thr Val Pro Leu
                165                 170                 175

Glu Arg Leu Gln His Arg Glu Arg Arg Asn Arg Gln Val Asn Pro Thr
            180                 185                 190

Asp Pro Leu Asn Ala Leu Arg Tyr Ala Glu Glu Ser Asp Ser Arg Ala
        195                 200                 205

Ala Gln Glu Asp Asp Gly Asp Met Asp Phe Glu Pro Ser Glu Gly Gln
210                 215                 220

Asn Ile Ser Arg Glu Thr Leu Val Ser Pro Ser Asp Asp Pro Trp
225                 230                 235                 240

Asp Leu Leu His Asp Thr Ser Pro Gly Ser Pro Arg Ile Ala Ala Ile
                245                 250                 255

Val Gly

<210> SEQ ID NO 277
<211> LENGTH: 756
<212> TYPE: DNA
<213> ORGANISM: Homo sapiens

<400> SEQUENCE: 277
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg caccccatca gaccatctac agtgccctga tgatcagatc agaggatgct     240
ggctttgtgg tgattacagg tgtgatgagc agaagatacc tctgcatgga tttcagaggc     300 aacattttg gatcacacta tttcgacccg agaactgca ggttccaaca ccagacgctg      360
gaaaacgggt acgacgtcta ccactctcct cagtatcact tcctggtcag tctgggccgg     420
gcgaagagag ccttcctgcc aggcatgaac ccaccccgt actcccagtt cctgtcccgg     480
aggaacgaga tccccctaat tcacttcaac ccccccatac cacggcggca cacccggagc     540
gccgaggacg actcggagcg ggacccctg aacgtgctga gccccggc ccggatgacc       600 ccggccccgg cctcctgttc acaggagctc ccgagcgccg aggacaacag cccgatggcc     660
agtgacccat taggggtggt cagggcggt cgagtgaaca cgcacgctgg gggaacgggc      720
ccggaaggct gccgccccctt cgccaagttc atctag                              756
```

<210> SEQ ID NO 278
<211> LENGTH: 756
<212> TYPE: DNA
<213> ORGANISM: Gorilla

<400> SEQUENCE: 278

| | |
|---|---|
| atgttggggg cccgcctcag gctctgggtc tgtgccttgt gcagcgtctg cagcttgagc | 60 |
| gtcctcagag cctatcccaa tgcctcccca ctgctcggct ccagctgggg tggcctgatc | 120 |
| cacctgtaca cagccacagc caggaacagc taccacctgc agatccacaa gaatggccat | 180 |
| gtggatggcg caccccatca gaccatctac agtgccctga tgatcagatc agaggatgct | 240 |
| ggctttgtgg tgattacagg tgtgatgagc agaagatacc tctgcatgga tttcagaggc | 300 |
| aacatttttg gatcacacta tttcgacccg gagaactgca ggttccaaca ccagacgctg | 360 |
| gaaaacgggt acgacgtcta ccactctcct cagtatcact tcctggtcag tctgggccgg | 420 |
| gcgaagagag ccttcctgcc aggcatgaac ccaccccgt actcccagtt cctgtcccgg | 480 |
| aggaacgaga tcccctcat tcacttcaac accccatac acggcggca cacccggagc | 540 |
| gccgaggacg actcggagcg ggacccctg aacgtgctga gccccgggc ccggatgacc | 600 |
| ccggccccgg cctcctgttc acaggagctc ccgagcgccg aggacaacag cccgatggcc | 660 |
| agtgacccat tagggggtggt caggggcggt cgagtgaaca cgtacgctgg gggaacgggc | 720 |
| ccggaaggct gccgcccctt ccccaagttc atctag | 756 |

<210> SEQ ID NO 279
<211> LENGTH: 756
<212> TYPE: DNA
<213> ORGANISM: Northern white-cheeked gibbon

<400> SEQUENCE: 279

| | |
|---|---|
| atgttggggg cccgcctcag gctctgggtc tgtgccttgt gcagcgtctg cagcatgagc | 60 |
| gtcctcagag cctatcccaa tgcctcccca ctgctcggct ccagctgggg tggcctgatc | 120 |
| cacctgtaca cagccacagc caggaacagc taccacctgc agatccacaa gaatggccat | 180 |
| gtggatggcg caccccatca gaccatctac agtgccctga tgatcagatc agaggatgct | 240 |
| ggctttgtgg tgattacagg tgtgatgagc agaagatacc tctgcatgga tttcagaggc | 300 |
| aacatttttg gatcacacta tttcaacccg gagaactgca ggttccaaca ccagacgctg | 360 |
| gaaaacgggt acgacgtcta ccactctcct cagcatcact tcctggtcag tctgggccgg | 420 |
| gccaagagag ccttcctgcc gggcatgaac ccaccccgt actcccagtt cctgtcccgg | 480 |
| aggaacgaga tccccctact tcacttcaac accccacac acggcggca cacccggagc | 540 |
| gccgaggacg actcggagcg ggacccctg aacgtgctga aacccgggc ccggatgacc | 600 |
| ccggccccgg cctcctgctc acaggagctc ctgagctccg aggacaacag cccgatggcc | 660 |
| agcgacccat tagggggtggt caggggcggt cgagtgaaca cgcacgctgg gggaacgggc | 720 |
| ccggaaggct gccgcccctt ccccaagttc atctag | 756 |

<210> SEQ ID NO 280
<211> LENGTH: 756
<212> TYPE: DNA
<213> ORGANISM: Rhesus monkey

<400> SEQUENCE: 280

| | |
|---|---|
| atgttggggg cccgcctcag gctctgggtc tgtgccttgt gcagcgtctg cagcatgagc | 60 |
| gtcatcagag cctatcccaa tgcctcccca ttgctcggct ccagctgggg tggcctgatc | 120 |

```
cacctgtaca cagccacagc caggaacagc taccacctgc agatccacaa gaatggccac    180
gtggatggcg caccccatca gaccatctac agtgccctga tgatcagatc agaggatgct    240
ggctttgtgg tgattacagg tgtgatgagc agaagatacc tctgcatgga tttcagaggc    300 aacattttg  gatcacacta tttcaacccg gagaactgca ggttccgaca ctggacgctg    360
gagaacggct acgacgtcta ccactctcct cagcatcact ttctggtcag tctgggccgg    420
gcgaagaggg ccttcctgcc aggcatgaac ccaccccct  actcccagtt cctgtcccgg    480
aggaacgaga tccccctcat ccacttcaac accccagac  cacggcggca cccggagc     540 gccgaggacg actcggagcg ggaccccctg aacgtgctga gccccgggc  ccggatgacc    600 ccggccccgg cctcctgctc acaggagctc ccgagcgccg aggacaacag cccggtggcc    660
agcgacccgt tagggtggt  caggggcggt cgggtgaaca cgcacgctgg gggaacgggc    720
ccggaagcct gccgccccett ccccaagttc atctag                              756
```

```
<210> SEQ ID NO 281
<211> LENGTH: 756
<212> TYPE: DNA
<213> ORGANISM: Crab-eating macaque

<400> SEQUENCE: 281
atgttggggg cccgcctcag gctctgggtc tgtgccttgt gcagcgtctg cagcatgagc     60
gtcatcagag cctatcccaa tgcctcccca ttgctcggct ccagctgggg tggcctgatc    120
cacctgtaca cagccacagc caggaacagc taccacctgc agatccacaa gaatggccac    180
gtggatggcg caccccatca gaccatctac agtgccctga tgatcagatc agaggatgct    240
ggctttgtgg tgattacagg tgtgatgagc agaagatacc tctgcatgga tttcagaggc    300 aacattttg  gatcacacta tttcaacccg gagaactgca ggttccgaca ctggacgctg    360
gagaacggct acgacgtcta ccactctcct cagcatcact ttctggtcag tctgggccgg    420
gcgaagaggg ccttcctgcc aggcatgaac ccaccccct  actcccagtt cctgtcccgg    480
aggaacgaga tccccctcat ccacttcaac accccagac  cacggcggca cccggagc     540 gccgaggacg actcggagcg ggaccccctg aacgtgctga gccccgggc  ccggatgacc    600 ccggccccgg cctcctgctc acaggagctc ccgagcgccg aggacaacag cccggtggcc    660
agcgacccgt tagggtggt  caggggcggt cgggtgaaca cgcacgctgg gggaacgggc    720
ccggaagcct gccgccccctt ccccaagttc atctag                              756
```

```
<210> SEQ ID NO 282
<211> LENGTH: 756
<212> TYPE: DNA
<213> ORGANISM: Chimpanzee

<400> SEQUENCE: 282
atgttggggg cccgcctcag gctctgggtc tgtgccttgt gcagtgtctg cagcgtgagc     60
gtcctcagag cctaccccaa tgcctcccca ctgctcggct ccagctgggg tggcctgatc    120
cacctgtaca cagccacagc caggaacagc taccacctgc agatccacaa gaatggccat    180
gtggatggcg caccccatca gaccatctac agtgccctga tgatcagatc agaggatgct    240
ggctttgtgg tgattacagg tgtgatgagc agaagatacc tctgcatgga tttcagaggc    300 aacattttg  gatcacacta tttcaacccg gagaactgca ggttccaaca ccagacgctg    360
gaaaacgggt acgacgtcta ctactctcct cagtatcact tcctggtcag tctgggccgg    420
```

```
gcgaagagag ccttcctgcc aagcatgaac ccaccccgt actcccagtt cctgtcccgg    480
aggaacgaga tccccctaat tcacttcaac accccatac cacggcggca cacccggagc    540
gccgaggacg actcggagcg ggacccctg aacgtgctga agcccgggc ccggatgacc    600 ccggccccgg cctcctgttc acaggagctc ccgagcgccg aggacaacag cccgatggcc    660
agtgacccat taggggtggt caggggcggt cgagtgaaca cgcacgctgg gggaacgggc    720
ccggaaggct gccgcccctt ccccaagttc atctag                              756
```

<210> SEQ ID NO 283
<211> LENGTH: 756
<212> TYPE: DNA
<213> ORGANISM: White-tufted-ear marmoset

<400> SEQUENCE: 283

```
atgttggggg cccgcctcag gctctgggtc tgtgccttgt gcagcgtctg cagcatgagc     60
gtcctcagag cctatcccaa tgcctcccca ctgcttgcct ccagctgggg tggcctgatc    120
cacctgtaca cagccacagc caggaacagc taccacctgc agatccacaa gaatggccat    180
gtggatggcg cacccatca gaccatctac agtgccctgc tgatcagatc agaggatgct    240
ggctttgtgt tgattacagg tgtgatgagc agaagatacc tctgcatgga tttcagaggc    300 aacattttg gatcacacta tttcaacccg gagaactgca ggttccgacc ccagaggctg    360
gagaacgggt acgacgtcta ccagtctcct cagcatcact tcctggtcag tctgggccgg    420
gcgaagaggg ccttcctgcc aggcatgaac ccaccccgt actcccagtt cctgtcccgg    480
aggaacgaga tcccctcat tcacttcaac accccaaac cgcggcggca cacccggagc    540
gccgaggacg accccggagct agaccccctg aacgtgctga agtcccgggt ccggatgacc    600
ccggccccgg cctcctgctc gcaggagctc ctgagcgccg aggacaacag cccggtgggc    660 agcgaccct tagggatggt ccggggtggt cgggtgaaca gccacgctga gggaacaggc    720
ccagaaggct gcagccccctt ccccaagctc atctag                            756
```

<210> SEQ ID NO 284
<211> LENGTH: 756
<212> TYPE: DNA
<213> ORGANISM: Elephant

<400> SEQUENCE: 284

```
atgttggggg cccgcctcag gctctgggtc tgcaccctgt gcagtgcctg cagcatgtgc     60
agtgtcagag cctatcccaa tgcctcccg ctgctccact ccagctgggg tggcctgacc    120
cacctgtaca cagccaccgc caggaacagc taccacctgc agatccacaa ggacggccat    180
gtggatggta cgccggacca gaccatctac agtgccctga taatcagatc agaggaggcc    240
ggcttcgtgg tgattacagg ggtgatgagt aggagatacc tctgtatgga tttcagaggc    300 aacattttg gatcgcatta cttcaaccca gagaactgca ggttcaaaca ctggacgctg    360
gaaaatggat atgacgtcta tcactctcct cagcatcatt tcctggtcag tctgggtcgc    420
gtgaagaagg ccttcctgcc aggcatgaac ccaccacctt actctcagtt cctgtcccgg    480
aggaatgaga tcccccttgat ttacttcaac accccccaagc ccggcggca cacccggagt    540 gccgaggatg actctgaacg ggacccactg aatgtgctga agccccggcc ccgtatgaca    600
cctgctccag cttcttgctc ccaggaactc ctgagtgctg aagacaacag cgtggtggcc    660 aatgacccctt taggagtggt cagaagcaat agggtcaaca cacatgctgg tgggataggt    720 gtggaaggt gccgcccctt ccccaagttc atctag                              756
```

<210> SEQ ID NO 285
<211> LENGTH: 750
<212> TYPE: DNA
<213> ORGANISM: Lesser hedgehog tenrec

<400> SEQUENCE: 285

```
atgttggggg cccacctcag actctgggtc tgtgccttgt gcagtgtgag cgccatgtac      60
cacgtcagag cctaccccaa cgcctccccg ctcctgggta ccagctgggc tggcctgacc     120
cacctgtaca cggcgacagc caggaacagc ttccacctgc agatccacaa ggatggccac     180
gtggacggca ccccccacca gaccatctac agtgccctga tgatccgatc agaggactct     240
ggcttcgtgg tgatcacagg ggtgatgagc aggagatacc tgtgtatgga tttcagaggc     300
aacattttg atcgcacta cttcactgcg gacagctgca ggttcagaca gcggacgctg     360
gagaacggct atgacgtcta ccactctcct cagcatcatt tcctgatcag cctgggccgg     420
gccaagaggg tcttcctgcc cggcatgaac ccgccgcctt actcccagtt cctgtcccga     480
aggaatgaga tcccctgat tcacttcaac acccccaggc cccggcggca cacggagt      540
gccgaggagg aagtggagca ggatccgctg aacgtgctga agcccaggcc ccggatgacg     600
ccggctccag cctcctgctc ccaggagctg cccagtgccg aagacaacag cgccctggcc     660
agcgacccgc tgggagtggt cagaggcaaa aagctcaaca cccatgctgt gggcatgggc     720
gcggaaagat gccgccccctt tcccaagttc                                     750
```

<210> SEQ ID NO 286
<211> LENGTH: 710
<212> TYPE: DNA
<213> ORGANISM: Hedgehog

<400> SEQUENCE: 286

```
atgttggggg cccacctggg tctggtggtc tgcgccctgg tcagcagagc ctatcccaat      60
gcctcgccac tgctgggctt cagctggggg ggcctgacac atctgtacac ggccacagcc     120
aggaacagct accacctgca gatccacaag gacggccacg tggacggctc gcctcagcag     180
accatctaca tgctggtttc gtgatgatca caggcgtgat gagtaggcgc tacctctgca     240
tggacttcag gagcaacatc tttggatcgc atcacttcgc ccctgagagc tgcaggttca     300
gacatcggac actggaaaac ggctatgacg tctaccactc cccccagcac catttcctgg     360
tcagcctggg ccgggccaag cgggccttcc tgccgggcac caaccccccca ccatactccc     420
agttttgtc ccggaggaac gaggttcccc tcatccactt caacacccc aggcccaggc     480
gtcacacccg cagcgccgag acaactcag agctggatcc cctgaacgtg ctgaagccca     540
ggccccgcat gaccccgcc ccagcctcct gctcccagga gcttccgagc gctgaggaca     600
acagcatggt ggccagtgac ccactgggtg tggtcagagc caacagagtg aacacacacg     660
cagggggcct gggtgtggac aagtgccgcc ccttccccaa gtttatctag                710
```

<210> SEQ ID NO 287
<211> LENGTH: 759
<212> TYPE: DNA
<213> ORGANISM: Bushbaby

<400> SEQUENCE: 287

```
atgctgggga cctgcctcag gctctgggtc tgtgccctgt gcagtgtttg cagcgtgagc      60
attgtcagag cctatcccaa cgcctcccca ctgctcagct ccagctgggg tggcctgacc     120
```

```
cacctgtaca cggcctcggc cagaaacagc taccacctgc agatccacaa ggatggccat      180
gtggacggca cccccacca gaccatctac agcgccctaa tgatcaggtc agaggatgct      240
ggcttcgtgg tgattacagg cgtgatgagc agaagatacc tctgtatgga tttcaaaggc      300
aacatttttg gatcacactc cttccacccc gagagctgca ggttcagaca ccggactctg      360
gagaacggct atgacgtcta cctctcgccg cagcatcact tcttggtcag cctgggccgc      420
tccaagaggc ccttcctgcc gggcatgaac ccgccccct tctcccagtt cctgtcgcgg      480
aggaacgaca tcccgctcat tcacttcaac accccccgcc cgcggagaca cccgcagc      540 gccgaggaca cgactcgga gctcgacccc ctgaacgtgc tgaagccgcg gccccgggcc      600
accccgggcc ccgcctcctg ctcgcaggag ctccccagcg ccgaggacaa cagcctggtg      660
gccagcgacc ctttaggggt ggtccgggc aacaggtga acgctcacgc cgggagggcc      720
ggcctggaca ggtgccgccc cttccccagg tatttctag                            759

<210> SEQ ID NO 288
<211> LENGTH: 759
<212> TYPE: DNA
<213> ORGANISM: Rabbit

<400> SEQUENCE: 288
atgttagggg cccggctcct ccggctcttg gtctgtgccc tgggcagtgt gtgcagctgg       60
tgtgtggtcc gagcctaccc tgacacctcc ccgctgctca gctccagctg gctggcctg      120 acccacctgt acacggccac cgccagaaac agctaccacc tgcagatcca aaggacggc      180 caagtggatg gcacacctca tcagaccatc tacagtgccc tgatgatcag atcggaggat      240
gctggcttcg tggtgataac aggtgtcatg agcaggaggt acctctgtat ggatttcaga      300
ggcaacattt ttggatcgca ttacttcgac ccccagaact gcaggttcag acacaggacg      360
ctggaaaacg ggtacgacgt ctaccactct ccggagcatc acttcctggt cagcctgggc      420
cgggccaaga ggcccttcct gccaggcatg aacccgccac cctattccca gttcctgtcc      480
cggaggaacg agatccccct gatccacttc aacacgccga ggccgcgaag cacacccgg      540 agcgccgagg acgcctggga gcaggacccg ctgaacgtgc tgaagcccag gttccggctg      600
accccggccc cagcctcctg ctcacaggag gcccaagtg ctgaagacaa tggcctggtg      660
gccagcgacc ccttcggagt gctccgggc aataggtga acatgcacgg gacaggatg      720 ggcccggaaa ggtgccacca tttccccaag ttcatctag                            759

<210> SEQ ID NO 289
<211> LENGTH: 741
<212> TYPE: DNA
<213> ORGANISM: Horse

<400> SEQUENCE: 289
atgtcagggc cctgccttgg gctcctggtc tacgtcctgt gctccgcagt gaaagcctat       60
cccaacgcct cccgctgct agactccagc tggggcagcc tgacccacct gtacacggcc      120
acagccagga acagctacca cctgcagatc acaaggatg ccacgtgga tggcacaccc      180 catcagacca tctacagtgc cctgatgatc agatcagagg atgctggctt tgtggtgata      240
acaggtgtga tgagcaggag atacctctgc atggacttca gggaaacat ttttggatca      300 catcacttca gccccgagag ctgcagcttc gacagcgga cgctggagaa cggctacgac      360
gtgtaccact cgccgcagca tcgcttcctc gtcagcctgg gccgcgccaa gagggccttc      420
ctgcccggca cgaaccccc gccctactcg cagttcctgt cccggaggaa cgagatcccc      480
```

```
ctggtccact tcaacacccc gcggccgcgg cggcacacgc gcagcgccga ggacaactcg    540
gagcgcgacc cgctgaacgt gctgaagccc cggccccgca tgaccccgc gccggcctcc    600 tgctcccagg agctcccgag cgccgaggac aacagcgtgc tggccagcga ccccttaggg    660
gtggtccgtg caacagggt gaacacgcac gcgggggcg cgggcgtgga gcgctgccgc    720
cccttcccca agttcttcta g                                              741
```

```
<210> SEQ ID NO 290
<211> LENGTH: 738
<212> TYPE: DNA
<213> ORGANISM: Giant panda

<400> SEQUENCE: 290
atgtcaggga cccgccttgg gctgctggtc tctgtcctgt gctgggtagg cagagcctat     60
cccaacacct ccccactgct cggctccagc tggggtggcc tgacccacct gtacacagcc    120
agcgccagga acagctacca cctgcagatc acaaggacg gccatgtgga tggcacaccc    180
catcagacca tctacagtgc cctgatgatc aggtcagagg atgccggctt tgtggtgata    240
acaggtgtga tgagtaggcg atacctctgt atggacctca gaggcaacat ctttggatcc    300
cacctcttca gcccggagag ctgcaggttc cgacagcgga cgctggaaaa cggctacgac    360
gtgtaccact cgccgcagca ccgcttcctc gtcagcctgg ccaggccaa gaggaccttc    420 ctgccgggga ccaacccgcc gccctactcc cagttcctgt cccggaggaa cgagatcccc    480
ctcatccact tcaacacccc caggccaagg cggcacacgc gcagcgccga ggacacggag    540
cgcgacccgt tgaacgtgct gaagcccagg ccccgcatga ccccgcccc ggcctcctgc    600 tcccaggagc tcccgagcgc cgaggacaac agtgtggtgg ccagcgaccc gttaggggtg    660
ctcagaggca accgggtgaa cgcgcacgcc ggggggatgg gcgtggacag gtgccgcccc    720
ttccccaagt tcatctag                                                  738
```

```
<210> SEQ ID NO 291
<211> LENGTH: 753
<212> TYPE: DNA
<213> ORGANISM: Pika

<400> SEQUENCE: 291 atgctgggg ggctggggct gtgggtctgt gtcctgggca gtgtgtgcag ctggcgtggg      60
gtccgtgcct atcccgacac ctccccgctg ctcggctcca gctggactgg cctgacccac    120
ctgtacacgg ccaccgccag gaacagcttc cacctgcaga tccacaagga tggccatgtg    180
gatggcacac cccagcagac catctatagt gccctgatga tcagatcaga ggatgccggc    240
ttcgtggtga taacaggtgt catgagcagg aggtacctct gtatggattt cagaggcaac    300
atcttcggat cgcattactt cgagccacag aactgcaggt tccagcagag gacgctggag    360
aacggctacg acatctacca ctctccgcag cacgacttcc tggtcagcct aggtcgggcc    420
aagaggccgt tcctgccagg catgaacccg ccaccctact cccagttcct gtctcggagg    480
aacgagattc cgctgatcct cttcaacacg cccaggcctc ggaggcacac ccgcagcgcg    540
gaggagggct gggagcggga ccctctgaat gtgctgaagt ccaggcccg aatgaccccg    600 gccccagcct cctgctcgcg ggaggccccc agtgccgaag acgacggcct gctggccagt    660
gaccccatgg gagtgctcag aggccatagg gtggatgtgc acggggtgg dacgggtagg    720 gacaggtgcc gcccgttccc caggttcatc tag                                 753
```

<210> SEQ ID NO 292
<211> LENGTH: 738
<212> TYPE: DNA
<213> ORGANISM: Cattle

<400> SEQUENCE: 292

| | | | | | | |
|---|---|---|---|---|---|---|
| atgctggggg | cccgcctggg | gctctgggtc | tgcaccctga | gctgtgtggt | ccaagcctat | 60 |
| cccaacagct | ccccgctgct | gggctccagc | tggggcggcc | tgacccacct | gtacacggcc | 120 |
| acggccagga | acagctacca | cctgcagatc | cacggagacg | ggcacgtaga | tggctccccg | 180 |
| cagcagactg | tctacagcgc | cctgatgatc | aggtcggagg | atgccggctt | cgtggtgata | 240 |
| acaggtgtga | tgagcaggcg | gtacctctgc | atggacttca | caggcaacat | ttttggatcc | 300 |
| catcacttca | gtccggagag | ctgccggttc | cggcagcgga | cactggagaa | cggctacgac | 360 |
| gtgtaccact | cgccgcagca | ccgcttcctc | gtcagcctgg | gccgggccaa | gcgcgccttc | 420 |
| ctgccgggca | ccaaccccgcc | cccatacgcg | cagttcctgt | cgcgcaggaa | cgagatcccg | 480 |
| ctgccgcact | tcgccgccac | cgcgcggccc | cggcgccaca | cgcgcagcgc | acacgacagc | 540 |
| ggggacccgc | tcagcgtgct | caagccgcgc | gcccgcgcca | cgcccgtgcc | cgccgcctgc | 600 |
| tcccaggagc | tgcccagcgc | cgaggactcc | ggccctgccg | ccagcgaccc | gctcggggtg | 660 |
| ctccgcggac | accgcctgga | cgtgcgcgcc | ggctccgcgg | gcgccgagcg | ctgccggccc | 720 |
| ttccccggct | tcgcctag | | | | | 738 |

<210> SEQ ID NO 293
<211> LENGTH: 735
<212> TYPE: DNA
<213> ORGANISM: Pig

<400> SEQUENCE: 293

| | | | | | | |
|---|---|---|---|---|---|---|
| atgctggggg | cccgcctcgg | gctctgggtc | tgcaccctgt | gctgtgcggc | cagagcctat | 60 |
| cccgacacct | ccccgctgct | gagctctggc | tggggcggcc | tgacccacct | gtacacggcc | 120 |
| acggccagga | acagctacca | cctgcagatc | cacaaggatg | ccacgtgga | tggctcaccc | 180 |
| caacagacca | tctacagtgc | cctaatgatc | aggtcggagg | acgcaggctt | cgtggtcata | 240 |
| acaggcgtga | tgagcaggag | atacctctgc | atggacttaa | ggggcaacat | ttttggatcg | 300 |
| ctgcacttca | gccccgagag | ctgcaggttc | cggcagcgga | cgctggagaa | cggctacgac | 360 |
| gtgtaccact | cgccgcacta | ccgcttcctc | gtcagcctgg | gccgggccaa | gcgggccttc | 420 |
| ctgccgggta | ccaaccccgcc | ccgtacgcg | cagttcttgt | cgcgcaggaa | cgagatcccg | 480 |
| ctgctgcact | tcgccaccgc | gcggccccgg | cgccacacgc | gcagcgcgca | cgacggcggg | 540 |
| gacccgctga | gcgtcctgaa | gccgcgcgcg | cgcgccacgc | ccgcgcccgt | ctcctgctcc | 600 |
| cgcgagctgc | ccagcgccga | ggacggcggc | cccgcggcca | gcgacccgct | cggggtgctc | 660 |
| cggggccagc | ggctgacgc | gcgcgctggg | gtgggggcg | ccgagcgctg | ccggcccttc | 720 |
| cccagcttcg | cctag | | | | | 735 |

<210> SEQ ID NO 294
<211> LENGTH: 939
<212> TYPE: DNA
<213> ORGANISM: Dog

<400> SEQUENCE: 294

| | | | | | | |
|---|---|---|---|---|---|---|
| atgtggacag | tggagttttt | cctgtttgat | gtcacagggc | caccctttaa | aagtctgagg | 60 |
| gaaaaaagga | gggaatctag | cctgggactt | tcacgcaaga | tacccacaaa | gaagaggaga | 120 |

```
aaaaggcctg tgaggcacag ccggggaatc aaggaggcag tgtcaggttt caaactccag      180
ccagccattc agagagctgt gatgtctggc acccgccttg gattcctggt ctctgtcctg      240
tgctgggtag tcagagccta ttccaacacc tccccgctgc tcggctccag ctggggtagc      300
ctaacccacc tgtatacggc cacagccagg aacagctacc acctgcagat ccacaaggac      360
ggccatgtgg atggcacacc tcatcagacc atctacagtg ccttgatgat ccggtcagag      420
gatgccggct tgtggtgat aacaggtgtg atgagtagga ggtacctctg tatggacttc       480
agaggcaaca tctttggatc acacctcttc agcccggaga gctgccggtt ccgacagcgg      540
acgctggaga acggctacga cgtgtaccac tccccgcagc accgcttcct cgtcagcctg      600
ggccaggcca gagggccctt cctgcccggc accaacccgc cgccctactc gcagttcctg      660
tcccggagga acgagatccc cctcgtgcac ttccacacgc ccaggccgcg gcggcacacg      720
cgcagcgccg aggccccgga gcgcgacccg ctgaacgtgc tgaagcccag gccgcgcttg      780
gcccccgccc cggcctcctg ctcgcaggag ctcccgagcg ccgaggaccc cggcgcgccg      840
gccagcgacc cgctcggggt gctcagggc cacagggcca acgcgcgcgc cggcggggtg       900
ggcgtggaca ggtgccgcgc cttccccacg cccatctag                             939

<210> SEQ ID NO 295
<211> LENGTH: 732
<212> TYPE: DNA
<213> ORGANISM: Domestic guinea pig

<400> SEQUENCE: 295
atgctgggga cctgccttgg gctcctggcc tgcaccgtga gcttagtagg agcctatcct       60
gatgcctccc cattgctcac ctccagctgg ggtggcctga tccatctgta cacggccaca      120
gccagaaaca gctaccatct gcagatccac aaagatggcc acatagatgg tgcaccctat      180
ccgaccatct acagtgccct gatgatcaga tcagaagatg ctgggttcgt cgtgataaca      240
ggggtcacaa gcaggagatt cctctgcatg gatttcagag caacatttt tggatctcac       300 cacttcaatc cccaagactg ccgattccaa caccgcacgc tggaaaacgg ttacgacgtc      360
tacctctctc ccgagcacca cttctgatc agcctgggca ggaccaagaa gttcttcctg       420
ccgggcacca acccaccgcc ctactcccag ttcctgtcgc gcaggaacga gctgcccctg      480
gcccgcttcg tcacgcccgg gccgcggcga cacacgcgca gcgcggagga ggaccagggc      540
cgcgacccgc tgagcgtgct caagcttcgg ccccgcgcca cgcccgcgcc cgcctcgtgc      600
tcgcaggagc tgcccagcgc ggaggacgcg gcccaggcca gcgaccccct gggcgtgctg      660
cggggcgcca gggtgcacgc gcacggcggg ccgcgccccg cgaggtgccg cccgggaccc      720
ggggccaagt aa                                                         732

<210> SEQ ID NO 296
<211> LENGTH: 756
<212> TYPE: DNA
<213> ORGANISM: Chinese hamster

<400> SEQUENCE: 296
atgctgggga cctgcctcag actcctggtg ggtgttctgt gtagtgcctg cagcctgggc       60
actgttagag cctatcctga cacctcccca ctgctcggct ccaattgggg cagcctgacc      120
cacctgtaca cagctacagc caggaacagt tatcacctac agatccacaa ggatggccgt      180
gtagatggca caccccatca gaccatctac agtgccctga tgattagatc agaggatgct      240
```

| | |
|---|---|
| ggcttcgtga tcataacagg agctgtgact agaaggttcc tttgtatgga tctcaggggc | 300 |
| aacattttg gatcgcatca cttcagcccg gagaactgca ggttccgcca gcggactctg | 360 |
| gagaatggct atgacgtcta cctgtcgcca cagcatcact acctggtgag cctgggccgc | 420 |
| gccaagcgcc ccttcgagcc cggcaccaac ccgcctccct tctcgcagtt cctggcgcgc | 480 |
| aggaacgagg tcccgctgct gcgcttccat accgcacggc cacggcgcca cacgcgcagc | 540 |
| gccgaggacc ctcccgagtg ggacccactg aacgtgctca gccgcggcc ccgtgccacg | 600 |
| cccgtgcccg tgtcctgctc gcgggagctg ccgagcgccg aggaaggtga cctcgcggcc | 660 |
| agtgacccac tgggcgtcct gcgcagaggc cgcggggatg ctcgcggggg cgcaggaggc | 720 |
| gtggaccggt gccgtcccrt tcccagattc gcctag | 756 |

<210> SEQ ID NO 297
<211> LENGTH: 543
<212> TYPE: DNA
<213> ORGANISM: Tree shrew

<400> SEQUENCE: 297

| | |
|---|---|
| gccctgctga tcaggccgga ggaggctggc ttcgcggtga tcacgggcgt gatgagcagg | 60 |
| agatacctct gcatggattt caggggcaac atttcggat cacacctctt cagcccggag | 120 |
| agctgcaggt tccggcagcg cgccctggag aacggctacg acgtctacca ccacccgcag | 180 |
| caccacttcc tggtcagcct gggcggccc aagagggcct tcgtgccagg cacgaacccg | 240 |
| ccccctact cccagttcct ggcccggaag aacgagatcc cgctcatcca cttcaacacc | 300 |
| ccgaagccgc ggcggcacac ccgcagcgca gggacaact cggggcgcga cccgctgaac | 360 |
| gtgctgaagc ccggccgcg catgacccccg gcgcccgcct cctgctcgca ggagctcccg | 420 |
| agtgccgagg acaacagcgt ggtggccagc gacccctggg gagtgctcag ggcaacagg | 480 |
| gtgaacacgc acgcggggg ctggggcgtg gaccgctgcc gccccttccc caggtttatc | 540 |
| tag | 543 |

<210> SEQ ID NO 298
<211> LENGTH: 756
<212> TYPE: DNA
<213> ORGANISM: Norway rat

<400> SEQUENCE: 298

| | |
|---|---|
| atgctggggg cctgcctcag actcctggtg ggcgctctgt gcaccgtctg cagcttgggc | 60 |
| actgctagag cctattcaga cacttcccca ctgcttggct ccaactgggg gagcctgacc | 120 |
| cacctgtaca cagctacagc caggaacagc tatcacctac agatccatag ggatggccat | 180 |
| gtagacggaa caccccatca gactatctac agtgccctga tgatcacatc agaggatgct | 240 |
| ggctccgtag tgataatagg ggccatgacc agaaggttcc tttgtatgga tctccgcggc | 300 |
| aacattttg gatcgtatca cttcagcccg gagaactgca gattccgcca gtggacgcta | 360 |
| gagaacggct acgacgtcta cctgtcaccg aagcatcact acctggtgag cttgggccgc | 420 |
| tccaagcgca tcttccagcc cggtaccaac ccgccgccct tctcgcagtt cctggcgcgc | 480 |
| aggaacgagg tcccgctgct gcacttctac accgcgcgcc cacggcgcca cacgcgcagc | 540 |
| gccgaggacc cgcccgagcg cgacccgctg aatgtgctca gccgcggcc ccgcgctact | 600 |
| cccataccgg tatcctgctc gcgagagcta ccgagtgcag aggaaggtgg ccccgcggcc | 660 |
| agcgaccccc tggagtgct gcgcagaggc cgcggggatg ctcgccgggg cgcgggaggc | 720 |
| acggatcggt gtcgcccctt tcccaggttc gtctag | 756 |

<210> SEQ ID NO 299
<211> LENGTH: 756
<212> TYPE: DNA
<213> ORGANISM: House mouse

<400> SEQUENCE: 299

| | | | | | |
|---|---|---|---|---|---|
| atgctaggga | cctgccttag | actcctggtg | ggcgcgctct | gcactgtctg | cagcttgggc | 60 |
| actgctagag | cctatccaga | cacttcccca | ttgcttggct | ccaactgggg | aagcctgacc | 120 |
| cacctgtaca | cggctacagc | caggaccagc | tatcacctac | agatccatag | ggatggtcat | 180 |
| gtagatggca | cccccatca | gaccatctac | agtgccctga | tgattacatc | agaggacgcc | 240 |
| ggctctgtgg | tgataacagg | agccatgact | cgaaggttcc | tttgtatgga | tctccacggc | 300 |
| aacattttg | gatcgcttca | cttcagccca | gagaattgca | agttccgcca | gtggacgctg | 360 |
| gagaatggct | atgacgtcta | cttgtcgcag | aagcatcact | acctggtgag | cctgggccgc | 420 |
| gccaagcgca | tcttccagcc | gggcaccaac | ccgccgccct | tctcccagtt | cctggcgcgc | 480 |
| aggaacgagg | tcccgctgct | gcacttctac | actgttcgcc | cacggcgcca | cacgcgcagc | 540 |
| gccgaggacc | cacccgagcg | cgacccactg | aacgtgctca | agccgcggcc | ccgcgccacg | 600 |
| cctgtgcctg | tatcctgctc | tcgcgagctg | ccgagcgcag | aggaaggtgg | ccccgcagcc | 660 |
| agcgatcctc | tggggtgct | gcgcagaggc | cgtggagatg | ctcgcggggg | cgcgggaggc | 720 |
| gcggataggt | gtcgccccctt | tcccaggttc | gtctag | | | 756 |

<210> SEQ ID NO 300
<211> LENGTH: 747
<212> TYPE: DNA
<213> ORGANISM: Megabat

<400> SEQUENCE: 300

| | | | | | |
|---|---|---|---|---|---|
| atgccgaggg | gcagcctagg | gctcctggtc | tgcatcctgt | gctgcagagc | ctatcccgat | 60 |
| gcctctccgc | tgcttagctc | cagcttgggg | ggcctgatcc | acctctacac | agccacagcc | 120 |
| aggaacggct | accacctgca | gatccacaag | gatggccatg | tggatggcac | accccatcag | 180 |
| accatctaca | gtgccctgat | gataagatca | gaggacagtg | gctttgtggt | gataataggt | 240 |
| gtgatgagta | gaagatacct | ctgcatggac | ttcaaaggca | acattttttgg | atcacatcac | 300 |
| ttcagccccg | agagctgcaa | gttccgccag | cgaacgctgg | agaatggcta | cgacgtgtat | 360 |
| cactcgcccc | agcatcactt | cttcgtcagc | ctgggccgag | ctaagagggc | cttcctgccg | 420 |
| ggcacgaacc | cccaccctta | ctcccagttc | ctgtcccgaa | ggaatgagat | cccctgttc | 480 |
| cagttcaaca | ccccgcggcc | gcggcggcac | acgcgcagcg | tggaggacta | caaagactac | 540 |
| gatttggacc | ccgacccgct | gaaagttctg | aggcccgtc | ccggtgggt | ccgcccctg | 600 |
| ccctcctgct | cccaggagct | cccgagtgcc | gaggacaaca | gcgtggtagc | caacgacccg | 660 |
| ttaggggtgc | tcaggcccag | cagggtaaac | atataccgtg | agagaatggg | caaggggagg | 720 |
| tgccgtcccc | accctgagtt | tgtctag | | | | 747 |

<210> SEQ ID NO 301
<211> LENGTH: 744
<212> TYPE: DNA
<213> ORGANISM: Microbat

<400> SEQUENCE: 301

| | | | | | |
|---|---|---|---|---|---|
| atgccagggg | cccgccttgg | gttgctggtc | tgcgtcctgg | ccctgcgctg | tgtggtcaga | 60 |

```
gcctatccca acgcctcccc actgctcggc tccagctggg gtggcctgac ccacctgtac      120
acggcctcag ccaggaacag ctaccacctg cagatccaca aggacggcca tgtggacggc      180 acacccatc agaccatcta cagtgccctg atgatcagat cagaggacgc tggctttgtg       240
gtgataactg gagtgatgag taggagatac ctctgcatgg actttagagg caacattttt      300
ggatcccttt ttttcagtcc aagtaatttc agtttccttg aatggaaaaa ggaaagtggg      360
atggaccatt ggataagcag acagacgcac ttcctcgtca gccctgggcc gagccaagag      420
ggccttcctg ccgggcacaa cccgccgccc tactcgcagt tcctgtcgcg aaacgagatc      480
ccgctcttcc acttcaacac gcccgcgccg cgcggcaca cgcgcagcgc cgaggagaac       540
tcggcggccg acccgctggt cgtgctgaag cccgtgccgc gcctgacgcc cccgcccgcc      600
tcctgctccc gggagctgag cagcgccgag acaacagcg tggcggccca cgacccgctc       660
ggggtgctgc ggagcagcaa cagggtgaac tcgcacgcgc cgcccccagg tccacctagg      720
acccgccaag gaatgcttct cgta                                            744
```

<210> SEQ ID NO 302
<211> LENGTH: 738
<212> TYPE: DNA
<213> ORGANISM: Tasmanian devil

<400> SEQUENCE: 302

```
atgtcagggg gttgcctcag gctcctattc tgtgccctgt gcagcttaag ggccatccaa      60
gccttcccca atgcttcccc cctgctcagc cttggctggg ggggtctgac tcacctctat      120
acggccacag ccaggaacag ctaccacctg cagatccaca agatggcca cgtggatggg       180 tctcctcatc aaaccatcta tagtgccttg atgatcagat cagaggatgc tgggctagtc      240
ataataactg gtgtgatgag caggagatat ctctgtatgg acattagggg caacatcttc      300
ggatcgcatt tcttcagccc agacaactgc aggttcaaac accggacatt agaaaatggg      360
tatgacatct atcactctcc ccagaacaac ttcctgatca gccttggcaa ggcaaagagg      420
gccttcctac cagggatgaa cccacctcct tactcccaat tcctgtctcg gagaaatgaa      480
atccccataa tacacttcaa tacacctgaa ccccaccggc ataccaggag tgctgagaac      540
agtcctgact tggacccaat gaatgtgctg aaactccgac caaggataac tccctgctcc      600
caggaacttc acagtgctga agagaacagt gtagtggatg atgacccttt ggaagtactc      660
agaaatagca atagattgaa gccctatcct ggcaggatga gtttggaaag atgcctccat      720
gtccccaagg cagcttaa                                                   738
```

<210> SEQ ID NO 303
<211> LENGTH: 576
<212> TYPE: DNA
<213> ORGANISM: Gray short-tailed opossum

<400> SEQUENCE: 303

```
atggcaaatt gtagagaaaa ggagctggag atgtacattt gtgccttgat gatcagatca      60
gaggatgctg ggctagtcat aataactggt gtgatgagca ggagatatct ctgtatggac      120
atcaggggca acatctttgg ttcgcatttc ttcaacccgg acaactgcaa gttcaagcac      180
cggacactag aaaatgggta tgacatctat cattctcccc agaacaactt cctgatcagc      240
cttggcaagg caaagagggc ctttctgcca ggcatgaatc cacctccgta ctctcaattc      300
ctgtctcgga agaatgagat ccccataatc cacttcaaca cacctgaacc ccaccggcac      360
accaggagtg ctgaaaacag tcctgacttg gacccaatga atgtgctgaa accccgacca      420
```

```
aggatgactc cctgctctca ggaactctac agtgctgaag agaacagtgt agtggatgat     480
gacccttggg aagtacttag aaatagcaat cgactgaagc ccttccctgg taggctgggt     540
ttagaaaggt gccaccatgt tcccaagact gattaa                                576
```

<210> SEQ ID NO 304
<211> LENGTH: 543
<212> TYPE: DNA
<213> ORGANISM: Armadillo

<400> SEQUENCE: 304

```
gccctgatga tcagctctga agatgctggc tttgtggtga taacaggtgt gatgagcagg      60
aggtacctct gtatggattt cagaggcaac attttttggat cgcacgactt caccccggac    120
agctgcaggt tccgccagcg cacgctggag aacggctacg acgtctacca ctcgccgcag    180
caccacttcc tcgtcagcct ggggcgggcc aagcgggcct tccagccggg ctccaacccg    240
ccgccctact cccagttcct gtcccgcagg aacgagatcc cgctgatgcg cttcagcacc    300
ccgcggccgc ggcggcacac gcgcagcgcc caggaccacg cggaccccga cccgctgagg    360
gtgctcaagc cccggctccg gctgaccccg gcccccgcct cctgctccca ggagctgccg    420
agcgacgagg acgacggcgc ggtggccagc gaccccctgc gcgtggtcct cggccgccgg    480
ccccacgcgc gggccgcggg cgcgggcggg gagcggtgcc gccccggccc gcagctcagc    540
tag                                                                  543
```

<210> SEQ ID NO 305
<211> LENGTH: 534
<212> TYPE: DNA
<213> ORGANISM: Wallaby

<400> SEQUENCE: 305

```
gccttgatga tcagatcaga ggacgctggg ctagtcataa taagtggtgt gatgagcagg      60
aggtatctct gtatggacct cagaggcaac atcttcggat cgcatttctt cagcccagac    120
aactgcaggt tcaaacaccg gacactagaa aatgggtatg acatctatca ctctccacag    180
aacaacctcc tgatcagcct tggcaaggca aaaagggcct tcctgccagg catgaaccca    240
cctccttact cccagttcct atctcggagg aatgagatcc ccataatcca cttcaataca    300
cctgaacccc gccggcacac caggagcgca gagaacagtc ctgacttgga cccaatgaat    360
gtgctgaaac cccgaccaag ggtgactccc tgctcccagg aactccgcag tgctgaagag    420
aacagtgtag tagatgatga ccctttggaa gtactcagaa atagtaatcg cctgaagccc    480
taccctggta gaatgagttt ggaaagatgc ctccaagtcc ccaaagctgc ttaa           534
```

<210> SEQ ID NO 306
<211> LENGTH: 771
<212> TYPE: DNA
<213> ORGANISM: Zebra finch

<400> SEQUENCE: 306

```
atggagtgga gagccactct ccagggcatt ccctgcagct ccctgctcct gctgctctgc      60
agcctaaagg cttcccttgc ctttcccaac tcctctccac tgctgagtcc cagctggggc    120
aatggagatc gcctgatgca cctctacacc gacaccgaga ggagcagctt ccacctccag    180
atcaacgctg atggctacat cgatggcgct cctcaccaaa ccatctacag tgccctaatg    240
atcaagtctg agggtgctgg ctcagtaata atcacaggtg tgaagagtgg acgctacctg    300
```

| | |
|---|---|
| tgtatggaca tgaaaggaaa tatatttggc tcgcattact tcagccaaga ggactgcatg | 360 |
| ttcaaccaca ggacgctgga aaatgggtac gatgtgtacc aatcccccaa acaccacttc | 420 |
| ttggtgagct taggcagagt taaacaagtc ttctcccctg gtatgaatcc accaccatac | 480 |
| tcccagtttc tgtccaggaa gaatgagatc cctctgttcc gattcaacac ccccgagccc | 540 |
| cacaggcaca ccaggagtgc agatgttgat cccgtagatc ctcaccagat cctggtcccg | 600 |
| cagaggaaga ccccagtgtt tggctccctg cagcagcagc cagcagactt ccccacatg | 660 |
| cccagggagc ccatgaggat caaccagaac gacgtggtga accccgatga tccccacgca | 720 |
| atgatggagg ccaggaggta cccaagcccc cgcttctaca tcacgagata a | 771 |

<210> SEQ ID NO 307
<211> LENGTH: 765
<212> TYPE: DNA
<213> ORGANISM: Chicken

<400> SEQUENCE: 307

| | |
|---|---|
| atgccacaca ccagtccctg cagctgcctg gagtacatgc tgcttgtgct ctgtatcctg | 60 |
| aaggctgcag tcgccttccc caactcctct ccgctgctga atcccagctg ggggaatgga | 120 |
| gatcagctga tgcacttgta cacttctaca gagaggaaca gcttccatct ccaaatcaat | 180 |
| gctgatggac acatcaatgg tgttcctcac caaaccattt acagtgcctt aatgatcaag | 240 |
| tctgagggtg ctggctgtgt aataatcaca ggtgtgaaga gtggacgcta cctatgcatg | 300 |
| gacatgaaag gagacatttt tggatcgtat tatttcagcc aagaggactg tgtgttcaac | 360 |
| caaaggacac tggaaaatgg atatgatgtg taccaatctc ccaagcacaa ttttctggtt | 420 |
| agcttgggca gaactaagca gttttcttc cctggtatga atccaccacc atactcccag | 480 |
| tttttgtcca ggagaaacga aatccctttg tttcgattca acacacctga accccacaga | 540 |
| aacactagaa gtgcagatgt cgatccactg gatcctcacc aaatcctggt cccacagaga | 600 |
| aaggtctctg cattagggtc tcagctgcag ctgcaaatgg acttttccca tgtgcccaga | 660 |
| gaacccatga gagtcaatca gaatgatgtg gtcaatccag atgacccaca tgctatgatg | 720 |
| gatgctagga ggtatgctag tcctcgcttt tacattacaa gataa | 765 |

<210> SEQ ID NO 308
<211> LENGTH: 765
<212> TYPE: DNA
<213> ORGANISM: Turkey

<400> SEQUENCE: 308

| | |
|---|---|
| atgccgcaca ccagtccctg cagctgcctg gagtacatgc tgcttgtgct ctgtatcctg | 60 |
| aaggctgcag tcagcttccc caactcctct ccactgctga atcccagctg ggggaacgga | 120 |
| gatcagctga tgcacttgta tacttctaca gagaggaaca gcttccatct tcaaatcaat | 180 |
| gctgatggcc acatcagtgg tgttccttac caaaccattt acagtgccct aatgatcaag | 240 |
| tctgagggtg ctggcagcgt tataatcaca ggtgtgaaga gtggacgcta cctatgcatg | 300 |
| gacatgaaag gagacatttt tggatcgcat tatttcagcc aagaggactg cgtgttcaac | 360 |
| caaagaacac tggaaaatgg atatgatgtg tatcaatctc ccaagcacaa ttttctggtt | 420 |
| agcttaggca gaactaagca gttttcttc cctggtatga atccaccacc gtactcccag | 480 |
| tttttgtcca ggagaaacga aatcccgttg tttcgattca acacacctga accccacaga | 540 |
| aacactagaa gtgcagatgt tgatccaatg gatcctcacc agatcctggt cccacagaga | 600 |
| aaggtctctg caatagagtc tcagctgcaa ctgcaaatgg acttttccca tgtgcccaga | 660 |

```
gaacccatga gagtcaatca gaacgatgtg gtcaacccag atgacccaca cgctatgatg      720
gatgccagga gatatgctag tcctcgcttt tacattacaa gataa                     765

<210> SEQ ID NO 309
<211> LENGTH: 729
<212> TYPE: DNA
<213> ORGANISM: Green anole

<400> SEQUENCE: 309
atggtccagg ctactctata cagcttcctc aaatatatgc tgcttgcaac atgtagctgg       60
aaagcaattg ctgctttccc caacgcatca cctttgctca gcctcaactg gggaaattca      120
gacagcctgc tacacttgta cacttccaca gcaagaaaca gcttccacct gcaaatccac      180
tccaatggct acgtggatgg aagtccgtat caaacaattt acagtgcctt gatgatcaaa      240
tctgaagttg ctggttatgt tataataaat ggtgtgaaaa gtggacgttt tctttgtatg      300
gatatgaatg ggaacatctt tggatcgcat ttcttcagtt atgaggactg cactttcaaa      360
cactgggtcc tggaaaatgg ttatgatgtt tatcagtctc ccaaatacaa ctaccttgtc      420
agcttaggaa aagcaaagca accattgttc cccaatatga atccaccacc ttactcccag      480
ttcttgtcca ggagaaatga aattcctttta gtccagttca acacaccgaa acctcacaga     540
cataccagaa gtgccaacgc ggatccctgc ggcagcatca tatcatcagg aaatattgcg      600
aaagaaaacc tacagttaca gccactaatg tataacacta aaatgaattc aaacagtgaa      660
gatgaagacc caaacagtgc aataatcaat agaagatttt tgagtcctag aacagatgtc      720
aggagctga                                                              729

<210> SEQ ID NO 310
<211> LENGTH: 750
<212> TYPE: DNA
<213> ORGANISM: Coelacanth

<400> SEQUENCE: 310
ctagagtccg ctcttcttgc gttttctatg gctatattct atagctttaa agctgtgagc       60
tcttttccaa attcttcgcc actgcttaac ccagtctggg gaaacactga caacctgata      120
cacctgtata cagcttctga gacgaacagc ttccacttgc agatcaactc cgatggacat      180
gtggatggta ctccacacca aaccgcttac agtgcactgc tgatcaagtc cgaggaggct      240
ggttctgtag ttatcctggg ggtgaagagt ggacgttacc tctgtatgga tatcaagggc      300
aatattattg gactgcatca cttcagcaag gaagactgta cattcaaaca agagggcttg      360
gaaaatggat tgatgtgct gcgctcacct aagcacaaca ttttggtcag ccttgacaag      420
actaaacgct cctacatccc gggtatgaac ctgccaccct actcacagtt tttatcccga      480
cagaatgaag tagctctgat caacttcatt aacacacctg acatacacag acatagtcga      540
aatgttgatg ttgatccttc agaccccat gggatgataa ttcagcctga tgtgggtgtt      600
tcatttcgta agtcttcatc tctgtttttca gatctgccca gagactccat gagaactagc      660
cataatggta tggatatggt tgatcctgct gacccacatg gaatgttaga ttccaggaga      720
agaccaagtc caaggttctt tgcaagatag                                       750

<210> SEQ ID NO 311
<211> LENGTH: 765
<212> TYPE: DNA
<213> ORGANISM: Western clawed frog
```

<400> SEQUENCE: 311

```
atgaccaagc agcaaactag actaggactg gtgctcactg ttcttgccag tataaaggtt    60
atatctgcct tccccaactc ttctccaata atcagtggcg gctgggggt ccctgacaga   120
ctgatgcacc tatatacggc cagtgactgg aacagcttcc acctacagat caaccatgat   180
ggaagcattg atggaacccc tacccaaacc atttacagtg caataatgat caaatcagaa   240
tccgctgggc acgtggttat tactgggtg aagactaatc ggtacctgtg catggataaa   300
agtgggaaca ttttggata tcacgacttc aaccacgacg actgcgtttt taagcacgag   360
actctggaga caactttga cgtttaccat tctccaaaac acaactttgt gatcagcctc   420
aaggagccca agcatcattt ccgcctcggc atggacctgc ccccttactc ccaattcctg   480
tccttggaga atgaaatccc cataaccaga ttcaatgctc cagagccgga atgagaatc   540
ccagagggca actttgctga ccccagcgac atcataaaga accccaggaa ctgggacttt   600
tcgcagtcta ttcataatcc atttcaggat gtgtggttgc cgttcccag cggttcatta   660
ccaatcatta gagcttcctt gccaattatt cataacaatg tgattaatac agatgaccct   720
gaagaaattg taaaaatgaa gagatacaga tatttcaaga ggtag               765
```

<210> SEQ ID NO 312
<211> LENGTH: 600
<212> TYPE: DNA
<213> ORGANISM: Cat

<400> SEQUENCE: 312

```
atgtcaggga cccgccttgg gctcctggtc tctgtcctgt gctgggtagt cagagcctat    60
cctaacacct ccccgctgct gggctccagc tggggtggcc tgacccacct gtacacggcc   120
acagccagga acagctacca cctgcagata cacaaggacg gccatgtgga tggcacaccc   180
catcagacca tctacagtgc cctgatgatc agatcggagg atgccggctt gtggtgata   240
acaggtgtga tgagtcagag gtacctctgt atggacttca gaggcaatat cttcggatcg   300
cacctcttca gccccgagag ctgcaggttc cgacagcgga cgctggaaaa cggctacgac   360
gtgtaccact ccccgcagca ccgcttccta gtcagcctgg gccggccaa gagggccttc   420
ctgccgggca ccaaccgcat gacccccgcg ccggcctcct gctcccagga gctcccaagc   480
gccgaggaca cgcgcgtggt ggccagcgac ccgttagggg tgctcagggg caacagggtg   540
aacgcgcacg ccgggggggat gggcgtggag aggtgccgcc ccttccccaa gttcaactag   600
```

<210> SEQ ID NO 313
<211> LENGTH: 750
<212> TYPE: DNA
<213> ORGANISM: Chinese softshell turtle

<400> SEQUENCE: 313

```
atgtcacagc ccagccagtg cagctgcctg aacttcatgc tgttcgtgct atgtagcttc    60
aaagctattg ctgcctttcc cttcttctct tcactgctga atcccagctg gggggaaacg   120
gatagtttga tacacctgta cacagctact gagaagaaca gcttccatct gcagatcaac   180
cctgatggtt atgttgacgg cacacctcac caaaccattt acagtgctct aatgatcaaa   240
tctgaggatg ctggctatgt ggtgataagt ggtgtaaaga gtgggcgcta cctatgtatg   300
gacattaaag gaaatatctt tggatcgcat tacttcagtc aagaggactg catgtttaaa   360
cacagaacac tggaaaatgg atatgatgtg taccagtctc ccaagcacaa cttcctggtc   420
agcctgggca ggaataaaca gcttttcttc cctggtatga atctgccacc atactcccag   480
```

```
tttttgccca ggagaaatga aatccctctg atccgattca acacacccga accccacagg      540
cacactagga atgcagatgt tgatcccctc cagattttga tccctcgggg agaggctttt      600
gacacaggac ctcagaggtt gcagactcac tttgatcacc tgcctagaga acccatgaga      660
atcaatccaa atgatgtagt cagcccggat gacccactcg ccatgatgga tgtcagaagg      720
aatgcaagtc cacgccttta cattacaaga                                       750
```

<210> SEQ ID NO 314
<211> LENGTH: 738
<212> TYPE: DNA
<213> ORGANISM: Ferret

<400> SEQUENCE: 314

```
atgtcagtga cccgtcttgg gctcctggtc tctgtcctgt gctgggtagt cagagcctat       60
cccaacgcct ccccgctgct cggctccagc tggggtggcc tgacccacct gtacacggcc      120
actgccagga acagctacca cctgcagatc acaaggatgc ccatgtggat ggcacacccc      180
caccagacca tctacagcgc cctgatgatc agatcagagg atgccggctt tgtggtgatc      240
acaggtgtga tgagcaggcg gtacctgtgt atggacttcc gaggcaacat ctttggatcc      300
cacctcttca gccccgagag ctgcaggttc cgacagcgga cactggaaaa cggctacgac      360
gtgtaccact ccccgcagca ccgcttcctc gtcagcctgg ccaagccaa gagggccttc       420 ctgccgggca ccaacccgcc gccctactcc cagtttctgt cccggaggaa tgagatcccc      480
ctcatccact tcaacacccc caggccgcgg cgtcacacgc gcagcgccga ggacatggag      540
cacgacccgt tgaacgtgct gaagccccgg ccccgcatga cccggccc ggcctcctgc        600 tcccaggagc tcccgagcgc cgaggacaac agtgtggtgg ccagcgaccc gttaggggtg      660
ctcagaggca accgggtgaa cgtgcacgcg ggggggatgg gcgtggacag gtgccgcccc      720 ctcccccaagt tcatctag                                                   738
```

<210> SEQ ID NO 315
<211> LENGTH: 618
<212> TYPE: DNA
<213> ORGANISM: Mouse lemur

<400> SEQUENCE: 315

```
atgctggggg cctgcctcag gctctgggtc tgtgccctgt gcagtgtctg cggcgtgagc       60
gtcgtcagag cctatcccaa cgcctccccg ctgctcgcct ccagctgggg tggcctgatc      120
cacctgtaca cggccacggc caggaacagc taccacctgc agatccacaa ggacggccat      180
gtggacggca caccccacca gaccatctac agtgccttga tgatcaggtc agaggatgct      240
ggctttgtgg tgatcacagg tgtgatgagc agaagatacc tctgcatgga tttcagaggc      300 aacattttg gatcacatgt cttcagcgcg gagagctgca ggttcagaca gcggacgctg      360
gagaacggct cgacgtgta ccagtcccct cagcaccact tcctggtcag cctgggccgc      420
gccaaagggg cctttccggc cggggcgaaa ccgccccct tccccagtt cctgccgcgg       480 gggaacgagg ctcccgggcg caaaacgcgg gggcccgagg aaaagggggc cccacaccct      540
ctccgcgggg tggaaagcgg gggccggaaa ggcggggccc cgcctctctg tttggagagg      600
ctctccagag cccgagag                                                    618
```

<210> SEQ ID NO 316
<211> LENGTH: 579
<212> TYPE: DNA

<213> ORGANISM: Orangutan

<400> SEQUENCE: 316

| | |
|---|---|
| atgcgcaatg agtctttgcc ctgcctggtt ttctccatag gtgccctgat gatcagatca | 60 |
| gaggatgctg gctttgtggt gattacaggt gtgatgagca aagatacct ctgcatggat | 120 |
| ttcagaggca acatttttgg atcacactat ttcaacccgg agaactgcag gttccaacac | 180 |
| cagacgctgg aaaacgggta tgacgtctac cactctcctc agcatcactt cctggtcagt | 240 |
| ctgggccggg tgaagagagc cttcctgcca ggcatgccac ccccgtactc ccagttcctg | 300 |
| tcccggagga acgagatccc cctaattcac ttcaacaccc ccgtaccacg gcggcacacc | 360 |
| cggagcgccg aggatgacac ggagcgggac ccctgaaag tgctgaagcc ccgggcccgg | 420 |
| atgaccccgg ccccggcctc ctgctcacag gagctcccga gctccgagga caacagcccg | 480 |
| atggccagcg acccattagg ggtggtcagg ggcggtcgag tgaacacgca cgctggggga | 540 |
| acgggcccgg aaggctgccg ccccttcccc aagttcatc | 579 |

<210> SEQ ID NO 317
<211> LENGTH: 564
<212> TYPE: DNA
<213> ORGANISM: Shrew

<400> SEQUENCE: 317

| | |
|---|---|
| atgtggggac tccgcctggg tctcttggtc ggcctcctgg gctgcgtgga cagagcctcc | 60 |
| ccgatgctgg cgtccagctg gggcggcctg acgcacctgt acacggccac ggccaggaac | 120 |
| agctaccacc tccagatcca caaggacggc ctggtcgacg gctccccgca gcagaccgtc | 180 |
| taccaccatt tcagcccgga gagctgccgc ttccagcagc gcacgctgga gaacggctac | 240 |
| gacgtgtacc agtccccgca gcaccgcttc ctcgtgagcc tgggccggcc caagcgcgcc | 300 |
| ttccagccgg cgccaacccc gccgccctac gcgcagttcc tggcgcgccg caacgaggtg | 360 |
| cccctggcgc gcttccacac gcccgcgccg cgccgccaca cgcgcagcgc gcacgacaac | 420 |
| ggcgacgccg acccgctcaa cgtgctggcg cctcgggccg ccgccgccgc ctcctgctcg | 480 |
| cacgagctgc ccagcgccga ggacaacagc gtggtggcca cgacccgct gggcgtcatc | 540 |
| cgcagcaacc gcttccgcac gcac | 564 |

<210> SEQ ID NO 318
<211> LENGTH: 792
<212> TYPE: DNA
<213> ORGANISM: Tetraodon

<400> SEQUENCE: 318

| | |
|---|---|
| atggacgtaa acagaaggat cggggtgaag gacgccttgc tggcgctcct gctcgcccctt | 60 |
| ctccagggat gcccctgggg ggaaacggct cccaacgcgt caccgctggt cggttccaac | 120 |
| tgggggaacc cgaggaggta cgttcacctt cagacatcca cagacatgag caacttctac | 180 |
| ttggagatca gactggatgg aaccgtgcgc aaaagcacag cccggacttc atacagtgtg | 240 |
| atttttactga aagccgacac gagggagcgc atcgccatcc tgggcgtcaa gagcaaccgt | 300 |
| tacctgtgta tggacctcga ggggagccca tttagctctc ccacctgcat cagggacgac | 360 |
| tgcttgttca accacagtct tctggagaac aaccgggacg tctactactc cagccggacc | 420 |
| ggcattctct tcaaccttga gggctcccgc caggtgttcg tggtgggcca gaacgtcccg | 480 |
| cagacctccc tcttcctgcc caggacgaac acggtgccgc tggagcgact ccttctgcac | 540 |
| agggacaagc ggaaccaggt ggtggacccc tctgacccgc accgcgtcgc cgtgggtcgc | 600 |

```
gccgaggagg gctcggactc ccgggccttg caggaggacg acgccgacct ggaggtggag    660
acagaggttg aggtcgggga cgacggacgc aacgcgtccc gggagcggct gcaggctccg    720
tccgatcacg acccctgggg cgtgttctcc tccaaccccg ggagccccg cagcagcggc     780 acggtgggct ga                                                        792
```

<210> SEQ ID NO 319
<211> LENGTH: 768
<212> TYPE: DNA
<213> ORGANISM: Tilapia

<400> SEQUENCE: 319

```
atggacgtca acaggcgaat ggggatgaga gacaccgtgc tggcgctctt tctcgctgtc    60
ttgcagggat ttcctctcgg ggatacggtc ccgaacccat cacctctggc tggatccaac   120 tggggaacc caaggagata cgtccacctg cagacatcca cagacctcaa taacttctac   180
ttggagatca gattagatgg gagtgtgcgc aaaactacgt ccaggagcac ctatagtgtg   240
attctactga aatctgaagc aagagatcgc gtcgccatcc tcggcgtcaa aagcagccgt   300
tacctatgca tggacctgga gggcaacccg ttcagctctc ctgtctgcct tcgggatgac   360
tgtctgttca accacaagct cctggagaac aaccgggacg tgtactactc cagccggaca   420
ggcatcttgt tcaacctgga gggctcccga caggtgtact cggtgggcca gaacctgccg   480
cagacctccc tcttcttgcc caggaaaaac accgtaccac tggagcgcct cctgctgcac   540
agggagaaga gaaaccgggg gcagacagaa gagggttcgg actcccggc cgtgccggag   600 gagctggagg aaagggaggt ggaaatggag acggaaatag aaacagaggt cggggatgac   660
ggacgcaacg tgtcccggga gaaactcgcg gctccatcca gccacgaccc ctggaacgtg   720
cacttctcca acccggccag ccccggagc accgggacag tgggctga                 768
```

<210> SEQ ID NO 320
<211> LENGTH: 777
<212> TYPE: DNA
<213> ORGANISM: Zebrafish

<400> SEQUENCE: 320

```
atgcgttgcg cactttccaa cctgcacatg ctgcattcat ccgtcctcgc gctgtggttc    60
acggctctcc agggactcag acctgcagat gcggccccca tccttctccc gctgctgggc   120
tccaactggg ggaacccgcg gagatacatc caccttcaga ccacttcaga cttaaacaac   180
tactacctgg agatcagccc gagtggacac gtgcgcaaaa ctacaaatcg gggctcatac   240
agtgtaatct tattgaaaac agaaagcaga gaccgtctgg cgatatttgg agtgaaaagt   300
aaccggtttt tgtgcatgga tacaggagga accccttttca catctacgat ctgcaataag   360
gaagactgtc ttttccacca caaactgttg gaaaaccatc gtgatgtgta ttactccact   420
aaacacagca tactgcttaa tctggacggg acaaacagg cgtttatagc gggacaaaac   480
ctccctcagt cgtctctctt cttgtcggag aagaacacgg ttccgctgga gcgcctgcag   540
catcgggagc gcaggaaccg gcaggtgaac ccaacagacc cgctgaacgc gctccggtac   600
gcggaggagt ctgattccag agccgcgcag gaggatgatg agacatgga ttttgagccc   660 tcagaaggtc aaaacatctc tagagaaacc cttgtttccc cttccgatga tgatccatgg   720
gatcttctgc acgacacgag ccctggaagt cctcggattg cagcaattgt cggataa      777
```

<210> SEQ ID NO 321

<211> LENGTH: 241
<212> TYPE: PRT
<213> ORGANISM: Artificial
<220> FEATURE:
<223> OTHER INFORMATION: Chimeric protein

<400> SEQUENCE: 321

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Asp Gln
        115                 120                 125

Asn Gly Ser Cys Val Arg Gly Pro Arg Thr His Tyr Gly Gln Lys Ala
    130                 135                 140

Ile Leu Phe Leu Pro Leu Arg Asn Glu Ile Pro Leu Ile His Phe Asn
145                 150                 155                 160

Thr Pro Ile Pro Arg Gln His Thr Gln Ser Ala Glu Asp Asp Ser Glu
                165                 170                 175

Arg Asp Pro Leu Asn Val Leu Lys Pro Arg Ala Arg Met Thr Pro Ala
            180                 185                 190

Pro Ala Ser Cys Ser Gln Glu Leu Pro Ser Ala Glu Asp Asn Ser Pro
        195                 200                 205

Met Ala Ser Asp Pro Leu Gly Val Val Arg Gly Gly Arg Val Asn Thr
    210                 215                 220

His Ala Gly Gly Thr Gly Pro Glu Gly Cys Arg Pro Phe Ala Lys Phe
225                 230                 235                 240

Ile

<210> SEQ ID NO 322
<211> LENGTH: 217
<212> TYPE: PRT
<213> ORGANISM: Artificial
<220> FEATURE:
<223> OTHER INFORMATION: Chimeric protein

<400> SEQUENCE: 322

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

```
Glu Glu Asn His Tyr Asn Thr Tyr Ile Ser Lys Lys His Ala Glu Lys
                85                  90                  95

Asn Trp Phe Val Gly Leu Asp Gln Asn Gly Ser Cys Val Arg Gly Pro
            100                 105                 110

Arg Thr His Tyr Gly Gln Lys Ala Ile Leu Phe Leu Pro Leu Arg Asn
        115                 120                 125

Glu Ile Pro Leu Ile His Phe Asn Thr Pro Ile Pro Arg Gln His Thr
    130                 135                 140

Gln Ser Ala Glu Asp Ser Glu Arg Asp Pro Leu Asn Val Leu Lys
145                 150                 155                 160

Pro Arg Ala Arg Met Thr Pro Ala Pro Ala Ser Cys Ser Gln Glu Leu
                165                 170                 175

Pro Ser Ala Glu Asp Asn Ser Pro Met Ala Ser Asp Pro Leu Gly Val
            180                 185                 190

Val Arg Gly Gly Arg Val Asn Thr His Ala Gly Gly Thr Gly Pro Glu
        195                 200                 205

Gly Cys Arg Pro Phe Ala Lys Phe Ile
    210                 215

<210> SEQ ID NO 323
<211> LENGTH: 242
<212> TYPE: PRT
<213> ORGANISM: Artificial
<220> FEATURE:
<223> OTHER INFORMATION: Chimeric protein

<400> SEQUENCE: 323

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Asp
        115                 120                 125

Gln Thr Gly Gln Tyr Val Leu Gly Ser Lys Thr Gly Pro Gly Gln Lys
    130                 135                 140

Ala Ile Leu Phe Leu Pro Met Arg Asn Glu Ile Pro Leu Ile His Phe
145                 150                 155                 160

Asn Thr Pro Ile Pro Arg Gln His Thr Gln Ser Ala Glu Asp Asp Ser
                165                 170                 175

Glu Arg Asp Pro Leu Asn Val Leu Lys Pro Arg Ala Arg Met Thr Pro
            180                 185                 190

Ala Pro Ala Ser Cys Ser Gln Glu Leu Pro Ser Ala Glu Asp Asn Ser
        195                 200                 205

Pro Met Ala Ser Asp Pro Leu Gly Val Val Arg Gly Gly Arg Val Asn
    210                 215                 220
```

```
Thr His Ala Gly Gly Thr Gly Pro Glu Gly Cys Arg Pro Phe Ala Lys
225                 230                 235                 240

Phe Ile

<210> SEQ ID NO 324
<211> LENGTH: 218
<212> TYPE: PRT
<213> ORGANISM: Artificial
<220> FEATURE:
<223> OTHER INFORMATION: Chimeric protein

<400> SEQUENCE: 324

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
                20                  25                  30

Asp Pro His Ile Lys Leu Gln Leu Gln Ala Glu Glu Arg Gly Val Val
            35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Asp Gln Thr Gly Gln Tyr Val Leu Gly
            100                 105                 110

Ser Lys Thr Gly Pro Gly Gln Lys Ala Ile Leu Phe Leu Pro Met Arg
    115                 120                 125

Asn Glu Ile Pro Leu Ile His Phe Asn Thr Pro Ile Pro Arg Gln His
130                 135                 140

Thr Gln Ser Ala Glu Asp Asp Ser Glu Arg Asp Pro Leu Asn Val Leu
145                 150                 155                 160

Lys Pro Arg Ala Arg Met Thr Pro Ala Pro Ala Ser Cys Ser Gln Glu
                165                 170                 175

Leu Pro Ser Ala Glu Asp Asn Ser Pro Met Ala Ser Asp Pro Leu Gly
            180                 185                 190

Val Val Arg Gly Gly Arg Val Asn Thr His Ala Gly Gly Thr Gly Pro
    195                 200                 205

Glu Gly Cys Arg Pro Phe Ala Lys Phe Ile
210                 215

<210> SEQ ID NO 325
<211> LENGTH: 723
<212> TYPE: DNA
<213> ORGANISM: Artificial
<220> FEATURE:
<223> OTHER INFORMATION: Nucleic acid sequence encoding chimeric protein

<400> SEQUENCE: 325
atggctgaag gggaaatcac caccttcaca gccctgaccg agaagtttaa tctgcctcca    60
gggaattaca agaagcccaa actcctctac tgtagcaacg ggggccactt cctgaggatc   120
cttccggatg gcacagtgga tgggacaagg gacaggagcg accagcacat tcagctgcag   180
ctcagtgcgg aaagcgtggg ggaggtgtat ataaagagta ccgagactgg ccagtacttg   240
gccatggaca ccgacgggct tttatacggc tcacagacac caaatgagga atgtttgttc   300
ctggaaaggc tggaggagaa ccattacaac acctatatat ccaagaagca tgcagagaag   360
```

```
aattggtttg ttggcctcga tcagaatggg agctgcgttc gcggtcctcg gactcactat    420
ggccagaaag caatcttgtt tctcccctg aggaacgaga tccccctaat tcacttcaac    480 accccatac cacggcagca cacccagagc gccgaggacg actcggagcg gaccccctg     540 aacgtgctga agccccgggc ccggatgacc ccggccccgg cctcctgttc acaggagctc    600
ccgagcgccg aggacaacag cccgatggcc agtgacccat taggggtggt caggggcggt    660
cgagtgaaca cgcacgctgg gggaacgggc cggaaggct gccgcccctt cgccaagttc     720
atc                                                                  723
```

<210> SEQ ID NO 326
<211> LENGTH: 651
<212> TYPE: DNA
<213> ORGANISM: Artificial
<220> FEATURE:
<223> OTHER INFORMATION: Nucleic acid sequence encoding chimeric protein

<400> SEQUENCE: 326

```
aagcccaaac tcctctactg tagcaacggg ggccacttcc tgaggatcct tccggatggc    60
acagtggatg ggacaaggga caggagcgac cagcacattc agctgcagct cagtgcggaa    120
agcgtggggg aggtgtatat aaagagtacc gagactggcc agtacttggc catggacacc    180
gacgggcttt tatacggctc acagaccaca aatgaggaat gtttgttcct ggaaaggctg    240
gaggagaacc attacaacac ctatatatcc aagaagcatg cagagaagaa ttggtttgtt    300
ggcctcgatc agaatgggag ctgcgttcgc ggtcctcgga ctcactatgg ccagaaagca    360
atcttgtttc tccccctgag gaacgagatc cccctaattc acttcaacac cccataccca   420
cggcagcaca cccagagcgc cgaggacgac tcggagcggg accccctgaa cgtgctgaag    480
ccccgggccc ggatgacccc ggccccggcc tcctgttcac aggagctccc gagcgccgag    540
gacaacagcc cgatggccag tgacccatta ggggtggtca ggggcggtcg agtgaacacg    600
cacgctgggg gaacgggccc ggaaggctgc cgcccttcg ccaagttcat c              651
```

<210> SEQ ID NO 327
<211> LENGTH: 726
<212> TYPE: DNA
<213> ORGANISM: Artificial
<220> FEATURE:
<223> OTHER INFORMATION: Nucleic acid sequence encoding chimeric protein

<400> SEQUENCE: 327

```
atggcagccg ggagcatcac cacgctgccc gccttgcccg aggatggcgg cagcggcgcc    60
ttcccgcccg gccacttcaa ggaccccaag cggctgtact gcaaaaacgg gggcttcttc    120
ctgcgcatcc accccgacgg ccgagttgac ggggtccggg agaagagcga ccctcacatc    180
aagctacaac ttcaagcaga agagagagga gttgtgtcta tcaaaggagt gtgtgctaac    240
cgttacctgg ctatgaagga agatggaaga ttactggctt ctaaatgtgt tacgatgagt    300
tgtttctttt ttgaacgatt ggaatctaat aactacaata cttaccggtc aaggaaatac    360
accagttggt atgtggcact ggatcagact gggcagtatg ttcttggatc caaaacagga    420
cctgggcaga aagctatact ttttcttcca atgaggaacg agatcccct aattcacttc    480 aacacccca taccacggca gcacacccag agcgccgagg acgactcgga gcgggacccc    540
ctgaacgtgc tgaagccccg ggccggatg acccgggccc cggcctcctg ttcacaggag    600
ctcccgagcg ccgaggacaa cagcccgatg gccagtgacc cattaggggt ggtcaggggc    660
```

```
ggtcgagtga acacgcacgc tgggggaacg ggcccggaag gctgccgccc cttcgccaag    720
ttcatc                                                               726
```

<210> SEQ ID NO 328
<211> LENGTH: 654
<212> TYPE: DNA
<213> ORGANISM: Artificial
<220> FEATURE:
<223> OTHER INFORMATION: Nucleic acid sequence encoding chimeric protein

<400> SEQUENCE: 328

```
cacttcaagg accccaagcg gctgtactgc aaaaacgggg gcttcttcct gcgcatccac    60
cccgacggcc gagttgacgg ggtccgggag aagagcgacc ctcacatcaa gctacaactt    120
caagcagaag agagaggagt tgtgtctatc aaaggagtgt gtgctaaccg ttacctggct    180
atgaaggaag atggaagatt actggcttct aaatgtgtta cggatgagtg tttctttttt    240
gaacgattgg aatctaataa ctacaatact taccggtcaa ggaaatacac cagttggtat    300
gtggcactgg atcagactgg gcagtatgtt cttggatcca aaacaggacc tgggcagaaa    360
gctatacttt tccttccaat gaggaacgag atcccctaa ttcacttcaa cacccccata    420
ccacggcagc acacccagag cgccgaggac gactcggagc gggaccccct gaacgtgctg    480
aagccccggg cccggatgac cccggccccg gcctcctgtt cacaggagct cccgagcgcc    540
gaggacaaca gcccgatggc cagtgaccca ttaggggtgg tcaggggcgg tcgagtgaac    600
acgcacgctg ggggaacggg cccggaaggc tgccgcccct cgccaagtt catc           654
```

<210> SEQ ID NO 329
<211> LENGTH: 1012
<212> TYPE: PRT
<213> ORGANISM: Homo sapiens

<400> SEQUENCE: 329

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190
```

```
His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
        290                 295                 300

Pro Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
        500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
        530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
        580                 585                 590

Phe Arg Phe Ser Leu Asp Trp Ala Leu Ile Leu Pro Leu Gly Asn Gln
        595                 600                 605
```

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
            660                 665                 670

Cys Phe Gln Glu Leu Gly His Val Lys Leu Trp Ile Thr Met Asn
        675                 680                 685

Glu Pro Tyr Thr Arg Asn Met Thr Tyr Ser Ala Gly His Asn Leu Leu
690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Met Gln Asn Tyr Ile Asn
            885                 890                 895

Glu Ala Leu Lys Ala His Ile Leu Asp Gly Ile Asn Leu Cys Gly Tyr
        900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975

His Thr Arg Lys Ser Leu Leu Ala Phe Ile Ala Phe Leu Phe Phe Ala
        980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 330
<211> LENGTH: 3039
<212> TYPE: DNA
<213> ORGANISM: Homo sapiens

<400> SEQUENCE: 330

| | | | | | |
|---|---|---|---|---|---|
| atgcccgcca | gcgccccgcc | gcgccgcccg | cggccgccgc | cgccgtcgct | gtcgctgctg | 60 |
| ctggtgctgc | tgggcctggg | cggccgccgc | ctgcgtgcgg | agccgggcga | cggcgcgcag | 120 |
| acctgggccc | gtttctcgcg | gcctcctgcc | cccgaggccg | cgggcctctt | ccagggcacc | 180 |
| ttccccgacg | gcttcctctg | ggccgtgggc | agcgccgcct | accagaccga | gggcggctgg | 240 |
| cagcagcacg | gcaagggtgc | gtccatctgg | gatacgttca | cccaccaccc | cctggcaccc | 300 |
| ccgggagact | cccggaacgc | cagtctgccg | ttgggcgccc | cgtcgccgct | gcagcccgcc | 360 |
| accgggacg | tagccagcga | cagctacaac | aacgtcttcc | gcgacacgga | ggcgctgcgc | 420 |
| gagctcgggg | tcactcacta | ccgcttctcc | atctcgtggg | cgcgagtgct | ccccaatggc | 480 |
| agcgcgggc | tccccaaccg | cgaggggctg | cgctactacc | ggcgcctgct | ggagcggctg | 540 |
| cgggagctgg | gcgtgcagcc | cgtggtcacc | ctgtaccact | gggacctgcc | ccagcgcctg | 600 |
| caggacgcct | acggcggctg | ggccaaccgc | gccctggccg | accacttcag | ggattacgcg | 660 |
| gagctctgct | tccgccactt | cggcggtcag | gtcaagtact | ggatcaccat | cgacaacccc | 720 |
| tacgtggtgg | cctggcacgg | ctacgccacc | gggcgcctgg | ccccggcat | ccggggcagc | 780 |
| ccgcggctcg | ggtacctggt | ggcgcacaac | ctcctcctgg | ctcatgccaa | agtctggcat | 840 |
| ctctacaata | cttctttccg | tcccactcag | ggaggtcagg | tgtccattgc | cctaagctct | 900 |
| cactggatca | atcctcgaag | aatgaccgac | cacagcatca | agaatgtca | aaatctctg | 960 |
| gactttgtac | taggttggtt | tgccaaaccc | gtatttattg | atggtgacta | tcccgagagc | 1020 |
| atgaagaata | acctttcatc | tattctgcct | gattttactg | aatctgagaa | aagttcatc | 1080 |
| aaaggaactg | ctgacttttt | tgctctttgc | tttggaccca | ccttgagttt | tcaactttg | 1140 |
| gaccctcaca | tgaagttccg | ccaattggaa | tctcccaacc | tgaggcaact | gctttcctgg | 1200 |
| attgaccttg | aatttaacca | tcctcaaata | tttattgtgg | aaaatggctg | gtttgtctca | 1260 |
| gggaccacca | agagagatga | tgccaaatat | atgtattacc | tcaaaaagtt | catcatggaa | 1320 |
| accttaaaag | ccatcaagct | ggatggggtg | gatgtcatcg | ggtataccgc | atggtccctc | 1380 |
| atggatggtt | tcgagtggca | cagaggttac | agcatcaggc | gtggactctt | ctatgttgac | 1440 |
| tttctaagcc | aggacaagat | gttgttgcca | aagtcttcag | ccttgttcta | ccaaaagctg | 1500 |
| atagagaaaa | atggcttccc | tcctttacct | gaaaatcagc | cctagaagg | gacatttccc | 1560 |
| tgtgactttg | cttggggagt | tgttgacaac | tacattcaag | tagataccac | tctgtctcag | 1620 |
| tttaccgacc | tgaatgttta | cctgtgggat | gtccaccaca | gtaaaaggct | tattaaagtg | 1680 |
| gatgggggttg | tgaccaagaa | gaggaaatcc | tactgtgttg | actttgctgc | catccagccc | 1740 |
| cagatcgctt | tactccagga | aatgcacgtt | acacattttc | gcttctcct | ggactgggcc | 1800 |
| ctgattctcc | ctctgggtaa | ccagtcccag | gtgaaccaca | ccatcctgca | gtactatcgc | 1860 |
| tgcatggcca | gcgagcttgt | ccgtgtcaac | atcaccccag | tggtggccct | gtggcagcct | 1920 |
| atggccccga | accaaggact | gccgcgcctc | ctggccaggc | agggcgcctg | ggagaacccc | 1980 |
| tacactgccc | tggcctttgc | agagtatgcc | cgactgtgct | ttcaagagct | cggccatcac | 2040 |
| gtcaagcttt | ggataacgat | gaatgagccg | tatacaagga | atatgacata | cagtgctggc | 2100 |
| cacaaccttc | tgaaggccca | tgccctggct | tggcatgtgt | acaatgaaaa | gtttaggcat | 2160 |

```
gctcagaatg ggaaaatatc catagccttg caggctgatt ggatagaacc tgcctgccct    2220
ttctcccaaa aggacaaaga ggtggctgag agagttttgg aatttgacat tggctggctg    2280
gctgagccca ttttcggctc tggagattat ccatgggtga tgagggactg gctgaaccaa    2340
agaaacaatt ttcttcttcc ttatttcact gaagatgaaa aaaagctaat ccagggtacc    2400
tttgactttt tggctttaag ccattatacc accatccttg tagactcaga aaagaagat    2460 ccaataaaat acaatgatta cctagaagtg caagaaatga ccgacatcac gtggctcaac    2520
tcccccagtc aggtggcggt agtgccctgg gggttgcgca aagtgctgaa ctggctgaag    2580
ttcaagtacg gagacctccc catgtacata atatccaatg aatcgatga cgggctgcat    2640 gctgaggacg accagctgag ggtgtattat atgcagaatt acataaacga agctctcaaa    2700
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttca cacccgaaag    2940 tctttactgg ctttcatagc ttttctattt tttgcttcta ttatttctct ctcccttata    3000
ttttactact cgaagaaagg cagaagaagt tacaaatag                            3039
```

<210> SEQ ID NO 331
<211> LENGTH: 1014
<212> TYPE: PRT
<213> ORGANISM: Mus musculus

<400> SEQUENCE: 331

```
Met Leu Ala Arg Ala Pro Pro Arg Arg Pro Pro Arg Leu Val Leu Leu
1               5                   10                  15

Arg Leu Leu Leu Leu His Leu Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
        115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
    210                 215                 220
```

```
Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
            245                 250                 255

Pro Gly Val Arg Gly Ser Ser Arg Leu Gly Tyr Leu Val Ala His Asn
                260                 265                 270

Leu Leu Leu Ala His Ala Lys Val Trp His Leu Tyr Asn Thr Ser Phe
                275                 280                 285

Arg Pro Thr Gln Gly Gly Arg Val Ser Ile Ala Leu Ser Ser His Trp
                290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
                340                 345                 350

Asp Phe Thr Glu Ser Glu Lys Arg Leu Ile Arg Gly Thr Ala Asp Phe
                355                 360                 365

Phe Ala Leu Ser Phe Gly Pro Thr Leu Ser Phe Gln Leu Leu Asp Pro
370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
                420                 425                 430

Met Tyr Tyr Leu Lys Lys Phe Ile Met Glu Thr Leu Lys Ala Ile Arg
                435                 440                 445

Leu Asp Gly Val Asp Val Ile Gly Tyr Thr Ala Trp Ser Leu Met Asp
450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
                500                 505                 510

Glu Asn Gln Pro Leu Glu Gly Thr Phe Pro Cys Asp Phe Ala Trp Gly
                515                 520                 525

Val Val Asp Asn Tyr Val Gln Val Asp Thr Thr Leu Ser Gln Phe Thr
530                 535                 540

Asp Pro Asn Val Tyr Leu Trp Asp Val His His Ser Lys Arg Leu Ile
545                 550                 555                 560

Lys Val Asp Gly Val Val Ala Lys Lys Arg Lys Pro Tyr Cys Val Asp
                565                 570                 575

Phe Ser Ala Ile Arg Pro Gln Ile Thr Leu Leu Arg Glu Met Arg Val
                580                 585                 590

Thr His Phe Arg Phe Ser Leu Asp Trp Ala Leu Ile Leu Pro Leu Gly
                595                 600                 605

Asn Gln Thr Gln Val Asn His Thr Val Leu His Phe Tyr Arg Cys Met
                610                 615                 620

Ile Ser Glu Leu Val His Ala Asn Ile Thr Pro Val Val Ala Leu Trp
625                 630                 635                 640
```

Gln Pro Ala Ala Pro His Gln Gly Leu Pro His Ala Leu Ala Lys His
                645                 650                 655

Gly Ala Trp Glu Asn Pro His Thr Ala Leu Ala Phe Ala Asp Tyr Ala
            660                 665                 670

Asn Leu Cys Phe Lys Glu Leu Gly His Trp Val Asn Leu Trp Ile Thr
        675                 680                 685

Met Asn Glu Pro Asn Thr Arg Asn Met Thr Tyr Arg Ala Gly His His
    690                 695                 700

Leu Leu Arg Ala His Ala Leu Ala Trp His Leu Tyr Asp Asp Lys Phe
705                 710                 715                 720

Arg Ala Ala Gln Lys Gly Lys Ile Ser Ile Ala Leu Gln Ala Asp Trp
                725                 730                 735

Ile Glu Pro Ala Cys Pro Phe Ser Gln Asn Asp Lys Glu Val Ala Glu
            740                 745                 750

Arg Val Leu Glu Phe Asp Ile Gly Trp Leu Ala Glu Pro Ile Phe Gly
        755                 760                 765

Ser Gly Asp Tyr Pro Arg Val Met Arg Asp Trp Leu Asn Gln Lys Asn
    770                 775                 780

Asn Phe Leu Leu Pro Tyr Phe Thr Glu Asp Glu Lys Lys Leu Val Arg
785                 790                 795                 800

Gly Ser Phe Asp Phe Leu Ala Val Ser His Tyr Thr Thr Ile Leu Val
                805                 810                 815

Asp Trp Glu Lys Glu Asp Pro Met Lys Tyr Asn Asp Tyr Leu Glu Val
            820                 825                 830

Gln Glu Met Thr Asp Ile Thr Trp Leu Asn Ser Pro Ser Gln Val Ala
        835                 840                 845

Val Val Pro Trp Gly Leu Arg Lys Val Leu Asn Trp Leu Arg Phe Lys
    850                 855                 860

Tyr Gly Asp Leu Pro Met Tyr Val Thr Ala Asn Gly Ile Asp Asp Asp
865                 870                 875                 880

Pro His Ala Glu Gln Asp Ser Leu Arg Ile Tyr Ile Lys Asn Tyr
                885                 890                 895

Val Asn Glu Ala Leu Lys Ala Tyr Val Leu Asp Asp Ile Asn Leu Cys
            900                 905                 910

Gly Tyr Phe Ala Tyr Ser Leu Ser Asp Arg Ser Ala Pro Lys Ser Gly
        915                 920                 925

Phe Tyr Arg Tyr Ala Ala Asn Gln Phe Glu Pro Lys Pro Ser Met Lys
    930                 935                 940

His Tyr Arg Lys Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
            980                 985                 990

Phe Thr Phe Ile Ile Ser Leu Ala Leu Ile Phe His Tyr Ser Lys Lys
        995                 1000                1005

Gly Gln Arg Ser Tyr Lys
    1010

<210> SEQ ID NO 332
<211> LENGTH: 3045
<212> TYPE: DNA
<213> ORGANISM: Mouse

<400> SEQUENCE: 332

```
atgctagccc gcgcccctcc tcgccgcccg ccgcggctgg tgctgctccg tttgctgttg        60
ctgcatctgc tgctgctcgc cctgcgcgcc cgctgcctga cgctgagcc  gggtcagggc       120
gcgcagacct gggctcgctt cgcgcgcgct cctgccccag aggccgctgg cctcctccac       180
gacaccttcc ccgacggttt cctctgggcg gtaggcagcg ccgcctatca gaccgagggc       240
ggctggcgac agcacggcaa aggcgcgtcc atctgggaca ctttcaccca tcactctggg       300
gcggccccgt ccgactcccc gatcgtcgtg gcgccgtcgg gtgccccgtc gcctcccctg       360
tcctccactg gagatgtggc cagcgatagt tacaacaacg tctaccgcga cacagagggg       420
ctgcgcgaac tggggtcac  ccactaccgc ttctccatat cgtgggcgcg ggtgctcccc       480
aatggcaccg cgggcactcc caaccgcgag gggctgcgct actaccggcg gctgctggag       540
cggctgcggg agctgggcgt gcagccggtg gttaccctgt accattggga cctgccacag       600
cgcctgcagg acacctatgg cggatgggcc aatcgcgccc tggccgacca tttcagggat       660
tatgccgagc tctgcttccg ccacttcggt ggtcaggtca agtactggat caccattgac       720
aaccctacg  tggtggcctg gcacgggtat gccaccgggc gcctggcccc gggcgtgagg       780
ggcagctcca ggctcgggta cctggttgcc cacaacctac ttttggctca tgccaaagtc       840
tggcatctct acaacacctc tttccgcccc acacagggag gccgggtgtc tatcgcctta       900
agctcccatt ggatcaatcc tcgaagaatg actgactata atatcagaga atgccagaag       960
tctcttgact ttgtgctagg ctggtttgcc aaacccatat ttattgatgg cgactaccca      1020
gagagtatga agaacaacct ctcgtctctt ctgcctgatt ttactgaatc tgagaagagg      1080
ctcatcagag gaactgctga ctttttttgct ctctccttcg gaccaacctt gagctttcag     1140
ctattggacc ctaacatgaa gttccgccaa ttggagtctc ccaacctgag gcagcttctg      1200
tcttggatag atctggaata taaccaccct ccaatattta ttgtggaaaa tggctggttt      1260
gtctcgggaa ccaccaaaag ggatgatgcc aaatatatgt attatctcaa gaagttcata      1320
atggaaacct taaaagcaat cagactggat ggggtcgacg tcattgggta caccgcgtgg      1380
tcgctcatgg acggtttcga gtggcatagg ggctacagca tccggcgagg actcttctac      1440
gttgactttc tgagtcagga caaggagctg ttgccaaagt cttcggcctt gttctaccaa      1500
aagctgatag aggacaatgg cttttcctcct ttacctgaaa accagcccct tgaagggaca     1560
tttccctgtg actttgcttg gggagttgtt gacaactacg ttcaagtgga cactactctc      1620
tctcagttta ctgacccgaa tgtctatctg tgggatgtgc atcacagtaa gaggcttatt      1680
aaagtagacg gggttgtagc caagaagaga aaaccttact gtgttgattt ctctgccatc      1740
cggcctcaga taaccttact tcgagaaatg cgggtcaccc actttcgctt ctccctggac      1800
tgggccctga tcttgcctct gggtaaccag acccaagtga ccacacggt tctgcacttc       1860
taccgctgca tgatcagcga gctggtgcac gccaacatca ctccagtggt ggccctgtgg      1920
cagccagcag ccccgcacca aggcctgcca catgcccttg caaaacatgg ggcctgggag      1980
aacccgcaca ctgctctggc gtttgcagac tacgcaaacc tgtgttttaa agagttgggt      2040
cactgggtca atctctggat caccatgaac gagccaaaca cacggaacat gacctatcgt      2100
gccgggcacc acctcctgag agcccatgcc ttggcttggc atctgtacga tgacaagttt      2160
agggcggctc agaaaggcaa atatccatc  gccttgcagg ctgactggat agaaccggcc      2220
tgcccttttct ctcaaaatga caaagaagtg gccgagagag ttttggaatt tgatataggc     2280
tggctggcag agcctatttt tggttccgga gattatccac gtgtgatgag ggactggctg      2340
```

```
aaccaaaaaa acaattttct tttgccctat ttcaccgaag atgaaaaaaa gctagtccgg   2400
ggttcctttg acttcctggc ggtgagtcat tacaccacca ttctggtaga ctgggaaaag   2460
gaggatccga tgaaatacaa cgattacttg gaggtacagg agatgactga catcacatgg   2520
ctcaactctc ccagtcaggt ggcagtggtg ccttggggc tgcgcaaagt gctcaactgg    2580
ctaaggttca agtacggaga cctcccgatg tatgtgacag ccaatggaat cgatgatgac   2640
ccccacgccg agcaagactc actgaggatc tattatatta agaattatgt gaatgaggct   2700
ctgaaagcct acgtgttgga cgacatcaac ctttgtggct actttgcgta ttcacttagt   2760
gatcgctcag ctcccaagtc tggcttttat cgatatgctg cgaatcagtt tgagcccaaa   2820
ccatctatga acattacag gaaaattatt gacagcaatg gcttcctggg ttctggaaca    2880
ctgggaaggt tttgtccaga agaatacact gtgtgcaccg aatgtggatt ttttcaaacc   2940
cggaagtctt tgctggtctt catctcgttt cttgttttta cttttattat ttctcttgct   3000
ctcatttttc actactccaa gaaaggccag agaagttata agtaa                   3045
```

<210> SEQ ID NO 333
<211> LENGTH: 216
<212> TYPE: PRT
<213> ORGANISM: Homo sapiens

<400> SEQUENCE: 333

Met Arg Ser Gly Cys Val Val His Val Trp Ile Leu Ala Gly Leu
1               5                   10                  15
Trp Leu Ala Val Ala Gly Arg Pro Leu Ala Phe Ser Asp Ala Gly Pro
            20                  25                  30
His Val His Tyr Gly Trp Gly Asp Pro Ile Arg Leu Arg His Leu Tyr
        35                  40                  45
Thr Ser Gly Pro His Gly Leu Ser Ser Cys Phe Leu Arg Ile Arg Ala
    50                  55                  60
Asp Gly Val Val Asp Cys Ala Arg Gly Gln Ser Ala His Ser Leu Leu
65                  70                  75                  80
Glu Ile Lys Ala Val Ala Leu Arg Thr Val Ala Ile Lys Gly Val His
                85                  90                  95
Ser Val Arg Tyr Leu Cys Met Gly Ala Asp Gly Lys Met Gln Gly Leu
            100                 105                 110
Leu Gln Tyr Ser Glu Glu Asp Cys Ala Phe Glu Glu Ile Arg Pro
        115                 120                 125
Asp Gly Tyr Asn Val Tyr Arg Ser Glu Lys His Arg Leu Pro Val Ser
    130                 135                 140
Leu Ser Ser Ala Lys Gln Arg Gln Leu Tyr Lys Asn Arg Gly Phe Leu
145                 150                 155                 160
Pro Leu Ser His Phe Leu Pro Met Leu Pro Met Val Pro Glu Glu Pro
                165                 170                 175
Glu Asp Leu Arg Gly His Leu Glu Ser Asp Met Phe Ser Ser Pro Leu
            180                 185                 190
Glu Thr Asp Ser Met Asp Pro Phe Gly Leu Val Thr Gly Leu Glu Ala
        195                 200                 205
Val Arg Ser Pro Ser Phe Glu Lys
    210                 215

<210> SEQ ID NO 334
<211> LENGTH: 209
<212> TYPE: PRT
<213> ORGANISM: Homo sapiens

<400> SEQUENCE: 334

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

CHIMERIC FIBROBLAST GROWTH FACTOR 23 PROTEINS AND METHODS OF USE

This application claims priority benefit of U.S. Provisional Patent Application No. 61/656,887, filed Jun. 7, 2012, and U.S. Provisional Patent Application No. 61/664,097, filed Jun. 25, 2012, each of which is hereby incorporated by reference in its entirety.

This invention was made with government support under grant numbers DE13686, DK077276, AG019712, DK091392, and DK067158 awarded by the U.S. National Institutes of Health. The government has certain rights in this invention.

FIELD OF THE INVENTION

The present invention relates to chimeric fibroblast growth factor ("FGF") proteins and uses thereof.

BACKGROUND OF THE INVENTION

Fibroblast growth factor (FGF) 23, is an endocrine regulator of phosphate homeostasis and vitamin D metabolism, and was originally identified as the mutated gene in patients with the phosphate wasting disorder "autosomal dominant hypophosphatemic rickets" (ADHR) (Anonymous, "Autosomal Dominant Hypophosphataemic Rickets is Associated with Mutations in FGF23," *Nat Genet* 26(3):345-348 (2000)). FGF23 inhibits reabsorption of phosphate in the renal proximal tubule by decreasing the abundance of the type II sodium-dependent phosphate transporters $NaP_i$-2A and $NaP_i$-2C in the apical brush border membrane (Baum et al., "Effect of Fibroblast Growth Factor-23 on Phosphate Transport in Proximal Tubules," *Kidney Int* 68(3):1148-1153 (2005); Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," *Am J Physiol Renal Physiol* 293(5):F1577-1583 (2007); Larsson et al., "Transgenic Mice Expressing Fibroblast Growth Factor 23 under the Control of the Alpha1 (I) Collagen Promoter Exhibit Growth Retardation, Osteomalacia, and Disturbed Phosphate Homeostasis," *Endocrinology* 145(7):3087-3094 (2004)). The phosphaturic activity of FGF23 is down-regulated by proteolytic cleavage at the $^{176}RXXR^{179}$ (SEQ ID NO: 233) motif, where "XX" is defined as "HT", corresponding to positions 177 and 178, respectively, of the FGF23 amino acid sequence, producing an inactive N-terminal fragment (Y25 to R179) and a C-terminal fragment (S180 to I251) (Goetz et al., "Molecular Insights into the Klotho-dependent, Endocrine Mode of Action of Fibroblast Growth Factor 19 Subfamily Members," *Mol Cell Biol* 27(9):3417-3428 (2007)). αKlotho, a protein first described as an aging suppressor (Kuro-o et al., "Mutation of the Mouse Klotho Gene Leads to a Syndrome Resembling Aging," *Nature* 390(6655):45-51 (1997)), is required by FGF23 in its target tissue in order to exert its phosphaturic activity (Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006)). αKlotho constitutively binds the cognate FGFRs of FGF23, and the binary FGFR-αKlotho complexes exhibit enhanced binding affinity for FGF23 ((Kurosu et al., "Regulation of Fibroblast Growth Factor-23 Signaling by Klotho," *J Biol Chem* 281 (10):6120-6123 (2006); Urakawa et al., "Klotho Converts Canonical FGF Receptor into a Specific Receptor for FGF23," *Nature* 444(7120):770-774 (2006)). In co-immunoprecipitation studies, it was demonstrated that the mature, full-length form of FGF23 (Y25 to I251) but not the inactive N-terminal fragment of proteolytic cleavage (Y25 to R179) binds to binary FGFR-αKlotho complexes (Goetz et al., "Molecular Insights into the Klotho-dependent, Endocrine Mode of Action of Fibroblast Growth Factor 19 Subfamily Members," *Mol Cell Biol* 27(9):3417-3428 (2007)).

It was further shown that the mature, full-length form of FGF23 (Y25 to I251) forms a stable ternary complex with the ectodomain of αKlotho and the ligand-binding domain of FGFR1c in solution (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). The ligand interacts with a de novo binding site generated at the composite receptor-coreceptor interface in the binary αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). The region on FGF23 that binds to this de novo site was mapped to the 72 amino acid long C-terminal tail, which follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). Thus, the N-terminal fragment of proteolytic cleavage (Y25 to R179) is metabolically inactive because it lacks the binding site for the αKlotho-FGFR complex. The C-terminal proteolytic fragment (S180 to I251), however, can compete with full-length FGF23 for binding to the αKlotho-FGFR complex to antagonize the metabolic activity of FGF23, because this fragment contains the binding site for the αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). These findings suggest a dual mechanism by which proteolytic cleavage at the RXXR motif inactivates FGF23: the cleavage removes the binding site for the αKlotho-FGFR complex from FGF23 and concomitantly generates an endogenous inhibitor of FGF23 Inhibition of this proteolytic cleavage by missense mutations at the RXXR motif in FGF23 leads to accumulation of full-length, bioactive FGF23, causing renal phosphate wasting disease in humans (Shimada et al., "Mutant FGF-23 Responsible for Autosomal Dominant Hypophosphatemic Rickets is Resistant to Proteolytic Cleavage and Causes Hypophosphatemia in vivo," Endocrinology 143:3179-3182 (2002); White et al., "Autosomal-dominant Hypophosphatemic Rickets (ADHR) Mutations Stabilize FGF-23," *Kidney Int* 60:2079-2086 (2001); White et al., "Autosomal Dominant Hypophosphataemic Rickets is Associated with Mutations in FGF23," *Nature Genet* 26:345-348 (2000)).

Conversely, enhanced FGF23 cleavage due to impaired O-glycosylation of FGF23 leads to a deficit in full-length FGF23, which manifests as hyperphosphatemia and soft tissue calcification in humans (Frishberg Y et al., "Hyperostosis-hyperphosphatemia Syndrome: a Congenital Disorder of O-glycosylation Associated with Augmented Processing of Fibroblast Growth Factor 23," *J Bone Miner Res* 22:235-242 (2007); Kato et al., "Polypeptide GalNAc-transferase T3 and Familial Tumoral Calcinosis. Secretion of Fibroblast Growth Factor 23 Requires β-glycosylation," *J Biol Chem* 281:18370-18377 (2006)). Familial tumoral calcinosis is an autosomal recessive metabolic disorder associated with hyperphosphatemia and soft tissue calcification. Missense mutations in either the UDP-N-acetyl-α-D-galactosamine: polypeptide N-acetylglactosaminyltransferase 3 (GALNT3) gene (Garringer et al., "Two Novel GALNT3 Mutations in Familial Tumoral Calcinosis," *Am Med Genet A* 143A:2390-2396 (2007)) or the FGF23 gene (Garringer et al., "Molecular Genetic and Biochemical Analyses of FGF23 Mutations in Familial Tumoral Calcinosis," *Am Physiol Endocrinol Metab* 295:E929-E937 (2008); Araya et al., "A Novel Mutation in Fibroblast Growth Factor 23 Gene as a Cause of Tumoral Calcinosis," *J Clin Endocrinol Metab* 90:5523-5527 (2005)) have been associated with familial tumoral calcinosis. There is a great need for suitable treatments for such patients.

The present invention is directed to overcoming these and other deficiencies in the art.

SUMMARY OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification.

Another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a C-terminal portion of FGF23 that includes an α-Klotho-FGFR complex binding domain to the modified FGF protein's C-terminus.

Yet another aspect of the present invention relates to a method of facilitating fibroblast growth factor receptor ("FGFR")-α-Klotho co-receptor complex formation. This method involves providing a cell that includes a α-Klotho co-receptor and an FGFR and providing a chimeric FGF protein. The chimeric FGF protein includes a C-terminal portion of FGF23 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-αKlotho co-receptor complex formation.

Yet a further aspect of the present invention relates to a method of screening for agents capable of facilitating fibroblast growth factor receptor ("FGFR")-αKlotho co-receptor complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves providing a binary αKlotho-FGFR complex and providing one or more candidate agents. This method further involves combining the chimeric FGF, the binary αKlotho-FGFR complex, and the one or more candidate agents under conditions permitting the formation of a ternary complex between the chimeric FGF and the binary αKlotho-FGFR complex in the absence of the one or more candidate agents. This method also involves identifying the one or more candidate agents that decrease ternary complex formation between the chimeric FGF and the binary αKlotho-FGFR compared to the ternary complex formation in the absence of the one or more candidate agents as suitable for treating the disorder.

Yet another aspect of the present invention relates to a modified FGF23 protein. The modified FGF23 protein includes an FGF23 protein that includes a modification to decrease binding affinity for heparin and/or heparan sulfate compared to an FGF23 protein without the modification.

Another aspect of the present invention relates to a method for treating a subject suffering from a disorder. This method involves selecting a subject suffering from the disorder and administering to the selected subject a therapeutically effective amount of a modified FGF23 protein that includes a modification to decrease binding affinity for heparin and/or heparan sulfate compared to an FGF23 protein without the modification.

Fibroblast growth factors (FGFs) 19, 21, and 23 are hormones that regulate in a Klotho co-receptor-dependent fashion major metabolic processes such as glucose and lipid metabolism (FGF21) and phosphate and vitamin D homeostasis (FGF23). The role of heparan sulfate glycosaminoglycan in the formation of the cell surface signaling complex of endocrine FGFs has remained unclear. To decipher the role of HS in endocrine FGF signaling, we generated FGF19 and FGF23 mutant ligands devoid of HS binding and compared their signaling capacity with that of wild-type ligands. The data presented herein show that the mutated ligands retain full metabolic activity demonstrating that HS does not participate in the formation of the endocrine FGF signaling complex. Here it is shown that heparan sulfate is not a component of the signal transduction unit of FGF19 and FGF23. A paracrine FGF is converted into an endocrine ligand by diminishing heparan sulfate binding affinity of the paracrine FGF and substituting its C-terminal tail for that of an endocrine FGF containing the Klotho co-receptor binding site in order to home the ligand into the target tissue. The ligand conversion provides a novel strategy for engineering endocrine FGF-like molecules for the treatment of metabolic disorders, including global epidemics such as type 2 diabetes and obesity.

BRIEF DESCRIPTION OF THE DRAWINGS

FIG. 1A shows interactions of FGF2 (schematic representation) with a heparin hexasaccharide (shown as sticks) as observed in the crystal structure of the 2:2 FGF2-FGFR1c dimer (PDB ID: 1FQ9; (Schlessinger et al., *Mol. Cell* 6:743-750 (2000), which is hereby incorporated by reference in its entirety)). The heparin hexasaccharide consists of three disaccharide units of 1→4 linked N-sulfated-6-O-sulfated D-glucosamine and 2-O-sulfated L-iduronic acid. Note that the heparin hexasaccharide interacts with both side chain and backbone atoms of residues in the HS-binding site of FGF2. Dashed lines denote hydrogen bonds. K128, R129, and K134, which make the majority of hydrogen bonds with the heparin hexasaccharide, are boxed. The β-strand nomenclature follows the original FGF1 and FGF2 crystal structures (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety). Please note that compared to the prototypical β-trefoil fold seen in soybean trypsin inhibitor (PDB ID: 1TIE; (Onesti et al., *J. Mol. Biol.* 217:153-176 (1991), which is hereby incorporated by reference in its entirety)) and interleukin 1β (PDB ID: 1I1B; (Finzel et al., *J. Mol. Biol.* 209:779-791 (1989), which is hereby incorporated by reference in its entirety)), the β10-β11 strand pairing in FGF2 and other paracrine FGFs is less well defined. FIGS. 1B and 1C show cartoon representation of the crystal structures of FGF19 (PDB ID: 2P23; (Goetz et al., *Mol. Cell Biol.* 27:3417-3428 (2007), which is hereby incorporated by reference in its entirety)) (FIG. 1B) and FGF23 (PDB ID: 2P39; (Goetz et al., *Mol. Cell Biol.* 27:3417-3428 (2007), which is hereby incorporated by reference in its entirety)) (FIG. 1C) shown in the same orientation as the FGF2 structure in FIG. 1A. Side chains of residues that map to the corresponding HS-binding sites of these ligands are shown as sticks. Residues selected for mutagenesis to knock out residual HS binding in FGF19 and FGF23 are boxed. NT and CT indicate N- and C-termini of the FGFs. FIG. 1D is a schematic of two working models for the endocrine FGF-FGFR-Klotho coreceptor signal transduction unit. A recent study on the ternary complex formation between FGF21, FGFR1c, and βKlotho supports the 1:2:1 model rather than the 2:2:2 model (Ming et al., *J. Biol. Chem.* 287:19997-20006 (2012), which is hereby incorporated by reference in its entirety). For comparison, a schematic of the paracrine FGF-FGFR-HS signaling unit is shown, which was made based on the crystal structure of the 2:2:2 FGF2-FGFR1c-HS complex (PDB ID: 1FQ9; (Schlessinger et al., *Mol. Cell* 6:743-750 (2000), which is hereby incorporated by reference in its entirety)). HS engages both paracrine FGF and receptor to enhance binding of FGF to its primary and secondary receptors thus promoting receptor dimerization. A question mark denotes whether or not HS is also a component of the endocrine FGF signaling complex.

FIG. 2 shows a sequence alignment of the endocrine FGFs, FGF1, and FGF2. The amino acid sequences of the mature human FGF19, FGF21, and FGF23 ligands are aligned. Also included in the alignment are the human sequences of FGF1 and FGF2, prototypical paracrine FGFs, which were used in the experiments described herein, in which FGF1 and FGF2 were converted into endocrine FGF ligands. Residue numbers corresponding to the human sequence of FGF1 (SEQ ID NO: 1) (GenBank Accession No. AAH32697, which is hereby incorporated by reference in its entirety), FGF2 (SEQ ID NO: 121) (GenBank Accession No. EAX05222, which is hereby incorporated by reference in its entirety), FGF19 (SEQ ID NO: 333) (GenBank Accession No. NP_005108, which is hereby incorporated by reference in its entirety), FGF21 (SEQ ID NO: 334) (GenBank Accession No. NP_061986, which is hereby incorporated by reference in its entirety), and FGF23 (SEQ ID NO: 233) (GenBank accession no. AAG09917, which is hereby incorporated by reference in its entirety) are in parenthesis to the left of the alignment. Secondary structure elements are labeled, and residues containing these elements for known secondary structures are boxed. Gaps (dashes) were introduced to optimize the sequence alignment. The β-trefoil core domain for known FGF crystal structures is shaded gray. Blue bars on top of the alignment indicate the location of the HS-binding regions. HS-binding residues selected for mutagenesis are shaded blue.

FIG. 3A shows an overlay of SPR sensorgrams illustrating heparin binding of FGF2, FGF19, FGF21, and FGF23 (left panel) and an exploded view of the binding responses for FGF19-, FGF21-, and FGF23-heparin interactions (right panel). Heparin was immobilized on a biosensor chip, and 400 nM of FGF2, FGF19, FGF21, or FGF23 were passed over the chip. Note that FGF19, FGF21, and FGF23 exhibit measurable, residual heparin binding and that differences in heparin binding exist between these three endocrine FGFs. FIGS. 3B-3D show overlays of SPR sensorgrams illustrating binding of FGF19 to heparin (FIG. 3B) and lack of interaction between the FGF19$^{K149A}$ mutant and heparin (FIG. 3C) and between the FGF19$^{K149A, R157A}$ mutant and heparin (FIG. 3D). Heparin was immobilized on a biosensor chip, and increasing concentrations of FGF19 were passed over the chip. Thereafter, FGF19$^{K149A}$ or FGF19$^{K149A, R157A}$ was injected over the heparin chip at the highest concentration tested for the wild-type ligand. FIGS. 3E-3G show overlays of SPR sensorgrams illustrating binding of FGF23 to heparin (FIG. 3E), poor interaction between the FGF23$^{R48A, N49A}$ mutant and heparin (FIG. 3F), and lack of interaction between the FGF23$^{R140A, R143A}$ mutant and heparin (FIG. 3G). Heparin was immobilized on a biosensor chip, and increasing concentrations of FGF23 were passed over the chip. FGF23$^{R48A, N49A}$ or FGF23$^{R140A, R143A}$ was then injected over the heparin chip at the highest concentration tested for the wild-type ligand.

FIG. 4A shows results of an immunoblot analysis of phosphorylation of FRS2α (pFRS2α) and 44/42 MAP kinase (p44/42 MAPK) in H4IIE hepatoma cells following stimulation with the FGF19$^{K149A}$ mutant, the FGF19$^{K149A, R157A}$ mutant, or wild-type FGF19. Numbers above the lanes give the amounts of protein added in ng ml$^{-1}$. Total 44/42 MAPK protein expression was used as a loading control. FIG. 4B shows results of an immunoblot analysis of phosphorylation of FRS2α (pFRS2α) and 44/42 MAP kinase (p44/42 MAPK) in a HEK293-αKlotho cell line following stimulation with the FGF23$^{R48A, N49A}$ mutant, the FGF23$^{R140A, R143A}$ mutant, or wild-type FGF23. Numbers above the lanes give the amounts of protein added in ng ml$^{-1}$. Total 44/42 MAPK and αKlotho protein expression were used as loading controls. FIG. 4C shows graphical results of a quantitative analysis of CYP7A1 and CYP8B1 mRNA expression in liver tissue from mice treated with FGF19$^{K149A}$, FGF19$^{K149A, R157A}$, FGF19, or vehicle. 1 mg of protein per kg of body weight was given. Data are presented as mean±SEM; ***, P<0.001 by Student's t test. FIG. 4D shows graphical results of analysis of serum phosphate concentrations (serum P$_i$) in mice before and 8 h after intraperitoneal injection of FGF23$^{R48A, N49A}$, FGF23$^{R140A, R143A}$, FGF23, or vehicle. Wild-type mice were given a single dose of protein (0.29 mg kg body weight$^{-1}$), whereas Fgf23 knockout mice received two doses of 0.71 mg kg body weight$^{-1}$ each. Data are presented as mean±SEM; *, P<0.05, and **, P<0.01 by ANOVA.

Figures 5A, 5B, 5C, 5D, 5E, 5F, 5G:
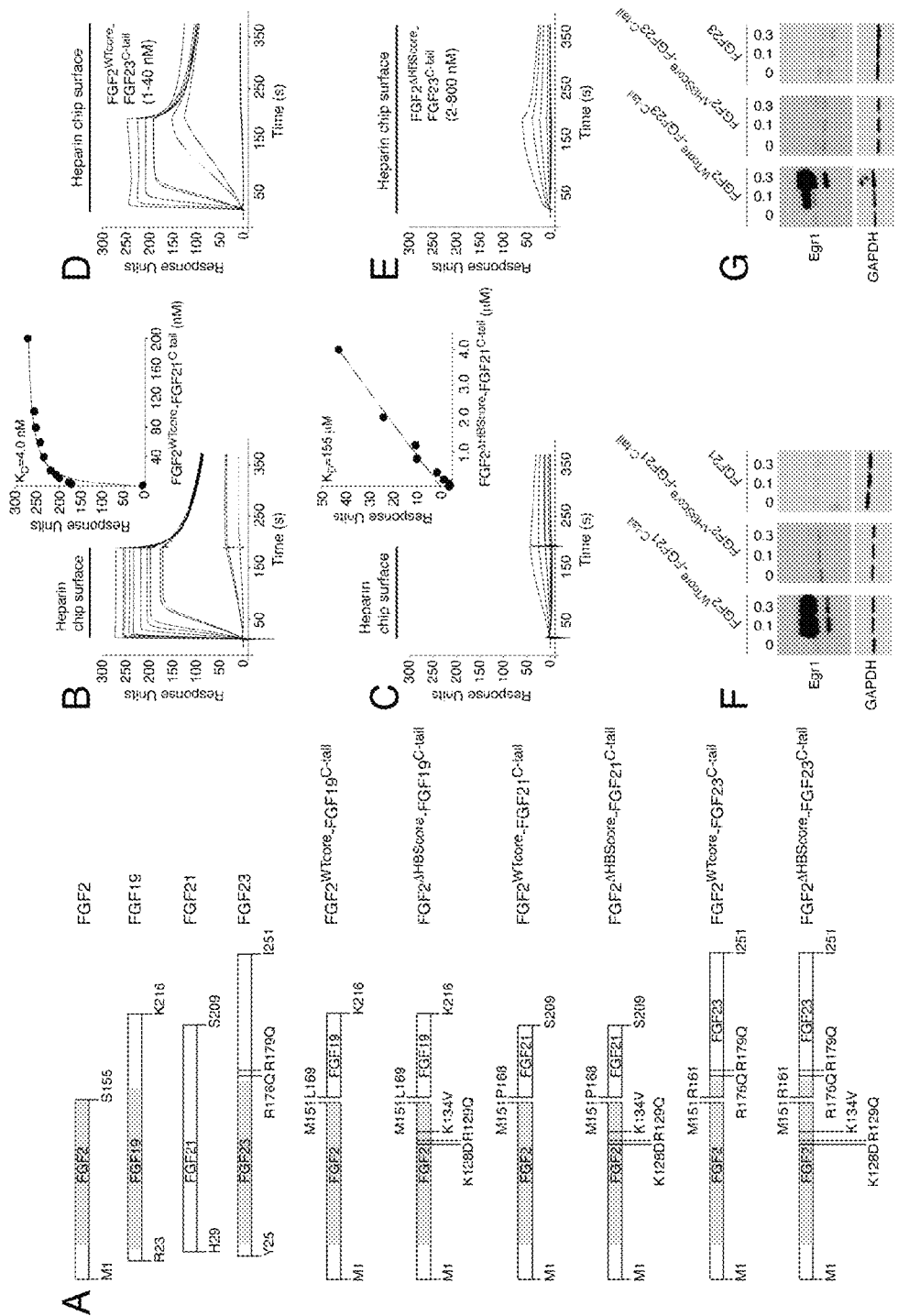

FIGS. 5A-5G show design and results relating to the conversion of FGF2 into an endocrine ligand. FIG. 5A is a schematic of human FGF2, FGF19, FGF21, FGF23, and engineered FGF2-FGF19, FGF2-FGF21, and FGF2-FGF23 chimeras. Amino acid boundaries of each ligand and of each component of the chimeras are labeled with residue letter and number. The β-trefoil core domain for the known ligand crystal structures is shaded gray. HS-binding residues mutated in the FGF2 portion of chimeras are labeled with residue letter and number. Also labeled are the arginine residues of the proteolytic cleavage site in the C-terminal region of FGF23 that were mutated to glutamine in both FGF23 and the FGF2-FGF23 chimeras. FIGS. 5B and 5C show overlays of SPR sensorgrams illustrating binding of FGF2$^{WTcore}$-FGF21$^{C-tail}$ (FIG. 5B) and FGF2$^{\Delta HBScore}$-FGF21$^{C-tail}$ (FIG. 5C) to heparin, and fitted saturation binding curves. Heparin was immobilized on a biosensor chip, and increasing concentrations of FGF2$^{WTcore}$-FGF21$^{C-tail}$ or FGF2$^{\Delta HBScore}$-FGF21$^{C-tail}$ were passed over the chip. Dissociation constants ($K_D$s) were derived from the saturation binding curves. FIGS. 5D and 5E show overlays of SPR sensorgrams illustrating binding of FGF2$^{WTcore}$-FGF23$^{C-tail}$ (FIG. 5D) and FGF2$^{\Delta HBScore}$-FGF23$^{C-tail}$ (FIG. 5E) to heparin. Increasing concentrations of FGF2$^{WTcore}$-FGF23$^{C-tail}$ or FGF2$^{\Delta HBScore}$-FGF23$^{C-tail}$ were passed over a chip containing immobilized heparin. FIGS. 5F and 5G show results of immunoblot analysis for Egr1 expression in HEK293 cells following stimulation with chimeras or native FGFs as denoted. Numbers above the lanes give the amounts of protein added in nanomolar. GAPDH protein expression was used as a loading control.

Figure 6:
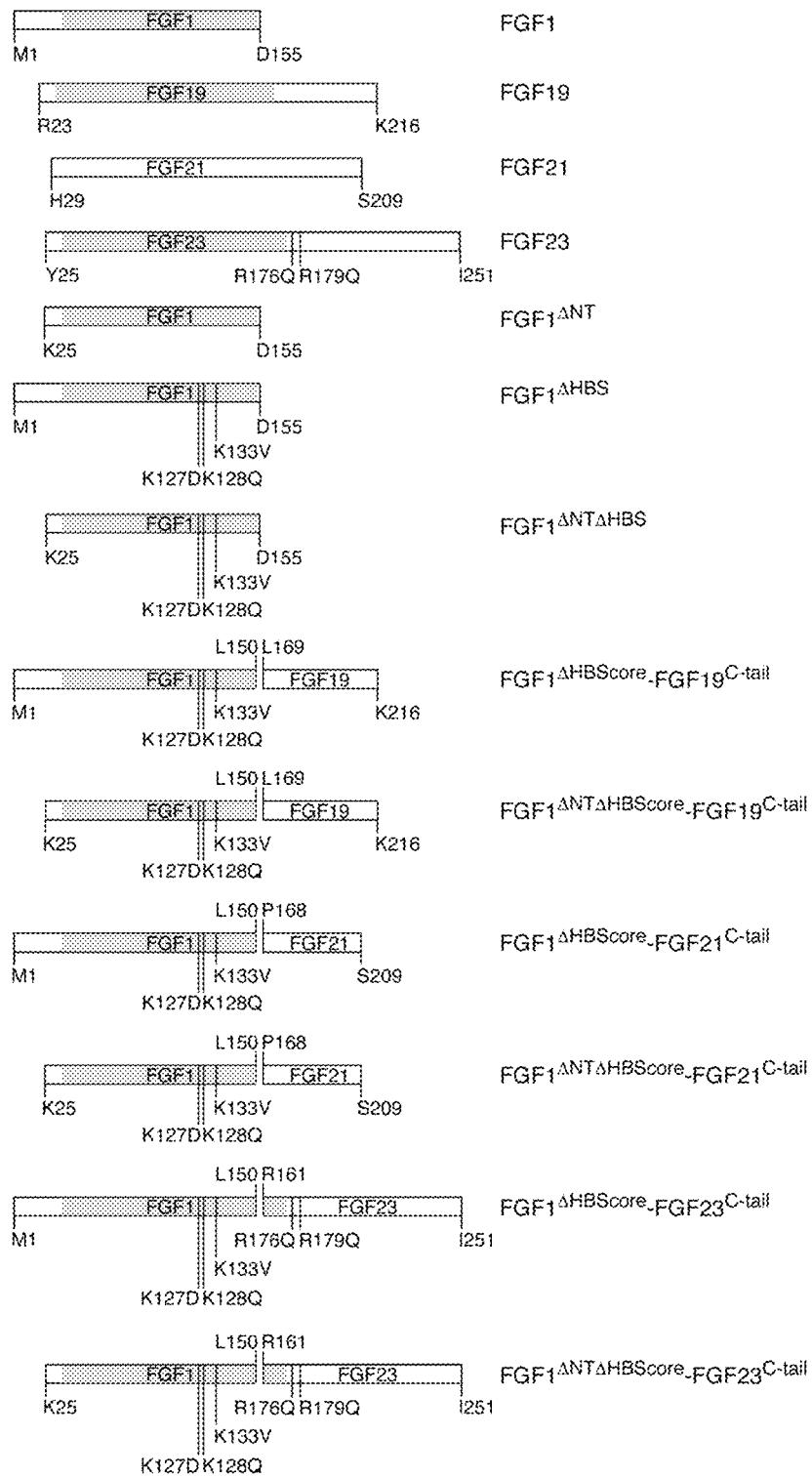

FIG. 6 is a schematic illustrating the conversion of FGF1 into an endocrine ligand. Shown are schematic drawings of human FGF1, FGF19, FGF21, FGF23, and exemplary FGF1-FGF19, FGF1-FGF21, and FGF1-FGF23 chimeras according to the present invention. Amino acid boundaries of each ligand and of each component of the chimeras are labeled with residue letter and number. The β-trefoil core domain for the known ligand crystal structures is shaded gray. HS-binding residues mutated in the FGF1 portion of chimeras are labeled with residue letter and number. Also labeled are the arginine residues of the proteolytic cleavage site in the C-terminal region of FGF23 that were mutated to glutamine in both FGF23 and the FGF1-FGF23 chimeras.

Figures 7A, 7B, 7C, 7D, 7E, 7F, 7G:
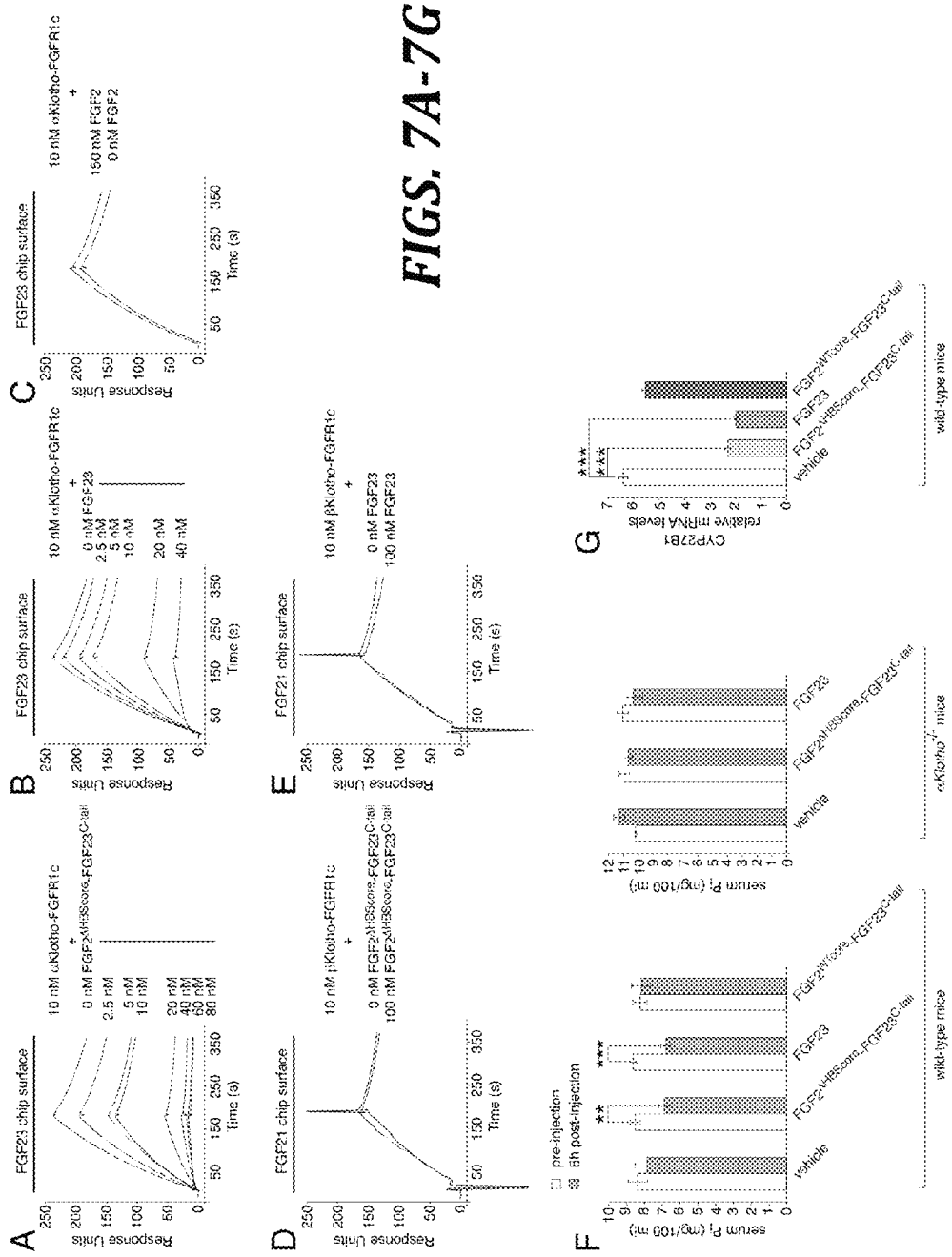

FIGS. 7A-7G show results demonstrating that the FGF2$^{\Delta HBScore}$-FGF23$^{C-tail}$ chimera exhibits FGF23-like activity. FIGS. 7A and 7B show overlays of SPR sensorgrams illustrating inhibition by FGF2$^{\Delta HBScore}$-FGF23$^{C-tail}$ (FIG. 7A) or FGF23 (FIG. 7B) of αKlotho-FGFR1c binding to FGF23 immobilized on a biosensor chip. Increasing concentrations of FGF2$^{\Delta HBScore}$-FGF23$^{C-tail}$ or FGF23 were mixed with a fixed concentration of αKlotho-FGFR1c complex, and the mixtures were passed over a FGF23 chip. FIG. 7C shows an overlay of SPR sensorgrams illustrating failure of FGF2 to inhibit αKlotho-FGFR1c binding to FGF23. FGF2 and αKlotho-FGFR1c complex were mixed at a molar ratio of 15:1, and the mixture was passed over a biosensor chip containing immobilized FGF23. FIGS. 7D and 7E show overlays of SPR sensorgrams illustrating no inhibition by FGF2$^{\Delta HBScore}$-FGF23$^{C-tail}$ (FIG. 7D) or FGF23 (FIG. 7E) of βKlotho-FGFR1c binding to FGF21. FGF2$^{\Delta HBScore}$-FGF23$^{C-tail}$ or FGF23 were mixed with βKlotho-FGFR1c complex at a molar ratio of 10:1, and the mixtures were passed over a biosensor chip containing immobilized FGF21. FIG. 7F shows analysis of serum phosphate concentrations (serum $P_i$) in mice before and 8 h after intraperitoneal injection of FGF2$^{\Delta HBScore}$-FGF23$^{C-tail}$, FGF2$^{WTcore}$-FGF23$^{C-tail}$, FGF23, or vehicle. Wild-type mice and αKlotho knockout mice were given 0.21 mg and 0.51 mg of protein, respectively, per kg of body weight. Data are presented as mean±SEM; , P<0.01; *, P<0.001 by ANOVA. FIG. 7G shows quantitative analysis of CYP27B1 mRNA expression in renal tissue from mice injected with FGF2$^{\Delta HBScore}$-FGF23$^{C-tail}$, FGF2$^{WTcore}$-FGF23$^{C-tail}$, FGF23, or vehicle. 0.21 mg of protein per kg of body weight were injected. Data are presented as mean±SEM; ***, P<0.001 by ANOVA.

Figures 8A, 8B, 8C, 8D, 8E, 8F, 8G:
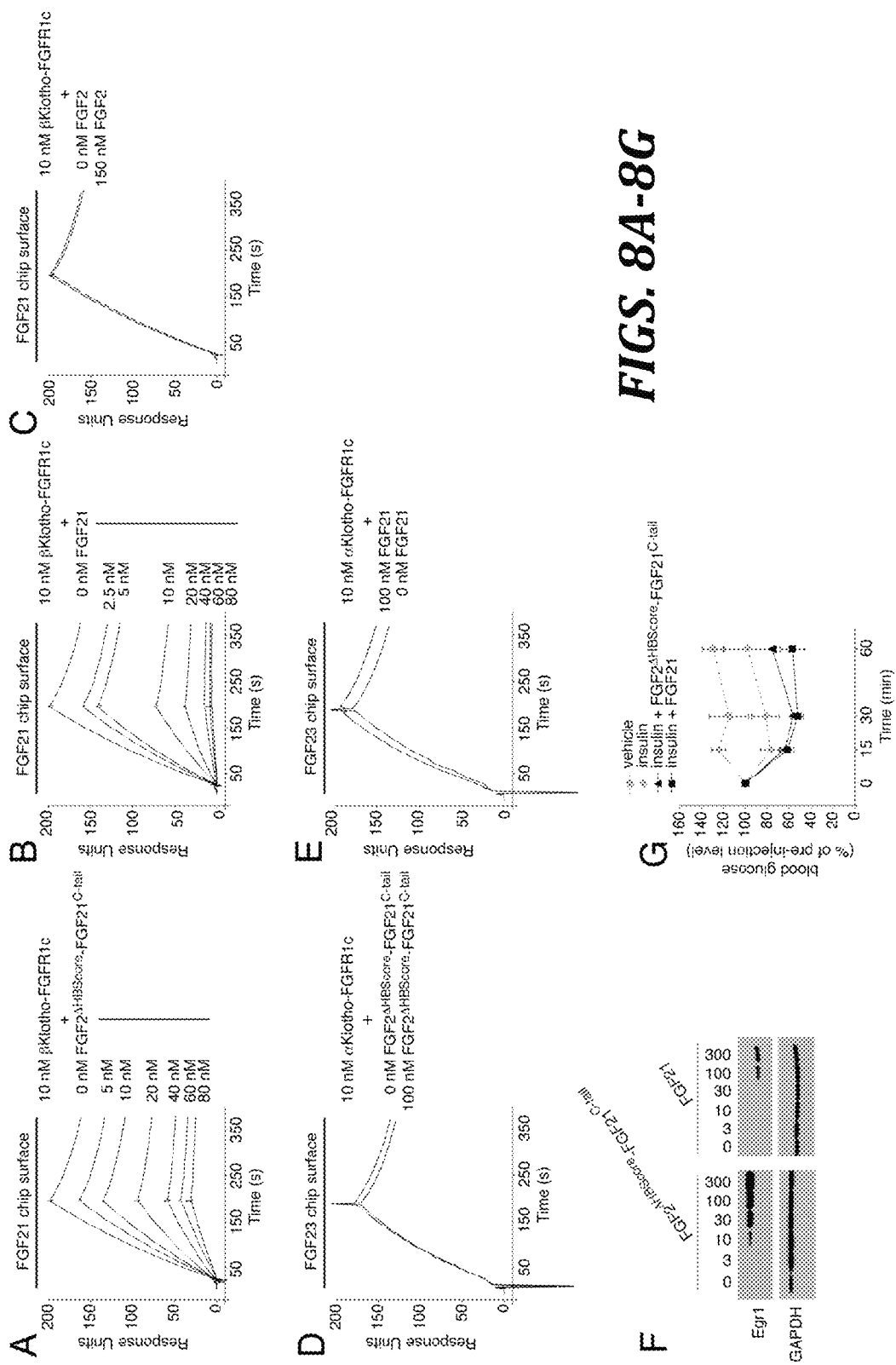

FIGS. 8A-8G show results demonstrating that the FGF2$^{\Delta HBScore}$-FGF21$^{C-tail}$ chimera exhibits FGF21-like activity. FIGS. 8A-8B show overlays of SPR sensorgrams illustrating inhibition by FGF2$^{\Delta HBScore}$-FGF21$^{C-tail}$ (FIG. 8A) or FGF21 (FIG. 8B) of βKlotho-FGFR1c binding to FGF21 immobilized on a biosensor chip. Increasing concentrations of FGF2$^{\Delta HBScore}$-FGF21$^{C-tail}$ or FGF21 were mixed with a fixed concentration of βKlotho-FGFR1c complex, and the mixtures were passed over a FGF21 chip. FIG. 8C shows an overlay of SPR sensorgrams illustrating failure of FGF2 to inhibit βKlotho-FGFR1c binding to FGF21. FGF2 and βKlotho-FGFR1c complex were mixed at a molar ratio of 15:1, and the mixture was passed over a biosensor chip containing immobilized FGF21. FIGS. 8D-8E show overlays of SPR sensorgrams illustrating no inhibition by FGF2$^{\Delta HBScore}$-FGF21$^{C-tail}$ (FIG. 8D) or FGF21 (FIG. 8E) of αKlotho-FGFR1c binding to FGF23. FGF2$^{\Delta HBScore}$-FGF21$^{C-tail}$ or FGF21 were mixed with αKlotho-FGFR1c complex at a molar ratio of 10:1, and the mixtures were passed over a biosensor chip containing immobilized FGF23. FIG. 8F shows results of immunoblot analysis for Egr1 expression in HEK293-βKlotho cells stimulated with FGF2$^{\Delta HBScore}$-FGF21$^{C-tail}$ or FGF21. Numbers above the lanes give the amounts of protein added in ng ml$^{-1}$. GAPDH protein expression was used as a loading control. Note that the FGF2$^{\Delta HBScore}$-FGF21$^{C-tail}$ chimera is more potent than native FGF21 at inducing Egr1 expression suggesting that the chimera has agonistic property. This is expected since the core domain of FGF2 has inherently greater binding affinity for FGFR than the core domain of FGF21 (see FIGS. 10A and 10C). FIG. 8G shows graphical results of analysis of blood glucose concentrations in mice before and at the indicated time points after intraperitoneal injection of insulin alone, insulin plus FGF2$^{\Delta HBScore}$-FGF21$^{C-tail}$ chimera, insulin plus FGF21, or vehicle alone. 0.5 units of insulin per kg of body weight and 0.3 mg of FGF21 ligand per kg of body weight were injected. Blood glucose concentrations are expressed as percent of pre-injection values. Data are presented as mean±SEM.

Figures 9A, 9B, 9C:
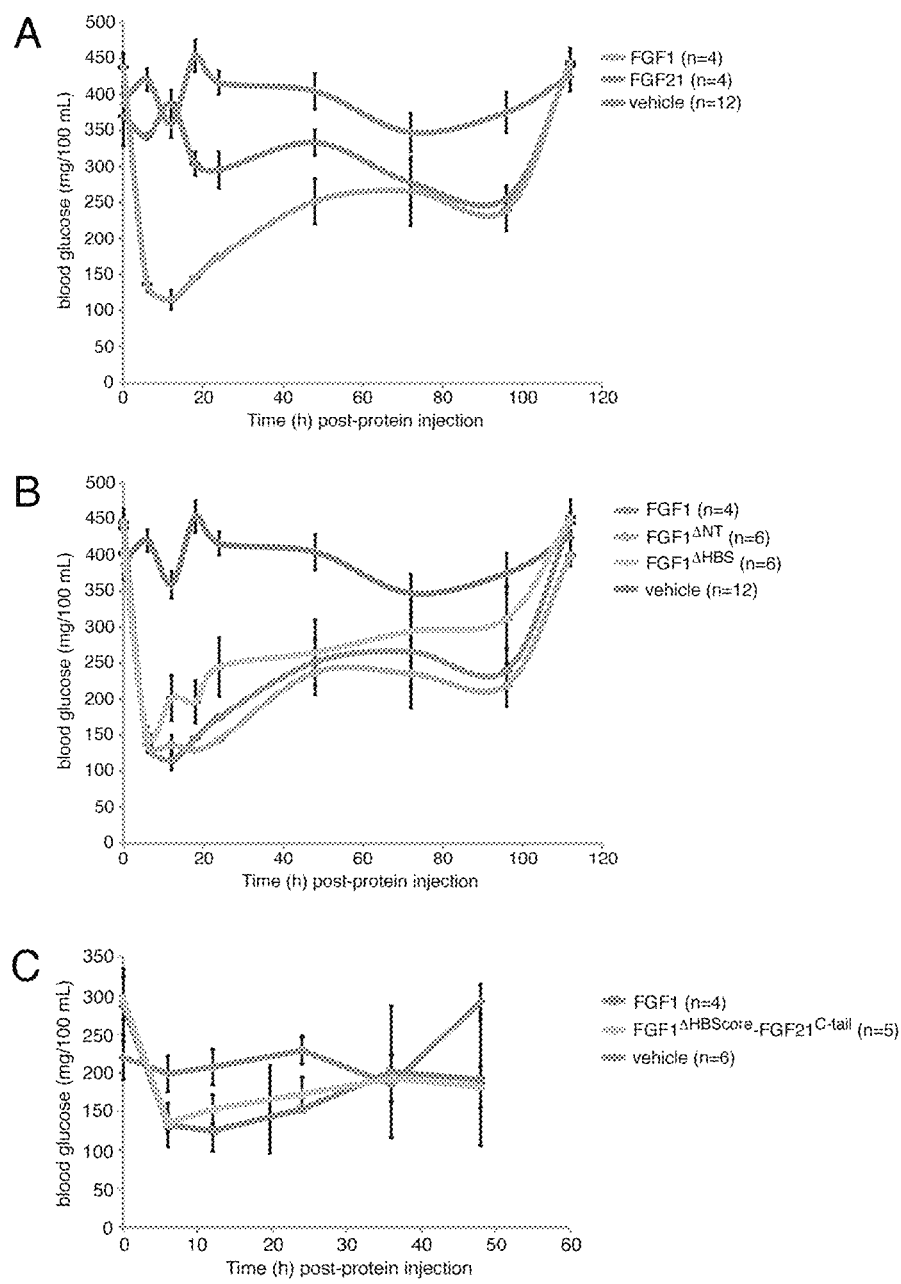

FIGS. 9A-9C show the glucose-lowering effects in ob/ob mice of FGF1 variants according to the present invention. FIG. 9A shows graphical results of analysis of blood glucose concentrations in ob/ob mice before and at the indicated time points after subcutaneous injection of FGF1 or FGF21. FIG. 9B shows graphical results of analysis of blood glucose concentrations in ob/ob mice before and at the indicated time points after subcutaneous injection of FGF1, FGF1$^{\Delta NT}$, or FGF1$^{\Delta HBS}$. FIG. 9C shows graphical results of analysis of blood glucose concentrations in ob/ob mice before and at the indicated time points after subcutaneous injection of FGF1 or FGF1$^{\Delta HBScore}$-FGF21$^{C-tail}$ chimera. For the experiments shown in FIGS. 9A-9C, ob/ob mice were injected with a bolus of 0.5 mg of FGF protein per kg of body weight. Data are presented as mean±SD.

Figures 10A, 10B, 10C, 10D, 10E, 10F:
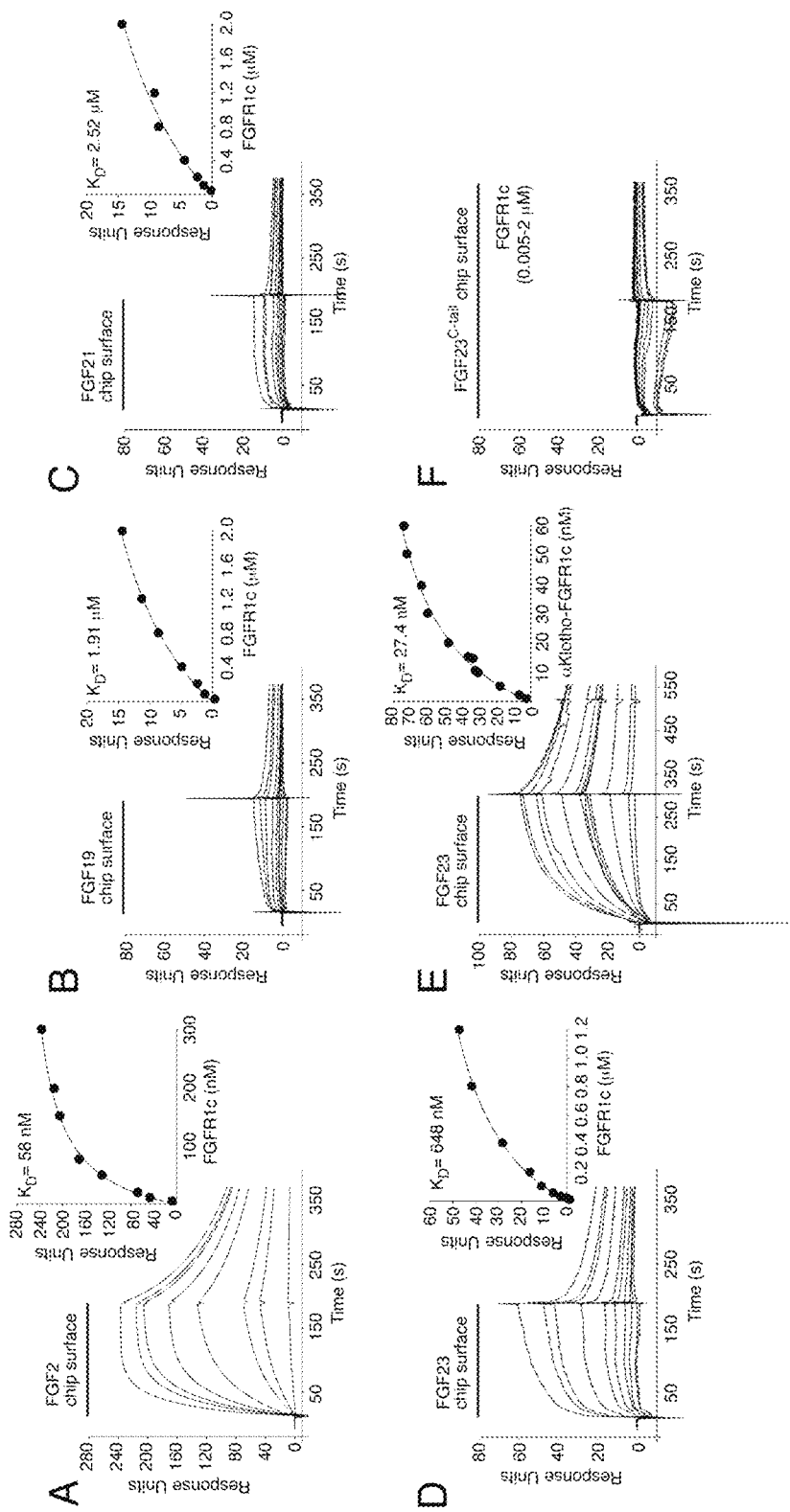

FIGS. 10A-10F show results demonstrating that endocrine FGFs have low binding affinity for FGFR1c compared to FGF2. FIGS. 10A-10D show overlays of SPR sensorgrams illustrating binding of FGFR1c to FGF2 (FIG. 10A), FGF19 (FIG. 10B), FGF21 (FIG. 10C), and FGF23 (FIG. 10D), and fitted saturation binding curves. Increasing concentrations of FGFR1c ligand-binding domain were passed over a biosensor chip containing immobilized FGF2, FGF19, FGF21, or FGF23. FIG. 10E shows an overlay of SPR sensorgrams illustrating binding of αKlotho-FGFR1c complex to FGF23. Increasing concentrations of αKlotho-FGFR1c complex were passed over a biosensor chip containing immobilized FGF23. FIG. 10F shows an overlay of SPR sensorgrams showing lack of interaction between the C-terminal tail peptide of FGF23 and FGFR1c. FGF23$^{C\text{-}tail}$ was immobilized on a biosensor chip and increasing concentrations of FGFR1c ligand-binding domain were passed over the chip. Dissociation constants ($K_D$s) given in FIGS. 10A-10E were derived from the saturation binding curves.

Figure 11:
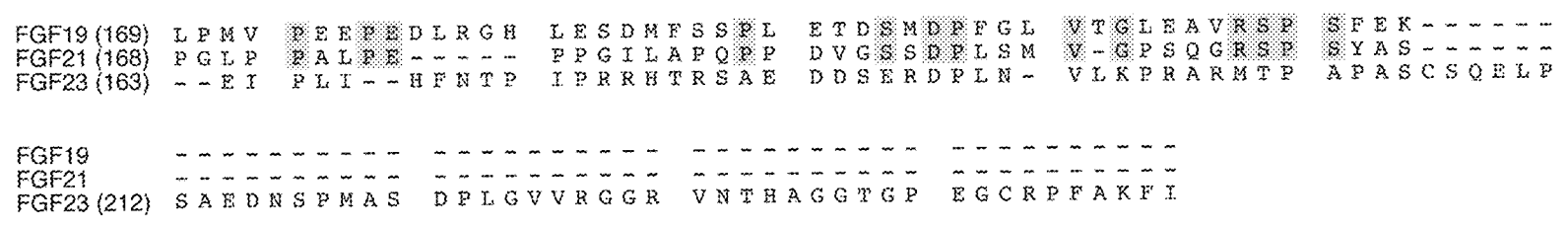

FIG. 11 shows an alignment of the C-terminal tail sequences of human FGF19 (GenBank Accession No. NP$_{13}$ 005108, which is hereby incorporated by reference in its entirety), FGF21 (GenBank Accession No. NP_061986, which is hereby incorporated by reference in its entirety), and FGF23 (GenBank accession no. AAG09917, which is hereby incorporated by reference in its entirety). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence.

DETAILED DESCRIPTION OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149: 121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331:1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115:1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs (β1-β12) and eleven β strands in endocrine FGFs (β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-3428 (2007); Asada et al., *Biochim. Biophys. Acta.* 1790:40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ. There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., *Sci. Signal* 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug Discov.* 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type I β-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A.* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583:19-24 (2009); Goetz et al., *Mol. Cell Biol.* 32:1944-1954 (2012), which are hereby incorporated by reference in their entirety).

FGF23 interacts with a de novo binding site generated at the composite receptor-coreceptor interface in the binary αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety). The region on FGF23 that binds to this de novo site was mapped to the 72 amino acid long C-terminal tail, which follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety). Thus, the N-terminal fragment of proteolytic cleavage of FGF23 (Y25 to R179) is metabolically inactive because it lacks the binding site for the αKlotho-FGFR complex. The C-terminal proteolytic fragment (S180 to I251), however, can compete with full-length FGF23 for binding to the αKlotho-FGFR complex to antagonize the metabolic activity of FGF23, because this fragment contains the binding site for the αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281:15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion and/or C-terminal portion, respectively. In some embodiments, the N-terminal portion and/or the C-terminal portion having such additional portion(s) will have enhanced and/or prolonged activity compared to the corresponding naturally occurring N-terminal portion and/or C-terminal portion, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

The portion of the paracrine FGF may be derived from any suitable paracrine FGF. Suitable paracrine FGFs in accordance with the present invention include FGF1, FGF2, and ligands of the FGF4 and FGF9 subfamilies. Certain embodiments of the present invention may include a full-length amino acid sequence of a paracrine FGF, rather than a portion of a paracrine FGF.

In one embodiment, the portion of the paracrine FGF is derived from a mammalian FGF. In one embodiment, the portion of the paracrine FGF is derived from a vertebrate FGF. In one embodiment, the portion of the paracrine FGF is derived from a human FGF. In one embodiment, the paracrine FGF is derived from a non-human mammalian FGF. In one embodiment, the portion of the paracrine FGF is derived from a non-human vertebrate FGF. In one embodiment, the paracrine FGF is derived from an ortholog of human FGF, or a polypeptide or protein obtained from one species that is the functional counterpart of a polypeptide or protein from a different species.

In one embodiment according to the present invention, the portion of the paracrine FGF of the chimeric protein includes an N-terminal portion of the paracrine FGF.

In one embodiment, the paracrine FGF is FGF1. In one embodiment, the portion of the FGF1 is from human FGF1 having the following amino acid sequence (GenBank Accession No. AAH32697, which is hereby incorporated by reference in its entirety) (SEQ ID NO: 1):

In one embodiment, the portion of the paracrine FGF includes an amino acid sequence beginning at any one of residues 1 to 25 and ending at any one of residues 150 to 155 of SEQ ID NO: 1 (human FGF1). In one embodiment, the portion of the paracrine FGF includes amino acid residues 1-150, 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-150, 25-151, 25-152, 25-153, 25-154, or 25-155 of FGF1 (SEQ ID NO: 1). In one embodiment, the portion of the paracrine FGF includes amino acid residues 1-150 or 25-150 of SEQ ID NO: 1.

In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 150 to 155 of SEQ ID NO: 1 (human FGF1). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 150 to 155 of SEQ ID NO: 1 (human FGF1).

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill

```
  1 MAEGEITTFT ALTEKFNLPP GNYKKPKLLY CSNGGHFLRI LPDGTVDGTR DRSDQHIQLQ

61 LSAESVGEVY IKSTETGQYL AMDTDGLLYG SQTPNEECLF LERLEENHYN TYISKKHAEK

121 NWFVGLKKNG SCKRGPRTHY GQKAILFLPL PVSSD
``` in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In one embodiment of the present invention, the portion of the paracrine FGF of the chimeric protein is derived from an ortholog of human FGF1. In one embodiment, the portion of FGF1 is derived from *Papio Anubis, Pongo abelii, Callithrix jacchus, Equus caballus, Pan troglodytes, Loxodonta Africana, Canis lupus familiaris, Ailuropoda mela-* noleuca, Saimiri boliviensis boliviensis, Sus scrofa, Otolemur garnettii, Rhinolophus ferrumequinum, Sorex araneus, Oryctolagus cuniculus, Cricetulus griseus, Sarcophilus harrisii, Mus musculus, Cavia porcellus, Monodelphis domestica, Desmodus rotundus, Bos taurus, Ornithorhynchus anatinus, Taeniopygia guttata, Dasypus novemcinctus, Xenopus Silurana tropicalis, Heterocephalus glaber, Pteropus alecto, Tupaia chinensis, Columba livia, Ovis aries, Gallus gallus, Vicugna pacos, Anolis carolinensis, Otolemur garnettii, Felis catus, Pelodiscus sinensis, Latimeria chalumnae, Tursiops truncates, Mustela putorius furo, Nomascus leucogenys, Gorilla gorilla, Erinaceus europaeus, Procavia capensis, Dipodomys ordii, Petromyzon marinus, Echinops telfairi, Macaca mulatta, Pteropus vampyrus, Myotis lucifugus, Microcebus murinus, Ochotona princeps, Rattus norvegicus, Choloepus hoffmanni, Ictidomys tridecemlineatus, Tarsius syrichta, Tupaia belangeri, Meleagris gallopavo, Macropus eugenii, or Danio rerio. The portions of an ortholog of human paracrine FGF1 include portions corresponding to the above-identified amino acid sequences of human FGF1. Corresponding portions may be determined by, for example, sequence analysis and structural analysis.

In one embodiment, the portion of the FGF1 of the chimeric protein of the present invention is derived from an ortholog of human FGF1 having the amino acid sequence shown in Table 1.

TABLE 1

Amino acid sequence of human FGF1 (SEQ ID NO: 1) (GenBank accession no. AAH32697, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of Papio anubis (olive baboon) FGF1 (SEQ ID NO: 2) (GenBank accession no. NP_001162557, which is hereby incorporated by reference in its entirety):

```
  1 MAEGEITTFT ALTEKFNLPP ANYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of Pongo abelii (Sumatran orangutan) FGF1 (SEQ ID NO: 3) (GenBank accession no. NP_001127073, which is hereby incorporated by reference in its entirety)

```
 60                                                                  M
 61 AEGEITTFTA LTEKFNLPPG NYKKPKLLYC SNGGHFLRIL PDGTVDGTRD RSDQHIQLQL
121 SAESVGEVYI KSTETGQYLA MDTDGLLYGS QTPNEECLFL ERLEENHYNT YISKKHAEKN
181 WFVGLKKNGS CKRGPRTHYG QKAILFLPLP VSSD
```

Amino acid sequence of Callithrix jacchus (white-tufted-ear marmoset) FGF1 (SEQ ID NO: 4) (GenBank accession no. XP_002744341, which is hereby incorporated by reference in its entirety):

```
  1 MAEGEITTFT ALTEKFDLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of Equus caballus (horse) FGF1 (SEQ ID NO: 5) (GenBank accession no. NP_001157358, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of Pan troglodytes (chimpanzee) FGF1 (SEQ ID NO: 6) (GenBank accession no. JAA29511, which is hereby incorporated by reference in its entirety):

```
  1 MAEGEITTFT ALTEKFNLPS GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of Loxodonta africana (elephant) FGF1 (SEQ ID NO: 7) (GenBank accession no. XP_003404621, which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKGTETGQYL AMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Canis lupus familiaris* (dog) FGF1
(SEQ ID NO: 8) (GenBank accession no. XP_849274,
which is hereby incorporated by reference in its entirety):

```
  1 MAEGEITTFT ALTEKFNLPP GNYMKPKLLY CSNGGHFLRI LPDGTVDGTR DRSDQHIQLQ
 61 LSAESVGEVY IKSTETGQYL AMDTDGLLYS QTPNEECLF LERLEENHYN TYTSKKHAEK
121 NWFVGLKKNG SCKRGPRTHY GQKAILFLPL PVSSD
```

Amino acid sequence of *Ailuropoda melanoleuca* (giant panda)
FGF1 (SEQ ID NO: 9) (GenBank accession no. XP_002912581,
which is hereby incorporated by reference in its entirety):

```
  1 MAEGEITTFT ALTEKFNLPA GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Saimiri boliviensis boliviensis*
(Bolivian squirrel monkey) FGF1 (SEQ ID NO: 10) (GenBank
accession no. XP_003920596, which is hereby
incorporated by reference in its entirety):

```
  1 MAEGEITTFT ALTEKFDLPP GNYKKPKLLY CSNGGHFLRI LPDGTVDGTR DRSDLHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Sus scrofa* (pig) FGF1
(SEQ ID NO: 11) (GenBank accession no. XP_003124058,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTSGLLYG SQTPSEECLF LERLEENHYN TYTSKKHAEK
121 NWFVGLKKNG SCKRGPRTHY GQKAILFLPL PVSSD
```

Amino acid sequence of *Otolemur garnettii* (small-eared galago)
FGF1 (SEQ ID NO: 12) (GenBank accession no. XP_003782135,
which is hereby incorporated by reference in its entirety):

```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Rhinolophus ferrumequinum* (greater
horseshoe bat) FGF1 (SEQ ID NO: 13) (GenBank accession no.
ACC62496, which is hereby incorporated by reference
in its entirety):

```
  1 MAEGEVTTFT ALTEKFNLPT GNYKKPKLLY CSNGGHFLRI LPDGTVDGTR DKSDQHIQLQ
 61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD
```

Amino acid sequence of *Sorex araneus* (European shrew) FGF1
(SEQ ID NO: 14) (GenBank accession no. ACE75805, which is
hereby incorporated by reference in its entirety):

```
  1 MAEGEITTFG ALMEKFNLPP GNYKKPKLLY CSNGGHFLRI LPDGTVDGTR DRSDQHIQLQ
 61 LSAESVGEVY IKSTETGHYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Oryctolagus cuniculus* (rabbit) FGF1
(SEQ ID NO: 15) (GenBank accession no. NP_001164959,
which is hereby incorporated by reference in its entirety):

```
  1 MAEGEVTTFT ALTEKFNLPA GNYKLPKLLY CSNGGHFLRI LPDGTVDGTR DRSDQHIQLQ
 61 LSAESVGEVY IKSTETGQYL AMDTDGLLYG SQTPSEECLF LERLEENHYN TYTSKKHAEK
121 NWFVGLKKNG SCKRGPRTHY GQKAILFLPL PVSSD
```

Amino acid sequence of *Cricetulus griseus* (Chinese hamster)
FGF1 (SEQ ID NO: 16) (GenBank accession no. XP_003502469,
which is hereby incorporated by reference in its entirety):

```
  1 MAEGEITTFS ALTERFNLPP GNYKKPKLLY CSNGGHFLRI LPDGTVDGTR DRSDQHIQLQ
 61 LSAESAGEVY IKGTETGQYR NMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Sarcophilus harrisii* (Tasmanian devil)
FGF1 (SEQ ID NO: 17) (GenBank accession no. XP_003756738,
which is hereby incorporated by reference in its entirety):

```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTDGLLYG SQTPTEECLF LERLEENHYN TYISKKHAEK
121 NWFVGLKKNG SCKRGPRTHY GQKAILFLPL PVSSE
```

Amino acid sequence of *Mus musculus* (house mouse) FGF1
(SEQ ID NO: 18) (GenBank accession no. NP_034327,
which is hereby incorporated by reference in its entirety):

```
  1 MAEGEITTFA ALTERFNLPL GNYKKPKLLY CSNGGHFLRI LPDGTVDGTR DRSDQHIQLQ
 61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD
```

Amino acid sequence of *Cavia porcellus* (domestic guinea pig)
FGF1 (SEQ ID NO: 19) (GenBank accession no. XP_003477242,
which is hereby incorporated by reference in its entirety):

```
  1 MAEGEITTFA ALTEKFNLPP GNYKKPKLLY CSNGGHFLRI LPDGTVDGTR DRSDQHIQLQ
 61 LSAEGVGEVY IQSTETGQYL AMDTDGLLYG SQTPSEECLF LERLEENHYN TYTSKKHVEK
121 NWFVGLKKNG SCKRGPRTHY GQKAILFLPL PVSD
```

Amino acid sequence of *Monodelphis domestica* (gray short-tailed
opossum) FGF1 (SEQ ID NO: 20) (GenBank accession no.
XP_001368921, which is hereby incorporated by
reference in its entirety):

```
  1 MAEGEITTFT ALTERFNLPL GNYKKPKLLY CSNGGHFLRI LPDGKVDGTR DRNDQHIQLQ
 61 LSTESVGEVY IKSTESGQYL AMDTDGLLYG SQTPSEECLF LERLEENHYN TYTSKKHAEK
121 NWFVGLKKNG SCKKGPRTHY GQKAILFLPL PVSSE
```

Amino acid sequence of *Desmodus rotundus* (common vampire bat)
FGF1 (SEQ ID NO: 21) (GenBank accession no. JAA45191, which
is hereby incorporated by reference in its entirety):

```
  1 MAEGEVTTFT ALTEKFNLPL ESYKKPKLLY CSNGGHFLRI LPDGTVDGTR DKSDQHIQLQ
 61 LSAESVGEVY IKSTGSGQYL AMDSAGLLYG SQTPNEECLF LERLEENHYN TYTSKKHAEK
121 NWFVGLKKNG SCKRGPRTHY GQKAILFLPL PVNSD
```

Amino acid sequence of *Bos taurus* (cattle) FGF1 (SEQ ID NO: 22)
(GenBank accession no. NP_776480, which is hereby
incorporated by reference in its entirety):

```
  1 MAEGETTTFT ALTEKFNLPL GNYKKPKLLY CSNGGYFLRI LPDGTVDGTK DRSDQHIQLQ
 61 LCAESIGEVY IKSTETGQFL AMDTDGLLYG SQTPNEECLF LERLEENHYN TYISKKHAEK
121 HWFVGLKKNG RSKLGPRTHF GQKAILFLPL PVSSD
```

Amino acid sequence of *Ornithorhynchus anatinus* (platypus)
FGF1 (SEQ ID NO: 23) (GenBank accession no. XP_001514861,
which is hereby incorporated by reference in its entirety):

```
  1 MAEGEITTFT ALMEKFDLPL GNYKKPRLLY CSNGGYFLRI QPDGKVDGTR DRSDQHIQLQ
 61 LSAESVGEVY IKSTESGHYL AMDTEGLLYG SQAPSEDCLF LERLEENHYN TYVSKKHAEK
121 NWFVGLKKNG SCKRGPRTHY GQKAILFLPL PVASD
```

Amino acid sequence of *Taeniopygia guttata* (zebra finch) FGF1
(SEQ ID NO: 24) (GenBank accession no. XP_002193287,
which is hereby incorporated by reference in its entirety):

```
  1 MAEGEITTFS ALTEKFNLPP GNYKKPKLLY CSNGGHFLRI LPDGTVDGTR DRSDQHIQLQ
 61 LSAESVGVVH IQSTQSGQYL AMDTNGLLYG SQLPPGECLF LERLEENHYN TYVSKMHADK
121 NWFVGLKKNG TSKLGPRTHY GQKAILFLPL PVAAD
```

Amino acid sequence of *Dasypus novemcinctus* (nine-banded
armadillo) FGF1 (SEQ ID NO: 25) (GenBank accession no.
ACO06224, which is hereby incorporated by reference
in its entirety):

```
  1 MAEGEITTFM ALMEKFNLPL ENYKHPRLLY CRNGGHFLRI LPDGTVDGTR DRSDQHIQLQ
 61 LSAESVGEVY IKSAETGQYL AMDTDGLLYG SETPSEECLF MEKLEENNYN TYISKKHAEK
121 KWFVGLKKDG SSKRGPQTHY GQKAILFLPL PVSSD
```

TABLE 1-continued

Amino acid sequence of *Xenopus Silurana tropicalis* (western clawed frog) FGF1(SEQ ID NO: 26) (GenBank accession no. ACJ50585, which is hereby incorporated by reference in its entirety):

```
  1 MAEGDITTFN PIAESFSLPI GNYKKPKLLY CNNGGYFLRI LPDGVVDGTR DRDDLYITLK
 61 LSAQSQGEVH IKSTETGSYL AMDSSGQLYG TLTPNEESLF LETLEENHYN TYKSKKYAEN
121 NWFVGIKKNG ASKKGSRTHY GQKAILFLPL PASPD
```

Amino acid sequence of *Heterocephalus glaber* (naked mole-rat) FGF1 (SEQ ID NO: 27) (GenBank accession no. EHA99379, which is hereby incorporated by reference in its entirety):

```
  1 MAEGEITTFT ALTEKFNLPP GNYKKPKLLY CSNGGHFLRI LPDGKVDGTR DRSDQHIQLQ
 61 LSAEGVGEVY IKSTETGQYL AMDTDGLLYG SQTASEECLF LERLEENHYN TYISKKHAEK
121 NWFVGLKKNG SCKRGPRTHY GQKAILFLPL PVSSD
```

Amino acid sequence of *Pteropus alecto* (black flying fox) FGF1 (SEQ ID NO: 28) (GenBank accession no. ELK02961, which is hereby incorporated by reference in its entirety):

```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

Amino acid sequence of *Tupaia chinensis* (Chinese tree shrew) FGF1 (SEQ ID NO: 29) (GenBank accession no. ELW69091, which is hereby incorporated by reference in its entirety):

```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Columba livia* (rock pigeon) FGF1 (SEQ ID NO: 30) (GenBank accession no. EMC79997, which is hereby incorporated by reference in its entirety):

```
  1 MAEGEITTFT ALTEKFNLPP GNYKKPKLLY CSNGGHFLRI LPDGKVDGTR DRSDQHIQLQ
 61 LSAESVGEVY IKSTQSGQYL AMDPTGLLYG SQLLGEECLF LERIEENHYN TYVSKKHADK
121 NWFVGLKKNG NSKLGPRTHY GQKAILFLPL PVSAD
```

Amino acid sequence of *Ovis aries* (sheep) FGF1 (SEQ ID NO: 31) (GenBank accession no. XP_004008958, which is hereby incorporated by reference in its entirety):

```
  1 MAEGETTTFR ALTEKFNLPL GNYKKPKLLY CSNGGYFLRI LPDGRVDGTK DRSDQHIQLQ
 61 LYAESIGEVY IKSTETGQFL AMDTNGLLYG SQTPSEECLF LERLEENHYN TYISKKHAEK
121 NWFIGLKKNG SSKLGPRTHF GQKAILFLPL PVSSD
```

Amino acid sequence of *Gallus gallus* (chicken) FGF1 (SEQ ID NO: 32) (GenBank accession no. NP_990511, which is hereby incorporated by reference in its entirety):

```
  1 MAEGEITTFT ALTERFGLPL GNYKKPKLLY CSNGGHFLRI LPDGKVDGTR DRSDQHIQLQ
 61 LSAEDVGEVY IKSTASGQYL AMDTNGLLYG SQLPGEECLF LERLEENHYN TYISKKHADK
121 NWFVGLKKNG NSKLGPRTHY GQKAILFLPL PVSAD
```

Amino acid sequence of *Vicugna pacos* (alpaca) FGF1 (SEQ ID NO: 33) (Ensembl accession no. ENSVPAP00000007810; partial sequence corresponding to human FGF1 residues 58 to 155, which is hereby incorporated by reference in its entirety):

```
  1 QLQLSAESVG EVYIKSTETG QYLAMDTDGL LHGSQTPNEE CLFLERLEEN HYNTYTSKKH
 61 AEKNWFVGLK KNGSCKRGPR THYGQKAILF LPLPVSSD
```

Amino acid sequence of *Anolis carolinensis* (anole lizard) FGF1 (SEQ ID NO: 34) (Ensembl accession no. ENSACAP00000013203, which is hereby incorporated by reference in its entirety):

```
  1 MAEGEITTFT ALTERFALPM ENYKKPKLLY CSNGGHFLRI LPDGKVDGTM DRNDSYIQLL
 61 LTAEDVGVVY IKGTETGQYL AMDANGHLYG SQLPTEECLF VETLEENHYN TYTSKMHGDK
121 KWYVGLKKNG KGKLGPRTHR GQKAILFLPL PVSPD
```

TABLE 1-continued

Amino acid sequence of *Otolemur garnettii* (bushbaby) FGF1
(SEQ ID NO: 35) (Ensembl accession no. ENSOGAP00000004540,
which is hereby incorporated by reference in its entirety):

```
  1 MAEGEITTFT ALTEKFNLPL GNYKKPKLLY CSNGGHFLRI LPDGTVDGTQ DRSDQHIQLQ
 61 LSAESVGEVY IKSTQTGQYL AMDSDGLLYG SQTPNEECLF LERLEENHYN TYVSKKHAEK
121 NWFVGLKKNG SCKRGPRTHY GQKAILFLPL PVSSD
```

Amino acid sequence of *Felis catus* (cat) FGF1 (SEQ ID NO: 36)
(Ensembl accession no. ENSFCAP00000008457, which is hereby
incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Pelodiscus sinensis* (Chinese
softshell turtle) FGF1 (SEQ ID NO: 37) (Ensembl accession
no. ENSPSIP00000016356, which is hereby incorporated by
reference in its entirety):

```
  1 MAEGEITTFT ALTEKFNLPL GNYKNPKLLY CSNGGYFLRI HPDGKVDGTR DRSDQHIQLQ
 61 LSAESVGEVY IKSTESGQFL AMDANGLLYG SLSPSEECLF LERMEENHYN TYISKKHADK
121 NWFVGLKKNG SCKLGPRTHY GQKAVLFLPL PVSAD
```

Amino acid sequence of *Latimeria chalumnae* (coelacanth)
FGF1 (SEQ ID NO: 38) (Ensembl accession no. ENSLACP00000015106,
which is hereby incorporated by reference in its entirety):

```
  1 MAEDKITTLK ALAEKFNLPM GNYKKAKLLY CSNGGYFLRI PPDGKVEGIR ERSDKYIQLQ
 61 MNAESLGMVS IKGVEAGQYL AMNTNGLLYG SQSLTEECLF MEKMEENHYN TYRSKTHADK
121 NWYVGIRKNG SIKPGPRTHI GQKAVLFLPL PASSD
```

Amino acid sequence of *Tursiops truncatus* (dolphin) FGF1
(SEQ ID NO: 39) (Ensembl accession no. ENSTTRP00000004470,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYASKKHAEK
121 NWFVGLKKNG SCKRGPRTHY GQKAILFLPL PVSSD
```

Amino acid sequence of *Mustela putorius furo* (ferret) FGF1
(SEQ ID NO: 40) (Ensembl accession no. ENSMPUP00000007888,
which is hereby incorporated by reference in its entirety):

```
  1 MAEGEITTFT ALMEKFNLPA GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Nomascus leucogenys* (gibbon) FGF1
(SEQ ID NO: 41) (Ensembl accession no. ENSNLEP00000011873,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Gorilla gorilla* (gorilla) FGF1
(SEQ ID NO: 42) (Ensembl accession no. ENSGGOP00000017663,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYISKKHAEK
121 NWFVGLKKNG SCKRGPRTHY GQKAILFLPL PVSSD
```

Amino acid sequence of *Erinaceus europaeus* (hedgehog)
FGF1 (SEQ ID NO: 43) (Ensembl accession no. ENSEEUP00000005318,
which is hereby incorporated by reference in its entirety):

```
  1 MAEGEITTFT ALTEKFNLPL GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

TABLE 1-continued

Amino acid sequence of *Procavia capensis* (hyrax) FGF1
(SEQ ID NO: 44) (Ensembl accession no. ENSPCAP00000010969,
which is hereby incorporated by reference in its entirety)
(partial sequence corresponding to human FGF1
residues 1 to 91):

```
  1 MAEGEITTFT ALTEKFNLPL ENYKKPKLLY CSNGGHFLRI LPDGTVDGTR DRSDQHIQLQ
 61 LSAESVGEVY IKGTETGQYL AMDTDGLLYG S
```

Amino acid sequence of *Dipodomys ordii* (kangaroo rat)
FGF1 (SEQ ID NO: 45) (Ensembl accession no. ENSDORP00000006889,
which is hereby incorporated by reference in its entirety)
(partial sequence corresponding to human FGF1 residues
1 to 16 and 58 to 155):

```
  1 MAEGEITTFT ALTERF---- ---------- ---------- ---------- -------QLQ
 61 LSAESVGEVY IKSTETGQYL AMDADGLLYG SQTPDEECLF LERLEENHYN TYIAKKHAEK
121 NWFVGLKKNG SCKRGPRTHY GQKAILFLPL PVSSD
```

Amino acid sequence of *Petromyzon marinus* (lamprey) FGF1
(SEQ ID NO: 46) (Ensembl accession no. ENSPMAP00000010683,
which is hereby incorporated by reference in its entirety)
(partial sequence corresponding to human FGF1
residues 1 to 93):

```
  1 MEVGHIGTLP VVPAGPVFPG SFKEPRRLYC RSAGHHLQIL GDGTVSGTQD ENEPHAVLQL
 61 QAVRRGVVTI RGLCAERFLA MSTEGHLYGA VR
```

Amino acid sequence of *Echinops telfairi* (lesser hedgehog
tenrec) FGF1 (SEQ ID NO: 47) (Ensembl accession no.
ENSETEP00000014504, which is hereby incorporated by
reference in its entirety) (partial sequence corresponding to
human FGF1 residues 58 to 155)

```
  1 QLKLVAESVG VVYIKSIKTG QYLAMNPDGL LYGSETPEEE CLFLETLEEN HYTTFKSKKH
 61 VEKNWFVGLR KNGRVKIGPR THQGQKAILF LPLPVSSD
```

Amino acid sequence of *Macaca mulatta* (rhesus monkey) FGF1
(SEQ ID NO: 48) (Ensembl accession no. ENSMMUP00000030943,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Pteropus vampyrus* (megabat) FGF1
(SEQ ID NO: 49) (Ensembl accession no. ENSPVAP00000004349,
which is hereby incorporated by reference in its entirety):

```
  1 MAEGEVTTFT ALTERFNLPP GNYKKPKLLY CSNGGHFLRI LPDGTVDGTR DKSDQHIQLQ
 61 LSAESVGEVY IKSTESGQYL AMDSDGLLYG SQTPDEDCLF LERLEENHYN TYTSKKHAEK
121 NWFVGLKKNG SCKRGPRTHY GQKAILFLPL PVSSD
```

Amino acid sequence of *Myotis lucifugus* (microbat) FGF1
(SEQ ID NO: 50) (Ensembl accession no. ENSMLUP00000006481,
which is hereby incorporated by reference in its entirety):

```
  1 MAEGEVTTFT ALTERFNLPL ENYKKPKLLY CSNGGHFLRI LPDGTVDGTR DRSDQHIQLQ
 61 LSAESVGEVY IKSTESGQYL AMDSDGLLYG SQTPNEECLF LERLEENHYN TYTSKKHAEK
121 NWFVGLKKNG SCKRGPRTHY GQKAILFLPL PVSSD
```

Amino acid sequence of *Microcebus murinus* (mouse lemur)
FGF1 (SEQ ID NO: 51) (Ensembl accession no. ENSMICP00000008602,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESAGEVY IKSTQTGRYL AMDADGLLYG SQTPNEECLF LERLEENHYN TYVSKKHAEK
121 NWFVGLKKNG SCKRGPRTHY GQKAILFLPL PVSSD
```

Amino acid sequence of *Ochotona princeps* (pika) FGF1
(SEQ ID NO: 52) (Ensembl accession no. ENSOPRP00000011739,
which is hereby incorporated by reference in its entirety):

```
  1 MAEGEVTTFS ALTEKFNLPG GNYKLPKLLY CSNGGHFLRI LPDGTVDGTR DRSDLH----
 61 -------EVF IKSTETGQYL AMDTDGLLYG SQTPSEECLF LERLEENHYN TYTSKKHAEK
121 NWFVGIKKNG SCKRGPRTHY GQKAILFLPL PVSSD
```

TABLE 1-continued

Amino acid sequence of *Rattus norvegicus* (rat) FGF1
(SEQ ID NO: 53) (Ensembl accession no. ENSRNOP00000018577,
which is hereby incorporated by reference in its entirety):

```
  1 MAEGEITTFA ALTERFNLPL GNYKKPKLLY CSNGGHFLRI LPDGTVDGTR DRSDQHIQLQ
 61 LSAESAGEVY IKGTETGQYL AMDTEGLLYG SQTPNEECLF LERLEENHYN TYTSKKHAEK
121 NWFVGLKKNG SCKRGPRTHY GQKAILFLPL PVSSD
```

Amino acid sequence of *Choloepus hoffmanni* (sloth) FGF1
(SEQ ID NO: 54) (Ensembl accession no. ENSCHOP00000010964,
which is hereby incorporated by reference in its entirety):

```
  1 MAEGEITTFT ALMEKFNLPP GNYMKPKLLY CSNGGHFLRI LPDGTVDGTR DRSDLHIQLQ
 61 LSAESVGEVY IKSAETGQYL AMDTGGLLYG SQTPSEECLF LERLEENHYN TYVSKKHAEK
121 NWFVGLKKNG SSKRGPRTHY GQKAILFLPL PVSSD
```

Amino acid sequence of *Ictidomys tridecemlineatus* (squirrel)
FGF1 (SEQ ID NO: 55) (Ensembl accession no. ENSSTOP00000021782,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYTSKKHAEK
121 NWFVGLKKNG SCKRGPRTHY GQKAILFLPL PVSSD
```

Amino acid sequence of *Tarsius syrichta* (tarsier) FGF1
(SEQ ID NO: 56) (Ensembl accession no. ENSTSYP00000006804,
which is hereby incorporated by reference in its entirety):

```
  1 MAEGEITTFT ALTEKFNLPP GNYKKPKLLY CSNGGHFLRI LPDGTVDGTR DRSDQHIQLQ
 61 LSAESVGEVY IKSTETGQYL AMDTDGLLYG SQTPNEECLF LERLEENHYN TYVSKKHAEK
121 NWFVGLKKNG SCKRGPRTHY GQKAILFLPL PVSSD
```

Amino acid sequence of *Tupaia belangeri* (tree shrew) FGF1
(SEQ ID NO: 57) (Ensembl accession no. ENSTBEP00000010264,
which is hereby incorporated by reference in its entirety):

```
  1 MAEGEITTFA ALTEKFDLPP GNYKKPKLLY CSNGGHFLRI LPDGTVDGTR DRSDQHIQLQ
 61 LTAENVGEVY IKSTETGQYL AMDADGLLYG SQTPNEECLF LERLEENHYN TYISKKHAEK
121 NWFVALKKNG SCKLGPRTHY GQKAILFLPL PVSSD
```

Amino acid sequence of *Meleagris gallopavo* (turkey) FGF1
(SEQ ID NO: 58) (Ensembl accession no. ENSMGAP00000016398;
partial sequence corresponding to human FGF1 residues 1 to 56,
which is hereby incorporated by reference in its entirety):

```
  1 MAEGEITTFT ALTERFGLPL GNYKKPKLLY CSNGGHFLRI LPDGKVDGTR DRSDQH
```

Amino acid sequence of *Macropus eugenii* (wallaby) FGF1
(SEQ ID NO: 59) (Ensembl accession no. ENSMEUP00000015084,
which is hereby incorporated by reference in its entirety):

```
  1 MAEGEITTFT ALTERFNLPL GNYKKPKLLY CSNGGHFLRI LPDGKVDGTR DRNDQHIQLQ
 61 LSAESVGEVY IKSTESGQYL AMDTNGLLYG SQTPSEECLF LERLEENHYN TYISKKHAEK
121 NWFVGLKKNG SCKRGPRTHY GQKAILFLPL PVSSE
```

Amino acid sequence of *Danio rerio* (zebrafish) FGF1
(SEQ ID NO: 60) (Ensembl accession no. ENSDARP00000008825,
which is hereby incorporated by reference in its entirety):

```
  1 MTEADIAVKS SPRDYKKLTR LYCMNGGFHL QILADGTVAG AADENTYSIL RIKATSPGVV
 61 VIEGSETGLY LSMNEHGKLY ASSLVTDESY FLEKMEENHY NTYQSQKHGE NWYVGIKKNG
121 KMKRGPRTHI GQKAIFFLPR QVEQEED
```

As noted above, the portion of the paracrine FGF may be modified to decrease binding affinity for heparin and/or heparan sulfate compared to the portion without the modification. In one embodiment, the modified portion of the paracrine FGF includes one or more substitutions, additions, or deletions.

In one embodiment, the one or more substitutions are located at one or more amino acid residues of SEQ ID NO: 1 selected from N33, K127, K128, N129, K133, R134, R137, Q142, K143, and combinations thereof. In one embodiment, the one or more substitutions are selected from N33T, K127D, K128Q, N129T, K133V, R134L, R137H, Q142M, K143T/L/I, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. Amino acid residues corresponding to those of SEQ ID NO:1 may be determined by, for example, sequence analysis and structural analysis.

Also encompassed within the present invention are portions of paracrine FGFs other than FGF1 (e.g., FGF2, FGF4, FGF5, FGF6, FGF9, FGF16, and FGF20). The portions derived from paracrine FGFs other than FGF1 include portions corresponding to the above-identified amino acid sequences of FGF1. Corresponding portions may be determined by, for example, sequence analysis and structural analysis.

It will be understood that the portion of the paracrine FGF according to the present invention may be derived from a nucleotide sequence that encodes a paracrine FGF protein. For example, in one embodiment, the nucleotide sequence is the nucleotide sequence that encodes human FGF1 (GenBank Accession No. BC032697, which is hereby incorporated by reference in its entirety) (SEQ ID NO: 61), as follows:

```
 91                     ATGGCTGAAG GGGAAATCAC CACCTTCACA
121 GCCCTGACCG AGAAGTTTAA TCTGCCTCCA GGGAATTACA AGAAGCCCAA ACTCCTCTAC
181 TGTAGCAACG GGGGCCACTT CCTGAGGATC CTTCCGGATG GCACAGTGGA TGGGACAAGG
241 GACAGGAGCG ACCAGCACAT TCAGCTGCAG CTCAGTGCGG AAAGCGTGGG GGAGGTGTAT
301 ATAAAGAGTA CCGAGACTGG CCAGTACTTG GCCATGGACA CCGACGGGCT TTTATACGGC
361 TCACAGACAC CAAATGAGGA ATGTTTGTTC CTGGAAAGGC TGGAGGAGAA CCATTACAAC
421 ACCTATATAT CCAAGAAGCA TGCAGAGAAG AATTGGTTTG TTGGCCTCAA GAAGAATGGG
481 AGCTGCAAAC GCGGTCCTCG GACTCACTAT GGCCAGAAAG CAATCTTGTT TCTCCCCCTG
541 CCAGTCTCTT CTGATTAA
```

In another embodiment of the present invention, the portion of the paracrine FGF of the chimeric protein may be derived from a nucleotide sequence that encodes an ortholog of human FGF1. Nucleotide sequences that encode FGF1 orthologs are shown in Table 2.

TABLE 2

Olive Baboon FGF1 gene coding sequence (1-155) (SEQ ID NO: 62)
(GenBank accession no. NM_001169086, which is hereby
incorporated by reference in its entirety):

```
  1 ATGGCTGAAG GGGAAATCAC CACGTTCACA GCCCTGACCG AGAAGTTTAA TCTGCCTCCA
 61 GCGAATTACA AGAAGCCCAA ACTGCTCTAC TGTAGCAACG GGGGACACTT CTTGAGGATC
121 CTTCCGGATG GCACAGTGGA TGGGACAAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAGAA CCATTACAAC ACCTACATAT CCAAGAAGCA CGCAGAGAAG
361 AATTGGTTTG TTGGCCTCAA GAAGAATGGA AGCTGCAAAC GTGGTCCTCG GACTCACTAT
421 GGCCAGAAAG CAATCTTGTT TCTTCCCCTG CCAGTCTCTT CTGATTAA
```

Sumatran orangutan FGF1 gene coding sequence (60-214) (SEQ ID NO: 63)
(GenBank accession no. NM_001133601, which is hereby
incorporated by reference in its entirety):

```
211                     ATGGCTGAAG GGGAAATCAC CACCTTCACA
241 GCCCTGACCG AGAAGTTTAA TCTGCCTCCA GGGAATTACA AGAAGCCCAA ACTCCTCTAC
301 TGTAGCAACG GGGGCCACTT CTTGAGGATC CTTCCGGATG GCACAGTGGA TGGGACAAGG
361 GACAGGAGCG ACCAGCACAT TCAGCTGCAG CTCAGTGCGG AAAGCGTGGG GGAGGTGTAT
421 ATAAAGAGTA CCGAGACTGG CCAGTACTTG GCCATGGACA CCGACGGGCT TTTATACGGC
481 TCACAGACAC CAAATGAGGA ATGTTTGTTC CTGGAAAGGC TGGAGGAGAA CCATTACAAC
541 ACCTATATAT CCAAGAAGCA TGCAGAGAAG AATTGGTTTG TTGGCCTCAA GAAGAATGGA
601 AGCTGCAAAC GCGGTCCTCG GACTCACTAT GGCCAGAAAG CAATCTTGTT TCTCCCCCTG
661 CCAGTCTCTT CCGATTAA
```

White-tufted-ear marmoset FGF1 gene coding sequence (1-155)
(SEQ ID NO: 64) (GenBank accession no. XM_002744295,
which is hereby incorporated by reference in its entirety):

```
130           A TGGCTGAAGG GGAAATCACC ACCTTCACAG CCCTGACCGA GAAGTTTGAT
181 CTGCCTCCAG GGAATTACAA GAAGCCCAAA CTCCTCTACT GTAGCAATGG GGGCCACTTC
241 TTGAGGATCC TTCCGGATGG CACAGTGGAT GGGACAAGGG ACAGGAGCGA CCAGCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAGAGGCT GGAGGAGAAC CATTACAACA CCTATATATC CAAGAAACAT
481 GCAGAGAAGA ATTGGTTTGT CGGCCTCAAG AAGAATGGAA GCTGTAAACG TGGTCCTCGG
541 ACTCACTATG GTCAGAAAGC GATCTTGTTT CTCCCCCTGC CAGTTTCTTC TGATTAA
```

TABLE 2-continued

Horse FGF1 gene coding sequence (1-155) (SEQ ID NO: 65)
(GenBank accession no. NM_001163886, which is hereby
incorporated by reference in its entirety):

```
 34                          ATGGCTG AAGGAGAAAT CACAACCTTC
 61 ACGGCCCTGA CCGAGAAGTT TAATCTGCCT CCAGGGAATT ACAAGAAGCC CAAACTCCTC
121 TACTGTAGCA ATGGGGCCA CTTCCTGAGG ATCCTTCCAG ATGGCACAGT GGATGGGACA
181 AGGGACAGGA GCGACCAGCA CATTCAGCTG CAGCTCAGTG CGGAAAGCGT GGGGGAGGTG
241 TATATAAAGA GTACCGAGAC TGGCCAGTAC TTGGCCATGG ACACCGACGG GCTGTTGTAC
301 GGCTCACAGA CACCCAAACGA GGAATGTTTG TTCCTGGAAA GGCTGGAGGA AAACCATTAC
361 AACACCTACA CATCCAAGAA GCATGCAGAG AAGAACTGGT TCGTTGGTCT CAAGAAGAAT
421 GGGAGCTGCA AACGCGGTCC TCGGACTCAC TATGGGCAGA AGCAATCTT GTTTCTTCCC
481 CTGCCCGTCT CCTCTGACTA A
```

Chimpanzee FGF1 gene coding sequence (1-155) (SEQ ID NO: 66) (GenBank
accession no. GABD01003589, which is hereby incorporated by reference
in its entirety):

```
 80          A TGGCTGAAGG GGAAATCACC ACCTTCACAG CCCTGACCGA
121 GAAGTTTAAT CTGCCTTCAG GGAATTACAA GAAGCCCAAA CTCCTCTACT GTAGCAACGG
181 GGGCCACTTC CTGAGGATCC TTCCGGATGG CACAGTGGAT GGGACAAGGG ACAGGAGCGA
241 CCAGCACATT CAGCTGCAGC TCAGTGCGGA AAGCGTGGGG GAGGTGTATA TAAAGAGTAC
301 CGAGACTGGC CAGTACTTGG CCATGGACAC CGACGGGCTT TTATACGGCT CACAGACACC
361 AAATGAGGAA TGTTTGTTCC TGGAACGGCT GGAGGAGAAC CATTACAACA CCTATATATC
421 CAAGAAGCAT GCAGAGAAGA ATTGGTTTGT TGGCCTCAAG AAGAATGGAA GCTGCAAACG
481 CGGTCCTCGG ACTCACTATG GCCAGAAAGC AATCTTGTTT CTCCCCCTGC CAGTCTCTTC
541 CGATTAA
```

Elephant FGF1 gene coding sequence (1-155) (SEQ ID NO: 67) (GenBank
accession no. XM_003404573, which is hereby incorporated by reference in
its entirety):

```
  1 ATGGCCGAAG GGGAAATCAC AACTTTCACA GCCCTGACGA GAAGTTCAA CCTGCCTCCA
 61 GGGAATTACA AGAAGCCCAA ACTCCTCTAC TGTAGCAATG GAGGTCACTT CTTAAGGATC
121 CTTCCAGATG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAAAA CCATTACAAC ACCTACACAT CCAAGAAGCA CGCAGAGAAG
361 AATTGGTTCG TTGGTCTCAA GAAGAATGGA AGCTGCAAAC GCGGTCCTCG GACTCACTAT
421 GGCCAGAAAG CAATCTTGTT TCTCCCCCTG CCAGTCTCCT CTGATTAA
```

Dog FGF1 gene coding sequence (1-155) (SEQ ID NO: 68) (GenBank accession
no. XM_844181, which is hereby incorporated by reference in its
entirety):

```
164                             ATGGCTG AAGGGGAAAT
181 CACAACCTTC ACTGCCCTGA CGGAGAAGTT TAATCTGCCT CCGGGGAATT ACATGAAGCC
241 CAAACTCCTC TACTGTAGCA ACGGGGCCA CTTCCTGAGG ATCCTTCCAG ATGGCACAGT
301 GGATGGGACA AGGGACAGGA GCGACCAGCA CATTCAGCTG CAGCTCAGTG CGGAAAGCGT
361 GGGGGAGGTG TATATAAAGA GCACCGAGAC TGGCCAGTAC TTGGCCATGG ACACCGATGG
421 GCTTCTGTAC GGCTCACAGA CACCGAATGA GGAATGTTTG TTCCTGGAAA GGCTGGAGGA
481 AAACCATTAC AACACCTACA CATCCAAGAA GCATGCAGAA AAAATTGGT TGTTGGTCT
541 CAAGAAGAAT GGAGCTGCA AACGCGGTCC TCGGACTCAC TATGGTCAAA AGCAATTTT
601 GTTTCTCCCC CTGCCAGTGT CCTCTGATTA A
```

Giant panda FGF1 gene coding sequence (1-155) (SEQ ID NO: 69) (GenBank
accession no. XM_002912535, which is hereby incorporated by reference in
its entirety):

```
146                       ATGGC TGAAGGGGAG ATCACAACCT TCACCGCCCT
181 GACGGAGAAG TTTAATCTGC CTGCGGGGAA TTACAAGAAG CCCAAACTCC TCTACTGTAG
241 CAACGGGGGC CACTTCCTGA GGATCCTTCC AGATGGCACA GTGGACGGGA CAGGGGACAG
301 GAGCGACCAG CACATTCAAC TGCAGCTCAG CGCGGAAAGC GTAGGGGAGG TGTACATAAA
361 GAGCACCGAG ACCGGCCAGT ACTTGGCCAT GGACACCGAT GGGCTTCTGT ACGGCTCACA
421 GACACCAAAT GAGGAATGTT TGTTCCTGGA AAGGCTGGAG GAAAACCATT ACAACACCTA
481 CACATCCAAG AAGCACGCGG AGAAGAATTG GTTTGTTGGT CTCAAGAAGA ATGGAAGCTG
541 CAAACGTGGT CCTCGGACTC ACTATGGCCA GAAAGCAATT CTGTTTCTCC CCTGCCAGT
601 CTCCTCTGAT TAA
```

Bolivian squirrel monkey FGF1 gene coding sequence (1-155)
(SEQ ID NO: 70) (GenBank accession no. XM_003920547,
which is hereby incorporated by reference in its entirety):

```
130         A TGGCTGAAGG GGAAATCACC ACCTTTACAG CCCTGACCGA GAAGTTTGAT
181 CTGCCTCCAG GGAATTACAA GAAGCCCAAA CTCCTCTACT GTAGCAACGG GGGCCACTTC
241 TTGAGGATCC TTCCGGATGG CACAGTGGAT GGGACCAGGG ACAGGAGCGA TCTTCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAAAGGCT GGAGGAGAAC CATTACAACA CCTATATATC CAAGAAACAC
```

TABLE 2-continued

```
481 GCAGAGAAGA ATTGGTTTGT TGGCCTCAAG AAGAATGGAA GCTGCAAGCG CGGTCCTCGG
541 ACTCACTATG GCCAGAAAGC AATCTTGTTT CTCCCCCTGC CAGTCTCTTC TGATTAA
```

Pig FGF1 gene coding sequence (1-155) (SEQ ID NO: 71) (GenBank accession no. XM_003124010, which is hereby incorporated by reference in its entirety):

```
 35                                          ATGGCT GAAGGCGAAA TCACAACCTT
 61 CACGGCCCTG ACCGAGAAGT TTAATCTGCC TCCAGGAAAT TACAAGAAGC CCAAGCTCCT
121 CTACTGCAGC AACGGGGGCC ATTTCCTCAG GATCCTTCCA GATGGCACAG TGGATGGGAC
181 CAGGGACAGG AGCGACCAGC ACATTCAGCT GCAGCTCAGT GCGGAAAGCG TGGGGGAGGT
241 GTATATAAAG AGTACGGAGA CTGGCCAGTA CTTGGCCATG GACACCAGCG GCTTTTGTA
301 CGGCTCACAG ACACCCAGTG AGGAGTGTTT GTTCCTGGAG AGGCTGGAGG AAAACCATTA
361 CAATACCTAC ACATCCAAGA AGCACGCAGA GAAGAACTGG TTCGTTGGCC TCAAGAAGAA
421 TGGAAGCTGC AAACGCGGTC CTCGGACTCA CTATGGCCAG AAAGCCATCC TGTTTCTCCC
481 CCTGCCAGTA TCCTCGGATT AA
```

Small-eared galago FGF1 gene coding sequence (1-155) (SEQ ID NO: 72) (GenBank accession no. XM_003782087, which is hereby incorporated by reference in its entirety):

```
 28                                       ATG GCTGAAGGGG AAATCACAAC CTTCACAGCC
 61 CTCACAGAGA AGTTTAATCT GCCTCTAGGA AATTACAAGA AGCCCAAGCT CCTCTACTGT
121 AGCAACGGGG GTCACTTTCT GAGGATCCTG CCGGATGGCA CCGTGGATGG GACACAAGAC
181 AGGAGCGACC AGCACATTCA GCTGCAGCTC AGTGCGGAAA GCGTGGGGGA GGTGTATATA
241 AAGAGTACCC AGACTGGCCA GTACTTGGCC ATGGACTCCG ACGGGCTTTT ATACGGCTCA
301 CAAACACCAA ATGAGGAATG CCTGTTCCTG GAACGGCTGG AGGAAAACCA TTACAACACC
361 TATGTGTCCA AGAAGCACGC CGAGAAGAAT TGGTTTGTCG GTCTCAAGAA GAACGGAAGT
421 TGCAAACGTG GTCCTCGGAC TCACTACGGC CAGAAAGCAA TCTTGTTTCT CCCCCTGCCA
481 GTCTCCTCTG ATTAA
```

Greater horseshoe bat FGF1 gene coding sequence (1-155) (SEQ ID NO: 73) (GenBank accession no. DP000705, which is hereby incorporated by reference in its entirety):

```
190120                                            T TAATCAGAGG AGACTGGCAG
190141 GGGGAGAAAC AGGATTGCTT TCTGGCCATA GTGAGTCCGA GGACCGCGCT TGCAGCTTCC
190201 ATTCTTCTTG AGCCCAACGA ACCAATTCTT TTCTGCGTGC TTCTTGGACG TGTAGGTGTT
190261 GTAATGGTTT TCCTCCAGCC TTTTCCAGGA CAGACATTCC TCATTTGGTG TCTG
194466       TGAGC CGTACAAAAG CCCGTCGGAG TCCATGGCCA AGTACTGGCC ACTCTCGGTG
194521 CTCTTTATAT ACACCTCCCC CACGCTTTCC GCACTGAGCT GCAGCTGAA
208114                                          TGTGCTG GTCACTCTTG TCCCTTGTCC
208141 CATCCACTGT GCCATCTGGA AGGATCCTCA GGAAGTGGCC CCCGTTGCTG CAGTAGAGAA
208201 GTTTGGGTTT CTTGTAATTC CCTGTAGGCA GATTAAACTT CTCAGTAAGG GCTGTGAACG
208261 TGGTGACTTC CCCTTCGGCC AT
```

European shrew FGF1 gene coding sequence (1-155) (SEQ ID NO: 74) (GenBank accession no. DP000767, which is hereby incorporated by reference in its entirety):

```
138344                               CTAGTCG GAGGAGACGG
138361 GCAGGGGGAG AAACAAGATC GCTTTCTGGC CGTAGTGAGT CCGGGGACCA CGCTTGCAGC
138421 TTCCGTTCTT CTTCAGACCA ACAAACCAAT TCTTCTCGGC ATGCTTGGAG GAGGTATAGG
138481 TGTTGTAATG GTTTTCCTCC AGCCTTTCCA GAAACAGACA TTCCTCATTC GGTGTTTG
143512                                               TGAGCCGTA
143521 TAAAAGCCCG TCGGTGTCCA TGGCCAAGTA ATGGCCAGTC TCCGTGCTCT TTATATACAC
143581 CTCCCCCACG CTTTCCGCAC TGAGCTGCAG CTGAA
157009                                            TG TGCTGGTCGC
157021 TGCGGTCCCT GGTCCCATCC ACTGTGCCGT CCGGGAGGAT GCGCAGGAAG TGGCCCCCGT
157081 TGCTGCAGTA CAGGAGTTTG GGCTTCTTGT AGTTCCCTGG TGGCAGGTTA AACTTCTCCA
157141 TGAGGGCCCC AAAGGTGGTG ATCTCCCCCT CGGCCAT
```

Rabbit FGF1 gene coding sequence (1-155) (SEQ ID NO: 75) (GenBank accession no. NM_001171488, which is hereby incorporated by reference in its entirety):

```
  1 ATGGCTGAGG GGGAGGTCAC CACCTTCACA GCCCTGACCG AGAAGTTCAA CCTGCCTGCA
 61 GGGAACTACA AGTTGCCCAA ACTCCTCTAC TGCAGCAACG GGGCCACTT CCTGAGGATC
121 CTGCCGGACG GCACTGTGGA CGGCACAAGG GACAGGAGCG ACCAGCACAT TCAGCTGCAG
181 CTGAGTGCGG AAAGCGTGGG GGAGGTGTAT ATAAAGAGTA CGGAGACCGG CCAGTACTTG
241 GCCATGGACA CCGACGGCCT TTTATACGGC TCGCAAACGC CAGTGAGGA GTGTTTGTTC
301 CTGGAACGGC TGGAGGAGAA CCACTACAAC ACCTACGTG CCAAGAAGCA CGCCGAGAAG
361 AACTGGTTCG TGGGGCTGAA GAAAAACGGG AGCTGCAAGC GCGGTCCTCG GACTCACTAC
421 GGCCAGAAAG CCATCTTGTT CCTCCCCCTG CCGGTCTCCT CCGACTAA
```

TABLE 2-continued

Chinese hamster FGF1 gene coding sequence (1-155) (SEQ ID NO: 76)
(GenBank accession no. XM_003502421, which is hereby
incorporated by reference in its entirety):

```
  1 ATGGCTGAAG GAGAAATCAC CACCTTCTCA GCCCTGACAG AGAGATTTAA TCTGCCTCCA
 61 GGAAACTACA AGAAGCCCAA ACTGCTCTAC TGCAGCAACG GGGCCACTT CTTGAGGATC
121 CTTCCAGATG GCACAGTGGA TGGGACAAGG GACAGGAGTG ACCAGCACAT TCAGCTGCAG
181 CTGAGTGCGG AAAGCGCGGG CGAAGTGTAT ATAAAGGGTA CAGAGACAGG CCAGTACAGG
241 AACATGGACA CGGATGGCCT TTTATACGGC TCACAGACAC CAAATGAAGA ATGCCTGTTC
301 CTGGAAAGGC TGGAAGAAAA CCATTACAAC ACTTATATCA TCCAAGAAGCA CGCAGAGAAG
361 AACTGGTTTG TGGGCCTCAA GAAAAACGGG AGCTGCAAGC GTGGTCCTCG GACTCACTAT
421 GGCCAGAAAG CAATCTTGTT TCTCCCCCTG CCTGTATCTT CTGACTAG
```

Tasmanian devil FGF1 gene coding sequence (1-155) (SEQ ID NO: 77)
(GenBank accession no. XM_003756690, which is hereby
incorporated by reference in its entirety):

```
 24                       ATGGCCG AAGGGGAGAT CACAACCTTC ACAGCCCTGA
 61 CCGAAAGATT TAATCTGCCA CTGGGGAATT ACAAGAAGCC CAAGCTTCTC TACTGTAGCA
121 ATGGGGGCCA CTTTTTGAGG ATTCTTCCTG ATGGTAAAGT GGATGGGACA AGGGACAGAA
181 ATGATCAACA CATTCAACTG CAACTAAGCG CGGAAAGCGT GGGTGAGGTG TATATAAAGA
241 GCACTGAGTC TGGCCAGTAT TTGGCTATGG ACACCGATGG ACTTTTATAC GGCTCACAGA
301 CACCCACTGA AGAATGCTTG TTCCTGGAGA GATTGGAGGA GAATCATTAC AACACCTACA
361 TATCAAAGAA GCATGCGGAG AAAAATTGGT TTGTGGGCCT CAAGAAAAAT GGAAGCTGCA
421 AAAGAGGTCC CAGGACTCAC TATGGCCAGA AAGCCATCCT CTTCCTTCCC CTCCCTGTGT
481 CCTCTGAGTA A
```

House mouse FGF1 gene coding sequence (1-155) (SEQ ID NO: 78)
(GenBank accession no. NM_010197, which is hereby
incorporated by reference in its entirety):

```
188         ATG GCTGAAGGGG AGATCACAAC CTTCGCAGCC CTGACCGAGA GGTTCAACCT
241 GCCTCTAGGA AACTACAAAA AGCCCAAACT GCTCTACTGC AGCAACGGGG CCACTTCTT
301 GAGGATCCTT CCTGATGGCA CCGTGGATGG GACAAGGGAC AGGAGCGACC AGCACATTCA
361 GCTGCAGCTC AGTGCGAAAA GTGCGGGCGA AGTGTATATA AAGGGTACGG AGACCGGCCA
421 GTACTTGGCC ATGGACACCG AAGGGCTTTT ATACGGCTCG CAGACACCAA ATGAGGAATG
481 TCTGTTCCTG GAAAGGCTGG AAGAAAACCA TTATAACACT TACACCTCCA AGAAGCATGC
541 GGAGAAGAAC TGGTTTGTGG GCCTCAAGAA GAACGGGAGC TGTAAGCGCG GTCCTCGGAC
601 TCACTATGGC CAGAAAGCCA TCTTGTTTCT GCCCCTCCCG GTGTCTTCTG ACTAG
```

Domestic guinea pig FGF1 gene coding sequence (1-154) (SEQ ID NO: 79)
(GenBank accession no. XM_003477194, which is hereby incorporated by
reference in its entirety):

```
  1 ATGGCTGAAG GAGAAATCAC AACTTTTGCA GCCCTGACTG AGAAGTTTAA TCTGCCTCCA
 61 GGGAATTATA AGAAGCCCAA ACTGCTCTAC TGCAGCAATG GGGCCACTT CCTGAGGATC
121 CTTCCAGACG GCACAGTGGA CGGCACAAGA GACAGGAGCG ACCAGCACAT TCAGCTGCAG
181 CTCAGTGCGG AAGGCGTGGG GGAGGTGTAT ATACAGAGCA CCGAGACCGG CCAGTACTTG
241 GCCATGGACA CCGACGGGCT TTTATACGGC TCACAGACAC CAAGTGAGGA ATGCTTGTTC
301 CTGGAAAGGC TGGAGGAAAA CCATTACAAC ACCTACACAT CCAAGAAGCA TGTGGAGAAG
361 AATTGGTTTG TTGGCCTCAA GAAGAACGGA AGCTGCAAGC GTGGTCCTCG GACTCACTAT
421 GGCCAGAAAG CAATCTTGTT CCTCCCCTTG CCAGTCTCTG ATTAG
```

Gray short-tailed opossum FGF1 gene coding sequence (1-155)
(SEQ ID NO: 80) (GenBank accession no. XM_001368884,
which is hereby incorporated by reference in its entirety):

```
  1 ATGGCCGAAG GGAGATCAC AACCTTCACA GCCCTGACTG AAAGATTTAA CCTGCCACTG
 61 GGGAATTACA AGAAACCCAA GCTTCTCTAC TGTAGCAATG GGGCCATTT CTTGAGGATC
121 CTTCCTGATG GCAAAGTGGA TGGGACACGG GACAGAAATG ATCAACACAT TCAACTGCAG
181 CTGAGCACGG AAAGTGTGGG TGAGGTGTAT ATAAGAGCA CTGAGTCTGG CCAGTATTTG
241 GCTATGGACA CCGATGGACT TTTATATGGC TCACAGACAC CCAGTGAAGA ATGCTTGTTT
301 CTGGAGAGGT TGGAGGAGAA TCATTACAAC ACCTACACAT CGAAGAAGCA TGCAGAGAAA
361 AATTGGTTTG TTGGTCTCAA GAAGAATGGA AGCTGCAAAA AGGGTCCCAG GACTCACTAC
421 GGCCAGAAAG CCATCCTGTT CCTTCCCCTC CCTGTGTCCT CTGAGTAA
```

Common vampire bat FGF1 gene coding sequence (1-155) (SEQ ID NO: 81)
(GenBank accession no. GABZ01008334, which is hereby incorporated by
reference in its entirety):

```
  1 ATGGCTGAAG GGAAGTCAC CACGTTCACA GCTCTGACTG AGAGTTTAA TCTGCCTCTG
 61 GAGAGTTACA AGAAGCCCAA ACTTCTCTAC TGCAGCAACG GTGGCCACTT CCTGAGGATC
121 CTTCCAGATG GTACAGTGGA TGGGACAAGG GACAAGAGCG ACCAGCACAT TCAGCTGCAG
181 CTCAGTGCGG AAAGCGTGGG GGAGGTGTAC ATAAAGAGCA CCGGGAGTGG CCAGTACTTG
241 GCCATGGACT CCGCCGGGCT TTTGTATGGC TCACAGACAC CAAATGAGGA ATGTTTGTTC
301 CTGGAAAGGC TGGAGGAAAA CCATTACAAC ACCTACACAT CCAAGAAGCA TGCAGAAAAG
361 AATTGGTTCG TGGGGCTCAA GAAGAATGGA AGCTGCAAGC GTGGCCCCG GACTCATTAT
421 GGCCAGAAAG CAATCTTGTT TCTCCCCCTG CCAGTCAACT CTGATTAA
```

TABLE 2-continued

Cattle FGF1 gene coding sequence (1-155) (SEQ ID NO: 82) (GenBank accession no. NM_174055, which is hereby incorporated by reference in its entirety):

```
 918                      ATG GCTGAAGGAG AAACCACGAC CTTCACGGCC CTGACTGAGA
 961 AGTTTAACCT GCCTCTAGGC AATTACAAGA AGCCCAAGCT CCTCTACTGC AGCAACGGGG
1021 GCTACTTCCT GAGAATCCTC CCAGATGGCA CAGTGGATGG GACGAAGGAC AGGAGCGACC
1081 AGCACATTCA GCTGCAGCTC TGTGCGGAAA GCATAGGGGA GGTGTATATT AAGAGTACGG
1141 AGACTGGCCA GTTCTTGGCC ATGGACACCG ACGGGCTTTT GTACGGCTCA CAGACACCCA
1201 ATGAGGAATG TTTGTTCCTG GAAAGGTTGG AGGAAAACCA TTACAACACC TACATATCCA
1261 AGAAGCATGC AGAGAAGCAT TGGTTCGTTG GTCTCAAGAA GAACGGAAGG TCTAAACTCG
1321 GTCCTCGGAC TCACTTCGGC CAGAAAGCCA TCTTGTTTCT CCCCCTGCCA GTCTCCTCTG
1381 ATTAA
```

Platypus FGF1 gene coding sequence (1-155) (SEQ ID NO: 83) (GenBank accession no. XM_001514811, which is hereby incorporated by reference in its entirety):

```
  1 ATGGCGGAGG GTGAAATCAC CACGTTCACA GCCCTGATGG AGAAGTTCGA CCTACCCCTG
 61 GGCAACTACA AAAAGCCTAG GCTGCTCTAC TGCAGCAATG GCGGCTACTT CCTGCGCATC
121 CAGCCAGACG GTAAAGTGGA CGGGACCAGG GATCGGAGCG ATCAGCACAT TCAACTGCAG
181 CTAAGCGCGG AAAGCGTGGG CGAGGTGTAT ATAAAGAGCA CCGAGTCTGG CCACTATTTG
241 GCTATGGACA CCGAAGGACT TTTATATGGC TCACAGGCAC CAGTGAAGA CTGCTTGTTC
301 CTGGAGCGGC TGGAGGAGAA CCACTATAAC ACGTACGTGT CCAAGAAGCA CGCTGAGAAG
361 AATTGGTTTG TCGGTCTCAA GAAGAACGGG AGCTGCAAAC GAGGTCCCCG GACTCACTAC
421 GGCCAGAAAG CCATCCTCTT CCTCCCGCTC CCCGTGGCAT CCGACTAG
```

Zebra finch FGF1 gene coding sequence (1-155) (SEQ ID NO: 84) (GenBank accession no. XM_002193251, which is hereby incorporated by reference in its entirety):

```
  1 ATGGCCGAGG GGGAGATCAC CACCTTCAGC GCCCTGACGG AGAAGTTCAA CCTGCCCCCG
 61 GGGAACTACA AGAAGCCCAA ACTGCTGTAC TGCAGCAACG GGGGCATTT CCTGCGCATC
121 CTCCCGGACG GCACCGTGGA TGGCACCAGG GACCGCAGCG ACCAGCACAT TCAGCTCCAG
181 CTGAGTGCAG AGAGCGTGGG GGTGGTGCAC ATCCAGAGCA CCCAGTCGGG GCAGTACCTG
241 GCCATGGACA CCAACGGGCT GCTCTACGGC TCGCAGCTGC CACCCGGTGA GTGTCTGTTC
301 CTGGAAAGGC TGGAGGAGAA CCATTACAAC ACCTACGTCT CCAAAATGCA CGCGGACAAG
361 AACTGGTTTG TGGGGCTGAA GAAGAACGGG ACAAGCAAGC TGGGCCCGCG GACTCACTAC
421 GGCCAGAAGG CGATCCTGTT CCTGCCGCTG CCCGTGGCGG CCGACTGA
```

Nine-banded armadillo FGF1 gene coding sequence (1-155) (SEQ ID NO: 85) (GenBank accession no. DP001080, which is hereby incorporated by reference in its entirety):

```
178389          TT AATCAGAGGA GACTGGCAGG GGAAGAAACA AGATAGCTTT CTGGCCATAG
178441 TGAGTCTGAG GACCACGTTT GCTGCTTCCG TCCTTCTTGA GACCAACAAA CCATTTCTTC
178501 TCTGCATGCT TCTTGGATAT GTAGGTGTTG TAATTGTTTT CTTCCAGCTT TTCCATGAAC
178561 AAGCATTCCT CACTTGGTGT CTC
182873                                                         TGAGCCAT
182881 ATAAAAGCCC GTCGGTGTCC ATGGCTAAGT ACTGGCCGGT CTCTGCACTC TTTATATACA
182941 CCTCCCCCAC GCTTTCCGCA CTGAGCTGCA GCTGAA
197786                         TGTGT TGGTCGCTCC TGTCCCTTGT CCCATCCACC
197821 GTGCCATCTG GAAGGATCCT CAAGAAGTGG CCCCCGTTTC TGCAGTAGAG GAGTCTGGGG
197881 TGCTTGTAAT TTTCTAGGGG CAGGTTGAAC TTCTCCATCA GGGCCATGAA GGTTGTGATC
197941 TCCCCTTCAG CCAT
```

*Xenopus Silurana tropicalis* FGF1 gene coding sequence (1-155) (SEQ ID NO: 86) (GenBank accession no. FJ428265, which is hereby incorporated by reference in its entirety):

```
  1 ATGGCAGAGG GAGACATCAC AACATTCAAC CCCATTGCAG AGTCCTTCAG TCTTCCAATT
 61 GGCAACTACA AGAAACCAAA ACTTCTGTAC TGTAATAATG GAGGGTATTT TTTGCGCATC
121 CTCCCAGATG GGGTTGTGGA TGGAACAAGA GACAGAGATG ACCTTTACAT TACACTGAAG
181 TTAAGCGCAC AAAGCCAAGG GGAGGTGCAT ATCAAAAGCA CAGAGACAGG GAGTTACTTA
241 GCCATGGACT CCAGTGGACA GTTGTATGGA ACTCTCACAC CAAATGAAGA AAGCCTGTTT
301 CTGGAGACAT TAGAAGAGAA TCACTATAAC ACATACAAGT CAAAGAAGTA TGCAGAAAAT
361 AACTGGTTTG TGGGGATAAA GAAGAACGGG GCAAGCAAAA AGGGATCAAG GACTCACTAT
421 GGACAAAAAG CCATCCTTTT TCTGCCGCTG CCAGCATCAC CTGACTAG
```

*Heterocephalus glaber* FGF1 gene coding sequence (1-155) (SEQ ID NO: 87) (generated using SMS Reverse Translate tool on the ExPASy Bioinformatics Resource website (www.expasy.org):

```
  1 ATGGCGGAAG GCGAAATTAC CACCTTTACC GCGCTGACCG AAAAATTTAA CCTGCCGCCG
 61 GGCAACTATA AAAAACCGAA ACTGCTGTAT TGCAGCAACG GCGGCCATTT TCTGCGCATT
121 CTGCCGGATG GCAAAGTGGA TGGCACCCGC GATCGCAGCG ATCAGCATAT TCAGCTGCAG
181 CTGAGCGCGG AAGGCGTGGG CGAAGTGTAT ATTAAAAGCA CCGAAACCGG CCAGTATCTG
241 GCGATGGATA CCGATGGCCT GCTGTATGGC AGCCAGACCG CGAGCGAAGA ATGCCTGTTT
```

TABLE 2-continued

```
301 CTGGAACGCC TGGAAGAAAA CCATTATAAC ACCTATATTA GCAAAAAACA TGCGGAAAAA
361 AACTGGTTTG TGGGCCTGAA AAAAAACGGC AGCTGCAAAC GCGGCCCGCG CACCCATTAT
421 GGCCAGAAAG CGATTCTGTT TCTGCCGCTG CCGGTGAGCA GCGAT
```

Black flying fox FGF1 gene coding sequence (1-155) (SEQ ID NO: 88)
(generated using SMS Reverse Translate tool on the ExPASy Bioinformatics
Resource website (www.expasy.org)):

```
  1 ATGGCGGAAG GCGAAGTGAC CACCTTTACC GCGCTGACCG AACGCTTTAA CCTGCCGCCG
 61 GGCAACTATA AAAAACCGAA ACTGCTGTAT TGCAGCAACG GCGGCCATTT TCTGCGCATT
121 CTGCCGGATG GCACCGTGGA TGGCACCCGC GATAAAAGCG ATCAGCATAT TCAGCTGCAG
181 CTGAGCGCGG AAAGCGTGGG CGAAGTGTAT ATTAAAAGCA CCGAAAGCGG CCAGTATCTG
241 GCGATGGATA GCGATGGCCT GCTGTATGGC AGCCAGACCC CGGATGAAGA TTGCCTGTTT
301 CTGGAACGCC TGGAAGAAAA CCATTATAAC ACCTATACCA GCAAAAAACA TGCGGAAAAA
361 AACTGGTTTG TGGGCCTGAA AAAAAACGGC AGCTGCAAAC GCGGCCCGCG CACCCATTAT
421 GGCCAGAAAG CGATTCTGTT TCTGCCGCTG CCGGTGAGCA GCGAT
```

Chinese tree shrew FGF1 gene coding sequence (1-155) (SEQ ID NO: 89)
(generated using SMS Reverse Translate tool on the ExPASy Bioinformatics
Resource website (www.expasy.org)):

```
  1 ATGGCGGAAG GCGAAATTAC CACCTTTGCG GCGCTGACCG AAAAATTTGA TCTGCCGCCG
 61 GGCAACTATA AAAAACCGAA ACTGCTGTAT TGCAGCAACG GCGGCCATTT TCTGCGCATT
121 CTGCCGGATG GCACCGTGGA TGGCACCCGC GATCGCAGCG ATCAGCATAT TCAGCTGCAG
181 CTGACCGCGG AAAACGTGGG CGAAGTGTAT ATTAAAAGCA CCGAAACCGG CCAGTATCTG
241 GCGATGGATG CGGATGGCCT GCTGTATGGC AGCCAGACCC CGAACGAAGA ATGCCTGTTT
301 CTGGAACGCC TGGAAGAAAA CCATTATAAC ACCTATATTA GCAAAAAACA TGCGGAAAAA
361 AACTGGTTTG TGGCGCTGAA AAAAAACGGC AGCTGCAAAC TGGGCCCGCG CACCCATTAT
421 GGCCAGAAAG CGATTCTGTT TCTGCCGCTG CCGGTGAGCA GCGAT
```

Rock pigeon FGF1 gene coding sequence (1-155) (SEQ ID NO: 90) (generated
using SMS Reverse Translate tool on the ExPASy Bioinformatics Resource
website (www.expasy.org)):

```
  1 ATGGCGGAAG GCGAAATTAC CACCTTTACC GCGCTGACCG AAAAATTTAA CCTGCCGCCG
 61 GGCAACTATA AAAAACCGAA ACTGCTGTAT TGCAGCAACG GCGGCCATTT TCTGCGCATT
121 CTGCCGGATG GCAAAGTGGA TGGCACCCGC GATCGCAGCG ATCAGCATAT TCAGCTGCAG
181 CTGAGCGCGG AAAGCGTGGG CGAAGTGTAT ATTAAAAGCA CCCAGAGCGG CCAGTATCTG
241 GCGATGGATC CGACCGGCCT GCTGTATGGC AGCCAGCTGC TGGGCGAAGA ATGCCTGTTT
301 CTGGAACGCA TTGAAGAAAA CCATTATAAC ACCTATGTGA GCAAAAAACA TGCGGATAAA
361 AACTGGTTTG TGGGCCTGAA AAAAAACGGC AACAGCAAAC TGGGCCCGCG CACCCATTAT
421 GGCCAGAAAG CGATTCTGTT TCTGCCGCTG CCGGTGAGCG CGGAT
```

Sheep FGF1 gene coding sequence (1-155) (SEQ ID NO: 91)
(GenBank accession no. XM_004008909, which is
hereby incorporated by reference in its entirety):

```
361 ATGGCTGAAG GAGAAACCAC AACCTTCAGG GCCCTGACTG AGAAGTTTAA CCTGCCTCTA
421 GGCAATTACA AGAAGCCCAA GCTCCTCTAT TGCAGCAACG GGGCTACTT CCTGAGAATC
481 CTCCCAGATG GCAGAGTGGA TGGGACGAAG GACAGGAGCG ACCAGCACAT TCAGCTGCAG
541 CTCTATGCGG AAAGCATAGG GGAGGTGTAT ATTAAGAGTA CGGAGACTGG CCAGTTCTTG
601 GCCATGGACA CCAACGGGCT TTTGTACGGC TCACAAACAC CCAGTGAGGA ATGTTTGTTC
661 CTGGAAAGGC TGGAGGAAAA CCATTATAAC ACCTACATAT CCAAGAAGCA TGCAGAGAAG
721 AATTGGTTCA TTGGTCTCAA GAAGAACGGA AGCTCCAAAC TCGGTCCTCG GACTCACTTC
781 GGCCAGAAAG CCATCTTGTT TCTCCCCCTG CCAGTTTCCT CTGATTAA
```

Chicken FGF1 gene coding sequence (1-155) (SEQ ID NO: 92) (GenBank
accession no. NM_205180, which is hereby incorporated
by reference in its entirety):

```
 52                                                            ATGGCCGAG
 61 GGGGAGATAA CCACCTTCAC CGCCCTGACC GAGCGCTTCG GCCTGCCGCT GGGCAACTAC
121 AAGAAGCCCA ACTCCTGTA CTGCAGCAAC GGGGGCCACT TCCTACGGAT CTGCCGGAC
181 GGCAAGGTGG ACGGGACGCG GGACCGGAGT GACCAGCACA TTCAGCTGCA GCTCAGCGCG
241 GAAGATGTGG GCGAGGTCTA TATAAAGAGC ACAGCGTCGG GGCAGTACCT GGCAATGGAC
301 ACCAACGGGC TCCTGTATGG CTCGCAGCTA CCAGGCGAGG AGTGCTTGTT CCTTGAGAGG
361 CTCGAGGAGA ACCATTACAA CACATACATC TCCAAAAAGC ACGCAGACAA GAACTGGTTC
421 GTCGGGCTGA AGAAAAACGG GAACAGCAAG CTGGGCCGC GGACTCACTA TGGGCAAAAG
481 GCGATCCTCT TCCTCCCATT GCCGGTGTCG GCTGACTGA
```

Alpaca FGF1 gene coding sequence (1-155, excluding 1-57) (SEQ ID NO: 93)
(Ensembl accession no. ENSVPAT00000008395, which is hereby incorporated
by reference in its entirety):

```
  1 CAGCTGCAGC TCAGTGCGGA AAGCGTGGGG GAGGTGTATA TAAAGAGTAC CGAGACTGGC
 61 CAGTACTTGG CCATGGACAC CGACGGGCTT TTGCACGGCT CACAGACACC AAATGAGGAA
121 TGTTTGTTCC TGGAAAGGCT GGAGGAGAAC CATTACAACA CCTACACGTC CAAGAAGCAC
181 GCCGAAAAGA ATTGGTTTGT TGGTCTCAAG AAGAATGGAA GCTGCAAACG CGGTCCTCGG
241 ACTCACTACG GCCAGAAGGC GATCTTGTTT CTCCCCTTGC CAGTCTCCTC TGATTAA
```

TABLE 2-continued

Anole lizard FGF1 gene coding sequence (1-155) (SEQ ID NO: 94) (Ensembl accession no. ENSACAT00000013467, which is hereby incorporated by reference in its entirety):

```
  1 ATGGCTGAAG GTGAAATAAC AACATTCACA GCCTTGACCG AGAGGTTTGC TCTCCCAATG
 61 GAGAATTACA AGAAGCCCAA ACTCCTGTAT TGCAGCAATG GAGGCCACTT CCTGAGGATC
121 CTTCCAGATG GAAAAGTGGA TGGCACCATG GACCGGAATG ACAGCTATAT TCAGTTGCTG
181 TTAACAGCAG AAGATGTGGG TGTGGTATAT ATAAAAGGCA CTGAGACCGG GCAGTACTTG
241 GCCATGGATG CCAATGGACA TTTATATGGC TCGCAGTTGC CAACAGAAGA GTGTTTATTT
301 GTGGAAACGC TGGAAGAAAA CCATTACAAT ACATATACCT CAAAGATGCA TGGCGATAAG
361 AAGTGGTATG TTGGCTTGAA AAAGAATGGG AAAGGCAAAC TGGGGCCACG GACTCATCGC
421 GGCCAAAAGG CAATACTTTT CCTTCCACTG CCAGTATCAC CTGATTAG
```

Bushbaby FGF1 gene coding sequence (1-155) (SEQ ID NO: 95) (Ensembl accession no. ENSOGAT00000005081, which is hereby incorporated by reference in its entirety):

```
  1 ATGGCTGAAG GGGAAATCAC AACCTTCACA GCCCTCACAG AGAAGTTTAA TCTGCCTCTA
 61 GGAAATTACA AGAAGCCCAA GCTCCTCTAC TGTAGCAACG GGGTCACTT TCTGAGGATC
121 CTGCCGGATG GCACCGTGGA TGGGACACAA GACAGGAGCG ACCAGCACAT TCAGCTGCAG
181 CTCAGTGCGG AAAGCGTGGG GGAGGTGTAT ATAAAGAGTA CCCAGACTGG CCAGTACTTG
241 GCCATGGACT CCGACGGGCT TTTATACGGC TCACAAACAC CAAATGAGGA ATGCCTGTTC
301 CTGGAACGGC TGGAGGAAAA CCATTACAAC ACCTATGTGT CCAAGAAGCA CGCCGAGAAG
361 AATTGGTTTG TCGGTCTCAA GAAGAACGGA AGTTGCAAAC GTGGTCCTCG GACTCACTAC
421 GGCCAGAAAG CAATCTTGTT TCTCCCCCTG CCAGTCTCCT CTGATTAA
```

Cat FGF1 gene coding sequence (1-155) (SEQ ID NO: 96) (Ensembl accession no. ENSFCAT00000009123, which is hereby incorporated by reference in its entirety):

```
  1 ATGGCTGAAG GGGAAATCAC AACCTTCACG GCCCTGACGG AGAGTTCAA TCTGCCTCCA
 61 GGGAATTACA AGAAACCCAA ACTCCTCTAC TGTAGCAACG GGGCCACTT CCTGAGGATC
121 CTTCCAGATG GCACAGTGGA TGGGACGAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTGTACGGC TCACAGACAC CAATGTTGTT C
301 CTGGAAAGGC TGGAAGAAAA CCATTACAAC ACCTACACAT CCAAGAAGCA CGCAGAAAAG
361 AATTGGTTTG TGGGTCTCAA GAAGAATGGA AGCTGCAAAC GCGGTCCCCG GACTCACTAT
421 GGCCAGAAGG CAATTTTGTT TCTCCCCCTG CCAGTCTCCT CTGATTAA
```

Chinese softshell turtle FGF1 gene coding sequence (1-155) (SEQ ID NO: 97) (Ensembl accession no. ENSPSIT00000016432, which is hereby incorporated by reference in its entirety):

```
131           ATGGCTGAAG GGGAAATAAC AACGTTCACC GCCCTGACCG AAAAATTCAA
181 CCTTCCCCTG GGGAATTACA AGAATCCCAA ACTCTTATAT TGCAGCAATG GAGGCTACTT
241 CTTGAGGATA CATCCAGATG GCAAAGTAGA TGGGACAAGG GACCGAAGTG ACCAACACAT
301 TCAGCTGCAG CTAAGTGCGG AAAGCGTGGG TGAGGTATAT ATAAAGAGCA CTGAGTCTGG
361 ACAGTTTTTG GCTATGGACG CCAATGGACT TTTATATGGA TCACTGTCAC CGAGTGAGGA
291 ATGCTTATTC TTGGAAAGAA TGGAAGAAAA TCATTATAAC ACCTACATCT CCAAGAAGCA
351 TGCAGACAAG AACTGGTTCG TTGGCTTAAA GAAGAATGGA AGCTGCAAAC TGGGACCGCG
411 GACGCACTAC GGCCAAAAGG CCGTCCTTTT CCTTCCACTG CCAGTGTCAG CTGATTAA
```

Coelacanth FGF1 gene coding sequence (1-155) (SEQ ID NO: 98) (Ensembl accession no. ENSLACT00000015212, which is hereby incorporated by reference in its entirety):

```
  1 ATGGCTGAAG ACAAAATAAC AACACTGAAG GCCTTGGCTG AAAAATTTAA CCTTCCTATG
 61 GGAAATTACA AGAAAGCAAA ACTCCTCTAC TGCAGCAACG GAGGGTATTT CCTGCGAATA
121 CCCCCAGACG GGAAAGTGGA AGGAATTAGA GAACGAAGCG ACAAGTACAT TCAGCTGCAA
181 ATGAATGCAG AAAGTTTAGG CATGGTGTCT ATAAAGGGTG TGGAGGCAGG GCAATACCTA
241 GCTATGGAATA CAAATGGACT CCTGTATGGA TCAGTCGAG ATGCCTTTTC
301 ATGGAAAAGA TGGAAGAAAA CCACTACAAC ACATACAGGT CTAAGCACAC TGCAGATAAA
361 AACTGGTATG TTGGCATTAG AAAGAACGGT AGCATCAAAC CAGGACCAAG GACTCACATT
421 GGCCAAAAGG CTGTTCTTTT TCTCCCTCTG CCTGCCTCGA GTGATTAG
```

Dolphin FGF1 gene coding sequence (1-155) (SEQ ID NO: 99) (Ensembl accession no. ENSTTRT00000004742, which is hereby incorporated by reference in its entirety):

```
  1 ATGGCTGAAG GGGAAATCAC AACCTTCACA GCCCTGACCG AGAAGTTTAA TCTGCCTCCA
 61 GGGAATTACA AGAAGCCCAA ACTCCTCTAC TGTAGCAACG GGGCCACTT CCTGAGGATC
121 CTTCCAGATG GCACAGTGGA TGGGACAAGG GACAGGAGTG ACCAGCACAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTGTACGGC TCACAGACAC CAATGAGGA ATGTTTGTTC
301 CTGGAAAGGT TGGAGGAAAA CCATTACAAC ACCTACGCAT CCAAGAAGCA TGCAGAAAAG
361 AATTGGTTCG TTGGTCTCAA GAAGAACGGA AGCTGCAAAC GCGGTCCTCG GACTCACTAC
421 GGCCAGAAAG CAATCTTGTT TCTCCCCCTG CCAGTCTCCT CCGATTAA
```

TABLE 2-continued

Ferret FGF1 gene coding sequence (1-155) (SEQ ID NO: 100) (Ensembl accession no. ENSMPUT00000008013, which is hereby incorporated by reference in its entirety):

```
  1                               ATGGCT GAAGGGGAAA TCACAACCTT
 61 CACAGCCCTG ATGGAGAAGT TTAATCTGCC TGCGGGGAAT TACAAGAAGC CCAAACTCCT
121 CTACTGTAGC AATGGGGGCC ACTTCCTGAG GATCCTTCCA GATGGCACAG TGGACGGCAC
181 AAGGGACAGG AGCGACCAGC ACATTCAGCT GCAGCTCAGT GCGGAAAGCG TGGGGGAGGT
241 GTACATAAAG AGTACCGAGA CTGGCCAGTA CTTGCCCATG GACACCGATG GCTTTTGTA
301 CGGCTCACAA ACACCAAATG AGGAATGTCT GTTCCTGGAA AGGCTGGAGG AAAACCATTA
361 CAACACCTAC ACATCCAAGA AGCACGCTGA GAAGAATTGG TTTGTAGGTC TCAAGAAGAA
421 CGGAAGCTGC AAACGCGGTC CTCGGACTCA CTATGGCCAG AAAGCAATTC TGTTTCTCCC
481 CCTGCCAGTC TCCTCTGATT AA
```

Gibbon FGF1 gene coding sequence (1-155) (SEQ ID NO: 101) (Ensembl accession no. ENSNLET00000012455, which is hereby incorporated by reference in its entirety):

```
241                                ATGG CCGAAGGGGA
301 AATCACCACC TTCACAGCCC TGACCGAGAA GTTTAATCTG CCTCCAGGGA ATTACAAGAA
361 GCCCAAACTC CTCTACTGTA GCAACGGGGG CCACTTCTTG AGGATCCTTC CGGATGGCAC
421 AGTGGATGGG ACAAGGGACA GGAGCGACCA GCACATTCAG CTGCAGCTCA GTGCGGAAAG
481 CGTGGGGGAG GTGTATATAA AGAGTACCGA GACTGGCCAG TACTTGGCCA TGGACACCGA
541 CGGGCTTTTA TACGGCTCAC AGACACCAAA TGAGGAATGT TTGTTCCTGG AAAGGCTGGA
601 GGAGAACCAT TACAACACCT ATATATCCAA GAAGCATGCA GAGAAGAATT GGTTTGTTGG
661 CCTCAAGAAG AATGGAAGCT GCAAACGCGG TCCTCGGACT CACTATGGCC AGAAAGCAAT
721 CTTGTTTCTC CCCCTGCCAG TCTCTTCTGA TTAA
```

*Gorilla* FGF1 gene coding sequence (1-155) (SEQ ID NO: 102) (Ensembl accession no. ENSGGOT00000025344, which is hereby incorporated by reference in its entirety):

```
121                                ATGG CTGAAGGGGA
181 AATCACCACC TTCACAGCCC TGACCGAGAA GTTTAATCTG CCTCCAGGGA ATTACAAGAA
241 GCCCAAACTC CTCTACTGTA GCAATGGGGG CCACTTCTTG AGGATCCTTC CGGATGGCAC
301 AGTGGATGGG ACAAGGGACA GGAGCGACCA GCACATTCAG CTGCAGCTCA GTGCGGAAAG
361 CGTGGGGGAG GTGTATATAA AGAGTACCGA GACTGGCCAG TACTTGGCCA TGGACACCGA
421 CGGGCTTTTA TACGGCTCAC AGACACCAAA TGAGGAATGT TTGTTCCTGG AAAGGCTGGA
481 GGAGAACCAT TACAACACCT ATATATCCAA GAAGCATGCA GAGAAGAATT GGTTTGTTGG
541 CCTCAAGAAG AATGGAAGCT GCAAACGCGG TCCTCGGACT CACTATGGCC AGAAAGCAAT
601 CTTGTTTCTC CCCCTGCCAG TCTCTTCCGA TTAA
```

Hedgehog FGF1 gene coding sequence (1-155) (SEQ ID NO: 103) (Ensembl accession no. ENSEEUT00000005832, which is hereby incorporated by reference in its entirety):

```
  1 ATGGCTGAAG GAGAAATCAC CACCTTCACG GCCCTGACTG AGAAGTTTAA TCTGCCACTA
 61 GGGAATTACA AGAAGCCCAA GCTCCTCTAC TGTAGCAACG GGGCCACTT CCTGAGGATC
121 CTTCCAGATG GCACCGTGGA TGGGACAAGG ACAGGAGCG ACCAGCATAT TCAGCTGCAG
181 CTCAGTGCGG AAAGCGTGGG GGAGGTGTAT ATAAAGACGG CCGAGACTGG CCAGTACTTG
241 GCCATGGACA CCGACGGGCT TTTATACGGC TCACAAACAC CAAATGAGGA ATGTCTGTTC
301 CTTGAAAGGC TGGAAGAGAA CCATTACAAT ACCTACACAT CCAAGAAGCA TGCCGAGAAG
361 AACTGGTTTG TTGGCCTCAA GAAGAATGGA AGCTGCAAGC GTGGTCCTCG GACTCATTAT
421 GGCCAGAAAG CTATTTTGTT TCTCCCCCTG CCAGTTTCCT CTGATTAA
```

Hyrax FGF1 gene coding sequence (1-155, excluding 1-90) (SEQ ID NO: 104) (Ensembl accession no. ENSPCAT00000011746, which is hereby incorporated by reference in its entirety):

```
  1 ATGGCTGAAG GCGAAATCAC AACCTTCACA GCCCTGACTG AGAAGTTTAA CCTGCCACTA
 61 GAGAATTACA AGAAGCCCAA ACTCCTCTAC TGTAGCAACG GAGGCCACTT CCTGAGGATC
121 CTTCCGGACG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATATGGC TCA
```

Kangaroo rat FGF1 gene coding sequence (1-155, excluding 1-16 and 58-155) (SEQ ID NO: 105) (Ensembl accession no. ENSDORT00000007345, which is hereby incorporated by reference in its entirety):

```
  1 ATGGCTGAAG GGAAATCAC AACCTTCACA GCCCTGACGG AAAGGTTTAA ----------
    ---------- ---------- ---------- ---------- ---------- ----------
 51 ---------- ---------- ---------- ---------- ---------T TCAGCTGCAA
 62 CTGAGTGCGG AAAGCGTGGG GGAGGTCTAT ATAAAGAGCA CCGAGACTGG CCAATACTTG
122 GCCATGGATG CCGACGGGCT TTTATACGGC TCACAGACAC CTGATGAAGA ATGCTTGTTC
182 CTGGAGAGGC TGGAAGAAAA TCATTATAAC ACCTACATAG CCAAGAAACA TGCTGAAAAG
242 AATTGGTTTG TCGGCCTCAA AAAGAATGGA AGCTGCAAGC GTGGTCCTCG GACTCACTAT
302 GGCCAGAAAG CAATCCTGTT CCTCCCCTTG CCTGTCTCCT CTGATTAG
```

TABLE 2-continued

Lamprey FGF1 gene coding sequence (1-155, excluding 94-155) (SEQ ID
NO: 106) (Ensembl accession no. ENSPMAT00000010729, which is hereby
incorporated by reference in its entirety):

```
  1 ATGGAGGTGG GCCACATCGG CACGCTGCCC GTGGTCCCCG CGGGGCCCGT GTTCCCCGGC
 61 AGTTTCAAGG AGCCACGGCG CCTCTACTGC CGCAGCGCGG CCACCACCT CCAGATCCTG
121 GGGGACGGCA CCGTGAGTGG CACCCAGGAC GAGAACGAGC CCCACGCCGT TCTGCAGCTG
181 CAGGCGGTGC GCCGCGGGGT GGTGACGATC CGTGGGCTCT GCGCCGAGAG GTTCCTCGCC
241 ATGAGCACGG AGGGACACCT GTACGGGCG GTGAGG
```

Lesser hedgehog tenrec FGF1 gene coding sequence (1-155, excluding 1-57)
(SEQ ID NO: 107) (Ensembl accession no. ENSETET00000017851, which is
hereby incorporated by reference in its entirety):

```
  1 CAGCTGAAGC TCGTTGCCGA AAGCGTGGGG GTGGTGTATA TAAAGAGCAT CAAGACCGGC
 61 CAGTACTTGG CCATGAACCC CGACGGGCTT TTATACGGCT CCGAGACCCC AGAGGAAGAA
121 TGCTTGTTCC TGGAAACGCT GGAGGAAAAC CACTACACCA CCTTCAAATC TAAGAAGCAC
181 GTAGAGAAGA ATTGGTTCGT TGGTCTCCGG AAGAATGGAA GGGTCAAGAT CGGGCCTCGG
241 ACTCACCAAG GCCAGAAAGC AATCTTGTTC CTGCCCCTCC GGTGTCCTC TGATTAA
```

Rhesus monkey FGF1 gene coding sequence (1-155) (SEQ ID NO: 108)
(Ensembl accession no. ENSMMUT00000033070, which is hereby
incorporated by reference in its entirety):

```
 36                                              ATGGC TGAAGGGGAA ATCACCACGT
 61 TCACAGCCCT GACCGAGAAG TTTAATCTGC CTCCAGGGAA TTACAAGAAG CCCAAACTGC
121 TCTACTGTAG CAATGGGGGC CACTTCTTGA GGATCCTTCC GGATGGCACA GTGGATGGGA
181 CAAGGGACAG GAGCGACCAG CACATTCAGC TGCAGCTCAG TGCGGAAAGC GTGGGGGAGG
241 TGTATATAAA GAGTACCGAG ACTGGCCAGT ACTTGGCCAT GGACACCGAC GGGCTTTTAT
301 ACGGCTCACA GACACCCAAT GAGGAATGTT TGTTCCTGGA AAGGCTGGAG GAGAACCATT
361 ACAACACCTA TATATCCAAG AAGCACGCAG AGAAGAATTG GTTTGTTGGC CTCAAGAAGA
421 ATGGAAGCTG CAAACGTGGT CCTCGGACTC ACTATGGCCA GAAAGCAATC TTGTTTCTTC
481 CCCTGCCAGT CTCTTCTGAT TAA
```

Megabat FGF1 gene coding sequence (1-155) (SEQ ID NO: 109) (Ensembl
accession no. ENSPVAT00000004596, which is hereby incorporated by
reference in its entirety):

```
  1 ATGGCCGAGG GGGAAGTCAC GACGTTCACG GCCCTGACCG AGAGGTTTAA CCTGCCTCCA
 61 GGGAATTACA AGAAGCCCAA ACTTCTCTAC TGCAGCAACG GGGCCACTT CCTGAGGATC
121 CTCCCAGATG GCACAGTGGA TGGGACAAGG GACAAGAGCG ACCAGCACAT TCAGCTGCAG
181 CTCAGTGCGG AAAGTGTGGG GGAGGTGTAT ATAAAGAGCA CCGAGAGTGG CCAGTACTTG
241 GCCATGGACT CCGACGGGCT TTTGTACGGC TCACAGACAC CAGATGAGGA CTGTTTGTTC
301 CTGGAAAGGC TGGAGGAAAA CCATTACAAC ACCTACACAT CCAAGAAGCA CGCAGAGAAG
361 AATTGGTTTG TTGGGCTCAA GAAGAATGGA AGCTGCAAGC GCGGTCCCCG GACTCACTAC
421 GGCCAGAAAG CGATCCTGTT TCTCCCCCTG CCAGTCTCCT CTGATTAG
```

Microbat FGF1 gene coding sequence (1-155) (SEQ ID NO: 110) (Ensembl
accession no. ENSMLUT00000007098, which is hereby incorporated by
reference in its entirety):

```
 66         ATGGC TGAGGGGGAA GTCACCACAT TCACGGCCCT GACCGAGAGG TTCAATCTGC
121 CTCTGGAGAA CTACAAGAAG CCCAAGCTTC TCTACTGCAG CAACGGGGC CACTTCCTGC
181 GGATCCTCCC AGACGGCACC GTGGACGGGA CGAGGGACAG GAGCGACCAG CACATTCAGC
241 TGCAGCTCAG TGCGGAAAGC GTGGGGGAGG TGTATATAAA GAGCACCGAG AGTGGCCAGT
301 ACTTGGCCAT GGACTCCGAC GGGCTTTTGT ACGGCTCACA ACACCCAAT GAGGAATGTT
361 TGTTCCTGGA AAGGCTGGAG GAGAACCACT ACAACACCTA CACGTCCAAG AAGCACGCAG
421 AAAAGAATTG GTTCGTTGGG CTCAAGAAGA ACGGAAGCTG CAAGCGTGGT CCTCGGACGC
481 ATTATGGCCA GAAAGCAATC TTGTTTCTCC CCCTGCCAGT CTCCTCCGAT TAA
```

Mouse lemur FGF1 gene coding sequence (1-155) (SEQ ID NO: 111) (Ensembl
accession no. ENSMICT00000009454, which is hereby incorporated by
reference in its entirety):

```
  1 ATGGCCGAAG GGAGATCAC AACCTTCACG GCCCTCACCG AGAAGTTTAA CCTGCCTCCG
 61 GGGAACTACA AGAAGCCCAA GCTCCTCTAC TGCAGCAACG GCGGCCACTT CCTGCGCATC
121 CTTCCCGACG GCACCGTGGA TGGCACGAGA GACAGGAGCG ACCAGCACAT TCAGCTGCAG
181 CTCAGTGCGG AAAGCGCGGG GGAGGTGTAT ATAAAGAGCA CCCAGACTGG CCGGTACTTG
241 GCCATGGACG CCGACGGGCT TTTATACGGC TCACAAACAC CAAATGAGGA ATGTTTGTTC
301 CTGGAAAGGC TGGAGGAAAA CCATTACAAC ACCTACGTAT CCAAGAAGCA CGCAGAGAAG
361 AATTGGTTTG TTGGCCTCAA GAAGAATGGA AGTTGCAAAC GCGGCCCCG GACTCACTAT
421 GGCCAGAAAG CAATCTTGTT TCTGCCCCTG CCAGTCTCCT CTGATTAA
```

Pika FGF1 gene coding sequence (1-155, excluding 57-67) (SEQ ID NO: 112)
(Ensembl accession no. ENSOPRT00000012854, which is hereby incorporated
by reference in its entirety):

```
  1 ATGGCCGAGG GAGAAGTCAC CACCTTCTCA GCCCTGACGG AGAAGTTCAA TCTGCCTGGA
 61 GGAAACTACA AGTTGCCCAA GCTCCTTTAC TGTAGCAACG GAGGCCACTT CCTGAGGATC
```

TABLE 2-continued

```
121   CTTCCAGATG GCACAGTGGA TGGGACCAGG GACAGGAGCG ACCTGCACA- ----------
170   ---------- ---------- -GAGGTGTTT ATAAAGAGTA CGGAGACTGG CCAGTACTTG
209   GCTATGGACA CCGATGGCCT TTTATATGGC TCGCAGACAC CCAGTGAGGA GTGTTTGTTC
269   CTGGAGCGGC TGGAGGAGAA CCACTACAAC ACCTACACAT CCAAGAAGCA TGCCGAGAAG
329   AACTGGTTTG TGGGCATCAA GAAGAATGGA AGCTGCAAGC GTGGTCCTCG GACTCACTAC
389   GGCCAGAAAG CCATCTTGTT TCTCCCTCTG CCAGTCTCTT CTGACTAA
```

Rat FGF1 gene coding sequence (1-155) (SEQ ID NO: 113) (Ensembl accession no. ENSRNOT00000018577, which is hereby incorporated by reference in its entirety):

```
268                      ATG GCCGAAGGGG AGATCACAAC CTTTGCAGCC
301   CTGACCGAGA GGTTCAATCT GCCTCTAGGG AACTACAAAA AACCCAAACT GCTCTACTGC
361   AGCAACGGGG GCCACTTCTT GAGGATTCTT CCCGATGGCA CCGTGGATGG GACCAGGGAC
421   AGGAGCGACC AGCACATTCA GCTGCAGCTC AGTGCGGAAA GCGCGGGCGA AGTGTATATA
481   AAGGGTACAG AGACTGGCCA GTACTTGGCC ATGGACACCG AAGGGCTTTT ATACGGCTCG
541   CAGACACCAA ATGAAGAATG CCTATTCCTG GAAAGGCTAG AAGAAAACCA TTATAACACT
601   TACACATCCA AGAAGCACGC GGAGAAGAAC TGGTTTGTGG GCCTCAAGAA GAACGGGAGT
661   TGTAAGCGCG GTCCTCGGAC TCACTACGGC CAGAAAGCCA TCTTGTTTCT CCCCCTCCCG
721   GTATCTTCTG ACTAA
```

Sloth FGF1 gene coding sequence (1-155) (SEQ ID NO: 114) (Ensembl accession no. ENSCHOT00000012416, which is hereby incorporated by reference in its entirety):

```
1     ATGGCTGAAG GGGAAATCAC AACCTTCACA GCTCTGATGG AGAAGTTTAA CCTGCCACCA
61    GGGAATTACA TGAAGCCCAA ACTCCTCTAC TGTAGCAACG GGGCCACTT CTTGAGGATC
121   CTTCCAGACG GCACAGTGGA TGGGACAAGG GACAGGAGCG ACCTGCACAT TCAGCTGCAG
181   CTCAGTGCGG AAAGCGTGGG GGAGGTGTAT ATAAAGAGTG CGGAGACCGG CCAGTACTTA
241   GCCATGGACA CCGGCGGGCT TTTATACGGC TCACAGACAC CAAGTGAGGA ATGCCTGTTC
301   CTAGAAAGGC TGGAGGAAAA CCATTACAAC ACCTACGTAT CCAAGAAGCA TGCGGAGAAG
361   AACTGGTTCG TTGGCCTAAA GAAGAATGGA AGCAGCAAAC GCGGCCCCCG GACTCACTAT
421   GGCCAGAAAG CCATCTTGTT TCTTCCCCTG CCAGTCTCCT CTGATTAA
```

Squirrel FGF1 gene coding sequence (1-155) (SEQ ID NO: 115) (Ensembl accession no. ENSSTOT00000029249, which is hereby incorporated by reference in its entirety):

```
1                                                                ATGG
5     CTGAAGGGGA AATCACAACC TTCACAGCCC TGACCGAGAA GTTCAATCTG CCTCCAGGGA
65    ACTACAAGAA GCCCAAACTG CTCTACTGTA GCAACGGAGG CCACTTCTTG AGGATCTTC
125   CTGATGGCAC AGTGGATGGG ACAAGAGACA GGAGCGACCA ACACATTCAG CTGCAGCTCA
185   GTGCGGAAAG CGTGGGGGAG GTGTATATAA AGAGTACCGA GACCGGCCAG TACTTGGCCA
245   TGGACACCGA CGGGCTTTTA TATGGCTCAC AGACCCCAAA TGAGGAATGC TTATTCCTGG
305   AAAGGCTGGA GGAAAACCAT TACAACACGT ACACATCCAA GAAGCATGCA GAGAAGAATT
365   GGTTTGTTGG CCTCAAGAAG AACGGAAGCT GCAAGCGCGG TCCCCGGACT CACTATGGCC
425   AGAAAGCGAT CTTGTTTCTC CCACTGCCTG TCTCCTCTGA TTAG
```

Tarsier FGF1 gene coding sequence (1-155) (SEQ ID NO: 116) (Ensembl accession no. ENSTSYT00000007425, which is hereby incorporated by reference in its entirety):

```
1     ATGGCCGAAG GGGAAATCAC AACCTTCACA GCCCTGACCG AGAAGTTCAA CCTGCCCCCG
61    GGGAATTACA AGAAGCCCAA ACTCCTCTAC TGCAGCAACG GGGCCACTT CTTGAGGATC
121   CTTCCGGATG GCACTGTGGA TGGAACGAGG GACAGGAGCG ACCAGCACAT TCAGCTGCAG
181   CTCAGCGCGG AAAGCGTGGG GGAGGTGTAT ATAAAGAGTA CCGAGACCGG CCAGTACTTG
241   GCCATGGACA CCGACGGGCT TTTGTACGGC TCACAGACAC CAAATGAGGA GTGTCTGTTC
301   CTGGAAAGGC TGGAAGAGAA TCATTACAAT ACCTACGTGT CCAAGAAGCA TGCGGAGAAG
361   AATTGGTTTG TCGGCCTCAA GAAGAATGGA AGCTGCAAAC GCGGTCCTCG GACTCACTAT
421   GGCCAGAAAG CAATCTTGTT TCTCCCCCTG CCAGTTTCCT CTGATTAA
```

Tree shrew FGF1 gene coding sequence (1-155) (SEQ ID NO: 117) (Ensembl accession no. ENSTBET00000011861, which is hereby incorporated by reference in its entirety):

```
1     ATGGCTGAAG GGGAAATCAC GACCTTCGCA GCCCTGACCG AGAAGTTTGA TCTGCCTCCA
61    GGGAATTACA AGAAGCCCAA ACTTCTCTAC TGTAGCAACG GGGCCATTT CTTGAGGATT
121   CTTCCAGATG GCACCGTGGA TGGGACAAGA GACAGGAGCG ACCAGCACAT TCAGCTGCAG
181   CTCACTGCGG AAAACGTGGG GGAGGTGTAC ATAAAGAGTA CGGAGACTGG CCAGTACTTG
241   GCCATGGACG CCGACGGGCT TTTATATGGC TCACAGACAC CAAACGAGGA TGTTTGTTC
301   CTGGAAAGGC TGGAGGAGAA CCATTACAAC ACCTACATAT CCAAGAAGCA CGCAGAGAAG
361   AATTGGTTTG TTGCCCTCAA GAAGAACGGA AGCTGCAAAC TCGGTCCTCG GACTCACTAT
421   GGCCAGAAAG CAATCTTGTT TCTCCCCCTG CCAGTCTCCT CTGATTAA
```

TABLE 2-continued

Turkey FGF1 gene coding sequence (1-155, excluding 57-155)
(SEQ ID NO: 118) (Ensembl accession no. ENSMGAT00000017372,
which is hereby incorporated by reference in its entirety):

```
  1  ATGGCCGAGG GGGAGATAAC CACCTTCACA GCCCTGACCG AGCGCTTCGG CCTGCCGCTG
 61  GGCAACTACA AGAAGCCCAA ACTCCTGTAC TGCAGCAACG GGGGCCACTT CCTACGGATC
121  CTGCCGGACG GCAAGGTGGA CGGGACGCGG GACCGGAGCG ACCAGCAC
```

Wallaby FGF1 gene coding sequence (1-155) (SEQ ID NO: 119)
(Ensembl accession no. ENSMEUT00000016544, which is hereby
incorporated by reference in its entirety):

```
  1  ATGGCCGAAG GGGAGATCAC AACCTTCACA GCCCTGACCG AAAGATTTAA CCTGCCACTG
 61  GGGAATTACA AGAAGCCCAA GCTTCTCTAC TGTAGCAATG GGGGCCACTT TTTGAGGATC
121  CTTCCTGATG GCAAAGTGGA TGGGACAAGG GACAGAAATG ATCAACACAT TCAACTGCAA
181  CTAAGCGCGG AAAGCGTGGG TGAGGTGTAT ATAAAGAGCA CTGAGTCTGG GCAGTATTTG
241  GCCATGGACA CCAATGGACT TTTATATGGC TCACAGACCC CCAGCGAAGA ATGCTTATTC
301  CTGGAGAGGT TGGAGGAGAA TCATTACAAC ACCTACATAT CAAAGAAGCA TGCGGAGAAA
361  AATTGGTTTG TTGGCCTCAA GAAGAACGGA AGTTGCAAAA GAGGTCCCAG GACTCACTAT
421  GGCCAGAAAG CCATCCTATT CCTTCCCCTC CCTGTGTCCT CTGAGTAA
```

Zebrafish FGF1 gene coding sequence (1-147) (SEQ ID NO: 120)
(Ensembl accession no. ENSDART00000005842, which is hereby
incorporated by reference in its entirety):

```
178                                                                ATG
181  ACCGAGGCCG ATATTGCGGT AAAGTCCAGC CCGCGCGACT ATAAAAAACT GACGCGGCTG
241  TACTGTATGA ATGGAGGATT TCACCTTCAG ATCCTGGCGG ACGGGACAGT GGCTGGAGCA
124  GCAGACGAAA ACACATACAG CATACTGCGC ATAAAAGCAA CAAGTCCAGG AGTGGTGGTG
184  ATCGAAGGAT CAGAAACAGG TCTTTACCTC TCGATGAATG AACATGGCAA GCTGTACGCT
244  TCATCATTAG TGACGGATGA AAGTTATTTC CTGGAGAAGA TGGAGGAAAA CCACTACAAC
304  ACATATCAGT CTCAAAAGCA CGGTGAAAAC TGGTACGTCG GAATAAAAAA GAACGGGAAA
364  ATGAAACGGG GCCCAAGAAC TCACATCGGA CAAAAGGCCA TTTTCTTTCT TCCACGACAG
424  GTGGAGCAGG AAGAGGACTG A
```

As noted above, also encompassed within the present invention are portions of paracrine FGFs other than FGF1 (e.g., FGF2, FGF4, FGF5, FGF6, FGF9, FGF16, and FGF20). The portions derived from paracrine FGF2 include portions corresponding to the above-identified amino acid sequences of FGF1. Corresponding portions may be determined by, for example, sequence analysis and structural analysis.

In one embodiment, the paracrine FGF is FGF2. In one embodiment, the portion of the FGF2 is derived from human FGF2 having the amino acid sequence of SEQ ID NO: 121 (GenBank Accession No. EAX05222, which is hereby incorporated by reference in its entirety), as follows:

```
  1  MAAGSITTLP ALPEDGGSGA FPPGHFKDPK RLYCKNGGFF LRIHPDGRVD GVREKSDPHI
 61  KLQLQAEERG VVSIKGVCAN RYLAMKEDGR LLASKCVTDE CFFFERLESN NYNTYRSRKY
121  TSWYVALKRT GQYKLGSKTG PGQKAILFLP MSAKS
```

In one embodiment, the portion of the paracrine FGF includes an amino acid sequence beginning at any one of residues 1 to 25 and ending at any one of residues 151 to 155 of SEQ ID NO: 121. In one embodiment, the portion of the paracrine FGF includes amino acid residues 1-151, 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-151, 25-152, 25-153, 25-154, or 25-155 of FGF2 (SEQ ID NO: 121). In one embodiment, the portion of the paracrine FGF includes amino acid residues 1-151 or 1-152 of SEQ ID NO: 121.

In one embodiment, the portion of the paracrine FGF of the chimeric protein includes an amino acid sequence that has at least 80%, at least 85%, at least 90%, at least 95%, at least 97% or at least 99% amino acid sequence identity to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 151 to 155 of SEQ ID NO: 121. In one embodiment, the portion of the paracrine FGF includes an amino acid sequence that has at least 80%, at least 85%, at least 90%, at least 95%, at least 97% or at least 99% amino acid sequence homology to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 151 to 155 of SEQ ID NO: 121.

Also encompassed within the present invention are portions of paracrine FGFs other than FGF2 (e.g., FGF1, FGF4, FGF5, FGF6, FGF9, FGF16, and FGF20). The portions derived from paracrine FGFs other than FGF2 include portions corresponding to the above-identified amino acid sequences of FGF2. Corresponding portions may be determined by, for example, sequence analysis and structural analysis.

In one embodiment of the present invention, the portion of the paracrine FGF is derived from an ortholog of a human paracrine FGF. In one embodiment of the present invention, the portion of the paracrine FGF of the chimeric protein is derived from an ortholog of human FGF2. In one embodiment, the portion of the FGF2 is derived from *Gorilla gorilla, Pongo abelii, Macaca mulatta, Pan troglodytes, Pan paniscus, Saimiri boliviensis boliviensis, Nomascus leucogenys, Equus caballus, Bos taurus, Papio Anubis, Vicugna pacos, Ovis aries, Capreolus capreolus, Loxodonta Africana, Sus scrofa, Ailuropoda melanoleuca, Choloepus hoffmanni, Bubalus bubalis, Canis lupus familiaris, Rattus norvegicus, Heterocephalus glaber, Otolemur garnettii, Mus musculus, Ictidomys tridecemlineatus, Felis catus, Cavia porcellus, Sarcophilus harrisii, Monodelphis domestica, Oryctolagus cuniculus, Meleagris gallopavo, Gallus gallus, Taeniopygia guttata, Cynops pyrrhogaster, Xenopus laevis, Didelphis albiventris, Myotis lucifugus, Anolis carolinensis, Dasypus novemcinctus, Tupaia belangeri, Xenopus silurana tropicalis, Latimeria chalumnae, Tetraodon nigroviridis, Gasterosteus aculeatus, Takifugu rubripes, Oncorhynchus mykiss, Salmo salar, Danio rerio, Oreochromis niloticus,* or *Oryzias latipes*. The portions of an ortholog of human paracrine FGF include portions corresponding to the above-identified amino acid sequences of FGF2. Corresponding portions may be determined by, for example, sequence analysis and structural analysis.

In one embodiment, the portion of the FGF2 of the chimeric protein of the present invention is derived from an ortholog of human FGF2 having the amino acid sequence shown in Table 3.

TABLE 3

Amino acid sequence of *Gorilla gorilla* (gorilla) FGF2
(SEQ ID NO: 122) (Ensembl accession no. ENSGGOP00000004720,
which is hereby incorporated by reference in its entirety):

```
104                                                MAAGSI TTLPALPEDG
120 GSGAFPPGHF KDPKRLYCKN GGFFLRIHPD GRVDGVREKS DPHIKLQLQA EERGVVSIKG
180 VCANRYLAMK EDGRLLASKC VTDECFFFER LESNNYNTYR SRKYTSWYVA LKRTGQYKLG
240 SKTGPGQKAI LFLPMSAKS
```

Amino acid sequence of *Pongo abelii* (sumatran orangutan) FGF2 (SEQ ID
NO: 123) (GenBank accession no. XP_002815172, which is hereby
incorporated by reference in its entirety):

```
168                                                   MAA GSITTLPALP
181 EDGGSGAFPP GHFKDPKRLY CKNGGFFLRI HPDGRVDGVR EKSDPHIKLQ LQAEERGVVS
241 IKGVCANRYL AMKEDGRLLA SKCVTDECFF FERLESNNYN TYRSRKYTSW YVALKRTGQY
301 KLGSKTGPGQ KAILFLPMSA KS
```

Amino acid sequence of *Macaca mulatta* (rhesus monkey) FGF2 (SEQ ID
NO: 124) (GenBank accession no. XP_001099284, which is hereby
incorporated by reference in its entirety):

```
 83                        MAAGSITT LPALPEDGGS GAFPPGHFKD PKRLYCKNGG
121 FFLRIHPDGR VDGVREKSDP HIKLQLQAEE RGVVSIKGVC ANRYLAMKED GRLLASKCVT
181 DECFFFERLE SNNYNTYRSR KYTSWYVALK RTGQYKLGSK TGPGQKAILF LPMSAKS
```

Amino acid sequence of *Pan troglodytes* (chimpanzee) FGF2 (SEQ ID
NO: 125) (GenBank accession no. NP_001103711, which is hereby
incorporated by reference in its entirety):

```
134              MAAGSIT TLPALPEDGG SGAFPPGHFK DPKRLYCKNG GFFLRIHPDG
181 RVDGVREKSD PHIKLQLQAE ERGVVSIKGV CANRYLAMKE DGRLLASKCV TDECFFFERL
241 ESNNYNTYRS RKYTSWYVAL KRTGQYKLGS KTGPGQKAIL FLPMSAKS
```

Amino acid sequence of *Pan paniscus* (Pygmy chimpanzee) FGF2 (SEQ ID
NO: 126) (GenBank accession no. XP_003816481, which is hereby
incorporated by reference in its entirety):

```
112                                                         MAAGSITTL
121 PALPEDGGSG AFPPGHFKDP KRLYCKNGGF FLRIHPDGRV DGVREKSDPH IKLQLQAEER
181 GVVSIKGVCA NRYLAMKEDG RLLASKCVTD ECFFFERLES NNYNTYRSRK YTSWYVALKR
241 TGQYKLGSKT GPGQKAILFL PMSAKS
```

Amino acid sequence of *Saimiri boliviensis boliviensis* (Bolivian
squirrel monkey) FGF2 (SEQ ID NO: 127) (GenBank accession no.
XP_003936290, which is hereby incorporated by reference in its
entirety):

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

TABLE 3-continued

Amino acid sequence of *Nomascus leucogenys* (Northern white-cheeked gibbon) FGF2 (SEQ ID NO: 128) (GenBank accession no. XP_003271404, which is hereby incorporated by reference in its entirety):

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Equus caballus* (horse) FGF2 (SEQ ID NO: 129) (GenBank accession no. NP_001182150, which is hereby incorporated by reference in its entirety):

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Bos taurus* (cattle) FGF2 (SEQ ID NO: 130) (GenBank accession no. NP_776481, which is hereby incorporated by reference in its entirety):

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MASKS
```

Amino acid sequence of *Papio anubis* (Olive baboon) FGF2 (SEQ ID NO: 131) (GenBank accession no. XP_003899210, which is hereby incorporated by reference in its entirety):

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

Amino acid sequence of *Vicugna pacos* (alpaca) FGF2 (SEQ ID NO: 132) (Ensembl accession no. ENSVPAP00000009804, which is hereby incorporated by reference in its entirety):

```
111                                                        MAAGSITTLP
121 ALPEDGGSGA FPPGHFKDPK RLYCKNGGFF LRIHPDGRVD GVREKSDPHI KLQLQAEERG
181 VVSIKGVCAN RYLAMKEDGR LLASKCVTDE CFFFERLESN NYNTYRSRKY SSWYVALKRT
241 GQYKLGPKTG PGQKAILFLP MSAKS
```

Amino acid sequence of *Ovis aries* (sheep) FGF2 (SEQ ID NO: 133) (GenBank accession no. NP_001009769, which is hereby incorporated by reference in its entirety):

```
  1 MAAGSITTLP ALPEDGGSSA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGPKTG PGQKAILFLP MSAKS
```

Amino acid sequence of *Capreolus capreolus* (Western roe deer) FGF2 (partial amino acid sequence corresponding to human FGF2 residues 42 to 149)(SEQ ID NO: 134) (GenBank accession no. AAF73226, which is hereby incorporated by reference in its entirety):

```
  1 RIHPDGRVDG VREKSDPHIK LQLQAEERGV VSIKGVCANR YLAMKEDGRL LASKCVTDEC
 61 FFFERLESNN YNTYRSRKYS SWYVALKRTG QYKLGPKTGP GQKAILFL
```

Amino acid sequence of *Loxodonta africana* (elephant) FGF2 (partial amino acid sequence corresponding to human FGF2 residues 60 to 155) (SEQ ID NO: 135) (Ensembl accession no. ENSLAFP00000008249, which is hereby incorporated by reference in its entirety):

```
  1 VKLQLQAEER GVVSIKGVCA NRYLAMKEDG RLLASRCVTD ECFFFERLES NNYNTYRSRK
 61 YTSWYVALKR TGQYKLGSKT GPGQKAILFL PMSAKS
```

Amino acid sequence of *Sus scrofa* (pig) FGF2 (partial amino acid sequence corresponding to human FGF2 residues 36 to 155) (SEQ ID NO: 136) (GenBank accession no. CAE11791 and Ensembl accession no. ENSSSCP00000009695, which is hereby incorporated by reference in its entirety):

```
  1 NGGFFLRIHP DGRVDGVREK SDPHIKLQLQ AEERGVVSIK GVCANRYLAM KEDGRLLASK
 61 CVTDECFFFE RLESNNYNTY RSRKYSSWYV ALKRTGQYKL GPKTGPGQKA ILFLPMSAKS
```

TABLE 3-continued

Amino acid sequence of *Ailuropoda melanoleuca* (panda) FGF2 (partial amino acid sequence corresponding to human FGF2 residues 60 to 155) (SEQ ID NO: 137) (Ensembl accession no. ENSAMEP00000018489, which is hereby incorporated by reference in its entirety):

```
  1 VKLQLQAEER GVVSIKGVCA NRYLAMKEDG RLLASKCVTD ECFFFERLES NNYNTYRSRK
 61 YSSWYVALKR TGQYKLGPKT GPGQKAILFL PMSAKS
```

Amino acid sequence of *Choloepus hoffmanni* (sloth) FGF2 (SEQ ID NO: 138) (Ensembl accession no. ENSCHOP00000010051, which is hereby incorporated by reference in its entirety):

```
 14                                                        MAAGSIT
 21 TLPALPEDGG SGALPPGHFK DPKRLYCKNG GFFLRIHPDG RVDGVREKSD PHIKLQLQAE
 81 ERGVVSIKGV CANRYLAMKE DGRLQASKCV TDECFFFERL ESNNYNTYRS RKYSSWYVAL
141 KRTGQYKLGP KTGPGQKAIL FLPMSAKS
```

Amino acid sequence of *Bubalus bubalis* (water buffalo) FGF2 (SEQ ID NO: 139) (GenBank accession no. AFH66795, which is hereby incorporated by reference in its entirety):

```
  1 MAAGSITTLP PLPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESS NYNTYRSRKY
121 SSWYVALKRT GQYKLGPKTG PGQKAILFLP MSAKS
```

Amino acid sequence of *Canis lupus familiaris* (dog) FGF2 (SEQ ID NO: 140) (GenBank accession no. XP_003432529, which is hereby incorporated by reference in its entirety):

```
 40                                          M AAGSITTLPA LPEDGGSGAF
 61 PPGHFKDPKR LYCKKGGFFL RIHPDGRVDG VREKSDPHVK LQLQAEERGV SIKGVCANR
121 YLAMKEDGRL LASKCVTDEC FFFERLESNN YNTYRSRKYS SWYVALKRTG QYKLGPKTGP
181 GQKAILFLPM SAKS
```

Amino acid sequence of *Rattus norvegicus* (Norway rat) FGF2 (SEQ ID NO: 141) (GenBank accession no. NP_062178, which is hereby incorporated by reference in its entirety):

```
  1 MAAGSITSLP ALPEDGGGAF PPGHFKDPKR LYCKNGGFFL RIHPDGRVDG VREKSDPHVK
 61 LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

Amino acid sequence of *Heterocephalus glaber* (naked mole-rat) FGF2 (partial amino acid sequence corresponding to human FGF2 residues 22 to 155) (SEQ ID NO: 142) (GenBank accession no. EHB17407, which is hereby incorporated by reference in its entirety):

```
  1 ppghfkdpkr lycknggffl rihpdgrvdg vreksdphvk lqlqaeergv vsikgvcanr
 61 ylamkedgrl laskcvtdec ffferlesnn yntyrsrkys swyvalkrtg qyklgsktgp
121 gqkailflpm saks
```

Amino acid sequence of *Otolemur garnettii* (bushbaby) FGF2 (SEQ ID NO: 143) (Ensembl accession no. ENSOGAP00000021960, which is hereby incorporated by reference in its entirety):

```
 52                                                       MAAGSITTL
 61 PSLPEDGGSD AFPPGHFKDP KRLYCKNGGF FLRIHPDGRV DGVREKSDPY IKLQLQAEER
121 GVVSIKGVCA NRYLAMKEDG RLLASKLITD ECFFFERLES NNYNTYRSRK YSSWYVALKR
181 TGQYKLGSKT GPGQKAILFL PMSAKS
```

Amino acid sequence of *Mus musculus* (house mouse) FGF2 (SEQ ID NO: 144) (GenBank accession no. NP_032032, which is hereby incorporated by reference in its entirety):

```
  1 MAAGSITSLP ALPEDGGAAF PPGHFKDPKR LYCKNGGFFL RIHPDGRVDG VREKSDPHVK
 61 LQLQAEERGV VSIKGVCANR YLAMKEDGRL LASKCVTEEC FFFERLESNN YNTYRSRKYS
121 SWYVALKRTG QYKLGSKTGP GQKAILFLPM SAKS
```

Amino acid sequence of *Ictidomys tridecemlineatus* (squirrel) FGF2 (partial amino acid sequence corresponding to human FGF2 residues 12 to 155) (SEQ ID NO: 145) (Ensembl accession no. ENSSTOP00000015653, which is hereby incorporated by reference in its entirety):

```
  1 LPEDGGGAF PPGHFKDPKR LYCKNGGFFL RIHPDGRVDG VREKSDPHIK LQLQAEDRGV
 61 VSIKGVCANR YLAMKEDGRL LASKCVTDEC FFFERLESNN YNTYRSRKYS SWYVALKRTG
121 QYKLGSKTGP GQKAILFLPM SAKS
```

TABLE 3-continued

Amino acid sequence of *Felis catus* (domestic cat) FGF2 (partial
amino acid sequence corresponding to human FGF2 residues 25 to 130)
(SEQ ID NO: 146) (GenBank accession no. ABY47638, which is
hereby incorporated by reference in its entirety):

```
  1 HFKDPKRLYC KNGGFFLRIH PDGRVDGVRE KSDPHIKLQL QAEERGVVSI KGVCANRYLA
 61 MKEDGRLLAS KCVTDECFFF ERLESNNYNT YRSRKYSSWY VALKRT
```

Amino acid sequence of *Cavia porcellus* (guinea pig) FGF2 (partial
amino acid sequence corresponding to human FGF2 residues 60 to 155)
(SEQ ID NO: 147) (Ensembl accession no. ENSCPOP00000004847, which is
hereby incorporated by reference in its entirety):

```
  1 VKLQLQAEDR GVVSIKGVCA NRYLAMKEDG RLLASKCVTD ECFFFERLES NNYNTYRSRK
 61 YSSWYVALKR TGQYKLGSKT GPGQKAILFL PMSAKS
```

Amino acid sequence of *Sarcophilus harrisii* (Tasmanian devil) FGF2
(SEQ ID NO: 148) (Ensembl accession no. ENSSHAP00000012215, which is
hereby incorporated by reference in its entirety):

```
 48                                                     MAA GSITTLPALA
 61 GDGASGGAFP PGHFQDPKRL YCKNGGFFLR IHPDGHVDGI REKSDPHIKL QLQAEERGVV
121 SIKGVCANRY LAMKEDGRLL ALKCVTEECF FFERLESNNY NTYRSRKYSN WYVALKRTGQ
181 YKLGSKTGPG QKAILFLPMS AKS
```

Amino acid sequence of *Monodelphis domestica* (gray short-tailed
opossum) FGF2 (SEQ ID NO: 149) (GenBank accession no. NP_001029148,
which is hereby incorporated by reference in its entirety):

```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFL PMSAKS
```

Amino acid sequence of *Oryctolagus cuniculus* (rabbit) FGF2 (SEQ ID
NO: 150) (GenBank accession no. XP_002717284, which is hereby
incorporated by reference in its entirety):

```
  1 MAAESITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 SSWYVALKRT GQYKLGSKTG PGQKAILFLP MSAKS
```

Amino acid sequence of *Meleagris gallopavo* (turkey) FGF2 (partial
amino acid sequence corresponding to human FGF2 residues 31 to 155)
(SEQ ID NO: 151) (Ensembl accession no. ENSMGAP00000010977, which is
hereby incorporated by reference in its entirety):

```
  1 RLYCKNGGFF LRINPDGRVD GVREKSDPHI KLQLQAEERG VVSIKGVSAN RFLAMKEDGR
 61 LLALKCATEE CFFFERLESN NYNTYRSRKY SDWYVALKRT GQYKPGPKTG PGQKAILFLP
121 MSAKS
```

Amino acid sequence of *Gallus gallus* (chicken) FGF2 (SEQ ID NO: 152)
(GenBank accession no. NP_990764

```
  1 maagaagsit tlpalpddgg ggafppghfk dpkrlyckng gfflrinpdg rvdgvreksd
 61 PHIKLQLQAE ERGVVSIKGV SANRFLAMKE DGRLLALKCA TEECFFFERL ESNNYNTYRS
121 RKYSDWYVAL KRTGQYKPGP KTGPGQKAIL FLPMSAKS
```

Amino acid sequence of *Taeniopygia guttata* (zebra finch) FGF2
(SEQ ID NO: 153) (GenBank accession no. XP_002188397,
which is hereby incorporated by reference in its entirety):

```
  1 MAAAGGIATL PDGGSGAFP PGHFKDPKRL YCKNGGFFLR INPDGKVDGV REKSDPHIKL
 61 QLQAEERGVV SIKGVSANRF LAMKEDGRLL ALKYATEECF FFERLESNNY NTYRSRKYSD
121 WYVALKRTGQ YKPGPKTGPG QKAILFLPMS AKS
```

Amino acid sequence of *Cynops pyrrhogaster* (Japanese firebelly newt)
FGF2 (SEQ ID NO: 154) (GenBank accession no. BAB63249, which
is hereby incorporated by reference in its entirety):

```
  1 MAAGSITSLP ALPEDGNGGT FTPGGFKEPK RLYCKNGGFF LRINSDGKVD GAREKSDSYI
 61 KLQLQAEERG VVSIKGVCAN RYLAMKDDGR LMALKWITDE CFFFERLESN NYNTYRSRKY
121 SDWYVALKRT GQYKNGSKTG AGQKAILFLP MSAKS
```

TABLE 3-continued

Amino acid sequence of *Xenopus laevis* (African clawed frog) FGF2
(SEQ ID NO: 155) (GenBank accession no. NP_001093341,
which is hereby incorporated by reference in its entirety):

```
  1 MAAGSITTLP TESEDGGNTP FSPGSFKDPK RLYCKNGGFF LRINSDGRVD GSRDKSDSHI
 61 KLQLQAVERG VVSIKGITAN RYLAMKEDGR LTSLRCITDE CFFFERLEAN NYNTYRSRKY
121 SSWYVALKRT GQYKNGSSTG PGQKAILFLP MSAKS
```

Amino acid sequence of *Didelphis albiventris* (white-eared opossum)
FGF2 (SEQ ID NO: 156) (GenBank accession no. ABL77404,
which is hereby incorporated by reference in its entirety):

```
  1 MAAGSITTLP ALSGDGGGGG AFPPGHFKDP KRLYCKNGGF FLRIHPDGRV DGIREKSDPN
 61 IKLQLQAEER GVVSIKGVCA NRYLAMKEDG RLLALKYVTE ECFFFERLES NNYNTYRSRK
121 YSNWYVALKR TGQYKLGSKT GPGQKAILFS PCLLRC
```

Amino acid sequence of *Myotis lucifugus* (microbat) FGF2 (partial
amino acid sequence corresponding to human FGF2 residues 60
to 155) (SEQ ID NO: 157) (Ensembl accession no. ENSMLUP00000017859,
which is hereby incorporated by reference in its entirety):

```
  1 VKLQLQAEER GVVSIKGVCA NRYLAMKEDG RLQASKCVTD ECFFFERLES NNYNTYRSRK
 61 YSSWYVALKR NGQYKLGPKT GPGQKAILFL PMSAKS
```

Amino acid sequence of *Anolis carolinensis* (anole lizard) FGF2
(partial amino acid sequence corresponding to human FGF2 residues 16
to 155) (SEQ ID NO: 158) (Ensembl accession no. ENSACAP00000011657,
which is hereby incorporated by reference in its entirety):

```
  1 AAAASFPPGP FKDPKRLYCK NGGFFLRINP DGGVDGVREK SDPNIKLLLQ AEERGVVSIK
 61 GVCANRFLAM NEDGRLLALK YVTDECFFFE RLESNNYNTY RSRKYRDWYI ALKRTGQYKL
121 GPKTGRGQKA ILFLPMSAKS
```

Amino acid sequence of *Dasypus novemcinctus* (armadillo) FGF2
(partial amino acid sequence corresponding to human FGF2 residues
1 to 94) (SEQ ID NO: 159) (Ensembl accession no. ENSDNOP00000011351,
which is hereby incorporated by reference in its entirety):

```
124     MAAGSIT TLPALPEDGG SGAFPPGHFK DPKRLYCKNG GFFLRIHPDG RVDGVREKSD
181 PNIKLQLQAE ERGVVSIKGV CANRYLAMRE DGRLQAS
```

Amino acid sequence of *Tupaia belangeri* (tree shrew) FGF2 (SEQ ID
NO: 160) (Ensembl accession no. ENSTBEP00000000985, which is hereby
incorporated by reference in its entirety):

```
  1 AGVRAEREEA PGSGDSRGTD PAARSLIRRP DAAAREALLG ARSRVQGSST SWPASSRTGI
 61 KLPDDSGQGM GGYPLDRPSR STGRGLGGAP DPAVKLQLQA EERGVVSIKG VCANRYLAMK
121 EDGRLLASKC VTDECFFFER LESNNYNTYR SRKYSSWYVA LKRTGQYKLG SKTGPGQKAI
181 LFLPMSAKS
```

Amino acid sequence of *Xenopus silurana tropicalis* (western clawed
frog) FGF2 (SEQ ID NO: 161) (GenBank accession no. NP_001017333,
which is hereby incorporated by reference in its entirety):

```
  1 MAAGSITTLP TESEDGNTPF PPGNFKDPKR LYCKNGGYFL RINSDGRVDG SRDKSDLHIK
 61 LQLQAVERGV VSIKGITANR YLAMKEDGRL TSLKCITDEC FFYERLEANN YNTYRSRKNN
121 SWYVALKRTG QYKNGSTTGP GQKAILFLPM SAKS
```

Amino acid sequence of *Latimeria chalumnae* (coelacanth) FGF2 (SEQ ID
NO: 162) (Ensembl accession no. ENSLACP00000019200, which is hereby
incorporated by reference in its entirety):

```
  1 MAAGGITTLP AVPEDGGSST FPPGNFKEPK RLYCKNGGYF LRINPDGRVD GTREKNDPYI
 61 KLQLQAESIG VVSIKGVCSN RYLAMNEDCR LFGLKYPTDE CFFHERLESN NYNTYRSKKY
121 SDWYVALKRT GQYKPGPKTG LGQKAILFLP MSAKS
```

Amino acid sequence of *Tetraodon nigroviridis* (spotted green
pufferfish) FGF2 (SEQ ID NO: 163) (GenBank accession no. CAG04681,
which is hereby incorporated by reference in its entirety):

```
 34                                    MATGGIT TLPSTPEDGG SSGFPPGSFK
 61 DPKRLYCKNG GFFLRIKSDG VVDGIREKSD PHIKLQLQAT SVGEVVIKGV CANRYLAMNR
121 DGRLFGTKRA TDECHFLERL ESNNYNTYRS RKYPTMFVGL TRTGQYKSGS KTGPGQKAIL
181 FLPMSAKC
```

TABLE 3-continued

Amino acid sequence of *Gasterosteus aculeatus* (stickleback) FGF2
(SEQ ID NO: 164) (Ensembl accession no. ENSGACP00000022078,
which is hereby incorporated by reference in its entirety):

```
  1 MATAGFATLP STPEDGGSGG FTPGGFKDPK RLYCKNGGFF LRIRSDGGVD GIREKSDAHI
 61 KLQIQATSVG EVVIKGVCAN RYLAMNRDGR LFGVRRATDE CYFLERLESN NYNTYRSRKY
121 PGMYVALKRT GQYKSGSKTG PGQKAILFLP MSAKC
```

Amino acid sequence of *Takifugu rubripes* (fugu rubripes) FGF2
(SEQ ID NO: 165) (GenBank accession no. CAD19830, which is
hereby incorporated by reference in its entirety):

```
  1 MATGGITTLP STPEDGGSGG FPPGSFKDPK RLYCKNGGFF LRIRSDGAVD GTREKTDPHI
 61 KLQLQATSVG EVVIKGVCAN RYLAMNRDGR LFGMKRATDE CHFLERLESN NYNTYRSRKY
121 PNMFVGLTRT GNYKSGTKTG PCQKAILFLP MSAKY
```

Amino acid sequence of *Oncorhynchus mykiss* (rainbow trout) FGF2 (SEQ
ID NO: 166) (GenBank accession no. NP_001118008, which is hereby
incorporated by reference in its entirety):

```
  1 MATGEITTLP ATPEDGGSGG FLPGNFKEPK RLYCKNGGYF LRINSNGSVD GIRDKNDPHN
 61 KLQLQATSVG EVVIKGVSAN RYLAMNADGR LFGPRRTTDE CYFMERLESN NYNTYRSRKY
121 PEMYVALKRT GQYKSGSKTG PGQKAILFLP MSARR
```

Amino acid sequence of *Salmo salar* (salmon) FGF2 (SEQ ID NO: 167)
(GenBank accession no. ACJ02099, which is hereby incorporated by
reference in its entirety):

```
  1 MATGEITTLP ATPEDGGSGG FPPGNFKDPK RLYCKNGGYF LRINSNGSVD GIREKNDPHK
 61 QPQFVRAWTL QGVKRSTGML AHVDSNASHN CVKVAGCSLG EFGSMSNRPH NRRPRVATPA
121 QDLHIRLLHL RDRLKPATRT ADKTEEYFCL
```

Amino acid sequence of *Danio rerio* (zebrafish) FGF2 (SEQ ID NO: 168)
(GenBank accession no. AAP32155, which is hereby incorporated by
reference in its entirety):

```
  1 MATGGITTLP AAPDAENSSF PAGSFRDPKR LYCKNGGFFL RINADGRVDG ARDKSDPHIR
 61 LQLQATAVGE VLIKGICTNR FLAMNADGRL FGTKRTTDEC YFLERLESNN YNTYRSRKYP
121 DWYVALKRTG QYKSGSKTSP GQKAILFLPM SAKC
```

Amino acid sequence of *Oreochromis niloticus* (Nile tilapia) FGF2
(SEQ ID NO: 169) (GenBank accession no. XP_003443412,
which is hereby incorporated by reference in its entirety):

```
  1 MATGGITTLP ATPEDGGSSG FPPGNFKDPK RLYCKNGGFF LRIKSDGGVD GIREKNDPHI
 61 KLQLQATSVG EVVIKGICAN RYLAMNRDGR LFGARRATDE CYFLERLESN NYNTYRSRKY
121 PNMYVALKRT GQYKSGSKTG PGQKAILFLP MSAKC
```

Amino acid sequence of *Oryzias latipes* (medaka) FGF2 (SEQ ID
NO: 170) (Ensembl accession no. ENSORLP00000025834,
which is hereby incorporated by reference in its entirety):

```
  1 MATGEITTLP SPAENSRSDG FPPGNYKDPK RLYCKNGGLF LRIKPDGGVD GIREKKDPHV
 61 KLRLQATSAG EVVIKGVCSN RYLAMHGDGR LFGVRQATEE CYFLERLESN NYNTYRSKKY
121 PNMYVALKRT GQYKPGNKTG PGQKAILFLP MSAKY
```

As noted above, the portion of the paracrine FGF may be modified to decrease binding affinity for heparin and/or heparan sulfate compared to the portion without the modification. In one embodiment, the modification of the paracrine FGF includes one or more substitutions, additions, or deletions.

In one embodiment, the modification is one or more substitutions located at one or more amino acid residues of SEQ ID NO: 121 selected from N36, K128, R129, K134, K138, Q143, K144, C78, C96, and combinations thereof. In one embodiment, the one or more substitutions are selected from N36T, K128D, R129Q, K134V, K138H, Q143M, K144T/L/I, C78S, C96S, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. Amino acid residues corresponding to those of SEQ ID NO: 121 may be determined by, for example, sequence analysis and structural analysis.

It will be understood that the portion of the paracrine FGF according to the present invention may be derived from a nucleotide sequence that encodes a paracrine FGF protein. For example, in one embodiment, nucleotide sequence is the nucleotide sequence that encodes human FGF2 (GenBank Accession No. NM_002006, which is hereby incorporated by reference in its entirety) (SEQ ID NO: 171), as follows:

```
468                                          ATG GCAGCCGGGA
481  GCATCACCAC GCTGCCCGCC TTGCCCGAGG ATGGCGGCAG CGGCGCCTTC CCGCCCGGCC
541  ACTTCAAGGA CCCCAAGCGG CTGTACTGCA AAAACGGGGG CTTCTTCCTG CGCATCCACC
601  CCGACGGCCG AGTTGACGGG GTCCGGGAGA GAGCGACCC TCACATCAAG CTACAACTTC
661  AAGCAGAAGA GAGAGGAGTT GTGTCTATCA AAGGAGTGTG TGCTAACCGT TACCTGGCTA
721  TGAAGGAAGA TGGAAGATTA CTGGCTTCTA AATGTGTTAC GGATGAGTGT TTCTTTTTTG
781  AACGATTGGA ATCTAATAAC TACAATACTT ACCGGTCAAG GAAATACACC AGTTGGTATG
841  TGGCACTGAA ACGAACTGGG CAGTATAAAC TTGGATCCAA AACAGGACCT GGGCAGAAAG
901  CTATACTTTT TCTTCCAATG TCTGCTAAGA GCTGA
```

In another embodiment of the present invention, the portion of the paracrine FGF of the chimeric protein may be derived from a nucleotide sequence that encodes an ortholog of human FGF2. Nucleotide sequences that encode FGF2 orthologs are shown in Table 4.

TABLE 4

Gorilla FGF2 gene coding sequence (amino acids ("aa") 104-258) (SEQ ID NO: 172) (Ensembl accession no. ENSGGOT00000004842, which is hereby incorporated by reference in its entirety):

```
310               ATGGCAGCC GGGAGCATCA CCACGCTGCC CGCCTTGCCC GAGGATGGCG
359  GCAGCGGCGC CTTCCCGCCC GGCCACTTCA AGGACCCCAA GCGGCTGTAC TGCAAAAACG
419  GGGGCTTCTT CCTGCGCATC CACCCCGACG GCCGAGTTGA CGGGGTCCGG GAGAAGAGCG
479  ACCCTCACAT CAAGCTACAA CTTCAAGCAG AAGAGAGAGG AGTTGTGTCT ATCAAAGGAG
539  TGTGTGCTAA CCGTTACCTT GCTATGAAGG AAGATGGAAG ATTACTGGCT TCTAAATGTG
599  TTACGGATGA GTGTTTCTTT TTTGAACGAT TGGAATCTAA TAACTACAAT ACTTACCGGT
659  CAAGGAAATA CACCAGTTGG TATGTGGCAC TGAAACGAAC TGGGCAGTAT AAACTTGGAT
719  CCAAAACAGG ACCTGGGCAG AAAGCTATAC TTTTTCTTCC AATGTCTGCT AAGAGCTGA
```

Sumatran orangutan FGF2 gene coding sequence (aa 168-322) (SEQ ID NO: 173) (GenBank accession no. XM_002815126, which is hereby incorporated by reference in its entirety):

```
504                   ATGGCAG CCGGGAGCAT CACCACGCTG CCCGCCTTGC
541  CCGAGGATGG CGGCAGCGGC GCCTTCCCGC CGGGCCACTT CAAGGACCCC AAGCGGCTGT
601  ACTGCAAAAA CGGGGGCTTC TTCCTGCGCA TCCACCCCGA CGGCCGAGTT GACGGGGTCC
661  GAGAGAAGAG CGACCCTCAC ATCAAACTAC AACTTCAAGC AGAAGAAAGA GGAGTTGTGT
721  CTATCAAAGG AGTGTGTGCT AACCGCTACC TTGCTATGAA GGAAGATGGA AGATTACTGG
781  CTTCTAAATG TGTTACGGAT GAGTGTTTCT TTTTTGAACG ATTGGAATCT AATAACTACA
841  ATACTTACCG GTCAAGGAAA TACACCAGTT GGTATGTGGC ACTGAAACGA ACTGGGCAGT
901  ATAAACTTGG ATCCAAAACA GGACCTGGGC AGAAAGCTAT ACTTTTTCTT CCAATGTCTG
961  CTAAGAGCTG A
```

Rhesus monkey FGF2 gene coding sequence (aa 83-237) (SEQ ID NO: 174) (GenBank accession no. XM_001099284, which is hereby incorporated by reference in its entirety):

```
247         ATGG CAGCCGGGAG CATCACCACG CTGCCCGCCT TGCCCGAGGA TGGCGGCAGC
301  GGCGCCTTCC CGCCTGGCCA CTTCAAGGAC CCCAAGCGGC TGTACTGCAA AAACGGGGGC
361  TTCTTCCTGC GCATTCACCC CGACGGCCGA GTTGACGGGG TCCGGGAGAA GAGCGACCCT
421  CACATCAAAT TACAACTTCA AGCAGAAGAG AGAGGAGTTG TGTCTATCAA AGGAGTGTGT
481  GCTAACCGTT ACCTTGCTAT GAAGGAAGAT GGAAGATTAC TGGCTTCTAA ATGTGTTACA
541  GATGAGTGTT TCTTTTTTGA ACGATTGGAA TCTAATAACT ACAATACTTA CCGGTCAAGG
601  AAATACACCA GTTGGTATGT GGCACTGAAA CGAACTGGGC AATATAAACT TGGATCCAAA
661  ACAGGACCTG GCAGAAAGC TATACTTTTT CTTCCAATGT CTGCTAAGAG CTGA
```

Chimpanzee FGF2 gene coding sequence (aa 134-288) (SEQ ID NO: 175) (GenBank accession no. NM_001110241, which is hereby incorporated by reference in its entirety):

```
400                                        A TGGCAGCCGG GAGCATCACC
421  ACGCTGCCCG CCTTGCCCGA GGATGGCGGC AGCGGCGCCT TCCCGCCCGG CCACTTCAAG
481  GACCCCAAGC GGCTGTACTG CAAAAACGGG GGCTTCTTCC TGCGCATCCA CCCCGACGGC
541  CGAGTTGACG GGGTCCGGGA GAAGAGCGAC CCTCACATCA AGCTACAACT TCAAGCAGAA
601  GAGAGAGGAG TTGTGTCTAT CAAGGAGTG TGTGCTAACC GTTACCTTGC TATGAAGGAA
661  GATGGAAGAT TACTGGCTTC TAAATGTGTT ACGGATGAGT GTTTCTTTTT TGAACGATTG
721  GAATCTAATA ACTACAATAC TTACCGGTCA AGGAAATACA CCAGTTGGTA TGTGGCACTG
781  AAACGAACTG GGCAGTATAA ACTTGATCC AAAACAGGAC CTGGGCAGAA AGCTATACTT
841  TTTCTTCCAA TGTCTGCTAA GAGCTGA
```

TABLE 4-continued

Pygmy chimpanzee FGF2 gene coding sequence (112-266) (SEQ ID NO: 176)
(GenBank accession no. XM_003816433, which is hereby incorporated by
reference in its entirety):

```
334                                           ATGGCAG CCGGGAGCAT CACCACGCTG
361 CCCGCCTTGC CCGAGGATGG CGGCAGCGGC GCCTTCCCGC CCGGCCACTT CAAGGACCCC
421 AAGCGGCTGT ACTGCAAAAA CGGGGGCTTC TTCCTGCGCA TCCACCCCGA CGGCCGAGTT
481 GACGGGGTCC GGGAGAAGAG CGACCCTCAC ATCAAGCTAC AACTTCAAGC AGAAGAGAGA
541 GGAGTTGTGT CTATCAAAGG AGTGTGTGCT AACCGTTACC TTGCTATGAA GGAAGATGGA
601 AGATTACTGG CTTCTAAATG TGTTACGGAT GAGTGTTTCT TTTTTGAACG ATTGGAATCT
661 AATAACTACA ATACTTACCG GTCAAGGAAA TACACCAGTT GGTATGTGGC ACTGAAACGA
721 ACTGGGCAGT ATAAACTTGG ATCCAAAACA GGACCTGGGC AGAAAGCTAT ACTTTTTCTT
781 CCAATGTCTG CTAAGAGCTG A
```

Bolivian squirrel monkey FGF2 gene coding sequence (1-155)
(SEQ ID NO: 177) (GenBank accession no. XM_003936241,
which is hereby incorporated by reference in its entirety):

```
 23                          ATGGCAGC CGGGAGCATC ACCACGCTGC CCGCCCTGCC
 61 CGAAGACGGC GGCAGCGGCG CCTTCCCGCC CGGCCACTTC AAAGACCCCA AGCGGCTGTA
121 CTGCAAAAAC GGGGGCTTCT TCCTGCGAAT CCACCCCGAC GGCCGAGTGG ACGGGGTCCG
181 GGAGAAGAGC GACCCTCACA TCAAACTACA ACTTCAAGCA AGAGAGAGAG GAGTTGTATC
241 TATCAAAGGA GTGTGTGCTA ACCGTTACCT TGCTATGAAG GAAGATGGAA GATTACTGGC
301 TTCTAAATGT GTTACGGACG AGTGTTTCTT TTTTGAACGA TTGGAATCTA ATAACTACAA
361 TACTTACCGA TCAAGGAAAT ACACCAGTTG GTATGTGGCA CTGAAACGAA CTGGGCAGTA
421 TAAACTTGGA TCCAAAACAG GACCTGGGCA GAAAGCTATA CTTTTTCTTC CAATGTCTGC
481 TAAGAGCTGA
```

Northern white-cheeked gibbon FGF2 gene coding sequence (aa 1-155)
(SEQ ID NO: 178) (GenBank accession no. XM_003271356, which is
hereby incorporated by reference in its entirety):

```
435                                              ATG GCAGCCGGGA
481 GCATCACCAC GCTGCCCGCC TTGCCGGAGG ATGGCGGCAG CGGCGCCTTC CCGCCCGGCC
541 ACTTCAAGGA CCCCAAGCGG CTGTACTGCA AAAACGGGGG TTTCTTCCTG CGCATCCACC
601 CCGACGGTCG AGTTGACGGG GTCCGGGAGA AGAGCGACCC TCACATCAAA CTACAACTTC
661 AAGCAGAAGA GAGAGGAGTT GTGTCTATCA AAGGAGTGTG TGCTAACCGT TACCTTGCTA
721 TGAAGGAAGA TGGAAGATTA CTGGCTTCTA AATGTGTTAC GGATGAGTGT TTCTTTTTTG
781 AACGATTGGA ATCTAATAAC TACAATACTT ACCGGTCAAG GAAATACACC AGTTGGTATG
841 TGGCACTGAA ACGAACTGGG CAGTATAAAC TTGGATCCAA AACAGGACCT GGGCAGAAAG
901 CTATACTTTT TCTTCCAATG TCTGCTAAGA GCTGA
```

Horse FGF2 gene coding sequence (aa 1-155) (SEQ ID NO: 179) (GenBank
accession no. NM_001195221, which is hereby incorporated by reference in
its entirety):

```
 54                                                         ATGGCAG
 61 CCGGGAGCAT CACCACGCTG CCCGCCCTGC CGAGGACGG CGGCAGCGGC GCCTTCCCGC
121 CCGGCCACTT CAAGGACCCC AAGCGGCTCT ACTGCAAAAA CGGGGGCTTC TTCCTGCGCA
181 TCCACCCCGA CGGCCGAGTG GACGGGGTCC GGGAGAAGAG CGACCCTCAC ATCAAACTAC
241 AACTTCAAGC AGAAGAGAGA GGGGTTGTGT CTATCAAAGG AGTGTGTGCG AACCGTTATC
301 TTGCTATGAA GGAAGATGGA AGGTTACTGG CTTCTAAATG TGTTACGGAC GAGTGTTTCT
361 TTTTTGAACG ATTGGAATCT AATAACTACA ATACTTACCG GTCAAGGAAA TACTCCAGTT
421 GGTATGTGGC CCTGAAACGA ACGGGGCAGT ATAAACTTGG ACCCAAAACA GGACCTGGAC
481 AGAAAGCTAT ACTTTTTCTT CCAATGTCTG CTAAGAGCTG A
```

Cattle FGF2 gene coding sequence (aa 1-155) (SEQ ID NO: 180) (GenBank
accession no. NM_174056, which is hereby incorporated by reference
in its entirety):

```
104                                            ATGGCCG CCGGGAGCAT
121 CACCACGCTG CCAGCCCTGC CGGAGGACGG CGGCAGCGGC GCTTTCCCGC CGGGCCACTT
181 CAAGGACCCC AAGCGGCTGT ACTGCAAGAA CGGGGGCTTC TTCCTGCGCA TCCACCCCGA
241 CGGCCGAGTG GACGGGGTCC GCGAGAAGAG CGACCCACAC ATCAAACTAC AACTTCAAGC
301 AGAAGAGAGA GGGGTTGTGT CTATCAAAGG AGTGTGTGCA AACCGTTACC TTGCTATGAA
361 AGAAGATGGA AGATTACTAC CTTCTAAATG TGTTACAGAC GAGTGTTTCT TTTTTGAACG
421 ATTGGAGTCT AATAACTACA ATACTTACCG GTCAAGGAAA TACTCCAGTT GGTATGTGGC
481 ACTGAAACGA ACTGGGCAGT ATAAACTTGG ACCCAAAACA GGACCTGGGC AGAAAGCTAT
541 ACTTTTTCTT CCAATGTCTG CTAAGAGCTG A
```

Olive baboon FGF2 gene coding sequence (1-155) (SEQ ID NO: 181) (GenBank
accession no. XM_003899161, which is hereby incorporated by reference in
its entirety):

```
467                                                ATGG CAGCCGGGAG
481 CATCACCACG CTGCCCGCCT TGCCCGAGGA TGGCGGCAGC GGCGCCTTCC CGCCCGGCCA
541 CTTCAAGGAC CCCAAGCGGC TGTACTGCAA AAACGGGGGC TTCTTCCTGC GCATTCACCC
601 CGACGGCCGA GTTGACGGG TCCGGGAGAA GAGCGACCCT CACATCAAAT ACAACTTCA
661 AGCAGAAGAG AGAGGAGTTG TGTCTATCAA AGGAGTGTGT GCTAACCGTT ACCTTGCTAT
```

TABLE 4-continued

```
721  GAAGGAAGAT GGAAGATTAC TGGCTTCTAA ATGTGTTACG GATGAGTGTT TCTTTTTTGA
781  ACGATTGGAA TCTAATAACT ACAATACTTA CCGGTCAAGG AAATACACCA GTTGGTATGT
841  GGCACTGAAA CGAACTGGGC AGTATAAACT TGGATCCAAA ACAGGACCTG GGCAGAAAGC
901  TATACTTTTT CTTCCAATGT CTGCTAAGAG CTGA
```

Alpaca FGF2 gene coding sequence (aa 111-265) (SEQ ID NO: 182) (Ensembl accession no. ENSVPAT00000010536, which is hereby incorporated by reference in its entirety):

```
341                                 ATGGCAGCTG GGAGCATCAC CACGCTGCCC
361  GCCCTGCCGG AGGACGGCGG CAGCGGCGCC TTCCCGCCCG GCCACTTCAA GGACCCCAAG
421  CGGTTGTACT GCAAAAACGG GGGCTTCTTC CTGCGCATCC ACCCCGACGG CCGAGTGGAC
481  GGGGTCCGGG AGAAGAGCGA CCCTCACATC AAACTACAAC TTCAAGCAGA AGAGAGAGGG
541  GTCGTGTCTA TCAAAGGAGT GTGTGCAAAC CGTTACCTTG CTATGAAGGA AGATGGAAGA
601  TTACTGGCTT CTAAATGTGT CACAGACGAG TGTTTCTTTT TTGAACGATT GGAATCTAAT
661  AACTACAATA CTTACCGGTC AAGGAAATAC TCCAGTTGGT ATGTGGCACT GAAACGAACT
721  GGGCAGTACA AACTTGGACC CAAAACAGGA CCTGGGCAGA AAGCTATACT TTTCCTTCCA
781  ATGTCTGCTA AGAGCTGA
```

Sheep FGF2 gene coding sequence (aa 1-155) (SEQ ID NO: 183) (GenBank accession no. NM_001009769, which is hereby incorporated by reference in its entirety):

```
  1  ATGGCCGCCG GGAGCATCAC CACGCTGCCA GCCCTGCCGG AGGACGGCGG CAGCAGCGCT
 61  TTCCCGCCCG GCCACTTTAA GGACCCCAAG CGGCTGTACT GCAAGAACGG GGGCTTCTTC
121  CTGCGCATCC ACCCCGACGG CCGAGTGGAC GGGGTCCGCG AGAAGAGCGA CCCTCACATC
181  AAACTACAAC TTCAAGCAGA AGAGAGAGGG GTTGTGTCTA TCAAAGGAGT GTGTGCAAAC
241  CGTTACCTTG CTATGAAAGA AGATGGAAGA TTACTAGCTT CTAAATGTGT TACAGACGAG
301  TGTTTCTTTT TTGAACGATT GGAGTCTAAT AACTACAACA CTTACCGGTC AAGGAAATAC
361  TCCAGTTGGT ATGTGGCACT GAAACGAACT GGGCAGTATA AACTTGGACC CAAAACAGGA
421  CCTGGGCAGA AAGCTATACT TTTTCTTCCA ATGTCTGCTA AGAGCTGA
```

Western roe deer FGF2 gene coding sequence (1-108; partial amino acid sequence corresponding to human FGF2 residues 42 to 149) (SEQ ID NO: 184) (GenBank accession no. AF152587, which is hereby incorporated by reference in its entirety):

```
  1  GCGCATCCAC CCCGACGGCC GAGTGGACGG GGTCCGCGAG AAGAGTGACC CTCACATCAA
 61  ACTACAACTT CAAGCAGAAG AGAGGGGT TGTGTCTATC AAAGGAGTGT GTGCGAACCG
121  TTATCTTGCT ATGAAAGAAG ACGGAAGATT ATTGGCTTCA AATGTGTTA CAGACGAATG
181  TTTCTTTTTT GAACGATTGG AGTCTAATAA CTACAATACT TACCGGTCAA GGAAATACTC
241  CAGTTGGTAT GTGGCACTGA ACGAACTGG GCAGTATAAA CTTGGACCCA AACAGGACC
301  TGGGCAGAAA GCTATACTTT TTCTT
```

Elephant FGF2 gene coding sequence (1-96; partial amino acid sequence corresponding to human FGF2 residues 60 to 155) (SEQ ID NO: 185) (Ensembl accession no. ENSLAFT00000008249, which is hereby incorporated by reference in its entirety):

```
  1  GTTAAACTAC AGCTTCAAGC AGAAGAGAGA GGTGTTGTGT CTATCAAAGG AGTGTGTGCC
 61  AACCGTTATC TGGCTATGAA GGAAGATGGA AGATTGCTGG CTTCTAGATG TGTGACAGAT
121  GAATGTTTCT TCTTTGAACG ACTGGAATCT AATAACTACA ATACTTACCG GTCAAGGAAA
181  TACACCAGTT GGTATGTGGC ACTGAAACGA ACGGGGCAGT ATAAACTTGG ATCCAAAACA
241  GGACCTGGAC AGAAAGCTAT ACTTTTTCTT CCCATGTCTG CTAAGAGC
```

Pig FGF2 gene coding sequence (1-120; partial amino acid sequence corresponding to human FGF2 residues 36 to 155) (SEQ ID NO: 186) (GenBank accession no. AJ577089 and Ensembl accession no. ENSSSCT00000009952, which is hereby incorporated by reference in its entirety):

```
  1  GAACGGGGGC TTCTTCCTGC GCATCCACCC CGACGGCCGA GTGGATGGGG TCCGGGAGAA
 61  GAGCGACCCT CACATCAAAC TACAACTTCA AGCAGAAGAG AGAGGGGTTG TGTCTATCAA
121  AGGAGTGTGT GCAAACCGTT ATCTTGCTAT GAAGGAAGAT GGAAGATTAC TGGCTTCTAA
181  ATGTGTTACA GACGAGTGTT TCTTTTTTGA ACGACTGGAA TCTAATAACT ACAATACTTA
241  CCGGTCGAGG AAATACTCCA GTTGGTATGT GGCACTGAAA CGAACTGGGC AGTATAAACT
301  TGGACCCAAA ACAGGACCTG GGCAGAAAGC TATACTTTTT CTTCCAATGT CTGCTAAGAG
361  C
```

Panda FGF2 gene coding sequence (1-96; partial amino acid sequence corresponding to human FGF2 residues 60 to 155) (SEQ ID NO: 187) (Ensembl accession no. ENSAMET00000019232, which is hereby incorporated by reference in its entirety):

```
  1  GTCAAACTGC AACTTCAAGC GGAAGAGAGA GGGGTTGTAT CCATCAAAGG AGTATGTGCA
 61  AATCGCTATC TTGCCATGAA GGAAGATGGA AGATTACTGG CTTCTAAATG TGTTACCGAT
121  GAGTGTTTCT TTTTTGAGCG ACTGGAATCT AATAACTACA ATACTTACCG GTCAAGGAAA
181  TACTCCAGTT GGTATGTGGC ACTGAAACGA ACTGGGCAGT ATAAACTTGG ACCCAAAACA
241  GGACCTGGGC AGAAAGCTAT ACTTTTTCTT CCAATGTCTG CTAAGAGC
```

TABLE 4-continued

Sloth FGF2 gene coding sequence (aa 14-168) (SEQ ID NO: 188) (Ensembl accession no. ENSCHOT00000011394, which is hereby incorporated by reference in its entirety):

```
 40                                          A TGGCAGCCGG GAGCATCACC
 61 ACGCTGCCCG CCCTGCCCGA GGACGGAGGC AGCGGCGCCT TACCGCCCGG CCACTTCAAA
121 GATCCCAAGC GGCTCTACTG CAAAAACGGG GGCTTCTTCC TGCGTATCCA TCCCGACGGC
181 AGAGTGGACG GGGTCCGGGA GAAGAGCGAC CCCCACATCA AACTACAACT TCAAGCAGAA
241 GAGAGAGGGG TTGTGTCTAT CAAAGGTGTG TGTGCAAACC GATATCTTGC TATGAAGGAA
301 GATGGAAGAT TACAGGCTTC TAAATGTGTA ACGGACGAGT GTTTCTTTTT TGAACGATTG
361 GAATCTAATA ACTACAATAC GTACCGATCA AGGAAATACT CCAGTTGGTA TGTGGCACTG
421 AAACGAACTG GGCAATATAA ACTTGGACCC AAAACAGGAC CTGGGCAGAA AGCCATACTT
481 TTTCTTCCAA TGTCTGCTAA GAGCTGA
```

Water buffalo FGF2 gene coding sequence (aa 1-155) (SEQ ID NO: 189) (GenBank accession no. JQ326277, which is hereby incorporated by reference in its entirety):

```
  1 ATGGCCGCCG GGAGCATCAC CACGCTGCCA CCCCTGCCGG AGGACGGCGG CAGCGGCGCT
 61 TTCCCGCCCG GCCACTTCAA GGACCCCAAG CGGCTGTACT GCAAGAACGG GGGCTTCTTC
121 CTGCGCATCC ACCCCGACGG CCGAGTGGAC GGGGTCCGGA AGAAGAGCGA CCCCACACTA
181 AAACTACAAC TTCAAGCAGA AGAGAGAGGG GTTGTGTCTA TCAAAGGAGT GTGTGCAAAC
241 CGTTACCTTG CTATGAAAGA AGATGGAAGA TTACTAGCTT CCAAATGTGT TACAGACGAG
301 TGTTTCTTTT TTGAACGATT GGAGTCTAGT AACTACAATA CTTACCGGTC AAGGAAATAC
361 TCCAGTTGGT ATGTGGCACT GAAACGAACT GGGCAGTATA ACTTGGACC CAAAACAGGA
421 CCTGGGCAGA AAGCTATACT TTTTCTTCCA ATGTCTGCTA AGAGCTGA
```

Dog FGF2 gene coding sequence (aa 40-194) (SEQ ID NO: 190) (GenBank accession no. XM_003432481, which is hereby incorporated by reference in its entirety):

```
118                                                                ATG
121 GCAGCCGGGA GCATCACCAC GCTGCCCGCC CTGCCGGAGG ACGGCGGCAG CGGCGCCTTC
181 CCGCCCGGCC ACTTCAAGGA CCCCAAGAGG CTGTACTGCA AAAAGGGGG CTTCTTCCTG
241 CGGATCCACC CCGACGGCCG GGTGGACGGG GTCCGGGAGA GAGCGATCC CCACGTCAAA
301 TTGCAACTTC AAGCAGAAGA GAGAGGCGTT GTGTCCATCA AGGAGTATG TGCAAATCGC
361 TATCTTGCTA TGAAGGAAGA TGGAAGATTA CTGGCTTCTA AATGTGTTAC TGACGAGTGC
421 TTCTTTTTTG AACGATTGGA ATCTAATAAC TACAATATCT ACCGGTCAAG GAAATACTCC
481 AGTTGGTATG TGGCACTGAA ACGAACTGGG CAGTATAAAC TTGGACCAAA AACAGGACCT
541 GGGCAGAAAG CTATACTTTT TCTTCCAATG TCTGCTAAGA GCTGA
```

Norway rat FGF2 gene coding sequence (aa 1-154) (SEQ ID NO: 191) (GenBank accession no. NM_019305, which is hereby incorporated by reference in its entirety):

```
533                                                          ATGGCTGC
541 CGGCAGCATC ACTTCGCTTC CCGCACTGCC GGAGGACGGG GGCGGCGCCT TCCCACCCGG
601 CCACTTCAAG GATCCCAAGC GGCTCTACTG CAAGAACGGC GGCTTCTTCC TGCGCATCCA
661 TCCAGACGGC CGCGTGGACG GCGTCCGGGA GAAGAGCGAC CCACACGTCA AACTACAGCT
721 CCAAGCAGAA GAGAGAGGAG TTGTGTCCAT CAAGGGAGTG TGTGCGAACC GTTACCTGGC
781 TATGAAGGAA GATGGACGGC TGCTGGCTTC TAAGTGTGTT ACAGAAGAGT GTTTCTTCTT
841 TGAACGCCTG GAGTCCAATA ACTACAACAC TTACCGGTCA CGGAAATACT CCAGTTGGTA
901 TGTGGCACTG AAACGAACTG GGCAGTATAA ACTCGGATCC AAAACGGGGC CTGGACAGAA
961 GGCCATACTG TTTCTTCCAA TGTCTGCTAA GAGCTGA
```

Naked mole-rat FGF2 gene coding sequence (1-134; partial amino acid sequence corresponding to human FGF2 residues 22 to 155) (SEQ ID NO: 192) (GenBank accession no. JH173674, which is hereby incorporated by reference in its entirety):

```
378500          C CACCCGGCCA CTTCAAGGAC CCAAAGCGGC
378531 TGTACTGCAA AAACGGGGGC TTCTTCCTGC GCATCCACCC CGACGGCCGC
378581 GTGGACGGGG TCCGGGAGAA GAGCGACCCT CACG
418784    TCAAACT ACAACTTCAA GCAGAAGAGA GAGGAGTTGT GTCTATTAAG
418831 GGAGTGTGTG CGAACCGTTA CCTTGCTATG AAGGAAGATG GAAGATTACT
418881 GGCTTCT
433983    AAATGTGT TACAGATGAG TGTTTCTTTT TTGAACGATT GGAATCTAAT
434031 AACTACAATA CTTATCGGTC AAGGAAATAC TCCAGTTGGT ATGTGGCACT
434081 GAAACGAACT GGACAATATA AACTTGGATC CAAAACAGGA CCGGGGCAGA
434131 AAGCTATACT TTTTCTTCCA ATGTCTGCTA AGAGCTGA
```

Bushbaby FGF2 gene coding sequence (aa 52-206) (SEQ ID NO: 193) (Ensembl accession no. ENSOGAT00000025228, which is hereby incorporated by reference in its entirety):

```
154                             ATGGCAG CCGGGAGCAT CACCACGCTG
181 CCCTCCCTGC CCGAGGACGG CGGCAGCGAC GCCTTTCCGC CCGGCCACTT CAAGGACCCC
241 AAGCGACTGT ACTGCAAAAA CGGGGGCTTC TTCCTGCGCA TCCACCCCGA CGGCCGAGTG
301 GACGGGGTCC GGGAGAAGAG CGACCCTTAC ATCAAACTAC AACTTCAAGC AGAAGAGAGA
361 GGAGTTGTGT CTATCAAAGG AGTGTGTGCG AACCGTTACC TTGCTATGAA GGAAGACGGA
```

TABLE 4-continued

```
421 AGATTGCTGG CTTCTAAATT GATTACAGAC GAGTGCTTCT TTTTTGAACG ACTGGAATCT
481 AATAACTACA ATACTTACCG GTCAAGAAAA TACTCCAGTT GGTATGTGGC ACTGAAACGA
541 ACTGGACAGT ATAAACTTGG ATCCAAAACA GGACCTGGGC AGAAAGCTAT ACTTTTTCTT
601 CCAATGTCTG CTAAGAGCTG A
```

House mouse FGF2 gene coding sequence (aa 1-154) (SEQ ID NO: 194)
(GenBank accession no. NM_008006, which is hereby
incorporated by reference in its entirety):

```
198                    ATG GCTGCCAGCG GCATCACCTC GCTTCCCGCA CTGCCGGAGG
241 ACGGCGGCGC CGCCTTCCCA CCAGGCCACT TCAAGGACCC CAAGCGGCTC TACTGCAAGA
301 ACGGCGGCTT CTTCCTGCGC ATCCATCCCG ACGGCCGCGT GGATGGCGTC CGCGAGAAGA
361 GCGACCCACA CGTCAAACTA CAACTCCAAG CAGAAGAGAG AGGAGTTGTG TCTATCAAGG
421 GAGTGTGTGC CAACCGGTAC CTTGCTATGA AGGAAGATGG ACGGCTGCTG GCTTCTAAGT
481 GTGTTACAGA AGAGTGTTTC TTCTTTGAAC GACTGGAATC TAATAACTAC AATACTTACC
541 GGTCACGGAA ATACTCCAGT TGGTATGTGG CACTGAAACG AACTGGGCAG TATAAACTCG
601 GATCCAAAAC GGGACCTGGA CAGAAGGCCA TACTGTTTCT TCCAATGTCT GCTAAGAGCT
661 GA
```

Squirrel FGF2 gene coding sequence (1-144; partial amino acid sequence
corresponding to human FGF2 residues 12 to 155) (SEQ ID NO: 195)
(Ensembl accession no. ENSSTOT00000022105, which is
hereby incorporated by reference in its entirety):

```
  1 CTGCCCGAGG ACGGCGGCGG CGGCGCCTTC CCGCCCGGCC ACTTTAAGGA CCCCAAGCGG
 61 CTCTACTGCA AAAACGGAGG CTTCTTCCTG CGCATCCACC CCGACGGCCG AGTGGACGGG
121 GTCCGGGAGA AGAGCGACCC CCACATCAAG CTCCAGCTTC AAGCCGAAGA CCGAGGGGTT
181 GTGTCCATCA AGGGAGTGTG TGCAAACCGA TACCTGGCCA TGAAGGAGGA CGGGAGGCTC
241 CTGGCTTCTA AATGTGTTAC GGACGAGTGT TTCTTTTTTG AACGACTGGA ATCAAATAAC
301 TACAATACTT ACCGGTCAAG GAAATACTCC AGTTGGTATG TGGCCCTGAA ACGAACAGGG
361 CAGTATAAAC TTGGATCCAA AACAGGACCT GGGCAGAAAG CTATACTTTT TCTTCCAATG
421 TCTGCTAAGA GC
```

Domestic cat FGF2 gene coding sequence (1-106; partial amino acid
sequence corresponding to human FGF2 residues 25 to 130) (SEQ ID
NO: 196) (GenBank accession no. EU314952, which is hereby
incorporated by reference in its entirety):

```
  1 CCACTTCAAG GACCCCAAGC GTCTGTACTG CAAAAACGGG GGCTTCTTCC TGCGCATCCA
 61 CCCCGACGGC CGAGTGGATG GGGTCCGGGA GAAGAGCGAC CCTCACATCA AACTGCAACT
121 TCAGGCAGAA GAGAGAGGGG TTGTGTCCAT CAAAGGAGTC TGTGCAAACC GCTATCTTGC
181 CATGAAGGAA GATGGAAGAT TACTGGCTTC TAAATGTGTT ACGGACGAGT GTTTCTTTTT
241 TGAACGATTG GAATCTAATA ACTACAATAC TTATCGGTCA AGGAAATACT CCAGCTGGTA
301 TGTGGCACTG AAACGAAC
```

Guinea pig FGF2 gene coding sequence (1-96; partial amino acid sequence
corresponding to human FGF2 residues 60 to 155) (SEQ ID NO: 197)
(Ensembl accession no. ENSCPOT00000005443, which is hereby
incorporated by reference in its entirety):

```
  1 GTTAAACTAC AACTTCAAGC CGAAGACAGA GGAGTTGTGT CTATCAAGGG AGTCTGTGCG
 61 AACCGTTACC TTGCTATGAA GGAAGACGGA AGATTATTGG CTTCCAAATG TGTTACAGAT
121 GAATGTTTCT TTTTTGAACG ACTGGAATCT AATAACTACA ACACTTACCG GTCAAGGAAA
181 TACTCCAGTT GGTATGTGGC ACTGAAACGA ACTGGACAAT ATAAACTTGG GTCCAAAACA
241 GGACCAGGGC AGAAAGCCAT ACTTTTTCTT CCAATGTCTG CGAAGAGC
```

Tasmanian devil FGF2 gene coding sequence (aa 48-203) (SEQ ID NO: 198)
(Ensembl accession no. ENSSHAP00000012215, which is hereby incorporated
by reference in its entirety):

```
142                    ATGGCCGCG GGCAGCATCA CCACGTTGCC GGCCCTGGCC
181 GGGGATGGAG CCAGCGGGGG CGCCTTTCCC CCGGGCCACT TCCAGGACCC CAAGCGGCTG
241 TACTGCAAGA ACGGAGGCTT CTTCTTGCGC ATCCATCCCG ACGGTCACGT GGACGGCATC
301 CGCGAGAAGA GCGATCCGCA CATTAAACTT CAGCTTCAGG CAGAAGAGAG AGGAGTAGTG
361 TCTATTAAAG GAGTTTGTGC CAACCGCTAT CTTGCCATGA AGAGGATGG CAGATTACTG
421 GCTCTGAAAT GTGTGACTGA AGAGTGTTTC TTCTTTGAAC GTCTAGAGTC AACAATTAC
481 AACACTTATC GCTCAAGGAA ATACTCCAAT TGGTATGTGG CATTGAAACG CACAGGCCAG
541 TATAAGCTTG GATCCAAGAC TGGACCAGGG CAGAAAGCCA TCCTTTTCCT TCCCATGTCT
601 GCTAAGAGCT GA
```

Gray short-tailed opossum FGF2 gene coding sequence (aa 1-155) (SEQ ID
NO: 199) (GenBank accession no. NM_001033976, which is
hereby incorporated by reference in its entirety):

```
 29                         AT GGCCGCAGGC AGCATCACCA CGCTGCCAGC
 61 CCTGTCCGGG GACGGAGGCG GCGGGGGCGC CTTTCCCCCG GGCCACTTCA AGGACCCCAA
121 GCGGCTGTAC TGCAAGAACG GAGGCTTCTT CCTGCGCATC CACCCCGACG GCCGTGTGGA
181 CGGCATCCGC GAGAAGAGCG ACCCGAACAT TAAACTACAA CTTCAGGCAG AAGAGAGAGG
241 AGTGGTGTCT ATTAAAGGAG TATGTGCCAA TCGCTATCTT GCCATGAAGG AAGATGGAAG
301 ATTATTGGCT TTGAAATATG TGACCGAAGA GTGTTTCTTT TTCGAACGCT TGGAGTCCAA
```

TABLE 4-continued

```
361 CAACTACAAC ACTTATCGCT CGAGGAAATA TTCCAATTGG TACGTGGCAC TGAAACGAAC
421 GGGGCAGTAC AAGCTTGGAT CCAAGACTGG CCCGGGGCAG AAAGCCATCC TTTTCCTCCC
481 CATGTCTGCT AAGAGCTGA
```

Rabbit FGF2 gene coding sequence (aa 1-155) (SEQ ID NO: 200) (GenBank accession no. XM_002717238, which is hereby incorporated by reference in its entirety):

```
  1 ATGGCAGCCG AGAGCATCAC CACGCTGCCC GCCCTGCCGG AGGATGGAGG CAGCGGCGCC
 61 TTCCCGCCCG GCCACTTCAA GGACCCCAAG CGGCTGTACT GCAAAAACGG GGGTTTCTTC
121 CTGCGTATCC ACCCCGACGG CCGCGTGGAC GGGGTCCGGG AGAAGAGCGA CCCACACATC
181 AAATTACAAC TTCAAGCAGA AGAGAGAGGA GTTGTATCCA TCAAAGGTGT GTGTGCAAAC
241 CGTTACCTTG CTATGAAGGA AGATGGAAGA CTGCTGGCTT CTAAATGTGT TACAGACGAG
301 TGCTTCTTTT TTGAACGACT GGAGTCTAAT AACTACAATA CTTACCGGTC AAGGAAATAT
361 TCCAGCTGGT ATGTGGCACT GAAACGAACT GGGCAGTATA AACTTGGATC CAAAACAGGA
421 CCTGGGCAGA AGGCTATACT TTTTCTTCCA ATGTCTGCTA AGAGCTGA
```

Turkey FGF2 gene coding sequence (1-125; partial amino acid sequence corresponding to human FGF2 residues 31 to 155) (SEQ ID NO: 201) (Ensembl accession no. ENSMGAT00000011845, which is hereby incorporated by reference in its entirety):

```
  1 CGGCTCTACT GTAAGAACGG CGGCTTCTTC CTGCGCATCA ATCCCGACGG CAGAGTGGAC
 61 GGCGTCCGCG AGAAGAGCGA TCCGCACATC AAACTGCAGC TTCAGGCAGA AGAAAGAGGA
121 GTGGTATCAA TCAAAGGTGT AAGTGCAAAC CGCTTTCTGG CTATGAAGGA GGATGGCAGA
181 TTGCTGGCAC TGAAATGTGC AACAGAAGAA TGTTTCTTTT TTGAGCGTTT GGAATCTAAT
241 AATTATAACA CTTACCGGTC ACGGAAGTAC TCTGATTGGT ATGTGGCACT GAAAAGAACT
301 GGACAGTACA AGCCCGACC AAAAACTGGA CCTGGACAGA AGCTATCCT TTTTCTTCCA
361 ATGTCTGCTA AAAGC
```

*Gallus gallus* FGF2 gene coding sequence (aa 1-158) (SEQ ID NO: 202) (GenBank accession no. NM_205433, which is hereby incorporated by reference in its entirety):

```
 98                                                   ATG GCGGCGGGGG CGGCGGGGAG
121 CATCACCACG CTGCCGGCGC TGCCCGACGA CGGGGGCGGC GGCGCTTTTC CCCCCGGGCA
181 CTTCAAGGAC CCCAAGCGGC TCTACTGCAA GAACGGCGGC TTCTTCCTGC GCATCAACCC
241 CGACGGCAGG GTGGACGGCG TCCGCGAGAA GAGCGATCCG CACATCAAAC TGCAGCTTCA
301 AGCAGAAGAA AGAGGAGTAG TATCAATCAA AGGCGTAAGT GCAAACCGCT TTCTGGCTAT
361 GAAGGAGGAT GGCAGATTGC TGGCACTGAA ATGTGCAACA GAGGAATGTT TCTTTTTCGA
421 GCGCTTGGAA TCTAATAACT ATAACACTTA CCGGTCACGG AAGTACTCTG ATTGGTATGT
481 GGCACTGAAA AGGACTGGAC AGTACAAGCC CGGACCAAAA ACTGGACCTG GACAGAAAGC
541 TATCCTTTTT CTTCCAATGT CTGCTAAAAG CTGA
```

Zebra finch FGF2 gene coding sequence (aa 1-153) (SEQ ID NO: 203) (GenBank accession no. XM_002188361, which is hereby incorporated by reference in its entirety):

```
  1 ATGGCGGCGG CGGGGGGCAT CGCTACGCTG CCCGACGACG GCGGCAGCGG CGCCTTTCCC
 61 CCGGGGCACT TCAAGGACCC CAAGCGCCTG TACTGCAAGA ACGGCGGCTT CTTCCTGCGC
121 ATCAACCCCG ACGGGAAGGT GGACGGCGTC CGCGAGAAGA GCGACCCGCA CATCAAGCTG
181 CAGCTTCAGG CGGAGGAACG AGGAGTGGTG TCCATCAAAG GTGTCAGTGC AATCGCTTC
241 CTGGCCATGA AGAGGATGG CAGATTGCTG GCCTTGAAAT ATGCAACAGA GAATGTTTC
301 TTTTTTGAAC GTTTGGAATC CAATAACTAT AACACTTACC GGTCACGGAA ATACTCGGAT
361 TGGTATGTGG CACTGAAAAG AACTGGACAG TACAAACCTG GACCAAAAAC TGGACCTGGA
421 CAGAAAGCTA TCCTTTTCCT TCCTATGTCT GCTAAAAGCT GA
```

Japanese firebelly newt FGF2 gene coding sequence (aa 1-155) (SEQ ID NO: 204) (GenBank accession no. AB064664, which is hereby incorporated by reference in its entirety):

```
384                              ATGGCTG CTGGGAGCAT CACCAGTCTC CCTGCCCTAC
421 CCGAGGACGG GAATGGCGGC ACCTTCACAC CCGGCGGATT CAAAGAGCCG AAGAGGCTGT
481 ACTGCAAGAA CGGGGGCTTC TTTCTCCGGA TCAACTCCGA CGGCAAGGTG GACGGAGCCC
541 GGGAGAAGAG CGACTCCTAC ATTAAACTGC AGCTTCAAGC AGAAGAGCGC GGTGTGGTGT
601 CCATCAAGGG AGTATGTGCA AACCGCTATC TCGCTATGAA GGATGATGGC AGGCTGATGG
661 CGCTGAAATG GATAACCGAT GAATGCTTCT TTTTCGAGCG ACTGGAGTCC AACAACTATA
721 ACACGTATCG ATCACGGAAA TATTCCGATT GGTATGTGGC GCTGAAAAGA ACTGGGCAAT
781 ACAAAAATGG ATCAAAAACC GGAGCAGGAC AGAAAGCAAT CCTTTTTCTA CCCATGTCGG
841 CCAAGAGTTG A
```

African clawed frog FGF2 gene coding sequence (aa 1-155) (SEQ ID NO: 205) (GenBank accession no. NM_001099871, which is hereby incorporated by reference in its entirety):

```
335                                          ATGGCG GCAGGGAGCA TCACAACTCT
361 GCCAACTGAA TCCGAGGATG GGGAAACAC TCCTTTTTCA CCAGGGAGTT TTAAAGACCC
421 CAAGAGGCTC TACTGCAAGA ACGGGGGCTT CTTCCTCAGG ATAAACTCAG ACGGGAGAGT
481 GGACGGGTCA AGGGACAAAA GTGACTCGCA CATAAAATTA CAGCTACAAG CTGTAGAGCG
541 GGGAGTGGTA TCAATAAAGG GAATCACTGC AAATCGCTAC CTTGCCATGA AGGAAGATGG
```

TABLE 4-continued

```
601  GAGATTAACA TCGCTGAGGT GTATAACAGA TGAATGCTTC TTTTTTGAAC GACTGGAAGC
661  TAATAACTAC AACACTTACC GGTCTCGGAA ATACAGCAGC TGGTATGTGG CACTAAAGCG
721  AACCGGGCAG TACAAAAATG GATCGAGCAC TGGACCGGGA CAAAAAGCTA TTTTATTTCT
781  CCCAATGTCC GCAAAGAGCT GA
```

White-eared opossum FGF2 gene coding sequence (aa 1-156) (SEQ ID
NO: 206) (GenBank accession no. EF057322, which is hereby
incorporated by reference in its entirety):

```
  1  ATGGCAGCAG GCAGCATCAC CACATTGCCG GCCCTGTCCG GGGACGGAGG CGGCGGGGGA
 61  GCCTTTCCTC CAGGCCACTT CAAGGACCCC AAGCGGCTGT ACTGCAAGAA CGGAGGCTTC
121  TTCCTGCGCA TCCACCCCGA CGGCCGCGTG GACGGCATCC GCGAGAAGAG CGACCCGAAC
181  ATTAAACTAC AACTTCAGGC AGAAGAGAGA GGAGTAGTGT CTATTAAAGG AGTATGTGCC
241  AACCGATATC TTGCCATGAA GGAGGATGGC AGATTATTGG CTTTGAAATA TGTGACCGAA
301  GAGTGTTTCT TTTTTGAACG TTTGGAGTCC AACAACTACA ACACTTATCG CTCAAGAAAA
361  TATTCCAATT GGTATGTGGC ACTGAAACGA ACGGGGCAGT ATAAGCTTGG ATCCAAGACT
421  GGCCCGGGGC AGAAAGCCAT CCTTTTCTCC CCATGTCTGC TAAGATGCTG A
```

Microbat FGF2 gene coding sequence (1-96; partial amino acid sequence
corresponding to human FGF2 residues 60 to 155) (SEQ ID NO: 207)
(Ensembl accession no. ENSMLUT00000027717, which is hereby
incorporated by reference in its entirety):

```
  1  GTCAAACTCC AACTTCAAGC AGAAGAGAGA GGGGTCGTGT CTATCAAAGG AGTGTGTGCC
 61  AACCGCTATC TCGCTATGAA GGAGGACGGC CGGTTACAGG CTTCTAAATG TGTTACGGAT
121  GAGTGTTTCT TTTTTGAACG GTTGGAATCC AATAACTACA ACACTTACCG GTCAAGAAAG
181  TACTCCAGTT GGTATGTGGC ATTGAAGCGG AATGGGCAGT ATAAACTTGG ACCCAAAACA
241  GGACCTGGCC AGAAAGCCAT ACTTTTTCTT CCCATGTCTG CTAAGAGC
```

Anole lizard FGF2 gene coding sequence (1-140; partial amino acid
sequence corresponding to human FGF2 residues 16 to 155) (SEQ ID
NO: 208) (Ensembl accession no. ENSACAT00000011897, which is
hereby incorporated by reference in its entirety):

```
  1  GCGGCGGCGG CCTCTTTCCC CCCGGGCCCC TTCAAGGACC CCAAGCGCCT CTACTGCAAG
 61  AACGGGGGCT TCTTCCTGCG GATCAACCCC GACGGCGGCG TGGACGGCGT CCGAGAGAAG
121  AGCGACCCCA ACATCAAATT GCTGCTCCAG GCAGAGGAGA GAGGTGTAGT GTCCATCAAA
181  GGTGTATGCG CAAACCGTTT CCTGGCTATG AATGAAGACG GTCGATTGTT AGCACTGAAA
241  TACGTAACAG ATGAATGCTT CTTTTTTGAA CGCTTGGAAT CTAATAATTA CAATACTTAT
301  CGGTCTCGTA AATACCGTGA TTGGTACATT GCACTGAAAC GAACTGGTCA GTACAAACTT
361  GGACCAAAAA CTGGACGAGG CCAGAAAGCT ATCCTTTTCC TTCCAATGTC TGCCAAAAGT
```

Armadillo FGF2 gene coding sequence (124-217; partial amino acid
sequence corresponding to human FGF2 residues 1 to 94) (SEQ ID
NO: 209) (Ensembl accession no. ENSDNOT00000014647,
which is hereby incorporated by reference in its entirety):

```
361           A TGGCAGCCGG GAGCATCACC ACGCTGCCCG CTCTGCCCGA GGACGGCGGC
421  AGCGGCGCCT TCCCGCCGGG CCACTTCAAG GACCCCAAGC GGCTGTACTG CAAAAACGGG
481  GGCTTCTTCC TGCGCATCCA TCCCGACGGC CGAGTGGATG GGGTCCGGGA GAAGAGCGAC
541  CCTAACATCA AACTACAACT TCAAGCAGAA GAGAGAGGGG TCGTGTCTAT CAAAGGCGTG
601  TGTGCGAACC GTTACCTTGC TATGCGGGAA GACGGAAGAC TCCAGGCGTC T
```

Tree shrew FGF2 gene coding sequence (1-189) (SEQ ID NO: 210) (Ensembl
accession no. ENSTBET00000001143, which is hereby incorporated by
reference in its entirety):

```
  1  GCGGGGGTTA GAGCTGAGAG GGAGGAGGCA CCGGGGAGCG GTGACAGCCG GGGGACCGAT
 61  CCCGCCGCGC GTTCGCTCAT CAGGAGGCCG GATGCTGCAG CGCGAGAGGC GCTTCTTGGA
121  GCCAGGAGCC GGGTTCAGGG CAGCTCCACC TCCTGGCCAG CCTCGTCACG AACCGGGATC
181  AAGTTGCCGG ACGACTCAGG TCAAGGAATG GCGGCTATC CTCTGGACCG CCCGAGCCGG
241  AGCACAGGGC GAGGGCTGGG CGGTGCCCCG GACCCTGCCG TAAAACTACA GCTTCAAGCG
301  GAAGAGAGAG GGGTCGTGTC TATCAAAGGA GTGTGTGCAA ACCGTTACCT GGCCATGAAG
361  GAGGATGGGC GACTGCTGGC TTCTAAATGT GTTACAGATG AGTGTTTCTT TTTTGAACGA
421  CTGGAATCTA ATAACTACAA TACTTACCGG TCCCGAAAGT ACTCCAGCTG GTATGTGGCA
481  CTGAAACGAA CTGGGCAGTA TAAACTTGGA TCCAAAACAG GACCTGGGCA GAAAGCTATA
541  CTTTTTCTTC CAATGTCTGC TAAAAGC
```

Western clawed frog FGF2 gene coding sequence (aa 1-154) (SEQ ID NO:
211) (GenBank accession no. NM_001017333, which is
hereby incorporated by reference in its entirety):

```
171                                                             ATGGCAGCAG
181  GAAGCATCAC AACCCTACCA ACCGAATCTG AGGATGGAAA CACTCCTTTC CCACCGGGGA
241  ACTTAAGGA CCCCAAGAGG CTCTACTGCA AGAATGGGGG CTACTTCCTC AGGATTAACT
301  CAGACGGGAG AGTGGACGGA TCAAGGGATA AAAGTGACTT ACACATAAAA TTACAGCTAC
361  AAGCAGTAGA GCGGGGAGTG GTATCAATAA AGGGAATCAC TGCAAATCGC TACCTTGCCA
421  TGAAGGAAGA TGGGAGATTA ACATCGCTGA AGTGTATAAC AGATGAATGC TTCTTTTATG
481  AACGATTGGA AGCTAATAAC TACAACACTT ACCGGTCTCG GAAAACAAC AGCTGGTATG
```

TABLE 4-continued

```
541 TGGCACTAAA GCGAACTGGG CAGTATAAAA ATGGATCGAC CACTGGACCA GGACAAAAAG
601 CTATTTTGTT TCTCCCAATG TCAGCAAAAA GCTGA
```

Coelacanth FGF2 gene coding sequence (aa 1-155) (SEQ ID NO: 212)
(Ensembl accession no. ENSLACT00000019333, which is hereby
incorporated by reference in its entirety):

```
  1                    ATGGCTGCGG GAGGAATCAC TACCCTGCCG GCGGTACCTG
 41 AGGATGGAGG CAGCAGCACC TTCCCTCCAG GAAACTTCAA GGAGCCCAAG AGACTTTACT
101 GTAAGAATGG AGGCTATTTC TTAAGGATAA ACCCCGATGG AAGAGTGGAT GGAACAAGGG
161 AGAAAAATGA TCCTTATATA AAATTACAAC TGCAAGCTGA ATCTATAGGA GTGGTGTCGA
221 TAAAGGGAGT TGTTCAAAC CGTTACCTAG CGATGAATGA AGACTGTAGA CTTTTTGGAT
281 TGAAATATCC AACGGATGAA TGTTTCTTCC ATGAGAGGCT GGAGTCCAAC AACTACAATA
341 CTTATCGTTC AAAGAAGTAT TCGGATTGGT ATGTGGCGCT GAAACGGACT GGTCAGTACA
401 AACCTGGGCC AAAAACTGGA CTGGGACAAA AAGCAATCCT TTTCCTTCCG ATGTCTGCCA
461 AGAGTTGA
```

Spotted green pufferfish FGF2 gene coding sequence (aa 34-188) (SEQ ID
NO: 213) (Ensembl accession no. ENSTNIT00000016254, which is hereby
incorporated by reference in its entirety):

```
  1 ATGGCCACGG GAGGGATCAC GACGCTTCCA TCCACACCTG AAGACGGCGG CAGCAGCGGC
 61 TTTCCTCCCG GCAGCTTCAA GGATCCCAAA AGGCTCTACT GTAAAAACGG AGGTTTCTTC
121 CTGAGGATCA AGTCCGACGG GGTCGTGGAC GGAATCCGGG AGAAGAGTGA CCCCCACATA
181 AAGCTTCAGC TCCAGGCGAC CTCTGTGGGG GAGGTGGTCA TCAAGGGGGT GTGCGCTAAC
241 CGCTATCTGG CCATGAACAG AGATGGACGG CTGTTCGGAA CGAAACGAGC CACGGACGAA
301 TGCCATTTCT TAGAGCGGCT TGAGAGCAAC AACTACAACA CTTACCGCTC CAGGAAGTAC
361 CCAACCATGT TTGTGGGACT GACGCGGACG GGCCAGTACA AGTCTGGGAG CAAAACTGGA
421 CCGGGCCAAA AGGCCATCCT TTTTCTTCCG ATGTCCGCCA ATGCTAA
```

Stickleback FGF2 gene coding sequence (aa 1-155) (SEQ ID NO: 214)
(Ensembl accession no. ENSGACT00000022120, which is hereby
incorporated by reference in its entirety):

```
  1                 AT GGCCACGGCA GGCTTCGCGA CGCTTCCCTC CACGCCCGAA
 43 GACGGCGGCA GCGGCGGCTT CACCCCCGGG GGATTCAAGG ATCCCAAGAG CTGTACTGC
103 AAAAACGGGG GCTTCTTCTT GAGGATCAGG TCCGACGGAG GTGTAGATGG AATCAGGGAG
163 AAGAGCGACG CCCACATAAA GCTCCAAATC CAGGCGACGT CGGTGGGGGA GGTGGTCATC
223 AAAGGAGTCT GTGCCAACCG CTATCTGGCC ATGAACAGAG ACGGCCGGCT GTTCGGAGTG
283 AGACGGGCGA CGGACGAATG CTACTTCCTG GAGCGGCTGG AGAGTAACAA CTACAACACC
343 TACCGCTCCA GGAAGTACCC CGGCATGTAC GTGGCTCTGA AGCGGACCGG CCAGTACAAG
403 TCCGGGAGCA AAACCGGACC CGGTCAAAAG GCCATTCTGT TCCTCCCCAT GTCGGCTAAG
463 TGCTAA
```

*Fugu rubripes* FGF2 gene coding sequence (aa 1-155) (SEQ ID NO: 215)
(Ensembl accession no. ENSTRUT00000022363, which is hereby incorporated
by reference in its entirety):

```
127       ATGG CCACGGGAGG GATCACAACA CTTCCATCCA CACCTGAAGA CGGCGGCAGC
181 GGCGGTTTTC CTCCCGGGAG CTTCAAGGAT CCCAAAAGGC TGTACTGTAA AAACGGCGGC
241 TTCTTCCTGA GGATCAGGTC CGACGGGGCC GTGGACGGAA CCCGGGAGAA GACTGACCCC
301 CACATAAAGC TTCAGCTCCA GGCGACCTCT GTGGGGGAGG TGGTCATCAA GGGGGTTTGT
361 GCTAATCGTT ATCTGGCCAT GAACAGAGAT GGACGACTGT TTGGAATGAA ACGAGCGACG
421 GATGAATGCC ACTTCTTAGA GCGGCTCGAG AGCAACAACT ACAACACCTA CCGCTCCAGG
481 AAGTACCCCA ACATGTTTGT GGGACTGACG CGAACTGGCA ACTACAAGTC TGGGACTAAA
541 ACTGGACCGG GCCAAAAGGC CATCCTCTTT CTTCCGATGT CGGCCAAATA CTAA
```

Rainbow trout FGF2 gene coding sequence (aa 1-155) (SEQ ID NO: 216)
(GenBank accession no. NM_001124536, which is hereby incorporated by
reference in its entirety):

```
390                         A TGGCCACAGG AGAAATCACC ACTCTACCCG
421 CCACACCTGA AGATGGAGGC AGTGGCGGCT TCCTTCCAGG AAACTTTAAG GAGCCCAAGA
481 GGTTGTACTG TAAAAATGGA GGCTACTTCT TGAGGATAAA CTCAACGGA AGCGTGGACG
541 GGATCAGAGA TAAGAACGAC CCCCACAATA AGCTTCAACT CCAGGCGACC TCAGTGGGGG
601 AAGTAGTAAT CAAAGGGGTC TCAGCCAACC GCTATCTGGC CATGAATGCA GATGGAAGAC
661 TGTTTGGACC GAGACGGACA ACAGATGAAT GCTACTTCAT GGAGAGGCTG GAGAGTAACA
721 ACTACAACAC CTACCGCTCT CGAAAGTACC CTGAAATGTA TGTGGCACTG AAAAGGACTG
781 GCCAGTACAA GTCAGGATCC AAAACTGGAC CCGGCCAAAA AGCCATCCTC TTCCTCCCCA
841 TGTCAGCCAG ACGCTGA
```

Salmon FGF2 gene coding sequence (1-150) (SEQ ID NO: 217) (GenBank
accession no. EU816603, which is hereby incorporated by reference in its
entirety):

```
 99402                         ATGGCCACA GGAGAAATCA
 99421 CCACTCTACC CGCCACACCT GAAGATGGAG GCAGTGGCGG CTTCCCTCCA GGAAACTTTA
 99481 AGGATCCCAA GAGGCTGTAC TGTAAAAACG GGGGCTACTT CTTGAGAATA AACTCTAATG
 99541 GAAGCGTGGA CGGGATCCGA GAGAAGAACG ACCCCCACA
100968                                                   AAC AGCCTCAATT
```

TABLE 4-continued

```
100981 TGTCAGGGCA TGGACTCTTC AAGGTGTCAA ACGTTCCACA GGGATGCTGG CCCATGTTGA
101041 CTCCAACGCT TCCCACAATT GTGTCAAGGT GGCTGGATGT TCTTTGGGAG
101845                    AATTTG GCAGTATGTC CAACCGGCCT CATAACCGCA
101881 GACCACGTGT AGCTACACCA GCCCAGGACC TCCACATCCG GCTTCTTCAT CTACGGGATC
101941 GTCTGAAACC AGCCACCCGA ACAGCTGATA AAACTGAGGA GTATTTCTGT CTGTAA
```

Zebrafish FGF2 gene coding sequence (aa 1-154) (SEQ ID NO: 218) (GenBank accession no. AY269790, which is hereby incorporated by reference in its entirety):

```
  43                                        ATGGCCAC CGGAGGGATC
  61 ACCACACTCC CGGCCGCTCC GGACGCCGAA AACAGCAGCT TTCCCGCGGG CAGCTTCAGG
 121 GATCCCAAGC GCCTGTACTG CAAAAACGGA GGATTCTTCC TGCGGATCAA CGCGGACGGC
 181 CGAGTGGACG GAGCCCGAGA CAAGAGCGAC CCGCACATTC GTCTGCAGCT GCAGGCGACG
 241 GCAGTGGGTG AAGTACTCAT TAAAGGCATC TGTACCAACC GTTTCCTTGC CATGAACGCA
 301 GACGGACGAC TGTTCGGACA GAAAAGGACC ACAGATGAAT GTTATTTCCT GGAGCGCCTG
 361 GAGTCCAACA ACTACAACAC ATACGATCCC CGCAAGTATC CCGACTGGTA CGTGGCTCTG
 421 AAGAGAACCG GCCAGTATAA AAGCGGCTCT AAAACCAGCC CGGGACAGAA GGCCATCCTG
 481 TTTCTGCCCA TGTCGGCCAA ATGCTGA
```

Nile tilapia FGF2 gene coding sequence (aa 1-155) (SEQ ID NO: 219) (GenBank accession no. XM_003443364, which is hereby incorporated by reference in its entirety):

```
   1 ATGGCCACGG GAGGAATCAC AACACTTCCC GCTACACCTG AAGACGGCGG CAGCAGCGGC
  61 TTTCCTCCTG GGAACTTCAA GGACCCTAAA AGGCTGTACT GTAAAAATGG TGGCTTCTTC
 121 TTGAGGATAA AATCTGATGG AGGAGTGGAT GGAATACGAG AGAAAAACGA CCCCCACATA
 181 AAGCTTCAAC TCCAGGCGAC CTCAGTGGGA GAAGTGGTCA TCAAAGGGAT TTGTGCAAAC
 241 CGATATCTGG CAATGAACAG AGATGGACGA CTGTTTGGAG CGAGAAGAGC AACAGATGAG
 301 TGCTACTTCT TAGAGCGGCT CGAGAGCAAC AACTACAACA CCTACCGCTC CAGGAAGTAC
 361 CCAAACATGT ACGTGGCGCT GAAGCGGACT GGCCAGTACA AGTCTGGAAG CAAAACTGGA
 421 CCGGGTCAAA AGGCAATTCT CTTTCTCCCA ATGTCTGCTA AATGCTAA
```

Medaka FGF2 gene coding sequence (aa 1-155) (SEQ ID NO: 220) (Ensembl accession no. ENSORLT00000025835, which is hereby incorporated by reference in its entirety):

```
   1 ATGGCTACGG GAGAAATCAC AACACTTCCC TCCCCAGCTG AAAACAGCAG AAGCGATGGC
  61 TTTCCTCCAG GGAACTACAA GGATCCTAAG AGGCTCTACT GTAAAAATGG AGGTTTGTTT
 121 TTGAGGATTA AACCTGATGG AGGAGTGGAT GGAATCCGGG AAAAAAAAGA TCCCCACGTT
 181 AAGCTTCGCC TTCAGGCTAC CTCAGCGGGA GAGGTGGTGA TCAAAGGAGT TGTTCAAAC
 241 AGATATCTGG CGATGCATGG AGATGGACGT CTATTTGGAG TGAGACAAGC AACAGAGGAA
 301 TGCTACTTCT TGGAGCGACT AGAGAGCAAC AACTATAACA CCTATCGCTC TAAAAAGTAC
 361 CCAAACATGT ACGTGGCACT GAAGCGGACA GGCCAGTACA AACCTGGAAA CAAAACTGGA
 421 CCAGGTCAAA AGGCCATTCT CTTTCTGCCT ATGTCTGCCA AGTACTAA
```

As noted above, also encompassed within the present invention are portions of paracrine FGFs other than FGF1 and/or FGF2 (e.g., FGF4, FGF5, FGF6, FGF9, FGF16, and FGF20). The portion of the paracrine FGF may be from human FGF4, FGF5, FGF6, FGF9, FGF16, and/or FGF20 having the amino acid sequences shown in Table 5, or orthologs thereof

TABLE 5

Amino acid sequence of human FGF4 (SEQ ID NO: 221) (GenBank accession no. NP_001998, which is hereby incorporated by reference in its entirety):

```
   1 MSGPGTAAVA LLPAVLLALL APWAGRGGAA APTAPNGTLE AELERRWESL VALSLARLPV
  61 AAQPKEAAVQ SGAGDYLLGI KRLRRLYCNV GIGFHLQALP DGRIGGAHAD TRDSLLELSP
 121 VERGVVSIFG VASRFFVAMS SKGKLYGSPF FTDECTFKEI LLPNNYNAYE SYKYPGMFIA
 181 LSKNGKTKKG NRVSPTMKVT HFLPRL
```

Amino acid sequence of human FGF5 (SEQ ID NO: 222) (GenBank Accession No. NP_004455, which is hereby incorporated by reference in its entirety):

```
   1 MSLSFLLLLF FSHLILSAWA HGEKRLAPKG QPGPAATDRN PRGSSSRQSS SSAMSSSSAS
  61 SSPAASLGSQ GSGLEQSSFQ WSPSGRRTGS LYCRVGIGFH LQIYPDGKVN GSHEANMLSV
 121 LEIFAVSQGI VGIRGVFSNK FLAMSKKGKL HASAKFTDDC KFRERFQENS YNTYASAIHR
 181 TEKTGREWYV ALNKRGKAKR GCSPRVKPQH ISTHFLPRFK QSEQPELSFT VTVPEKKKPP
 241 SPIKPKIPLS APRKNTNSVK YRLKFRFG
```

TABLE 5-continued

Amino acid sequence of human FGF6(SEQ ID NO: 223)
(NP_066276,
which is hereby incorporated by reference in its entirety):

```
  1 MALGQKLFIT MSRGAGRLQG TLWALVFLGI LVGMVVPSPA GTRANNTLLD SRGWGTLLSR
 61 SRAGLAGEIA GVNWESGYLV GIKRQRRLYC NVGIGFHLQV LPDGRISGTH EENPYSLLEI
121 STVERGVVSL FGVRSALFVA MNSKGRLYAT PSFQEECKFR ETLLPNNYNA YESDLYQGTY
181 IALSKYGRVK RGSKVSPIMT VTHFLPRI
```

Amino acid sequence of human FGF9(SEQ ID NO: 224)
(GenBank accession no. NP_002001,
which is hereby incorporated by reference in its entirety):

```
  1 MAPLGEVGNY FGVQDAVPFG NVPVLPVDSP VLLSDHLGQS EAGGLPRGPA VTDLDHLKGI
 61 LRRRQLYCRT GFHLEIFPNG TIQGTRKDHS RFGILEFISI AVGLVSIRGV DSGLYLGMNE
121 KGELYGSEKL TQECVFREQF EENWYNTYSS NLYKHVDTGR RYYVALNKDG TPREGTRTKR
181 HQKFTHFLPR PVDPDKVPEL YKDILSQS
```

Amino acid sequence of human FGF16(SEQ ID NO: 225)
(GenBank accession no. NP_003859,
which is hereby incorporated by reference in its entirety):

```
  1 MAEVGGVFAS LDWDLHGFSS SLGNVPLADS PGFLNERLGQ IEGKLQRGSP TDFAHLKGIL
 61 RRRQLYCRTG FHLEIFPNGT VHGTRHDHSR FGILEFISLA VGLISIRGVD SGLYLGMNER
121 GELYGSKKLT RECVFREQFE ENWYNTYAST LYKHSDSERQ YYVALNKDGS PREGYRTKRH
181 QKFTHFLPRP VDPSKLPSMS RDLFHYR
```

Amino acid sequence of human FGF20(SEQ ID NO: 226)
(GenBank accession no. NP_062825,
which is hereby incorporated by reference in it entirety):

```
  1 MAPLAEVGGF LGGLEGLGQQ VGSHFLLPPA GERPPLLGER RSAAERSARG GPGAAQLAHL
 61 HGILRRRQLY CRTGFHLQIL PDGSVQGTRQ DHSLFGILEF ISVAVGLVSI RGVDSGLYLG
121 MNDKGELYGS EKLTSECIFR EQFEENWYNT YSSNIYKHGD TGRRYFVALN KDGTPRDGAR
181 SKRHQKFTHF LPRPVDPERV PELYKDLLMY T
```

It will be understood that the portion of the paracrine FGF according to the present invention may be derived from a nucleotide sequence that encodes human FGF4, FGF5, FGF6, FGF9, FGF16, and/or FGF20 having the nucleotide sequences shown in Table 6, or orthologs thereof.

TABLE 6

Human FGF4 gene coding sequence (1-206) (SEQ ID NO: 227)
(GenBank accession no. NM_002007,
which is hereby incorporated by reference in its entirety):

```
320                    A TGTCGGGGCC CGGGACGGCC GCGGTAGCGC TGCTCCCGGC
361 GGTCCTGCTG GCCTTGCTGG CGCCCTGGGC GGGCCGAGGG GGCGCCGCCG CACCCACTGC
421 ACCCAACGGC ACGCTGGAGG CCGAGCTGGA GCGCCGCTGG GAGAGCCTGG TGGCGCTCTC
481 GTTGGCGCGC CTGCCGGTGG CAGCGCAGCC CAAGGAGGCG GCCGTCCAGA GCGGCGCCGG
541 CGACTACCTG CTGGGCATCA AGCGGCTGCG GCGGCTCTAC TGCAACGTGG GCATCGGCTT
601 CCACCTCCAG GCGCTCCCCG ACGGCCGCAT CGGCGGCGCG CACGCGGACA CCCGCGACAG
661 CCTGCTGGAG CTCTCGCCCG TGGAGCGGGG CGTGGTGAGC ATCTTCGGCG TGGCCAGCCG
721 GTTCTTCGTG GCCATGAGCA GCAAGGGCAA GCTCTATGGC TCGCCCTTCT TCACCGATGA
781 GTGCACGTTC AAGGAGATTC TCCTTCCCAA CAACTACAAC GCCTACGAGT CCTACAAGTA
841 CCCCGGCATG TTCATCGCCC TGAGCAAGAA TGGGAAGACC AAGAAGGGGA ACCGAGTGTC
901 GCCCACCATG AAGGTCACCC ACTTCCTCCC CAGGCTGTGA
```

Human FGF5 gene coding sequence (1-268) (SEQ ID NO: 228)
(GenBank Accession No. NM_004464,
which is hereby incorporated by reference in its entirety):

```
238                                                              ATG
241 AGCTTGTCCT TCCTCCTCCT CCTCTTCTTC AGCCACCTGA TCCTCAGCGC CTGGGCTCAC
301 GGGGAGAAGC GTCTCGCCCC CAAAGGGCAA CCCGGACCCG CTGCCACTGA TAGGAACCCT
361 AGAGGCTCCA GCAGCAGACA GAGCAGCAGT AGCGCTATGT CTTCCTCTTC TGCCTCCTCC
421 TCCCCCGCAG CTTCTCTGGG CAGCCAAGGA AGTGGCTTGG AGCAGAGCAG TTTCCAGTGG
481 AGCCCCTCGG GGCGCCGGAC CGGCAGCCTC TACTGCAGAG TGGGCATCGG TTTCCATCTG
541 CAGATCTACC CGGATGGCAA AGTCAATGGA TCCCACGAAG CCAATATGTT AAGTGTTTTG
601 GAAATATTTG CTGTGTCTCA GGGGATTGTA GGAATACGAG GAGTTTTCAG CAACAAATTT
661 TTAGCGATGT CAAAAAAAGG AAAACTCCAT GCAGTGCCA AGTTCACAGA TGACTGCAAG
721 TTCAGGGAGC GTTTTCAAGA AAATAGCTAT AATACCTATG CCTCAGCAAT ACATAGAACT
781 GAAAAAACAG GGCGGAGTG GTATGTGGCC CTGAATAAAA GAGGAAAAGC CAAACGAGGG
841 TGCAGCCCCC GGGTTAAACC CCAGCATATC TCTACCCATT TTCTGCCAAG ATTCAAGCAG
```

TABLE 6-continued

```
 901 TCGGAGCAGC CAGAACTTTC TTTCACGGTT ACTGTTCCTG AAAAGAAAAA GCCACCTAGC
 961 CCTATCAAGC CAAAGATTCC CCTTTCTGCA CCTCGGAAAA ATACCAACTC AGTGAAATAC
1021 AGACTCAAGT TTCGCTTTGG ATAA
```

Human FGF6 gene coding sequence (1-208) (SEQ ID NO: 229)
(NM_020996,
which is hereby incorporated by reference in its entirety):

```
  45                                                ATGGCC CTGGGACAGA
  61 AACTGTTCAT CACTATGTCC CGGGGAGCAG GACGTCTGCA GGGCACGCTG TGGGCTCTCG
 121 TCTTCCTAGG CATCCTAGTG GGCATGGTGG TGCCCTCGCC TGCAGGCACC CGTGCCAACA
 181 ACACGCTGCT GGACTCGAGG GGCTGGGGCA CCCTGCTGTC CAGGTCTCGC GCGGGGCTAG
 241 CTGGAGAGAT TGCCGGGGTG AACTGGGAAA GTGGCTATTT GGTGGGGATC AAGCGGCAGC
 301 GGAGGCTCTA CTGCAACGTG GGCATCGGCT TCCACCTCCA GGTGCTCCCC GACGGCCGGA
 361 TCAGCGGGAC CCACGAGGAG AACCCCTACA GCCTGCTGGA AATTTCCACT GTGGAGCGAG
 421 GCGTGGTGAG TCTCTTTGGA GTGAGAAGTG CCCTCTTCGT TGCCATGAAC AGTAAAGGAA
 481 GATTGTACGC AACGCCCAGC TTCCAAGAAG AATGCAAGTT CAGAGAAACC TCCTGCCCA
 541 ACAATTACAA TGCCTACGAG TCAGACTTGT ACCAAGGGAC CTACATTGCC CTGAGCAAAT
 601 ACGGACGGGT AAAGCGGGGC AGCAAGGTGT CCCCGATCAT GACTGTCACT CATTTCCTTC
 661 CCAGGATCTA A
```

Human FGF9 gene coding sequence (1-208)(SEQ ID NO: 230)
(GenBank accession no. NM_002010,
which is hereby incorporated by reference in its entirety):

```
 838                                                          ATG
 841 GCTCCCTTAG GTGAAGTTGG GAACTATTTC GGTGTGCAGG ATGCGGTACC GTTTGGGAAT
 901 GTGCCCGTGT TGCCGGTGGA CAGCCCGGTT TTGTTAAGTG ACCACCTGGG TCAGTCCGAA
 961 GCAGGGGGGC TCCCCAGGGG ACCCGCAGTC ACGGACTTGG ATCATTTAAA GGGGATTCTC
1021 AGGCGGAGGC AGCTATACTG CAGGACTGGA TTTCACTTAG AAATCTTCCC CAATGGTACT
1081 ATCCAGGGAA CCAGGAAAGA CCACAGCCGA TTTGGCATTC TGGAATTTAT CAGTATAGCA
1141 GTGGGCCTGG TCAGCATTCG AGGCGTGGAC AGTGGACTCT ACCTCGGGAT GAATGAGAAG
1201 GGGGAGCTGT ATGGATCAGA AAAACTAACC CAAGAGTGTG TATTCAGAGA ACAGTTCGAA
1261 GAAAACTGGT ATAATACGTA CTCATCAAAC CTATATAAGC ACGTGGACAC TGGAAGGCGA
1321 TACTATGTTG CATTAAATAA AGATGGGACC CCGAGAGAAG GGACTAGGAC TAAACGGCAC
1381 CAGAAATTCA CACATTTTTT ACCTAGACCA GTGGACCCCG ACAAAGTACC TGAACTGTAT
1441 AAGGATATTC TAAGCCAAAG TTGA
```

Human FGF16 gene coding sequence (1-207) (SEQ ID NO: 231)
(GenBank accession no. NM_003868,
which is hereby incorporated by reference in its entirety):

```
   1 ATGGCAGAGG TGGGGGGCGT CTTCGCCTCC TTGGACTGGG ATCTACACGG CTTCTCCTCG
  61 TCTCTGGGGA ACGTGCCCTT AGCTGACTCC CCAGGTTTCC TGAACGAGCG CCTGGGCCAA
 121 ATCGAGGGGA AGCTGCAGCG TGGCTCACCC ACAGACTTCG CCCACCTGAA GGGGATCCTG
 181 CGGCGCCGCC AGCTCTACTG CCGCACCGGC TTCCACCTGG AGATCTTCCC CAACGGCACG
 241 GTGCACGGGA CCCGCCACGA CCACAGCCGC TTCGGAATCC TGGAGTTTAT CAGCCTGGCT
 301 GTGGGGCTGA TCAGCATCCG GGGAGTGGAC TCTGGCCTGT ACCTAGGAAT GAATGAGCGA
 361 GGAGAACTCT ATGGGTCGAA GAAACTCACA CGTGAATGTG TTTTCCGGGA ACAGTTTGAA
 421 GAAAACTGGT ACAACACCTA TGCCTCAACC TTGTACAAAC ATTCGGACTC AGAGAGACAG
 481 TATTACGTGG CCCTGAACAA AGATGGCTCA CCCCGGGAGG GATACAGGAC TAAACGACAC
 541 CAGAAATTCA CTCACTTTTT ACCCAGGCCT GTAGATCCTT CTAAGTTGCC CTCCATGTCC
 601 AGAGACCTCT TCACTATAG GTAA
```

Human FGF20 gene coding sequence (1-211) (SEQ ID NO: 232)
(GenBank accession no. NM_019851,
which is hereby incorporated by reference in its entirety):

```
 134            ATGGCTC CCTTAGCCGA AGTCGGGGGC TTTCTGGGCG GCCTGGAGGG
 181 CTTGGGCCAG CAGGTGGGTT CGCATTTCCT GTTGCCTCCT GCCGGGGAGC GGCCGCCGCT
 241 GCTGGGCGAG CGCAGGAGCG CGGCGGAGCG GAGCGCGCGC GGCGGGCCGG GGGCTGCGCA
 301 GCTGGCGCAC CTGCACGGCA TCCTGCGCCG CCGGCAGCTC TATTGCCGCA CCGGCTTCCA
 361 CCTGCAGATC CTGCCCGACG GCAGCGTGCA GGGCACCCGG CAGGACCACA GCCTCTTCGG
 421 TATCTTGGAA TTCATCAGTG TGGCAGTGGG ACTGGTCAGT ATTAGAGGTG TGGACAGTGG
 481 TCTCTATCTT GGAATGAATG ACAAAGGAGA ACTCTATGGA TCAGAGAAAC TTACTTCCGA
 541 ATGCATCTTT AGGGAGCAGT TTGAAGAGAA CTGGTATAAC ACCTATTCAT CTAACATATA
 601 TAAACATGGA GACACTGGCC GCAGGTATTT TGTGGCACTT AACAAAGACG GAACTCCAAG
 661 AGATGGCGCC AGGTCCAAGA GGCATCAGAA ATTTACACAT TTCTTACCTA GACCAGTGGA
 721 TCCAGAAAGA GTTCCAGAAT TGTACAAGGA CCTACTGATG TACACTTGA
```

As noted above, the chimeric protein includes a portion of a paracrine FGF coupled to a C-terminal region derived from an FGF23. FGF23 is an endocrine FGF that was cloned by Itoh et al. at Kyoto University (WO 01/66596 to Itoh et al., which is hereby incorporated by reference in its entirety). FGF23 mRNA is expressed mainly in the brain, preferentially in the ventrolateral thalamic nucleus. It is also expressed in the thymus at low levels (Yamashita et al., "Identification of a Novel Fibroblast Growth Factor, FGF-23, Preferentially Expressed in the Ventrolateral Thalamic Nucleus of the Brain," *Biochem Biophys Res Comm* 277(2): 494-498 (2000), which is hereby incorporated by reference in its entirety). The tissue with the highest level of FGF23 expression is bone (osteocytes and osteoblasts), where it is highly expressed during phases of active bone remodeling (Riminucci et al., "FGF-23 in Fibrous Dysplasia of Bone and its Relationship to Renal Phosphate Wasting," *J Clin Invest* 112:683-692 (2003), which is hereby incorporated by reference in its entirety). Expression of FGF23 in dendritic cells has also been reported (Katoh et al., "Comparative Genomics on Mammalian Fgf6-Fgf23 Locus.," *Int J Mol Med* 16(2):355-358 (2005), which is hereby incorporated by reference in its entirety). See also Zhang et al., "Receptor Specificity of the Fibroblast Growth Factor Family," *J Biol Chem* 281(23):15694-15700; Yu et al., "Analysis of the Biochemical Mechanisms for the Endocrine Actions of Fibroblast Growth Factor-23," *Endocrinology* 146(11): 4647-4656, which are hereby incorporated by reference in their entirety.

In one embodiment the C-terminal region of the FGF23 molecule includes an α-Klotho-FGFR complex binding domain. In one embodiment, the C-terminal region is from human FGF23 having the amino acid sequence of SEQ ID NO: 233 (GenBank accession no. AAG09917, which is hereby incorporated by reference in its entirety), as follows:

```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

In one embodiment, the C-terminal portion from FGF23 of the chimeric protein according to the present invention includes an amino acid sequence beginning at any of amino acid residues 161-180 and ending at any of amino acid residues 200-251 of SEQ ID NO: 233. In one embodiment, the C-terminal portion from FGF23 of the chimeric protein according to the present invention comprises amino acid residues 161-200, 162-200, 163-200, 164-200, 165-200, 166-200, 167-200, 168-200, 169-200, 170-200, 171-200, 172-200, 173-200, 174-200, 175-200, 176-200, 177-200, 178-200, 179-200, 180-200, 161-205, 162-205, 163-205, 164-205, 165-205, 166-205, 167-205, 168-205, 169-205, 170-205, 171-205, 172-205, 173-205, 174-205, 175-205, 176-205, 177-205, 178-205, 179-205, 180-205, 161-251, 162-251, 163-251, 164-251, 165-251, 166-251, 167-251, 168-251, 169-251, 170-251, 171-251, 172-251, 173-251, 174-251, 175-251, 176-251, 177-251, 178-251, 179-251, or 180-251 of SEQ ID NO: 233.

In one embodiment, the C-terminal portion from FGF23 of the chimeric protein according to the present invention includes one or more deletions or substitutions while retaining the ability to bind the binary α-Klotho-FGFR complex. In one embodiment, the C-terminal portion from FGF23 of the chimeric protein according to the present invention includes a substitution at amino acid residues (or amino acid residues corresponding to) R176 and/or R179 of SEQ ID NO:233. In one embodiment, the R176 substitution is a R176Q/W substitution and/or the R179 substitution is a R179Q/W substitution. In one embodiment, the C-terminal portion from FGF23 of the chimeric protein according to the present invention includes amino acid residues 161-200, 162-200, 163-200, 164-200, 165-200, 166-200, 167-200, 168-200, 169-200, 170-200, 171-200, 172-200, 173-200, 174-200, 175-200, 176-200, 177-200, 178-200, 179-200, 180-200, 161-205, 162-205, 163-205, 164-205, 165-205, 166-205, 167-205, 168-205, 169-205, 170-205, 171-205, 172-205, 173-205, 174-205, 175-205, 176-205, 177-205, 178-205, 179-205, 180-205, 161-251, 162-251, 163-251, 164-251, 165-251, 166-251, 167-251, 168-251, 169-251, 170-251, 171-251, 172-251, 173-251, 174-251, 175-251, 176-251, 177-251, 178-251, 179-251, or 180-251 of SEQ ID NO: 233, where one or both of R176 and R179 are substituted. In one embodiment, the R176 substitution is a R176Q/W substitution and/or the R179 substitution is a R179Q/W substitution.

In one embodiment, the FGF23 according to the present invention is from a mammal. In one embodiment, the FGF23 according to the present invention is from a vertebrate. It will be understood that this includes orthologs of human FGF23, or a polypeptide or protein obtained from one species that is the functional counterpart of a polypeptide or protein from a different species. In one embodiment of the present invention, the FGF23 according to the present invention is from *Gorilla gorilla, Nomascus leucogenys, Macaca mulatta, Macaca fascicularis, Pan troglodytes, Callithrix jacchus, Loxodonta Africana, Erinaceus telfairi, Erinaceus europaeus, Otolemur garnettii, Oryctolagus cuniculus, Equus caballus, Ailuropoda melanoleuca, Ochotona princeps, Bos taurus, Sus scrofa, Canis lupus familiaris, Cavia porcellus, Cricetulus griseus, Tupaia belangeri, Rattus norvegicus, Mus musculus, Pteropus vampyrus, Myotis lucifugus, Sarcophilus harrisii, Monodelphis domestica, Dasypus novemcinctus, Macropus eugenii, Taeniopygia guttata, Gallus gallus, Meleagris gallopavo, Anolis carolinensis, Latimeria chalumnae, Xenopus silurana tropicalis, Felis catus, Pelodiscus sinensis, Mustela putorius furo, Microcebus murinus, Pongo abelii, Sorex araneus, Tetraodon nigroviridis, Oreochromis niloticus,* or *Danio rerio.*

In one embodiment, FGF23 according to the present invention is from a non-human FGF23 (or an FGF23 ortholog) having an amino acid sequence as shown in Table 7. The portions of an ortholog of human FGF23 of a chimeric protein according to the present invention include portions corresponding to the above-identified amino acid sequences of human FGF23. Corresponding portions may be determined by, for example, sequence analysis and structural analysis.

TABLE 7

Amino acid sequence of *Gorilla gorilla* (gorilla)
FGF23 (SEQ ID NO: 234)
(Ensembl accession no. ENSGGOP00000002917,
which is hereby incorporated by reference in its entirety):

```
  1 MLGARLRLWV CALCSVCSLS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTRS
181 AEDDSERDPL NVLKPRARMT PAPASCSQEL PSAEDNSPMA SDPLGVVRGG RVNTYAGGTG
241 PEGCRPFPKF I
```

Amino acid sequence of *Nomascus leucogenys*
(Northern white-cheeked gibbon) FGF23 (SEQ ID
NO: 235) (GenBank accession no. XP_003273749,
which is hereby incorporated by reference in its entirety):

```
  1 MLGARLRLWV CALCSVCSMS VLRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFQHQTL
121 ENGYDVYHSP QHHFLVSLGR AKRAFLPGMN PPPYSQFLSR RNEIPLLHFN TPTPRRHTRS
181 AEDDSERDPL NVLKPRARMT PAPASCSQEL LSSEDNSPMA SDPLGVVRGG RVNTHAGGTG
241 PEGCRPFPKF I
```

Amino acid sequence of *Macaca mulatta* (rhesus monkey)
FGF23 (SEQ ID NO: 236) (GenBank accession
no. NP_001181066,
which is hereby incorporated by reference in its entirety):

```
  1 MLGARLRLWV CALCSVCSMS VIRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFRHWTL
121 ENGYDVYHSP QHHFLVSLGR AKRAFLPGMN PPPYSQFLSR RNEIPLIHFN TPRPRRHTRS
181 AEDDSERDPL NVLKPRARMT PAPASCSQEL PSAEDNSPVA SDPLGVVRGG RVNTHAGGTG
241 PEACRPFPKF I
```

Amino acid sequence of *Macaca fascicularis*
(crab-eating macaque) FGF23 (SEQ ID NO:
237) (GenBank accession no. EHH66001,
which is hereby incorporated by reference in its entirety):

```
  1 MLGARLRLWV CALCSVCSMS VIRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFRHWTL
121 ENGYDVYHSP QHHFLVSLGR AKRAFLPGMN PPPYSQFLSR RNEIPLIHFN TPRPRRHTRS
181 AEDDSERDPL NVLKPRARMT PAPASCSQEL PSAEDNSPVA SDPLGVVRAG RVNTHAGGTG
241 PEACRPFPKF I
```

Amino acid sequence of *Pan troglodytes* (chimpanzee)
FGF23 (SEQ ID NO: 238) (GenBank
accession no. XP_001157070,
which is hereby incorporated by reference in its entirety):

```
  1 MLGARLRLWV CALCSVCSVS VLRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFQHQTL
121 ENGYDVYYSP QYHFLVSLGR AKRAFLPSMN PPPYSQFLSR RNEIPLIHFN TPIPRRHTRS
181 AEDDSERDPL NVLKPRARMT PAPASCSQEL PSAEDNSPMA SDPLGVVRGG RVNTHAGGTG
241 PEGCRPFPKF I
```

Amino acid sequence of *Callithrix jacchus*
(white-tufted-ear marmoset) FGF23 (SEQ ID
NO: 239) (GenBank accession no. XP_002752281,
which is hereby incorporated by reference in its entirety):

```
  1 MLGARLRLWV CALCSVCSMS VLRAYPNASP LLASSWGGLI HLYTATARNS YHLQIHKNGH
 61 VDGAPHQTIY SALLIRSEDA GFVVITGVMS RRYLCMDFRG NIFGSHYFNP ENCRFRPQRL
121 ENGYDVYQSP QHHFLVSLGR AKRAFLPGMN PPPYSQFLSR RNEIPLIHFN TPKPRRHTRS
181 AEDDPELDPL NVLKSRVRMT PAPASCSQEL LSAEDNSPVG SDPLGMVRGG RVNSHAEGTG
241 PEGCSPFPKL I
```

Amino acid sequence of *Loxodonta africana*
(elephant) FGF23 (SEQ ID NO: 240)
(GenBank accession no. XP_003410677,
which is hereby incorporated by reference in its entirety):

```
  1 MLGARLRLWV CTLCSACSMC SVRAYPNASP LLHSSWGGLT HLYTATARNS YHLQIHKDGH
 61 VDGTPDQTIY SALIIRSEEA GFVVITGVMS RRYLCMDFRG NIFGSHYFNP ENCRFKHWTL
121 ENGYDVYHSP QHHFLVSLGR VKKAFLPGMN PPPYSQFLSR RNEIPLIYFN TPKPRRHTRS
181 AEDDSERDPL NVLKPRPRMT PAPASCSQEL LSAEDNSVVA NDPLGVVRSN RVNTHAGGIG
241 VERCRPFPKF I
```

TABLE 7-continued

Amino acid sequence of *Erinaceus telfairi*
(lesser hedgehog tenrec) FGF23 (SEQ ID NO:
241) (Ensembl accession no. ENSETEP00000001298,
which is hereby incorporated by reference in its entirety):

```
  1 MLGAHLRLWV CALCSVSAMY HVRAYPNASP LLGTSWAGLT HLYTATARNS FHLQIHKDGH
 61 VDGTPHQTIY SALMIRSEDS GFVVITGVMS RRYLCMDFRG NIFGSHYFTA DSCRFRQRTL
121 ENGYDVYHSP QHHFLISLGR AKRVFLPGMN PPPYSQFLSR RNEIPLIHFN TPRPRRHTRS
181 AEEEVEQDPL NVLKPRPRMT PAPASCSQEL PSAEDNSALA SDPLGVVRGK KLNTHAVGMG
241 AERCRPFPKF
```

Amino acid sequence of *Erinaceus europaeus*
(hedgehog) FGF23 (SEQ ID NO: 242) (Ensembl
accession no. ENSEEUP00000007211,
which is hereby incorporated by reference in its entirety):

```
  1 MLGAHLGLVV CALVSRAYPN ASPLLGFSWG GLTHLYTATA RNSYHLQIHK DGHVDGSPQQ
 61 TIY------- --AGFVMITG VMSRRYLCMD FRSNIFGSHH FAPESCRFRH RTLENGYDVY
121 HSPQHHFLVS LGRAKRAFLP GTNPPPYSQF LSRRNEVPLI HFNTPRPRRH TRSAEDNSEL
181 DPLNVLKPRP RMTPAPASCS QELPSAEDNS MVASDPLGVV RANRVNTHAG GLGVDKCRPF
241 PKFI
```

Amino acid sequence of *Otolemur garnettii*
(bushbaby) FGF23 (SEQ ID NO: 243) (Ensembl
accession no. ENSOGAP00000004657,
which is hereby incorporated by reference in its entirety):

```
  1 MLGTCLRLWV CALCSVCSVS IVRAYPNASP LLSSSWGGLT HLYTASARNS YHLQIHKDGH
 61 VDGTPHQTIY SALMIRSEDA GFVVITGVMS RRYLCMDFKG NIFGSHSFHP ESCRFRHRTL
121 ENGYDVYLSP QHHFLVSLGR SKRPFLPGMN PPPFSQFLSR RNDIPLIHFN TPRPRRHTRS
181 AEDNDSELDP LNVLKPRPRA TPGPASCSQE LPSAEDNSLV ASDPLGVVRG NRVNAHAGRA
241 GLDRCRPFPR YF
```

Amino acid sequence of *Oryctolagus cuniculus*
(rabbit) FGF23 (SEQ ID
NO: 244) (GenBank accession no. XP_002712872,
which is hereby incorporated by reference in its entirety):

```
  1 MLGARLLRLL VCALGSVCSW CVVRAYPDTS PLLSSSWAGL THLYTATARN SYHLQIHKDG
 61 QVDGTPHQTI YSALMIRSED AGFVVITGVM SRRYLCMDFR GNIFGSHYFD PQNCRFRHRT
121 LENGYDVYHS PEHHFLVSLG RAKRPFLPGM NPPPYSQFLS RRNEIPLIHF NTPRPRRHTR
181 SAEDAWEQDP LNVLKPRFRL TPAPASCSQE APSAEDNGLV ASDPFGVLRG NRVNMHGDRM
241 GPERCHHFPK FI
```

Amino acid sequence of *Equus caballus*
(horse) FGF23 (SEQ ID NO: 245) (GenBank
accession no. XP_001491469,
which is hereby incorporated by reference in its entirety):

```
  1 MSGPCLGLLV YVLCSAVKAY PNASPLLDSS WGSLTHLYTA TARNSYHLQI HKDGHVDGTP
 61 HQTIYSALMI RSEDAGFVVI TGVMSRRYLC MDFRGNIFGS HHFSPESCSF RQRTLENGYD
121 VYHSPQHRFL VSLGRAKRAF LPGTNPPPYS QFLSRRNEIP LVHFNTPRPR RHTRSAEDNS
181 ERDPLNVLKP RPRMTPAPAS CSQELPSAED NSVLASDPLG VVRGNRVNTH AGGAGVERCR
241 PFPKFF
```

Amino acid sequence of *Ailuropoda melanoleuca*
(giant panda) FGF23 (SEQ ID NO: 246)
(GenBank accession no. XP_002920496,
which is hereby incorporated by reference in its entirety):

```
  1 MSGTRLGLLV SVLCWVGRAY PNTSPLLGSS WGGLTHLYTA SARNSYHLQI HKDGHVDGTP
 61 HQTIYSALMI RSEDAGFVVI TGVMSRRYLC MDLRGNIFGS HLFSPESCRF RQRTLENGYD
121 VYHSPQHRFL VSLGQAKRTF LPGTNPPPYS QFLSRRNEIP LIHFNTPRPR RHTRSAEDTE
181 RDPLNVLKPR PRMTPAPASC SQELPSAEDN SVVASDPLGV LRGNRVNAHA GGMGVDRCRP
241 FPKFI
```

Amino acid sequence of *Ochotona princeps*
(pika) FGF23 (SEQ ID NO: 247)
(Ensembl accession no. ENSOPRP00000006546,
which is hereby incorporated by reference in its entirety):

```
  1 MLGGLGLWVC VLGSVCSWRG VRAYPDTSPL LGSSWTGLTH LYTATARNSF HLQIHKDGHV
 61 DGTPQQTIYS ALMIRSEDAG FVVITGVMSR RYLCMDFRGN IFGSHYFEPQ NCRFQQRTLE
121 NGYDIYHSPQ HDFLVSLGRA KRPFLPGMNP PPYSQFLSRR NEIPLILFNT PRPRRHTRSA
181 EEGWERDPLN VLKSRPRMTP APASCSREAP SAEDDGLLAS DPMGVLRGHR VDHGGGTGR
241 DRCRPFPRFI
```

TABLE 7-continued

Amino acid sequence of *Bos taurus* (cattle)
FGF23 (SEQ ID NO: 248) (GenBank
accession no. XP_002687926,
which is hereby incorporated by reference in its entirety):

```
  1 MLGARLGLWV CTLSCVVQAY PNSSPLLGSS WGGLTHLYTA TARNSYHLQI HGDGHVDGSP
 61 QQTVYSALMI RSEDAGFVVI TGVMSRRYLC MDFTGNIFGS HHFSPESCRF RQRTLENGYD
121 VYHSPQHRFL VSLGRAKRAF LPGTNPPPYA QFLSRRNEIP LPHFAATARP RRHTRSAHDS
181 GDPLSVLKPR ARATPVPAAC SQELPSAEDS GPAASDPLGV LRGHRLDVRA GSAGAERCRP
241 FPGFA
```

Amino acid sequence of *Sus scrofa* (pig)
FGF23 (SEQ ID NO: 249) (GenBank
accession no. XP_001926560,
which is hereby incorporated by reference in its entirety):

```
  1 MLGARLGLWV CTLCCAARAY PDTSPLLSSG WGGLTHLYTA TARNSYHLQI HKDGHVDGSP
 61 QQTIYSALMI RSEDAGFVVI TGVMSRRYLC MDLRGNIFGS LHFSPESCRF RQRTLENGYD
121 VYHSPHYRFL VSLGRAKRAF LPGTNPPPYA QFLSRRNEIP LLHFATARPR RHTRSAHDGG
181 DPLSVLKPRA RATPAPVSCS RELPSAEDGG PAASDPLGVL RGQRLDARAG VGGAERCRPF
241 PSFA
```

Amino acid sequence of *Canis lupus
familiaris* (dog) FGF23 (SEQ ID NO: 250) (GenBank
accession no. XP_854580,
which is hereby incorporated by reference in its entirety):

```
  1 MWTVEFFLFD VTGPPFKSLR EKRRESSLGL SRKIPTKKRR KRPVRHSRGI KEAVSGFKLQ
 61 PAIQRAVMSG TRLGFLVSVL CWVVRAYSNT SPLLGSSWGS LTHLYTATAR NSYHLQIHKD
121 GHVDGTPHQT IYSALMIRSE DAGFVVITGV MSRRYLCMDF RGNIFGSHLF SPESCRFRQR
181 TLENGYDVYH SPQHRFLVSL GQAKRAFLPG TNPPPYSQFL SRRNEIPLVH FHTPRPRRHT
241 RSAEAPERDP LNVLKPRPRL APAPASCSQE LPSAEDPGAP ASDPLGVLRG HRANARAGGV
301 GVDRCRAFPT PI
```

Amino acid sequence of *Cavia porcellus*
(domestic guinea pig) FGF23 (SEQ ID NO: 251)
(GenBank accession no. XP_003463346,
which is hereby incorporated by reference in its entirety):

```
  1 MLGTCLGLLA CTVSLVGAYP DASPLLTSSW GGLIHLYTAT ARNSYHLQIH KDGHIDGAPY
 61 PTIYSALMIR SEDAGFVVIT GVTSRRFLCM DFRGNIFGSH HFNPQDCRFQ HRTLENGYDV
121 YLSPEHHFLI SLGRTKKFFL PGTNPPPYSQ FLSRRNELPL ARFVTPGPRR HTRSAEEDQG
181 RDPLSVLKLR PRATPAPASC SQELPSAEDA AQASDPLGVL RGARVHAHGG PRPARCRPGP
241 GAK
```

Amino acid sequence of *Cricetulus griseus*
(Chinese hamster) FGF23 (SEQ ID NO: 252)
(GenBank accession no. XP_003496132,
which is hereby incorporated by reference in its entirety):

```
  1 MLGTCLRLLV GVLCSACSLG TVRAYPDTSP LLGSNWGSLT HLYTATARNS YHLQIHKDGR
 61 VDGTPHQTIY SALMIRSEDA GFVIITGAVT RRFLCMDLRG NIFGSHHFSP ENCRFRQRTL
121 ENGYDVYLSP QHHYLVSLGR AKRPFEPGTN PPPFSQFLAR RNEVPLLRFH TARPRRHTRS
181 AEDPPEWDPL NVLKPRPRAT PVPVSCSREL PSAEEGDLAA SDPLGVLRRG RGDARGGAGG
241 VDRCRPFPRF A
```

Amino acid sequence of *Tupaia belangeri*
(tree shrew) FGF23 (SEQ ID NO: 253)
(Ensembl accession no. ENSTBEP00000014220,
which is hereby incorporated by reference in its entirety):

```
  1 ALLIRPEEAG FAVITGVMSR RYLCMDFRGN IFGSHLFSPE SCRFRQRALE NGYDVYHHPQ
 61 HHFLVSLGRP KRAFVPGTNP PPYSQFLARK NEIPLIHFNT PKPRRHTRSA EDNSGRDPLN
121 VLKPRPRMTP APASCSQELP SAEDNSVVAS DPLGVLRGNR VNTHAGGWGV DRCRPFPRFI
```

Amino acid sequence of *Rattus norvegicus*
(Norway rat) FGF23 (SEQ ID NO: 254)
(GenBank accession no. NP_570110,
which is hereby incorporated by reference in its entirety):

```
  1 MLGACLRLLV GALCTVCSLG TARAYSDTSP LLGSNWGSLT HLYTATARNS YHLQIHRDGH
 61 VDGTPHQTIY SALMITSEDA GSVVIIGAMT RRFLCMDLRG NIFGSYHSP ENCRFRQWTL
121 ENGYDVYLSP KHHYLVSLGR SKRIFQPGTN PPPFSQFLAR RNEVPLLHFY TARPRRHTRS
181 AEDPPERDPL NVLKPRPRAT PIPVSCSREL PSAEEGPAA SDPLGVLRRG RGDARRGAGG
241 TDRCRPFPRF V
```

TABLE 7-continued

Amino acid sequence of *Mus musculus*
(house mouse) FGF23 (SEQ ID NO: 255)
(GenBank accession no. AAI20606,
which is hereby incorporated by reference in its entirety):

```
  1 MLGTCLRLLV GALCTVCSLG TARAYPDTSP LLGSNWGSLT HLYTATARTS YHLQIHRDGH
 61 VDGTPHQTIY SALMITSEDA GSVVITGAMT RRFLCMDLHG NIFGSLHFSP ENCKFRQWTL
121 ENGYDVYLSQ KHHYLVSLGR AKRIFQPGTN PPPFSQFLAR RNEVPLLHFY TVRPRRHTRS
181 AEDPPERDPL NVLKPRPRAT PVPVSCSREL PSAEEGGPAA SDPLGVLRRG RGDARGGAGG
241 ADRCRPFPRF V
```

Amino acid sequence of *Pteropus vampyrus*
(megabat) FGF23 (SEQ ID NO: 256)
(Ensembl accession no. ENSPVAP00000000222,
which is hereby incorporated by reference in its entirety):

```
  1 MPRGSLGLLV CILCCRAYPD ASPLLSSSLG GLIHLYTATA RNGYHLQIHK DGHVDGTPHQ
 61 TIYSALMIRS EDSGFVVIIG VMSRRYLCMD FKGNIFGSHH FSPESCKFRQ RTLENGYDVY
121 HSPQHHFFVS LGRAKRAFLP GTNPPPYSQF LSRRNEIPLF QFNTPRPRRH TRSVEDYKDY
181 DLDPDPLKVL RPRPRWVPAL PSCSQELPSA EDNSVVANDP LGVLRPSRVN IYRERMGKGR
241 CRPHPEFV
```

Amino acid sequence of *Myotis lucifugus*
(microbat) FGF23 (SEQ ID NO: 257)
(Ensembl accession no. ENSMLUP00000017312,
which is hereby incorporated by reference in its entirety):

```
  1 MPGARLGLLV CVLALRCVVR AYPNASPLLG SSWGGLTHLY TASARNSYHL QIHKDGHVDG
 61 TPHQTIYSAL MIRSEDAGFV VITGVMSRRY LCMDFRGNIF GSLFFSPSNF SFLEWKKESG
121 MDHWISRQTH FLVSPGPSQE GLPAGHNPPP YSQFLSRNEI PLFHFNTPAP RRHTRSAEEN
181 SAADPLVVLK PVPRLTPPPA SCSRELSSAE DNSVAAHDPL GVLRSSNRVN SHAPPPGPPR
241 TRQGMLLV
```

Amino acid sequence of *Sarcophilus harrisii*
(Tasmanian devil) FGF23 (SEQ ID NO: 258)
(Ensembl accession no. ENSSHAP00000010151,
which is hereby incorporated by reference in its entirety):

```
  1 MSGGCLRLLF CALCSLRAIQ AFPNASPLLS LGWGGLTHLY TATARNSYHL QIHKDGHVDG
 61 SPHQTIYSAL MIRSEDAGLV IITGVMSRRY LCMDIRGNIF GSHFFSPDNC RFKHRTLENG
121 YDIYHSPQNN FLISLGKAKR AFLPGMNPPP YSQFLSRRNE IPIIHFNTPE PHRHTRSAEN
181 SPDLDPMNVL KLRPRITPCS QELHSAEENS VVDDDPLEVL RNSNRLKPYP GRMSLERCLH
241 VPKAA
```

Amino acid sequence of *Monodelphis domestica*
(gray short-tailed opossum) FGF23 (SEQ ID NO:
259) (GenBank accession no. XP_001372436,
which is hereby incorporated by reference in its entirety):

```
  1 MANCREKELE MYICALMIRS EDAGLVIITG VMSRRYLCMD IRGNIFGSHF FNPDNCKFKH
 61 RTLENGYDIY HSPQNNFLIS LGKAKRAFLP GMNPPPYSQF LSRKNEIPII HFNTPEPHRH
121 TRSAENSPDL DPMNVLKPRP RMTPCSQELY SAEENSVVDD DPLEVLRNSN RLKPFPGRLG
181 LERCHHVPKT D
```

Amino acid sequence of *Dasypus novemcinctus*
(armadillo) FGF23 (SEQ ID NO: 260) (Ensembl
accession no. ENSDNOP00000004491,
which is hereby incorporated by reference in its entirety):

```
  1 ALMISSEDAG FVVITGVMSR RYLCMDFRGN IFGSHDFTPD SCRFRQRTLE NGYDVYHSPQ
 61 HHFLVSLGRA KRAFQPGSNP PPYSQFLSRR NEIPLMRFST PRPRRHTRSA QDHADPDPLR
121 VLKPRLRLTP APASCSQELP SDEDDGAVAS DPLRVVLGRR PHARAAGAGG ERCRPGPQLS
```

Amino acid sequence of *Macropus eugenii*
(wallaby) FGF23 (SEQ ID NO: 261)
(Ensembl accession no. ENSMEUP00000003725,
which is hereby incorporated by reference in its entirety):

```
  1 ALMIRSEDAG LVIISGVMSR RYLCMDLRGN IFGSHFFSPD NCRFKHRTLE NGYDIYHSPQ
 61 NNLLISLGKA KRAFLPGMNP PPYSQFLSRR NEIPIIHFNT PEPRRHTRSA ENSPDLDPMN
121 VLKPRPRVTP CSQELRSAEE NSVVDDDPLE VLRNSNRLKP YPGRMSLERC LQVPKAA
```

Amino acid sequence of *Taeniopygia guttata*
(zebra finch) FGF23 (SEQ ID NO: 262) (GenBank
accession no. XP_002190520

```
  1 MEWRATLQGI PCSSLLLLLC SLKASLAFPN SSPLLSPSWG NGDRLMHLYT DTERSSFHLQ
 61 INADGYIDGA PHQTIYSALM IKSEGAGSVI ITGVKSGRYL CMDMKGNIFG SHYFSQEDCM
121 FNHRTLENGY DVYQSPKHHF LVSLGRVKQV FSPGMNPPPY SQFLSRKNEI PLFRFNTPEP
```

TABLE 7-continued

```
181 HRHTRSADVD PVDPHQILVP QRKTPVFGSL QQQPADFPHM PREPMRINQN DVVNPDDPHA
241 MMEARRYPSP RFYITR
```

Amino acid sequence of *Gallus gallus*
(chicken) FGF23 (SEQ ID NO: 263)
(GenBank accession no. XP_425663,
which is hereby incorporated by reference in its entirety):

```
  1 MPHTSPCSCL EYMLLVLCIL KAAVAFPNSS PLLNPSWGNG DQLMHLYTST ERNSFHLQIN
 61 ADGHINGVPH QTIYSALMIK SEGAGCVIIT GVKSGRYLCM DMKGDIFGSY YFSQEDCVFN
121 QRTLENGYDV YQSPKHNFLV SLGRTKQVFF PGMNPPPYSQ FLSRRNEIPL FRFNTPEPHR
181 NTRSADVDPL DPHQILVPQR KVSALGSQLQ LQMDFSHVPR EPMRVNQNDV VNPDDPHAMM
241 DARRYASPRF YITR
```

Amino acid sequence of *Meleagris gallopavo*
(turkey) FGF23 (SEQ ID NO: 264) (GenBank
accession no. XP_003202623,
which is hereby incorporated by reference in its entirety):

```
  1 MPHTSPCSCL EYMLLVLCIL KAAVSFPNSS PLLNPSWGNG DQLMHLYTST ERNSFHLQIN
 61 ADGHISGVPY QTIYSALMIK SEGAGSVIIT GVKSGRYLCM DMKGDIFGSH YFSQEDCVFN
121 QRTLENGYDV YQSPKHNFLV SLGRTKQVFF PGMNPPPYSQ FLSRRNEIPL FRFNTPEPHR
181 NTRSADVDPM DPHQILVPQR KVSAIESQLQ LQMDFSHVPR EPMRVNQNDV VNPDDPHAMM
241 DARRYASPRF YITR
```

Amino acid sequence of *Anolis carolinensis*
(green anole) FGF23 (SEQ ID NO: 265)
(GenBank accession no. XP_003221411,
which is hereby incorporated by reference in its entirety):

```
  1 MVQATLYSFL KYMLLATCSW KAIAAFPNAS PLLSLNWGNS DSLLHLYTST ARNSFHLQIH
 61 SNGYVDGSPY QTIYSALMIK SEVAGYVIIN GVKSGRFLCM DMNGNIFGSH FFSYEDCTFK
121 HWVLENGYDV YQSPKYNYLV SLGKAKQPLF PNMNPPPYSQ FLSRRNEIPL VQFNTPKPHR
181 HTRSANADPC GSIISSGNIA KENLQLQPLM YNTKMNSNSE DEDPNSAIIN RRFLSPRTDV
241 RS
```

Amino acid sequence of *Latimeria chalumnae*
coelacanth) FGF23 (SEQ ID NO: 266) (Ensembl
accession no. ENSLACP00000020506,
which is hereby incorporated by reference in its entirety):

```
  1 LESALLAFSM AIFYSFKAVS SFPNSSPLLN PVWGNTDNLI HLYTASETNS FHLQINSDGH
 61 VDGTPHQTAY SALLIKSEEA GSVVILGVKS GRYLCMDIKG NIIGLHHFSK EDCTFKQEGL
121 ENGFDVLRSP KHNILVSLDK TKRSYIPGMN LPPYSQFLSR QNEVALINFI NTPDIHRHSR
181 NVDVDPSDPH GMIIQPDVGV SFRKSSSLFS DLPRDSMRTS HNGMDMVDPA DPHGMLDSRR
241 RPSPRFFAR
```

Amino acid sequence of *Xenopus silurana*
tropicalis (western clawed frog) FGF23 (SEQ
ID NO: 267) (GenBank accession no.
XP_002940351,
which is hereby incorporated by reference in its entirety):

```
  1 MTKQQTRLGL VLTVLASIKV ISAFPNSSPI ISGGWGVPDR LMHLYTASDW NSFHLQINHD
 61 GSIDGTPTQT IYSAIMIKSE SAGHVVITGV KTNRYLCMDK SGNIFGYHDF NHDDCVFKHE
121 TLENNFDVYH SPKHNFVISL KEPKHHFRLG MDLPPYSQFL SLENEIPITR FNAPEPEMRI
181 PEGNFADPSD IIKNPRNWDF SQSIHNPFQD VWLPFPSGSL PIIRASLPII HNNVINTDDP
241 EEIVKMKRYR YFKR
```

Amino acid sequence of *Felis catus* (cat)
FGF23 (SEQ ID NO: 268) (Ensembl
accession no. ENSFCAP00000000128,
which is hereby incorporated by reference in its entirety):

```
  1 MSGTRLGLLV SVLCWVVRAY PNTSPLLGSS WGGLTHLYTA TARNSYHLQI HKDGHVDGTP
 61 HQTIYSALMI RSEDAGFVVI TGVMSQRYLC MDFRGNIFGS HLFSPESCRF RQRTLENGYD
121 VYHSPQHRFL VSLGPAKRAF LPGTNRMTPA PASCSQELPS AEDSGVVASD PLGVLRGNRV
181 NAHAGGMGVE RCRPFPKFN
```

Amino acid sequence of *Pelodiscus sinensis*
(Chinese softshell turtle) FGF23 (SEQ ID NO:
269) (Ensembl accession no. ENSPSIP00000012755,
which is hereby incorporated by reference in its entirety):

```
  1 MSQPSQCSCL NFMLFVLCSF KAIAAFPFFS SLLNPSWGET DSLIHLYTAT EKNSFHLQIN
 61 PDGYVDGTPH QTIYSALMIK SEDAGYVVIS GVKSGRYLCM DIKGNIFGSH YFSQEDCMFK
121 HRTLENGYDV YQSPKHNFLV SLGRNKQAFF PGMNLPPYSQ FLPRRNEIPL IRFNTPEPHR
181 HTRNADVDPL QILIPRGEAF DTGPQRLQTH FDHLPREPMR INPNDVVSPD DPLAMMDVRR
241 NASPRLYITR
```

TABLE 7-continued

Amino acid sequence of *Mustela putorius*
furo (Ferret) FGF23 (SEQ ID NO: 270) (Ensembl
accession no. ENSMPUP00000009243,
which is hereby incorporated by reference in its entirety):

```
  1 MSVTRLGLLV SVLCWVVRAY PNASPLLGSS WGGLTHLYTA TARNSYHLQI HKDGHVDGTP
 61 HQTIYSALMI RSEDAGFVVI TGVMSRRYLC MDFRGNIFGS HLFSPESCRF RQRTLENGYD
121 VYHSPQHRFL VSLGQAKRAF LPGTNPPPYS QFLSRRNEIP LIHFNTPRPR RHTRSAEDME
181 HDPLNVLKPR PRMTPAPASC SQELPSAEDN SVVASDPLGV LRGNRVNVHA GGMGVDRCRP
241 LPKFI
```

Amino acid sequence of *Microcebus murinus*
(Mouse lemur) FGF23 (SEQ ID NO: 271)
(Ensembl accession no. ENSMICP00000004444,
which is hereby incorporated by reference in its entirety):

```
  1 MLGACLRLWV CALCSVCGVS VVRAYPNASP LLASSWGGLI HLYTATARNS YHLQIHKDGH
 61 VDGTPHQTIY SALMIRSEDA GFVVITGVMS RRYLCMDFRG NIFGSHVFSA ESCRFRQRTL
121 ENGFDVYQSP QHHFLVSLGR AKGAFPAGAK PPPFPQFLPR GNEAPGRKTR GPEEKGAPHP
181 LRGVESGGRK GGAPPLCLER LSRARE
```

Amino acid sequence of *Pongo abelii*
(Orangutan) FGF23 (SEQ ID NO: 272)
(Ensembl accession no. ENSPPYP00000005881,
which is hereby incorporated by reference in its entirety)
(partial sequence corresponding to human
FGF23 residues 23 to 37 and 72 to 251):

```
  1 M--------- ---------- --RN--ESLP CLVFSIG--- ---------- ----------
 61 ---------- -ALMIRSEDA GFVVITGVMS RRYLCMDFRG NIFGSHYFNP ENCRFQHQTL
121 ENGYDVYHSP QHHFLVSLGR VKRAFLPGM- PPPYSQFLSR RNEIPLIHFN TPVPRRHTRS
181 AEDDTERDPL KVLKPRARMT PAPASCSQEL PSSEDNSPMA SDPLGVVRGG RVNTHAGGTG
241 PEGCRPFPKF I
```

Amino acid sequence of *Sorex araneus*
(Shrew) FGF23 (SEQ ID NO: 273)
(Ensembl accession no. ENSSARP00000007042,
which is hereby incorporated by reference in its entirety)
(partial sequence corresponding to human FGF23
residues 1 to 18, 28 to 70, 106 to 197, and 201 to 235):

```
  1 MWGLRLGLLV GLLGCVDR-- -------ASP MLASSWGGLT HLYTATARNS YHLQIHKDGL
 61 VDGSPQQTVY ---------- ---------- ---------- -----HHFSP ESCRFQQRTL
121 ENGYDVYQSP QHRFLVSLGR PKRAFQPGAN PPPYAQFLAR RNEVPLARFH TPAPRRHTRS
181 AHDNGDADPL NVLAPRA--- AAAASCSHEL PSAEDNSVVA SDPLGVIRSN RFRTH
```

Amino acid sequence of *Tetraodon nigroviridis*
(Tetraodon) FGF23 (SEQ ID NO: 274)
(Ensembl accession no. ENSTNIP00000014355,
which is hereby incorporated by reference in its entirety):

```
  1 MDVNRRIGVK DALLALLLAL LQGCPLGETA PNASPLVGSN WGNPRRYVHL QTSTDMSNFY
 61 LEIRLDGTVR KSTARTSYSV ILLKADTRER IAILGVKSNR YLCMDLEGSP FSSPTCIRDD
121 CLFNHSLLEN NRDVYYSSRT GILFNLEGSR QVFVVGQNVP QTSLFLPRTN TVPLERLLLH
181 RDKRNQVVDP SDPHRVAVGR AEEGSDSRAL QEDDADLEVE TEVEVGDDGR NASRERLQAP
241 SDHDPWGVFS SNPGSPRSSG TVG
```

Amino acid sequence of *Oreochromis niloticus*
(Tilapia) FGF23 (SEQ ID NO: 275)
(Ensembl accession no. ENSONIP00000000020,
which is hereby incorporated by reference in its entirety):

```
  1 MDVNRRMGMR DTVLALFLAV LQGFPLGDTV PNPSPLAGSN WGNPRRYVHL QTSTDLNNFY
 61 LEIRLDGSVR KTTSRSTYSV ILLKSEARDR VAILGVKSSR YLCMDLEGNP FSSPVCLRDD
121 CLFNHKLLEN NRDVYYSSRT GILFNLEGSR QVYSVGQNLP QTSLFLPRKN TVPLERLLLH
181 REKRNRGQTE EGSDSRAVPE ELEEREVEME TEIETEVGDD GRNVSREKLA APSSHDPWNV
241 HFSNPASPRS TGTVG
```

Amino acid sequence of *Danio rerio*
(Zebrafish) FGF23 (SEQ ID NO: 276) (Ensembl
accession no. ENSDARP00000067387,
which is hereby incorporated by reference in its entirety):

```
  1 MRCALSNLHM LHSSVLALWF TALQGLRPAD AAPNPSPLLG SNWGNPRRYI HLQTTSDLNN
 61 YYLEISPSGH VRKTTNRGSY SVILLKTESR DRLAIFGVKS NRFLCMDTGG TLFTSTICNK
121 EDCLFHHKLL ENHRDVYYST KHSILLNLDG DKQAFIAGQN LPQSSLFLSE KNTVPLERLQ
181 HRERRNQVN PTDPLNALRY AEESDSRAAQ EDDGDMDFEP SEGQNISRET LVSPSDDDPW
241 DLLHDTSPGS PRIAAIVG
```

In certain embodiments according to the present invention, the C-terminal portion of FGF23 of the chimeric protein of the present invention includes a polypeptide sequence that has at least 80%, at least 85%, at least 90%, at least 95%, at least 97%, or at least 99% amino acid sequence identity to the amino acid sequence of SEQ ID NO: 233.

It will be understood that the FGF23 according to the present invention may be from a nucleotide sequence that encodes an FGF23 protein (e.g., those encoding orthologs) from a mammal or even a non-mammalian species. For example, a nucleotide sequence encoding a mammalian or non-mammalian FGF23 protein according to the present invention may include, but is not limited to, those FGF-encoding nucleotide sequences shown in Table 8.

TABLE 8

Human FGF23 gene coding sequence (1-251) (SEQ ID NO: 277)
(GenBank accession no. AF263537,
which is hereby incorporated by reference in its entirety)

```
147                      ATGT TGGGGGCCCG CCTCAGGCTC TGGGTCTGTG
181 CCTTGTGCAG CGTCTGCAGC ATGAGCGTCC TCAGAGCCTA TCCCAATGCC TCCCCACTGC
241 TCGGCTCCAG CTGGGGTGGC CTGATCCACC TGTACACAGC CACAGCCAGG AACAGCTACC
301 ACCTGCAGAT CCACAAGAAT GGCCATGTGG ATGGCGCACC CCATCAGACC ATCTACAGTG
361 CCCTGATGAT CAGATCAGAG GATGCTGGCT TTGTGGTGAT TACAGGTGTG ATGAGCAGAA
421 GATACCTCTG CATGGATTTC AGAGGCAACA TTTTTGGATC ACACTATTTC GACCCGGAGA
481 ACTGCAGGTT CCAACACCAG ACGCTGGAAA ACGGGTACGA CGTCTACCAC TCTCCTCAGT
541 ATCACTTCCT GGTCAGTCTG GGCCGGGCGA AGAGAGCCTT CCTGCCAGGC ATGAACCCAC
601 CCCCGTACTC CCAGTTCCTG TCCCGGAGGA ACGAGATCCC CCTAATTCAC TTCAACACCC
661 CCATACCACG GCGGCACACC CGGAGCGCCG AGGACGACTC GGAGCGGGAC CCCCTGAACG
721 TGCTGAAGCC CCGGGCCCGG ATGACCCCGG CCCCGGCCTC CTGTTCACAG GAGCTCCCGA
781 GCGCCGAGGA CAACAGCCCG ATGGCCAGTG ACCCATTAGG GGTGGTCAGG GGCGGTCGAG
841 TGAACACGCA CGCTGGGGGA ACGGGCCCGG AAGGCTGCCG CCCCTTCGCC AAGTTCATCT
901 AG
```

Gorilla FGF23 gene coding sequence (1-251) (SEQ ID NO: 278)
(Ensembl accession no. ENSGGOT00000002983,
which is hereby incorporated by reference in its entirety)

```
1                        ATGT TGGGGGCCCG CCTCAGGCTC TGGGTCTGTG
35  CCTTGTGCAG CGTCTGCAGC TTGAGCGTCC TCAGAGCCTA TCCCAATGCC TCCCCACTGC
95  TCGGCTCCAG CTGGGGTGGC CTGATCCACC TGTACACAGC CACAGCCAGG AACAGCTACC
155 ACCTGCAGAT CCACAAGAAT GGCCATGTGG ATGGCGCACC CCATCAGACC ATCTACAGTG
215 CCCTGATGAT CAGATCAGAG GATGCTGGCT TTGTGGTGAT TACAGGTGTG ATGAGCAGAA
275 GATACCTCTG CATGGATTTC AGAGGCAACA TTTTTGGATC ACACTATTTC GACCCGGAGA
335 ACTGCAGGTT CCAACACCAG ACGCTGGAAA ACGGGTACGA CGTCTACCAC TCTCCTCAGT
395 ATCACTTCCT GGTCAGTCTG GGCCGGGCGA AGAGAGCCTT CCTGCCAGGC ATGAACCCAC
455 CCCCGTACTC CCAGTTCCTG TCCCGGAGGA ACGAGATCCC CCTCATTCAC TTCAACACCC
515 CCATACCACG GCGGCACACC CGGAGCGCCG AGGACGACTC GGAGCGGGAC CCCCTGAACG
575 TGCTGAAGCC CCGGGCCCGG ATGACCCCGG CCCCGGCCTC CTGTTCACAG GAGCTCCCGA
635 GCGCCGAGGA CAACAGCCCG ATGGCCAGTG ACCCATTAGG GGTGGTCAGG GGCGGTCGAG
695 TGAACACGTA CGCTGGGGGA ACGGGCCCGG AAGGCTGCCG CCCCTTCCCC AAGTTCATCT
755 AG
```

Northern white-cheeked gibbon FGF23 gene coding sequence
(1-251) (SEQ ID NO: 279) (GenBank accession no.
XM_003273701,
which is hereby incorporated by reference in its entirety)

```
140              A TGTTGGGGGC CCGCCTCAGG CTCTGGGTCT GTGCCTTGTG
181 CAGCGTCTGC AGCATGAGCG TCCTCAGAGC CTATCCCAAT GCCTCCCCAC TGCTCGGCTC
241 CAGCTGGGGT GGCCTGATCC ACCTGTACAC AGCCACAGCC AGGAACAGCT ACCACCTGCA
301 GATCCACAAG AATGGCCATG TGGATGGCGC ACCCCATCAG ACCATCTACA GTGCCCTGAT
361 GATCAGATCA GAGGATGCTG GCTTTGTGGT GATTACAGGT GTGATGAGCA GAAGATACCT
421 CTGCATGGAT TTCAGAGGCA ACATTTTTGG ATCACACTAT TTCAACCCGG AGAACTGCAG
481 GTTCCAACAC CAGACGCTGG AAAACGGGTA CGACGTCTAC CACTCTCCTC AGCATCACTT
541 CCTGGTCAGT CTGGGCCGGG CCAAGAGAGC CTTCCTGCCG GGCATGAACC CACCCCCGTA
601 CTCCCAGTTC CTGTCCCGGA GGAACGAGAT CCCCCTACTT CACTTCAACA CCCCCACACC
661 ACGGCGGCAC ACCCGGAGCG CCGAGGACGA CTCGGAGCGG GACCCCCTGA ACGTGCTGAA
721 ACCCCGGGCC CGGATGACCC CGGCCCCGGC CTCCTGCTCA CAGGAGCTCC TGAGCTCCGA
781 GGACAACAGC CCGATGGCCA GCGACCCATT AGGGGTGGTC AGGGGCGGTC GAGTGAACAC
841 GCACGCTGGG GAACGGGCC CGGAAGGCTG CCGCCCCTTC CCCAAGTTCA TCTAG
```

Rhesus monkey FGF23 gene coding sequence (1-251) (SEQ
ID NO: 280) (GenBank accession no. NM_001194137,
which is hereby incorporated by reference in its entirety)

```
69            AT GTTGGGGGCC CGCCTCAGGC TCTGGGTCTG TGCCTTGTGC AGCGTCTGCA
121 GCATGAGCGT CATCAGAGCC TATCCCAATG CCTCCCCATT GCTCGGCTCC AGCTGGGGTG
181 GCCTGATCCA CCTGTACACA GCCACAGCCA GGAACAGCTA CCACCTGCAG ATCCACAAGA
241 ATGGCCACGT GGATGGCGCA CCCCATCAGA CCATCTACAG TGCCCTGATG ATCAGATCAG
301 AGGATGCTGG CTTTGTGGTG ATTACAGGTG TGATGAGCAG AAGATACCTC TGCATGGATT
361 TCAGAGGCAA CATTTTTGGA TCACACTATT TCAACCCGGA GAACTGCAGG TTCCGACACT
421 GGACGCTGGA GAACGGCTAC GACGTCTACC ACTCTCCTCA GCATCACTTT CTGGTCAGTC
```

TABLE 8-continued

```
481 TGGGCCGGGC GAAGAGGGCC TTCCTGCCAG GCATGAACCC ACCCCCCTAC TCCCAGTTCC
541 TGTCCCGGAG GAACGAGATC CCCCTCATCC ACTTCAACAC CCCCAGACCA CGGCGGCACA
601 CCCGGAGCGC CGAGGACGAC TCGGAGCGGG ACCCCCTGAA CGTGCTGAAG CCCCGGGCCC
661 GGATGACCCC GGCCCCGGCC TCCTGCTCAC AGGAGCTCCC GAGCGCCGAG GACAACAGCC
721 CGGTGGCCAG CGACCCGTTA GGGGTGGTCA GGGGCGGTCG GGTGAACACG CACGCTGGGG
781 GAACGGGCCC GGAAGCCTGC CGCCCCTTCC CCAAGTTCAT CTAG
```

Crab-eating macaque FGF23 gene coding sequence (1-251) (SEQ
ID NO: 281) (GenBank accession no. ENSMMUT00000020999,
which is hereby incorporated by reference in its entirety)

```
  1            ATGTTG GGGGCCCGCC TCAGGCTCTG GGTCTGTGCC TTGTGCAGCG
 47 TCTGCAGCAT GAGCGTCATC AGAGCCTATC CCAATGCCTC CCCATTGCTC GGCTCCAGCT
107 GGGGTGGCCT GATCCACCTG TACACAGCCA CAGCCAGGAA CAGCTACCAC CTGCAGATCC
167 ACAAGAATGG CCACGTGGAT GGCGCACCCC ATCAGACCAT CTACAGTGCC CTGATGATCA
227 GATCAGAGGA TGCTGGCTTT GTGGTGATTA CAGGTGTGAT GAGCAGAAGA TACCTCTGCA
287 TGGATTTCAG AGGCAACATT TTTGGATCAC ACTATTTCAA CCCGGAGAAC TGCAGGTTCC
347 GACACTGGAC GCTGGAGAAC GGCTACGACG TCTACCACTC TCCTCAGCAT CACTTTCTGG
407 TCAGTCTGGG CCGGGCGAAG AGGGCCTTCC TGCCAGGCAT GAACCCACCC CCTACTCCC
467 AGTTCCTGTC CCGGAGGAAC GAGATCCCCC TCATCCACTT CAACACCCCC AGACCACGGC
527 GGCACACCCG GAGCGCCGAG GACGACTCGG AGCGGGACCC CCTGAACGTG CTGAAGCCCC
587 GGGCCCGGAT GACCCCGGCC CCGGCCTCCT GCTCACAGGA GCTCCCGAGC GCCGAGGACA
647 ACAGCCCGGT GGCCAGCGAC CCGTTAGGGG TGGTCAGGGG CGGTCGGGTG AACACGCACG
707 CTGGGGGAAC GGGCCCGGAA GCCTGCCGCC CCTTCCCCAA GTTCATCTAG
```

Chimpanzee FGF23 gene coding sequence (1-251) (SEQ ID NO:
282) (GenBank accession no. XM_001157070,
which is hereby incorporated by reference in its entirety)

```
141                      ATGTTGGGGG CCCGCCTCAG GCTCTGGGTC TGTGCCTTGT
181 GCAGTGTCTG CAGCGTGAGC GTCCTCAGAG CCTACCCCAA TGCCTCCCCA CTGCTCGGCT
241 CCAGCTGGGG TGGCCTGATC CACCTGTACA CAGCCACAGC CAGGAACAGC TACCACCTGC
301 AGATCCACAA GAATGGCCAT GTGGATGGCG CACCCCATCA GACCATCTAC AGTGCCCTGA
361 TGATCAGATC AGAGGATGCT GGCTTTGTG TGATTACAGG TGTGATGAGC AGAAGATACC
421 TCTGCATGGA TTTCAGAGGC AACATTTTTG GATCACACTA TTTCAACCCG GAGAACTGCA
481 GGTTCCAACA CCAGACGCTG GAAAACGGGT ACGACGTCTA CTACTCTCCT CAGTATCACT
541 TCCTGGTCAG TCTGGGCCGG GCGAAGAGAG CCTTCCTGCC AAGCATGAAC CCACCCCCGT
601 ACTCCCAGTT CCTGTCCCGG AGGAACGAGA TCCCCCTAAT TCACTTCAAC ACCCCCATAC
661 CACGGCGGCA CACCCGGAGC GCCGAGGACG ACTCGGAGCG GGACCCCCTG AACGTGCTGA
721 AGCCCCGGGC CCGGATGACC CCGGCCCCGG CCTCCTGTTC ACAGGAGCTC CCGAGCGCCG
781 AGGACAACAG CCCGATGGCC AGTGACCCAT AGGGGTGGT CAGGGGCGGT CGAGTGAACA
841 CGCACGCTGG GGGAACGGGC CGGAAGGCT GCCGCCCCTT CCCCAAGTTC ATCTAG
```

White-tufted-ear marmoset FGF23 gene coding sequence
(1-251) (SEQ ID NO: 283) (GenBank
accession no. XM_002752235,
which is hereby incorporated by reference in its entirety)

```
  1 ATGTTGGGGG CCCGCCTCAG GCTCTGGGTC TGTGCCTTGT GCAGCGTCTG CAGCATGAGC
 61 GTCCTCAGAG CCTATCCCAA TGCCTCCCCA CTGCTTGCCT CCAGCTGGGG TGGCCTGATC
121 CACCTGTACA CAGCCACAGC CAGGAACAGC TACCACCTGC AGATCCACAA GAATGGCCAT
181 GTGGATGGCG CACCCCATCA GACCATCTAC AGTGCCCTGC TGATCAGATC AGAGGATGCT
241 GGCTTTGTG TGATTACAGG TGTGATGAGC AGAAGATACC TCTGCATGGA TTTCAGAGGC
301 AACATTTTTG GATCACACTA TTTCAACCCG GAGAACTGCA GGTTCCGACC CCAGAGGCTG
361 GAGAACGGGT ACGACGTCTA CCAGTCTCCT CAGCATCACT TCCTGGTCAG TCTGGGCCGG
421 GCGAAGAGGG CCTTCCTGCC AGGCATGAAC CCACCCCCGT ACTCCCAGTT CCTGTCCCGG
481 AGGAACGAGA TCCCCCTCAT TCACTTCAAC ACCCCCAAAC CGCGGCGGCA CACCCGGAGC
541 GCCGAGGACG ACCCGGAGCT AGACCCCCTG AACGTGCTGA AGTCCCGGGT CCGGATGACC
601 CCGGCCCCGG CCTCCTGCTC GCAGGAGCTC CTGAGCGCCG AGGACAACAG CCCGGTGGGC
661 AGCGACCCCT TAGGGATGGT CCGGGGTGGT CGGGTGAACA GCCACGCTGA GGGAACAGGC
721 CCAGAAGGCT GCAGCCCCTT CCCCAAGCTC ATCTAG
```

Elephant FGF23 gene coding sequence (1-251) (SEQ ID NO:
284) (GenBank accession no. XM_003410629,
which is hereby incorporated by reference in its entirety)

```
  1 ATGTTGGGGG CCCGCCTCAG GCTCTGGGTC TGCACCCTGT GCAGTGCCTG CAGCATGTGC
 61 AGTGTCAGAG CCTATCCCAA TGCCTCCCCG CTGCTCCACT CCAGCTGGGG TGGCCTGACC
121 CACCTGTACA CAGCCACCGC CAGGAACAGC TACCACCTGC AGATCCACAA GGACGGCCAT
181 GTGGATGGTA CGCCGGACCA GACCATCTAC AGTGCCCTGA TAATCAGATC AGAGGAGGCC
241 GGCTTCGTGG TGATTACAGG GGTGATGAGT AGAGATACC TCTGTATGGA TTTCAGAGGC
301 AACATTTTTG GATCGCATTA CTTCAACCCA GAGAACTGCA GGTTCAAACA CTGGACGCTG
361 GAAAATGGAT ATGACGTCTA TCACTCTCCT CAGCATCATT TCCTGGTCAG TCTGGGTCGC
421 GTGAAGAAGG CCTTCCTGCC AGGCATGAAC CCACCACCTT ACTCTCAGTT CCTGTCCCGG
481 AGGAATGAGA TCCCCTTGAT TTACTTCAAC ACCCCCAAGC CGCGGCGGCA CACCCGGAGT
541 GCCGAGGATG ACTCTGAACG GGACCCACTG AATGTGCTGA AGCCCCGGCC CCGTATGACA
601 CCTGCTCCAG CTTCTTGCTC CCAGGAACTC CTGAGTGCTG AAGACAACAG CGTGGTGGCC
661 AATGACCCTT AGGAGTGGT CAGAAGCAAT AGGGTCAACA CACATGCTGG TGGGATAGGT
721 GTGGAAAGGT GCCGCCCCTT CCCCAAGTTC ATCTAG
```

TABLE 8-continued

Lesser hedgehog tenrec FGF23 gene coding sequence (1-250)
(SEQ ID NO: 285) (Ensembl accession no. ENSETET00000001609,
which is hereby incorporated by reference in its entirety)

```
  1 ATGTTGGGGG CCCACCTCAG ACTCTGGGTC TGTGCCTTGT GCAGTGTGAG CGCCATGTAC
 61 CACGTCAGAG CCTACCCCAA CGCCTCCCCG CTCCTGGGTA CCAGCTGGGC TGGCCTGACC
121 CACCTGTACA CGGCGACAGC CAGGAACAGC TTCCACCTGC AGATCCACAA GGATGGCCAC
181 GTGGACGGCA CCCCCCACCA GACCATCTAC AGTGCCCTGA TGATCCGATC AGAGGACTCT
241 GGCTTCGTGG TGATCACAGG GGTGATGAGC AGGAGATACC TGTGTATGGA TTTCAGAGGC
301 AACATTTTTG GATCGCACTA CTTCACTGCG GACAGCTGCA GGTTCAGACA GCGGACGCTG
361 GAGAACGGCT ATGACGTCTA CCACTCTCCT CAGCATCATT TCCTGATCAG CCTGGGCCGG
421 GCCAAGAGGG TCTTCCTGCC CGGCATGAAC CCGCCGCCTT ACTCCCAGTT CCTGTCCCGA
481 AGGAATGAGA TCCCCCTGAT TCACTTCAAC ACCCCCAGGC CCCGGCGGCA CACACGGAGT
541 GCCGAGGAGG AAGTGGAGCA GGATCCGCTG AACGTGCTGA AGCCCAGGCC CCGGATGACG
601 CCGGCTCCAG CCTCCTGCTC CCAGGAGCTG CCCAGTGCCG AAGACAACAG CGCCCTGGCC
661 AGCGACCCGC TGGGAGTGGT CAGAGGCAAA AAGCTCAACA CCCATGCTGT GGGCATGGGC
721 GCGGAAAGAT GCCGCCCCTT TCCCAAGTTC
```

Hedgehog FGF23 gene coding sequence (1-63 and 73-244)
(SEQ ID NO: 286) (Ensembl accession
no. ENSEEUT00000007917,
which is hereby incorporated by reference in its entirety)

```
  1 ATGTTGGGGG CCCACCTGGG TCTGGTGGTC TGCGCCCTGG TCAGCAGAGC CTATCCCAAT
 61 GCCTCGCCAC TGCTGGGCTT CAGCTGGGGG GGCCTGACCA ATCTGTACAC GGCCACAGCC
121 AGGAACAGCT ACCACCTGCA GATCCACAAG GACGGCCACG TGGACGGCTC GCCTCAGCAG
181 ACCATCTACA ---------- ---------- -----TGCTG GTTTCGTGAT GATCACAGGC
241 GTGATGAGTA GGCGCTACCT CTGCATGGAC TTCAGGAGCA ACATCTTTGG ATCGCATCAC
301 TTCGCCCCTG AGAGCTGCAG GTTCAGACAT CGGACACTGG AAAACGGCTA TGACGTCTAC
361 CACTCCCCCC AGCACCATTT CCTGGTCAGC CTGGGCCGGG CCAAGCGGGC CTTCCTGCCG
421 GGCACCAACC CCCCACCATA CTCCCAGTTT TTGTCCCGGA GGAACGAGGT TCCCCTCATC
481 CACTTCAACA CCCCCAGGCC CAGGCGTCAC ACCCGCAGCG CCGAGGACAA CTCAGAGCTG
541 GATCCCCTGA ACGTGCTGAA GCCCAGGCCC CGCATGACCC CGCCCCAGCC CTCCTGCTCC
601 CAGGAGCTTC CGAGCGCTGA GGACAACAGC ATGGTGGGCA GTGACCCACT GGGTGTGGTC
661 AGAGCCAACA GAGTGAACAC ACACGCAGGG GGCCTGGGTG TGGACAAGTG CCGCCCCTTC
721 CCCAAGTTTA TCTAG
```

Bushbaby FGF23 gene coding sequence (1-252) (SEQ ID NO:
287) (Ensembl accession no. ENSOGAT00000005213,
which is hereby incorporated by reference in its entirety)

```
  1 ATGCTGGGGA CCTGCCTCAG GCTCTGGGTC TGTGCCCTGT GCAGTGTTTG CAGCGTGAGC
 61 ATTGTCAGAG CCTATCCCAA CGCCTCCCCA CTGCTCAGCT CCAGCTGGGG TGGCCTGACC
121 CACCTGTACA CGGCCTCGGC CAGAAACAGC TACCACCTGC AGATCCACAA GGATGGCCAT
181 GTGGACGGCA CACCCCACCA GACCATCTAC AGCGCCCTAA TGATCAGGTC AGAGGATGCT
241 GGCTTCGTGG TGATTACAGG CGTGATGAGC AGAAGATACC TCTGTATGGA TTTCAAAGGC
301 AACATTTTTG GATCACACTC CTTCCACCCC GAGAGCTGCA GGTTCAGACA CCGGACTCTG
361 GAGAACGGCT ATGACGTCTA CCCTCTCGCC CAGCATCACT TCTTGGTCAG CCTGGGCCGC
421 TCCAAGAGGC CCTTCCTGCC GGGCATGAAC CCGCCCCCCT TCTCCCAGTT CCTGTCGCGG
481 AGGAACGACA TCCCGCTCAT TCACTTCAAC ACCCCCCAGC CGCGGAGACA CACCCGCAGC
541 GCCGAGGACA ACGACTCGGA GCTCGACCCC CTGAACGTGC TGAAGCCGCG GCCCCGGGCC
601 ACCCCGGGCC CCGCCTCCTG CTCGCAGGAG CTCCCCAGCG CCGAGGACAA CAGCCTGGTG
661 GCCAGCGACC CTTTAGGGGT GGTCCGGGGC AACAGGGTGA ACGCTCACGC CGGGAGGGCC
721 GGCCTGGACA GGTGCCGCCC CTTCCCCAGG TATTTCTAG
```

Rabbit FGF23 gene coding sequence (1-252) (SEQ ID NO: 288)
(GenBank accession no. XM_002712826,
which is hereby incorporated by reference in its entirety)

```
  1 ATGTTAGGGG CCCGGCTCCT CCGGCTCTTG GTCTGTGCCC TGGGCAGTGT GTGCAGCTGG
 61 TGTGTGGTCC GAGCCTACCC TGACACCTCC CCGCTGCTCA GCTCCAGCTG GCTGGCCTG
121 ACCCACCTGT ACACGGCCAC CGCCAGAAAC AGCTACCACC TGCAGATCCA CAAGGACGGC
181 CAAGTGGATG GCACACCTCA TCAGACCATC TACAGTGCCC TGATGATCAG ATCGGAGGAT
241 GCTGGCTTCG TGGTGATAAC AGGTGTGATG AGCAGGAGGT ACCTCTGTAT GGATTTCAGA
301 GGCAACATTT TTGGATCGCA TTACTTCGAC CCCCAGAACT GCAGGTTCAG ACACAGGACG
361 CTGGAAAACG GGTACGACGT CTACCACTCT CCGGAGCATC ACTTCCTGGT CAGCCTGGGC
421 CGGGCCAAGA GGCCCTTCCT GCCAGGCATG AACCCGCCAC CCTATTCCCA GTTCCTGTCC
481 CGGAGGAACG AGATCCCCCT GATCCACTTC AACACGCCGA GGCCGCGAAG GCACACCCGG
541 AGCGCCGAGG ACGCCTGGGA GCAGGACCCG CTGAACGTGC TGAAGCCCAG GTTCCGGCTG
601 ACCCCGGCCC CAGCCTCCTG CTCACAGGAG GCCCAAGTG CTGAAGACAA TGGCCTGGTG
661 GCCAGCGACC CCTTCGGAGT GCTCCGGGGC AATAGGGTGA ACATGCACGG GGACAGGATG
721 GGCCCGGAAA GGTGCCACCA TTTCCCCAAG TTCATCTAG
```

Horse FGF23 gene coding sequence (1-246) (SEQ ID NO: 289)
(GenBank accession no. XM_001491419,
which is hereby incorporated by reference in its entirety)

```
  1 ATGTCAGGGC CCTGCCTTGG GCTCCTGGTC TACGTCCTGT GCTCCGCAGT GAAAGCCTAT
 61 CCCAACGCCC CCCGCTGCT AGACTCCAGC TGGGGCAGCC TGACCCACCT GTACACGGCC
121 ACAGCCAGGA ACAGCTACCA CCTGCAGATC ACAAGGATG CCACGTGGA TGGCACACCC
```

TABLE 8-continued

```
181 CATCAGACCA TCTACAGTGC CCTGATGATC AGATCAGAGG ATGCTGGCTT TGTGGTGATA
241 ACAGGTGTGA TGAGCAGGAG ATACCTCTGC ATGGACTTCA GAGGAAACAT TTTTGGATCA
301 CATCACTTCA GCCCCGAGAG CTGCAGCTTC CGACAGCGGA CGCTGGAGAA CGGCTACGAC
361 GTGTACCACT CGCCGCAGCA TCGCTTCCTC GTCAGCCTGG GCCGCGCCAA GAGGGCCTTC
421 CTGCCCGGCA CGAACCCCCC GCCCTACTCG CAGTTCCTGT CCCGGAGGAA CGAGATCCCC
481 CTGGTCCACT TCAACACCCC GCGGCCGCGG CGGCACACGC GCAGCGCCGA GGACAACTCG
541 GAGCGCGACC CGCTGAACGT GCTGAAGCCC CGGCCCCGCA TGACCCCGC GCCGGCCTCC
601 TGCTCCCAGG AGCTCCCGAG CGCCGAGGAC AACAGCGTGC TGGCCAGCGA CCCCTTAGGG
661 GTGGTCCGTG GCAACAGGGT GAACACGCAC GCGGGGGGCG CGGGCGTGGA GCGCTGCCGC
721 CCCTTCCCCA AGTTCTTCTA G
```

Giant panda FGF23 gene coding sequence (1-245) (SEQ ID NO: 290) (GenBank accession no. XM_002920450, which is hereby incorporated by reference in its entirety)

```
  1 ATGTCAGGGA CCCGCCTTGG GCTGCTGGTC TCTGTCCTGT GCTGGGTAGG CAGAGCCTAT
 61 CCCAACACCT CCCCACTGCT CGGCTCCAGC TGGGGTGGCC TGACCCACCT GTACACGGCC
121 AGCGCCAGGA ACAGCTACCA CCTGCAGATC CACAAGGACG GCCATGTGGA TGGCACACCC
181 CATCAGACCA TCTACAGTGC CCTGATGATC AGGTCAGAGG ATGCCGGCTT TGTGGTGATA
241 ACAGGTGTGA TGAGTAGGCG ATACCTCTGT ATGGACCTCA GAGGCAACAT CTTTGGATCC
301 CACCTCTTCA GCCCGGAGAG CTGCAGGTTC CGACAGCGGA CGCTGGAAAA CGGCTACGAC
361 GTGTACCACT CGCCGCAGCA CCGCTTCCTC GTCAGCCTGG GCCAGGCCAA GAGGACCTTC
421 CTGCCGGGGA CCAACCCGCC GCCCTACTCC CAGTTCCTGT CCCGGAGGAA CGAGATCCCC
481 CTCATCCACT TCAACACCCC CAGGCCAAGG CGGCACACGC GCAGCGCCGA GGACACGGAG
541 CGCGACCCGT TGAACGTGCT GAAGCCCAGG CCCCGCATGA CCCCCGCCCC GGCCTCCTGC
601 TCCCAGGAGC TCCCGAGCGC CGAGGACAAC AGTGTGGTGG CCAGCGACCC GTTAGGGGTG
661 CTCAGAGGCA ACCGGGTGAA CGCGCACGCC GGGGGGATGG GCGTGGACAG GTGCCGCCCC
721 TTCCCCAAGT TCATCTAG
```

Pika FGF23 gene coding sequence (1-250) (SEQ ID NO: 291) (Ensembl accession no. ENSOPRT00000007149, which is hereby incorporated by reference in its entirety)

```
  1 ATGCTGGGGG GGCTGGGGCT GTGGGTCTGT GTCCTGGGCA GTGTGTGCAG CTGGCGTGGG
 61 GTCCGTGCCT ATCCCGACAC CTCCCCGCTG CTCGGCTCCA GCTGGACTGG CCTGACCCAC
121 CTGTACACGG CCACCGCCAG GAACAGCTTC CACCTGCAGA TCCACAAGGA TGGCCATGTG
181 GATGGCACAC CCCAGCAGAC CATCTATAGT GCCCTGATGA TCAGATCAGA GGATGCCGGC
241 TTCGTGGTGA TAACATTAGGTGT CATGAGCAGG AGGTACCTCT GTATGGATTT CAGAGGCAAC
301 ATCTTCGGAT CGCATTACTT CGAGCCACAC AACTGCAGGT TCCAGCAGAG GACGCTGGAG
361 AACGGCTACG ACATCTACCA CTCTCCGCAG CACGACTTCC TGGTCAGCCT AGGTCGGGCC
421 AAGAGGCCGT TCCTGCCAGG CATGAACCCG CCACCCTACT CCCAGTTCCT GTCTCGGAGG
481 AACGAGATTC CGCTGATCCT CTTCAACACG CCCAGGCCTG GGAGGCACAC CCGCAGCGCG
541 GAGGAGGGCT GGGAGCGGGA CCCTCTGAAT GTGCTGAAGT CCAGGCCCCG AATGACCCCG
601 GCCCCAGCCT CCTGCTCGCG GGAGGCCCCC AGTGCCGAAG ACGACGGCCT GCTGGCCAGT
661 GACCCCATGG GAGTGCTCAG AGGCCATAGG GTGGATGTGC ACGGGGGTGG GACGGGTAGG
721 GACAGGTGCC GCCCGTTCCC CAGGTTCATC TAG
```

Cattle FGF23 gene coding sequence (1-245) (SEQ ID NO: 292) (GenBank accession no. XM_002687880, which is hereby incorporated by reference in its entirety)

```
  1 ATGCTGGGGG CCCGCCTGGG GCTCTGGGTC TGCACCCTGA CTGTGTGGT CCAAGCCTAT
 61 CCCAACAGCT CCCCGCTGCT GGGCTCCAGC TGGGGCGGCC TGACCCACCT GTACACGGCC
121 ACGGCCAGGA ACAGCTACCA CCTGCAGATC CACGGAGACG GGCACGTAGA TGGCTCCCCG
181 CAGCAGACTG TCTACAGCGC CCTGATGATC AGGTCGGAGG ATGCCGGCTT CGTGGTGATA
241 ACAGGTGTGA TGAGCAGGCG GTACCTCTGC ATGGACTTCA CAGGCAACAT TTTTGGATCC
301 CATCACTTCA GTCCGGAGAG CTGCCGGTTC CGGCAGCGGA CACTGGAGAA CGGCTACGAC
361 GTGTACCACT CGCCGCAGCA CCGCTTCCTC GTCAGCCTGG GCCGGGCCAA GCGCGCCTTC
421 CTGCCCGGCA CCAACCCGCC CCCATACGCG CAGTTCCTGT CGCGCAGGAA CGAGATCCCG
481 CTGCCGCACT CGCCGCCAC CGCGCGGCCC GGCGCCACA CGCGCAGCGC ACACGACAGC
541 GGGGACCCGC TCAGCGTGCT CAAGCCGCGC GCCCGCGCCA CGCCCGTGCC CGCCGCCTGC
601 TCCCAGGAGC TGCCCAGCGC CGAGGACTCC GGCCCTGCCG CCAGCGACCC GCTCGGGGTG
661 CTCCGCGGAC ACCGCCTGGA CGTGCGCGCC GGCTCCGCGG GCGCCGAGCG CTGCCGGCCC
721 TTCCCCGGCT TCGCCTAG
```

Pig FGF23 gene coding sequence (1-244) (SEQ ID NO: 293) (GenBank accession no. XM_001926525, which is hereby incorporated by reference in its entirety)

```
  1 ATGCTGGGGG CCCGCCTCGG GCTCTGGGTC TGCACCCTGT GCTGTGCGGC CAGAGCCTAT
 61 CCCGACACCT CCCCGCTGCT GAGCTCTGGC TGGGGCGGCC TGACCCACCT GTACACGGCC
121 ACGGCCAGGA ACAGCTACCA CCTGCAGATC CACAAGGATG CCACGTGGA TGGCTCACCC
181 CAACAGACCA TCTACAGTGC CCTAATGATC AGGTCGGAGG ACGCAGGCTT CGTGGTCATA
241 ACAGGCGTGA TGAGCAGGAG ATACCTCTGC ATGGACTTAA GGGCAACAT TTTTGGATCG
301 CTGCACTTCA GCCCCGAGAG CTGCAGGTTC CGGCAGCGGA CGCTGGAGAA CGGCTACGAC
361 GTGTACCACT CGCCGCACTA CCGCTTCCTC GTCAGCCTGG GCCGGGCCAA GCGGGCCTTC
421 CTGCCGGGTA CCAACCCGCC CCGTACGCG CAGTTCTTGT CGCGCAGGAA CGAGATCCCG
481 CTGCTGCACT CGCCGCACCGC GCGGCCCGG CGCCACACGC GCAGCGCGCA CGACGGCGGG
541 GACCCGCTGA GCGTCCTGAA GCCGCGCGCG CGCGCCACGC CCGCGCCCGT CTCCTGCTCC
601 CGCGAGCTGC CCAGCGCCGA GGACGGCGG CCCGCGGCCA GCGACCCGCT CGGGGTGCTC
```

TABLE 8-continued

```
661 CGGGGCCAGC GGCTGGACGC GCGCGCTGGG GTGGGGGGCG CCGAGCGCTG CCGGCCCTTC
721 CCCAGCTTCG CCTAG
```

Dog FGF23 gene coding sequence (1-312) (SEQ ID NO: 294)
(GenBank accession no. XM_849487,
which is hereby incorporated by reference in its entirety)

```
  1 ATGTGGACAG TGGAGTTTTT CCTGTTTGAT GTCACAGGGC CACCCTTTAA AAGTCTGAGG
 61 GAAAAAAGGA GGGAATCTAG CCTGGGACTT TCACGCAAGA TACCCACAAA GAAGAGGAGA
121 AAAAGGCCTG TGAGGCACAG CCGGGGAATC AAGGAGGCAG TGTCAGGTTT CAAACTCCAG
181 CCAGCCATTC AGAGAGCTGT GATGTCTGGC ACCCGCCTTG GATTCCTGGT CTCTGTCCTG
241 TGCTGGGTAG TCAGAGCCTA TTCCAACACC TCCCCGCTGC TCGGCTCCAG CTGGGGTAGC
301 CTAACCCACC TGTATACGGC CACAGCCAGG AACAGCTACC ACCTGCAGAT CCACAAGGAC
361 GGCCATGTGG ATGGCACACC TCATCAGACC ATCTACAGTG CCTTGATGAT CCGGTCAGAG
421 GATGCCGGCT TTGTGGTGAT AACAGGTGTG ATGAGTAGGA GGTACCTCTG TATGGACTTC
481 AGAGGCAACA TCTTTGGATC ACACCTCTTC AGCCCGGAGA GCTGCCGGTT CCGACAGCGG
541 ACGCTGGAGA ACGGCTACGA CGTGTACCAC TCCCCGCAGC ACCGCTTCCT CGTCAGCCTG
601 GGCCAGGCCA GAGGGCCTT CCTGCCCGGC ACCAACCCGC CGCCCTACTC GCAGTTCCTG
661 TCCCGGAGGA ACGAGATCCC CCTCGTGCAC TTCCACACGC CCAGGCCGCG GCGGCACACG
721 CGCAGCGCCG AGGCCCCGGA GCGCGACCCG CTGAACGTGC TGAAGCCCAG GCCGCGCTTG
781 GCCCCCGCCC CGGCCTCCTG CTCGCAGGAG CTCCCGAGCG CCGAGGACCC CGGCGCGCCG
841 GCCAGCGACC CGCTCGGGGT GCTCAGGGGC CACAGGGCCA ACGCGCGCGC CGGCGGGGTG
901 GGCGTGGACA GGTGCCGCGC CTTCCCCACG CCCATCTAG
```

Domestic guinea pig FGF23 gene coding sequence (1-243)
(SEQ ID NO: 295) (GenBank accession no.
XM_003463298,
which is hereby incorporated by reference in its entirety)

```
  1 ATGCTGGGGA CCTGCCTTGG GCTCCTGGCC TGCACCGTGA GCTTAGTAGG AGCCTATCCT
 61 GATGCCTCCC CATTGCTCAC CTCCAGCTGG GGTGGCCTGA TCCATCTGTA CACGGCCACA
121 GCCAGAAACA GCTACCATCT GCAGATCCAC AAAGATGGCA ACATAGATGG TGCACCCTAT
181 CCGACCATCT ACAGTGCCCT GATGATCAGA TCAGAAGATG CTGGGTTCGT CGTGATAACA
241 GGGGTCACAA GCAGGAGATT CCTCTGCATG GATTTCAGAG CAACATTTT TGGATCTCAC
301 CACTTCAATC CCCAAGACTG CCGATTCCAA CACCGCACGC TGGAAAACGG TTACGACGTC
361 TACCTCTCTC CCGAGCACCA CTTTCTGATC AGCCTGGGCA GGACCAAGAA GTTCTTCCTG
421 CCGGGCACCA ACCCACCGCC CTACTCCCAG TTCCTGTCGC GCAGGAACGA GCTGCCCCTG
481 GCCCGCTTCG TCACGCCCGG GCCGCGGCGA CACACGCGCA GCGCGGAGGA GGACCAGGGC
541 CGCGACCCGC TGAGCGTGCT CAAGCTTCGG CCCCGCGCCA CGCCCGCGCC CGCCTCGTGC
601 TCGCAGGAGC TGCCCAGCGC GGAGGACGCG CCCAGGCCA GCGACCCCCT GGGCGTGCTG
661 CGGGGCGCCA GGGTGCACGC GCACGGCGGG CCGCGCCCCG CGAGGTGCCG CCCGGGACCC
721 GGGGCCAAGT AA
```

Chinese hamster FGF23 gene coding sequence (1-251) (SEQ
ID NO: 296) (GenBank accession no. XM_003496084,
which is hereby incorporated by reference in its entirety)

```
  1 ATGCTGGGGA CCTGCCTCAG ACTCCTGGTG GGTGTTCTGT GTAGTGCCTG CAGCCTGGGC
 61 ACTGTTAGAG CCTATCCTGA CACCTCCCCA CTGCTCGGCT CCAATTGGGG CAGCCTGACC
121 CACCTGTACA CAGCTACAGC CAGGAACAGT TATCACCTAC AGATCCACAA GGATGGCCGT
181 GTAGATGGCA CACCCCATCA GACCATCTAC AGTGCCCTGA TGATTAGATC AGAGGATGCT
241 GGCTTCGTGA TCATAACAGG AGCTGTGACT AGAAGGTTCC TTTGTATGGA TCTCAGGGGC
301 AACATTTTTG GATCGCATCA CTTCAGCCCG GAGAACTGCA GGTTCCGCCA GCGGACTCTG
361 GAGAATGGCT ATGACGTCTA CCTGTCGCCA CAGCATCACT ACCTGGTGAG CCTGGGCCGC
421 GCCAAGCGCC CCTTCGAGCC CGGCACCAAC CCGCCTCCCT TCTCGCAGTT CCTGGCGCGC
481 AGGAACGAGG TCCCGCTGCT GCGCTTCCAT ACCGCACGGC CACGGCGCCA CACGCGCAGC
541 GCCGAGGACC CTCCCGAGTG GGACCCACTG AACGTGCTCA AGCCGCGGCC CCGTGCCACG
601 CCCGTGCCCG TGTCCTGCTC GCGGGAGCTG CCGAGCGCCG AGGAAGGTGA CCTCGCGGCC
661 AGTGACCCAC TGGGCGTCCT GCGCAGAGGC CGCGGGGATG CTCGCGGGGG CGCAGGAGGC
721 GTGGACCGGT GCCGTCCCTT TCCCAGATTC GCCTAG
```

Tree shrew FGF23 gene coding sequence (1-180) (SEQ ID
NO: 297) (Ensembl accession no. ENSTBET00000016365,
which is hereby incorporated by reference in its entirety)

```
  1 GCCCTGCTGA TCAGGCCGGA GGAGGCTGGC TTCGCGGTGA TCACGGGCGT GATGAGCAGG
 61 AGATACCTCT GCATGGATTT CAGGGGCAAC ATTTTCGGAT CACACCTCTT CAGCCCGGAG
121 AGCTGCAGGT TCCGGCAGCG CGCCCTGGAG AACGGCTACG ACGTGTACCA CCACCCGCAG
181 CACCACTTCC TGGTCAGCCT GGGCCGGCCC AAGAGGGCCT TCGTGCCAGG CACGAACCCG
241 CCCCCCTACT CCCAGTTCCT GGCCCGGAAG AACGAGATCC CGCTCATCCA CTTCAACACC
301 CCGAAGCCGC GGCGGCACAC CCGCAGCGCA GAGGACAACT CGGGGCGCGA CCCGCTGAAC
361 GTGCTGAAGC CCCGGCCGCG CATGACCCCG CGCCCGCCT CCTGCTCGCA GGAGCTCCCG
421 AGTGCCGAGG ACAACAGCGT GGTGGCCAGC GACCCCCTGG GAGTGCTCAG GGCAACAGG
481 GTGAACACGC ACGCGGGGGG CTGGGCGTG GACCGCTGCC GCCCCTTCCC CAGGTTTATC
541 TAG
```

TABLE 8-continued

Norway rat FGF23 gene coding sequence (1-251) (SEQ
ID NO: 298) (GenBank accession no. NM_130754,
which is hereby incorporated by reference in its entirety)

```
  1 ATGCTGGGGG CCTGCCTCAG ACTCCTGGTG GGCGCTCTGT GCACCGTCTG CAGCTTGGGC
 61 ACTGCTAGAG CCTATTCAGA CACTTCCCCA CTGCTTGGCT CCAACTGGGG GAGCCTGACC
121 CACCTGTACA CAGCTACAGC CAGGAACAGC TATCACCTAC AGATCCATAG GGATGGCCAT
181 GTAGACGGAA CACCCCATCA GACTATCTAC AGTGCCCTGA TGATCACATC AGAGGATGCT
241 GGCTCCGTAG TGATAATAGG GGCCATGACC AGAAGGTTCC TTTGTATGGA TCTCCGCGGC
301 AACATTTTTG GATCGTATCA CTTCAGCCCG GAGAACTGCA GATTCCGCCA GTGGACGCTA
361 GAGAACGGCT ACGACGTCTA CCTGTCACCG AAGCATCACT ACCTGGTGAG CTTGGGCCGC
421 TCCAAGCGCA TCTTCCAGCC CGGTACCAAC CCGCCGCCCT TCTCGCAGTT CCTGGCGCAC
481 AGGAACGAGG TCCCGCTGCT GCACTTCTAC ACCGCGCGCC CACGGCGCCA CACGCGCAGC
541 GCCGAGGACC CGCCCGAGCG CGACCCGCTG AATGTGCTCA AGCCGCGGCC CCGCGCTACT
601 CCCATACCGG TATCCTGCTC GCGAGAGCTA CCGAGTGCAG AGGAAGGTGG CCCCGCGGCC
661 AGCGACCCCC TGGGAGTGCT GCGCAGAGGC CGCGGGGATG CTCGCCGGGG CGCGGGAGGC
721 ACGGATCGGT GTCGCCCCTT TCCCAGGTTC GTCTAG
```

House mouse FGF23 gene coding sequence (1-251) (SEQ ID
NO: 299) (GenBank accession no. BC120605,
which is hereby incorporated by reference in its entirety)

```
 24                    ATGCTAG GGACCTGCCT TAGACTCCTG GTGGGCGCGC
 61 TCTGCACTGT CTGCAGCTTG GGCACTGCTA GAGCCTATCC AGACACTTCC CCATTGCTTG
121 GCTCCAACTG GGGAAGCCTG ACCCACCTGT ACACGGCTAC AGCCAGGACC AGCTATCACC
181 TACAGATCCA TAGGGATGGT CATGTAGATG CACCCCCCA TCAGACCATC TACAGTGCCC
241 TGATGATTAC ATCAGAGGAC GCCGGCTCTG TGGTGATAAC AGGAGCCATG ACTCGAAGGT
301 TCCTTTGTAT GGATCTCCAC GGCAACATTT TTGGATCGCT TCACTTCAGC CCAGAGAATT
361 GCAAGTTCCG CCAGTGGACG CTGGAGAATG GCTATGACGT CTACTTGTCG CAGAAGCATC
421 ACTACCTGGT GAGCCTGGGC CGCGCCAAGC GCATCTTCCA GCCGGGCACC AACCCGCCGC
481 CCTTCTCCCA GTTCCTGGCG CGCAGGAACG AGGTCCCGCT GCTGCACTTC TACACTGTTC
541 GCCCACGGCG CCACACGCGC AGCGCCGAGG ACCCACCCGA GCGCGACCCA CTGAACGTGC
601 TCAAGCCGCG GCCCCGCGCC ACGCCTGTGC CTGTATCCTG CTCTCGCGAG CTGCCGAGCG
661 CAGAGGAAGG TGGCCCCGCA GCCAGCGATC CTCTGGGGGT GCTGCGCAGA GGCCGTGGAG
721 ATGCTCGCGG GGGCGCGGGA GGCGCGGATA GGTGTCGCCC CTTTCCCAGG TTCGTCTAG
```

Megabat FGF23 gene coding sequence (1-248) (SEQ ID
NO: 300) (Ensembl accession no. ENSPVAT00000000244,
which is hereby incorporated by reference in its entirety)

```
  1 ATGCCGAGGG GCAGCCTAGG GCTCCTGGTC TGCATCCTGT GCTGCAGAGC CTATCCCGAT
 61 GCCTCTCCGC TGCTTAGCTC CAGCTTGGGG GGCCTGATCC ACCTCTACAC AGCCACAGCC
121 AGGAACGGCT ACCACCTGCA GATCCACAAG GATGGCCATG TGGATGGCAC ACCCCATCAG
181 ACCATCTACA GTGCCCTGAT GATAAGATCA GAGGACAGTG GCTTTGTGGT GATAATAGGT
241 GTGATGAGTA GAAGATACCT CTGCATGGAC TTCAAAGGCA ACATTTTTGG ATCACATCAC
301 TTCAGCCCCG AGAGCTGCAA GTTCCGCCAG CGAACGCTGG AGAATGGCTA CGACGTGTAT
361 CACTCGCCCC AGCATCACTT CTTCGTCAGC CTGGGCCGAG CTAAGAGGGC CTTCCTGCCG
421 GGCACGAACC CCCCACCTTA CTCCCAGTTC CTGTCCCGAA GGAATGAGAT CCCCCTGTTC
481 CAGTTCAACA CCCCGCGGCC GCGGCGGCAC ACGCGCAGTG TGGAGGACTA CAAAGACTAC
541 GATTTGGACC CCGACCCGCT GAAAGTTCTG AGGCCCCGTC CCCGGTGGGT CCCCGCCCTG
601 CCCTCCTGCT CCCAGGAGCT CCCGAGTGCC GAGGACAACA GCGTGGTAGC CAACGACCCG
661 TTAGGGGTGC TCAGGCCCAG CAGGGTAAAC ATATACCGTG AGAGAATGGG CAAGGGGAGG
721 TGCCGTCCCC ACCCTGAGTT TGTCTAG
```

Microbat FGF23 gene coding sequence (1-248) (SEQ ID
NO: 301) (Ensembl accession no. ENSMLUT00000031180,
which is hereby incorporated by reference in its entirety)

```
  1 ATGCCAGGGG CCCGCCTTGG GTTGCTGGTC TGCGTCCTGG CCCTGCGCTG TGTGGTCAGA
 61 GCCTATCCCA ACGCCTCCCC ACTGCTCGGC TCCAGCTGGG GTGGCCTGAC CCACCTGTAC
121 ACGGCCTCAG CCAGGAACAG CTACCACCTG CAGATCCACA AGGACGGCCA TGTGGACGGC
181 ACACCCCATC AGACCATCTA CAGTGCCCTG ATGATCAGAT CAGAGGACGC TGGCTTTGTG
241 GTGATAACTG GAGTGATGAG TAGGAGATAC CTCTGCATGG ACTTTAGAGG CAACATTTTT
301 GGATCCCTTT TTTTCAGTCC AAGTAATTTC AGTTTCCTTG AATGGAAAAA GGAAAGTGGG
361 ATGGACCATT GGATAAGCAG ACAGACGCAC TTCCTCGTCA GCCCTGGGCC GAGCCAAGAG
421 GGCCTTCCTG CCGGGCACAA CCCGCCGCCC TACTCGCAGT TCCTGTCGCG AAACGAGATC
481 CCGCTCTTCC ACTTCAACAC GCCCGCGCCG CGCGGCACA CGCGCAGCGC CGAGGAGAAC
541 TCGGCGGCCG ACCCGCTGGT CGTGCTGAAG CCCGTGCCGC GCCTGACGCC CCGCCCGCC
601 TCCTGCTCCC GGGAGCTGAG CAGCGCCGAG GACAACAGCG TGGCGGCCCA CGACCCGCTC
661 GGGGTGCTGC GGAGCAGCAA CAGGGTGAAC TCGCACGCGC CGCCCCCAGG TCCACCTAGG
721 ACCCGCCAAG GAATGCTTCT CGTA
```

Tasmanian devil FGF23 gene coding sequence (1-245) (SEQ
ID NO: 302) (Ensembl accession no. ENSSHAT00000010240,
which is hereby incorporated by reference in its entirety)

```
  1 ATGTCAGGGG GTTGCCTCAG GCTCCTATTC TGTGCCCTGT GCAGCTTAAG GGCCATCCAA
 61 GCCTTCCCCA ATGCTTCCCC CCTGCTCAGC CTTGGCTGGG GGGTCTGAC TCACCTCTAT
121 ACGGCCACAG CCAGGAACAG CTACCACCTG CAGATCCACA AAGATGGCCA CGTGGATGGG
```

TABLE 8-continued

```
181 TCTCCTCATC AAACCATCTA TAGTGCCTTG ATGATCAGAT CAGAGGATGC TGGGCTAGTC
241 ATAATAACTG GTGTGATGAG CAGGAGATAT CTCTGTATGG ACATTAGGGG CAACATCTTC
301 GGATCGCATT TCTTCAGCCC AGACAACTGC AGGTTCAAAC ACCGGACATT AGAAAATGGG
361 TATGACATCT ATCACTCTCC CCAGAACAAC TTCCTGATCA GCCTTGGCAA GGCAAAGAGG
421 GCCTTCCTAC CAGGGATGAA CCCACCTCCT TACTCCCAAT TCCTGTCTCG GAGAAATGAA
481 ATCCCCATAA TACACTTCAA TACACCTGAA CCCCACCGGC ATACCAGGAG TGCTGAGAAC
541 AGTCCTGACT TGGACCCAAT GAATGTGCTG AAACTCCGAC AAGGATAAC TCCCTGCTCC
601 CAGGAACTTC ACAGTGCTGA AGAGAACAGT GTAGTGGATG ATGACCCTTT GGAAGTACTC
661 AGAAATAGCA ATAGATTGAA GCCCTATCCT GGCAGGATGA GTTTGGAAAG ATGCCTCCAT
721 GTCCCCAAGG CAGCTTAA
```

Gray short-tailed opossum FGF23 gene coding sequence
(1-191) (SEQ ID NO: 303) (GenBank accession
no. XM_001372399,
which is hereby incorporated by reference in its entirety)

```
  1 ATGGCAAATT GTAGAGAAAA GGAGCTGGAG ATGTACATTT GTGCCTTGAT GATCAGATCA
 61 GAGGATGCTG GCTAGTCAT AATAACTGGT GTGATGAGCA GGAGATATCT CTGTATGGAC
121 ATCAGGGGCA ACATCTTTGG TTCGCATTTC TTCAACCCGG ACAACTGCAA GTTCAAGCAC
181 CGGACACTAG AAAATGGGTA TGACATCTAT CATTCTCCCC AGAACAACTT CCTGATCAGC
241 CTTGGCAAGG CAAAGAGGGC CTTTCTGCCA GGCATGAATC CACCTCCGTA CTCTCAATTC
301 CTGTCTCGGA AGAATGAGAT CCCCATAATC CACTTCAACA CACCTGAACC CCACCGGCAC
361 ACCAGGAGTG CTGAAAACAG TCCTGACTTG GACCCAATGA ATGTGCTGAA ACCCCGACCA
421 AGGATGACTC CCTGCTCTCA GGAACTCTAC AGTGCTGAAG AGAACAGTGT AGTGGATGAT
481 GACCCTTTGG AAGTACTTAG AAATAGCAAT CGACTGAAGC CCTTCCCTGG TAGGCTGGGT
541 TTAGAAAGGT GCCACCATGT TCCCAAGACT GATTAA
```

Armadillo FGF23 gene coding sequence (1-180) (SEQ
ID NO: 304) (Ensembl accession no. ENSDNOT00000005805,
which is hereby incorporated by reference in its entirety)

```
  1 GCCCTGATGA TCAGCTCTGA AGATGCTGGC TTTGTGGTGA TAACAGGTGT GATGAGCAGG
 61 AGGTACCTCT GTATGGATTT CAGAGGCAAC ATTTTTGGAT CGCACGACTT CACCCCGGAC
121 AGCTGCAGGT TCCGCCAGCG CACGCTGGAG AACGGCTACG ACGTCTACCA CTCGCCGCAG
181 CACCACTTCC TCGTCAGCCT GGGGCGGGCC AAGCGGGCCT TCCAGCCGGG CTCCAACCCG
241 CCGCCCTACT CCCAGTTCCT GTCCCGCAGG AACGAGATCC CGCTGATGCG CTTCAGCACC
301 CCGCGGCCGC GGCGGCACAC GCGCAGCGCC CAGGACCACG CGGACCCCGA CCCGCTGAGG
361 GTGCTCAAGC CCCGGCTCCG GCTGACCCCG GCCCCCGCCT CCTGCTCCCA GGAGCTGCCG
421 AGCGACGAGG ACGACGGCGC GGTGCCAGC GACCCCCTGC GCGTGGTCCT CGGCCGCCGG
481 CCCCACGCGC GGGCCGCGGG CGCGGGCGGG GAGCGGTGCC GCCCCGGCCC GCAGCTCAGC
541 TAG
```

Wallaby FGF23 gene coding sequence (1-177) (SEQ ID
NO: 305) (Ensembl accession no. ENSMEUT00000004101,
which is hereby incorporated by reference in its entirety)

```
  1 GCCTTGATGA TCAGATCAGA GGACGCTGGG CTAGTCATAA TAAGTGGTGT GATGAGCAGG
 61 AGGTATCTCT GTATGGACCT CAGAGGCAAC ATCTTCGGAT CGCATTTCTT CAGCCCAGAC
121 AACTGCAGGT TCAAACACCG GACACTAGAA AATGGGTATG ACATCTATCA CTCTCCACAG
181 AACAACCTCC TGATCAGCCT TGGCAAGGCA AAAAGGGCCT TCTGCCAGG CATGAACCCA
241 CCTCCTTACT CCCAGTTCCT ATCTCGGAGG AATGAGATCC CCATAATCCA CTTCAATACA
301 CCTGAACCCC GCCGGCACAC CAGGAGCGCA GAGAACAGTC CTGACTTGGA CCCAATGAAT
361 GTGCTGAAAC CCCGACCAAG GGTGACTCCC TGCTCCAGG AACTCCGCAG TGCTGAAGAG
421 AACAGTGTAG TAGATGATGA CCCTTTGGAA GTACTCAGAA ATAGTAATCG CCTGAAGCCC
481 TACCCTGGTA GAATGAGTTT GGAAAGATGC CTCCAAGTCC CAAAGCTGC TTAA
```

Zebra finch FGF23 gene coding sequence (1-256) (SEQ
ID NO: 306) (GenBank accession no. XM_002190484,
which is hereby incorporated by reference in its entirety)

```
  1 ATGGAGTGGA GAGCCACTCT CCAGGGCATT CCCTGCAGCT CCCTGCTCCT GCTGCTCTGC
 61 AGCCTAAAGG CTTCCCTTGC CTTTCCCAAC TCCTCTCCAC TGCTGAGTCC CAGCTGGGGC
121 AATGGAGATC GCCTGATGCA CCTCTACACC GACACCGAGA GGAGCAGCTT CCACCTCCAG
181 ATCAACGCTG ATGGCTACAT CGATGGCGCT CCTCACCAAA CCATCTACAG TGCCCTAATG
241 ATCAAGTCTG AGGGTGCTGG CTCAGTAATA ATCACAGGTG TGAAGAGTGG ACGCTACCTG
301 TGTATGGACA TGAAAGGAAA TATATTTGGC TCGCATTACT TCAGCCAAGA GGACTGCATG
361 TTCAACCACA GGACGCTGGA AAATGGGTAC GATGTGTACC AATCCCCCAA ACACCACTTC
421 TTGGTGAGCT TAGGCAGAGT TAAACAAGTC TTCTCCCCTG GTATGAATCC ACCACCATAC
481 TCCCAGTTTC TGTCCAGGAA GAATGAGATC CCTCTGTTCC GATTCAACAC CCCCGAGCCC
541 CACAGGCACA CCAGGAGTGC AGATGTTGAT CCCGTAGATC CTCACCAGAT CCTGGTCCCG
601 CAGAGGGAAGA CCCCAGTGTT TGGCTCCCTG CAGCAGCAGC AGCAGACTT TCCCCACATG
661 CCCAGGGAGC CCATGGAGGAT CAACCAGAAC GACGTGGTGA ACCCCGATGA TCCCCACGCA
721 ATGATGGAGG CCAGGAGGTA CCCAAGCCCC CGCTTCTACA TCACGAGATA A
```

Chicken FGF23 gene coding sequence (1-254) (SEQ ID
NO: 307) (GenBank accession no. XM_425663,
which is hereby incorporated by reference in its entirety)

```
  1 ATGCCACACA CCAGTCCCTG CAGCTGCCTG GAGTACATGC TGCTTGTGCT CTGTATCCTG
 61 AAGGCTGCAG TCGCCTTCCC CAACTCCTCT CCGCTGCTGA ATCCCAGCTG GGGGAATGGA
```

TABLE 8-continued

```
121 GATCAGCTGA TGCACTTGTA CACTTCTACA GAGAGGAACA GCTTCCATCT CCAAATCAAT
181 GCTGATGGAC ACATCAATGG TGTTCCTCAC CAAACCATTT ACAGTGCCTT AATGATCAAG
241 TCTGAGGGTG CTGGCTGTGT AATAATCACA GGTGTGAAGA GTGGACGCTA CCTATGCATG
301 GACATGAAAG GAGACATTTT TGGATCGTAT TATTTCAGCC AAGAGGACTG TGTGTTCAAC
361 CAAAGGACAC TGGAAAATGG ATATGATGTG TACCAATCTC CCAAGCACAA TTTTCTGGTT
421 AGCTTGGGCA GAACTAAGCA AGTTTTCTTC CCTGGTATGA ATCCACCACC ATACTCCCAG
481 TTTTTGTCCA GGAGAAACGA AATCCCTTTG TTTCGATTCA ACACACCTGA ACCCCACAGA
541 AACACTAGAA GTGCAGATGT CGATCCACTG GATCCTCACC AAATCCTGGT CCCACAGAGA
601 AAGGTCTCTG CATTAGGGTC TCAGCTGCAG CTGCAAATGG ACTTTTCCCA TGTGCCCAGA
661 GAACCCATGA GAGTCAATCA GAATGATGTG GTCAATCCAG ATGACCCACA TGCTATGATG
721 GATGCTAGGA GGTATGCTAG TCCTCGCTTT TACATTACAA GATAA
```

Turkey FGF23 gene coding sequence (1-254) (SEQ ID
NO: 308) (GenBank accession no. XM_003202575,
which is hereby incorporated by reference in its entirety)

```
  1 ATGCCGCACA CCAGTCCCTG CAGCTGCCTG GAGTACATGC TGCTTGTGCT CTGTATCCTG
 61 AAGGCTGCAG TCAGCTTCCC CAACTCCTCT CCACTGCTGA ATCCCAGCTG GGGGAACGGA
121 GATCAGCTGA TGCACTTGTA TACTTCTACA GAGAGGAACA GCTTCCATCT TCAAATCAAT
181 GCTGATGGCC ACATCAGTGG TGTTCCTTAC CAAACCATTT ACAGTGCCCT AATGATCAAG
241 TCTGAGGGTG CTGGCAGCGT TATAATCACA GGTGTGAAGA GTGGACGCTA CCTATGCATG
301 GACATGAAAG GAGACATTTT TGGATCGCAT TATTTCAGCC AAGAGGACTG CGTGTTCAAC
361 CAAAGAACAC TGGAAAATGG ATATGATGTG TATCAATCTC CCAAGCACAA TTTTCTGGTT
421 AGCTTAGGCA GAACTAAGCA AGTTTTCTTC CCTGGTATGA ATCCACCACC GTACTCCCAG
481 TTTTTGTCCA GGAGAAACGA AATCCCGTTG TTTCGATTCA ACACACCTGA ACCCCACAGA
541 AACACTAGAA GTGCAGATGT TGATCCAATG GATCCTCACC AGATCCTGGT CCCACAGAGA
601 AAGGTCTCTG CAATAGAGTC TCAGCTGCAA CTGCAAATGG ACTTTTCCCA TGTGCCCAGA
661 GAACCCATGA GAGTCAATCA GAACGATGTG GTCAACCCAG ATGACCCACA CGCTATGATG
721 GATGCCAGGA GATATGCTAG TCCTCGCTTT TACATTACAA GATAA
```

Green anole FGF23 gene coding sequence (1-242) (SEQ ID
NO: 309) (GenBank accession no. XM_003221363,
which is hereby incorporated by reference in its entirety)

```
  1 ATGGTCCAGG CTACTCTATA CAGCTTCCTC AAATATATGC TGCTTGCAAC ATGTAGCTGG
 61 AAAGCAATTG CTGCTTTCCC CAACGCATCA CCTTTGCTCA GCCTCAACTG GGGAAATTCA
121 GACAGCCTGC TACACTTGTA CACTTCCACA GCAAGAAACA GCTTCCACCT GCAAATCCAC
181 TCCAATGGCT ACGTGGATGG AAGTCCGTAT CAAACAATTT ACAGTGCCTT GATGATCAAA
241 TCTGAAGTTG CTGGTTATGT TATAATAAAT GGTGTGAAAA GTGGACGTTT TCTTTGTATG
301 GATATGAATG GGAACATCTT TGGATCGCAT TTCTTCAGTT ATGAGGACTG CACTTTCAAA
361 CACTGGGTCC TGGAAAATGG TTATGATGTT TATCAGTCTC CCAAATACAA CTACCTTGTC
421 AGCTTAGGAA AAGCAAAGCA ACCATTGTTC CCCAATATGA ATCCACCACC TTACTCCCAA
481 TTCTTGTCCA GGAGAAATGA AATTCCTTTA GTCCAGTTCA ACACACCGAA ACCTCACAGA
541 CATACCAGAA GTGCCAACGC GGATCCCTGC GGCAGCATCA TATCATCAGG AAATATTGCG
601 AAAGAAAACC TACAGTTACA GCCACTAATG TATAACACTA AAATGAATTC AAACAGTGAA
661 GATGAAGACC CAAACAGTGC AATAATCAAT AGAAGATTTT TGAGTCCTAG AACAGATGTC
721 AGGAGCTGA
```

Coelacanth FGF23 gene coding sequence (1-249) (SEQ
ID NO: 310) (Ensembl accession no. ENSLACT00000020646,
which is hereby incorporated by reference in its entirety)

```
  1 CTAGAGTCCG CTCTTCTTGC GTTTTCTATG GCTATATTCT ATAGCTTTAA AGCTGTGAGC
 61 TCTTTTTCCAA ATTCTTGCCC ACTGCTTAAC CCAGTCTGGG GAAACACTGA CAACCTGATA
121 CACCTGTATA CAGCTTCTGA GACGAACAGC TTCCACTTGC AGATCAACTC CGATGGACAT
181 GTGGATGGTA CTCCACACCA AACCGCTTAC AGTGCACTGC TGATCAAGTC CGAGGAGGCT
241 GGTTCTGTAG TTATCCTGGG GGTGAAGAGT GGACGTTACC TCTGTATGGA TATCAAGGGC
301 AATATTATTG GACTGCATCA CTTCAGCAAG GAAGACTGTA CATTCAAACA AGAGGGCTTG
361 GAAAATGGAT TTGATGTGCT GCGCTCACCT AAGCACAACA TTTTGGTCAG CCTTGACAAG
421 ACTAAACGCT CCTACATCCC GGGTATGAAC CTGCCACCTT ACTCACAGTT TTTATCCCGA
481 CAGAATGAAG TAGCTCTGAT CAACTTCATT AACACACCTG ACATACACAG ACATAGTCGA
541 AATGTTGATG TTGATCCTTC AGACCCCCAT GGGATGATAA TTCAGCCTGA TGTGGGTGTT
601 TCATTTCGTA AGTCTTCATC TCTGTTTTCA GATCTGCCCA GAGACTCCAT GAGAACTAGC
661 CATAATGGTA TGGATATGGT TGATCCTGCT GACCCACATG GAATGTTAGA TTCCAGGAGA
721 AGACCAAGTC CAAGGTTCTT TGCAAGATAG
```

Western clawed frog FGF23 gene coding sequence (1-254)
(SEQ ID NO: 311) (GenBank accession no.
XM_002940305,
which is hereby incorporated by reference in its entirety)

```
 25                         ATGACC AAGCAGCAAA CTAGACTAGG ACTGGTGCTC
 61 ACTGTTCTTG CCAGTATAAA GGTTATATCT GCCTTCCCCA ACTCTTCTCC AATAATCAGT
121 GGCGGCTGGG GGGTCCCTGA CAGACTGATG CACCTATATA CGGCCAGTGA CTGGAACAGC
181 TTCCACCTAC AGATCAACCA TGATGGAAGC ATTGATGGAA CCCTACCCA AACCATTTAC
241 AGTGCAATAA TGATCAAATC AGAATCCGCT GGGCACGTGG TTATTACTGG GGTGAAGACT
301 AATCGGTACC TGTGCATGGA TAAAGTGGG ACATTTTTG GATATCACGA CTTCAACCAC
361 GACGACTGCG TTTTTAAGCA CGAGACTCTG GAGAACAACT TTGACGTTTA CCATTCTCCA
421 AAACACAACT TTGTGATCAG CCTCAAGGAG CCCAAGCATC ATTTCCGCCT CGGCATGGAC
481 CTGCCCCCTT ACTCCCAATT CCTGTCCTTG GAGAATGAAA TCCCCATAAC CAGATTCAAT
```

TABLE 8-continued

```
541 GCTCCAGAGC CGGAAATGAG AATCCCAGAG GGCAACTTTG CTGACCCCAG CGACATCATA
601 AAGAACCCCA GGAACTGGGA CTTTTCGCAG TCTATTCATA ATCCATTTCA GGATGTGTGG
661 TTGCCGTTCC CCAGCGGTTC ATTACCAATC ATTAGAGCTT CCTTGCCAAT TATTCATAAC
721 AATGTGATTA ATACAGATGA CCCTGAAGAA ATTGTAAAAA TGAAGAGATA CAGATATTTC
781 AAGAGGTAG
```

Cat FGF23 gene coding sequence (1-199) (SEQ ID NO: 312)
(Ensembl accession no. ENSFCAT00000000141,
which is hereby incorporated by reference in its entirety)

```
  1 ATGTCAGGGA CCCGCCTTGG GCTCCTGGTC TCTGTCCTGT GCTGGGTAGT CAGAGCCTAT
 61 CCTAACACCT CCCCGCTGCT GGGCTCCAGC TGGGGTGGCC TGACCCACCT GTACACGGCC
121 ACAGCCAGGA ACAGCTACCA CCTGCAGATA CACAAGGACG GCCATGTGGA TGGCACACCC
181 CATCAGACCA TCTACAGTGC CCTGATGATC AGATCGGAGG ATGCCGGCTT TGTGGTGATA
241 ACAGGTGTGA TGAGTCAGAG GTACCTCTGT ATGGACTTCA GAGGCAATAT CTTCGGATCG
301 CACCTCTTCA GCCCCGAGAG CTGCAGGTTC CGACAGCGGA CGCTGGAAAA CGGCTACGAC
361 GTGTACCACT CCCCGCAGCA CCGCTTCCTA GTCAGCCTGG GCCCGGCCAA GAGGGCCTTC
421 CTGCCGGGCA CCAACCGCAT GACCCCCGCG CCGGCCTCCT GCTCCCAGGA GCTCCCAAGC
481 GCCGAGGACA GCGGCGTGGT GGCCAGCGAC CCGTTAGGGG TGCTCAGGGG CAACAGGGTG
541 AACGCGCACG CCGGGGGGAT GGGCGTGGAG AGGTGCCGCC CCTTCCCCAA GTTCAACTAG
```

Chinese softshell turtle FGF23 gene coding sequence
(1-250) (SEQ ID NO: 313) (Ensembl accession no.
ENSPSIT00000012816,
which is hereby incorporated by reference in its entirety)

```
 98                                     ATG TCACAGCCCA GCCAGTGCAG
121 CTGCCTGAAC TTCATGCTGT TCGTGCTATG TAGCTTCAAA GCTATTGCTG CCTTTCCCTT
181 CTTCTCTTCA CTGCTGAATC CCAGCTGGGG GGAAACGGAT AGTTTGATAC ACCTGTACAC
241 AGCTACTGAG AAGAACAGCT TCCATCTGCA GATCAACCCT GATGGTTATG TTGACGGCAC
301 ACCTCACCAA ACCATTTACA GTGCTCTAAT GATCAAATCT GAGGATGCTG GCTATGTGGT
361 GATAAGTGGT GTAAAGAGTG GGCGCTACCT ATGTATGGAC ATTAAAGGAA ATATCTTTGG
421 ATCGCATTAC TTCAGTCAAG AGGACTGCAT GTTTAAACAC AGAACACTGG AAAATGGATA
481 TGATGTGTAC CAGTCTCCCA AGCACAACTT CCTGGTCAGC CTGGGCAGGA ATAAACAAGC
541 TTTCTTCCCT GGTATGAATC TGCCACCATA CTCCCAGTTT TTGCCCAGGA GAAATGAAAT
601 CCCTCTGATC CGATTCAACA CACCCGAACC CCACAGGCAC ACTAGGAATG CAGATGTTGA
661 TCCCCTCCAG ATTTTGATCC CTCGGGGAGA GGCTTTTGAC ACAGGACCTC AGAGGTTGCA
721 GACTCACTTT GATCACCTGC CTAGAGAACC CATGAGAATC AATCCAAATG ATGTAGTCAG
781 CCCGGATGAC CCACTCGCCA TGATGGATGT CAGAAGGAAT GCAAGTCCAC GCCTTTACAT
841 TACAAGA
```

Ferret FGF23 gene coding sequence (1-245) (SEQ ID NO: 314)
(Ensembl accession no. ENSMPUT00000009396,
which is hereby incorporated by reference in its entirety)

```
186     ATGTC AGTGACCCGT CTTGGGCTCC TGGTCTCTGT CCTGTGCTGG GTAGTCAGAG
241 CCTATCCCAA CGCCTCCCCG CTGCTCGGCT CCAGCTGGGG TGGCCTGACC CACCTGTACA
301 CGGCCACTGC CAGGAACAGC TACCACCTGC AGATCCACAA GGATGGCCAT GTGGATGGCA
361 CACCCCACCA GACCATCTAC AGCGCCCTGA TGATCAGATC AGAGGATGCC GGCTTTGTGG
421 TGATCACAGG TGTGATGAGC AGGCGGTACC TGTGTATGGA CTTCCGAGGC AACATCTTTG
481 GATCCCACCT CTTCAGCCCC GAGAGCTGCA GGTTCCGACA GCGGACACTG GAAAACGGCT
541 ACGACGTGTA CCACTCCCCG CAGCACCGCT TCCTCGTCAG CCTGGGCCAA GCCAAGAGGG
601 CCTTCCTGCC GGGCACCAAC CGCCGCCCCT ACTCCCAGTT TCTGTCCCGG AGGAATGAGA
661 TCCCCCTCAT CCACTTCAAC ACCCCCAGGC CGCGGCGTCA CACGCGCAGC GCCGAGGACA
721 TGGAGCACGA CCCGTTGAAC GTGCTGAAGC CCCGGCCCCG CATGACCCCG GCCCCGGCCT
781 CCTGCTCCCA GGAGCTCCCG AGCGCCGAGG ACAACAGTGT GGTGGCCAGC GACCCGTTAG
841 GGGTGCTCAG AGGCAACCGG GTGAACGTGC ACGCGGGGGG GATGGGCGTG GACAGGTGCC
901 GCCCCCTCCC CAAGTTCATC TAG
```

Mouse lemur FGF23 gene coding sequence (1-206)
(SEQ ID NO: 315) (Ensembl accession no.
ENSMICT00000004875,
which is hereby incorporated by reference in its entirety)

```
  1 ATGCTGGGGG CCTGCCTCAG GCTCTGGGTC TGTGCCCTGT GCAGTGTCTG CGGCGTGAGC
 61 GTCGTCAGAG CCTATCCCAA CGCCTCCCCG CTGCTCGCCT CCAGCTGGGG TGGCCTGATC
121 CACCTGTACA CGGCCACGGC CAGGAACAGC TACCACCTGC AGATCCACAA GGACGGCCAT
181 GTGGACGGCA CACCCCACCA GACCATCTAC AGTGCCTTGA TGATCAGGTC AGAGGATGCT
241 GGCTTTGTGG TGATCACAGG TGTGATGAGC AGAAGATACC TCTGCATGGA TTTCAGAGGC
301 AACATTTTTG GATCACATGT CTTCAGCGCG GAGAGCTGCA GGTTCAGACA GCGGACGCTG
361 GAGAACGGCT TCGACGTGTA CCAGTCCCCT CAGCACCACT TCCTGGTCAG CCTGGGCCGC
421 GCCAAGGGGG CCTTTCCGGC CGGGGCGAAA CCGCCCCCCT TCCCCAGTT CCTGCCGCGG
481 GGGAACGAGG CTCCCGGGCG CAAAACGCGG GGGCCCGAGG AAAAAGGGGC CCACACCCT
541 CTCCGCGGGG TGGAAAGCGG GGGCCGGAAA GGCGGGGCCC GCCTCTCTG TTTGGAGAGG
601 CTCTCCAGAG CCCGAGAG
```

TABLE 8-continued

Orangutan FGF23 gene coding sequence (1-251,
excluding 2-22 and 38-71) (SEQ ID NO: 316)
(Ensembl accession no. ENSPPYT00000006110,
which is hereby incorporated by reference in its entirety)

```
  1 ATG------- ---------- ---------- ---------- ---------- ----------
 61 ------CGCA AT------GA GTCTTTGCCC TGCCTGGTTT TCTCCATAGG T---------
121 ---------- ---------- ---------- ---------- ---------- ----------
181 ---------- ---------- ---------- GCCCTGATGA TCAGATCAGA GGATGCTGGC
241 TTTGTGGTGA TTACAGGTGT GATGAGCAGA AGATACCTCT GCATGGATTT CAGAGGCAAC
301 ATTTTTGGAT CACACTATTT CAACCCGGAG AACTGCAGGT TCCAACACCA GACGCTGGAA
361 AACGGGTATG ACGTCTACCA CTCTCCTCAG CATCACTTCC TGGTCAGTCT GGGCCGGGTG
421 AAGAGAGCCT TCCTGCCAGG CATG---CCA CCCCCGTACT CCCAGTTCCT GTCCCGGAGG
481 AACGAGATCC CCTAATTCA CTTCAACACC CCCGTACCAC GGCGGCACAC CCGGAGCGCC
541 GAGGATGACA CGGAGCGGGA CCCCCTGAAA GTGCTGAAGC CCCGGGCCCG GATGACCCCG
601 GCCCCGGCCT CCTGCTCACA GGAGCTCCCG AGCTCCGAGG ACAACAGCCC GATGGCCAGC
661 GACCCATTAG GGGTGGTCAG GGGCGGTCGA GTGAACACGC ACGCTGGGGG AACGGGCCCG
721 GAAGGCTGCC GCCCCTTCCC CAAGTTCATC
```

Shrew FGF23 gene coding sequence (1-251,
excluding 19-27, 71-105, 198-200, and 236-251)
(SEQ ID NO: 317) (Ensembl accession no. ENSSART00000007775,
which is hereby incorporated by reference in its entirety)

```
  1 ATGTGGGGAC TCCGCCTGGG TCTCTTGGTC GGCCTCCTGG GCTGCGTGGA CAGA------
 61 GCCTCCCCGA TGCTGGCGTC CAGCTGGGGC GGCCTGACGC ACCTGTACAC GGCCACGGCC
121 AGGAACAGCT ACCACCTCCA GATCCACAAG GACGGCCTGG TCGACGGCTC CCCGCAGCAG
181 ACCGTCTAC- ---------- ---------- ---------- ---------- ----------
241 ---------- ---------- ---------- ---------- ---------- ----CACCAT
301 TTCAGCCCGG AGAGCTGCCG CTTCCAGCAG CGCACGCTGG AGAACGGCTA CGACGTGTAC
361 CAGTCCCCGC AGCACCGCTT CCTCGTGAGC CTGGGCCGGC CCAAGCGCGC CTTCCAGCCG
421 GGCGCCAACC CGCCGCCCTA CGCGCAGTTC CTGGCGCGCC GCAACGAGGT GCCCCTGGCG
481 CGCTTCCACA CGCCCGCGCC GCGCCGCCAC ACGCGCAGCG CGCACGACAA CGGCGACGCC
541 GACCCGCTCA ACGTGCTGGC GCCTCGGGCC ---------G CCGCCGCCGC CTCCTGCTCG
601 CACGAGCTGC CCAGCGCCGA GGACAACAGC GTGGTGGCCA GCGACCCGCT GGGCGTCATC
661 CGCAGCAACC GCTTCCGCAC GCAC
```

Tetraodon FGF23 gene coding sequence (1-263) (SEQ
ID NO: 318) (Ensembl accession no. ENSTNIT00000014553,
which is hereby incorporated by reference in its entirety)

```
  1 ATGGACGTAA ACAGAAGGAT CGGGGTGAAG GACGCCTTGC TGGCGCTCCT GCTCGCCCTT
 61 CTCCAGGGAT GCCCCCTGGG GGAAACGGCT CCCAACGCGT CACCGCTGGT CGGTTCCAAC
121 TGGGGGAACC CGAGGAGGTA CGTTCACCTT CAGACATCCA CAGACATGAG CAACTTCTAC
181 TTGGAGATCA GACTGGATGG AACCGTGCGC AAAAGCACAG CCCGGACTTC ATACAGTGTG
241 ATTTTACTGA AAGCCGACAC GAGGGAGCGC ATCGCCATCC TGGGCGTCAA GAGCAACCGT
301 TACCTGTGTA TGGACCTCGA GGGGAGCCCA TTTAGCTCTC CCACCTGCAT CAGGGACGAC
361 TGCTTGTTCA ACCACAGTCT TCTGGAGAAC AACCGGACG TCTACTACTC CAGCCGGACC
421 GGCATTCTCT TCAACCTTGA GGGCTCCCGC CAGGTGTTCG TGGTGGGCCA GAACGTCCCG
481 CAGACCTCCC TCTTCCTGCC CAGGACGAAC ACGGTGCCGC TGGAGCGACT CCTTCTGCAC
541 AGGGACAAGC GGAACCAGGT GGTGGACCCC TCTGACCCGC ACCGCGTCGC CGTGGGTCGC
601 GCCGAGGAGG GCTCGGACTC CCGGGCCTTG CAGGAGGACG ACGCCGACCT GGAGGTGGAG
661 ACAGAGGTTG AGGTCGGGGA CGACGGACGC AACGCGTCCC GGGAGCGGCT GCAGGCTCCG
721 TCCGATCACG ACCCCTGGGG CGTGTTCTCC TCCAACCCCG GGAGCCCCCG CAGCAGCGGC
781 ACGGTGGGCT GA
```

Tilapia FGF23 gene coding sequence (1-255) (SEQ ID
NO: 319) (Ensembl accession no. ENSONIT00000000020,
which is hereby incorporated by reference in its entirety)

```
 472                                                           ATGGACGTC
 481 AACAGGCGAA TGGGGATGAG AGACACCGTG CTGGCGCTCT TTCTCGCTGT CTTGCAGGGA
 541 TTTCCTCTCG GGGATACGGT CCCGAACCCA TCACCTCTGG CTGGATCCAA CTGGGGGAAC
 601 CCAAGGAGAT ACGTCCACCT GCAGACATCC ACAGACCTCA ATAACTTCTA CTTGGAGATC
 661 AGATTAGATG GGAGTGTGCG CAAAACTACG TCCAGGAGCA CCTATAGTGT GATTCTACTG
 721 AAATCTGAAG CAAGAGATCG CGTCGCCATC CTCGGCGTCA AAAGCAGCCG TTACCTATGC
 781 ATGGACCTGG AGGGCAACCC GTTCAGCTCT CCTGTCTGCC TTCGGGATGA CTGTCTGTTC
 841 AACCACAAGC TCCTGGAGAA CAACCGGGAC GTGTACTACT CCAGCCGGAC AGGCATCTTG
 901 TTCAACCTGG AGGGCTCCCG ACAGGTGTAC TCGGTGGGCC AGAACCTGCC GCAGACCTCC
 961 CTCTTCTTGC CCAGGAAAAA CACCGTACCA CTGGAGCGCC TCCTGCTGCA CAGGGAGAAG
1021 AGAAACCGGG GGCAGACAGA AGAGGGTTCG GACTCCCGGG CCGTGCCGGA GGAGCTGGAG
1081 GAAAGGGAGG TGGAAATGGA GACGGAAATA GAAACAGAGG TCGGGGATGA CGGACGCAAC
1141 GTGTCCCGGG AGAAACTCGC GGCTCCATCC AGCCACGACC CCTGGAACGT GCACTTCTCC
1201 AACCCGGCCA GCCCCGGAG CACCGGGACA GTGGGCTGA
```

TABLE 8-continued

Zebrafish FGF23 gene coding sequence (1-258) (SEQ ID
NO: 320) (Ensembl accession no. ENSDART00000067388,
which is hereby incorporated by reference in its entirety)

```
 79                     AT GCGTTGCGCA CTTTCCAACC TGCACATGCT GCATTCATCC
121 GTCCTCGCGC TGTGGTTCAC GGCTCTCCAG GGACTCAGAC CTGCAGATGC GGCCCCCAAT
103 CCTTCTCCGC TGCTGGGCTC CAACTGGGGG AACCCGCGGA GATACATCCA CCTTCAGACC
163 ACTTCAGACT TAAACAACTA CTACCTGGAG ATCAGCCCGA GTGGACACGT GCGCAAAACT
223 ACAAATCGGG GCTCATACAG TGTAATCTTA TTGAAAACAG AAAGCAGAGA CCGTCTGGCG
283 ATATTTGGAG TGAAAAGTAA CCGGTTTTTG TGCATGGATA CAGGAGGAAC CCTTTTCACA
343 TCTACGATCT GCAATAAGGA AGACTGTCTT TTCCACCACA AACTGTTGGA AAACCATCGT
403 GATGTGTATT ACTCCACTAA ACACAGCATA CTGCTTAATC TGGACGGGGA CAAACAGGCG
463 TTTATAGCGG GACAAAACCT CCCTCAGTCG TCTCTCTTCT TGTCGGAGAA GAACACGGTT
523 CCGCTGGAGC GCCTGCAGCA TCGGGAGCGC AGGAACCGGC AGGTGAACCC AACAGACCCG
583 CTGAACGCGC TCCGGTACGC GGAGGAGTCT GATTCCAGAG CCGCGCAGGA GGATGATGGA
643 GACATGGATT TTGAGCCCTC AGAAGGTCAA AACATCTCTA GAGAAACCCT TGTTTCCCCT
703 TCCGATGATG ATCCATGGGA TCTTCTGCAC GACACGAGCC CTGGAAGTCC TCGGATTGCA
763 GCAATTGTCG GATAA
```

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

In one embodiment, the chimeric protein of the present invention includes the amino acid sequence of SEQ ID NO: 321, SEQ ID NO: 322, SEQ ID NO: 323, or SEQ ID NO: 324, as shown in Table 9.

TABLE 9

| Description of Chimeric Protein | Sequence |
|---|---|
| Amino acid sequence of a FGF1/FGF23 chimera composed of residues M1 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 321<br>MAEGEITTFT ALTEKFNLPP GNYKKPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK<br>NWFVGLDQNG SCVRGPRTHY GQKAILFLPL<br>**RNEIPLIHFN TPIPR*Q*HT*Q*S AEDDSERDPL<br>NVLKPRARMT PAPASCSQEL PSAEDNSPMA<br>SDPLGVVRGG RVNTHAGGTG PEGCRPFAKF I** |
| Amino acid sequence of a FGF1/FGF23 chimera composed of residues K25 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 322<br>                          KPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK<br>NWFVGLDQNG SCVRGPRTHY GQKAILFLPL<br>**RNEIPLIHFN TPIPR*Q*HT*Q*S AEDDSERDPL<br>NVLKPRARMT PAPASCSQEL PSAEDNSPMA<br>SDPLGVVRGG RVNTHAGGTG PEGCRPFAKF I** |
| Amino acid sequence of a FGF2/FGF23 chimera composed of residues M1 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 323<br>MAAGSITTLP ALPEDGGSGA FPPGHFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVALDQT GQYVLGSKTG PGQKAILFLP<br>**MRNEIPLIHF NTPIPR*Q*HT*Q* SAEDDSERDP<br>LNVLKPRARM TPAPASCSQE LPSAEDNSPM<br>ASDPLGVVRG GRVNTHAGGT GPEGCRPFAK<br>FI** |
| Amino acid sequence of a FGF2/FGF23 chimera composed of residues H25 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 324<br>                          HFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVALDQT GQYVLGSKTG PGQKAILFLP<br>**MRNEIPLIHF NTPIPR*Q*HT*Q* SAEDDSERDP<br>LNVLKPRARM TPAPASCSQE LPSAEDNSPM<br>ASDPLGVVRG GRVNTHAGGT GPEGCRPFAK<br>FI** |

Chimeric proteins according to the present invention may be isolated proteins or polypeptides. The isolated chimeric proteins of the present invention may be prepared for use in accordance with the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 325, SEQ ID NO: 326, SEQ ID NO: 327, or SEQ ID NO: 328 (as shown in Table 10).

TABLE 10

| Description of Chimeric Protein | Sequence |
| --- | --- |
| Nucleotide sequence of a FGF1/FGF23 chimera composed of residues M1 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 325<br>ATGGCTGAAG GGGAAATCAC CACCTTCACA<br>GCCCTGACCG AGAAGTTTAA TCTGCCTCCA<br>GGGAATTACA AGAAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>AGGAACGAGA TCCCCCTAAT TCACTTCAAC<br>ACCCCCATAC CACGG*CA*GCA CACC*CA*GAGC<br>GCCGAGGACG ACTCGGAGCG GGACCCCCTG<br>AACGTGCTGA AGCCCCGGGC CCGGATGACC<br>CCGGCCCCGG CCTCCTGTTC ACAGGAGCTC<br>CCGAGCGCCG AGGACAACAG CCCGATGGCC<br>AGTGACCCAT TAGGGTGGT CAGGGGCGGT<br>CGAGTGAACA CGCACGCTGG GGGAACGGGC<br>CCGGAAGGCT GCCGCCCCTT CGCCAAGTTC<br>ATC |
| Nucleotide sequence of a FGF1/FGF23 chimera composed of residues K25 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 326<br>AAGCCCAA ACCCCCATAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTCGA TCAGAATGGG<br>AGCTGCGTTC GCGGTCCTCG GACTCACTAT<br>GGCCAGAAAG CAATCTTGTT TCTCCCCCTG<br>AGGAACGAGA TCCCCCTAAT TCACTTCAAC<br>ACCCCCATAC CACGG*CA*GCA CACC*CA*GAGC<br>GCCGAGGACG ACTCGGAGCG GGACCCCCTG<br>AACGTGCTGA AGCCCCGGGC CCGGATGACC<br>CCGGCCCCGG CCTCCTGTTC ACAGGAGCTC<br>CCGAGCGCCG AGGACAACAG CCCGATGGCC<br>AGTGACCCAT TAGGGTGGT CAGGGGCGGT<br>CGAGTGAACA CGCACGCTGG GGGAACGGGC<br>CCGGAAGGCT GCCGCCCCTT CGCCAAGTTC<br>ATC |
| Nucleotide sequence of a FGF2/FGF23 chimera composed of residues M1 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 327<br>ATG GCAGCCGGGA<br>GCATCACCAC GCTGCCCGCC TTGCCCGAGG<br>ATGGCGGCAG CGGCGCCTTC CCGCCCGGCC<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG |

TABLE 10-continued

| Description of Chimeric Protein | Sequence |
|---|---|
| | TGGCACTGGA TCAGACTGGG CAGTATGTTC<br>TTGGATCCAA AACAGGACCT GGGCAGAAAG<br>CTATACTTTT TCTTCCAATG AGGAACGAGA<br>TCCCCCTAAT TCACTTCAAC ACCCCCATAC<br>CACGG*CAG*CA CAC*CCAG*AGC GCCGAGGACG<br>ACTCGGAGCG GGACCCCCTG AACGTGCTGA<br>AGCCCCGGGC CCGGATGACC CCGGCCCCGG<br>CCTCCTGTTC ACAGGAGCTC CCGAGCGCCG<br>AGGACAACAG CCCGATGGCC AGTGACCCAT<br>TAGGGGTGGT CAGGGGCGGT CGAGTGAACA<br>CGCACGCTGG GGGAACGGGC CCGGAAGGCT<br>GCCGCCCCTT CGCCAAGTTC ATC |
| Nucleotide sequence of a FGF2/FGF23 chimera composed of residues H25 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 328<br>C<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTG<br>AACGATTGGA ATCTAATAAC TACAATACTT<br>ACCGGTCAAG GAAATACACC AGTTGGTATG<br>TGGCACTGGA TCAGACTGGG CAGTATGTTC<br>TTGGATCCAA AACAGGACCT GGGCAGAAAG<br>CTATACTTTT TCTTCCAATG AGGAACGAGA<br>TCCCCCTAAT TCACTTCAAC ACCCCCATAC<br>CACGG*CAG*CA CAC*CCAG*AGC GCCGAGGACG<br>ACTCGGAGCG GGACCCCCTG AACGTGCTGA<br>AGCCCCGGGC CCGGATGACC CCGGCCCCGG<br>CCTCCTGTTC ACAGGAGCTC CCGAGCGCCG<br>AGGACAACAG CCCGATGGCC AGTGACCCAT<br>TAGGGGTGGT CAGGGGCGGT CGAGTGAACA<br>CGCACGCTGG GGGAACGGGC CCGGAAGGCT<br>GCCGCCCCTT CGCCAAGTTC ATC |

Another aspect of the present invention relates to a nucleic acid construct including a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors including such nucleic acid molecules and host cells including such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, 1 pp, and the like, may be used to direct high levels of transcription of adjacent DNA segments. Additionally, a hybrid trp-lacUV 5 (tac) promoter or other E. coli promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

In one particular embodiment of the present invention, the pharmaceutical composition according to the present invention is administered with another hypophosphatemic agent, a phosphate binder, a vitamin D antagonist, an analgesic, and/or an anti-inflammatory agent.

The pharmaceutical composition according to the present invention can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

Another aspect of the present invention relates to a method for treating a subject suffering from a disorder. This method involves selecting a subject suffering from the disorder and administering the pharmaceutical composition according to the present invention to the selected subject under conditions effective to treat the disorder. In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification.

Accordingly, another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Suitable chimeric proteins for use in accordance with this aspect of the present invention are described above and throughout the present application.

In one embodiment, the selected subject is a mammal. In one embodiment, the selected subject is a human. In another embodiment, the selected subject is a rodent.

In one embodiment, the chimeric FGF protein is effective for treating disorders associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the chimeric FGF protein is effective for treating disorders associated with soft tissue calcification. In one embodiment, the chimeric FGF protein normalizes vitamin D metabolism and/or phosphate metabolism. In one embodiment, the chimeric FGF protein ameliorates soft tissue calcification.

The chimeric protein of the present invention or pharmaceutical composition thereof can be used to treat a number of conditions. In one embodiment, the condition is one which the therapeutic outcome includes a decrease in circulating phosphate levels. In one embodiment, the condition is one which the therapeutic outcome includes a decrease in circulating levels of bioactive vitamin D. Each of these parameters can be measured by standard methods, for example, by performing blood tests for phosphate and vitamin D.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification. In one embodiment, the disorder is tumoral calcinosis (also referred to as hyperphosphatemic familial tumoral calcinosis, Online Mendelian Inheritance in Man, ID 211900 (purl.bioontology.org/ontology/OMIM/211900), which is hereby incorporated by reference in its entirety). In one embodiment, the disorder is associated with hyperostosis, diaphysitis, arterial aneurysms, dental abnormalities, and/or angioid streaks of the retina.

Familial tumoral calcinosis is an autosomal recessive metabolic disorder associated with hyperphosphatemia and soft tissue calcification. Missense mutations in either the UDP-N-acetyl-α-D-galactosamine:polypeptide N-acetylgalactosaminyltransferase 3 (GALNT3) gene (Garringer et al., "Two Novel GALNT3 Mutations in Familial Tumoral Calcinosis," *Am J Med Genet A* 143A:2390-2396 (2007)) or the FGF23 gene (Garringer et al., "Molecular Genetic and Biochemical Analyses of FGF23 Mutations in Familial Tumoral Calcinosis," *Am J Physiol Endocrinol Metab* 295: E929-E937 (2008); Araya et al., "A Novel Mutation in Fibroblast Growth Factor 23 Gene as a Cause of Tumoral Calcinosis," *J Clin Endocrinol Metab* 90:5523-5527 (2005), each of which is hereby incorporated by reference in its entirety) have been associated with familial tumoral calcinosis. All patients with familial tumoral calcinosis have abnormally high plasma levels of the C-terminal proteolytic fragment of FGF23 but abnormally low plasma levels of intact, full-length FGF23. The excess C-terminal FGF23 fragment may aggravate hyperphosphatemia, and the resulting soft tissue calcification, by antagonizing the action of any residual, functional FGF23 ligand in these patients. Thus, the chimeric and modified proteins according to the present invention are FGF23 agonists that provide a causative form of treatment for these patients.

In one embodiment, the chimeric protein of the present invention or pharmaceutical composition thereof is administered with a pharmaceutically-acceptable carrier.

The chimeric protein according to the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. Formulations including chimeric proteins according to the present invention may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions including the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 µg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. Guidance as to particular dosages and methods of delivery of proteins is provided in the literature; see, for example, U.S. Pat. Nos. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," Nat. Med. 2:795-799 (1996); Yasuda, "Sustained Release Formulation of Interferon," Biomed. Ther. 27:1221-1223 (1993); Hora et al., "Controlled Release of Interleukin-2 from Biodegradable Microspheres," Nat. Biotechnol. 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

In some embodiments, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is a hypophosphatemic agent, a phosphate binder, a vitamin D antagonist, an analgesic, and/or an anti-inflammatory agent.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a C-terminal portion of FGF23 that includes a α-Klotho-FGFR complex binding domain to the modified FGF protein's C-terminus, whereby a chimeric FGF protein possessing enhanced endocrine activity is made.

Suitable C-terminal portions of FGF23 are described above. In one embodiment, the C-terminal region from FGF23 is derived from a mammalian FGF23. In one embodiment, the C-terminal region derived from FGF23 is from a vertebrate FGF23.

In one embodiment, the chimeric FGF protein has greater binding affinity for FGFR than native FGF23. In one embodiment the chimeric FGF protein possesses enhanced endocrine activity compared to the chimeric FGF protein in the absence of the modification or the α-Klotho-FGFR complex binding domain. In one embodiment, the native endocrine FGF ligand having the α-Klotho co-receptor-FGFR binding domain is native FGF23. In one embodiment, the FGFR is FGFR1c, FGFR3c, or FGFR4.

In one embodiment, the chimeric FGF protein has greater stability than a native endocrine FGF ligand possessing the α-Klotho-FGFR complex binding domain. In one embodiment, increasing the stability includes an increase in thermal stability of the protein as compared to either wild type protein or native endocrine FGF ligand. In one embodiment, increasing the stability includes increasing the half-life of the protein in the blood circulation as compared to wild type or native protein or native endocrine FGF ligand.

In one embodiment, the FGF is derived from a mammalian FGF. In one embodiment, the FGF is derived from a vertebrate FGF. In one embodiment, the FGF protein is a paracrine FGF molecule. In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

In one embodiment, the chimeric FGF protein normalizes vitamin D metabolism and/or phosphate metabolism.

Suitable methods of generating chimeric proteins according to the present invention include standard methods of synthesis known in the art, as described above.

Yet another aspect of the present invention relates to a method of facilitating fibroblast growth factor receptor ("FGFR")-α-Klotho co-receptor complex formation. This method involves providing a cell that includes a α-Klotho co-receptor and an FGFR and providing a chimeric FGF protein. The chimeric FGF protein includes a C-terminal portion of FGF23 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-αKlotho co-receptor complex formation.

The portion of the paracrine FGF may also be modified to alter receptor-binding specificity and/or receptor-binding affinity of the FGF, as noted above. Suitable portions of the paracrine FGFs for use in accordance with the present invention, as well as modifications to receptor-binding specificity and/or receptor-binding affinity of the FGF are described above. Suitable modifications to the paracrine FGFs for use in accordance with the present invention are also described above. Suitable C-terminal portions from FGF23 are described above and throughout the present application.

In one embodiment according to the present invention, α-Klotho is mammalian αKlotho. In one embodiment, α-Klotho is human or mouse α-Klotho. In one particular embodiment of the present invention, α-Klotho is human or mouse αKlotho having the amino acid sequence of SEQ ID NO: 329 (i.e., GenBank Accession No. NP_004786, which is hereby incorporated by reference in its entirety) or SEQ ID NO: 331 (i.e., GenBank Accession No. NP_038851, which is hereby incorporated by reference in its entirety), respectively, as follows:

```
SEQ ID NO: 329:
   1 MPASAPPRRP RPPPPSLSLL LVLLGLGGRR LRAEPGDGAQ TWARFSRPPA PEAAGLFQGT

61 FPDGFLWAVG SAAYQTEGGW QQHGKGASIW DTFTHHPLAP PGDSRNASLP LGAPSPLQPA

121 TGDVASDSYN NVFRDTEALR ELGVTHYRFS ISWARVLPNG SAGVPNREGL RYYRRLLERL

181 RELGVQPVVT LYHWDLPQRL QDAYGGWANR ALADHFRDYA ELCFRHFGGQ VKYWITIDNP

241 YVVAWHGYAT GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP DFTESEKKFI

361 KGTADFFALC FGPTLSFQLL DPHMKFRQLE SPNLRQLLSW IDLEFNHPQI FIVENGWFVS

421 GTTKRDDAKY MYYLKKFIME TLKAIKLDGV DVIGYTAWSL MDGFEWHRGY SIRRGLFYVD

481 FLSQDKMLLP KSSALFYQKL IEKNGFPPLP ENQPLEGTFP CDFAWGVVDN YIQVDTTLSQ

541 FTDLNVYLWD VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL LARQGAWENP

661 YTALAFAEYA RLCFQELGHH VKLWITMNEP YTRNMTYSAG HNLLKAHALA WHVYNEKFRH

721 AQNGKISIAL QADWIEPACP FSQKDKEVAE RVLEFDIGWL AEPIFGSGDY PWVMRDWLNQ

781 RNNFLLPYFT EDEKKLIQGT FDFLALSHYT TILVDSEKED PIKYNDYLEV QEMTDITWLN

841 SPSQVAVVPW GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS NGFPGPETLE

961 RFCPEEFTVC TECSFFHTRK SLLAFIAFLF FASIISLSLI FYYSKKGRRS YK

SEQ ID NO: 331:
   1 MLARAPPRRP PRLVLLRLLL LHLLLLALRA RCLSAEPGQG AQTWARFARA PAPEAAGLLH

61 DTFPDGFLWA VGSAAYQTEG GWRQHGKGAS IWDTFTHHSG AAPSDSPIVV APSGAPSPPL

121 SSTGDVASDS YNNVYRDTEG LRELGVTHYR FSISWARVLP NGTAGTPNRE GLRYYRRLLE

181 RLRELGVQPV VTLYHWDLPQ RLQDTYGGWA NRALADHFRD YAELCFRHFG GQVKYWITID

241 NPYVVAWHGY ATGRLAPGVR GSSRLGYLVA HNLLLAHAKV WHLYNTSFRP TQGGRVSIAL
```

```
301 SSHWINPRRM TDYNIRECQK SLDFVLGWFA KPIFIDGDYP ESMKNNLSSL LPDFTESEKR

361 LIRGTADFFA LSFGPTLSFQ LLDPNMKFRQ LESPNLRQLL SWIDLEYNHP PIFIVENGWF

421 VSGTTKRDDA KYMYYLKKFI METLKAIRLD GVDVIGYTAW SLMDGFEWHR GYSIRRGLFY

481 VDFLSQDKEL LPKSSALFYQ KLIEDNGFPP LPENQPLEGT FPCDFAWGVV DNYVQVDTTL

541 SQFTDPNVYL WDVHHSKRLI KVDGVVAKKR KPYCVDFSAI RPQITLLREM RVTHFRFSLD

601 WALILPLGNQ TQVNHTVLHF YRCMISELVH ANITPVVALW QPAAPHQGLP HALAKHGAWE

661 NPHTALAFAD YANLCFKELG HWVNLWITMN EPNTRNMTYR AGHHLLRAHA LAWHLYDDKF

721 RAAQKGKISI ALQADWIEPA CPFSQNDKEV AERVLEFDIG WLAEPIFGSG DYPRVMRDWL

781 NQKNNFLLPY FTEDEKKLVR GSFDFLAVSH YTTILVDWEK EDPMKYNDYL EVQEMTDITW

841 LNSPSQVAVV PWGLRKVLNW LRFKYGDLPM YVTANGIDDD PHAEQDSLRI YYIKNYVNEA

901 LKAYVLDDIN LCGYFAYSLS DRSAPKSGFY RYAANQFEPK PSMKHYRKII DSNGFLGSGT

961 LGRFCPEEYT VCTECGFFQT RKSLLVFISF LVFTFIISLA LIFHYSKKGQ RSYK
```

In one particular embodiment of the present invention, α-Klotho is human or mouse α-Klotho encoded by a nucleotide sequence having the nucleotide sequences of SEQ ID NO: 330 (GenBank Accession No. NM_04795, which is hereby incorporated by reference in its entirety) and SEQ ID NO: 332 (GenBank Accession No. NM_013823, which is hereby incorporated by reference in its entirety), as follows:

```
SEQ ID NO: 330 (human αKlotho gene coding sequence):
    9         AT GCCCGCCAGC GCCCCGCCGC CCGCCCGCG GCCGCCGCCG CCGTCGCTGT

61 CGCTGCTGCT GGTGCTGCTG GGCCTGGGCG CCGCCGCCT GCGTGCGGAG CCGGGCGACG

121 GCGCGCAGAC CTGGGCCCGT TTCTCGCGGC CTCCTGCCCC GAGGCCGCG GGCCTCTTCC

181 AGGGCACCTT CCCCGACGGC TTCCTCTGGG CCGTGGGCAG CGCCGCCTAC CAGACCGAGG

241 GCGGCTGGCA GCAGCACGGC AAGGGTGCGT CCATCTGGGA TACGTTCACC CACCACCCCC

301 TGGCACCCCC GGGAGACTCC CGGAACGCCA GTCTGCCGTT GGGCGCCCCG TCGCCGCTGC

361 AGCCCGCCAC CGGGGACGTA GCCAGCGACA GCTACAACAA CGTCTTCCGC GACACGGAGG

421 CGCTGCGCGA GCTCGGGGTC ACTCACTACC GCTTCTCCAT CTCGTGGGCG CGAGTGCTCC

481 CCAATGGCAG CGCGGGCGTC CCCAACCGCG AGGGGCTGCG CTACTACCGG CGCCTGCTGG

541 AGCGGCTGCG GGAGCTGGGC GTGCAGCCCG TGGTCACCCT GTACCACTGG GACCTGCCCC

601 AGCGCCTGCA GGACGCCTAC GGCGGCTGGG CCAACCGCGC CCTGGCCGAC CACTTCAGGG

661 ATTACGCGGA GCTCTGCTTC CGCCACTTCG GCGGTCAGGT CAAGTACTGG ATCACCATCG

721 ACAACCCCTA CGTGGTGGCC TGGCACGGCT ACGCCACCGG GCGCCTGGCC CCCGGCATCC

781 GGGGCAGCCC GCGGCTCGGG TACCTGGTGG CGCACAACCT CCTCCTGGCT CATGCCAAAG

841 TCTGGCATCT CTACAATACT TCTTTCCGTC CCACTCAGGG AGGTCAGGTG TCCATTGCCC

901 TAAGCTCTCA CTGGATCAAT CCTCGAAGAA TGACCGACCA CAGCATCAAA GAATGTCAAA

961 AATCTCTGGA CTTTGTACTA GGTTGGTTTG CCAAACCCGT ATTTATTGAT GGTGACTATC

1021. CCGAGAGCAT GAAGAATAAC CTTTCATCTA TTCTGCCTGA TTTTACTGAA TCTGAGAAAA

1081 AGTTCATCAA AGGAACTGCT GACTTTTTTG CTCTTTGCTT TGGACCCACC TTGAGTTTTC

1141 AACTTTTGGA CCCTCACATG AAGTTCCGCC AATTGGAATC TCCCAACCTG AGGCAACTGC

1201 TTTCCTGGAT TGACCTTGAA TTTAACCATC CTCAAATATT TATTGTGGAA AATGGCTGGT

1261 TTGTCTCAGG GACCACCAAG AGAGATGATG CCAAATATAT GTATTACCTC AAAAAGTTCA
```

```
-continued
1321  TCATGGAAAC CTTAAAAGCC ATCAAGCTGG ATGGGGTGGA TGTCATCGGG TATACCGCAT
1381  GGTCCCTCAT GGATGGTTTC GAGTGGCACA GAGGTTACAG CATCAGGCGG GGACTCTTCT
1441  ATGTTGACTT TCTAAGCCAG GACAAGATGT TGTTGCCAAA GTCTTCAGCC TTGTTCTACC
1501  AAAAGCTGAT AGAGAAAAAT GGCTTCCCTC CTTTACCTGA AAATCAGCCC CTAGAAGGGA
1561  CATTTCCCTG TGACTTTGCT TGGGGAGTTG TTGACAACTA CATTCAAGTA GATACCACTC
1621  TGTCTCAGTT TACCGACCTG AATGTTTACC TGTGGGATGT CCACCACAGT AAAAGGCTTA
1681  TTAAAGTGGA TGGGGTTGTG ACCAAGAAGA GGAAATCCTA CTGTGTTGAC TTTGCTGCCA
1741  TCCAGCCCCA GATCGCTTTA CTCCAGGAAA TGCACGTTAC ACATTTTCGC TTCTCCCTGG
1801  ACTGGGCCCT GATTCTCCCT CTGGGTAACC AGTCCCAGGT GAACCACACC ATCCTGCAGT
1861  ACTATCGCTG CATGGCCAGC GAGCTTGTCC GTGTCAACAT CACCCCAGTG GTGGCCCTGT
1921  GGCAGCCTAT GGCCCCGAAC CAAGGACTGC CGCGCCTCCT GGCCAGGCAG GGCGCCTGGG
1981  AGAACCCCTA CACTGCCCTG GCCTTTGCAG AGTATGCCCG ACTGTGCTTT CAAGAGCTCG
2041  GCCATCACGT CAAGCTTTGG ATAACGATGA ATGAGCCGTA TACAAGGAAT ATGACATACA
2101  GTGCTGGCCA AACCTTCTG AAGGCCCATG CCCTGGCTTG GCATGTGTAC AATGAAAAGT
2161  TTAGGCATGC TCAGAATGGG AAAATATCCA TAGCCTTGCA GGCTGATTGG ATAGAACCTG
2221  CCTGCCCTTT CTCCCAAAAG GACAAAGAGG TGGCTGAGAG AGTTTTGGAA TTTGACATTG
2281  GCTGGCTGGC TGAGCCCATT TTCGGCTCTG GAGATTATCC ATGGGTGATG AGGGACTGGC
2341  TGAACCAAAG AAACAATTTT CTTCTTCCTT ATTTCACTGA AGATGAAAAA AAGCTAATCC
2401  AGGGTACCTT TGACTTTTTG GCTTTAAGCC ATTATACCAC CATCCTTGTA GACTCAGAAA
2461  AAGAAGATCC AATAAAATAC AATGATTACC TAGAAGTGCA AGAAATGACC GACATCACGT
2521  GGCTCAACTC CCCCAGTCAG GTGGCGGTAG TGCCCTGGGG GTTGCGCAAA GTGCTGAACT
2581  GGCTGAAGTT CAAGTACGGA GACCTCCCCA TGTACATAAT ATCCAATGGA ATCGATGACG
2641  GGCTGCATGC TGAGGACGAC CAGCTGAGGG TGTATTATAT GCAGAATTAC ATAAACGAAG
2701  CTCTCAAAGC CCACATACTG GATGGTATCA ATCTTTGCGG ATACTTTGCT TATTCGTTTA
2761  ACGACCGCAC AGCTCCGAGG TTTGGCCTCT ATCGTTATGC TGCAGATCAG TTTGAGCCCA
2821  AGGCATCCAT GAAACATTAC AGGAAAATTA TTGACAGCAA TGGTTTCCCG GGCCCAGAAA
2881  CTCTGGAAAG ATTTTGTCCA GAAGAATTCA CCGTGTGTAC TGAGTGCAGT TTTTTTCACA
2941  CCCGAAAGTC TTTACTGGCT TTCATAGCTT TTCTATTTTT TGCTTCTATT ATTTCTCTCT
3001  CCCTTATATT TTACTACTCG AAGAAAGGCA GAAGAAGTTA CAAATAG
SEQ ID NO: 332 (murine αKlotho gene coding sequence):
  111                                                          ATGCTAGCCC
  121  GCGCCCCTCC TCGCCGCCCG CCGCGGCTGG TGCTGCTCCG TTTGCTGTTG CTGCATCTGC
  181  TGCTGCTCGC CCTGCGCGCC CGCTGCCTGA GCGCTGAGCC GGGTCAGGGC GCGCAGACCT
  241  GGGCTCGCTT CGCGCGCGCT CCTGCCCCAG AGGCCGCTGG CCTCCTCCAC GACACCTTCC
  301  CCGACGGTTT CCTCTGGGCG GTAGGCAGCG CCGCCTATCA GACCGAGGGC GGCTGGCGAC
  361  AGCACGGCAA AGGCGCGTCC ATCTGGGACA CTTTCACCCA TCACTCTGGG GCGGCCCCGT
  421  CCGACTCCCC GATCGTCGTG GCGCCGTCGG GTGCCCCGTC GCCTCCCCTG TCCTCCACTG
  481  GAGATGTGGC CAGCGATAGT TACAACAACG TCTACCGCGA CACAGAGGGG CTGCGCGAAC
  541  TGGGGGTCAC CCACTACCGC TTCTCCATAT CGTGGGCGCG GGTGCTCCCC AATGGCACCG
  601  CGGGCACTCC CAACCGCGAG GGGCTGCGCT ACTACCGGCG GCTGCTGGAG CGGCTGCGGG
  661  AGCTGGGCGT GCAGCCGGTG GTTACCCTGT ACCATTGGGA CCTGCCACAG CGCCTGCAGG
```

```
 721 ACACCTATGG CGGATGGGCC AATCGCGCCC TGGCCGACCA TTTCAGGGAT TATGCCGAGC
 781 TCTGCTTCCG CCACTTCGGT GGTCAGGTCA AGTACTGGAT CACCATTGAC AACCCCTACG
 841 TGGTGGCCTG GCACGGGTAT GCCACCGGGC GCCTGGCCCC GGGCGTGAGG GGCAGCTCCA
 901 GGCTCGGGTA CCTGGTTGCC CACAACCTAC TTTTGGCTCA TGCCAAAGTC TGGCATCTCT
 961 ACAACACCTC TTTCCGCCCC ACACAGGGAG GCCGGGTGTC TATCGCCTTA AGCTCCCATT
1021 GGATCAATCC TCGAAGAATG ACTGACTATA ATATCAGAGA ATGCCAGAAG TCTCTTGACT
1081 TTGTGCTAGG CTGGTTTGCC AAACCCATAT TTATTGATGG CGACTACCCA GAGAGTATGA
1141 AGAACAACCT CTCGTCTCTT CTGCCTGATT TTACTGAATC TGAGAAGAGG CTCATCAGAG
1201 GAACTGCTGA CTTTTTTGCT CTCTCCTTCG GACCAACCTT GAGCTTTCAG CTATTGGACC
1261 CTAACATGAA GTTCCGCCAA TTGGAGTCTC CCAACCTGAG GCAGCTTCTG TCTTGGATAG
1321 ATCTGGAATA TAACCACCCT CCAATATTTA TTGTGGAAAA TGGCTGGTTT GTCTCGGGAA
1381 CCACCAAAAG GGATGATGCC AAATATATGT ATTATCTCAA GAAGTTCATA ATGGAAACCT
1441 TAAAAGCAAT CAGACTGGAT GGGGTCGACG TCATTGGGTA CACCGCGTGG TCGCTCATGG
1501 ACGGTTTCGA GTGGCATAGG GGCTACAGCA TCCGGCGAGG ACTCTTCTAC GTTGACTTTC
1561 TGAGTCAGGA CAAGGAGCTG TTGCCAAAGT CTTCGGCCTT GTTCTACCAA AAGCTGATAG
1621 AGGACAATGG CTTTCCTCCT TTACCTGAAA ACCAGCCCCT TGAAGGGACA TTTCCCTGTG
1681 ACTTTGCTTG GGGAGTTGTT GACAACTACG TTCAAGTGGA CACTACTCTC TCTCAGTTTA
1741 CTGACCCGAA TGTCTATCTG TGGGATGTGC ATCACAGTAA GAGGCTTATT AAAGTAGACG
1801 GGGTTGTAGC CAAGAAGAGA AAACCTTACT GTGTTGATTT CTCTGCCATC CGGCCTCAGA
1861 TAACCTTACT TCGAGAAATG CGGGTCACCC ACTTTCGCTT CTCCCTGGAC TGGGCCCTGA
1921 TCTTGCCTCT GGGTAACCAG ACCCAAGTGA ACCACACGGT TCTGCACTTC TACCGCTGCA
1981 TGATCAGCGA GCTGGTGCAC GCCAACATCA CTCCAGTGGT GGCCCTGTGG CAGCCAGCAG
2041 CCCCGCACCA AGGCCTGCCA CATGCCCTTG CAAAACATGG GGCCTGGGAG AACCCGCACA
2101 CTGCTCTGGC GTTTGCAGAC TACGCAAACC TGTGTTTTAA AGAGTTGGGT CACTGGGTCA
2161 ATCTCTGGAT CACCATGAAC GAGCCAAACA CACGGAACAT GACCTATCGT GCCGGGCACC
2221 ACCTCCTGAG AGCCCATGCC TTGGCTTGGC ATCTGTACGA TGACAAGTTT AGGGCGGCTC
2281 AGAAAGGCAA AATATCCATC GCCTTGCAGG CTGACTGGAT AGAACCGGCC TGCCCTTTCT
2341 CTCAAAATGA CAAAGAAGTG GCCGAGAGAG TTTTGGAATT TGATATAGGC TGGCTGGCAG
2401 AGCCTATTTT TGGTTCCGGA GATTATCCAC GTGTGATGAG GGACTGGCTG AACCAAAAAA
2461 ACAATTTTCT TTTGCCCTAT TTCACCGAAG ATGAAAAAAA GCTAGTCCGG GGTTCCTTTG
2521 ACTTCCTGGC GGTGAGTCAT ACACCACCA TTCTGGTAGA CTGGGAAAAG GAGGATCCGA
2581 TGAAATACAA CGATTACTTG GAGGTACAGG AGATGACTGA CATCACATGG CTCAACTCTC
2641 CCAGTCAGGT GGCAGTGGTG CCTTGGGGGC TGCGCAAAGT GCTCAACTGG CTAAGGTTCA
2701 AGTACGGAGA CCTCCCGATG TATGTGACAG CCAATGGAAT CGATGATGAC CCCCACGCCG
2761 AGCAAGACTC ACTGAGGATC TATTATATTA AGAATTATGT GAATGAGGCT CTGAAAGCCT
2821 ACGTGTTGGA CGACATCAAC CTTTGTGGCT ACTTTGCGTA TTCACTTAGT GATCGCTCAG
2881 CTCCCAAGTC TGGCTTTTAT CGATATGCTG CGAATCAGTT TGAGCCCAAA CCATCTATGA
2941 AACATTACAG GAAAATTATT GACAGCAATG GCTTCCTGGG TTCTGGAACA CTGGGAAGGT
3001 TTTGTCCAGA AGAATACACT GTGTGCACCG AATGTGGATT TTTTCAAACC CGGAAGTCTT
```

```
3061 TGCTGGTCTT CATCTCGTTT CTTGTTTTTA CTTTTATTAT TTCTCTTGCT CTCATTTTTC

3121 ACTACTCCAA GAAAGGCCAG AGAAGTTATA AGTAA
```

In one embodiment, the FGFR is FGFR1c, FGFR3c, or FGFR4. In one embodiment of the present invention, the FGF receptor is FGFR1c receptor. In one particular embodiment, the FGFR1c receptor is the human FGFR1c receptor (GenBank Accession No. NP_075598, which is hereby incorporated by reference in its entirety). In another embodiment, the FGF receptor is FGFR3c receptor. In one particular embodiment, the FGFR3c receptor is the human FGFR3c receptor (GenBank Accession No. NP_000133, which is hereby incorporated by reference in its entirety). In another embodiment, the FGF receptor is FGFR4 receptor. In one particular embodiment, the FGFR4 receptor is the human FGFR4 receptor (GenBank Accession No. NP_002002, which is hereby incorporated by reference in its entirety).

In one embodiment, the method of facilitating FGFR-αKlotho co-receptor complex formation is carried out in vitro. In one embodiment, the method is carried out in a cell ectopically expressing αKlotho co-receptor and one or more of the cognate FGFRs of FGF23, which are FGFR1c, FGFR3c, and FGFR4. In one particular embodiment, the interleukin-3-dependent murine pro-B BaF3 cell line is used for ectopic expression of αKlotho co-receptor and one or more of the cognate FGFRs of FGF23. In one embodiment, the method is carried out in a cell endogenously expressing αKlotho co-receptor and one or more of the cognate FGFRs of FGF23. In one embodiment, the method is carried out in a renal cell, a parathyroid cell, a blood cell, a thymus cell, a pituitary cell, a hypothalamus-derived cell, a cell derived from the corpus striatum, and/or a cell derived from the cerebrum. In one particular embodiment, the method is carried out in a renal proximal tubule epithelial cell.

In one embodiment, the method of facilitating FGFR-αKlotho co-receptor complex formation is carried out in vivo. In one embodiment, the method is carried out in a mammal. In one particular embodiment, the mammal is a mouse. In one embodiment, the mouse is an fgf23-gene knockout mouse. In one embodiment, serum concentration of phosphate is used as readout for the method. In one embodiment, renal excretion of phosphate is used as readout for the method. In one embodiment, serum concentration of bioactive vitamin D is used as readout for the method. In one embodiment, renal expression of 1α-hydroxylase (CYP27B1) is used as readout for the method. In one embodiment, renal expression of NaP$_i$-2A and/or NaP$_i$-2C is used as readout for the method.

Yet a further aspect of the present invention relates to a method of screening for agents capable of facilitating fibroblast growth factor receptor ("FGFR")-αKlotho co-receptor complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves providing a binary αKlotho-FGFR complex and providing one or more candidate agents. This method further involves combining the chimeric FGF, the binary αKlotho-FGFR complex, and the one or more candidate agents under conditions permitting the formation of a ternary complex between the chimeric FGF and the binary αKlotho-FGFR complex in the absence of the one or more candidate agents. This method also involves identifying the one or more candidate agents that decrease ternary complex formation between the chimeric FGF and the binary αKlotho-FGFR compared to the ternary complex formation in the absence of the one or more candidate agents as suitable for treating the disorder.

In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

Suitable chimeric proteins for use in accordance with this aspect of the present invention are described above and throughout the present application. Suitable paracrine FGFs, as well as suitable modifications to decrease binding affinity for heparin and/or heparan sulfate, to alter receptor-binding specificity and/or to alter receptor-binding affinity compared to the portion without the modification, are also described above.

In one embodiment, the modulation is a competitive interaction between the chimeric FGF molecule and the one or more candidate agents for binding to the binary αKlotho-FGFR complex.

In one embodiment, the FGFR is FGFR1c, FGFR3c, or FGFR4.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification.

In one embodiment of the screening aspects of the present invention, a plurality of compounds or agents is tested. Candidate agents may include small molecule compounds or larger molecules (e.g., proteins or fragments thereof). In one embodiment, the candidate compounds are biomolecules. In one embodiment, the biomolecules are proteins. In one embodiment, the biomolecules are peptides. In one embodiment, the candidates are peptides or peptide mimetics having similar structural features to native FGF ligand. In one embodiment, the candidate agent is a second chimeric FGF molecule. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the modulation stabilizes the ternary complex between the chimeric FGF molecule and the binary αKlotho-FGFR complex. In one embodiment, the stabilization is compared to the native ternary complex.

In one embodiment, the modulation is an allosteric or kinetic modulation. In one embodiment, the allosteric or kinetic modulation is compared to the native ternary complex. Such stabilization or allosteric or kinetic modulation can be measured modulation determined according to methods known in the art (e.g., by use of surface plasmon resonance (SPR) spectroscopy experiments as described in the Examples infra).

In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with renal cells. In one particular embodiment, the renal cells are proximal tubule epithelial cells. In one embodiment, the cell-based assay is carried out with parathyroid cells. In one embodiment, the cell-based assay is carried out with blood cells. In one embodiment, the cell-based assay is carried out with thymus cells. In one embodiment, the cell-based assay is carried out with pituitary cells. In one embodiment, the cell-based assay is carried out with cells derived from the hypothalamus. In one embodiment, the cell-based assay is carried out with cells derived from the corpus striatum. In one embodiment, the cell-based assay is carried out with cells derived from the cerebrum. In one embodiment, inhibition of phosphate uptake by the cells is the assay readout. In one embodiment, repression of the $NaP_i$-2A gene and/or the $NaP_i$-2C gene is the assay readout. In one embodiment, reduction of NaPi-2A and/or $NaP_i$-2C protein expression is the assay readout. In one embodiment, reduction of NaPi-2A and/or $NaP_i$-2C protein in the cell membrane is the assay readout. In one embodiment, repression of the CYP27B1 gene is the assay readout. In one embodiment, a dose-response curve is generated for inhibition of phosphate uptake (repression of the $NaP_i$-2A gene and/or the $NaP_i$-2C gene, reduction of NaPi-2A and/or $NaP_i$-2C protein expression, reduction of NaPi-2A and/or $NaP_i$-2C protein in the cell membrane, repression of the CYP27B1 gene) by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF23. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF23.

In one embodiment of the screening aspects of the present invention, the cell-based assay is carried out with mammalian cells ectopically expressing αKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for αKlotho-dependent activation of FGF receptor by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF23. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF23.

In one embodiment of the screening aspects of the present invention, the surface plasmon resonance spectroscopy-based assay is carried out using the chimeric FGF protein as ligand coupled to a biosensor chip. In one embodiment, mixtures of the binary complex of FGFR ligand-binding domain and αKlotho ectodomain with increasing concentrations of a candidate compound are passed over a biosensor chip containing chimeric FGF protein. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for the chimeric FGF protein, the candidate compound has greater potency than the chimeric FGF protein and/or native FGF23. In one embodiment, an $IC_{50}$ value is derived from the inhibition-binding curve of a candidate compound to determine potency of the candidate compound. An $IC_{50}$ value smaller than that obtained for containing chimeric FGF protein identifies a candidate compound as more potent than the chimeric FGF protein and/or native FGF23. In one embodiment, the inhibition constant $K_i$ is determined for a candidate compound to determine potency of the candidate compound. A $K_i$ value smaller than that obtained for native FGF23 identifies a candidate compound as more potent than the chimeric FGF protein and/or native FGF23.

Yet another aspect of the present invention relates to a modified FGF23 protein. The modified FGF23 protein includes an FGF23 protein that includes a modification to decrease binding affinity for heparin and/or heparan sulfate compared to an FGF23 protein without the modification.

FGF23 proteins suitable for use in accordance with this aspect of the present invention include those described above (i.e., human FGF23 and orthologs thereof). In one embodiment, the modified FGF23 is derived from a mammalian FGF23. In one embodiment, the modified FGF23 protein includes an FGF protein that includes the amino acid sequence of SEQ ID NO: 233, where the modification includes a substitution at amino acid residues selected from R48, N49, R140, R143, and combinations thereof. In one embodiment, the modification includes one or more substitutions selected from R48A/G/S, N49A/G/S, R140A/G/S, R143A/G/S, and combinations thereof. In one embodiment, the modified FGF23 protein has an amino acid sequence that has at least 80%, at least 85%, at least 90%, at least 95%, at least 97% or at least 99% amino acid sequence identity or homology to the amino acid sequence of SEQ ID NO: 233. In one embodiment, the modified FGF23 protein has an amino acid sequence that has at least 80%, at least 85%, at least 90%, at least 95%, at least 97% or at least 99% amino acid sequence identity or homology to an ortholog of human FGF23 (SEQ ID NO:233). In one embodiment, the modified FGF23 includes a modification to decrease binding affinity for heparin and/or heparan sulfate compared to an FGF23 protein without the modification and retains biological activity of native FGF23. In one embodiment, the modified FGF23 includes a modification to decrease binding affinity for heparin and/or heparan sulfate compared to an FGF23 protein without the modification and retains the ability to bind a binary αKlotho-FGFR complex.

In one embodiment, the modification includes a substitution at amino acid residues corresponding to positions of SEQ ID NO: 233 selected from R48, N49, R140, R143, and combinations thereof. In one embodiment, the modification includes one or more substitutions selected from R48A/G/S, N49A/G/S, R140A/G/S, R143A/G/S, and combinations thereof.

Another aspect of the present invention relates to a pharmaceutical composition including the modified FGF23 protein according to the present invention and a pharmaceutically-acceptable carrier. Suitable pharmaceutical compositions, dosages, carriers and the like are described above.

In one embodiment, the pharmaceutical composition further includes a hypophosphatemic agent, a phosphate binder, a vitamin D antagonist, an analgesic, and/or an anti-inflammatory agent.

In one embodiment, the pharmaceutical composition further includes an organotropic targeting agent. In one embodiment, the targeting agent is covalently linked to the chimeric protein via a linker that is cleaved under physiological conditions.

As noted above, chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs).

In one embodiment, the modified FGF23 is fused at its N-terminus to an agent that increases the half-life of the modified FGF23 protein in circulation. In one embodiment, the agent that increases the half-life is a PEG molecule. In one embodiment, the agent that increases the half-life is an antibody fragment.

Another aspect of the present invention relates to a method for treating a subject suffering from a disorder. This method involves selecting a subject suffering from the disorder and administering to the selected subject a therapeutically effective amount of a modified FGF23 protein including a modification to decrease binding affinity for heparin and/or heparan sulfate compared to an FGF23 protein without the modification.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification. Such disorders and methods for evaluating those disorders are described above and will be known to those of skill in the art. Suitable modes of administration are also described above.

In one embodiment, the modified FGF23 protein is administered with a pharmaceutically-acceptable carrier.

In one embodiment, the selected subject is a mammal. In one embodiment, the selected subject is a human.

In one embodiment, the modified FGF23 protein is co-administered with a hypophosphatemic agent, a phosphate binder, a vitamin D antagonist, an analgesic, and/or an anti-inflammatory agent.

EXAMPLES

Example 1

Purification of FGF, FGFR, and Klotho Proteins

The N-terminally hexahistidine-tagged, mature form of human FGF19 (SEQ ID NO: 333) (R23 to K216), human FGF21 (SEQ ID NO: 334) (H29 to S209; FIG. 5A), and human FGF23 (Y25 to I251; FIG. 5A) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which is hereby incorporated by reference in its entirety). The amino acid sequence of human FGF19 (SEQ ID NO:333) (GenBank Accession No. NP_005108, which is hereby incorporated by reference in its entirety) is as follows:

```
  1 MRSGCVVVHV WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

The amino acid sequence of human FGF21 (SEQ ID NO: 334) (GenBank Accession No. NP_061986, which is hereby incorporated by reference in its entirety), as follows:

```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPALPEPPGI

181 LAPQPPDVGS SDPLSMVGPS QGRSPSYAS.
```

FIG. 11 shows an alignment of the C-terminal tail sequences of human FGF19, FGF21, and FGF23.

HS-binding site mutants of FGF19 (K149A) and FGF23 (R140A/R143A) were purified from bacterial inclusion bodies by similar protocols as the wild-type proteins. In order to minimize proteolysis of FGF23 wild-type and mutant proteins, arginine residues 176 and 179 of the proteolytic cleavage site $^{176}$RXXR$^{179}$ were replaced with glutamine as it occurs in the phosphate wasting disorder "autosomal dominant hypophosphatemic rickets" (ADHR) (White et al., Nat. Genet. 26:345-348 (2000); White et al., Kidney Int. 60:2079-2086 (2001), which are hereby incorporated by reference in their entirety). Human FGF1 (SEQ ID NO: 1) (M1 to D155; FIG. 6), N-terminally truncated human FGF1 (K25 to D155, termed FGF1$^{\Delta NT}$; FIG. 6), human FGF2 (SEQ ID NO: 121) (M1 to S155; FIG. 5A), and human FGF homologous factor 1B (FHF1B; M1 to T181) were purified by published protocols (Plotnikov et al., Cell 101:413-424 (2000); Olsen et al., J. Biol. Chem. 278:34226-34236 (2003), which are hereby incorporated by reference in their entirety).

Chimeras composed of the core domain of FGF2 (M1 to M151) and the C-terminal region of either FGF21 (P168 to S209) or FGF23 (R161 to I251) (termed FGF2$^{WTcore}$-FGF21$^{C\text{-}tail}$ and FGF2$^{WTcore}$-FGF23$^{C\text{-}tail}$, respectively; FIG. 5A) were purified by the same protocol as that for native FGF2 (Plotnikov et al., Cell 101:413-424 (2000), which is hereby incorporated by reference in its entirety). Analogous chimeras containing three mutations in the HS-binding site of the FGF2 core (K128D/R129Q/K134V) (termed FGF2$^{\Delta HBScore}$-FGF21$^{C\text{-}tail}$ and FGF2$^{\Delta HBScore}$-FGF23$^{C\text{-}tail}$ respectively, FIG. 5A) were purified from the soluble bacterial cell lysate fraction by ion-exchange and size-exclusion chromatographies. In order to minimize proteolysis of the chimeras containing the C-terminal sequence from R161 to I251 of FGF23, arginine residues 176 and 179 of the proteolytic cleavage site $^{176}$RXXR$^{179}$ located within this sequence were replaced with glutamine as it occurs in ADHR (White et al., Nat. Genet. 26:345-348 (2000); White et al., Kidney Int. 60:2079-2086 (2001), which are hereby incorporated by reference in their entirety). In addition, in order to prevent disulfide-mediated dimerization of FGF2 and chimeric FGF2 proteins, cysteine residues 78 and 96 were mutated to serine. An HS-binding site mutant of FGF1 (K127D/K128Q/K133V) (termed FGF1$^{\Delta HBScore}$; FIG. 6) and chimeras composed of the core domain of the HS-binding site mutant of FGF1 (M1 to L150, K127D/K128Q/K133V) and the C-terminal region of either FGF19 (L169 to K216) or FGF21 (P168 to S209) (termed FGF1$^{\Delta HBScore}$-FGF19$^{C\text{-}tail}$ and FGF1$^{\Delta HBScore}$-FGF21$^{C\text{-}tail}$, respectively; FIG. 6) were purified from the soluble bacterial cell lysate fraction by ion-exchange and size-exclusion chromatographies. The N-terminally hexahistidine-tagged C-terminal tail peptide of FGF23 (S180 to I251, termed FGF23$^{C\text{-}tail}$) was purified by a published protocol (Goetz et al., Proc. Nat'l. Acad. Sci. U.S.A. 107:407-412 (2010), which is hereby incorporated by reference in its entirety). The ligand-binding domain of human FGFR1c (D142 to R365) was refolded in vitro from bacterial inclusion bodies, and purified by published protocols (Ibrahimi et al., Hum. Mol. Genet. 13:2313-2324 (2004); Plotnikov et al., Cell 101:413-424 (2000), which are hereby incorporated by reference in their entirety). The ectodomain of murine αKlotho (A35 to K982) and the ectodomain of murine βKlotho (F53 to L995) were expressed in HEK293 cells as fusion proteins with a C-terminal FLAG tag (Kurosu et al., J. Biol. Chem. 281:6120-6123 (2006); Kurosu et al., Science 309:1829-1833 (2005), which are hereby incorporated by reference in their entirety). The binary complex of FGFR1c ligand-binding domain with αKlotho ectodomain (referred to as αKlotho-FGFR1c complex) was prepared by a published protocol (Goetz et al., Proc. Nat'l. Acad. Sci. U.S.A. 107:407-412 (2010), which is hereby incorporated by reference in its entirety). The binary complex of FGFR1c ligand-binding domain with βKlotho ectodomain (referred to as βKlotho-FGFR1c complex) was prepared in the same fashion as the αKlotho-FGFR1c complex.

Example 2

Analysis of FGF-Heparin and FGF-FGFR-α/βKlotho Interactions by Surface Plasmon Resonance Spectroscopy Surface plasmon resonance (SPR) experiments were performed on a Biacore 2000 instrument (Biacore AB), and the interactions were studied at 25° C. in HBS-EP buffer (10 mM HEPES-NaOH, pH 7.4, 150 mM NaCl, 3 mM EDTA, 0.005% (v/v) polysorbate 20). To study endocrine FGF-heparin interactions, a heparin chip was prepared by immobilizing biotinylated heparin (Sigma-Aldrich) on flow channels of a research-grade streptavidin chip (Biacore AB). The coupling density was ~5 fmol mm$^{-2}$ of flow channel. To measure binding of chimeric FGF2 proteins to heparin, biotinylated heparin was coupled to a streptavidin chip at an approximately 4-fold lower density as judged based on the binding responses obtained for FGF1. To study FGF-FGFR-α/βKlotho interactions, FGF chips were prepared by covalent coupling of FGF proteins through their free amino groups on flow channels of research grade CM5 chips (Biacore AB). Proteins were injected over a chip at a flow rate of 50 μl min$^{-1}$, and at the end of each protein injection (180 and 300 s, respectively), HBS-EP buffer (50 μl min$^{-1}$) was flowed over the chip to monitor dissociation for 180 or 240 s. The heparin chip surface was regenerated by injecting 50 μl of 2.0 M NaCl in 10 mM sodium acetate, pH 4.5. For FGF chips, regeneration was achieved by injecting 2.0 M NaCl in 10 mM sodium/potassium phosphate, pH 6.5. To control for nonspecific binding in experiments where an FGF ligand was immobilized on the chip, FHF1B, which shares structural similarity with FGFs but does not exhibit any FGFR binding (Olsen et al., J. Biol. Chem. 278:34226-34236 (2003), which is hereby incorporated by reference in its entirety), was coupled to the control flow channel of the chip (~15-30 fmol mm$^{-2}$). In experiments where heparin was immobilized on the chip, the control flow channel was left blank. The data were processed with BiaEvaluation software (Biacore AB). For each protein injection over the heparin chip, the nonspecific responses from the control flow channel were subtracted from the responses recorded for the heparin flow channel. Similarly, for each protein injection over a FGF chip, the nonspecific responses from the FHF1B control flow channel were subtracted from the responses recorded for the FGF flow channel. Where possible, equilibrium dissociation constants ($K_D$s) were calculated from fitted saturation binding curves. Fitted binding curves were judged to be accurate based on the distribution of the residuals (even and near zero) and $\chi^2$ (<10% of $R_{max}$).

To examine whether the K149A mutation abrogates residual heparin binding of FGF19, increasing concentrations of wild-type FGF19 were passed over a heparin chip. Thereafter, the FGF19$^{K149A}$ mutant was injected over the heparin chip at the highest concentration tested for the wild-type ligand. The effect of the R140A/R143A double mutation in the HS-binding site of FGF23 on residual heparin binding of FGF23 was examined in the same fashion as was the effect of the HS-binding site mutation in FGF19.

To verify that the K128D/R129Q/K134V triple mutation in the HS-binding site of the FGF2 core domain diminishes heparin-binding affinity of the FGF2 core, increasing concentrations of FGF2$^{\Delta HBScore}$-FGF21$^{C\text{-}tail}$ and FGF2$^{\Delta HBScore}$-FGF23$^{C\text{-}tail}$ were passed over a heparin chip. As a control, binding of FGF2$^{WTcore}$-FGF21$^{C\text{-}tail}$ and FGF2$^{WTcore}$-FGF23$^{C\text{-}tail}$ to heparin was studied.

To examine whether the FGF2$^{\Delta HBScore}$-FGF23$^{C\text{-}tail}$ chimera can compete with FGF23 for binding to the αKlotho-FGFR1c complex, FGF23 was immobilized on a chip (~16 fmol mm$^{-2}$ of flow channel). Increasing concentrations of FGF2$^{\Delta HBScore}$-FGF23$^{C\text{-}tail}$ were mixed with a fixed concentration of αKlotho-FGFR1c complex in HBS-EP buffer, and the mixtures were injected over the FGF23 chip. As controls, the binding competition was carried out with FGF23 or FGF2 as the competitor in solution. As an additional specificity control, competition of the FGF2$^{\Delta HBScore}$-FGF23$^{C\text{-}tail}$ chimera with FGF21 for binding to the αKlotho-FGFR1c complex was studied. αKlotho-FGFR1c complex was mixed with FGF2$^{\Delta HBScore}$-FGF23$^{C\text{-}tail}$ or FGF23 at a molar ratio of 1:10, and the mixture was injected over a chip containing immobilized FGF21 (~12 fmol mm$^{-2}$ of flow channel).

To test whether the FGF2$^{\Delta HBScore}$-FGF21$^{C\text{-}tail}$ chimera can compete with FGF21 for binding to the βKlotho-FGFR1c complex, increasing concentrations of FGF2$^{\Delta HBScore}$-FGF21$^{C\text{-}tail}$ were mixed with a fixed concentration of βKlotho-FGFR1c complex in HBS-EP buffer, and the mixtures were passed over a chip containing immobilized FGF21 (~19 fmol mm$^{-2}$ of flow channel). As controls, the binding competition was carried out with FGF21 or FGF2 as the competitor in solution. As an additional specificity control, competition of the FGF2$^{\Delta HBScore}$-FGF21$^{C\text{-}tail}$ chimera with FGF23 for binding to the αKlotho-FGFR1c complex was studied. αKlotho-FGFR1c complex was mixed with FGF2$^{\Delta HBScore}$-FGF21$^{C\text{-}tail}$ or FGF21 at a molar ratio of 1:10, and the mixture was injected over a chip containing immobilized FGF23 (~12 fmol mm$^{-2}$ of flow channel).

To measure binding of FGFR1c to each of the three endocrine FGFs, increasing concentrations of FGFR1c ligand-binding domain were injected over a chip containing immobilized FGF19, FGF21, and FGF23 (~30 fmol mm$^{-2}$ of flow channel). As a control, binding of FGFR1c to FGF2 immobilized on a chip was studied. As additional controls, binding of the αKlotho-FGFR1c complex to FGF23 and binding of FGFR1c to the C-terminal tail peptide of FGF23 was measured.

Example 3

Analysis of Phosphorylation of FRS2α and 44/42 MAP Kinase in Hepatoma and Epithelial Cell Lines To examine whether the FGF19$^{K149A}$ and FGF23$^{R140A/R143A}$ mutants can activate FGFR in a α/βKlotho-dependent fashion, induction of tyrosine phosphorylation of FGFR substrate 2α (FRS2α) and downstream activation of MAP kinase cascade was used as readout for FGFR activation. Subconfluent cells of the H4IIE rat hepatoma cell line, which endogenously expresses βKlotho (Kurosu et al., J. Biol. Chem. 282:26687-26695 (2007), which is hereby incorporated by reference in its entirety), were serum starved for 16 h and then stimulated for 10 min with the FGF19$^{K149A}$ mutant or wild-type FGF19 (0.2 ng ml$^{-1}$ to 2.0 μg ml$^{-1}$). Similarly, subconfluent cells of a HEK293 cell line ectopically expressing the transmembrane isoform of murine αKlotho (Kurosu et al., J. Biol. Chem. 281:6120-6123 (2006), which is hereby incorporated by reference in its entirety) were treated with the FGF23$^{R140A/R143A}$ mutant or wild-type FGF23 (0.1 to 100 ng ml$^{-1}$). After stimulation, the cells were lysed (Kurosu et al., Science 309:1829-1833 (2005), which is hereby incorporated by reference in its entirety), and cellular proteins were resolved on SDS-polyacrylamide gels and transferred to nitrocellulose membranes. The protein blots were probed with antibodies to phosphorylated FRS2α, phosphorylated 44/42 MAP kinase, total (phosphorylated and nonphosphorylated) 44/42 MAP kinase, and αKlotho. Except for the anti-αKlotho antibody (KM2119) (Kato et al., Biochem. Biophys. Res. Commun. 267:597-602 (2000), which is hereby incorporated by reference in its entirety), all antibodies were from Cell Signaling Technology.

Example 4

Analysis of Egr1 Protein Expression in an Epithelial Cell Line

To examine whether the FGF2$^{\Delta HBScore}$-FGF21$^{C\text{-}tail}$ and FGF2$^{\Delta HBScore}$-FGF23$^{C\text{-}tail}$ chimeras can activate FGFR in a HS-dependent fashion, induction of protein expression of the transcription factor early growth response 1 (Egr1), a known downstream mediator of FGF signaling, was used as readout for FGFR activation. HEK293 cells were serum starved overnight and then stimulated for 90 min with FGF2$^{\Delta HBScore}$-FGF21$^{C\text{-}tail}$ or FGF2$^{\Delta HBScore}$-FGF23$^{C\text{-}tail}$ (0.1 and 0.3 nM). Cell stimulation with FGF2$^{WTcore}$-FGF21$^{C\text{-}tail}$, FGF2$^{WTcore}$-FGF23$^{C\text{-}tail}$, FGF21, and FGF23 served as controls. To test whether the FGF2$^{\Delta HBScore}$-FGF21$^{C\text{-}tail}$ chimera can activate FGFR in a βKlotho-dependent fashion, HEK293 cells transfected with murine βKlotho were serum starved overnight and then stimulated for 90 min with FGF2$^{\Delta HBScore}$-FGF21$^{C\text{-}tail}$ or FGF21 (3 to 300 ng ml$^{-1}$). After stimulation, the cells were lysed (Kurosu et al., Science 309:1829-1833 (2005), which is hereby incorporated by reference in its entirety), and cellular proteins were resolved on SDS-polyacrylamide gels and transferred to nitrocellulose membranes. The protein blots were probed with antibodies to Egr1 and glyceraldehyde 3-phosphate dehydrogenase (GAPDH). The anti-Egr1 antibody was from Cell Signaling Technology and the anti-GAPDH antibody was from Abcam.

Example 5

Analysis of CYP7A1 and CYP8B1 mRNA Expression in Murine Liver Tissue

To examine the metabolic activity of the FGF19$^{K149A}$ mutant in vivo, 6- to 8-week old C57BL/6 mice were fasted overnight and then given intraperitoneally a single dose (1 mg kg body weight$^{-1}$) of FGF19$^{K149A}$ or FGF19 as a control. 6 h after the injection, the mice were sacrificed, and liver tissue was excised and frozen. Total RNA was isolated from liver tissue, and mRNA levels of cholesterol 7α-hydroxylase (CYP7A1) and sterol 12α-hydroxylase (CYP8B1) were measured using quantitative real time RT-PCR as described previously (Inagaki et al., *Cell Metab.* 2:217-225 (2005); Kim et al., *J. Lipid Res.* 48:2664-2672 (2007), which are hereby incorporated by reference in their entirety). The Institutional Animal Care and Use Committee at the University of Texas Southwestern Medical Center at Dallas had approved the experiments.

Example 6

Measurement of Serum Phosphate in Mice

The metabolic activity of the FGF23$^{R140A/R143A}$ mutant was examined both in normal mice and in Fgf23 knockout mice. 4- to 5-week old C57BL/6 mice were given intraperitoneally a single dose (0.29 mg kg body weight$^{-1}$) of FGF23$^{R140A/R143A}$ or FGF23 as a control. Before the injection and 8 h after the injection, blood was drawn from the cheek pouch and spun at 3,000×g for 10 min to obtain serum. Phosphate concentration in serum was measured using the Phosphorus Liqui-UV Test (Stanbio Laboratory). 6- to 8-week old Fgf23 knockout mice (Sitara et al., *Matrix Biol.* 23:421-432 (2004), which is hereby incorporated by reference in its entirety) (56) were given two injections of FGF23$^{R140A/R143A}$ or FGF23 at 8 h intervals (0.71 mg kg body weight$^{-1}$ each), and blood samples were collected for phosphate analysis before the first injection and 8 h after the second injection.

To test whether the FGF2$^{\Delta HBScore}$-FGF23$^{C\text{-}tail}$ chimera exhibits FGF23-like metabolic activity, 5- to 6-week old C57BL/6 mice were given a single injection of FGF2$^{\Delta HBScore}$-FGF23$^{C\text{-}tail}$ (0.21 mg kg body weight$^{-1}$). As controls, mice were injected with FGF2$^{WTcore}$-FGF23$^{C\text{-}tail}$ or FGF23. Before the injection and 8 h after the injection, blood samples were collected for measurement of serum phosphate. To confirm that αKlotho is required for the metabolic activity of the FGF2$^{\Delta HBScore}$-FGF23$^{C\text{-}tail}$ chimera, 7- to 8-week old αKlotho knockout mice (Lexicon Genetics) were injected once with FGF2$^{\Delta HBScore}$-FGF23$^{C\text{-}tail}$ or FGF23 as a control (0.51 mg kg body weight$^{-1}$). Before the injection and 8 h after the injection, blood samples were collected for phosphate analysis. The Harvard University Animal Care and Research committee board had approved all the experiments.

Example 7

Analysis of CYP27B1 mRNA Expression in Murine Renal Tissue

The ability of the FGF2$^{\Delta HBScore}$-FGF23$^{C\text{-}tail}$ chimera to reduce renal expression of 25-hydroxyvitamin D$_3$ 1α-hydroxylase (CYP27B1) was used as another readout for FGF23-like metabolic activity. C57BL/6 mice injected with FGF2$^{\Delta HBScore}$-FGF23$^{C\text{-}tail}$, FGF2$^{WTcore}$-FGF23$^{C\text{-}tail}$, or FGF23 were sacrificed 8 h after the protein injection, and renal tissue was excised and frozen. CYP27B1 mRNA levels in total renal tissue RNA were measured using real time quantitative PCR as described previously (Nakatani et al., *FASEB J.* 23:3702-3711 (2009); Ohnishi et al., *Kidney Int.* 75:1166-1172 (2009), which are hereby incorporated by reference in their entirety). The Harvard University Animal Care and Research committee board had approved the experiments.

Example 8

Insulin Tolerance Test in Mice

The ability of the FGF2$^{\Delta HBScore}$-FGF21$^{C\text{-}tail}$ chimera to potentiate the hypoglycemic effect of insulin was used as readout for FGF21-like metabolic activity (Ohnishi et al., *FASEB J.* 25:2031-2039 (2011), which is hereby incorporated by reference in its entirety). 8- to 12-week old C57BL/6 mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units kg body weight$^{-1}$) alone or insulin (0.5 units·kg body weight$^{-1}$) plus FGF2$^{\Delta HBScore}$-FGF21$^{C\text{-}tail}$ chimera (0.3 mg kg body weight$^{-1}$). As a control, mice were co-injected with insulin plus FGF21. At the indicated time points after the injection (FIG. 7G), blood was drawn from the tail vein. Glucose concentrations in the blood samples were determined using Bayer Contour® blood glucose test strips (Bayer Corp.). The Harvard University Animal Care and Research committee board had approved the experiments.

Example 9

Analysis of Blood Glucose in ob/ob Mice ob/ob mice were injected subcutaneously with FGF1$^{\Delta NT}$, FGF1$^{\Delta HBS}$, or FGF1$^{\Delta HBScore}$-FGF21$^{C\text{-}tail}$ chimera. Injection of native FGF1 or native FGF21 served as controls. A single bolus of 0.5 mg of protein per kg of body weight was injected. This dose was chosen on the basis that maximal efficacy of the hypoglycemic effect of native FGF1 is seen at this dose. Before the protein injection and at the indicated time points after the injection (FIGS. 9A-9C), blood glucose concentrations were measured using an OneTouch Ultra glucometer (Lifescan). The Institutional Animal Care and Use Committee at the Salk Institute for Biological Sciences at La Jolla had approved the experiments.

Example 10

Statistical Analysis

Data are expressed as mean±SEM. A Student's t test or analysis of variance (ANOVA) was used as appropriate to make statistical comparisons. A value of P<0.05 was considered significant.

Example 11

HS is Dispensable for the Metabolic Activity of FGF19 and FGF23

Figures 1A, 1B, 1C, 1D:
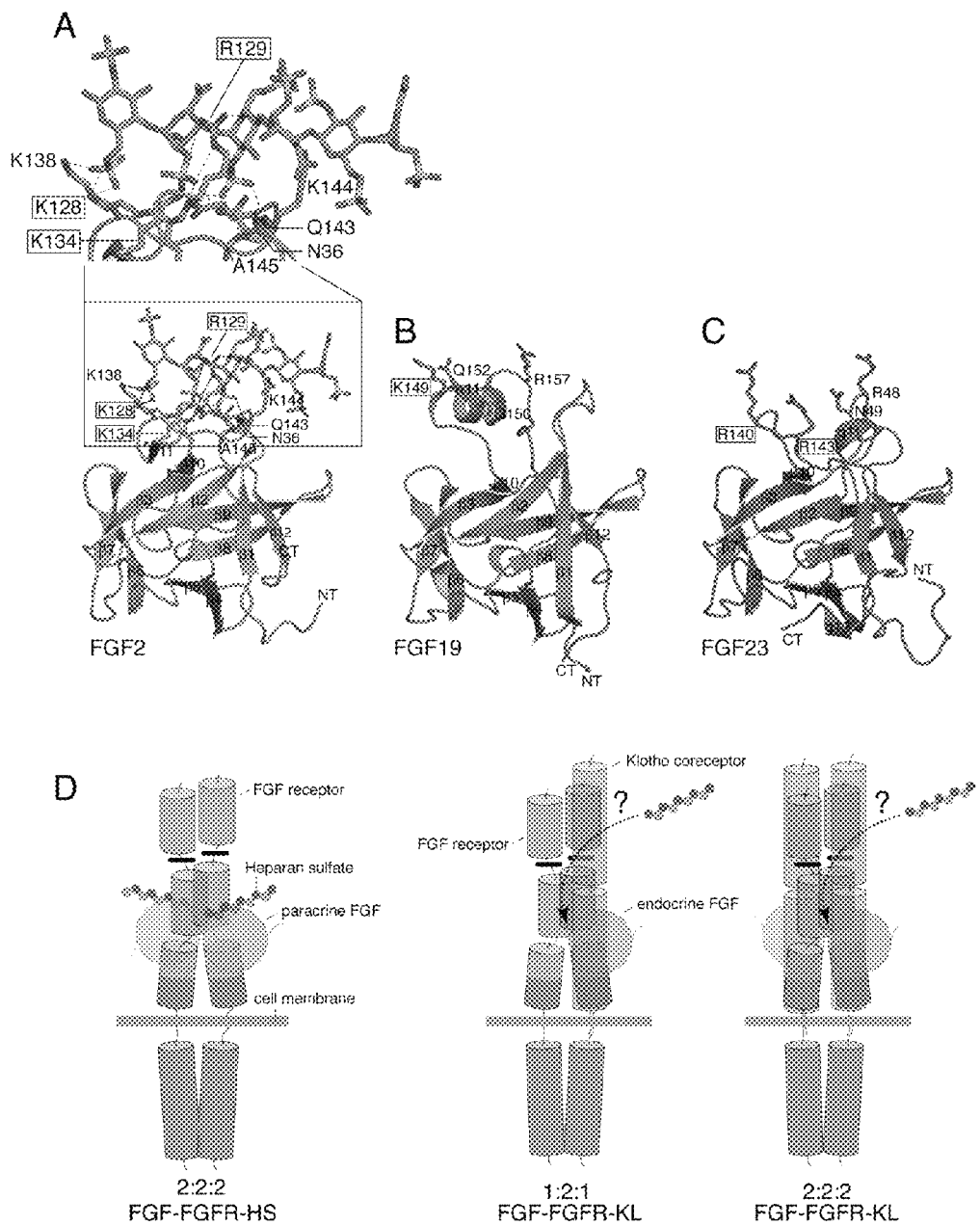
FIGS. 1A-1D are schematic diagrams showing side-by-side comparison of the HS-binding site of FGF2, FGF19, and FGF23, and working model of the endocrine FGF signaling complex.
Figure 2:
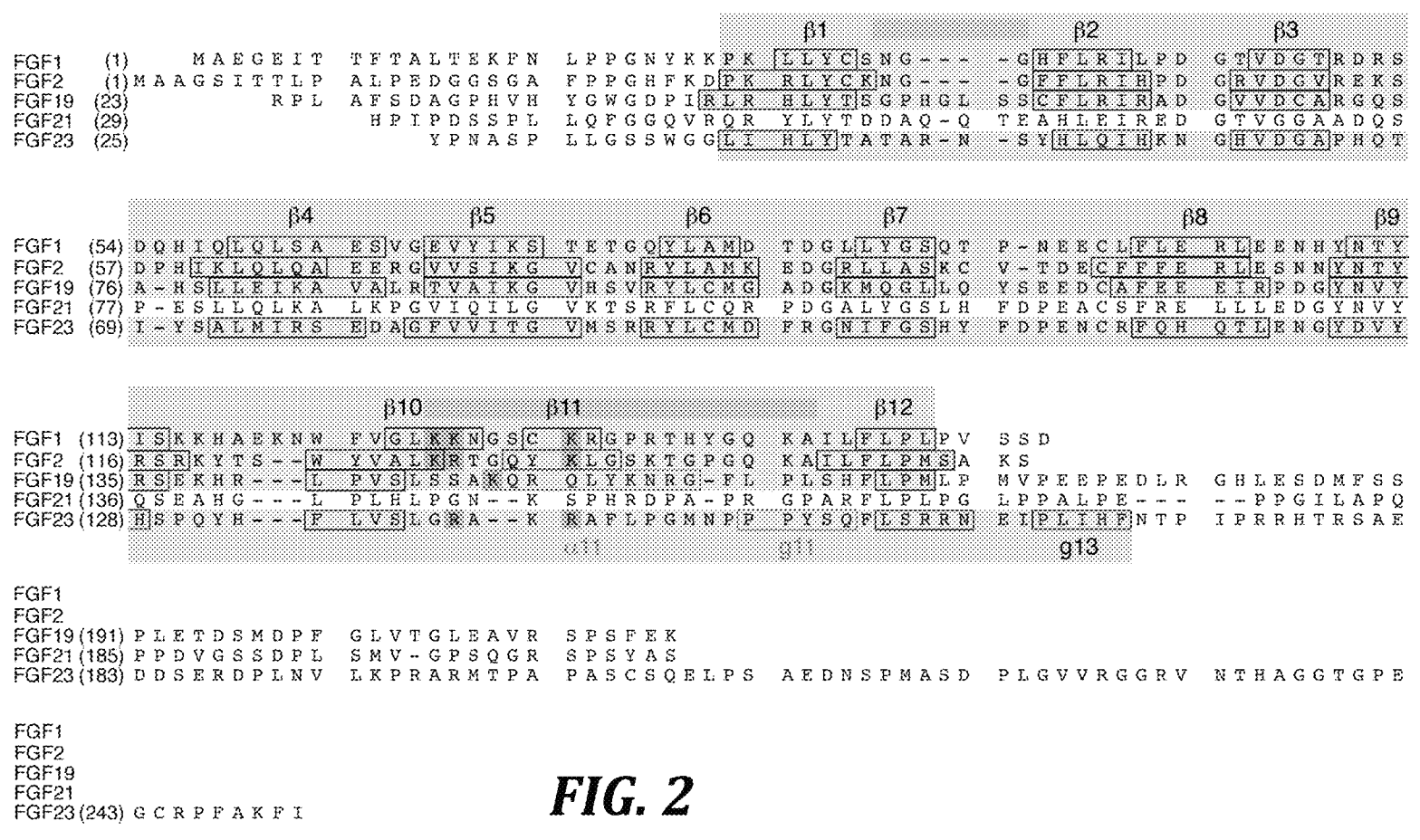
Figures 3A, 3B, 3C, 3D, 3E, 3F, 3G:
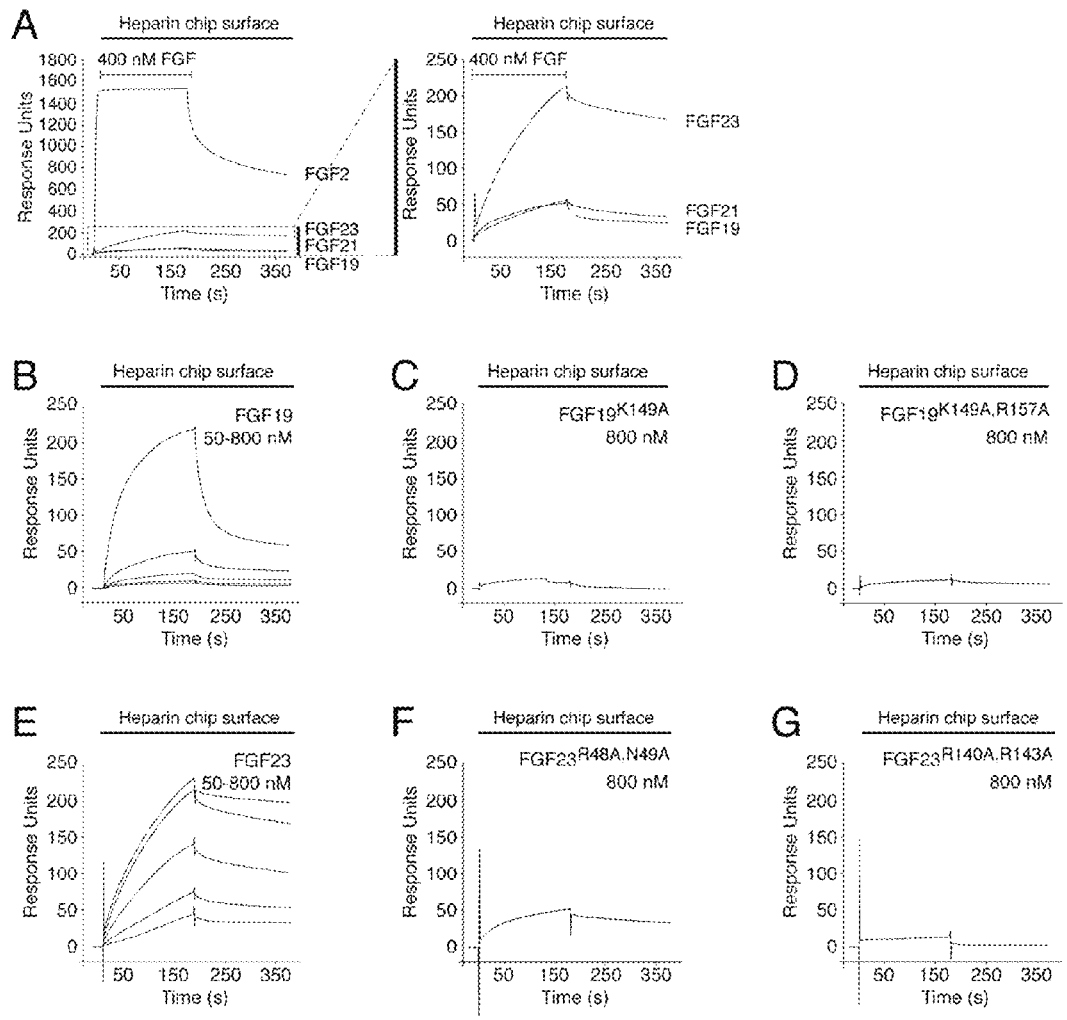
FIGS. 3A-3G show Surface plasmon resonance ("SPR") results relating to knockout of residual heparin binding in FGF19 and FGF23 by site-directed mutagenesis.

In order to engineer endocrine FGFs devoid of HS binding, the FGF19 crystal structure (PDB ID: 2P23; (Goetz et al., *Mol. Cell Biol.* 27:3417-3428 (2007), which is hereby incorporated by reference in its entirety) was compared with that of FGF2 bound to a heparin hexasaccharide (PDB ID: 1FQ9; (Schlessinger et al., *Mol. Cell* 6:743-750 (2000), which is hereby incorporated by reference in its entirety)). This analysis shows that solvent-exposed residues K149, Q150, Q152, and R157 of FGF19 lie at the corresponding HS-binding site of this ligand, and hence could account for the residual HS binding of FGF19 (FIGS. 1A, 1B, and 2). Likewise, comparative analysis of the FGF23 crystal structure (PDB ID: 2P39; (Goetz et al., *Mol. Cell Biol.* 27:3417-3428 (2007), which is hereby incorporated by reference in its entirety)) with that of heparin-bound FGF2 (PDB ID: 1FQ9; (Schlessinger et al., *Mol. Cell* 6:743-750 (2000), which is hereby incorporated by reference in its entirety)) points to R48, N49, R140, and R143 as candidates mediating the residual HS binding of this ligand (FIGS. 1A, 1C, and 2). In agreement with the structural predictions, replacement of K149 alone in FGF19 with alanine and combined substitution of R140 and R143 in FGF23 for alanine were sufficient to abolish residual HS binding of these ligands (FIGS. 3B-3G).

Figures 4A, 4B, 4C, 4D:
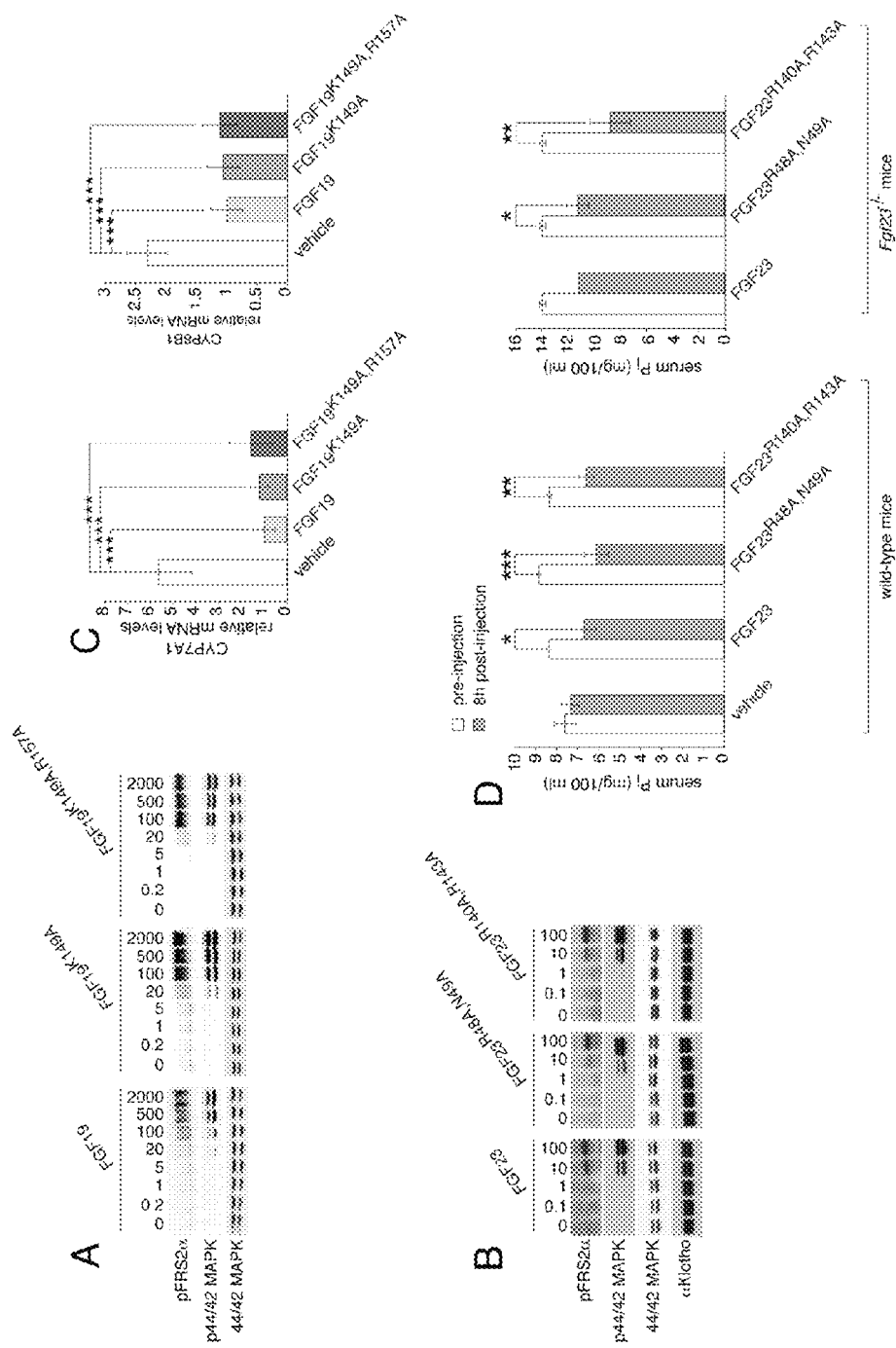
FIGS. 4A-4D show results demonstrating that HS is dispensable for the metabolic activity of FGF19 and FGF23.

To test the impact of knocking out residual HS binding of FGF19 on the signaling by this ligand, H4IIE hepatoma cells were stimulated with the $FGF19^{K149A}$ mutant or wild-type FGF19. H4IIE cells endogenously express FGFR4 and βKlotho (Kurosu et al., *J. Biol. Chem.* 282:26687-26695 (2007), which is hereby incorporated by reference in its entirety), the cognate receptor and co-receptor, respectively, for FGF19. The $FGF19^{K149A}$ mutant was as effective as wild-type FGF19 in inducing tyrosine phosphorylation of FRS2α and downstream activation of MAP kinase cascade (FIG. 4A). These data show that elimination of residual HS binding has no impact on the ability of FGF19 to signal in cultured cells. To test whether the same holds true for FGF23 signaling, HEK293 cells, which naturally express two of the three cognate receptors of FGF23, namely FGFR1c and FGFR3c (Kurosu et al., *J. Biol. Chem.* 281:6120-6123 (2006), which is hereby incorporated by reference in its entirety) were transfected with the transmembrane isoform of αKlotho, the co-receptor of FGF23. These cells were treated with the $FGF23^{R140A/R143A}$ double mutant or wild-type FGF23. The $FGF23^{R140A/R143A}$ mutant had the same capacity as wild-type FGF23 in inducing phosphorylation of FRS2α and downstream activation of MAP kinase cascade (FIG. 4B). These data show that similar to FGF19, FGF23 does not need to bind HS in order to activate FGFR in cultured cells.

To substantiate the findings in cells, the metabolic activity of wild-type and mutated ligands in vivo were compared. Mice were injected with the $FGF19^{K149A}$ mutant or wild-type FGF19 and liver gene expression of CYP7A1 and CYP8B1, which are key enzymes in the major bile acid biosynthetic pathway (Russell, D. W., *Annu. Rev. Biochem.* 72:137-174 (2003), which is hereby incorporated by reference in its entirety), was analyzed. Like wild-type FGF19, the $FGF19^{K149A}$ mutant markedly decreased CYP7A1 and CYP8B1 mRNA levels (FIG. 4C), demonstrating that knockout of residual HS binding does not affect the metabolic activity of FGF19. To examine whether residual HS binding is also dispensable for the metabolic activity of FGF23, mice were injected with the $FGF23^{R140A/R143A}$ mutant or wild-type FGF23 and serum phosphate concentrations were measured. The $FGF23^{R140A/R143A}$ mutant reduced serum phosphate as effectively as wild-type FGF23 (FIG. 4D). Moreover, when injected into Fgf23 knockout mice, the $FGF23^{R140A/R143A}$ mutant exhibited as much of phosphate-lowering activity as wild-type FGF23 (FIG. 4D). These data show that, as in the case of FGF19, abolishment of residual HS binding does not impact the metabolic activity of FGF23 leading to the conclusion that HS is not a component of the endocrine FGF signal transduction unit (FIG. 1D).

Example 12

Conversion of a Paracrine FGF Into an Endocrine Ligand Confirms that HS is Dispensable for the Metabolic Activity of Endocrine FGFs If HS is dispensable for the metabolic activity of endocrine FGFs, then it should be feasible to convert a paracrine FGF into an endocrine FGF by eliminating HS-binding affinity of the paracrine FGF and substituting its C-terminal tail for that of an endocrine FGF containing the Klotho co-receptor binding site. Reducing HS-binding affinity will allow the ligand to freely diffuse and enter the blood circulation while attaching the C-terminal tail of an endocrine FGF will home the ligand into its target tissues. FGF2, a prototypical paracrine FGF, was chosen for conversion into FGF23-like and FGF21-like ligands, respectively. FGF2 was selected as paracrine ligand for this protein engineering exercise because it preferentially binds to the "c" isoform of FGFR1, the principal receptor mediating the metabolic activity of FGF23 (Gattineni et al., *Am. J. Physiol. Renal Physiol.* 297:F282-291 (2009); Liu et al., *J. Am. Soc. Nephrol.* 19:2342-2350 (2008), which are hereby incorporated by reference in their entirety) and FGF21 (Kurosu et al., *J. Biol. Chem.* 282:26687-26695 (2007), which is hereby incorporated by reference in its entirety), respectively. In the crystal structure of heparin-bound FGF2 (PDB ID: 1FQ9; (Schlessinger et al., *Mol. Cell* 6:743-750 (2000), which is hereby incorporated by reference in its entirety)), K128, R129, and K134 mediate the majority of hydrogen bonds with heparin and hence mutation of these residues was predicted to cause a major reduction in HS-binding affinity of FGF2 (FIGS. 1A, 2, and 5A). Accordingly, these three residues were mutated and then the short C-terminal tail of the mutated FGF2 was replaced with the C-terminal tail of FGF23 (R161 to I251) or the C-terminal tail of FGF21 (P168 to S209) (FIG. 5A). The resulting chimeras were termed $FGF2^{\Delta HBScore}$-$FGF2^{C\text{-}tail}$ and $FGF2^{\Delta HBScore}$-$FGF21^{C\text{-}tail}$ (FIG. 5A). To demonstrate that reduction in HS-binding affinity is required for converting FGF2 into an endocrine ligand, two control chimeras were made in which the HS-binding site of the FGF2 core was left intact ($FGF2^{WTcore}$-$FGF23^{C\text{-}tail}$ and $FGF2^{WTcore}$-$FGF21^{C\text{-}tail}$; FIG. 5A).

Consistent with the structural prediction, $FGF2^{\Delta HBScore}$-$FGF23^{C\text{-}tail}$ and $FGF2^{\Delta HBScore}$-$FGF21^{C\text{-}tail}$ exhibited poor binding affinity for HS compared to the corresponding control chimeras with intact HS-binding site (FIGS. 5B-5E). Since HS is an obligatory cofactor in paracrine FGF signaling, the $FGF2^{\Delta HBScore}$-$FGF23^{C\text{-}tail}$ and $FGF2^{\Delta HBScore}$-$FGF21^{C\text{-}tail}$ chimeras were predicted to lose the ability to activate FGFR1c in an HS-dependent fashion. To test this, HEK293 cells, which endogenously express FGFR1c, were stimulated with $FGF2^{\Delta HBScore}$-$FGF23^{C\text{-}tail}$ or $FGF2^{WTcore}$-$FGF23^{C\text{-}tail}$. Induction of protein expression of the transcription factor Egr1, a known downstream mediator of FGF signaling, was used as readout for FGFR activation. As shown in FIG. 5G, the $FGF2^{\Delta HBScore}$-$FGF23^{C\text{-}tail}$ chimera, like native FGF23, was ineffective in inducing Egr1 expression at concentrations at which the $FGF2^{WTcore}$-$FGF23^{C\text{-}tail}$ chimera elicited a near maximal effect. The same observations were made for the FGF2$^{\Delta HBScore}$-FGF21$^{C\text{-}tail}$ chimera (FIG. 5F). These data show that, similar to native FGF23 and FGF21, the FGF2$^{\Delta HBScore}$-FGF23$^{C\text{-}tail}$ and FGF2$^{\Delta HBScore}$-FGF21$^{C\text{-}tail}$ chimeras lost the ability to activate FGFR in an HS-dependent, paracrine fashion.

To determine whether the FGF2$^{\Delta HBScore}$-FGF23$^{C\text{-}tail}$ and FGF2$^{\Delta HBScore}$-FGF21$^{C\text{-}tail}$ chimeras gained the ability to signal in a Klotho co-receptor-dependent, endocrine fashion, it was first analyzed whether these chimeras can form ternary complexes with FGFR1c and Klotho co-receptor. To this end, a SPR-based binding competition assay was employed. FGF23 was immobilized onto a SPR biosensor chip, and mixtures of a fixed concentration of binary αKlotho-FGFR1c complex with increasing concentrations of FGF2$^{\Delta HBScore}$-FGF23$^{C\text{-}tail}$ chimera were passed over the chip. FGF2$^{\Delta HBScore}$-FGF23$^{C\text{-}tail}$ competed, in a dose-dependent fashion, with immobilized FGF23 for binding to the αKlotho-FGFR1c complex (FIG. 7A), demonstrating that the chimera, like native FGF23 (FIG. 7B), is able to form a ternary complex with FGFR1c and αKlotho. To test whether the FGF2$^{\Delta HBScore}$-FGF21$^{C\text{-}tail}$ chimera can likewise form a ternary complex with FGFR1c and βKlotho, FGF21 was coupled to a SPR biosensor chip, and mixtures of the binary βKlotho-FGFR1c complex with FGF2$^{\Delta HBScore}$-FGF21$^{C\text{-}tail}$ were passed over the chip. FGF2$^{\Delta HBScore}$-FGF21$^{C\text{-}tail}$ effectively competed with immobilized FGF21 for binding to the βKlotho-FGFR1c complex (FIG. 8A), demonstrating that the chimera, like native FGF21 (FIG. 8B), is capable of binding to the binary complex of FGFR1c and βKlotho. Notably, native FGF2 failed to compete with FGF23 for binding to the αKlotho-FGFR1c complex (FIG. 7C), and with FGF21 for binding to the βKlotho-FGFR1c complex (FIG. 8C) since it lacks the Klotho co-receptor binding domain. To further confirm the binding specificity of the FGF2$^{\Delta HBScore}$-FGF2$^{C\text{-}tail}$ chimera for the αKlotho-FGFR1c complex, FGF2$^{\Delta HBScore}$-FGF2$^{C\text{-}tail}$ and βKlotho-FGFR1c complex were mixed at a molar ratio of 10:1, and the mixture was injected over a chip containing immobilized FGF21. FGF2$^{\Delta HBScore}$-FGF23$^{C\text{-}tail}$, like native FGF23, failed to compete with FGF21 for binding to the βKlotho-FGFR1c complex (FIGS. 7D and 7E). Similarly, the FGF2$^{\Delta HBScore}$-FGF21$^{C\text{-}tail}$ chimera, like native FGF21, failed to compete with FGF23 for binding to the αKlotho-FGFR1c complex (FIGS. 8D and 8E). For the FGF2$^{\Delta HBScore}$-FGF21$^{C\text{-}tail}$ chimera, we investigated whether it is able to activate FGFR1c in a βKlotho-dependent fashion in cells. HEK293 cells were transfected with βKlotho and then stimulated with FGF2$^{\Delta HBScore}$-FGF21$^{C\text{-}tail}$ or FGF21. Similar to native FGF21, the FGF2$^{\Delta HBScore}$-FGF21$^{C\text{-}tail}$ chimera induced Egr1 protein expression in HEK293-βKlotho cells (FIG. 8F), indicating that the chimera is capable of activating FGFR1c in the presence of βKlotho.

To provide definite proof for the ligand conversion, the metabolic activity of the chimeras in vivo was tested. Specifically, the ability of the FGF2$^{\Delta HBScore}$-FGF23$^{C\text{-}tail}$ chimera to lower serum phosphate and to reduce renal gene expression of CYP27B1, which catalyzes the conversion of vitamin D into its bioactive form, was examined. Mice were injected with FGF2$^{\Delta HBScore}$-FGF23$^{C\text{-}tail}$ or as controls, FGF23 or FGF2$^{WTcore}$-FGF23$^{C\text{-}tail}$, and serum phosphate concentrations and renal CYP27B 1 mRNA levels were measured. Similar to native FGF23, the FGF2$^{\Delta HBScore}$-FGF23$^{C\text{-}tail}$ chimera caused a decrease in serum phosphate in wild-type mice (FIG. 7F). The chimera also induced a marked decrease in CYP27B1 mRNA levels, just like the native FGF23 ligand (FIG. 7G). These data show that the FGF2$^{\Delta HBScore}$-FGF23$^{C\text{-}tail}$ chimera acts as an FGF23-like hormone. Importantly, the FGF2$^{WTcore}$-FGF23$^{C\text{-}tail}$ chimera failed to decrease serum phosphate or CYP27B1 mRNA levels (FIGS. 7F and 7G). This is expected because, owing to its high affinity for HS, this chimera should be trapped in the vicinity of the injection site and hence not be able to enter the blood circulation. Moreover, these data show that adding the Klotho co-receptor binding site is not sufficient to convert a paracrine FGF into an endocrine ligand. To confirm that the metabolic activity of the FGF2$^{\Delta HBScore}$-FGF23$^{C\text{-}tail}$ chimera is dependent on αKlotho, αKlotho knockout mice were injected with FGF2$^{\Delta HBScore}$-FGF23$^{C\text{-}tail}$ or FGF23 as a control, and serum concentrations of phosphate were measured. As shown in FIG. 7F, FGF2$^{\Delta HBScore}$-FGF23$^{C\text{-}tail}$ failed to lower serum phosphate, demonstrating that the chimera, like native FGF23 (FIG. 7F), requires αKlotho for metabolic activity.

To determine whether the FGF2$^{\Delta HBScore}$-FGF21$^{C\text{-}tail}$ chimera exhibits FGF21-like metabolic activity, its ability to potentiate the hypoglycemic effect of insulin was examined (Ohnishi et al., *FASEB J.* 25:2031-2039 (2011), which is hereby incorporated by reference in its entirety). Mice were injected with insulin plus FGF2$^{\Delta HBScore}$-FGF21$^{C\text{-}tail}$, insulin plus FGF21, or insulin alone, and blood glucose concentrations were monitored for up to one hour after the injection. Similar to FGF21, the FGF2$^{\Delta HBScore}$-FGF21$^{C\text{-}tail}$ chimera enhanced the hypoglycemic effect of insulin (FIG. 8G), demonstrating that the chimera acts as an FGF21-like hormone.

To substantiate further the concept of FGF ligand conversion, another FGF21-like ligand was engineered using FGF1 as paracrine FGF, and the metabolic activity of the engineered protein was tested in vivo in a mouse model of diabetes and obesity. Besides serving as an additional proof-of-concept, the use of FGF1 for this particular ligand conversion was appealing because FGF1 on its own plays an essential role in glucose metabolism (Jonker et al., "A PPARγ-FGF1 Axis is Required for Adaptive Adipose Remodelling and Metabolic Homeostasis," *Nature* 485:391-394 (2012), which is hereby incorporated by reference in its entirety). Notably, similar to FGF21, FGF1 is induced postprandially in gonadal white adipose tissue by the nuclear hormone receptor PPARγ (peroxisome proliferator activated receptor-γ) (Jonker et al., "A PPARγ-FGF1 Axis is Required for Adaptive Adipose Remodelling and Metabolic Homeostasis," *Nature* 485:391-394 (2012); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). FGF1 is required for the remodeling of adipose tissue to adjust to fluctuations in nutrient availability (Jonker et al., "A PPARγ-FGF1 Axis is Required for Adaptive Adipose Remodelling and Metabolic Homeostasis," *Nature* 485:391-394 (2012), which is hereby incorporated by reference in its entirety), and this process is influenced by FGF21 (Hotta et al., "Fibroblast Growth Factor 21 Regulates Lipolysis in White Adipose Tissue But is Not Required for Ketogenesis and Triglyceride Clearance in Liver," *Endocrinology* 150:4625-4633 (2009); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). As part of a positive feedback loop, FGF21 stimulates PPARγ activity in adipocytes (Dutchak et al., "Fibroblast Growth Factor-21 Regulates PPARγ Activity and the Antidiabetic Actions of Thiazolidinediones," *Cell* 148:556-

567 (2012), which is hereby incorporated by reference in its entirety), raising the intriguing possibility that FGF21 regulates FGF1 signaling in adipose tissue through PPARγ. An FGF1$^{\Delta HBScore}$-FGF21$^{C\text{-}tail}$ chimera was generated in the same manner as the FGF2$^{\Delta HBScore}$-FGF21$^{C\text{-}tail}$ chimera (FIGS. 5 and 6). Specifically, K127, K128, and K133 of FGF1, which correspond to the key HS-binding residues identified in the crystal structure of heparin-bound FGF2 (PDB ID: 1FQ9; (Schlessinger et al., *Mol. Cell* 6:743-750 (2000), which is hereby incorporated by reference in its entirety)), were mutated and then the short C-terminal tail of the mutated FGF1 was replaced with the C-terminal tail of FGF21 (P168 to S209) (FIG. 6). A full-length FGF1 protein harboring the HS-binding site mutations was used as a control (FIG. 6). Consistent with the structural prediction, this protein exhibited poor binding affinity for HS compared to wild-type FGF1 as evidenced by the fact that, unlike the wild-type ligand, the mutant protein did not bind to a Heparin sepharose column. A subcutaneous bolus injection of the FGF1$^{\Delta HBScore}$-FGF21$^{C\text{-}tail}$ chimera elicited a hypoglycemic effect in ob/ob mice (FIG. 9C), demonstrating that the chimera has metabolic activity. The effect was of similar magnitude as that observed for native FGF1 (FIG. 9C), which itself has a much greater hypoglycemic effect in ob/ob mice than native FGF21 (FIG. 9A). The HS-binding site mutant of FGF1, which was included as a control in these experiments, showed a similar hypoglycemic effect as the wild-type ligand (FIG. 9B), indicating that the loss in HS-binding affinity had no impact on the metabolic activity of FGF1. To alter the receptor-binding specificity of FGF1 such that FGF1 selectively binds to the "c" splice isoform of FGFR1, the principal receptor mediating the metabolic activity of FGF21, an N-terminally truncated FGF1 protein was made (FIG. 6). The truncated FGF1 ligand lacked twenty four residues from the N-terminus including the nine residues that are critical for the promiscuous binding of FGF1 to both splice isoforms of FGFR1-3 (Beenken et al., "Plasticity in Interactions of Fibroblast Growth Factor 1 (FGF1) N Terminus with FGF Receptors Underlies Promiscuity of FGF1," *J Biol Chem* 287(5):3067-3078 (2012), which is hereby incorporated by reference in its entirety). Based on the crystal structures of FGF1-FGFR complexes, the truncation was also predicted to reduce the receptor-binding affinity of FGF1, and hence the ligand's mitogenicity. The truncated FGF1 protein induced a similar hypoglycemic effect in ob/ob mice as native FGF1 did (FIG. 9B), indicating that the metabolic activity of FGF1 is mediated through the "c" splice isoform of FGFR. Together, these findings provide a starting point for engineering FGF1 ligands that have no mitogenicity but the same or enhanced metabolic activity compared to native FGF1.

The demonstrated ability to convert a paracrine FGF into an endocrine ligand by means of reducing HS-binding affinity of the paracrine FGF and adding the Klotho co-receptor binding site substantiates that HS does not participate in the formation of the endocrine FGF signal transduction unit. The dispensability of HS for the metabolic activity of endocrine FGFs has an intriguing implication as to how these FGFs have evolved to become hormones. It appears that these ligands have lost the requirement to bind HS in order to signal, while acquiring the ability to bind Klotho co-receptors, which is necessary to direct these ligands to their target organs.

In the target tissue, Klotho co-receptors constitutively associate with cognate receptors of endocrine FGFs to offset the inherently low receptor-binding affinity of endocrine FGFs (FIGS. 10B-10D; Kurosu et al., *J. Biol. Chem.* 282: 26687-26695 (2007); Kurosu et al., *J. Biol. Chem.* 281: 6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). This low binding affinity is due to the fact that key receptor-binding residues in the β-trefoil core of endocrine FGFs are replaced by residues that are suboptimal for receptor binding (Goetz et al., *Mol. Cell Biol.* 27:3417-3428 (2007), which is hereby incorporated by reference in its entirety). To measure the degree to which Klotho co-receptors enhance the receptor-binding affinity of endocrine FGFs, SPR experiments were conducted using FGF23 and FGFR1c and αKlotho co-receptor as an example (see FIGS. 10A-10F). The SPR data show that αKlotho enhances the affinity of FGF23 for FGFR1c by over 20-fold (FIGS. 10D and 10E). The affinity of FGF23 for FGFR1c in the presence of αKlotho is comparable to that of FGF2 for FGFR1c in the absence of its HS cofactor (FIGS. 10A and 10E). It should be noted, however, that HS further increases the binding affinity of FGF2 for FGFR1c by at least an order of magnitude (Pantoliano et al., *Biochemistry* 33:10229-10248 (1994); Roghani et al., *J. Biol. Chem.* 269:3976-3984 (1994), which are hereby incorporated by reference in their entirety). Hence, the receptor-binding affinity of FGF23 in the presence of αKlotho co-receptor still is lower than that of FGF2 in the presence of HS cofactor. These observations imply that the signaling capacity of the endocrine FGF signal transduction unit should be weaker than that of the paracrine FGF signaling unit. Indeed, cell-based studies show that even in the presence of their Klotho co-receptor, endocrine FGFs are inferior to paracrine FGFs at activating FGFR-induced intracellular signaling pathways (Kurosu et al., *J. Biol. Chem.* 282:26687-26695 (2007); Urakawa et al., *Nature* 444:770-774 (2006), which are hereby incorporated by reference in their entirety).

The finding that endocrine FGFs do not need to rely on HS for signaling has another important implication in regard to the role of Klotho co-receptors. Since FGFR dimerization is a prerequisite for FGF signaling in general, it is proposed that Klotho co-receptors not only enhance the binding affinity of endocrine ligand for receptor but also promote receptor dimerization upon ligand binding. In other words, Klotho co-receptors must fulfill the same dual role that HS plays in signaling by paracrine FGFs (FIG. 1D). The ligand conversion also provides the framework for the rational design of endocrine FGF-like molecules for the treatment of metabolic disorders. An FGF23-like molecule, for example, will be useful for the treatment of inherited or acquired hyperphosphatemia, and an FGF21-like molecule, for example, for the treatment of type 2 diabetes, obesity, and related metabolic disorders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A chimeric protein comprising:
an N-terminus coupled to a C-terminus, wherein the N-terminus comprises an FGF2 portion beginning at any one of residues 1 to 25 and ending at any one of residues 151-155 of SEQ ID NO: 121,
wherein the FGF2 amino acid positions corresponding to those selected from the group consisting of N36, K128, R129, K134, K138, Q143, K144, and combinations thereof are substituted to decrease binding affinity for heparin and/or heparan sulfate compared to FGF2 without the substitution, and
wherein the C-terminus comprises a C-terminal portion of an FGF23 comprising amino acid residues 161-251 of SEQ ID NO: 233.

2. The chimeric protein according to claim 1, wherein the FGF2 portion is amino acid residues 1-151 of SEQ ID NO: 121.

3. The chimeric protein according to claim 1, wherein the FGF2 portion is amino acid residues 25-151 of SEQ ID NO: 121.

4. The chimeric protein according to claim 1, wherein the FGF2 portion is amino acid residues 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 20-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-152, 25-153, 25-154, or 25-155 of SEQ ID NO: 121.

5. The chimeric protein according to claim 1, wherein the one or more substitutions are selected from the group consisting of N36T; K128D; R129Q; K134V; K138H; Q143M; K144T, K144L, or K144I ; and combinations thereof.

6. A pharmaceutical composition comprising the chimeric protein according to claim 1 and a pharmaceutically-acceptable carrier.

7. The pharmaceutical composition according to claim 6 further comprising:
a hypophosphatemic agent, a phosphate binder, a vitamin D antagonist, an analgesic and/or an anti-inflammatory agent.

8. The chimeric protein according to claim 1, wherein the chimeric protein comprises the amino acid sequence of SEQ ID NO:323 or SEQ ID NO:324.

9. The chimeric protein according to claim 1, wherein the one or more amino acid substitutions comprises a substitution at amino acid residue N36.

10. The chimeric protein according to claim 9, wherein the substitution is N36T.

11. The chimeric protein according to claim 1, wherein the one or more amino acid substitutions comprises a substitution at amino acid residue K128.

12. The chimeric protein according to claim 11, wherein the substitution is K128D.

13. The chimeric protein according to claim 1, wherein the one or more amino acid substitutions comprises a substitution at amino acid residue R129.

14. The chimeric protein according to claim 13, wherein the substitution is R129Q.

15. The chimeric protein according to claim 1, wherein the one or more amino acid substitutions comprises a substitution at amino acid residue K134.

16. The chimeric protein according to claim 15, wherein the substitution is K134V.

17. The chimeric protein according to claim 1, wherein the one or more amino acid substitutions comprises a substitution at amino acid residue K138.

18. The chimeric protein according to claim 17, wherein the substitution is K138H.

19. The chimeric protein according to claim 1, wherein the one or more amino acid substitutions comprises a substitution at amino acid residue Q143.

20. The chimeric protein according to claim 19, wherein the substitution is Q143M.

21. The chimeric protein according to claim 1, wherein the one or more amino acid substitutions comprises a substitution at amino acid residue K144.

22. The chimeric protein according to claim 21, wherein the substitution is K144T.

23. The chimeric protein according to claim 21, wherein the substitution is K144L.

24. The chimeric protein according to claim 21, wherein the substitution is K144I.

25. The chimeric protein of claim 1, wherein the one or more amino acid substitutions comprises substitutions at amino acid residues K128, R129, and K134.

26. The chimeric protein of claim 25, wherein the substitutions are K128D, R129Q, and K134V.

27. A method for decreasing circulating levels of phosphate and/or bioactive vitamin D in a subject suffering from a disorder, the method comprising:
    selecting a subject suffering from a disorder wherein the selected subject has a disorder associated with elevated blood levels of phosphate; elevated blood levels of bioactive vitamin D; or combinations thereof;
    providing a chimeric protein according to claim 1; and
    administering an amount of the chimeric protein to the selected subject effective to decrease circulating levels of phosphate and/or bioactive vitamin D in the selected subject.

28. The method according to claim 27, wherein the FGF2 portion is amino acid residues 1-151 of SEQ ID NO: 121.

29. The method according to claim 27, wherein the FGF2 portion is amino acid residues 25-151 of SEQ ID NO: 121.

30. The method according to claim 29, wherein the FGF2 portion is amino acid residues 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155, 15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-152, 25-153, 25-154, or 25-155 of SEQ ID NO: 121.

31. The method according to claim 27, wherein the one or more substitutions are selected from the group consisting of N36T; K128D; R129Q; K134V; K138H; Q143M; K144T, K144L, or K144I; and combinations thereof.

32. The method according to claim 27, wherein the administering is performed parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

33. The method according to claim 27, wherein the chimeric protein is administered with a pharmaceutically-acceptable carrier.

34. The method according to claim 27, wherein the selected subject is a mammal.

35. The method according to claim 27, wherein the selected subject is a human.

36. The method according to claim 27, wherein the chimeric protein is co-administered with a hypophosphatemic agent, a phosphate binder, a vitamin D antagonist, an analgesic and/or an anti-inflammatory agent.

37. The method according to claim 27, wherein the chimeric protein comprises the amino acid sequence of SEQ ID NO:323 or SEQ ID NO:324.

38. The method according to claim 27, wherein the selected subject has familial tumoral calcinosis.

39. The method according to claim 27, wherein the selected subject has hyperostosis-hyperphosphatemia syndrome.

40. The method according to claim 27, wherein the selected subject has hyperphosphatemia.

* * * * *

UNITED STATES PATENT AND TRADEMARK OFFICE
CERTIFICATE OF CORRECTION

PATENT NO. : 9,657,075 B2
APPLICATION NO. : 13/839051
DATED : May 23, 2017
INVENTOR(S) : Mohammadi et al.

Page 1 of 1

It is certified that error appears in the above-identified patent and that said Letters Patent is hereby corrected as shown below:

In the Specification

Column 1 at Lines 10-14, delete "This invention was made with government support under grant numbers DE13686, DK077276, AG019712, DK091392, and DK067158 awarded by the U.S. National Institutes of Health. The government has certain rights in this invention." and insert in its place --This invention was made with government support under DE13686 awarded by National Institutes of Health. The government has certain rights in the invention.--

Signed and Sealed this
Seventh Day of April, 2020

Andrei Iancu
*Director of the United States Patent and Trademark Office*